US012703692B2

(12) United States Patent
Brown et al.

(10) Patent No.: US 12,703,692 B2
(45) **Date of Patent: *Aug. 11, 2026**

(54) SMALL MOLECULE INHIBITORS OF MAMMALIAN SLC6A19 FUNCTION

(71) Applicant: Jnana Therapeutics Inc., Boston, MA (US)

(72) Inventors: Dean G. Brown, Hollis, NH (US); Giovanni Muncipinto, Cambridge, MA (US); Joshua Ethan Zweig, Somerville, MA (US); Long Vo Nguyen, Boston, MA (US); Mitchell T. Antalek, Medford, MA (US); Ryan A. Hollibaugh, Quincy, MA (US)

(73) Assignee: Jnana Therapeutics Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/224,208

(22) Filed: May 30, 2025

(65) Prior Publication Data

US 2025/0289798 A1 Sep. 18, 2025

Related U.S. Application Data

(63) Continuation of application No. 18/977,370, filed on Dec. 11, 2024, now Pat. No. 12,319,668, which is a (Continued)

(51) Int. Cl.

| | |
|---|---|
| ***C07D 401/04*** | (2006.01) |
| ***A61K 31/44*** | (2006.01) |
| ***A61K 31/4523*** | (2006.01) |
| ***A61K 31/4525*** | (2006.01) |
| ***A61K 31/453*** | (2006.01) |
| ***A61K 31/4535*** | (2006.01) |
| ***A61K 31/454*** | (2006.01) |
| ***A61K 31/4545*** | (2006.01) |
| ***A61K 31/497*** | (2006.01) |
| ***A61K 31/501*** | (2006.01) |
| ***A61K 31/506*** | (2006.01) |
| ***A61K 31/5377*** | (2006.01) |
| ***C07D 211/58*** | (2006.01) |
| ***C07D 401/06*** | (2006.01) |
| ***C07D 401/14*** | (2006.01) |
| ***C07D 403/04*** | (2006.01) |

(Continued)

(52) U.S. Cl.

CPC ........... *C07D 401/04* (2013.01); *A61K 31/44* (2013.01); *A61K 31/4523* (2013.01); *A61K 31/4525* (2013.01); *A61K 31/453* (2013.01); *A61K 31/4535* (2013.01); *A61K 31/454* (2013.01); *A61K 31/4545* (2013.01); *A61K 31/497* (2013.01); *A61K 31/501* (2013.01); *A61K 31/506* (2013.01); *A61K 31/5377* (2013.01); *C07D 211/58* (2013.01); *C07D 401/06* (2013.01); *C07D 401/14* (2013.01); *C07D 403/04* (2013.01); *C07D 405/06* (2013.01); *C07D 405/14* (2013.01); *C07D 409/06* (2013.01); *C07D 409/14* (2013.01); *C07D 413/04* (2013.01); *C07D 413/06* (2013.01); *C07D 413/12* (2013.01); *C07D 413/14* (2013.01); *C07D 417/04* (2013.01); *C07D 417/06* (2013.01); *C07D 417/14* (2013.01); *C07D 471/04* (2013.01); *C07D 487/04* (2013.01)

(58) Field of Classification Search

CPC .. C07D 211/58; C07D 401/06; C07D 401/14; C07D 403/04; C07D 405/06; C07D 405/14; C07D 409/06; C07D 409/14; C07D 413/04; C07D 413/06; C07D 413/12; C07D 413/14; C07D 417/04; C07D 417/06; C07D 417/14; C07D 471/04; C07D 487/04; C07D 401/04; A61K 31/4523; A61K 31/4525; A61K 31/453; A61K 31/4535; A61K 31/454; A61K 31/4545; A61K 31/497; A61K 31/501; A61K 31/506; A61K 31/5377; A61K 31/44

See application file for complete search history.

(56) References Cited

U.S. PATENT DOCUMENTS

| | | | |
|---|---|---|---|
| 6,288,077 | B1 | 9/2001 | De Nanteuil et al. |
| 6,500,844 | B1 | 12/2002 | Finke et al. |

(Continued)

FOREIGN PATENT DOCUMENTS

| | | | |
|---|---|---|---|
| WO | WO-2003/037894 | A1 | 5/2003 |
| WO | WO-2008/021927 | A2 | 2/2008 |

(Continued)

OTHER PUBLICATIONS

Desai J, Patel B, Darji B, et al. Discovery of novel, potent and orally efficacious inhibitor of neutral amino acid transporter B<sup>0</sup>AT1 (SLC6A19). Bioorganic & Medicinal Chemistry Letters. Dec. 2021;53:128421. DOI: 10.1016/j.bmcl.2021.128421. PMID: 34718128. (Year: 2021).*

(Continued)

*Primary Examiner* — Clinton A Brooks
*Assistant Examiner* — Josmalen M. Ramos-Lewis
(74) *Attorney, Agent, or Firm* — Foley Hoag LLP; Dana M. Gordon

(57) ABSTRACT

Disclosed are compounds, compositions, and methods useful for treating or preventing a disease or disorder associated with abnormal levels of amino acids by modulation of SLC6A19 transport.

30 Claims, 5 Drawing Sheets

Related U.S. Application Data continuation of application No. 18/281,138, filed as application No. PCT/US2022/019513 on Mar. 9, 2022.

(60) Provisional application No. 63/308,790, filed on Feb. 10, 2022, provisional application No. 63/159,271, filed on Mar. 10, 2021, provisional application No. 63/226,551, filed on Jul. 28, 2021, provisional application No. 63/234,487, filed on Aug. 18, 2021, provisional application No. 63/292,815, filed on Dec. 22, 2021.

(51) Int. Cl.

| | |
|---|---|
| ***C07D 405/06*** | (2006.01) |
| ***C07D 405/14*** | (2006.01) |
| ***C07D 409/06*** | (2006.01) |
| ***C07D 409/14*** | (2006.01) |
| ***C07D 413/04*** | (2006.01) |
| ***C07D 413/06*** | (2006.01) |
| ***C07D 413/12*** | (2006.01) |
| ***C07D 413/14*** | (2006.01) |
| ***C07D 417/04*** | (2006.01) |
| ***C07D 417/06*** | (2006.01) |
| ***C07D 417/14*** | (2006.01) |
| ***C07D 471/04*** | (2006.01) |
| ***C07D 487/04*** | (2006.01) |

(56) References Cited

U.S. PATENT DOCUMENTS

| | | | |
|---|---|---|---|
| 8,846,654 | B2 | 9/2014 | Janiak et al. |
| 9,346,853 | B2 | 5/2016 | Hoeferl-Prantz et al. |
| 10,934,299 | B2 | 3/2021 | Ioannidis et al. |
| 12,319,668 | B2 | 6/2025 | Brown |
| 2003/0114517 | A1 | 6/2003 | Greenlee et al. |
| 2004/0142416 | A1 | 7/2004 | Laipis et al. |
| 2004/0235823 | A1 | 11/2004 | Bridger et al. |
| 2007/0254915 | A1 | 11/2007 | Leleti et al. |
| 2009/0105259 | A1* | 4/2009 | Jeong .................. C07D 231/40 544/236 |
| 2015/0252021 | A1 | 9/2015 | Giuliano et al. |
| 2021/0238139 | A1 | 8/2021 | Poljak et al. |
| 2022/0213077 | A1 | 7/2022 | Tan et al. |
| 2024/0208923 | A1 | 6/2024 | Brown et al. |
| 2025/0084054 | A1 | 3/2025 | Brown et al. |
| 2025/0115570 | A1 | 4/2025 | Brown |
| 2025/0289797 | A1 | 9/2025 | Brown et al. |
| 2026/0001859 | A1 | 1/2026 | Brown et al. |
| 2026/0008753 | A1 | 1/2026 | Malona et al. |

FOREIGN PATENT DOCUMENTS

| | | | |
|---|---|---|---|
| WO | WO-2008/112022 | A1 | 9/2008 |
| WO | WO-2011/060396 | A1 | 5/2011 |
| WO | WO-2011/060397 | A1 | 5/2011 |
| WO | WO-2012/116176 | A2 | 8/2012 |
| WO | WO-2014/144130 | A2 | 9/2014 |
| WO | WO-2015/006492 | A1 | 1/2015 |
| WO | WO-2015/134839 | A1 | 9/2015 |
| WO | WO-2016/100050 | A1 | 6/2016 |
| WO | WO-2018/112136 | A1 | 6/2018 |
| WO | WO-2019/040106 | A2 | 2/2019 |
| WO | WO-2019/046303 | A1 | 3/2019 |
| WO | WO-2019/169153 | A1 | 9/2019 |
| WO | WO-2020/081572 | A1 | 4/2020 |
| WO | WO-2020/264176 | A1 | 12/2020 |
| WO | WO-2021/113682 | A1 | 6/2021 |
| WO | WO-2022/161972 | A1 | 8/2022 |
| WO | WO-2022/192370 | A1 | 9/2022 |
| WO | WO-2022/192545 | A1 | 9/2022 |
| WO | WO-2022/221227 | A1 | 10/2022 |
| WO | WO-2023/283213 | A1 | 1/2023 |
| WO | WO-2023/009663 | A1 | 2/2023 |
| WO | WO-2023/023242 | A1 | 2/2023 |
| WO | WO-2023/023255 | A1 | 2/2023 |
| WO | WO-2023/023532 | A3 | 5/2023 |
| WO | WO-2023/079294 | A1 | 5/2023 |
| WO | WO-2023/118252 | A1 | 6/2023 |
| WO | WO-2023/118875 | A1 | 6/2023 |
| WO | WO-2023/122134 | A1 | 6/2023 |
| WO | WO-2023/122140 | A1 | 6/2023 |
| WO | WO-2023/122267 | A2 | 6/2023 |
| WO | WO-2023/122780 | A2 | 6/2023 |
| WO | WO-2024/015569 | A2 | 1/2024 |
| WO | WO-2024/015574 | A1 | 1/2024 |
| WO | WO-2024/058926 | A1 | 3/2024 |
| WO | WO-2024/059005 | A1 | 3/2024 |
| WO | WO-2024/059205 | A1 | 3/2024 |
| WO | WO-2024/112830 | A1 | 5/2024 |
| WO | WO-2024/118721 | A1 | 6/2024 |
| WO | WO-2024/259100 | A2 | 12/2024 |
| WO | WO-2025/038421 | A1 | 2/2025 |
| WO | WO-2025/038949 | A1 | 2/2025 |

OTHER PUBLICATIONS

Caira, "Crystalline Polymorphism of Organic Compounds." Topics in Current Chemistry, vol. 198, p. 163-208.

CAS RN 2463865-94-1. Database Registry, Chemical Abstracts Service, "Urea, N-methyl-N'-(3-phenylcyclobutyl)-N-[1-(3-pyridazinyl)-3-piperidinyl]-," Aug. 27, 2020.

CAS RN 2467430-42-6. Database Registry, Chemical Abstracts Service, "Urea, N'-[(hexahydro-1-methyl-1H-azepin-3-yl)methyl]-N-methyl-N-[(2-methyl-5-thiazolyl)met hyl]-," Aug. 28, 2020.

CAS RN 2471803-01-5, Database Registry, Chemical Abstracts Service, "Urea, N'-[1-(3-fluoro-2-pyridinyl)-3-pyrrolidinyl]-N-methyl-N-(phenylmethyl)-," Sep. 3, 2020.

International Search Report and Written Opinion for International Application No. PCT/US23/32413 dated Feb. 6, 2024.

International Search Report and Written Opinion for International Application No. PCT/US22/19513 dated Jul. 7, 2022.

International Search Report and Written Opinion for International Application No. PCT/US22/53798 dated May 23, 2023.

International Search Report and Written Opinion for International Application No. PCT/US23/27766 dated Jan. 10, 2024.

International Search Report and Written Opinion for International Application No. PCT/US23/27774 dated Oct. 20, 2023.

International Search Report and Written Opinion for International Application No. PCT/US23/31169 dated Jan. 29, 2024.

International Search Report and Written Opinion for International Application No. PCT/US23/32752 dated Feb. 8, 2024.

International Search Report and Written Opinion for International Application No. PCT/US23/81526 dated Mar. 22, 2024.

International Search Report and Written Opinion for International Application No. PCT/US24/33808 dated Nov. 1, 2024.

International Search Report and Written Opinion for International Application No. PCT/US24/41648 dated Dec. 5, 2024.

International Search Report and Written Opinion for International Application No. PCT/US24/42724 dated Nov. 19, 2024.

Invitation to Pay Additional Fees for International Application No. PCT/US22/19513 dated May 10, 2022.

Invitation to Pay Additional Fees for International Application No. PCT/US22/53798 mailed Mar. 9, 2023.

Invitation to Pay Additional Fees for International Application No. PCT/US23/27766 dated Oct. 3, 2023.

Invitation to Pay Additional Fees for International Application No. PCT/US23/32413 dated Dec. 8, 2023.

Invitation to Pay Additional Fees for International Application No. PCT/US23/32752 dated Dec. 21, 2023.

Invitation to Pay Additional Fees for International Application No. PCT/US24/33808 dated Aug. 19, 2024.

Nguyen et al., "Synthesis and pharmacological evaluation of 1-phenyl-3-thiophenylurea derivatives as cannabinoid type-1 receptor allosteric modulators", Journal of medicinal chemistry 62.21: 9806-9823 (2019).

(56) References Cited

OTHER PUBLICATIONS

PubChem CID 100690760 "1-[(3S)-3-[3-(3,5-dimethylphenyl)-1,2,4-oxadiazol-5-yl]pyrrolidin-1-yl]propan-1-one" created Dec. 11, 2015.
PubChem CID 107653149 "3-Benzyl-1-methyl-1-(1-methylpiperidin-3-yl)urea" created Jan. 15, 2016.
PubChem CID 121579555 "N-(cyclopropylcarbamoyl)-2-(7,7-difluoro-3-azabicyclo[4.1.0]heptan-3-yl)propanamide" created Sep. 7, 2016.
Pubchem CID 122561404, "3-(1-ethylpiperidin-3-yl-)-1-methyl-1-[(3-methyl-1H-indol-2-yl-)methy]urea," Create date: Dec. 8, 2016.
PubChem CID 126820738 "3-(2,6-Dimethylphenyl)-1-methyl-1-(1-methylpyrrolidin-3-yl)urea" Apr. 25, 2017.
PubChem CID 138551861 "N-[[2-(4-ethoxyphenyl)-6-methyl-2-azabicyclo[4.1.0]heptan-4-yl]methyl]-3-hydroxy-N-methylpyrrolidine-1-carboxamide" created Jul. 20, 2019.
Pubchem CID 154705888 "1-Cyclopropyl-3-methyl-3-((5-methylisoxazol-3-yl)methyl)-1-(1-(methylsulfonyl)-5-phenylpiperidin-3-yl)urea" created Oct. 23, 2020.
Pubchem CID 165119963, "(3R)-3-[(4-chloro-2-flourophenyl)methylcarbamoyl-cyclopropylamino]-N-methylpiperidine-1-carboxamide," Create date: Oct. 7, 2022.
PubChem CID 60169214 "1-(1-Acetylpiperidin-4-yl)-1-methyl-3-(1-naphthalen-1-ylethyl)urea" created Sep. 24, 2012.
PubChem CID 60169315 "Tert-butyl 4-[methyl (1-naphthalen-1-ylethylcarbamoyl)amino]piperidine-1-carboxylate" created Sep. 24, 2012.
PubChem CID 61465137 "2-[Methyl-[(1-methylpyrrolidin-3-yl)carbamoyl]amino]benzoic acid" created Oct. 19, 2012.
Pubchem CID 72137915 "1-(1-Ethylpyrrolidin-3-yl)-3-(2-fluorophenyl)-1-methylurea", created Dec. 2, 2013.
PubChem CID 88127280 "(1S,6R)-2-[(4-carbamimidoylphenyl)methyl]-2-[(2R)-2-[carbamoyl(methyl)amino]-3-cyclohexylpropanoyl]-2-azoniabicyclo[4.1.0]heptane-1-carboxamide" created Feb. 12, 2015.
PubChem SID 132380186 "2-Methyl-4-[3-oxo-3-(3-pyrazol-1-ylpyrrolidin-1-yl)propyl]-1,4-benzoxazin-3-one" created Jan. 24, 2012.
PubChem SID 145028770 "AKOS008717507" dated Oct. 18, 2012.
PubChem SID 436009908 created Nov. 21, 2020.
PubChem SID 440678060 "3-[1-(1,3-dimethyl-2,4-dioxo-1,2,3,4-tetrahydropyrimidin-5-yl)piperidin-4-yl]-1-phenylurea" dated Feb. 24, 2021.
Supplementary European Search Report for EP Application No. 22767877.8 dated Feb. 28, 2025.
Yadav et al., "Novel Chemical Scaffolds to inhibit the Neutral Amino Acid Transporter BOAT1 (SLC6A19), a Potential Target to Treat Metabolic Disease," Frontiers in Pharmacology, 11: 1-13 (2020).
Supplementary European Search Report for EP Application No. 22912482.1 dated Sep. 15, 2025.
CAS RN 2197948-15-3, Database Registry, Chemical Abstracts Service, "1-Piperidinecarboxamide, 3-[[[1-methyl-1-[3-(1-methylethenyl)phenyl]ethyl]amino]carbonyl]amino]-N-(2-methylpropyl)-," Mar. 23, 2018.
CAS RN 2197948-16-4, Database Registry, Chemical Abstracts Service, "1-Piperidinecarboxamide, N-butyl-3-[[[1-methyl-1-[3-(1--methylethenyl)phenyl]ethyl]amino]carbonyl]amino]-," Mar. 23, 2018.
CAS RN 2198321-10-5, Database Registry, Chemical Abstracts Service, "1-Piperidinecarboxamide, 3-[[[1-methyl-1-[3-(1-methylethenyl)phenyl]ethyl]amino]carbonyl]amino]-N-2-propen-1-yl-," Mar. 25, 2018.
CAS RN 2198899-36-2, Database Registry, Chemical Abstracts Service, "1-Piperidinecarboxamide, N-methyl-3-[[[1-methyl-1-[3-(1-methylethenyl)phenyl]ethyl]amino]carbonyl]amino]-," Mar. 26, 2018.
CAS RN 2198943-64-3, Database Registry, Chemical Abstracts Service, "1-Piperidinecarboxamide, N-(3-methylbutyl)-3-[[]1-methyl-1-[3-(1-methylethenyl)phenyl]ethyl]amino]carbonyl]amino] -," Mar. 26, 2018.
CAS RN 2199714-33-3, Database Registry, Chemical Abstracts Service, "1-Piperidinecarboxarnide, 3-[[[1-methyl-1-[3-(1-methylethenyl)phenyl]ethyl]amino]carbonyl]amino]-N-(1-methylpropyl)-," Mar. 27, 2018.
CAS RN 2200630-45-9, Database Registry, Chemical Abstracts Service, "1-Piperidinecarboxamide, N-ethyl-3-[[[l-methyl-l-[3-(1-methylethenyl)phenyl]ethyl]amino]carbonyl]amino]-," Mar. 28, 2018.
CAS RN 2201962-28-7, Database Registry, Chemical Abstracts Service, "1-Piperidinecarboxamide, 3-[[[1-methyl-1-[3-(1-methylethenyl)phenyl]ethyl]amino]carbonyl]amino]-N-propyl-," Mar. 30, 2018.
CAS RN 2201962-31-2, Database Registry, Chemical Abstracts Service, "1-Piperidinecarboxamide, N-(1-methylethyl)-3-[[[1-methyl-1-[3-(1-methylethenyl)phenyl]ethyl]amino]carbonyl]amino]," Mar. 30, 2018.
Hollibaugh et al., U.S. Appl. No. 19/111,603 for "Treating PKU With Spiro-Substituted and Other Piperidine Inhibitors of SLC6A19 Function," filed Mar. 13, 2025.
Muncipinto et al., U.S. Appl. No. 19/492,917 for "Piperidine Inhibitor of SLC6A19 Function," filed Dec. 12, 2025.
Notice of Allowance for U.S. Appl. No. 19/224,188 dated Jan. 16, 2026.
Xu et al., "Molecular basis of inhibition of the amino acid transporter BOAT1 (SLC6A19)." Nature Communications 15 (2024): 7224.

* cited by examiner

FIG. 1

| Example | Category | | Example | Category | | Example | Category |
|---|---|---|---|---|---|---|---|
| 2 | A | | 31 | A | | 61 | B |
| 3 | A | | 32 | B | | 62 | B |
| 4 | A | | 33 | A | | 63 | A |
| 5 | A | | 34 | B | | 64 | E |
| 6 | A | | 35 | B | | 65 | A |
| 7 | A | | 36 | A | | 66 | B |
| 8 | D | | 37 | A | | 67 | B |
| 9 | A | | 38 | C | | 68 | C |
| 10 | C | | 39 | B | | 69 | B |
| 11 | B | | 40 | C | | 70 | B |
| 12 | B | | 41 | C | | 71 | C |
| 13 | E | | 42 | A | | 72 | C |
| 14 | C | | 43 | A | | 73 | C |
| 15 | B | | 44 | E | | 75 | C |
| 16 | B | | 45 | C | | 76 | B |
| 17 | A | | 46 | E | | 77 | D |
| 18 | A | | 47 | D | | 78 | B |
| 19 | B | | 48 | B | | 79 | B |
| 20 | B | | 49 | A | | 80 | E |
| 21 | A | | 50 | C | | 81 | B |
| 22 | C | | 51 | B | | 82 | A |
| 23 | A | | 52 | C | | 83 | A |
| 24 | C | | 53 | B | | 84 | A |
| 25 | B | | 54 | A | | 85 | A |
| 26 | C | | 55 | C | | 86 | D |
| 27 | C | | 56 | C | | 87 | B |
| 28 | B | | 57 | C | | 89 | A |
| 29 | A | | 58 | B | | 90 | E |
| 30 | E | | 59 | C | | 91 | C |
| 31 | A | | 60 | B | | 92 | B |

FIG. 1 (continued)

| Example | Category | | Example | Category | | Example | Category |
|---|---|---|---|---|---|---|---|
| 93 | E | | 123 | C | | 153 | B |
| 94 | E | | 124 | E | | 154 | B |
| 95 | C | | 125 | A | | 155 | C |
| 96 | B | | 126 | A | | 156 | B |
| 97 | A | | 127 | A | | 157 | B |
| 98 | E | | 128 | A | | 158 | B |
| 99 | A | | 129 | A | | 159 | B |
| 100 | B | | 130 | B | | 160 | C |
| 101 | C | | 131 | B | | 161 | C |
| 102 | B | | 132 | B | | 162 | B |
| 103 | A | | 133 | E | | 163 | B |
| 104 | A | | 134 | C | | 164 | D |
| 105 | A | | 135 | A | | 165 | C |
| 106 | D | | 136 | C | | 166 | B |
| 107 | C | | 137 | B | | 167 | B |
| 108 | E | | 138 | A | | 168 | D |
| 109 | C | | 139 | C | | 169 | B |
| 110 | B | | 140 | E | | 170 | B |
| 111 | B | | 141 | A | | 171 | E |
| 112 | C | | 142 | D | | 172 | A |
| 113 | D | | 143 | E | | 173 | A |
| 114 | B | | 144 | B | | 174 | E |
| 115 | B | | 145 | C | | 175 | A |
| 116 | A | | 146 | B | | 176 | B |
| 117 | B | | 147 | B | | 177 | C |
| 118 | D | | 148 | B | | 178 | C |
| 119 | B | | 149 | E | | 179 | C |
| 120 | B | | 150 | C | | 180 | C |
| 121 | B | | 151 | A | | 181 | C |
| 122 | A | | 152 | C | | 182 | C |

FIG. 1 (continued)

| Ex. | Category | Ex. | Category | Ex. | Category | Ex. | Category | Ex. | Category |
|---|---|---|---|---|---|---|---|---|---|
| 183 | B | 216 | A | 249 | B | 284 | A | 316 | A |
| 184 | A | 217 | B | 250 | B | 285 | B | 317 | A |
| 185 | A | 218 | C | 251 | E | 286 | A | 318 | A |
| 186 | C | 219 | A | 252 | B | 287 | A | 319 | A |
| 187 | B | 220 | A | 253 | E | 288 | A | 320 | A |
| 188 | C | 221 | B | 254 | D | 289 | A | 321 | A |
| 189 | B | 222 | A | 255 | C | 290 | A | 322 | A |
| 190 | B | 223 | B | 256 | C | 291 | A | 323 | B |
| 191 | C | 224 | C | 257 | C | 292 | A | 324 | B |
| 192 | B | 225 | A | 258 | C | 293 | A | 325 | B |
| 193 | B | 226 | C | 259 | C | 294 | A | 326 | A |
| 194 | B | 227 | A | 260 | D | 295 | A | 327 | A |
| 195 | A | 228 | C | 261 | C | 296 | B | 328 | E |
| 196 | D | 229 | C | 262 | B | 297 | A | 329 | E |
| 197 | B | 230 | A | 263 | C | 298 | C | 330 | E |
| 198 | A | 231 | B | 264 | B | 299 | C | 331 | C |
| 199 | A | 232 | D | 265 | D | 300 | B | 332 | E |
| 200 | D | 233 | E | 266 | D | 301 | C | 333 | C |
| 201 | B | 234 | C | 267 | B | 302 | B | 334 | D |
| 202 | B | 235 | C | 268 | C | 303 | C | 335 | C |
| 203 | C | 236 | C | 269 | C | 304 | B | 336 | D |
| 204 | B | 237 | B | 270 | C | 305 | A | 337 | A |
| 205 | C | 238 | B | 271 | D | 306 | B | 338 | B |
| 206 | B | 239 | C | 272 | A | 307 | A | 339 | B |
| 207 | B | 240 | C | 273 | C | 308 | A | 340 | C |
| 208 | A | 241 | B | 274 | E | 309 | B | 341 | B |
| 209 | B | 242 | B | 275 | D | 310 | A | 342 | D |
| 210 | D | 243 | C | 278 | A | 311 | A | 343 | A |
| 211 | B | 244 | B | 279 | A | 312 | A | - | - |
| 212 | B | 245 | B | 280 | A | 313 | A | - | - |
| 213 | A | 246 | B | 281 | A | 314 | A | - | - |
| 214 | A | 247 | E | 282 | A | 314A | B | - | - |
| 215 | B | 248 | C | 283 | A | 315 | A | - | - |

FIG. 2

| Example | Category |
|---|---|
| 344 | A |
| 345 | A |
| 346 | A |
| 347 | A |
| 348 | A |
| 349 | A |
| 350 | A |
| 351 | A |
| 352 | A |
| 353 | A |
| 354 | A |
| 355 | A |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | A |
| 369 | A |
| 370 | A |
| 371 | A |
| 372 | C |
| 373 | C |
| 374 | B |
| 375 | B |
| 376 | A |
| 377 | D |

FIG. 3

| Example | Category |
|---|---|
| 378 | A |
| 379 | A |
| 380 | A |
| 381 | A |
| 382 | A |
| 383 | A |
| 384 | A |
| 385 | A |
| 386 | A |
| 387 | A |
| 388 | A |
| 389 | A |
| 390 | A |
| 391 | A |
| 392 | A |
| 393 | A |
| 394 | A |
| 395 | A |
| 396 | A |
| 397 | A |
| 398 | A |
| 399 | A |
| 400 | A |

SMALL MOLECULE INHIBITORS OF MAMMALIAN SLC6A19 FUNCTION

RELATED APPLICATIONS

This application is a continuation of U.S. patent application Ser. No. 18/977,370, filed Dec. 11, 2024; which is a continuation U.S. patent application Ser. No. 18/281,138, filed Sep. 8, 2023; which is the 371 national stage application based on Patent Cooperation Treaty Application Serial No. PCT/US22/19513, filed Mar. 9, 2022; which claims the benefit of priority to U.S. Provisional Patent Application Ser. No. 63/308,790, filed Feb. 10, 2022; 63/292,815, filed Dec. 22, 2021; 63/234,487, filed Aug. 18, 2021; 63/226,551, filed Jul. 28, 2021; and 63/159,271, filed Mar. 10, 2021.

BACKGROUND

Phenylketonuria (PKU) is an inborn error of metabolism caused by mutations in phenylalanine hydroxylase (PAH), the enzyme responsible for metabolizing phenylalanine. PKU is an autosomal recessive metabolic disorder in which phenylalanine is not properly metabolized and results in abnormally high levels of plasma phenylalanine. People who have PKU have abnormally high blood levels of phenylalanine, which if untreated can lead to irreversible neurological damage resulting in a spectrum of complications such as intellectual disabilities, seizures, neurodevelopmental and behavioral disorders. PKU is difficult to treat because blood levels of phenylalanine are directly related to diet. Patients must adhere to a life-long and strict diet that impacts all aspects of patients' lives. Current standard of care are enzyme co-factor and enzyme substitution therapy but these therapies are not effective in all patients, and carry potential risk for adverse events.

The enzyme responsible for metabolizing phenylalanine, and thus maintaining phenylalanine homeostasis is phenylalanine hydroxylase (PAH). Loss-of-function (LOF) mutations at PAH gene at chromosome 12q23.2 are known to cause most forms of PKU. These LOF mutations resulting in PKU can be diagnosed as classical PKU (the most severe form), and "mild PKU" or "hyperphe" a less severe form. In addition to PAH, mutations in other enyzmes that affect phenylalanine metabolism, such as dihydropteridine reductase (DHPR), the enzyme responsible for synthesis of co-factors required for PAH activity, may also result in elevated levels of phenylalanine. In addition to diet, blood amino acid levels, including levels of phenylalanine, are regulated by SLC6A19. SCL6A19 is located in the proximal tubule of the kidney and is responsible for reabsorption of amino acids back into the blood.

SUMMARY

One aspect of the invention provides compounds, compositions, and methods useful for treating or preventing a disease or disorder associated with abnormal levels of amino acids by modulation of SLC6A19 transport.

Accordingly, provided herein is a compound having the structure of Formula (I):

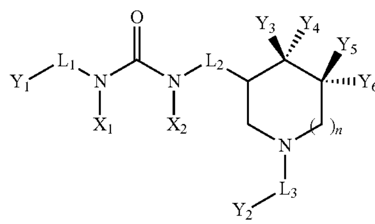

wherein:

n is 0, 1, or 2;

$L_1$ is absent or selected from -alkyl-, -hydroxyalkyl-, -cycloalkyl-, and -heteroaryl-$CH_2$—;

$L_2$ is absent or —$CH_2$—;

$L_3$ is absent or —C(O)—;

$X_1$ and $X_2$ are independently selected from —H, alkyl, haloalkyl, cycloalkyl, alkyl-cycloalkyl, and heterocyclyl; provided that $X_1$ and $X_2$ are not both —H;

$Y_1$ is selected from aryl and heteroaryl;

$Y_2$ is selected from alkyl, alkenyl, alkynyl, alkoxy, alkoxyalkyl, hydroxyalkyl, cycloalkyl, heterocyclyl, aryl, heteroaryl, —NH($Y_2$'), and —N($Y_2$")$_2$;

$Y_2$' is selected from —H, —OH, alkyl, alkoxy, alkoxyalkyl, and cycloalkyl;

each $Y_2$" is alkyl, or both instances taken together with the nitrogen atom to which they are bonded form a 5 or 6 membered heterocyclyl; and $Y_3$, $Y_4$, $Y_5$, and $Y_6$ are independently selected from —H, —OH, halide, alkyl, haloalkyl, and alkoxy; provided that $Y_3$ and $Y_4$ or $Y_5$ and $Y_6$ are not both —OH;

provided that when $L_3$ is —C(O)—, then $Y_2$ is not aryl; and the compound is not selected from:

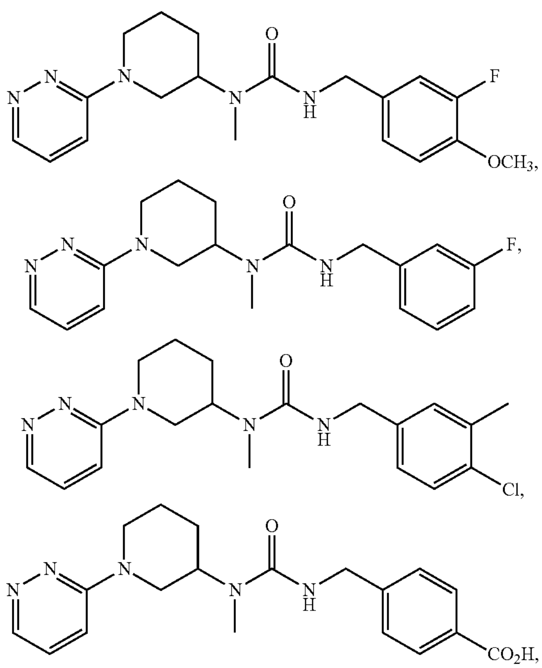

-continued

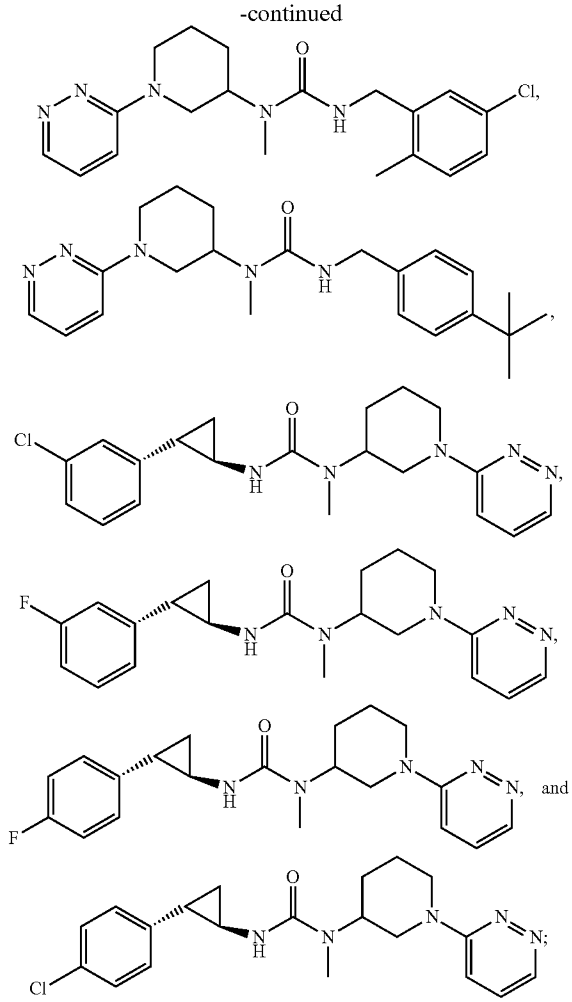

or a pharmaceutically acceptable salt thereof.

Another aspect of the invention relates to methods of treating or preventing a disease or disorder associated with a genetic defect in phenylalanine hydroxylase in a subject in need thereof comprising administering to the subject an effective amount of a compound of Formula (I).

Another aspect of the invention relates to methods of treating or preventing phenylketonuria, hyperphenylalaninemia, tyrosinemia, nonketotic hyperglycinemia, isovaleric acidemia, methylmalonic acidemia, propionic acidemia, maple syrup urine disease, DNAJC12 deficiency, urea cycle disorders, or hyperammonemia in a subject in need thereof comprising administering to the subject an effective amount of a compound of Formula (I).

Another aspect of the invention relates to methods of modulating SLC6A19 transport in a subject in need thereof comprising administering to the subject an effective amount of a compound of Formula (I).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

BRIEF DESCRIPTION OF THE DRAWINGS

FIG. 1 is a table summarizing isoleucine transport data for exemplary compounds of the invention. A=$IC_{50}$<500 nM; B=$IC_{50}$ 500 nM-1500 nM; C=$IC_{50}$ 1500 nM-5000 nM; D=$IC_{50}$ 5000 nM-10000 nM; E=$IC_{50}$>10000 nM.

FIG. 2 is a table summarizing isoleucine transport data for additional exemplary compounds of the invention. A=$IC_{50}$<500 nM; B=$IC_{50}$ 500 nM-1,500 nM; C=$IC_{50}$ 1,500 nM-5,000 nM; D=$IC_{50}$ 5,000 nM-10,000 nM; and E=$IC_{50}$>10,000 nM.

FIG. 3 is a table summarizing isoleucine transport data for additional exemplary compounds of the invention. A=$IC_{50}$<500 nM; B=$IC_{50}$ 500 nM-1,500 nM; C=$IC_{50}$ 1,500 nM-5,000 nM; D=$IC_{50}$ 5,000 nM-10,000 nM; and E=$IC_{50}$>10,000 nM.

DETAILED DESCRIPTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in "atropisomeric" forms or as "atropisomers." Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from a mixture of isomers. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as com starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound (s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "pharmaceutically acceptable cocrystals" refers to solid coformers that do not form formal ionic interactions with the small molecule.

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" or "subject" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "heteroalkyl" refers to an alkyl moiety as hereinbefore defined which contain one or more oxygen, sulfur, nitrogen, phosphorus, or silicon atoms in place of carbon atoms.

As used herein, the term "haloalkyl" refers to an alkyl group as hereinbefore defined substituted with at least one halogen.

As used herein, the term "hydroxyalkyl" refers to an alkyl group as hereinbefore defined substituted with at least one hydroxyl.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —$(CH_2)$—, ethylene —$(CH_2CH_2)$—, n-propylene —$(CH_2CH_2CH_2)$—, isopropylene —$(CH_2CH(CH_3))$—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Preferred cycloalkyls have from 3-10 carbon atoms in their ring structure, and more preferably have 3-6 carbons in the ring structure. Cycloalkyl groups may be substituted or unsubstituted.

As used herein, the term "halocycloalkyl" refers to an cycloalkyl group as hereinbefore defined substituted with at least one halogen.

"Cycloheteroalkyl" refers to an cycloalkyl moiety as hereinbefore defined which contain one or more oxygen, sulfur, nitrogen, phosphorus, or silicon atoms in place of carbon atoms. Preferred cycloheteroalkyls have from 4-8 carbon atoms and heteroatoms in their ring structure, and more preferably have 4-6 carbons and heteroatoms in the ring structure. Cycloheteroalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the definition of each expression, e.g., alkyl, m, n, etc., when it occurs more than once in any structure, is intended to be independent of its definition elsewhere in the same structure.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, a "small molecule" refers to an organic, inorganic, or organometallic compound typically having a molecular weight of less than about 1000. In some embodiments, a small molecule is an organic compound, with a size on the order of 1 nm. In some embodiments, small molecule drugs of the invention encompass oligopeptides and other biomolecules having a molecular weight of less than about 1000.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "modulate" includes up-regulation and down-regulation, e.g., enhancing or inhibiting a response.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

For purposes of this invention, the chemical elements are identified in accordance with the Periodic Table of the Elements, CAS version, Handbook of Chemistry and Physics, 67th Ed., 1986-87, inside cover.

Compounds of the Invention

One aspect of the invention relates to a compound of Formula (I):

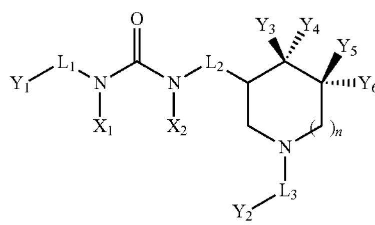

wherein:

n is 0, 1, or 2;

$L_1$ is absent or selected from -alkyl-, -hydroxyalkyl-, -cycloalkyl-, and -heteroaryl-$CH_2$—;

$L_2$ is absent or —$CH_2$—;

$L_3$ is absent or —C(O)—;

$X_1$ and $X_2$ are independently selected from —H, alkyl, haloalkyl, cycloalkyl, alkyl-cycloalkyl, and heterocyclyl; provided that $X_1$ and $X_2$ are not both —H;

$Y_1$ is selected from aryl and heteroaryl;

$Y_2$ is selected from alkyl, alkenyl, alkynyl, alkoxy, alkoxyalkyl, hydroxyalkyl, cycloalkyl, heterocyclyl, aryl, heteroaryl, —NH($Y_2$'), and —N($Y_2$")$_2$;

$Y_2$' is selected from —H, —OH, alkyl, alkoxy, alkoxyalkyl, hydroxyalkyl, and cycloalkyl;

each $Y_2$" is alkyl, or both instances taken together with the nitrogen atom to which they are bonded form a 5 or 6 membered heterocyclyl; and $Y_3$, $Y_4$, $Y_5$, and $Y_6$ are independently selected from —H, —OH, halide, alkyl, haloalkyl, and alkoxy; provided that $Y_3$ and $Y_4$ or $Y_5$ and $Y_6$ are not both —OH;

provided that when $L_3$ is —C(O)—, then $Y_2$ is not aryl; and the compound is not selected from:

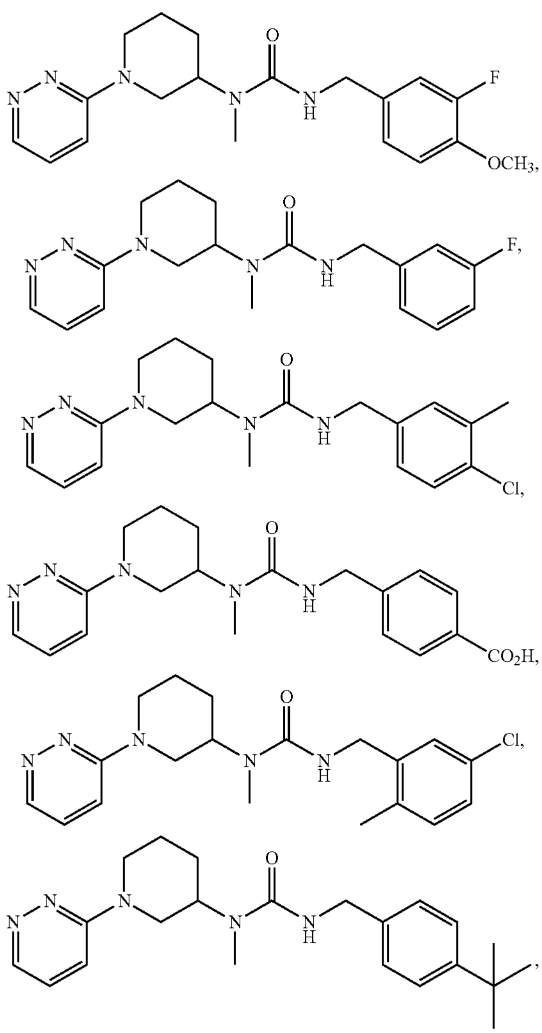

-continued

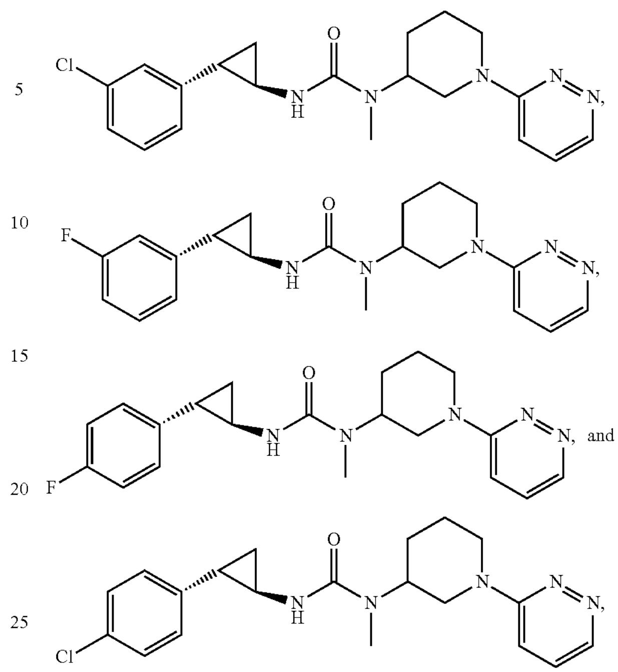

and or a pharmaceutically acceptable salt thereof.

In certain embodiments, the compound is also not selected from:

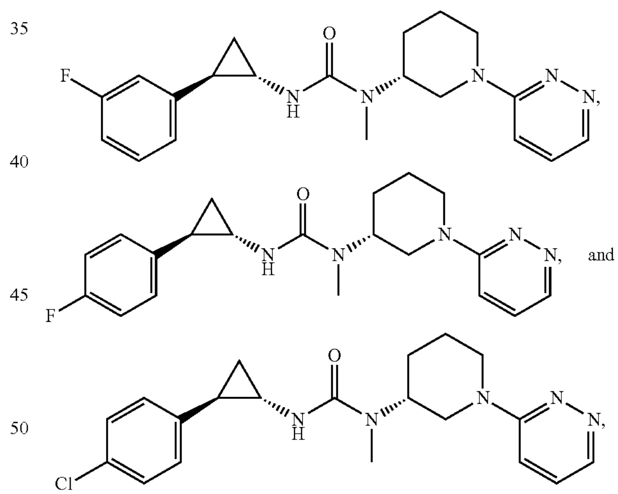

and or a pharmaceutically acceptable salt thereof.

In certain embodiments, the compound has the structure selected from:

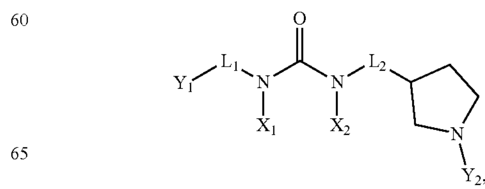

-continued

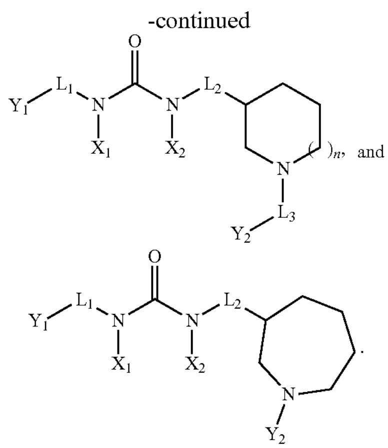

and

In certain embodiments, $Y_2'$ is selected from —H, —OH, alkyl, alkoxy, alkoxyalkyl, and cycloalkyl.

In certain embodiments, one of $X_1$ and $X_2$ is —H; and the other of $X_1$ and $X_2$ is selected from $C_1$-$C_4$ alkyl, haloalkyl, cycloalkyl, alkyl-cycloalkyl, and heterocyclyl.

In certain embodiments, one of $X_1$ and $X_2$ is —H; and the other of $X_1$ and $X_2$ is selected from $—CH_3$, $—CH_2CH_3$, $—CH_2CF_3$, $—CH_2CH_2CH_3$,

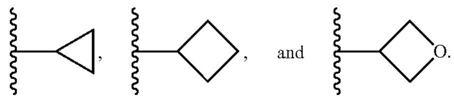

and

In certain embodiments, $X_1$ is —H and $X_2$ is $—CH_3$; $X_2$ is —H and $X_1$ is $—CH_3$; $X_1$ is —H and $X_2$ is

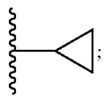 [SMILES: *C1CC1]

or $X_2$ is —H and $X_1$ is

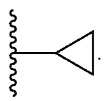

In certain embodiments, $L_1$ is absent. In other embodiments, $L_1$ is selected from -alkyl-, -hydroxyalkyl-, -cycloalkyl-, and -heteroaryl-$CH_2$—.

In certain embodiments, $L_1$ is selected from $—CH_2—$, $—C(H)(CH_3)—$, $—CH_2CH_2—$, and $—C(H)(OH)CH_2—$. In other embodiments, $L_1$ is

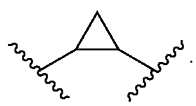 [SMILES: *C1CC1*]

In other embodiments, $L_1$ is selected from

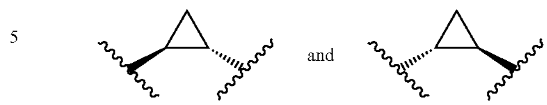

and

In other embodiments, $L_1$ is selected from

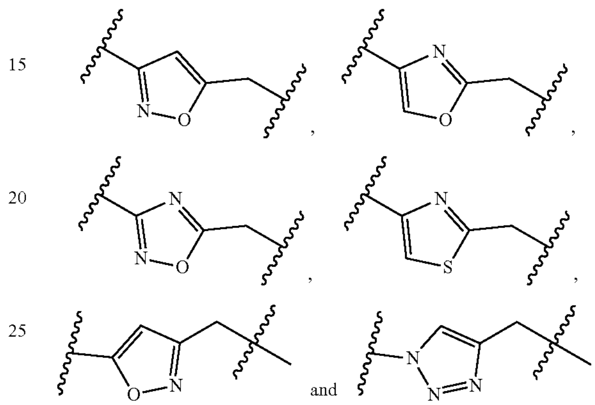

and

In certain embodiments, the compound is selected from:

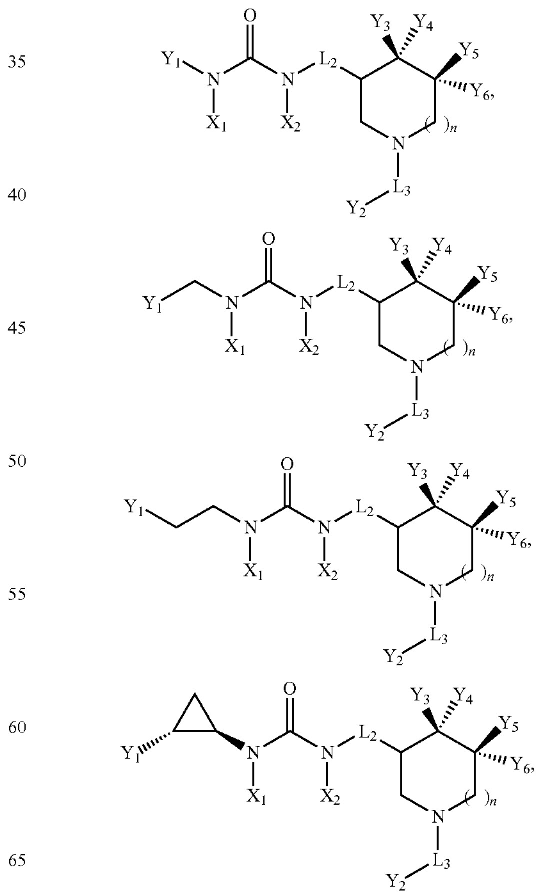

-continued

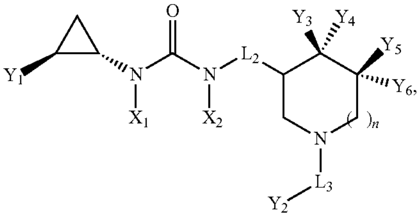

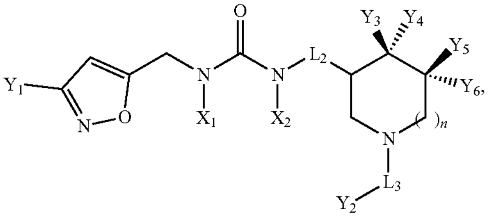

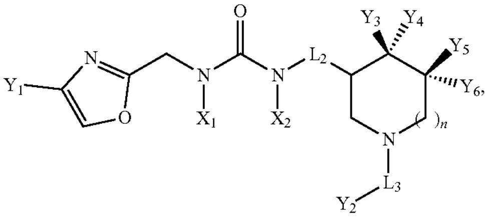

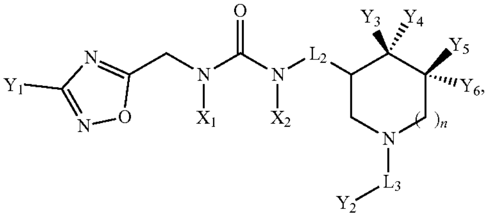

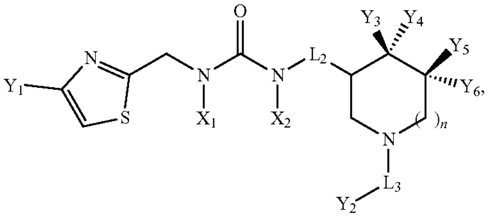

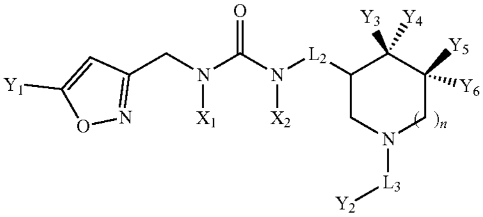

and

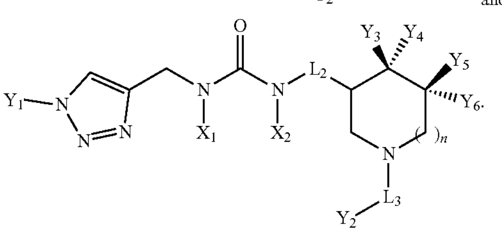

In certain embodiments, $Y_1$ is unsubstituted aryl, e.g. unsubstituted phenyl and unsubstituted naphthyl.

In certain embodiments, $Y_1$ is substituted aryl.

In certain embodiments, $Y_1$ is

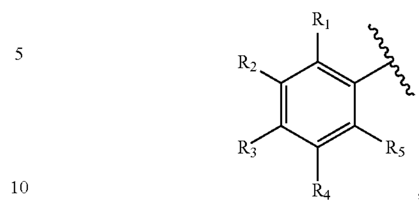

;

and $R_1$, $R_2$, $R_3$, $R_4$, and R are independently selected from —H, halogen, —CN, —$CF_3$, —$CHF_2$, —$CF_2CH_3$, —$OCF_3$, —$OCHF_2$, alkyl, haloalkyl, alkenyl, alkynyl, alkoxy, cycloalkyl, heterocyclyl, aryl, and heteroaryl; provided that one of $R_1$, $R_2$, $R_3$, $R_4$, and $R_5$ is not —H.

In certain embodiments, $R_1$, $R_2$, $R_3$, $R_4$, and $R_5$ are independently selected from —H, —F, —Cl, —Br, —CN, —$CH_3$, —$CH_2CH_3$, —$CF_3$, —$CHF_2$, —$CF_2CH_3$, —$OCH_3$, —$OCF_3$, —$OCHF_2$,

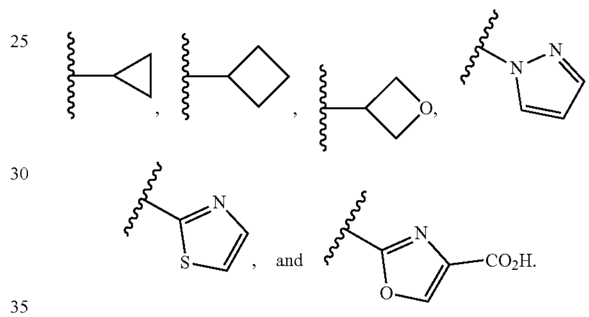

In certain embodiments, $R_1$, $R_2$, $R_3$, $R_4$, and $R_5$ are independently selected from —H, —F, —Cl, —Br, —CN, —$CH_3$, —$CH_2CH_3$, —$OCF_3$, and

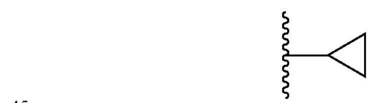

In certain embodiments, two of $R_1$, $R_2$, $R_3$, $R_4$, and $R_5$ are not —H. In other embodiments, three of $R_1$, $R_2$, $R_3$, $R_4$, and $R_5$ are not —H.

In certain embodiments, $Y_1$ is selected from

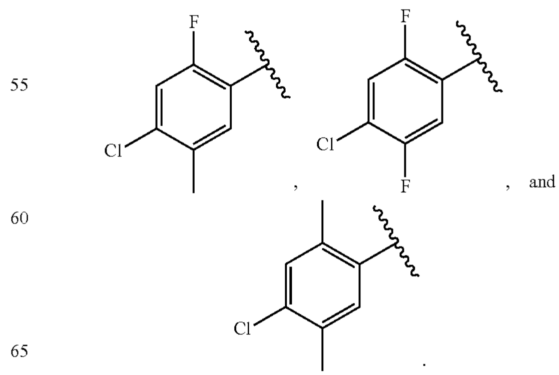

In certain embodiments, $Y_1$ is selected from $Y_1$ is selected from

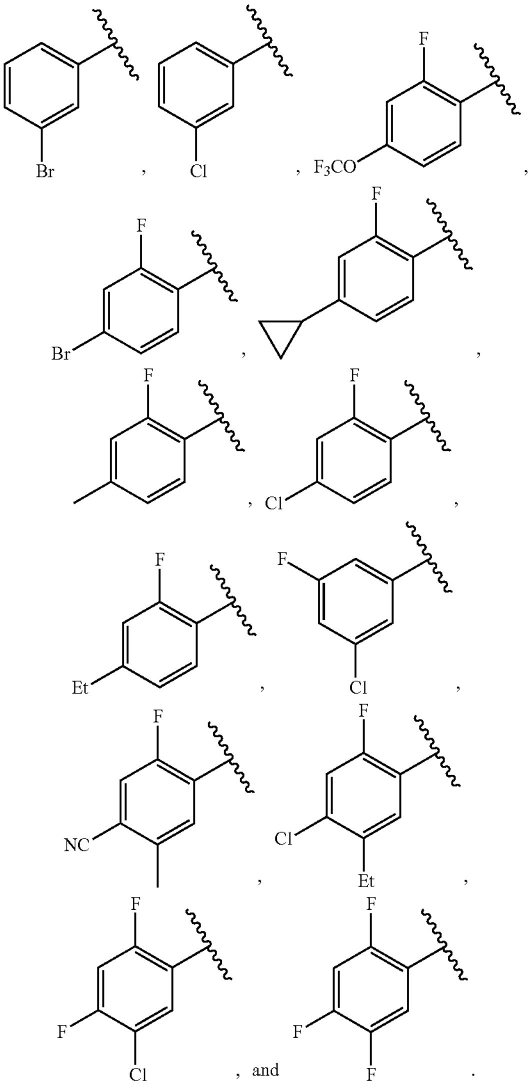

, , , , , , , , , , , and .

In certain embodiments, $Y_1$ is unsubstituted heteroaryl.

In certain embodiments, $Y_1$ is selected from

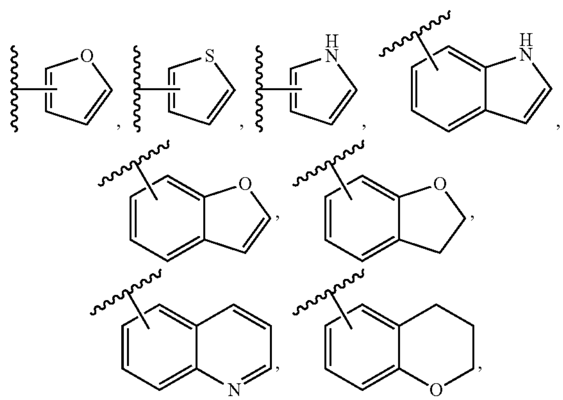

, , , , , , ,

-continued

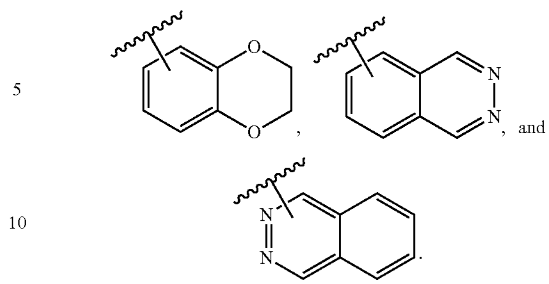

, , and .

In certain embodiments $Y_1$ is substituted heteroaryl.

In certain embodiments, $Y_1$ is selected from

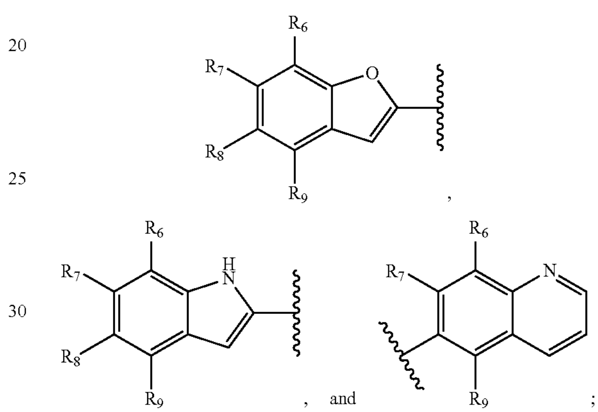

, , and ;

and each occurrence of $R_6$, $R_7$, $R_8$, and $R_9$ are independently selected from —H, halogen, —CN, —$OCF_3$, —$OCHF_2$, alkyl, haloalkyl, alkenyl, alkynyl, alkoxy, cycloalkyl, aryl, and heteroaryl; provided that at least one of $R_6$, $R_7$, $R_8$, and $R_9$ is not —H.

In certain embodiments, $L_2$ is absent. In other embodiments, $L_2$ is —$CH_2$—.

In certain embodiments, $L_3$ is absent. In other embodiments, $L_3$ is —C(O)—.

In certain embodiments, n is 0. In other embodiments, n is 1. In other embodiments, n is 2.

In certain embodiments, the compound is selected from:

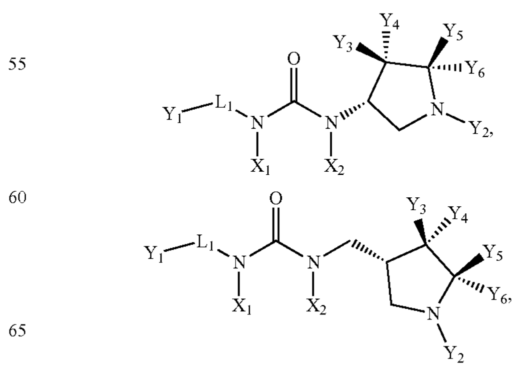

, ,

-continued
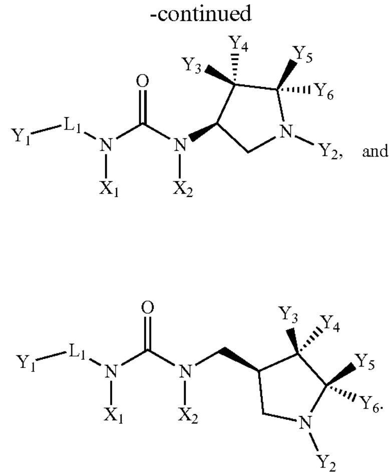
and
In certain embodiments, the compound is selected from:
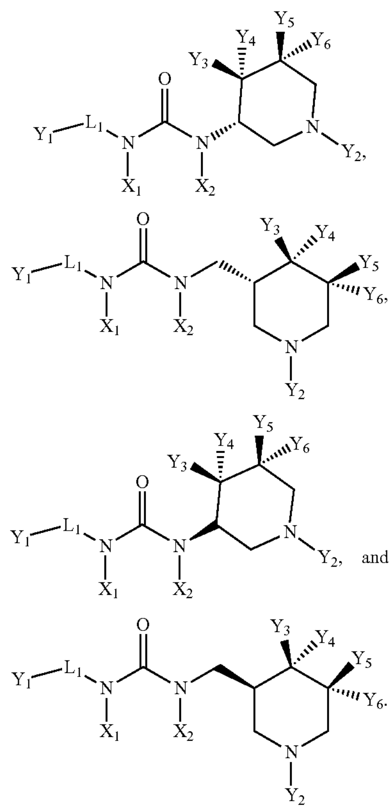
and
In certain embodiments, the compound is selected from:
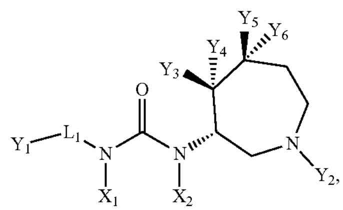
-continued
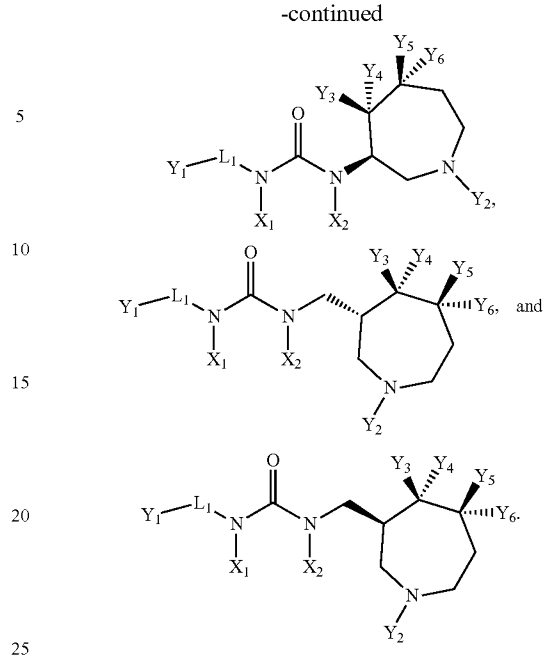
and
In certain embodiments, $Y_2$ is unsubstituted heteroaryl. In certain embodiments, $Y_2$ is selected from
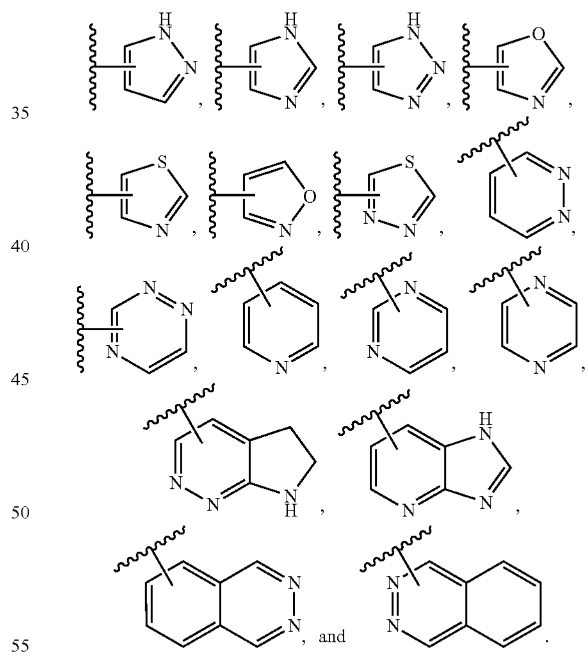
and
In certain embodiments, $Y_2$ is
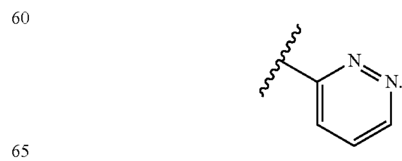

In certain embodiments, $Y_2$ is substituted heteroaryl.

In certain embodiments, $Y_2$ is

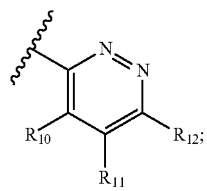

$R_{10}$, $R_{11}$, and $R_{12}$ are independently selected from —H, halogen, —CN, —OH, —$NH_2$, —$OCF_3$, —$OCHF_2$, —OAc, —NHAc, alkyl, haloalkyl, hydroxyalkyl, alkenyl, alkynyl, alkoxy, alkylamino cycloalkyl, aryl, heteroaryl, —C(O)$NR_{13}R_{14}$, —$CO_2R_{15}$, and —C(O)$NHSO_2R_{15}$; provided that at least one of $R_{10}$, $R_{11}$, and $R_{12}$ is not —H; and each occurrence of $R_{13}$, $R_{14}$, and $R_{15}$ is independently selected from —H, alkyl, aryl, and heteroaryl.

In certain embodiments, $Y_2$ is

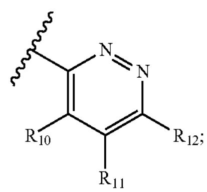

$R_{10}$, $R_{11}$, and $R_{12}$ are independently selected from —H, halogen, —CN, —OH, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —C(O)$NR_{13}R_{14}$, —$CO_2R_{15}$, and —C(O)$NHSO_2R_{15}$; provided that at least one of $R_{10}$, $R_{11}$, and $R_{12}$ is not —H; and each occurrence of $R_{13}$, $R_{14}$, and $R_{15}$ is independently selected from —H, alkyl, aryl, and heteroaryl.

In certain embodiments, $R_{10}$, $R_{11}$, and $R_{12}$ are independently selected from —H, —F, —Cl, —Br, —CN, —$CH_3$, —$CH_2CH_3$, —$CF_3$, —$CHF_2$, —$CF_2CH_3$, —$OCH_3$, —$OCF_3$, —$OCHF_2$, —OAc, —$NH_2$, —$NHCH_3$, —NHAc, —C(O)$NH_2$, —C(O)$NHCH_3$, —C(O)$NHCH_2CH_3$, —C(O)$NHSO_2CH_3$, —C(O)$NHSO_2CH_2CH_3$, —$CO_2H$, phenyl, cyclopropyl, cyclobutyl, imidazolyl, and tetrazolyl.

In certain embodiments, $R_{10}$ and $R_{12}$ are each —H; and $R_{11}$ is selected from —CN, —$CF_3$, —$CH_3$, —$OCH_3$, —$NH_2$, —$NHCH_3$, —NHAc, —$CO_2H$, —C(O)$NH_2$, —C(O)$NHCH_3$, —C(O)$NHCH_2CH_3$,

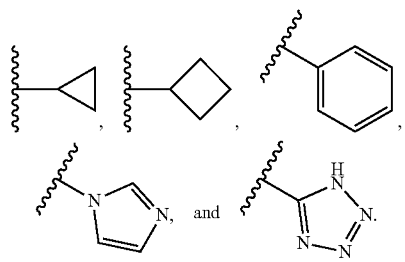

In certain embodiments, $R_1$ and $R_{12}$ are each —H; and $R_{10}$ is selected from —CN, —$CF_3$, —$CH_3$, —$OCH_3$, —$NH_2$, —$NHCH_3$, —NHAc, —$CO_2H$, —C(O)$NH_2$, —C(O)$NHCH_3$, —C(O)$NHCH_2CH_3$,

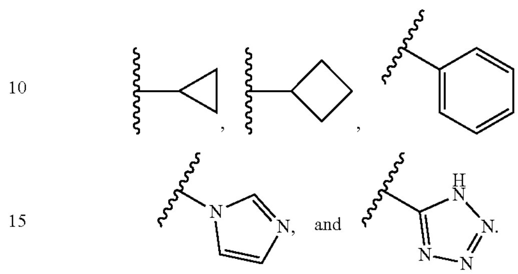

In certain embodiments, $R_{10}$ and $R_{11}$ are each —H; and $R_{12}$ is selected from —CN, —$CF_3$, —$CH_3$, —$OCH_3$, —$NH_2$, —$NHCH_3$, —NHAc, —$CO_2H$, —C(O)$NH_2$, —C(O)$NHCH_3$, —C(O)$NHCH_2CH_3$,

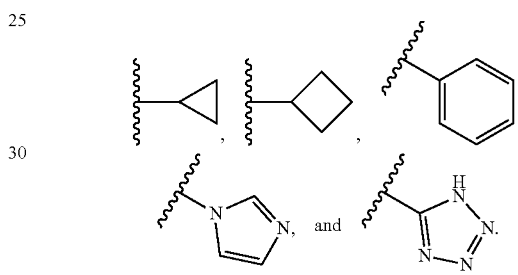

In certain embodiments, $Y_2$ is selected from

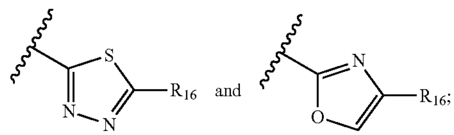

$R_{16}$ for each occurrence is independently selected from halogen, —CN, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —C(O)$NR_{13}R_{14}$, —$CO_2R_{15}$; and each occurrence of $R_{13}$, $R_{14}$, and $R_{15}$ is independently selected from —H, alkyl, aryl, and heteroaryl.

In certain embodiments, $R_{16}$ is selected from —CN, —$CH_3$, —$CF_3$, —C(O)$NH_2$, —$CO_2CH_2CH_3$, and

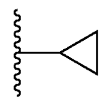

In certain embodiments, $Y_2$ is selected from

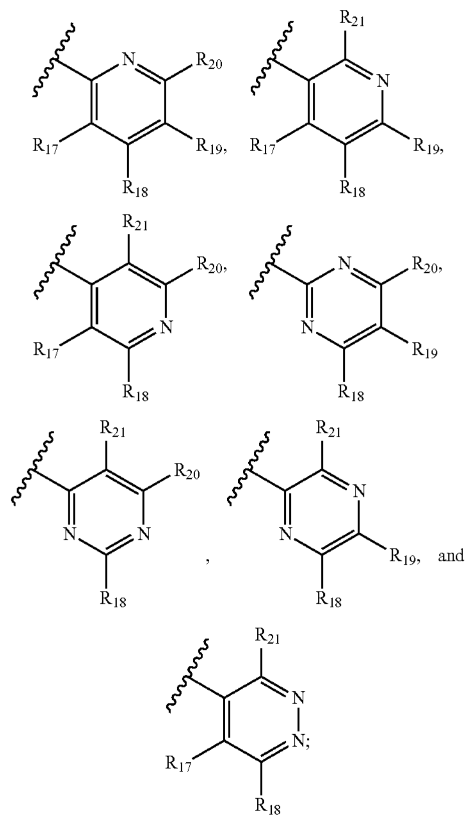

, and each occurrence of $R_{17}$, $R_{18}$, $R_{19}$, $R_{20}$, and $R_{21}$ is independently selected from —H, halogen, —CN, —$NH_2$, —$OCF_3$, —$OCHF_2$, —OAc, —NHAc, alkyl, haloalkyl, hydroxyalkyl, alkenyl, alkynyl, alkoxy, alkylamino cycloalkyl, aryl, heteroaryl, —C(O)$NR_{13}R_{14}$, and —$CO_2R_{15}$; provided that at least one of $R_{17}$, $R_{18}$, $R_{19}$, $R_{20}$, and $R_{21}$ is not —H; and each occurrence of $R_{13}$, $R_{14}$, and $R_{15}$ is independently selected from —H, alkyl, aryl, and heteroaryl.

In certain embodiments, $Y_2$ is selected from

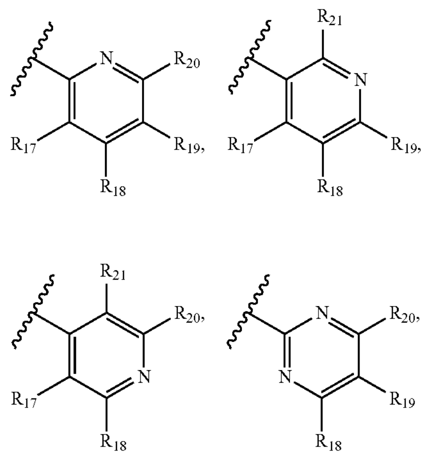

-continued

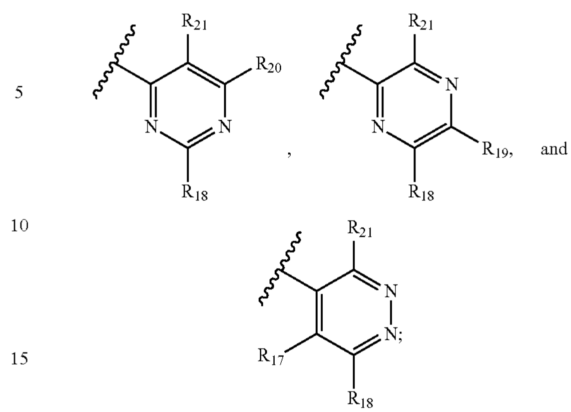

, and each occurrence of $R_{17}$, $R_{18}$, $R_{19}$, $R_{20}$, and $R_{21}$ is independently selected from —H, halogen, —CN, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —C(O)$NR_{13}R_{14}$, and —$CO_2R_{15}$; provided that at least one of $R_{17}$, $R_{18}$, $R_{19}$, $R_{20}$, and $R_{21}$ is not —H; and each occurrence of $R_{13}$, $R_{14}$, and $R_{15}$ is independently selected from —H, alkyl, aryl, and heteroaryl.

In certain embodiments, $R_{17}$, $R_{18}$, $R_{19}$, $R_{20}$, and $R_{21}$ are independently selected from —H, —CN, —$CH_3$, and —$OCH_3$.

In certain embodiments, $Y_2$ is selected from

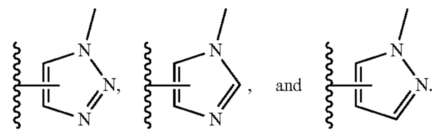

, and

In certain embodiments, the compound is selected from:

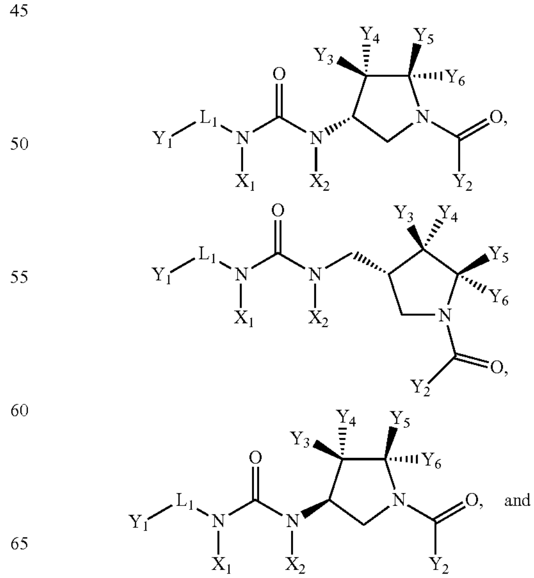

, and

-continued
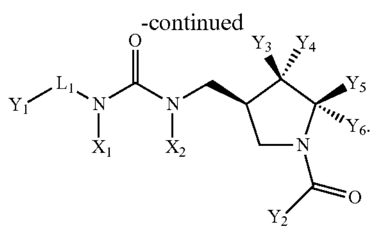
In certain embodiments, the compound is selected from:
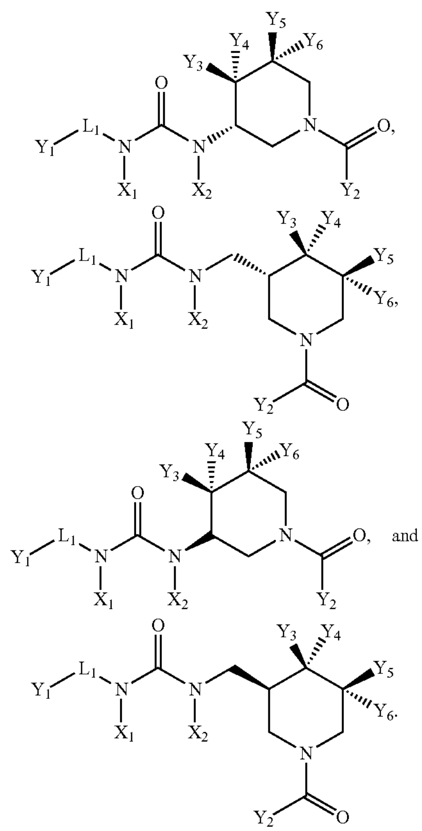
In certain embodiments, the compound is selected from:
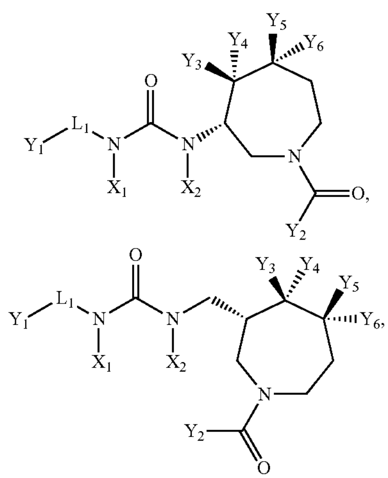
-continued
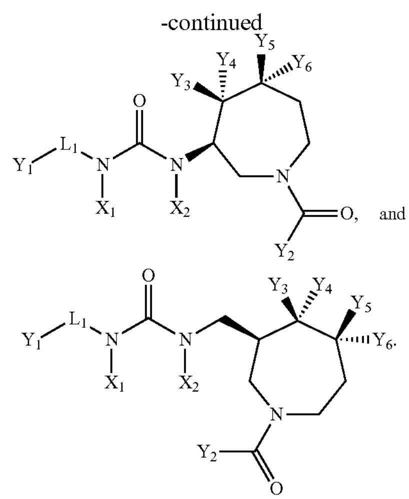
In certain embodiments, $Y_2$ is unsubstituted cycloalkyl or heterocyclyl.
In certain embodiments, $Y_2$ is selected from:
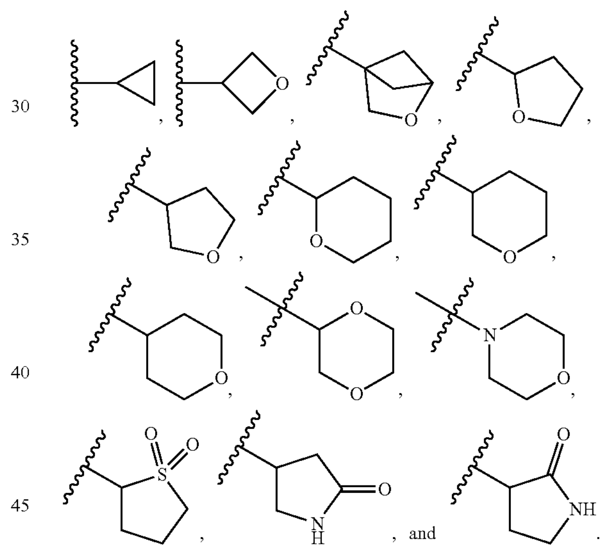
In certain embodiments, $Y_2$ is selected from:
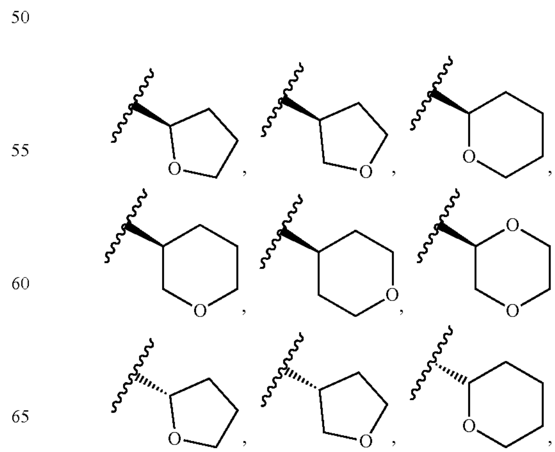

-continued

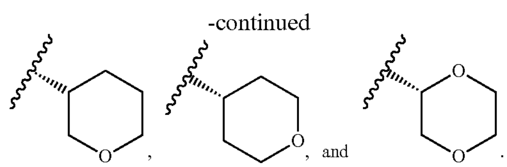

In certain embodiments, $Y_2$ is substituted cycloalkyl or heterocyclyl.

In certain embodiments, $Y_2$ is selected from

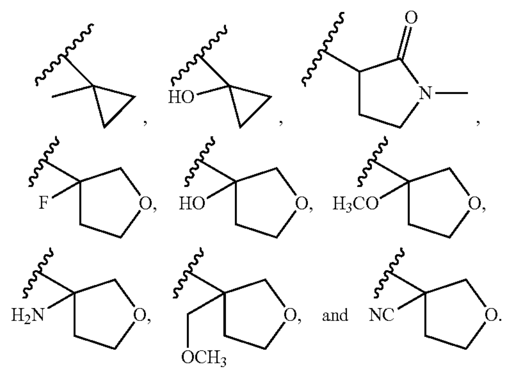

In certain embodiments, $Y_2$ is selected from alkyl, alkenyl, alkynyl, alkoxy, alkoxyalkyl, and hydroxyalkyl.

In certain embodiments, $Y_2$ is selected from —$CH_3$, —$CH_2CH(CH_3)_2$, —$CH_2CH_2C{\equiv}CH$, —$CH_2CH_2OCH_3$, —$C(H)(CH_3)CH_2OCH_3$, —$OCH_3$, —$CH_2OH$, —$CH_2CH_2OH$, —$C(CH_3)_2OH$, and —$CH_2OCH_3$.

In certain embodiments, $Y_2$ is selected from —$CH_2OH$ and —$CH_2CH_2OH$.

In certain embodiments, $Y_2$ is heteroaryl.

In certain embodiments, $Y_2$ is selected from

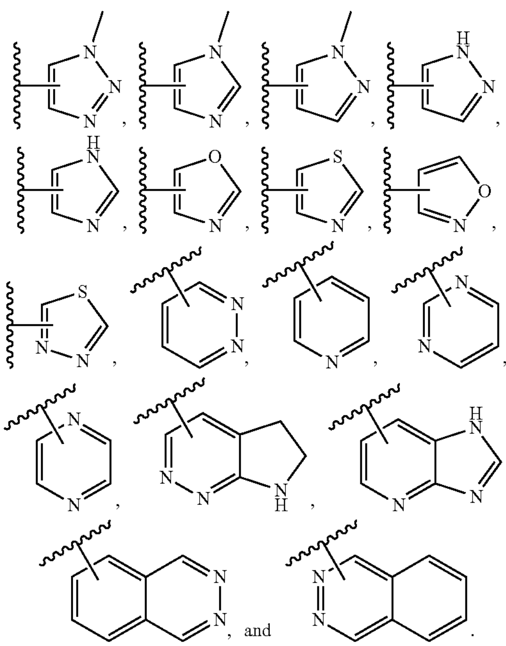

In certain embodiments, $Y_2$ is

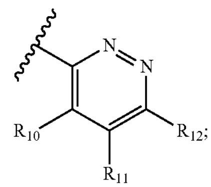

$R_{10}$, $R_{11}$, and $R_{12}$ are independently selected from —H, halogen, —CN, —OH, —$NH_2$, —$OCF_3$, —$OCHF_2$, —OAc, —NHAc, alkyl, haloalkyl, hydroxyalkyl, alkenyl, alkynyl, alkoxy, alkylamino cycloalkyl, aryl, heteroaryl, —$C(O)NR_{13}R_{14}$, and —$CO_2R_{15}$; and each occurrence of $R_{13}$, $R_{14}$, and $R_{15}$ is independently selected from —H, alkyl, aryl, and heteroaryl.

In certain embodiments, $Y_2$ is

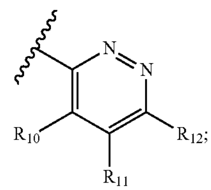

$R_{10}$, $R_{11}$, and $R_{12}$ are independently selected from —H, halogen, —CN, —OH, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —$C(O)NR_{13}R_{14}$, and —$CO_2R_{15}$; and each occurrence of $R_{13}$, $R_{14}$, and $R_{15}$ is independently selected from —H, alkyl, aryl, and heteroaryl.

In certain embodiments, at least one of $R_{10}$, $R_{11}$, and $R_{12}$ is not —H.

In certain embodiments, $Y_2$ is selected from

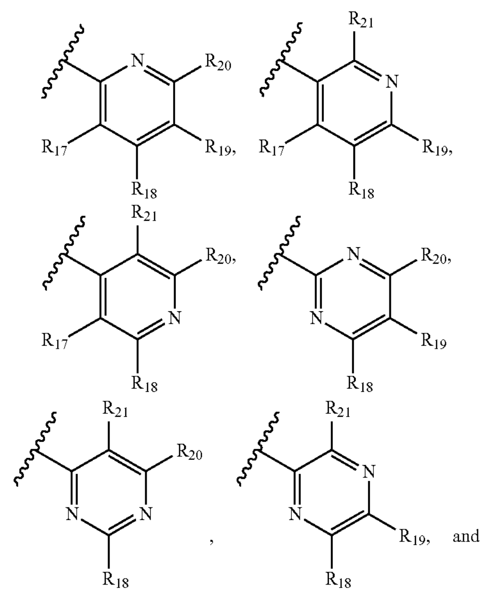

-continued

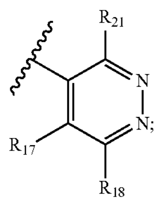

each occurrence of $R_{17}$, $R_{18}$, $R_{19}$, $R_{20}$, and $R_{21}$ is independently selected from —H, halogen, —CN, —$NH_2$, —$OCF_3$, —$OCHF_2$, —OAc, —NHAc, alkyl, haloalkyl, hydroxyalkyl, alkenyl, alkynyl, alkoxy, alkylamino cycloalkyl, aryl, heteroaryl, —C(O)$NR_{13}R_{14}$, and —$CO_2R_{15}$; and each occurrence of $R_{13}$, $R_{14}$, and $R_{15}$ is independently selected from —H, alkyl, aryl, and heteroaryl.

In certain embodiments, $Y_2$ is selected from

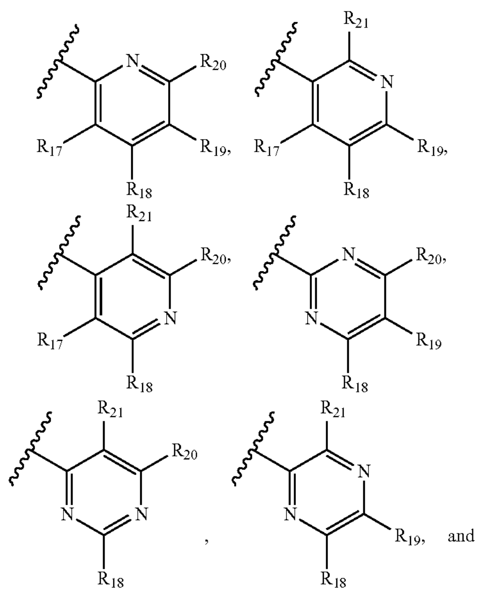

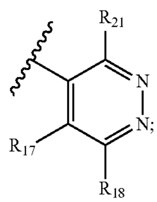

each occurrence of $R_{17}$, $R_{18}$, $R_{19}$, $R_{20}$, and $R_{21}$ is independently selected from —H, halogen, —CN, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —C(O)$NR_{13}R_{14}$, and —$CO_2R_{15}$; and each occurrence of $R_{13}$, $R_{14}$, and $R_{15}$ is independently selected from —H, alkyl, aryl, and heteroaryl.

In certain embodiments, at least one of $R_{17}$, $R_{18}$, $R_{19}$, $R_{20}$, and $R_{21}$ is not —H.

In certain embodiments, $Y_2$ is selected from

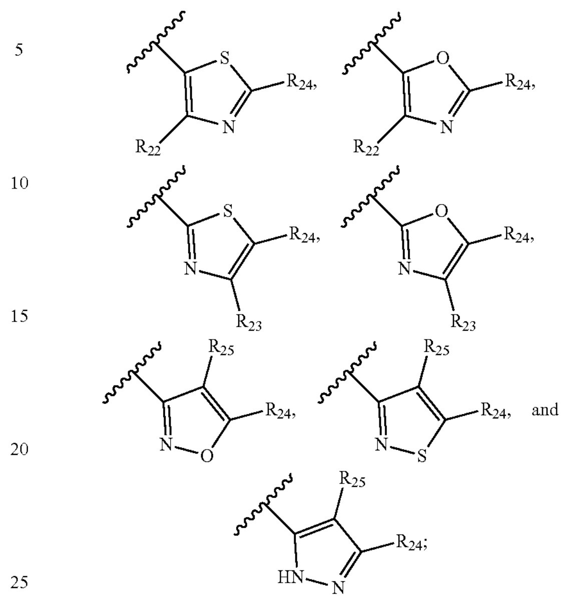

each occurrence of $R_{22}$, $R_{23}$, $R_{24}$, and $R_{25}$ is independently selected from —H, halogen, —CN, —$NH_2$, —$OCF_3$, —$OCHF_2$, —OAc, —NHAc, alkyl, haloalkyl, alkenyl, alkynyl, alkoxy, alkylamino cycloalkyl, aryl, heteroaryl, —C(O)$NR_{13}R_{14}$, and —$CO_2R_{15}$; and each occurrence of $R_{13}$, $R_{14}$, and $R_{15}$ is independently selected from —H, alkyl, aryl, and heteroaryl.

In certain embodiments, each occurrence of $R_{22}$, $R_{23}$, $R_{24}$, and $R_{25}$ is independently selected from —H, and —$CH_3$.

In certain embodiments, $Y_2$ is-NH($Y_2$') or $Y_2$ is-N($Y_2$")$_2$.

In certain embodiments, $Y_2$' is selected from —H, —OH, —$OCH_3$, —$CH_3$, —$CH_2CH_2OCH_3$, and

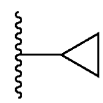

In certain embodiments, each $Y_2$" is —$CH_3$. In other embodiments, both $Y_2$" taken together with the nitrogen atom to which they are bonded form a morpholinyl.

In certain embodiments, wherein $Y_2$ is —NH($Y_2$').

In certain embodiments, $Y_2$' is selected from —H, alkyl, alkoxy, and hydroxyalkyl. In other embodiments, $Y_2$' is selected from —H, —$OCH_3$, —$CH_3$, and —$CH_2CH_2OH$.

In certain embodiments, $Y_2$' is H. In other embodiments, $Y_2$' is —$CH_3$. In other embodiments, $Y_2$' is —$CH_2CH_3$. In other embodiments, $Y_2$' is —$OCH_3$. In other embodiments, $Y_2$' is —$CH_2OH$. In other embodiments, $Y_2$' is —$CH_2CH_2OH$.

In certain embodiments, $Y_3$ and $Y_4$ are both —H or —F. In other embodiments, $Y_3$ is selected from —F, —$CF_3$, —OH and —$OCH_3$; and $Y_4$ is —H. In other embodiments, $Y_4$ is selected from —F, —$CF_3$, —OH and —$OCH_3$; and $Y_3$ is —H.

In certain embodiments, $Y_3$ and $Y_4$ are both —H. In other embodiments, $Y_3$ and $Y_4$ are both —F.

In certain embodiments, $Y_5$ and $Y_6$ are both —H or —F. In other embodiments, $Y_5$ is selected from —F, —$CF_3$, —OH and —$OCH_3$; and $Y_6$ is —H. In other embodiments, $Y_6$ is selected from —F, —$CF_3$, —OH and —$OCH_3$; and $Y_5$ is —H.
In certain embodiments, $Y_5$ and $Y_6$ are both —H. In other embodiments, $Y_5$ and $Y_6$ are both —F.
In some embodiments, the compound is selected from the following Table 1:
TABLE 1
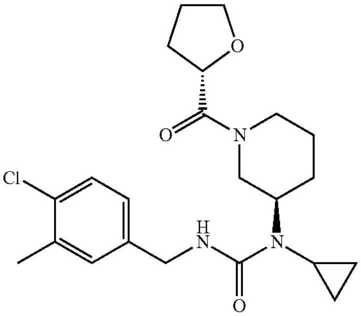 [SMILES: Cc1cc(CNC(=O)N(C2CC2)[C@@H]2CCCN(C(=O)[C@@H]3CCCO3)C2)ccc1Cl]
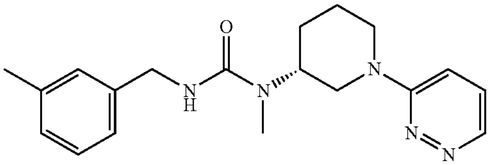 [SMILES: Cc1cccc(CNC(=O)N(C)[C@@H]2CCCN(c3cccnn3)C2)c1]
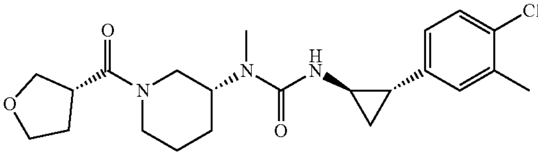 [SMILES: Cc1cc([C@@H]2C[C@H]2NC(=O)N(C)[C@@H]2CCCN(C(=O)[C@@H]3CCOC3)C2)ccc1Cl]
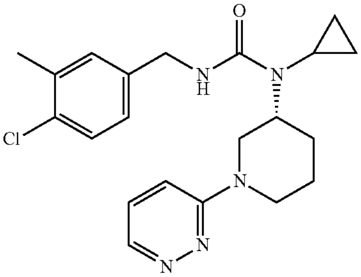 [SMILES: Cc1cc(CNC(=O)N(C2CC2)[C@@H]2CCCN(c3cccnn3)C2)ccc1Cl]
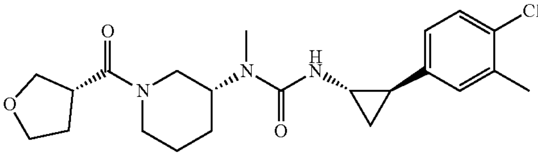 [SMILES: Cc1cc([C@H]2C[C@@H]2NC(=O)N(C)[C@@H]2CCCN(C(=O)[C@@H]3CCOC3)C2)ccc1Cl]
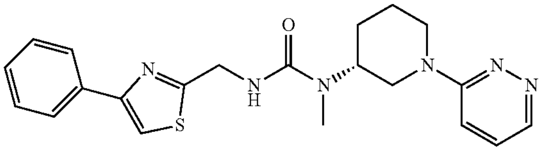 [SMILES: CN(C(=O)NCc1nc(-c2ccccc2)cs1)[C@@H]1CCCN(c2cccnn2)C1]
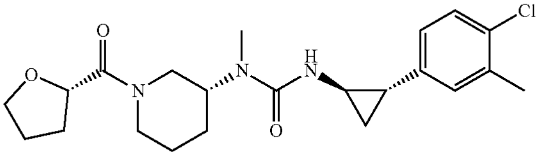 [SMILES: Cc1cc([C@@H]2C[C@H]2NC(=O)N(C)[C@@H]2CCCN(C(=O)[C@@H]3CCCO3)C2)ccc1Cl]
TABLE 1-continued
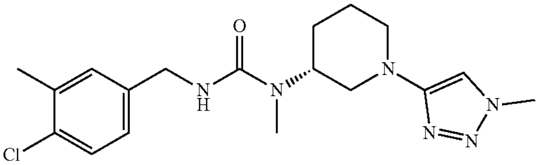 [SMILES: Cc1cc(CNC(=O)N(C)[C@@H]2CCCN(c3cn(C)nn3)C2)ccc1Cl]
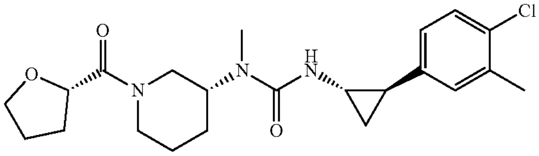 [SMILES: Cc1cc([C@H]2C[C@@H]2NC(=O)N(C)[C@@H]2CCCN(C(=O)[C@@H]3CCCO3)C2)ccc1Cl]
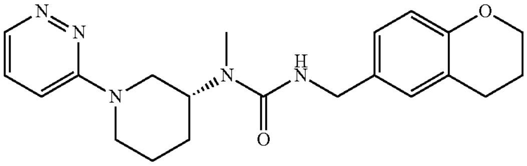 [SMILES: CN(C(=O)NCc1ccc2c(c1)CCCO2)[C@@H]1CCCN(c2cccnn2)C1]
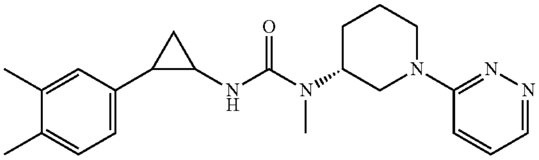 [SMILES: Cc1ccc(C2CC2NC(=O)N(C)[C@@H]2CCCN(c3cccnn3)C2)cc1C]
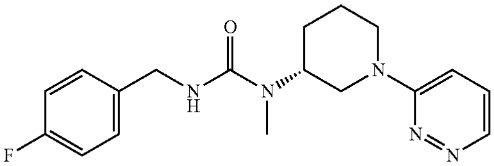 [SMILES: CN(C(=O)NCc1ccc(F)cc1)[C@@H]1CCCN(c2cccnn2)C1]
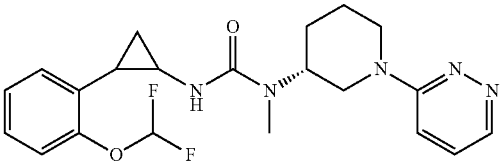 [SMILES: CN(C(=O)NC1CC1c1ccccc1OC(F)F)[C@@H]1CCCN(c2cccnn2)C1]
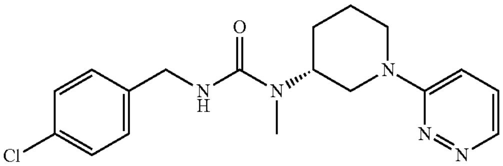 [SMILES: CN(C(=O)NCc1ccc(Cl)cc1)[C@@H]1CCCN(c2cccnn2)C1]
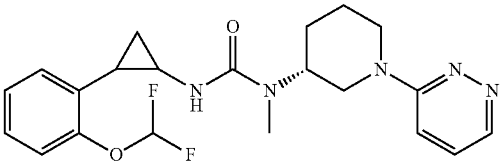 [SMILES: CN(C(=O)NC1CC1c1ccccc1OC(F)F)[C@@H]1CCCN(c2cccnn2)C1]
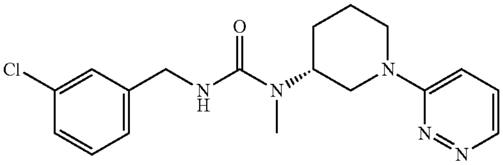 [SMILES: CN(C(=O)NCc1cccc(Cl)c1)[C@@H]1CCCN(c2cccnn2)C1]

TABLE 1-continued
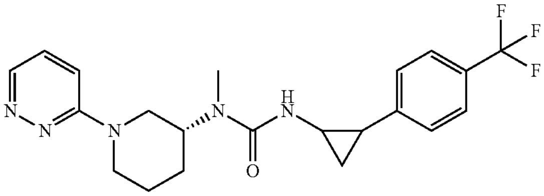 [SMILES: CN(C(=O)NC1CC1c1ccc(C(F)(F)F)cc1)[C@@H]1CCCN(c2cccnn2)C1]
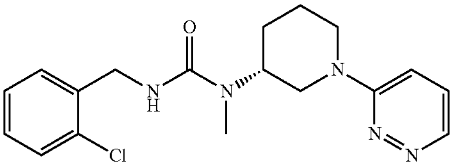 [SMILES: CN(C(=O)NCc1ccccc1Cl)[C@@H]1CCCN(c2cccnn2)C1]
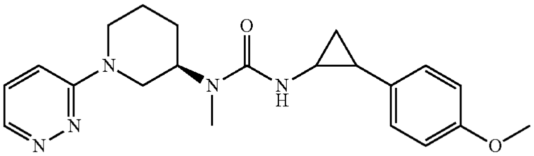 [SMILES: COc1ccc(C2CC2NC(=O)N(C)[C@@H]2CCCN(c3cccnn3)C2)cc1]
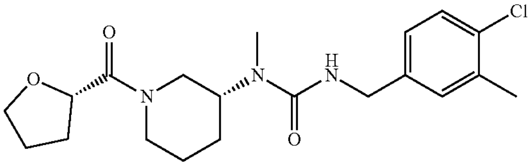 [SMILES: Cc1cc(CNC(=O)N(C)[C@@H]2CCCN(C(=O)[C@@H]3CCCO3)C2)ccc1Cl]
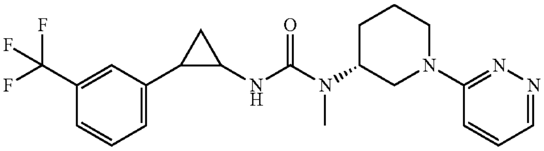 [SMILES: CN(C(=O)NC1CC1c1cccc(C(F)(F)F)c1)[C@@H]1CCCN(c2cccnn2)C1]
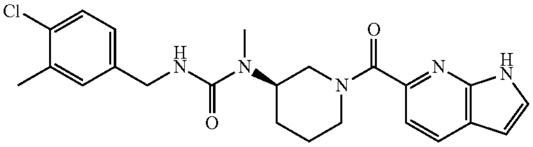 [SMILES: Cc1cc(CNC(=O)N(C)[C@@H]2CCCN(C(=O)c3ccc4cc[nH]c4n3)C2)ccc1Cl]
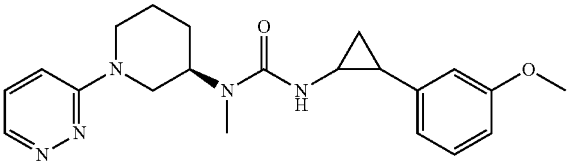 [SMILES: COc1cccc(C2CC2NC(=O)N(C)[C@@H]2CCCN(c3cccnn3)C2)c1]
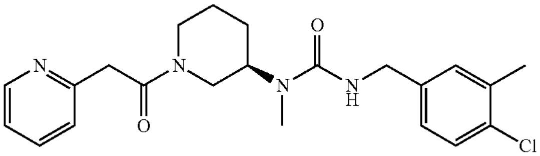 [SMILES: Cc1cc(CNC(=O)N(C)[C@@H]2CCCN(C(=O)Cc3ccccn3)C2)ccc1Cl]
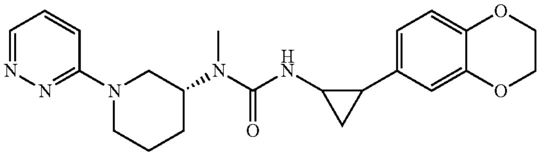 [SMILES: CN(C(=O)NC1CC1c1ccc2c(c1)OCCO2)[C@@H]1CCCN(c2cccnn2)C1]
TABLE 1-continued
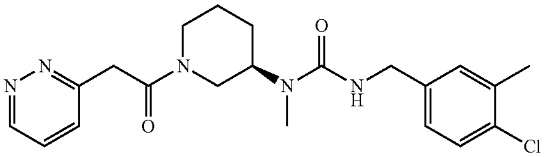 [SMILES: Cc1cc(CNC(=O)N(C)[C@@H]2CCCN(C(=O)Cc3cccnn3)C2)ccc1Cl]
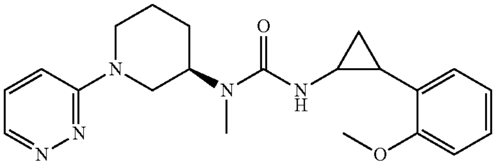 [SMILES: COc1ccccc1C1CC1NC(=O)N(C)[C@@H]1CCCN(c2cccnn2)C1]
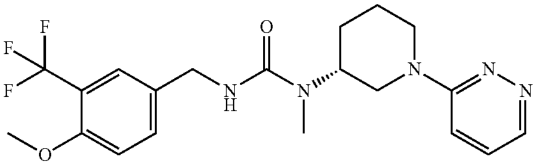 [SMILES: COc1ccc(CNC(=O)N(C)[C@@H]2CCCN(c3cccnn3)C2)cc1C(F)(F)F]
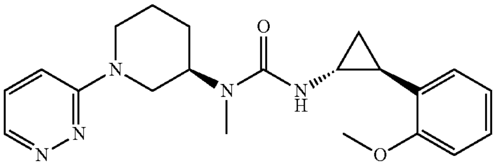 [SMILES: COc1ccccc1[C@@H]1C[C@H]1NC(=O)N(C)[C@@H]1CCCN(c2cccnn2)C1]
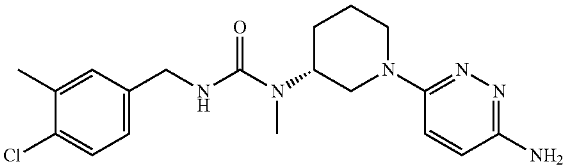 [SMILES: Cc1cc(CNC(=O)N(C)[C@@H]2CCCN(c3ccc(N)nn3)C2)ccc1Cl]
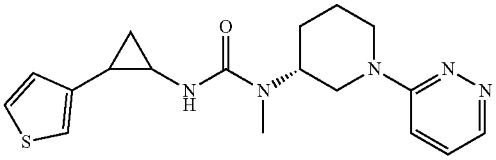 [SMILES: CN(C(=O)NC1CC1c1ccsc1)[C@@H]1CCCN(c2cccnn2)C1]
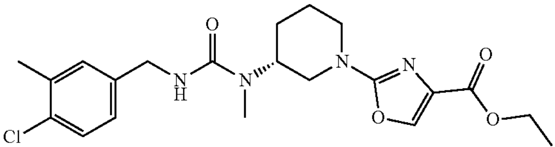 [SMILES: CCOC(=O)c1coc(N2CCC[C@@H](N(C)C(=O)NCc3ccc(Cl)c(C)c3)C2)n1]
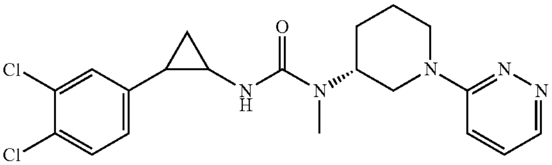 [SMILES: CN(C(=O)NC1CC1c1ccc(Cl)c(Cl)c1)[C@@H]1CCCN(c2cccnn2)C1]
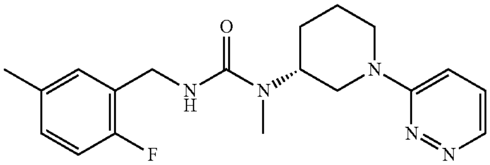 [SMILES: Cc1ccc(F)c(CNC(=O)N(C)[C@@H]2CCCN(c3cccnn3)C2)c1]

TABLE 1-continued
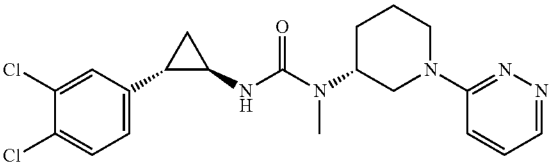 [SMILES: CN(C(=O)N[C@@H]1C[C@H]1c1ccc(Cl)c(Cl)c1)[C@@H]1CCCN(c2cccnn2)C1]
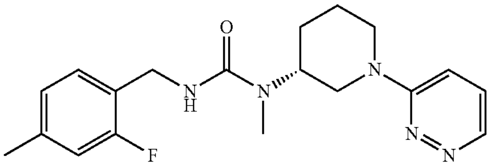 [SMILES: Cc1ccc(CNC(=O)N(C)[C@@H]2CCCN(c3cccnn3)C2)c(F)c1]
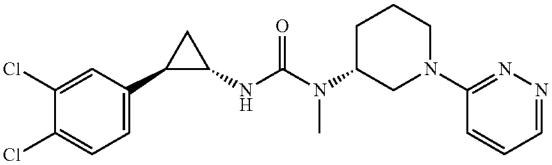 [SMILES: CN(C(=O)N[C@H]1C[C@@H]1c1ccc(Cl)c(Cl)c1)[C@@H]1CCCN(c2cccnn2)C1]
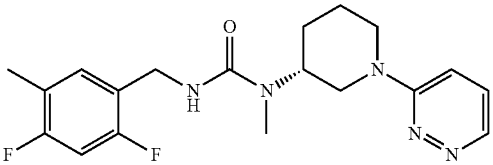 [SMILES: Cc1cc(CNC(=O)N(C)[C@@H]2CCCN(c3cccnn3)C2)c(F)cc1F]
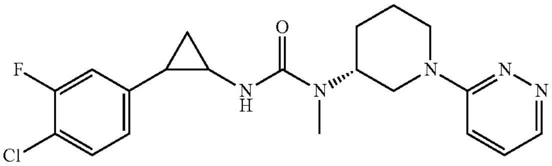 [SMILES: CN(C(=O)NC1CC1c1ccc(Cl)c(F)c1)[C@@H]1CCCN(c2cccnn2)C1]
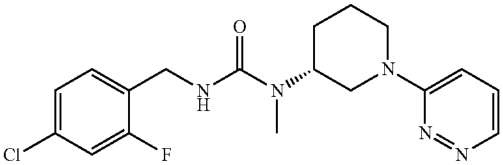 [SMILES: CN(C(=O)NCc1ccc(Cl)cc1F)[C@@H]1CCCN(c2cccnn2)C1]
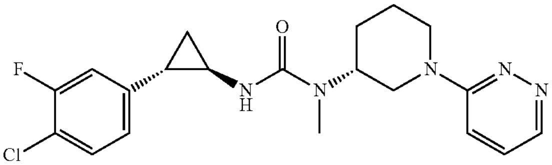
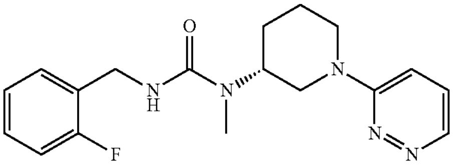 [SMILES: CN(C(=O)NCc1ccccc1F)[C@@H]1CCCN(c2cccnn2)C1]
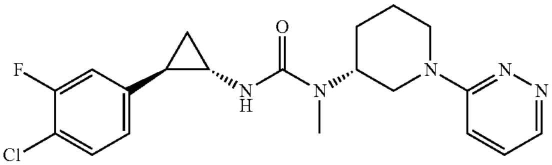 [SMILES: CN(C(=O)N[C@H]1C[C@@H]1c1ccc(Cl)c(F)c1)[C@@H]1CCCN(c2cccnn2)C1]
TABLE 1-continued
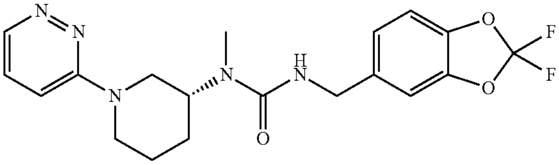 [SMILES: CN(C(=O)NCc1ccc2c(c1)OC(F)(F)O2)[C@@H]1CCCN(c2cccnn2)C1]
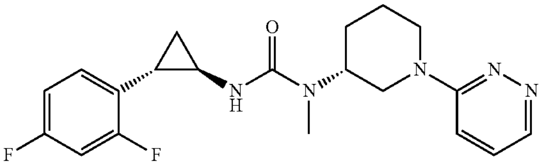 [SMILES: CN(C(=O)N[C@@H]1C[C@H]1c1ccc(F)cc1F)[C@@H]1CCCN(c2cccnn2)C1]
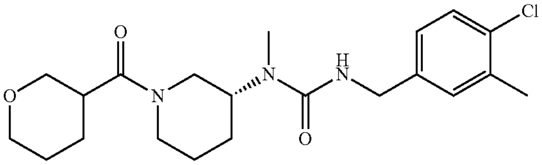 [SMILES: Cc1cc(CNC(=O)N(C)[C@@H]2CCCN(C(=O)C3CCCOC3)C2)ccc1Cl]
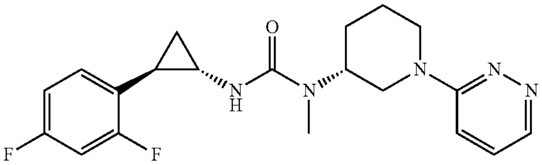 [SMILES: CN(C(=O)N[C@H]1C[C@@H]1c1ccc(F)cc1F)[C@@H]1CCCN(c2cccnn2)C1]
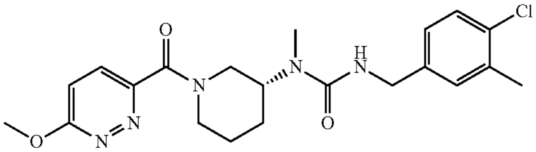
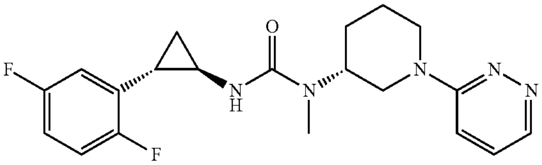 [SMILES: CN(C(=O)N[C@@H]1C[C@H]1c1cc(F)ccc1F)[C@@H]1CCCN(c2cccnn2)C1]
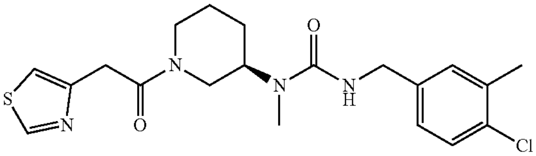 [SMILES: Cc1cc(CNC(=O)N(C)[C@@H]2CCCN(C(=O)Cc3cscn3)C2)ccc1Cl]
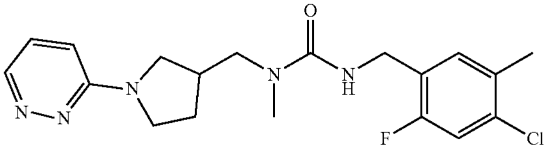 [SMILES: Cc1cc(CNC(=O)N(C)CC2CCN(c3cccnn3)C2)c(F)cc1Cl]
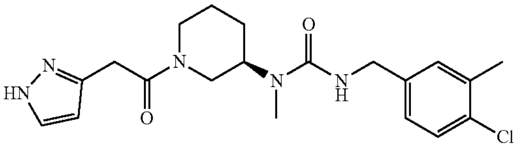 [SMILES: Cc1cc(CNC(=O)N(C)[C@@H]2CCCN(C(=O)Cc3cc[nH]n3)C2)ccc1Cl]

TABLE 1-continued
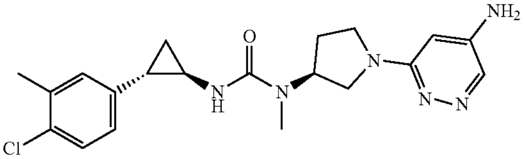 [SMILES: Cc1cc([C@@H]2C[C@H]2NC(=O)N(C)[C@H]2CCN(c3cc(N)cnn3)C2)ccc1Cl]
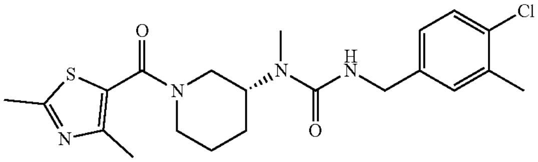
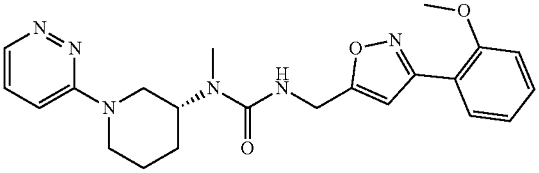 [SMILES: COc1ccccc1-c1cc(CNC(=O)N(C)[C@@H]2CCCN(c3cccnn3)C2)on1]
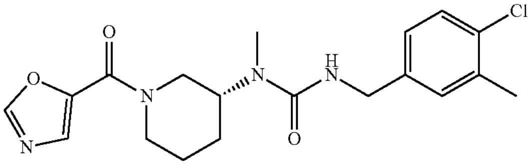
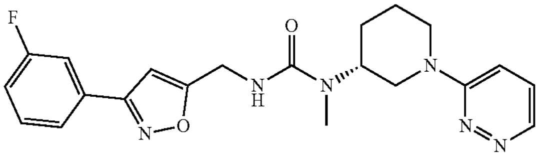 [SMILES: CN(C(=O)NCc1cc(-c2cccc(F)c2)no1)[C@@H]1CCCN(c2cccnn2)C1]
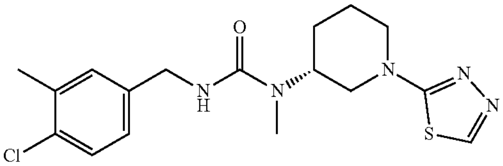 [SMILES: Cc1cc(CNC(=O)N(C)[C@@H]2CCCN(c3nncs3)C2)ccc1Cl]
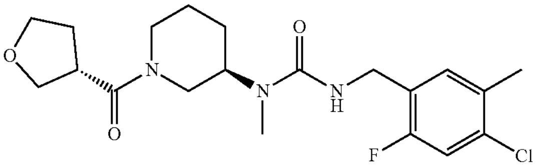 [SMILES: Cc1cc(CNC(=O)N(C)[C@@H]2CCCN(C(=O)[C@H]3CCOC3)C2)c(F)cc1Cl]
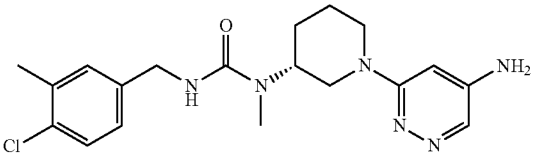 [SMILES: Cc1cc(CNC(=O)N(C)[C@@H]2CCCN(c3cc(N)cnn3)C2)ccc1Cl]
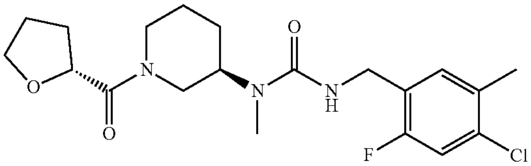 [SMILES: Cc1cc(CNC(=O)N(C)[C@@H]2CCCN(C(=O)[C@H]3CCCO3)C2)c(F)cc1Cl]
TABLE 1-continued
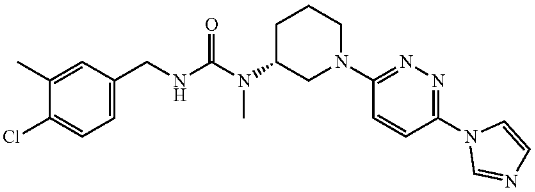 [SMILES: Cc1cc(CNC(=O)N(C)[C@@H]2CCCN(c3ccc(-n4ccnc4)nn3)C2)ccc1Cl]
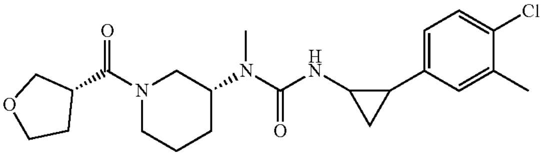 [SMILES: Cc1cc(C2CC2NC(=O)N(C)[C@@H]2CCCN(C(=O)[C@@H]3CCOC3)C2)ccc1Cl]
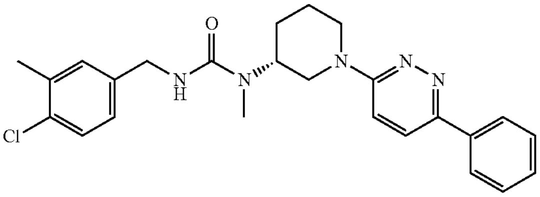 [SMILES: Cc1cc(CNC(=O)N(C)[C@@H]2CCCN(c3ccc(-c4ccccc4)nn3)C2)ccc1Cl]
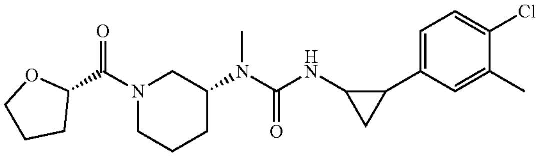 [SMILES: Cc1cc(C2CC2NC(=O)N(C)[C@@H]2CCCN(C(=O)[C@@H]3CCCO3)C2)ccc1Cl]
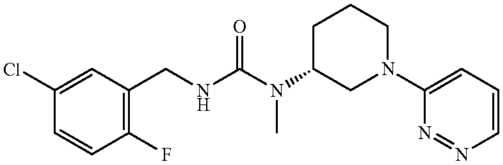 [SMILES: CN(C(=O)NCc1cc(Cl)ccc1F)[C@@H]1CCCN(c2cccnn2)C1]
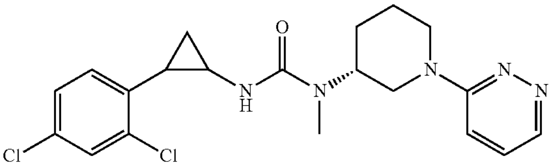 [SMILES: CN(C(=O)NC1CC1c1ccc(Cl)cc1Cl)[C@@H]1CCCN(c2cccnn2)C1]
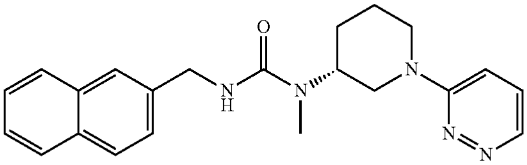 [SMILES: CN(C(=O)NCc1ccc2ccccc2c1)[C@@H]1CCCN(c2cccnn2)C1]
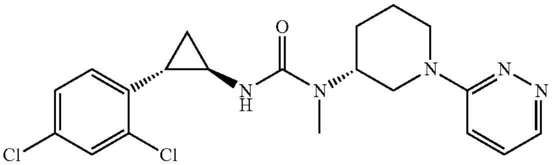 [SMILES: CN(C(=O)N[C@@H]1C[C@H]1c1ccc(Cl)cc1Cl)[C@@H]1CCCN(c2cccnn2)C1]
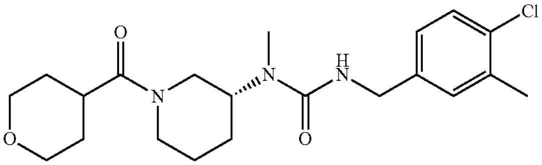 [SMILES: Cc1cc(CNC(=O)N(C)[C@@H]2CCCN(C(=O)C3CCOCC3)C2)ccc1Cl]

TABLE 1-continued
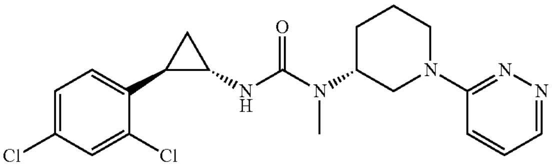 [SMILES: CN(C(=O)N[C@H]1C[C@@H]1c1ccc(Cl)cc1Cl)[C@@H]1CCCN(c2cccnn2)C1]
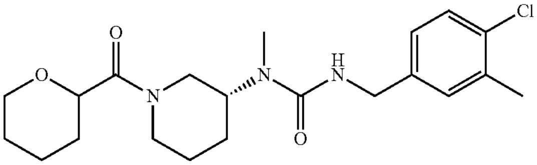 [SMILES: Cc1cc(CNC(=O)N(C)[C@@H]2CCCN(C(=O)C3CCCCO3)C2)ccc1Cl]
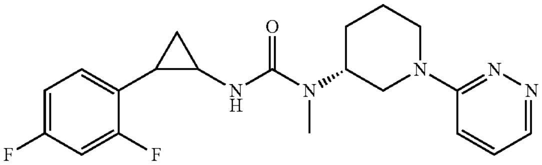 [SMILES: CN(C(=O)NC1CC1c1ccc(F)cc1F)[C@@H]1CCCN(c2cccnn2)C1]
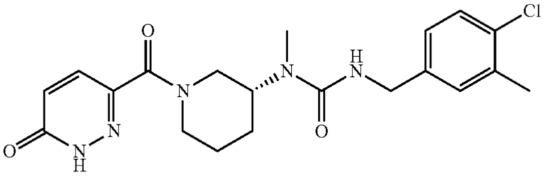 [SMILES: Cc1cc(CNC(=O)N(C)[C@@H]2CCCN(C(=O)c3ccc(=O)[nH]n3)C2)ccc1Cl]
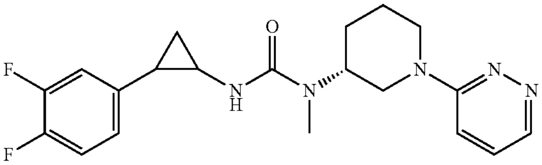 [SMILES: CN(C(=O)NC1CC1c1ccc(F)c(F)c1)[C@@H]1CCCN(c2cccnn2)C1]
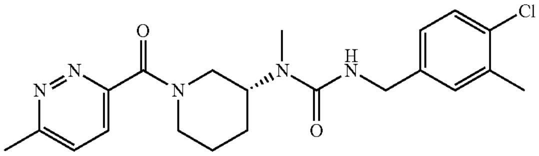 [SMILES: Cc1ccc(C(=O)N2CCC[C@@H](N(C)C(=O)NCc3ccc(Cl)c(C)c3)C2)nn1]
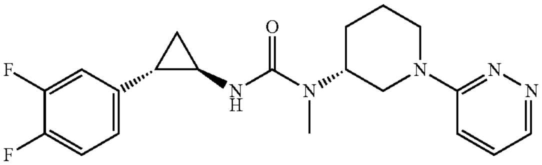 [SMILES: CN(C(=O)N[C@@H]1C[C@H]1c1ccc(F)c(F)c1)[C@@H]1CCCN(c2cccnn2)C1]
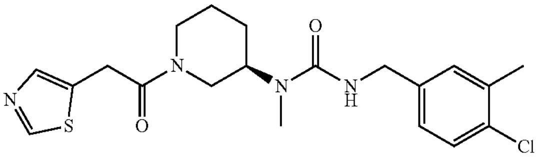 [SMILES: Cc1cc(CNC(=O)N(C)[C@@H]2CCCN(C(=O)Cc3cncs3)C2)ccc1Cl]
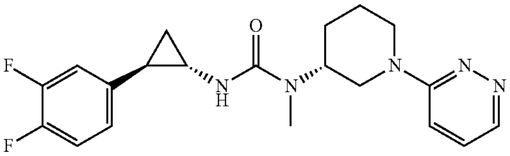 [SMILES: CN(C(=O)N[C@H]1C[C@@H]1c1ccc(F)c(F)c1)[C@@H]1CCCN(c2cccnn2)C1]
TABLE 1-continued
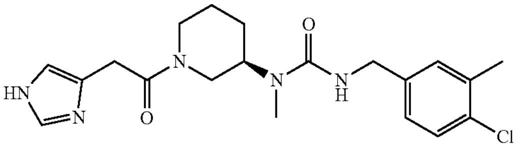 [SMILES: Cc1cc(CNC(=O)N(C)[C@@H]2CCCN(C(=O)Cc3c[nH]cn3)C2)ccc1Cl]
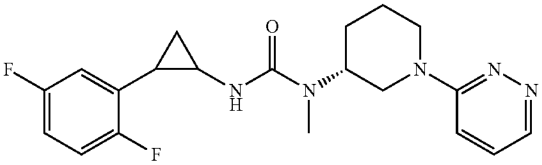 [SMILES: CN(C(=O)NC1CC1c1cc(F)ccc1F)[C@@H]1CCCN(c2cccnn2)C1]
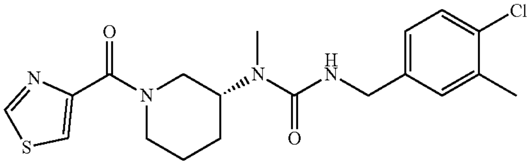
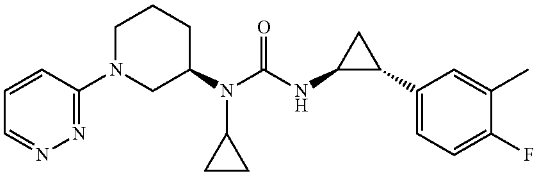 [SMILES: Cc1cc([C@H]2C[C@@H]2NC(=O)N(C2CC2)[C@@H]2CCCN(c3cccnn3)C2)ccc1F]
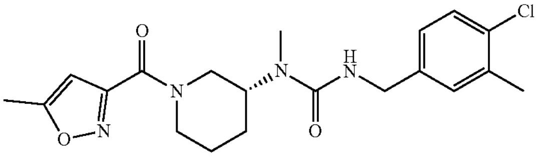 [SMILES: Cc1cc(C(=O)N2CCC[C@@H](N(C)C(=O)NCc3ccc(Cl)c(C)c3)C2)no1]
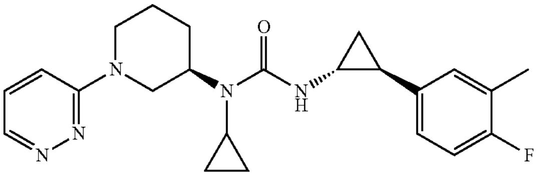 [SMILES: Cc1cc([C@@H]2C[C@H]2NC(=O)N(C2CC2)[C@@H]2CCCN(c3cccnn3)C2)ccc1F]
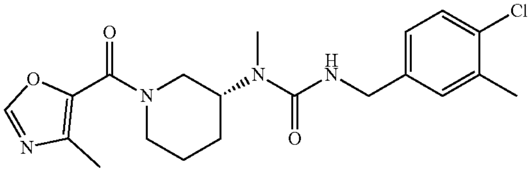 [SMILES: Cc1cc(CNC(=O)N(C)[C@@H]2CCCN(C(=O)c3ocnc3C)C2)ccc1Cl]
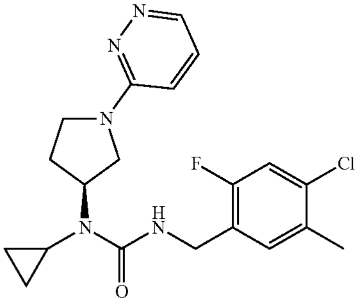 [SMILES: Cc1cc(CNC(=O)N(C2CC2)[C@H]2CCN(c3cccnn3)C2)c(F)cc1Cl]

TABLE 1-continued
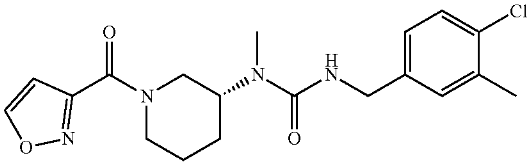
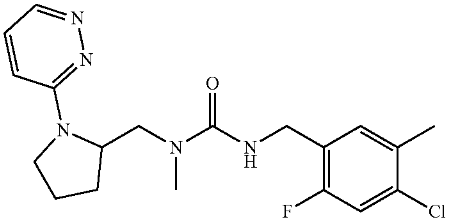 [SMILES: Cc1cc(CNC(=O)N(C)CC2CCCN2c2cccnn2)c(F)cc1Cl]
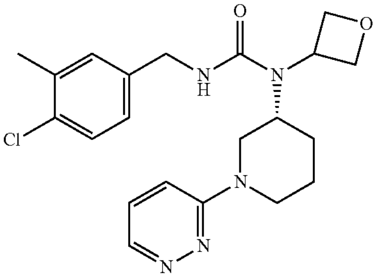 [SMILES: Cc1cc(CNC(=O)N(C2COC2)[C@@H]2CCCN(c3cccnn3)C2)ccc1Cl]
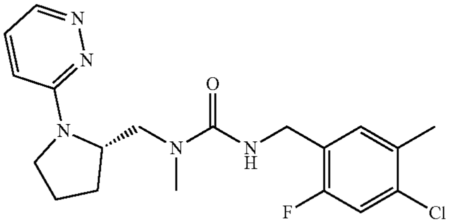 [SMILES: Cc1cc(CNC(=O)N(C)C[C@@H]2CCCN2c2cccnn2)c(F)cc1Cl]
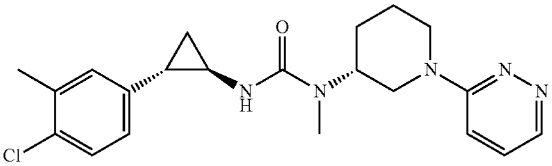 [SMILES: Cc1cc([C@@H]2C[C@H]2NC(=O)N(C)[C@@H]2CCCN(c3cccnn3)C2)ccc1Cl]
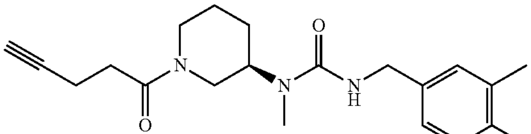
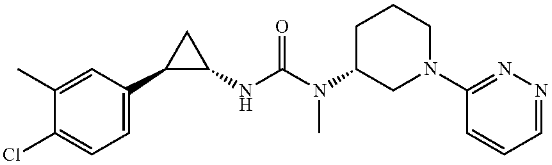 [SMILES: Cc1cc([C@H]2C[C@@H]2NC(=O)N(C)[C@@H]2CCCN(c3cccnn3)C2)ccc1Cl]
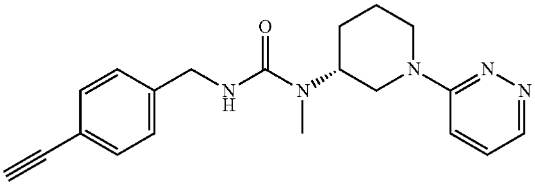
TABLE 1-continued
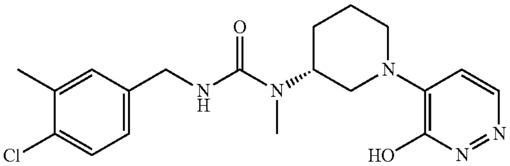 [SMILES: Cc1cc(CNC(=O)N(C)[C@@H]2CCCN(c3ccnnc3O)C2)ccc1Cl]
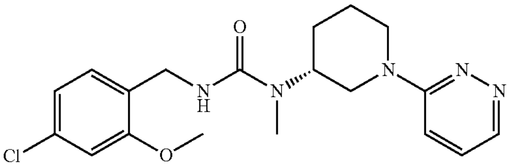 [SMILES: COc1cc(Cl)ccc1CNC(=O)N(C)[C@@H]1CCCN(c2cccnn2)C1]
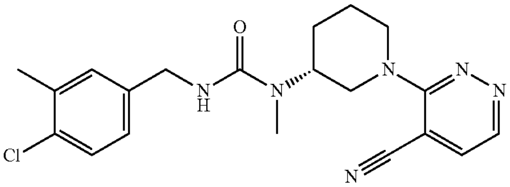 [SMILES: Cc1cc(CNC(=O)N(C)[C@@H]2CCCN(c3nnccc3C#N)C2)ccc1Cl]
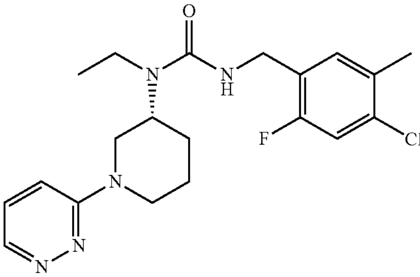 [SMILES: CCN(C(=O)NCc1cc(C)c(Cl)cc1F)[C@@H]1CCCN(c2cccnn2)C1]
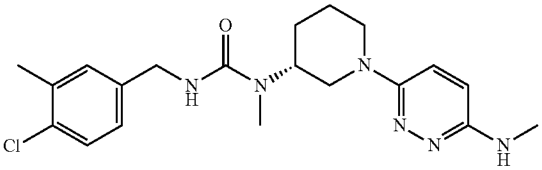
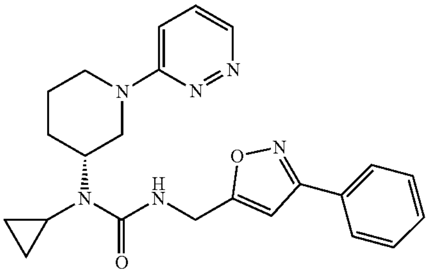 [SMILES: O=C(NCc1cc(-c2ccccc2)no1)N(C1CC1)[C@@H]1CCCN(c2cccnn2)C1]
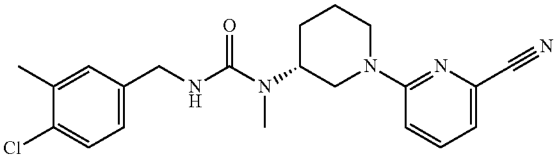 [SMILES: Cc1cc(CNC(=O)N(C)[C@@H]2CCCN(c3cccc(C#N)n3)C2)ccc1Cl]

TABLE 1-continued
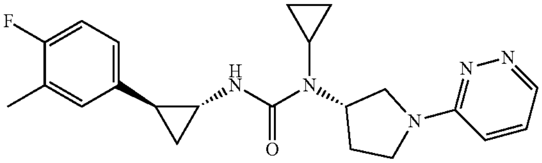 [SMILES: Cc1cc([C@@H]2C[C@H]2NC(=O)N(C2CC2)[C@H]2CCN(c3cccnn3)C2)ccc1F]
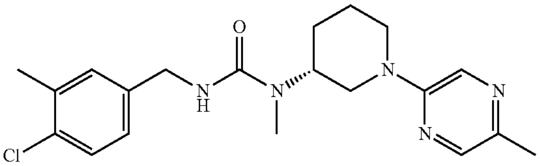 [SMILES: Cc1cnc(N2CCC[C@@H](N(C)C(=O)NCc3ccc(Cl)c(C)c3)C2)cn1]
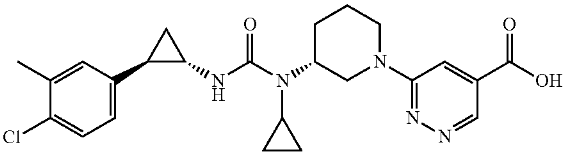 [SMILES: Cc1cc([C@H]2C[C@@H]2NC(=O)N(C2CC2)[C@@H]2CCCN(c3cc(C(=O)O)cnn3)C2)ccc1Cl]
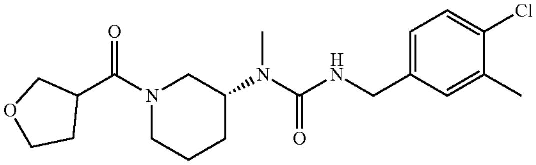 [SMILES: Cc1cc(CNC(=O)N(C)[C@@H]2CCCN(C(=O)C3CCOC3)C2)ccc1Cl]
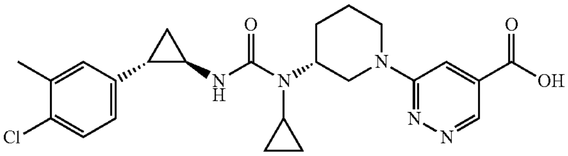 [SMILES: Cc1cc([C@@H]2C[C@H]2NC(=O)N(C2CC2)[C@@H]2CCCN(c3cc(C(=O)O)cnn3)C2)ccc1Cl]
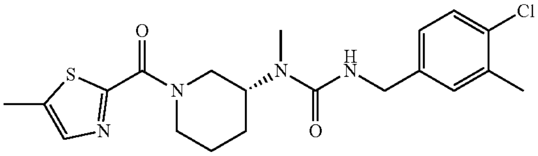 [SMILES: Cc1cnc(C(=O)N2CCC[C@@H](N(C)C(=O)NCc3ccc(Cl)c(C)c3)C2)s1]
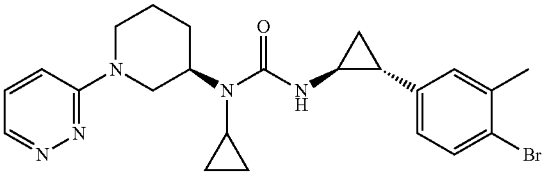 [SMILES: Cc1cc([C@H]2C[C@@H]2NC(=O)N(C2CC2)[C@@H]2CCCN(c3cccnn3)C2)ccc1Br]
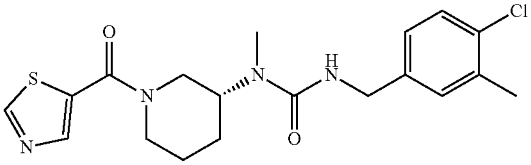 [SMILES: Cc1cc(CNC(=O)N(C)[C@@H]2CCCN(C(=O)c3cncs3)C2)ccc1Cl]
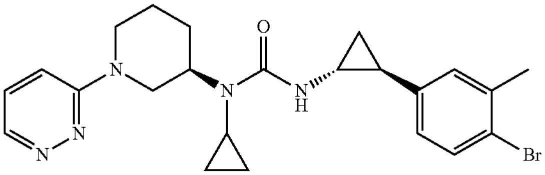 [SMILES: Cc1cc([C@@H]2C[C@H]2NC(=O)N(C2CC2)[C@@H]2CCCN(c3cccnn3)C2)ccc1Br]
TABLE 1-continued
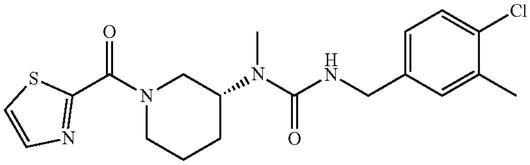 [SMILES: Cc1cc(CNC(=O)N(C)[C@@H]2CCCN(C(=O)c3nccs3)C2)ccc1Cl]
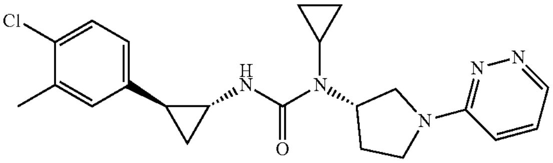 [SMILES: Cc1cc([C@@H]2C[C@H]2NC(=O)N(C2CC2)[C@H]2CCN(c3cccnn3)C2)ccc1Cl]
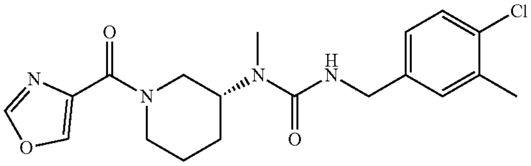 [SMILES: Cc1cc(CNC(=O)N(C)[C@@H]2CCCN(C(=O)c3cocn3)C2)ccc1Cl]
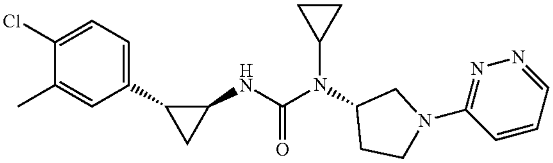 [SMILES: Cc1cc([C@H]2C[C@@H]2NC(=O)N(C2CC2)[C@H]2CCN(c3cccnn3)C2)ccc1Cl]
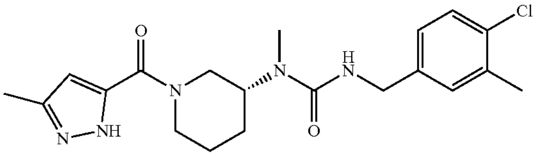 [SMILES: Cc1cc(C(=O)N2CCC[C@@H](N(C)C(=O)NCc3ccc(Cl)c(C)c3)C2)[nH]n1]
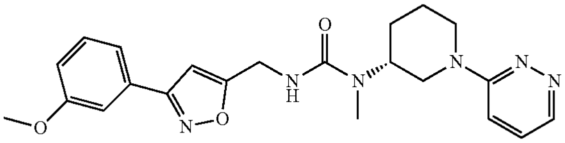 [SMILES: COc1cccc(-c2cc(CNC(=O)N(C)[C@@H]3CCCN(c4cccnn4)C3)on2)c1]
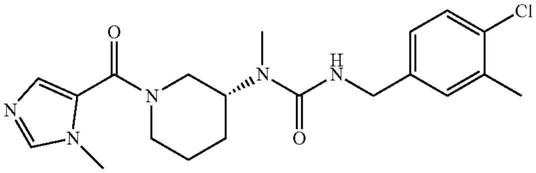 [SMILES: Cc1cc(CNC(=O)N(C)[C@@H]2CCCN(C(=O)c3cncn3C)C2)ccc1Cl]
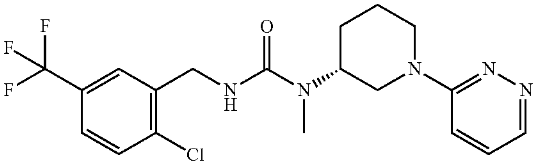 [SMILES: CN(C(=O)NCc1cc(C(F)(F)F)ccc1Cl)[C@@H]1CCCN(c2cccnn2)C1]
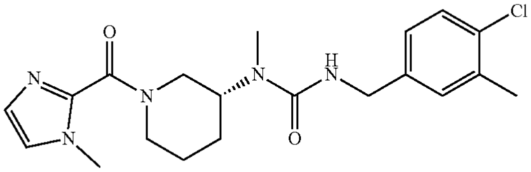 [SMILES: Cc1cc(CNC(=O)N(C)[C@@H]2CCCN(C(=O)c3nccn3C)C2)ccc1Cl]

TABLE 1-continued
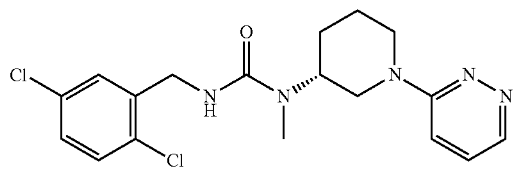 [SMILES: CN(C(=O)NCc1cc(Cl)ccc1Cl)[C@@H]1CCCN(c2cccnn2)C1]
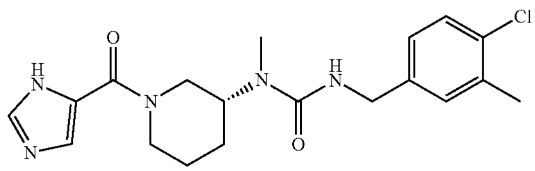
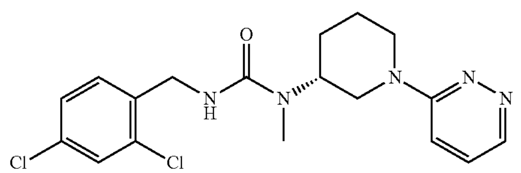 [SMILES: CN(C(=O)NCc1ccc(Cl)cc1Cl)[C@@H]1CCCN(c2cccnn2)C1]
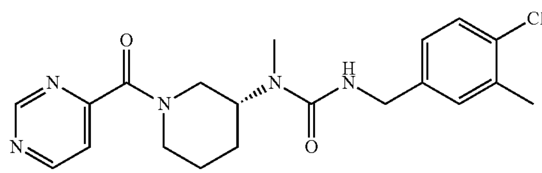 [SMILES: Cc1cc(CNC(=O)N(C)[C@@H]2CCCN(C(=O)c3ccncn3)C2)ccc1Cl]
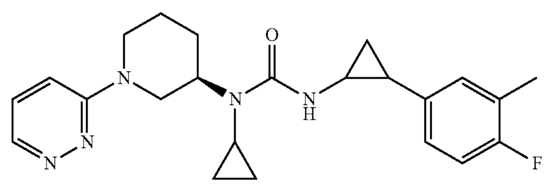 [SMILES: Cc1cc(C2CC2NC(=O)N(C2CC2)[C@@H]2CCCN(c3cccnn3)C2)ccc1F]
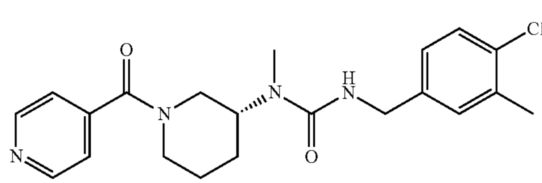 [SMILES: Cc1cc(CNC(=O)N(C)[C@@H]2CCCN(C(=O)c3ccncc3)C2)ccc1Cl]
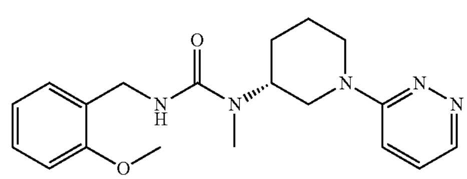 [SMILES: COc1ccccc1CNC(=O)N(C)[C@@H]1CCCN(c2cccnn2)C1]
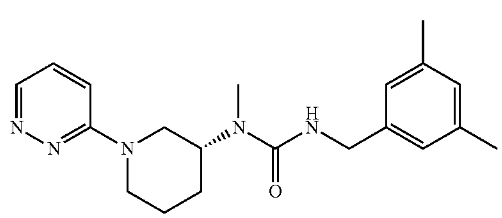 [SMILES: Cc1cc(C)cc(CNC(=O)N(C)[C@@H]2CCCN(c3cccnn3)C2)c1]
TABLE 1-continued
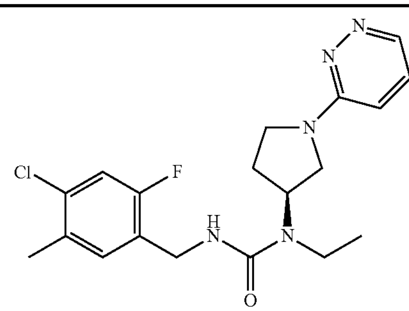
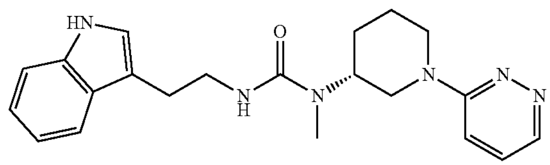 [SMILES: CN(C(=O)NCCc1c[nH]c2ccccc12)[C@@H]1CCCN(c2cccnn2)C1]
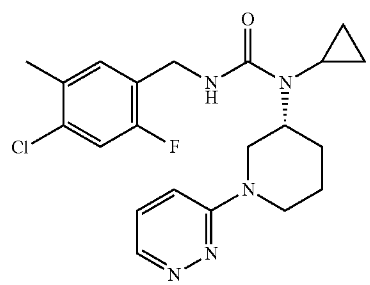 [SMILES: Cc1cc(CNC(=O)N(C2CC2)[C@@H]2CCCN(c3cccnn3)C2)c(F)cc1Cl]
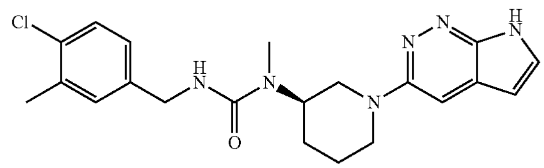 [SMILES: Cc1cc(CNC(=O)N(C)[C@@H]2CCCN(c3cc4cc[nH]c4nn3)C2)ccc1Cl]
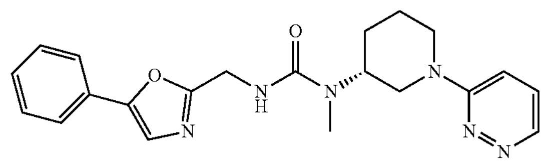 [SMILES: CN(C(=O)NCc1ncc(-c2ccccc2)o1)[C@@H]1CCCN(c2cccnn2)C1]
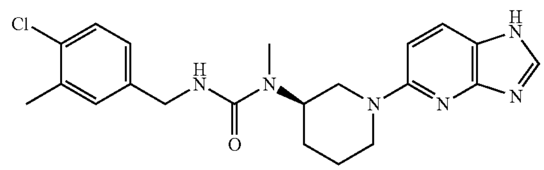 [SMILES: Cc1cc(CNC(=O)N(C)[C@@H]2CCCN(c3ccc4[nH]cnc4n3)C2)ccc1Cl]
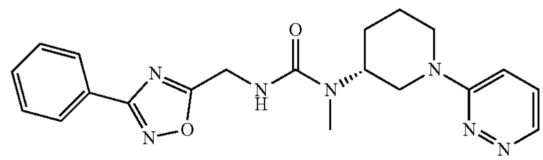 [SMILES: CN(C(=O)NCc1nc(-c2ccccc2)no1)[C@@H]1CCCN(c2cccnn2)C1]
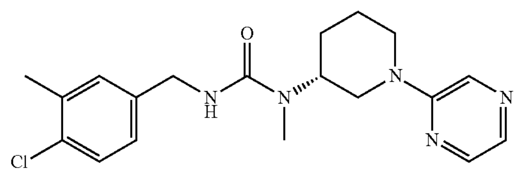 [SMILES: Cc1cc(CNC(=O)N(C)[C@@H]2CCCN(c3cnccn3)C2)ccc1Cl]

TABLE 1-continued
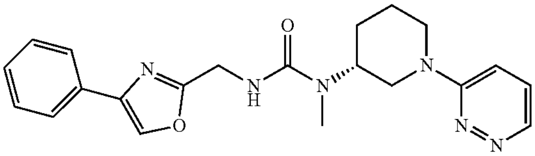 [SMILES: CN(C(=O)NCc1nc(-c2ccccc2)co1)[C@@H]1CCCN(c2cccnn2)C1]
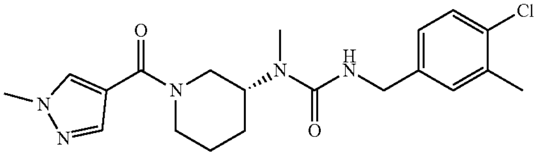 [SMILES: Cc1cc(CNC(=O)N(C)[C@@H]2CCCN(C(=O)c3cnn(C)c3)C2)ccc1Cl]
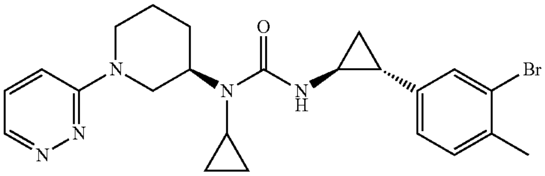 [SMILES: Cc1ccc([C@H]2C[C@@H]2NC(=O)N(C2CC2)[C@@H]2CCCN(c3cccnn3)C2)cc1Br]
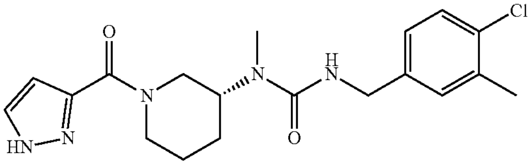
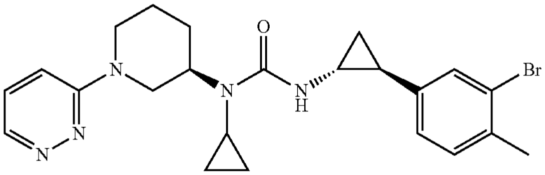 [SMILES: Cc1ccc([C@@H]2C[C@H]2NC(=O)N(C2CC2)[C@@H]2CCCN(c3cccnn3)C2)cc1Br]
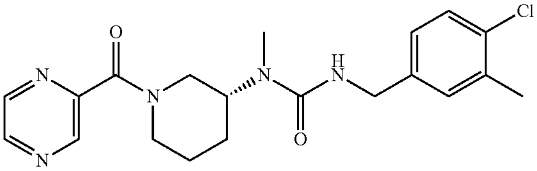 [SMILES: Cc1cc(CNC(=O)N(C)[C@@H]2CCCN(C(=O)c3cnccn3)C2)ccc1Cl]
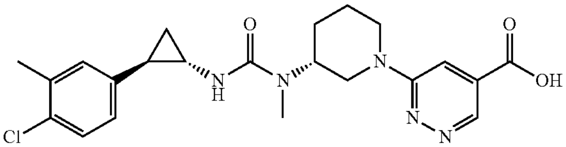 [SMILES: Cc1cc([C@H]2C[C@@H]2NC(=O)N(C)[C@@H]2CCCN(c3cc(C(=O)O)cnn3)C2)ccc1Cl]
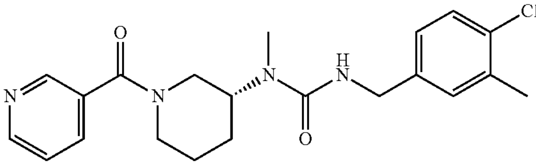 [SMILES: Cc1cc(CNC(=O)N(C)[C@@H]2CCCN(C(=O)c3cccnc3)C2)ccc1Cl]
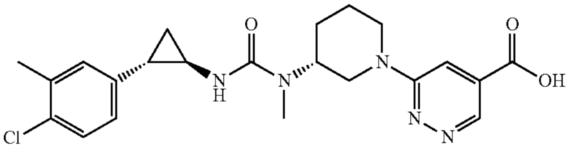 [SMILES: Cc1cc([C@@H]2C[C@H]2NC(=O)N(C)[C@@H]2CCCN(c3cc(C(=O)O)cnn3)C2)ccc1Cl]
TABLE 1-continued
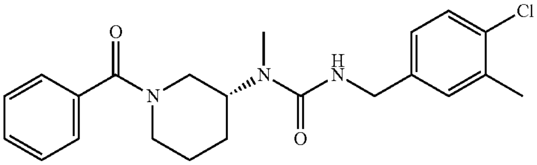 [SMILES: Cc1cc(CNC(=O)N(C)[C@@H]2CCCN(C(=O)c3ccccc3)C2)ccc1Cl]
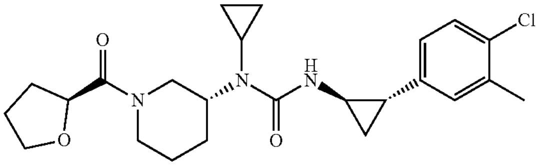 [SMILES: Cc1cc([C@@H]2C[C@H]2NC(=O)N(C2CC2)[C@@H]2CCCN(C(=O)[C@@H]3CCCO3)C2)ccc1Cl]
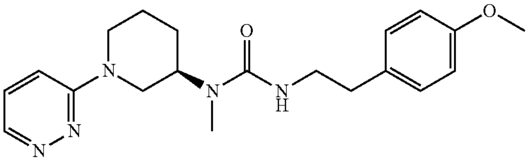 [SMILES: COc1ccc(CCNC(=O)N(C)[C@@H]2CCCN(c3cccnn3)C2)cc1]
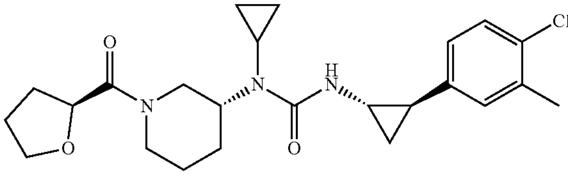 [SMILES: Cc1cc([C@H]2C[C@@H]2NC(=O)N(C2CC2)[C@@H]2CCCN(C(=O)[C@@H]3CCCO3)C2)ccc1Cl]
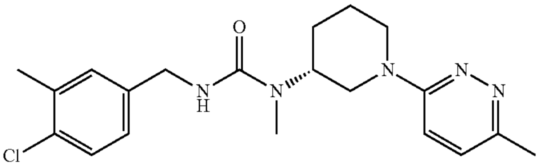
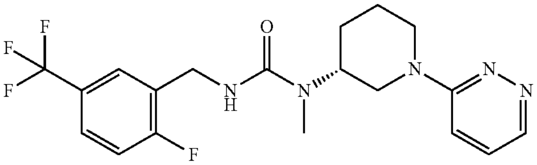 [SMILES: CN(C(=O)NCc1cc(C(F)(F)F)ccc1F)[C@@H]1CCCN(c2cccnn2)C1]
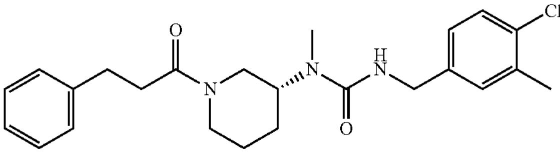 [SMILES: Cc1cc(CNC(=O)N(C)[C@@H]2CCCN(C(=O)CCc3ccccc3)C2)ccc1Cl]
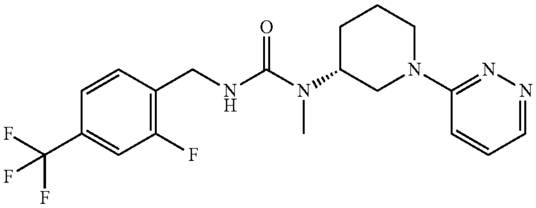 [SMILES: CN(C(=O)NCc1ccc(C(F)(F)F)cc1F)[C@@H]1CCCN(c2cccnn2)C1]
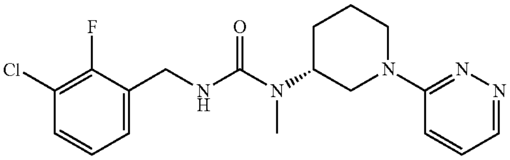 [SMILES: CN(C(=O)NCc1cccc(Cl)c1F)[C@@H]1CCCN(c2cccnn2)C1]

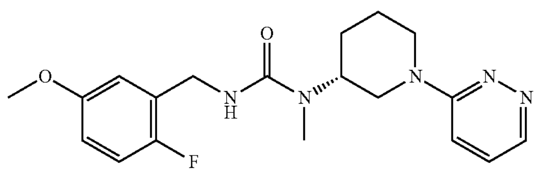 [SMILES: COc1ccc(F)c(CNC(=O)N(C)[C@@H]2CCCN(c3cccnn3)C2)c1]
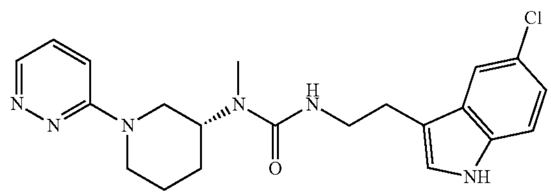 [SMILES: CN(C(=O)NCCc1c[nH]c2ccc(Cl)cc12)[C@@H]1CCCN(c2cccnn2)C1]
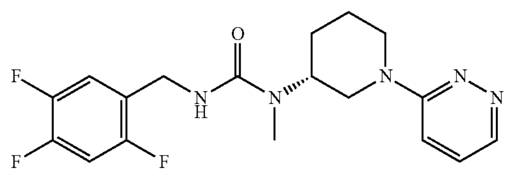 [SMILES: CN(C(=O)NCc1cc(F)c(F)cc1F)[C@@H]1CCCN(c2cccnn2)C1]
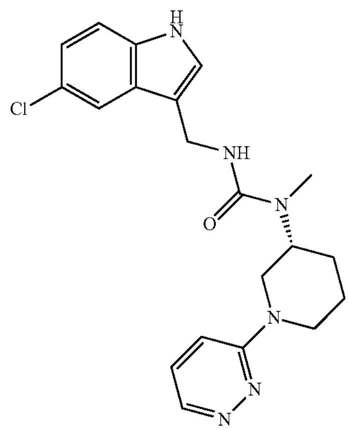 [SMILES: CN(C(=O)NCc1c[nH]c2ccc(Cl)cc12)[C@@H]1CCCN(c2cccnn2)C1]
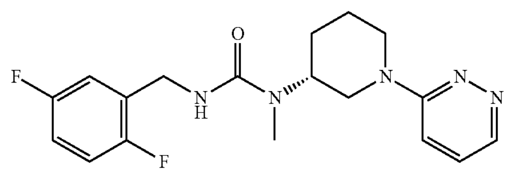 [SMILES: CN(C(=O)NCc1cc(F)ccc1F)[C@@H]1CCCN(c2cccnn2)C1]
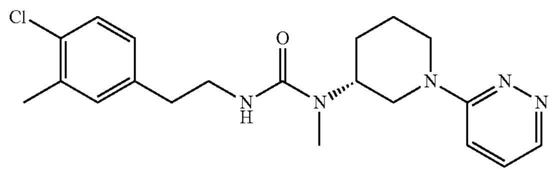 [SMILES: Cc1cc(CCNC(=O)N(C)[C@@H]2CCCN(c3cccnn3)C2)ccc1Cl]
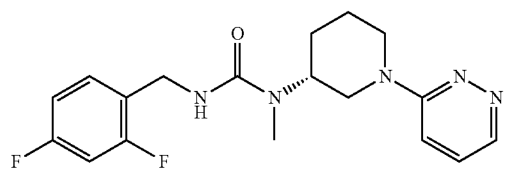 [SMILES: CN(C(=O)NCc1ccc(F)cc1F)[C@@H]1CCCN(c2cccnn2)C1]
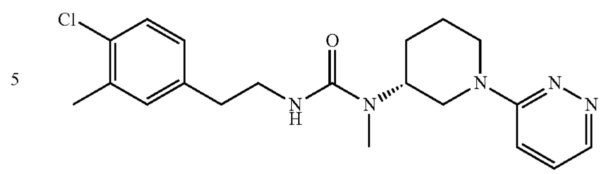
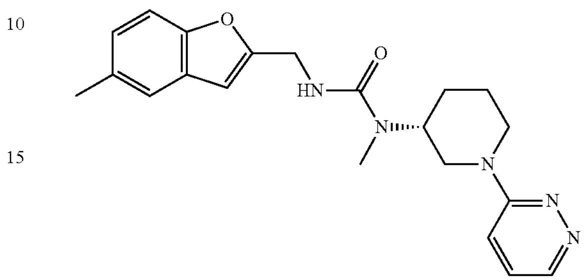
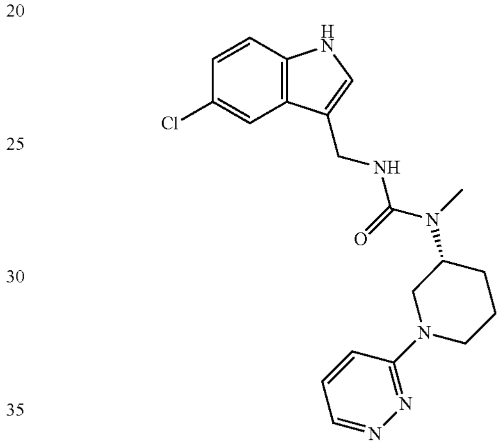
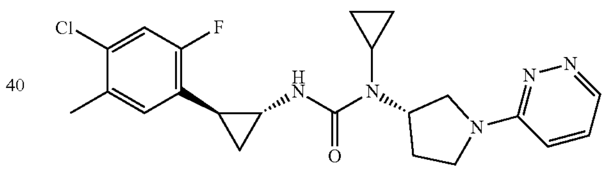
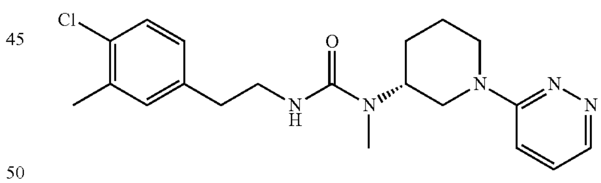
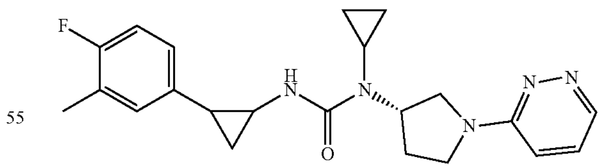
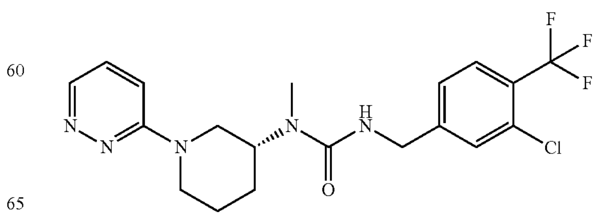

TABLE 1-continued
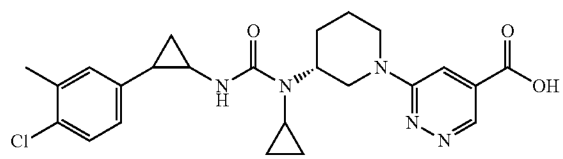 [SMILES: Cc1cc(C2CC2NC(=O)N(C2CC2)[C@@H]2CCCN(c3cc(C(=O)O)cnn3)C2)ccc1Cl]
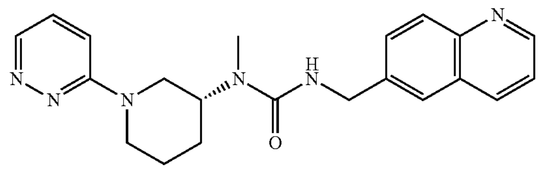 [SMILES: CN(C(=O)NCc1ccc2ncccc2c1)[C@@H]1CCCN(c2cccnn2)C1]
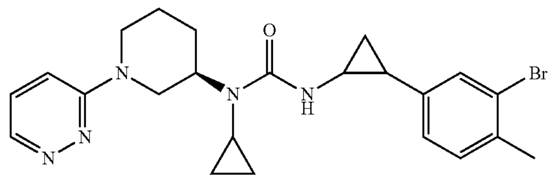 [SMILES: Cc1ccc(C2CC2NC(=O)N(C2CC2)[C@@H]2CCCN(c3cccnn3)C2)cc1Br]
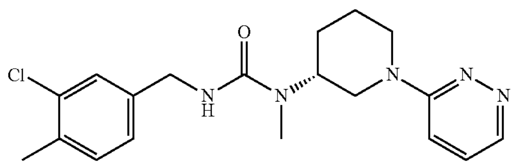 [SMILES: Cc1ccc(CNC(=O)N(C)[C@@H]2CCCN(c3cccnn3)C2)cc1Cl]
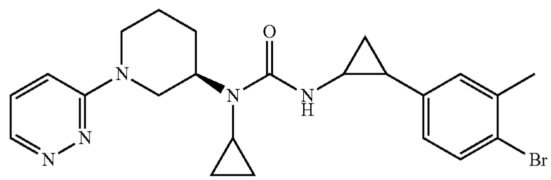 [SMILES: Cc1cc(C2CC2NC(=O)N(C2CC2)[C@@H]2CCCN(c3cccnn3)C2)ccc1Br]
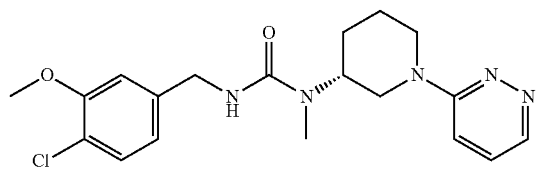 [SMILES: COc1cc(CNC(=O)N(C)[C@@H]2CCCN(c3cccnn3)C2)ccc1Cl]
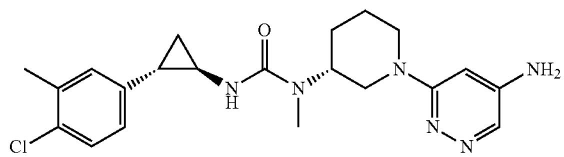 [SMILES: Cc1cc([C@@H]2C[C@H]2NC(=O)N(C)[C@@H]2CCCN(c3cc(N)cnn3)C2)ccc1Cl]
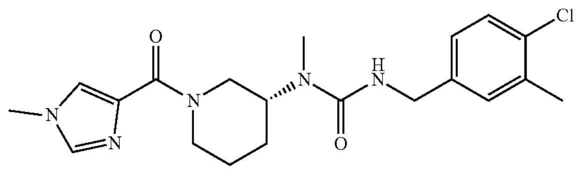 [SMILES: Cc1cc(CNC(=O)N(C)[C@@H]2CCCN(C(=O)c3cn(C)cn3)C2)ccc1Cl]
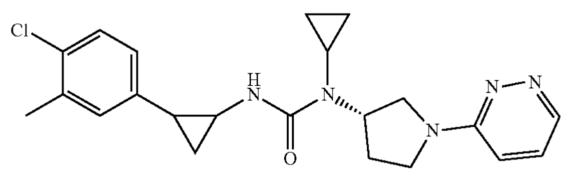 [SMILES: Cc1cc(C2CC2NC(=O)N(C2CC2)[C@H]2CCN(c3cccnn3)C2)ccc1Cl]
TABLE 1-continued
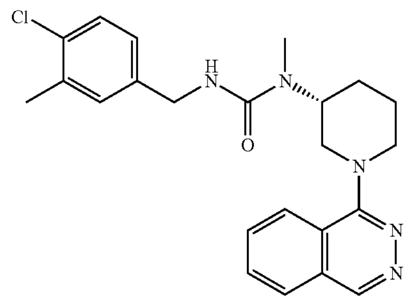 [SMILES: Cc1cc(CNC(=O)N(C)[C@@H]2CCCN(c3nncc4ccccc34)C2)ccc1Cl]
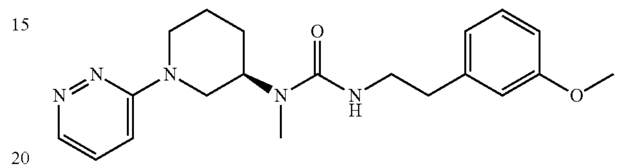
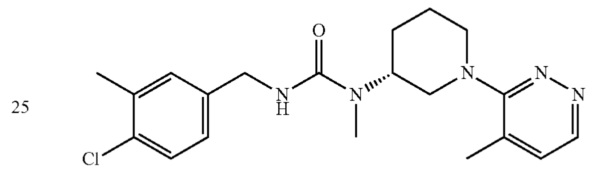
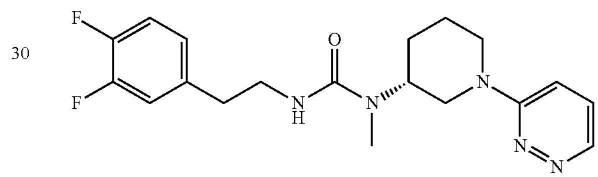
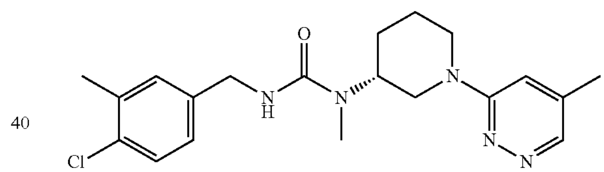
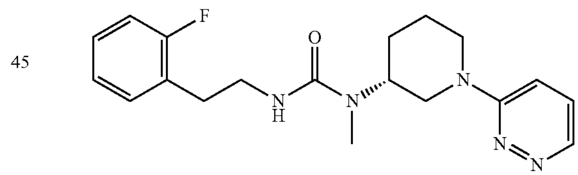
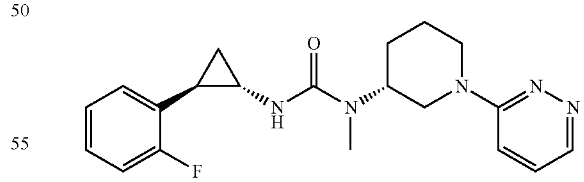
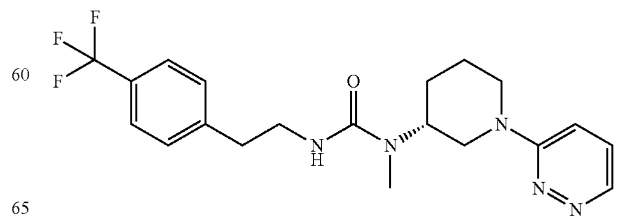

TABLE 1-continued
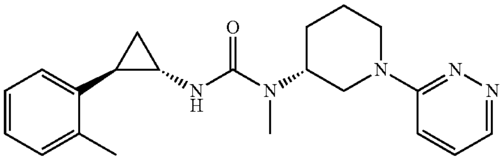 [SMILES: Cc1ccccc1[C@H]1C[C@@H]1NC(=O)N(C)[C@@H]1CCCN(c2cccnn2)C1]
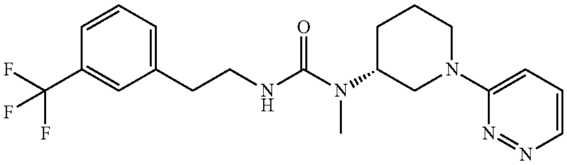 [SMILES: CN(C(=O)NCCc1cccc(C(F)(F)F)c1)[C@@H]1CCCN(c2cccnn2)C1]
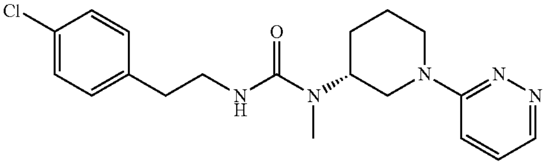 [SMILES: CN(C(=O)NCCc1ccc(Cl)cc1)[C@@H]1CCCN(c2cccnn2)C1]
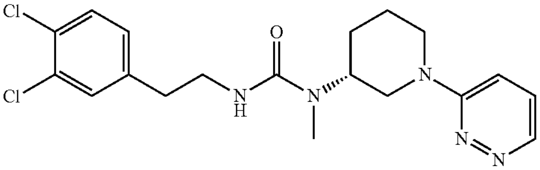 [SMILES: CN(C(=O)NCCc1ccc(Cl)c(Cl)c1)[C@@H]1CCCN(c2cccnn2)C1]
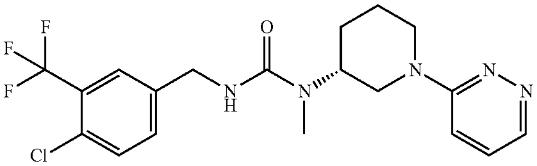
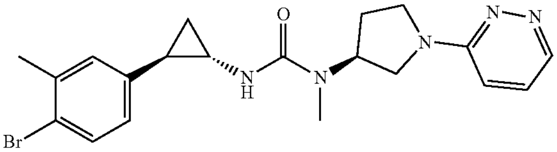 [SMILES: Cc1cc([C@H]2C[C@@H]2NC(=O)N(C)[C@H]2CCN(c3cccnn3)C2)ccc1Br]
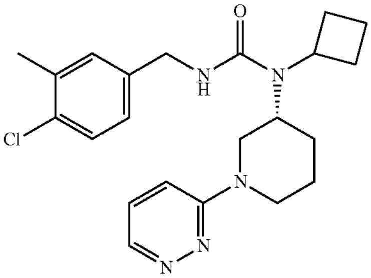 [SMILES: Cc1cc(CNC(=O)N(C2CCC2)[C@@H]2CCCN(c3cccnn3)C2)ccc1Cl]
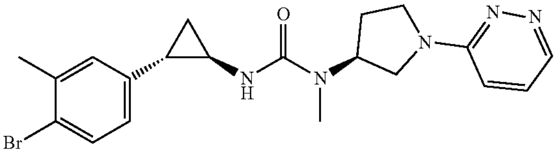 [SMILES: Cc1cc([C@@H]2C[C@H]2NC(=O)N(C)[C@H]2CCN(c3cccnn3)C2)ccc1Br]
TABLE 1-continued
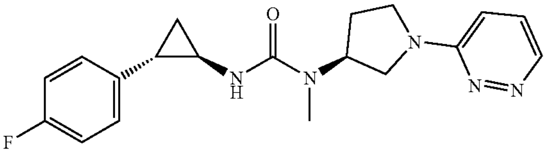 [SMILES: CN(C(=O)N[C@@H]1C[C@H]1c1ccc(F)cc1)[C@H]1CCN(c2cccnn2)C1]
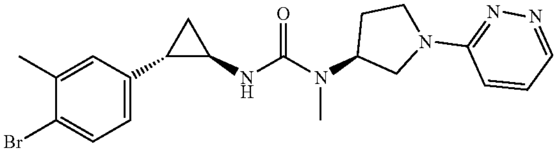 [SMILES: Cc1cc([C@@H]2C[C@H]2NC(=O)N(C)[C@H]2CCN(c3cccnn3)C2)ccc1Br]
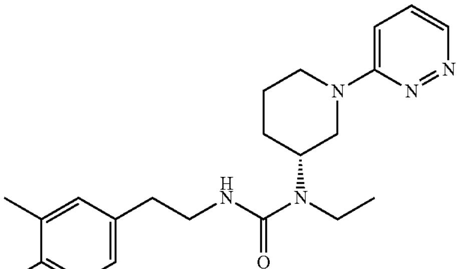
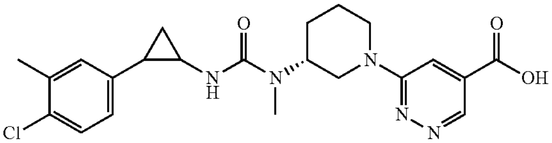 [SMILES: Cc1cc(C2CC2NC(=O)N(C)[C@@H]2CCCN(c3cc(C(=O)O)cnn3)C2)ccc1Cl]
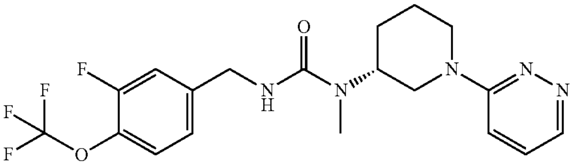 [SMILES: CN(C(=O)NCc1ccc(OC(F)(F)F)c(F)c1)[C@@H]1CCCN(c2cccnn2)C1]
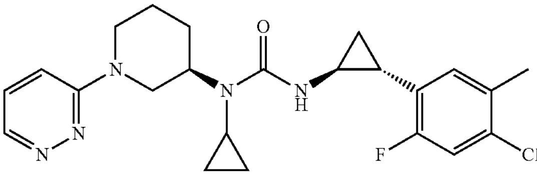 [SMILES: Cc1cc([C@H]2C[C@@H]2NC(=O)N(C2CC2)[C@@H]2CCCN(c3cccnn3)C2)c(F)cc1Cl]
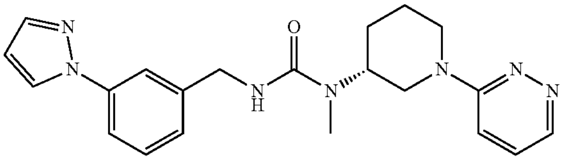 [SMILES: CN(C(=O)NCc1cccc(-n2cccn2)c1)[C@@H]1CCCN(c2cccnn2)C1]
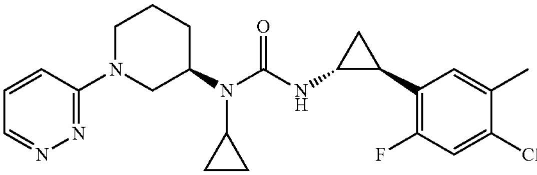 [SMILES: Cc1cc([C@@H]2C[C@H]2NC(=O)N(C2CC2)[C@@H]2CCCN(c3cccnn3)C2)c(F)cc1Cl]

TABLE 1-continued
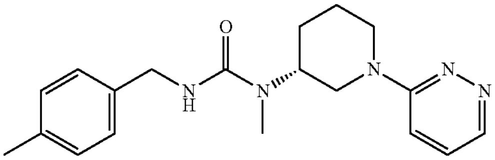 [SMILES: Cc1ccc(CNC(=O)N(C)[C@@H]2CCCN(c3cccnn3)C2)cc1]
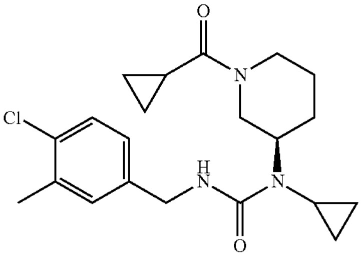 [SMILES: Cc1cc(CNC(=O)N(C2CC2)[C@@H]2CCCN(C(=O)C3CC3)C2)ccc1Cl]
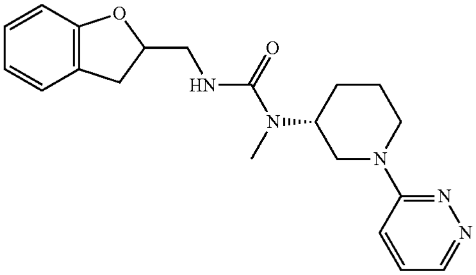 [SMILES: CN(C(=O)NCC1Cc2ccccc2O1)[C@@H]1CCCN(c2cccnn2)C1]
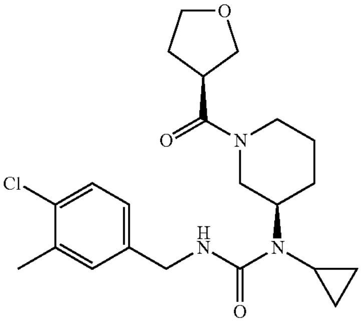 [SMILES: Cc1cc(CNC(=O)N(C2CC2)[C@@H]2CCCN(C(=O)[C@H]3CCOC3)C2)ccc1Cl]
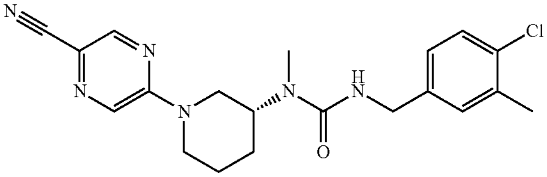 [SMILES: Cc1cc(CNC(=O)N(C)[C@@H]2CCCN(c3cnc(C#N)cn3)C2)ccc1Cl]
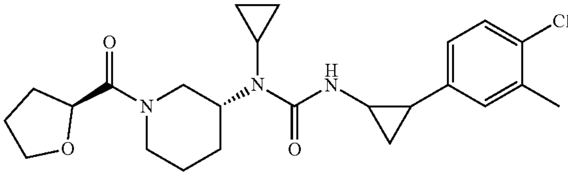 [SMILES: Cc1cc(C2CC2NC(=O)N(C2CC2)[C@@H]2CCCN(C(=O)[C@@H]3CCCO3)C2)ccc1Cl]
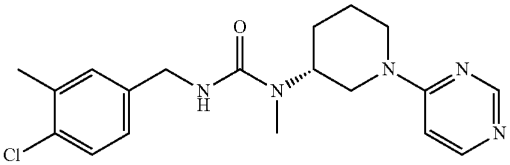 [SMILES: Cc1cc(CNC(=O)N(C)[C@@H]2CCCN(c3ccncn3)C2)ccc1Cl]
TABLE 1-continued
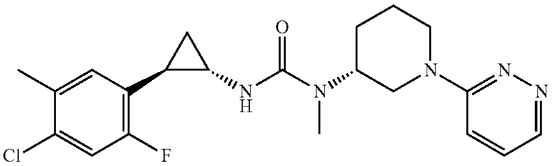 [SMILES: Cc1cc([C@H]2C[C@@H]2NC(=O)N(C)[C@@H]2CCCN(c3cccnn3)C2)c(F)cc1Cl]
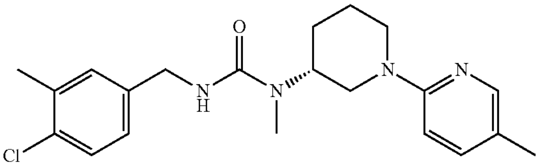 [SMILES: Cc1ccc(N2CCC[C@@H](N(C)C(=O)NCc3ccc(Cl)c(C)c3)C2)nc1]
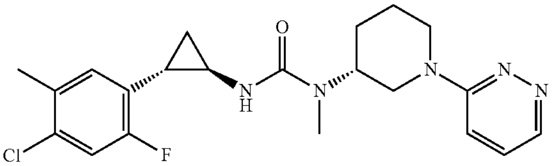 [SMILES: Cc1cc([C@@H]2C[C@H]2NC(=O)N(C)[C@@H]2CCCN(c3cccnn3)C2)c(F)cc1Cl]
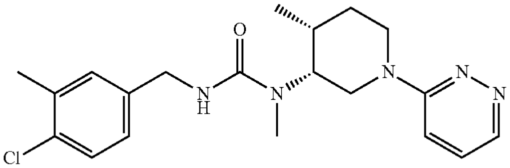 [SMILES: Cc1cc(CNC(=O)N(C)[C@H]2CN(c3cccnn3)CC[C@H]2C)ccc1Cl]
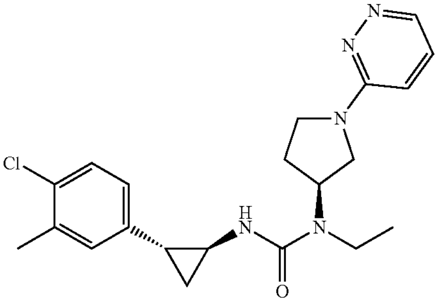 [SMILES: CCN(C(=O)N[C@H]1C[C@@H]1c1ccc(Cl)c(C)c1)[C@H]1CCN(c2cccnn2)C1]
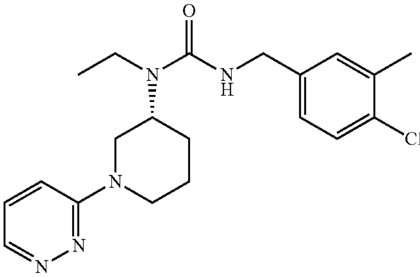 [SMILES: CCN(C(=O)NCc1ccc(Cl)c(C)c1)[C@@H]1CCCN(c2cccnn2)C1]
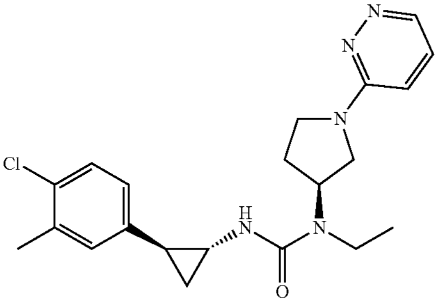 [SMILES: CCN(C(=O)N[C@@H]1C[C@H]1c1ccc(Cl)c(C)c1)[C@H]1CCN(c2cccnn2)C1]

TABLE 1-continued
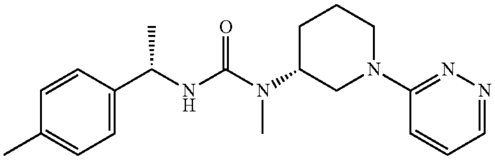 [SMILES: Cc1ccc([C@H](C)NC(=O)N(C)[C@@H]2CCCN(c3cccnn3)C2)cc1]
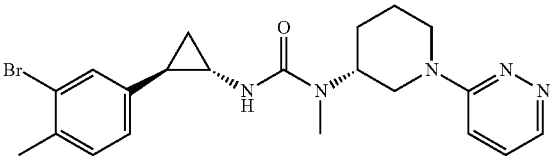 [SMILES: Cc1ccc([C@H]2C[C@@H]2NC(=O)N(C)[C@@H]2CCCN(c3cccnn3)C2)cc1Br]
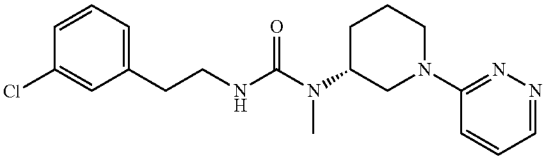 [SMILES: CN(C(=O)NCCc1cccc(Cl)c1)[C@@H]1CCCN(c2cccnn2)C1]
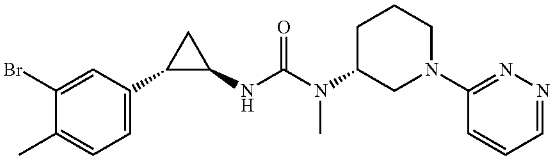 [SMILES: Cc1ccc([C@@H]2C[C@H]2NC(=O)N(C)[C@@H]2CCCN(c3cccnn3)C2)cc1Br]
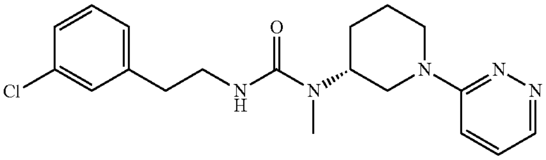 [SMILES: CN(C(=O)NCCc1cccc(Cl)c1)[C@@H]1CCCN(c2cccnn2)C1]
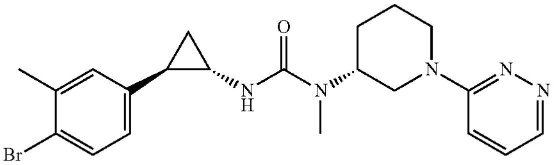
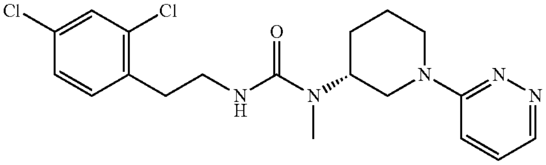 [SMILES: CN(C(=O)NCCc1ccc(Cl)cc1Cl)[C@@H]1CCCN(c2cccnn2)C1]
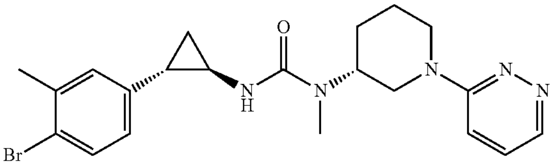 [SMILES: Cc1cc([C@@H]2C[C@H]2NC(=O)N(C)[C@@H]2CCCN(c3cccnn3)C2)ccc1Br]
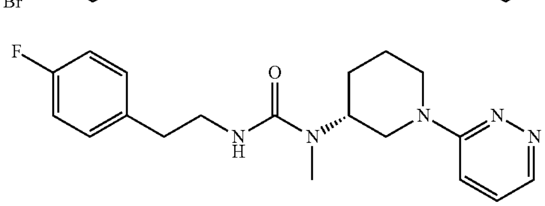
TABLE 1-continued
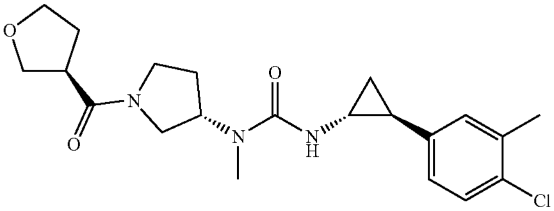 [SMILES: Cc1cc([C@@H]2C[C@H]2NC(=O)N(C)[C@H]2CCN(C(=O)[C@@H]3CCOC3)C2)ccc1Cl]
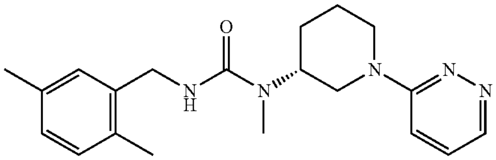 [SMILES: Cc1ccc(C)c(CNC(=O)N(C)[C@@H]2CCCN(c3cccnn3)C2)c1]
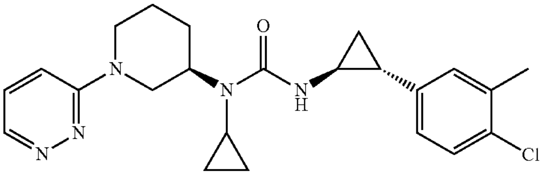
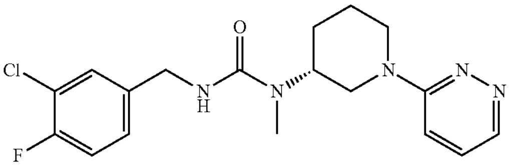 [SMILES: CN(C(=O)NCc1ccc(F)c(Cl)c1)[C@@H]1CCCN(c2cccnn2)C1]
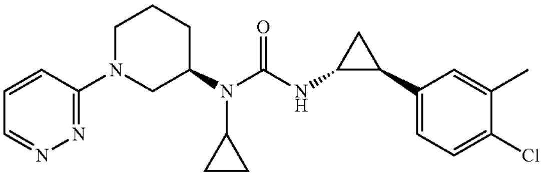 [SMILES: Cc1cc([C@@H]2C[C@H]2NC(=O)N(C2CC2)[C@@H]2CCCN(c3cccnn3)C2)ccc1Cl]
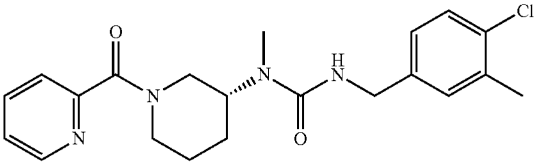 [SMILES: Cc1cc(CNC(=O)N(C)[C@@H]2CCCN(C(=O)c3ccccn3)C2)ccc1Cl]
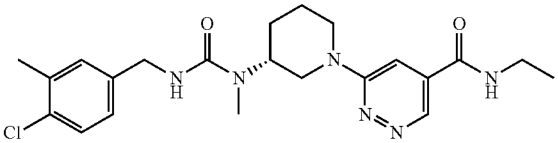 [SMILES: CCNC(=O)c1cnnc(N2CCC[C@@H](N(C)C(=O)NCc3ccc(Cl)c(C)c3)C2)c1]
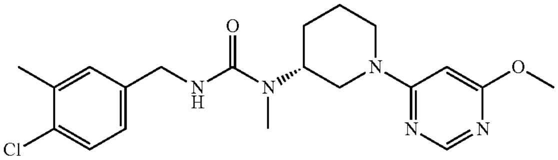
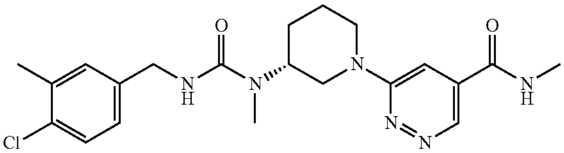

TABLE 1-continued
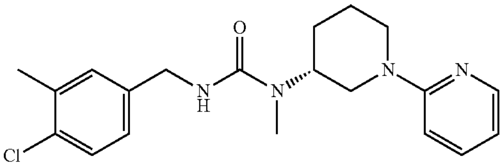 [SMILES: Cc1cc(CNC(=O)N(C)[C@@H]2CCCN(c3ccccn3)C2)ccc1Cl]
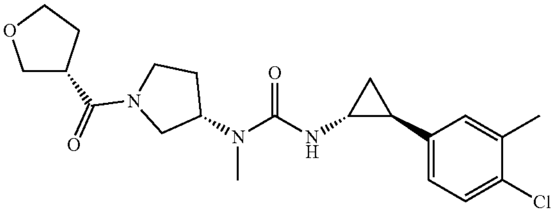 [SMILES: Cc1cc([C@@H]2C[C@H]2NC(=O)N(C)[C@H]2CCN(C(=O)[C@H]3CCOC3)C2)ccc1Cl]
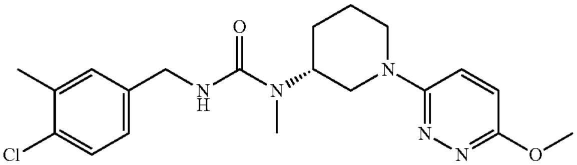
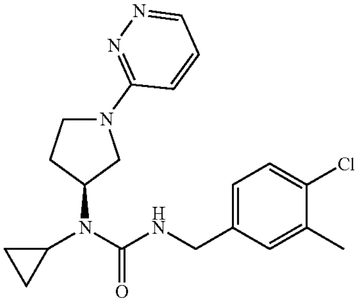 [SMILES: Cc1cc(CNC(=O)N(C2CC2)[C@H]2CCN(c3cccnn3)C2)ccc1Cl]
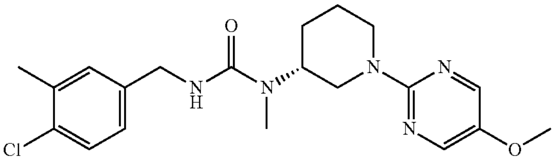
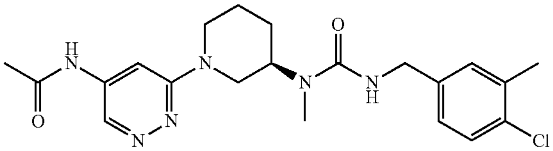 [SMILES: CC(=O)Nc1cnnc(N2CCC[C@@H](N(C)C(=O)NCc3ccc(Cl)c(C)c3)C2)c1]
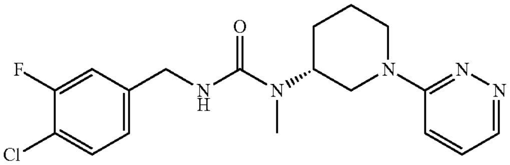 [SMILES: CN(C(=O)NCc1ccc(Cl)c(F)c1)[C@@H]1CCCN(c2cccnn2)C1]
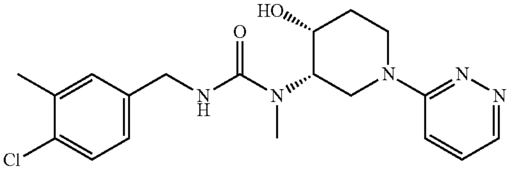 [SMILES: Cc1cc(CNC(=O)N(C)[C@H]2CN(c3cccnn3)CC[C@H]2O)ccc1Cl]
TABLE 1-continued
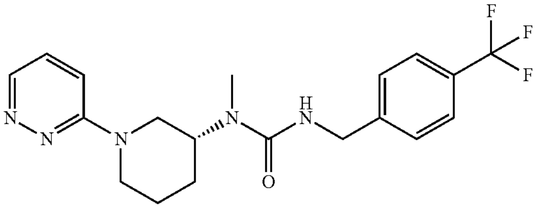 [SMILES: CN(C(=O)NCc1ccc(C(F)(F)F)cc1)[C@@H]1CCCN(c2cccnn2)C1]
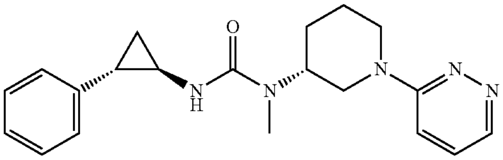 [SMILES: CN(C(=O)N[C@@H]1C[C@H]1c1ccccc1)[C@@H]1CCCN(c2cccnn2)C1]
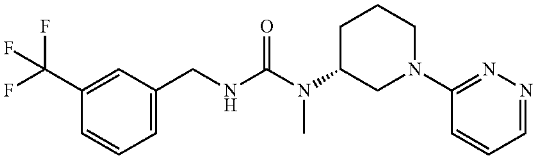 [SMILES: CN(C(=O)NCc1cccc(C(F)(F)F)c1)[C@@H]1CCCN(c2cccnn2)C1]
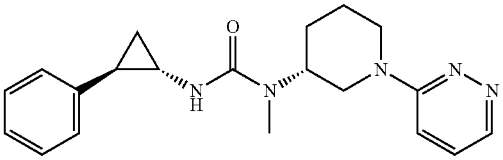 [SMILES: CN(C(=O)N[C@H]1C[C@@H]1c1ccccc1)[C@@H]1CCCN(c2cccnn2)C1]
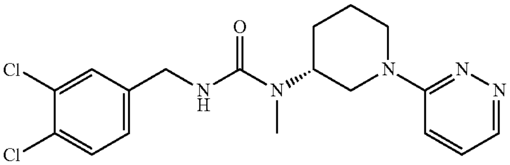 [SMILES: CN(C(=O)NCc1ccc(Cl)c(Cl)c1)[C@@H]1CCCN(c2cccnn2)C1]
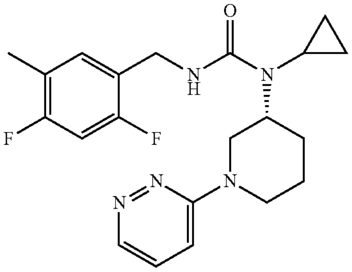 [SMILES: Cc1cc(CNC(=O)N(C2CC2)[C@@H]2CCCN(c3cccnn3)C2)c(F)cc1F]
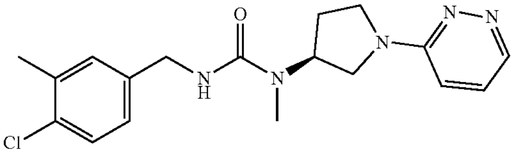 [SMILES: Cc1cc(CNC(=O)N(C)[C@H]2CCN(c3cccnn3)C2)ccc1Cl]
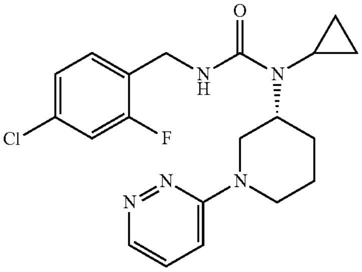 [SMILES: O=C(NCc1ccc(Cl)cc1F)N(C1CC1)[C@@H]1CCCN(c2cccnn2)C1]

TABLE 1-continued
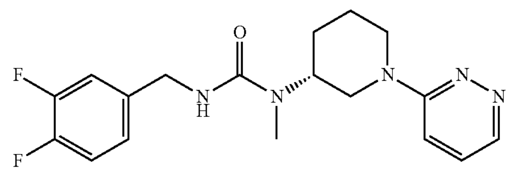 [SMILES: CN(C(=O)NCc1ccc(F)c(F)c1)[C@@H]1CCCN(c2cccnn2)C1]
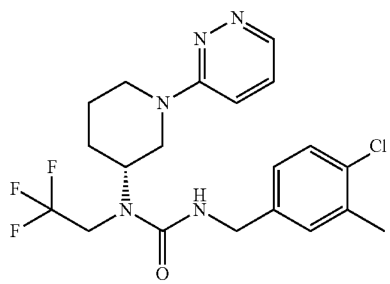 [SMILES: Cc1cc(CNC(=O)N(CC(F)(F)F)[C@@H]2CCCN(c3cccnn3)C2)ccc1Cl]
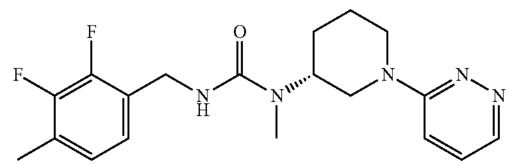 [SMILES: Cc1ccc(CNC(=O)N(C)[C@@H]2CCCN(c3cccnn3)C2)c(F)c1F]
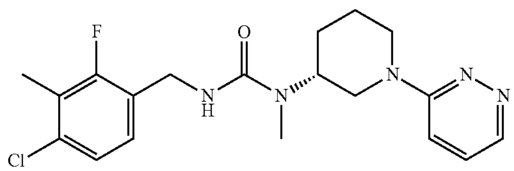 [SMILES: Cc1c(Cl)ccc(CNC(=O)N(C)[C@@H]2CCCN(c3cccnn3)C2)c1F]
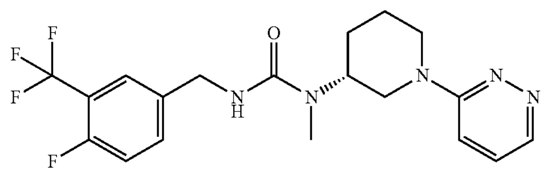 [SMILES: CN(C(=O)NCc1ccc(F)c(C(F)(F)F)c1)[C@@H]1CCCN(c2cccnn2)C1]
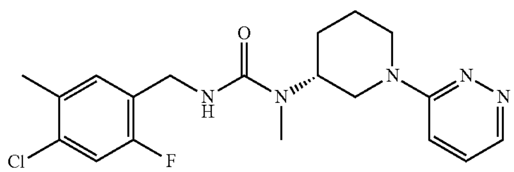 [SMILES: Cc1cc(CNC(=O)N(C)[C@@H]2CCCN(c3cccnn3)C2)c(F)cc1Cl]
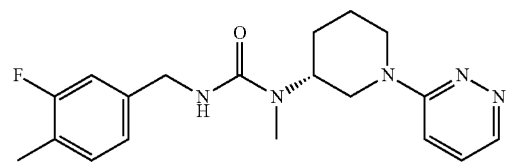 [SMILES: Cc1ccc(CNC(=O)N(C)[C@@H]2CCCN(c3cccnn3)C2)cc1F]
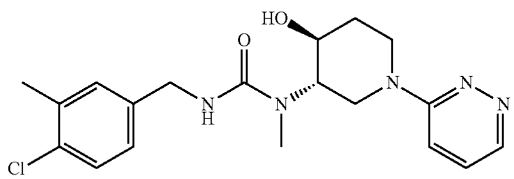 [SMILES: Cc1cc(CNC(=O)N(C)[C@H]2CN(c3cccnn3)CC[C@@H]2O)ccc1Cl]
TABLE 1-continued
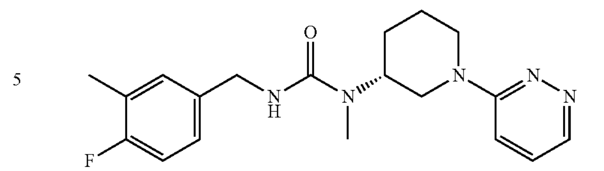
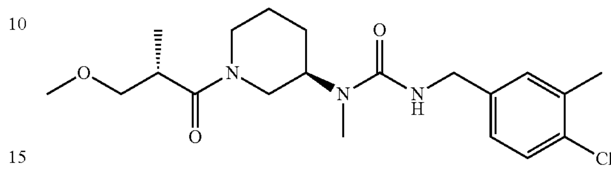
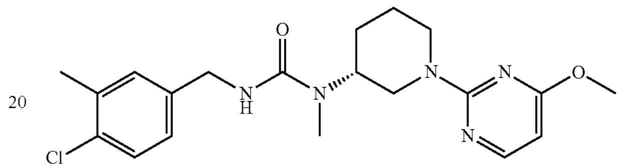
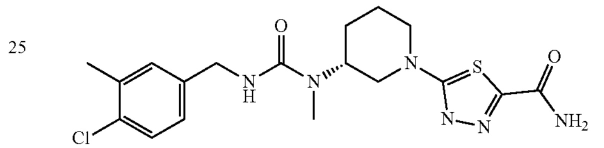
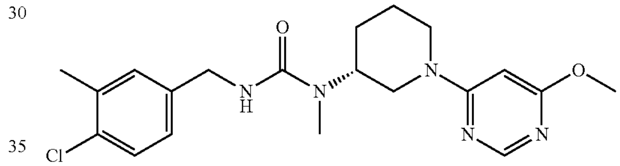
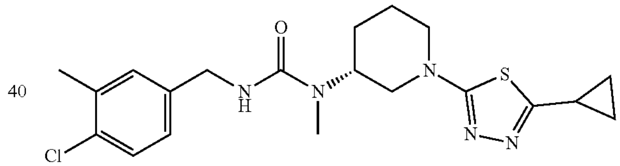
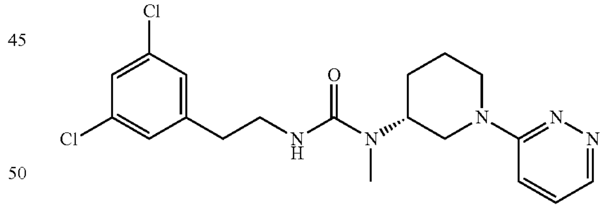
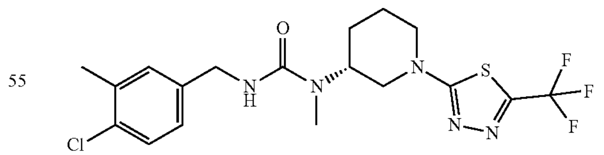
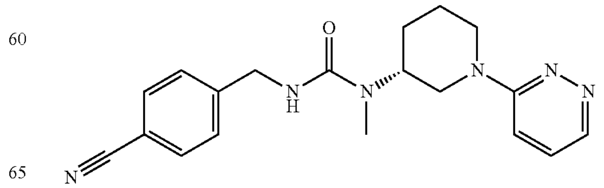

TABLE 1-continued
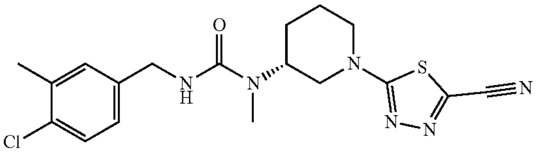 [SMILES: Cc1cc(CNC(=O)N(C)[C@@H]2CCCN(c3nnc(C#N)s3)C2)ccc1Cl]
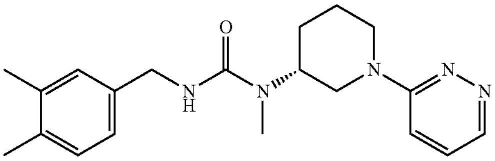 [SMILES: Cc1ccc(CNC(=O)N(C)[C@@H]2CCCN(c3cccnn3)C2)cc1C]
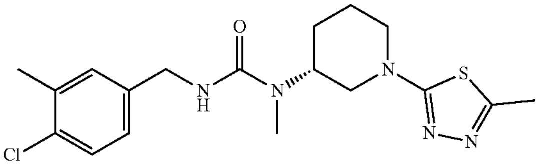 [SMILES: Cc1nnc(N2CCC[C@@H](N(C)C(=O)NCc3ccc(Cl)c(C)c3)C2)s1]
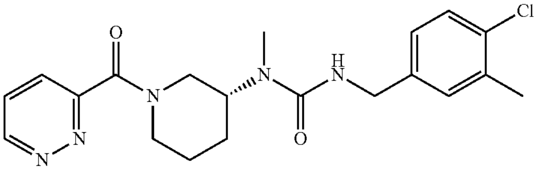 [SMILES: Cc1cc(CNC(=O)N(C)[C@@H]2CCCN(C(=O)c3cccnn3)C2)ccc1Cl]
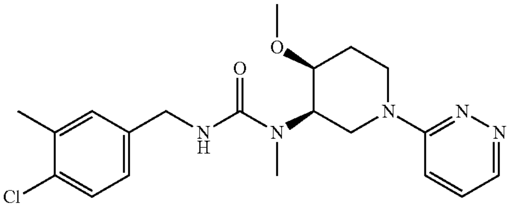 [SMILES: CO[C@H]1CCN(c2cccnn2)C[C@H]1N(C)C(=O)NCc1ccc(Cl)c(C)c1]
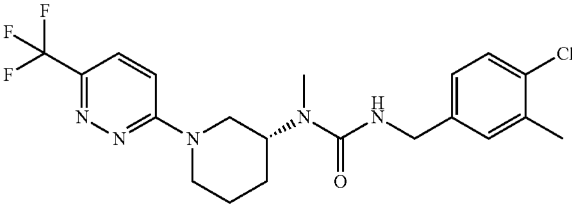 [SMILES: Cc1cc(CNC(=O)N(C)[C@@H]2CCCN(c3ccc(C(F)(F)F)nn3)C2)ccc1Cl]
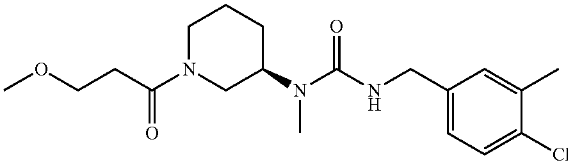 [SMILES: COCCC(=O)N1CCC[C@@H](N(C)C(=O)NCc2ccc(Cl)c(C)c2)C1]
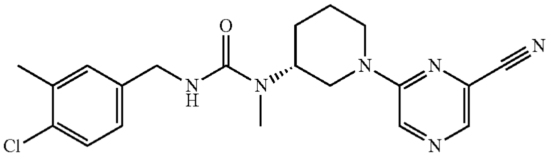 [SMILES: Cc1cc(CNC(=O)N(C)[C@@H]2CCCN(c3cncc(C#N)n3)C2)ccc1Cl]
TABLE 1-continued
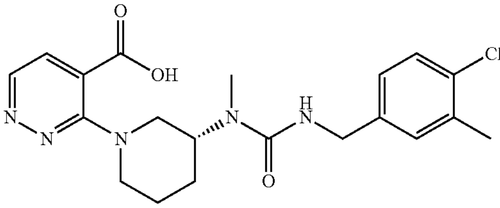 [SMILES: Cc1cc(CNC(=O)N(C)[C@@H]2CCCN(c3nnccc3C(=O)O)C2)ccc1Cl]
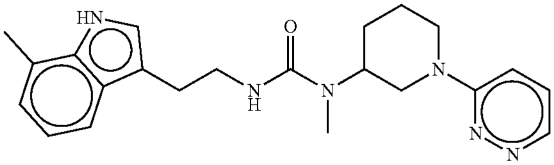
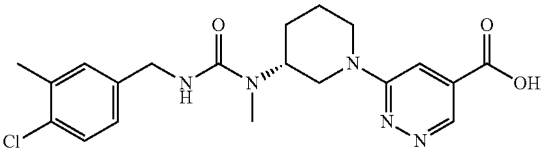 [SMILES: Cc1cc(CNC(=O)N(C)[C@@H]2CCCN(c3cc(C(=O)O)cnn3)C2)ccc1Cl]
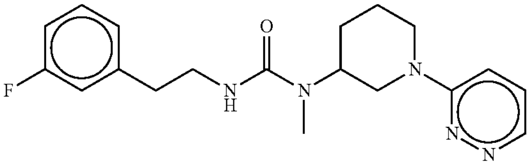
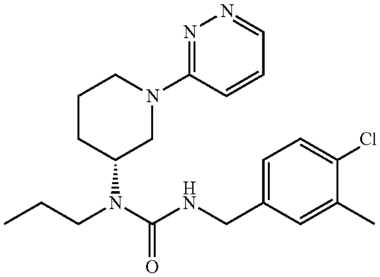 [SMILES: CCCN(C(=O)NCc1ccc(Cl)c(C)c1)[C@@H]1CCCN(c2cccnn2)C1]
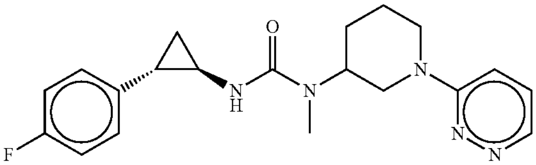
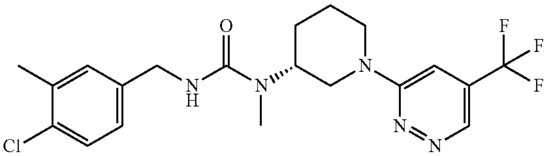 [SMILES: Cc1cc(CNC(=O)N(C)[C@@H]2CCCN(c3cc(C(F)(F)F)cnn3)C2)ccc1Cl]
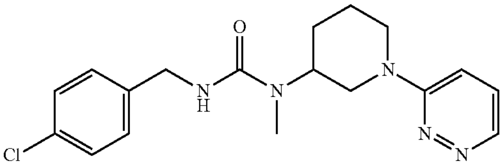

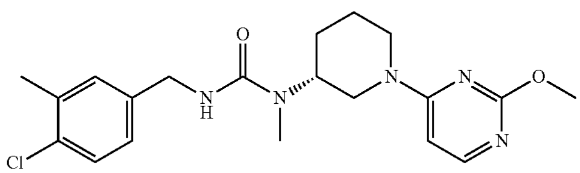
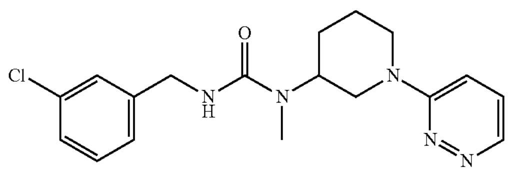 [SMILES: CN(C(=O)NCc1cccc(Cl)c1)C1CCCN(c2cccnn2)C1]
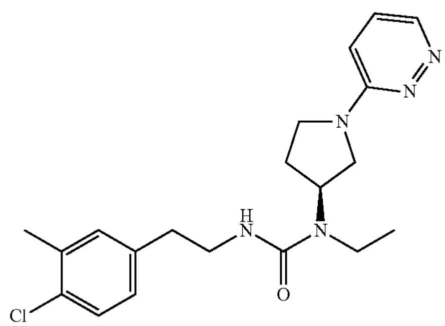 [SMILES: CCN(C(=O)NCCc1ccc(Cl)c(C)c1)[C@H]1CCN(c2cccnn2)C1]
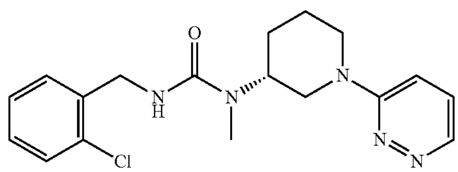 [SMILES: CN(C(=O)NCc1ccccc1Cl)[C@@H]1CCCN(c2cccnn2)C1]
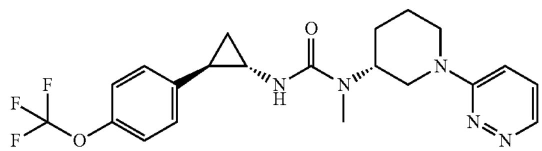 [SMILES: CN(C(=O)N[C@H]1C[C@@H]1c1ccc(OC(F)(F)F)cc1)[C@@H]1CCCN(c2cccnn2)C1]
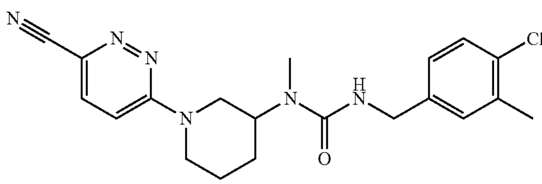 [SMILES: Cc1cc(CNC(=O)N(C)C2CCCN(c3ccc(C#N)nn3)C2)ccc1Cl]
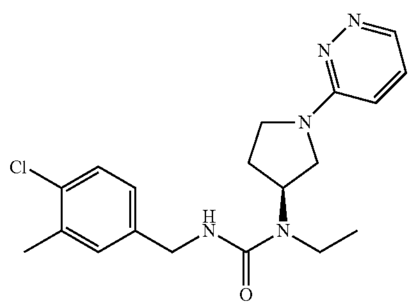 [SMILES: CCN(C(=O)NCc1ccc(Cl)c(C)c1)[C@H]1CCN(c2cccnn2)C1]
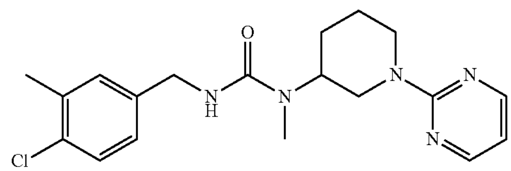 [SMILES: Cc1cc(CNC(=O)N(C)C2CCCN(c3ncccn3)C2)ccc1Cl]
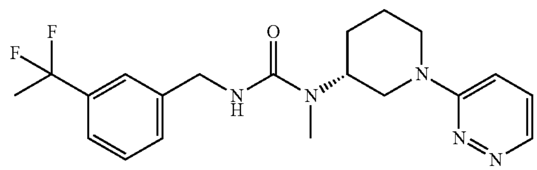 [SMILES: CN(C(=O)NCc1cccc(C(C)(F)F)c1)[C@@H]1CCCN(c2cccnn2)C1]
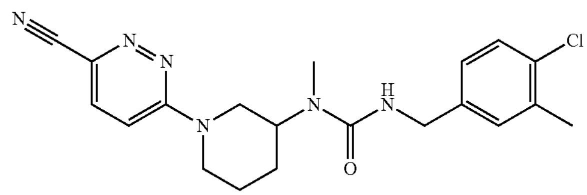 [SMILES: Cc1cc(CNC(=O)N(C)C2CCCN(c3ccc(C#N)nn3)C2)ccc1Cl]
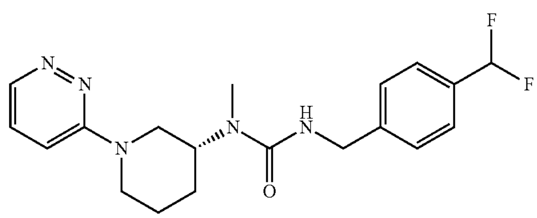 [SMILES: CN(C(=O)NCc1ccc(C(F)F)cc1)[C@@H]1CCCN(c2cccnn2)C1]
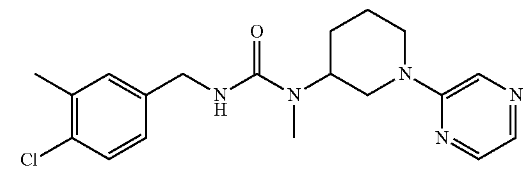 [SMILES: Cc1cc(CNC(=O)N(C)C2CCCN(c3cnccn3)C2)ccc1Cl]
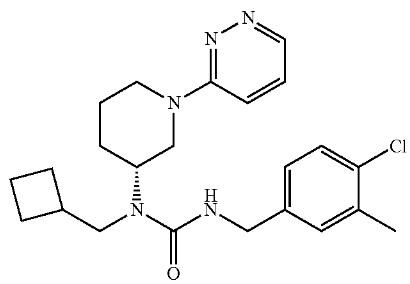 [SMILES: Cc1cc(CNC(=O)N(CC2CCC2)[C@@H]2CCCN(c3cccnn3)C2)ccc1Cl]
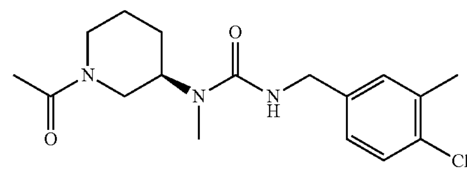 [SMILES: CC(=O)N1CCC[C@@H](N(C)C(=O)NCc2ccc(Cl)c(C)c2)C1]
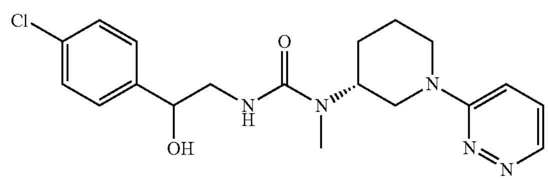 [SMILES: CN(C(=O)NCC(O)c1ccc(Cl)cc1)[C@@H]1CCCN(c2cccnn2)C1]

TABLE 1-continued
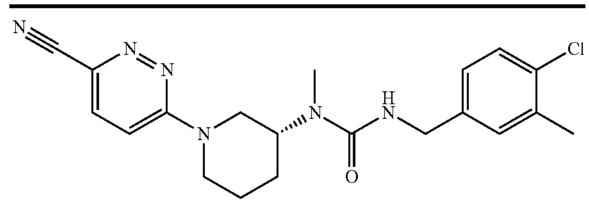
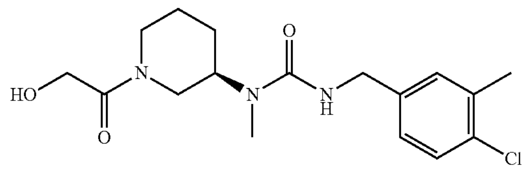 [SMILES: Cc1cc(CNC(=O)N(C)[C@@H]2CCCN(C(=O)CO)C2)ccc1Cl]
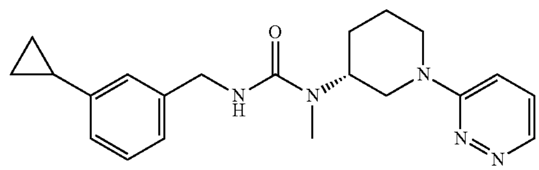 [SMILES: CN(C(=O)NCc1cccc(C2CC2)c1)[C@@H]1CCCN(c2cccnn2)C1]
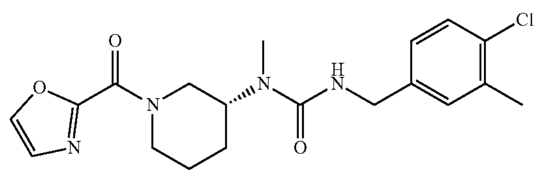 [SMILES: Cc1cc(CNC(=O)N(C)[C@@H]2CCCN(C(=O)c3ncco3)C2)ccc1Cl]
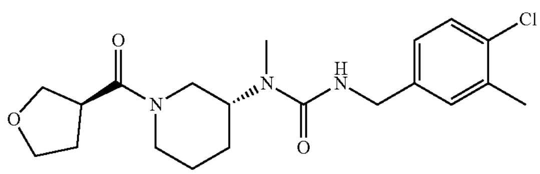 [SMILES: Cc1cc(CNC(=O)N(C)[C@@H]2CCCN(C(=O)[C@H]3CCOC3)C2)ccc1Cl]
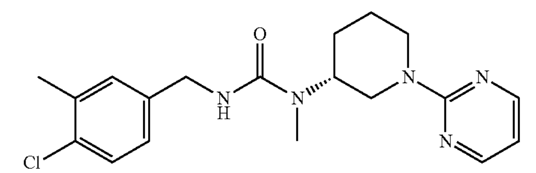 [SMILES: Cc1cc(CNC(=O)N(C)[C@@H]2CCCN(c3ncccn3)C2)ccc1Cl]
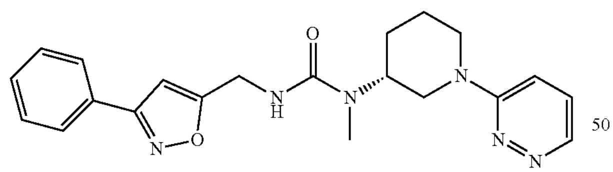
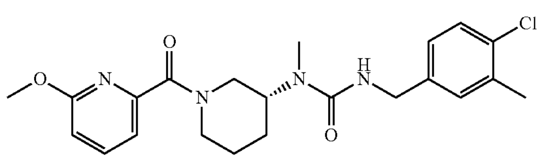
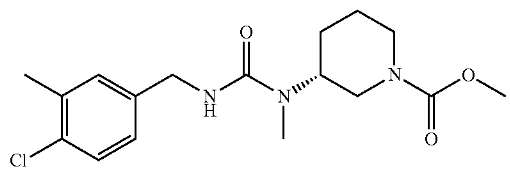
TABLE 1-continued
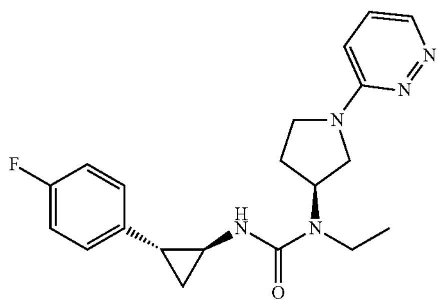 [SMILES: CCN(C(=O)N[C@H]1C[C@@H]1c1ccc(F)cc1)[C@H]1CCN(c2cccnn2)C1]
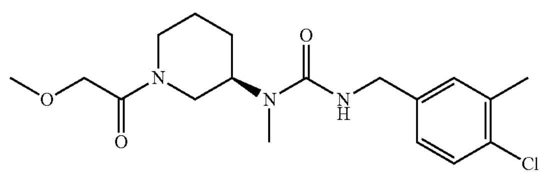 [SMILES: COCC(=O)N1CCC[C@@H](N(C)C(=O)NCc2ccc(Cl)c(C)c2)C1]
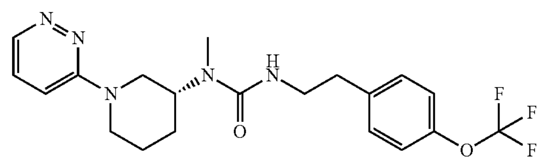 [SMILES: CN(C(=O)NCCc1ccc(OC(F)(F)F)cc1)[C@@H]1CCCN(c2cccnn2)C1]
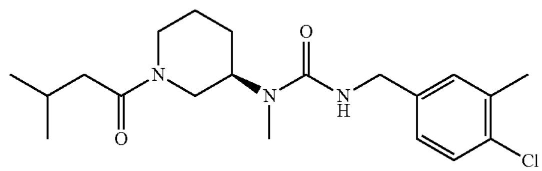 [SMILES: Cc1cc(CNC(=O)N(C)[C@@H]2CCCN(C(=O)CC(C)C)C2)ccc1Cl]
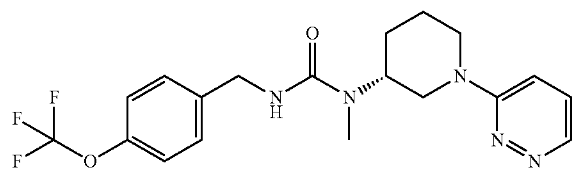 [SMILES: CN(C(=O)NCc1ccc(OC(F)(F)F)cc1)[C@@H]1CCCN(c2cccnn2)C1]
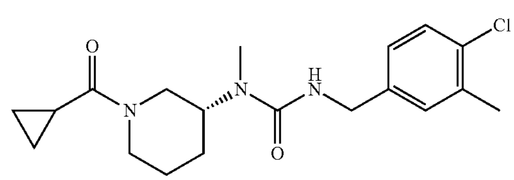 [SMILES: Cc1cc(CNC(=O)N(C)[C@@H]2CCCN(C(=O)C3CC3)C2)ccc1Cl]
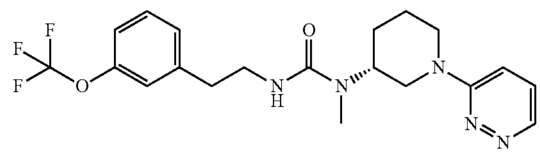 [SMILES: CN(C(=O)NCCc1cccc(OC(F)(F)F)c1)[C@@H]1CCCN(c2cccnn2)C1]
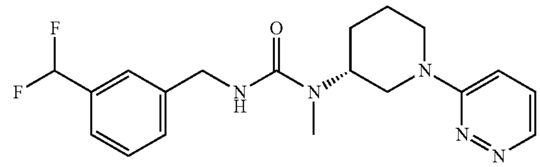 [SMILES: CN(C(=O)NCc1cccc(C(F)F)c1)[C@@H]1CCCN(c2cccnn2)C1]

TABLE 1-continued
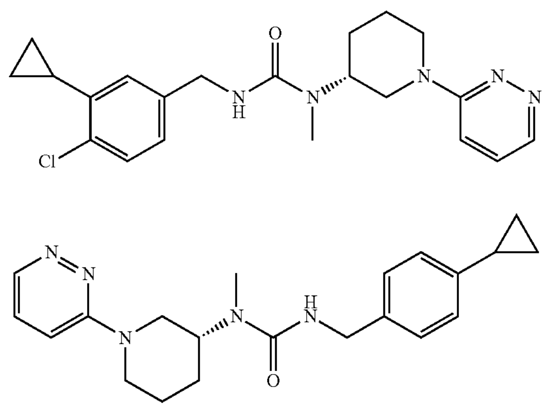
In some embodiments, the compound is selected from the following Table 2:
TABLE 2
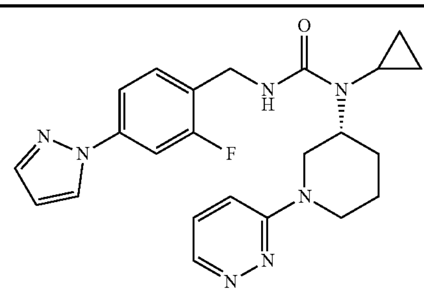
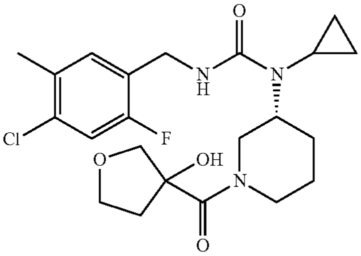 [SMILES: Cc1cc(CNC(=O)N(C2CC2)[C@@H]2CCCN(C(=O)C3(O)CCOC3)C2)c(F)cc1Cl]
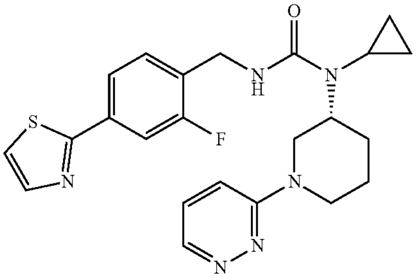 [SMILES: O=C(NCc1ccc(-c2nccs2)cc1F)N(C1CC1)[C@@H]1CCCN(c2cccnn2)C1]
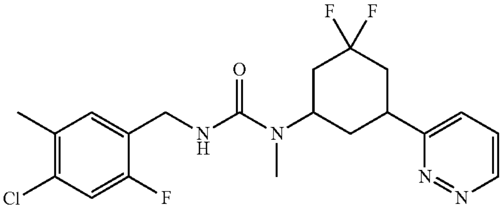 [SMILES: Cc1cc(CNC(=O)N(C)C2CC(c3cccnn3)CC(F)(F)C2)c(F)cc1Cl]
TABLE 2-continued
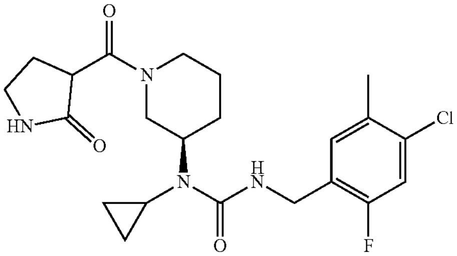 [SMILES: Cc1cc(CNC(=O)N(C2CC2)[C@@H]2CCCN(C(=O)C3CCNC3=O)C2)c(F)cc1Cl]
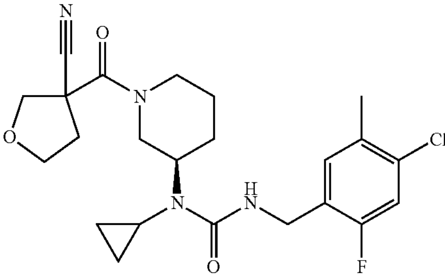 [SMILES: Cc1cc(CNC(=O)N(C2CC2)[C@@H]2CCCN(C(=O)C3(C#N)CCOC3)C2)c(F)cc1Cl]
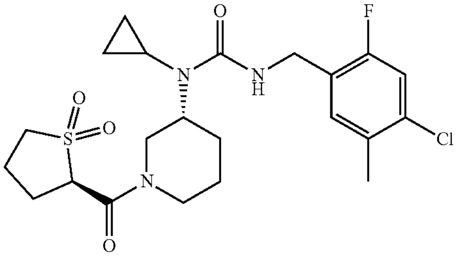 [SMILES: Cc1cc(CNC(=O)N(C2CC2)[C@@H]2CCCN(C(=O)[C@H]3CCCS3(=O)=O)C2)c(F)cc1Cl]
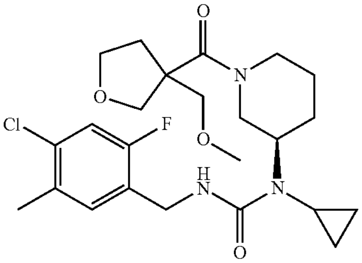 [SMILES: COCC1(C(=O)N2CCC[C@@H](N(C(=O)NCc3cc(C)c(Cl)cc3F)C3CC3)C2)CCOC1]
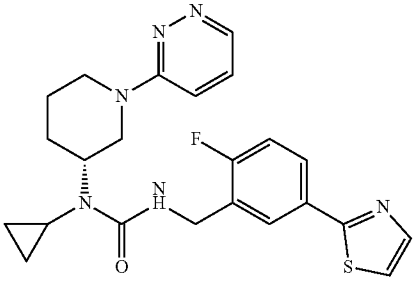 [SMILES: O=C(NCc1cc(-c2nccs2)ccc1F)N(C1CC1)[C@@H]1CCCN(c2cccnn2)C1]

TABLE 2-continued
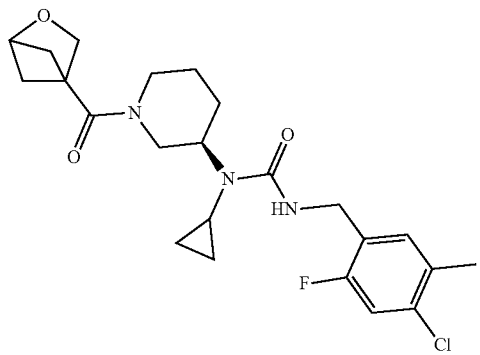 [SMILES: Cc1cc(CNC(=O)N(C2CC2)[C@@H]2CCCN(C(=O)C34COC(C3)C4)C2)c(F)cc1Cl]
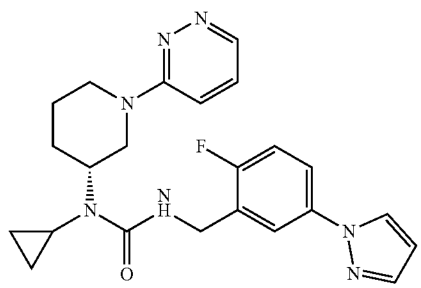 [SMILES: O=C(NCc1cc(-n2cccn2)ccc1F)N(C1CC1)[C@@H]1CCCN(c2cccnn2)C1]
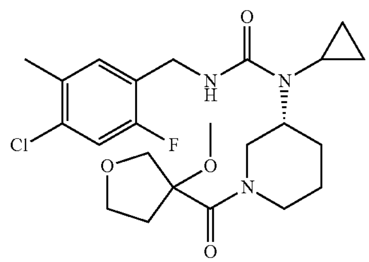 [SMILES: COC1(C(=O)N2CCC[C@@H](N(C(=O)NCc3cc(C)c(Cl)cc3F)C3CC3)C2)CCOC1]
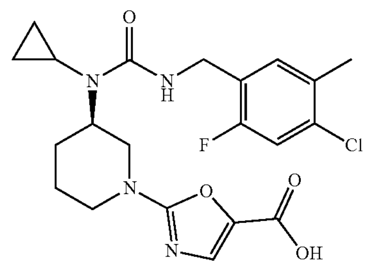 [SMILES: Cc1cc(CNC(=O)N(C2CC2)[C@@H]2CCCN(c3ncc(C(=O)O)o3)C2)c(F)cc1Cl]
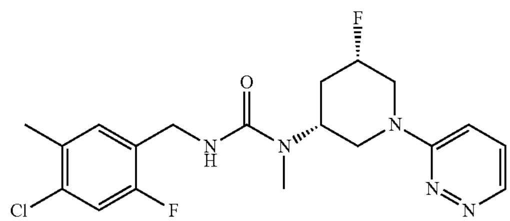 [SMILES: Cc1cc(CNC(=O)N(C)[C@@H]2C[C@H](F)CN(c3cccnn3)C2)c(F)cc1Cl]
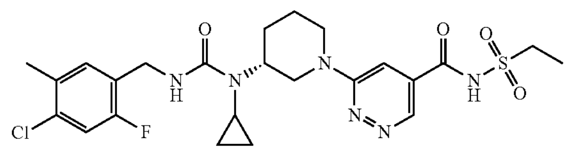 [SMILES: CCS(=O)(=O)NC(=O)c1cnnc(N2CCC[C@@H](N(C(=O)NCc3cc(C)c(Cl)cc3F)C3CC3)C2)c1]
TABLE 2-continued
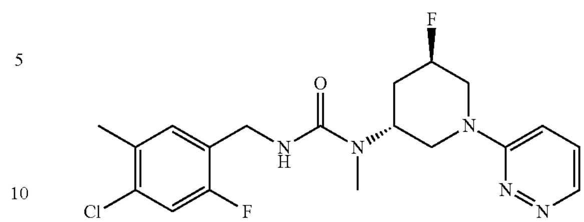
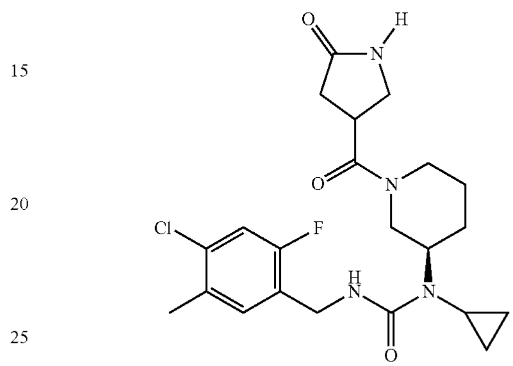
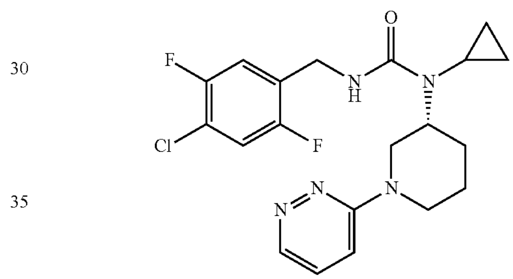
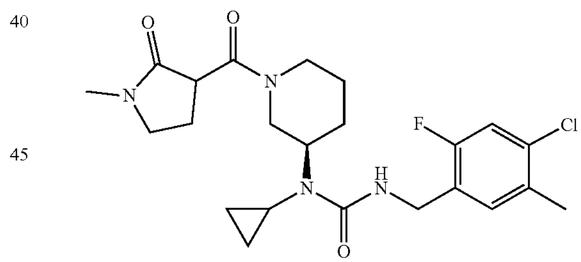
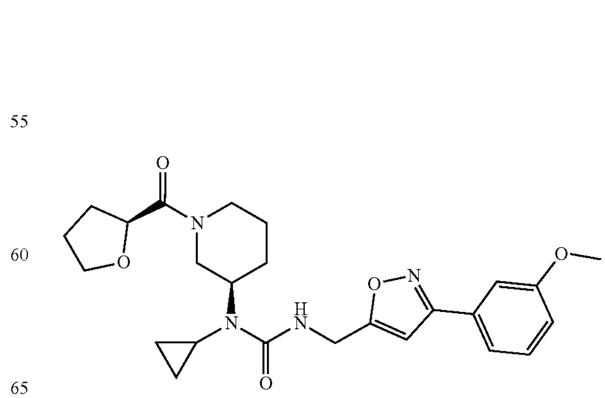

TABLE 2-continued
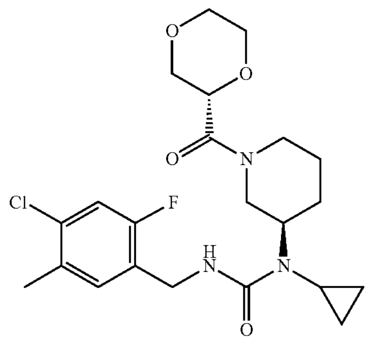 [SMILES: Cc1cc(CNC(=O)N(C2CC2)[C@@H]2CCCN(C(=O)[C@@H]3COCCO3)C2)c(F)cc1Cl]
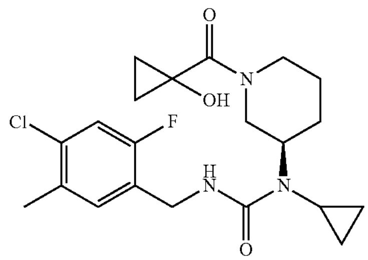 [SMILES: Cc1cc(CNC(=O)N(C2CC2)[C@@H]2CCCN(C(=O)C3(O)CC3)C2)c(F)cc1Cl]
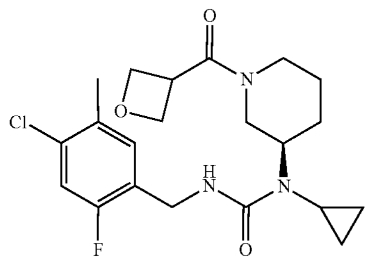 [SMILES: Cc1cc(CNC(=O)N(C2CC2)[C@@H]2CCCN(C(=O)C3COC3)C2)c(F)cc1Cl]
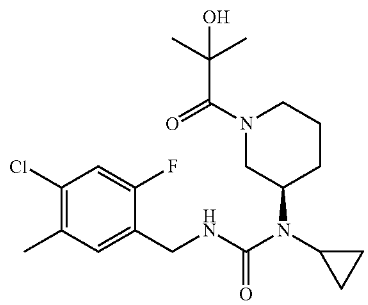 [SMILES: Cc1cc(CNC(=O)N(C2CC2)[C@@H]2CCCN(C(=O)C(C)(C)O)C2)c(F)cc1Cl]
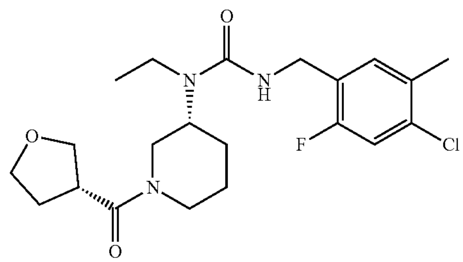 [SMILES: CCN(C(=O)NCc1cc(C)c(Cl)cc1F)[C@@H]1CCCN(C(=O)[C@@H]2CCOC2)C1]
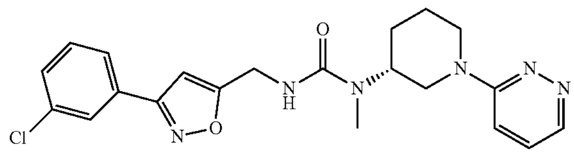 [SMILES: CN(C(=O)NCc1cc(-c2cccc(Cl)c2)no1)[C@@H]1CCCN(c2cccnn2)C1]
TABLE 2-continued
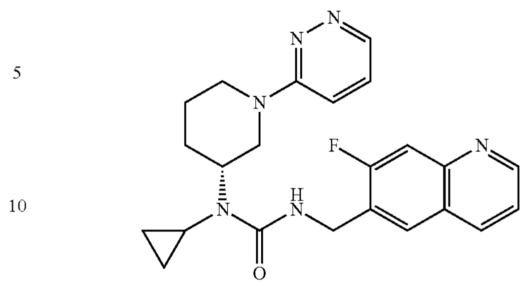
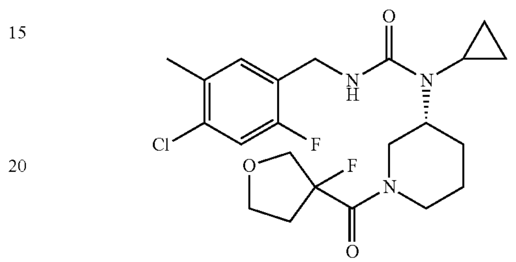
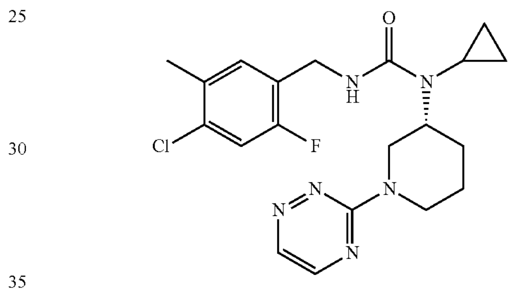
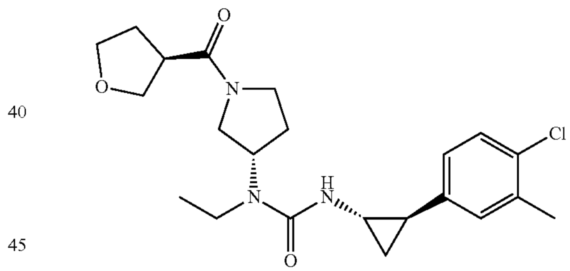
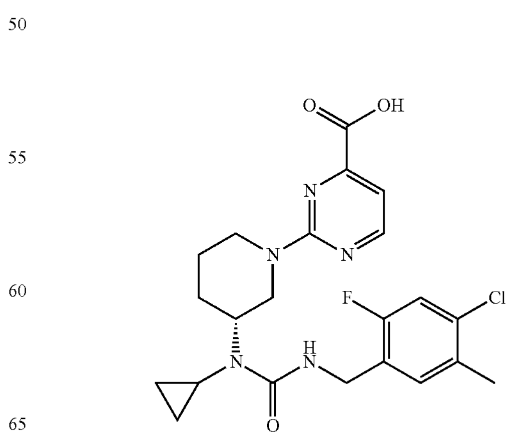

TABLE 2-continued
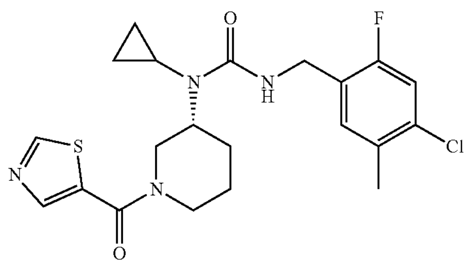 [SMILES: Cc1cc(CNC(=O)N(C2CC2)[C@@H]2CCCN(C(=O)c3cncs3)C2)c(F)cc1Cl]
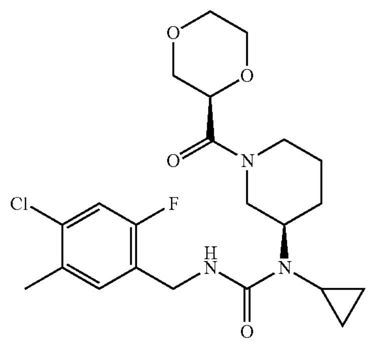 [SMILES: Cc1cc(CNC(=O)N(C2CC2)[C@@H]2CCCN(C(=O)[C@H]3COCCO3)C2)c(F)cc1Cl]
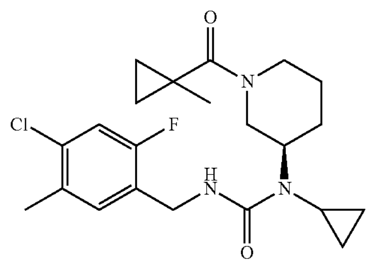 [SMILES: Cc1cc(CNC(=O)N(C2CC2)[C@@H]2CCCN(C(=O)C3(C)CC3)C2)c(F)cc1Cl]
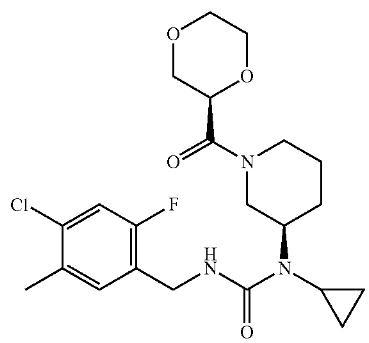 [SMILES: Cc1cc(CNC(=O)N(C2CC2)[C@@H]2CCCN(C(=O)[C@H]3COCCO3)C2)c(F)cc1Cl]
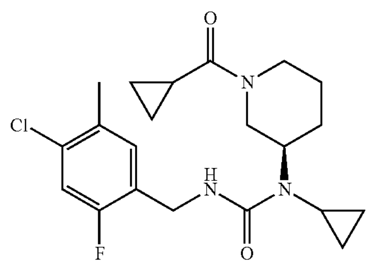 [SMILES: Cc1cc(CNC(=O)N(C2CC2)[C@@H]2CCCN(C(=O)C3CC3)C2)c(F)cc1Cl]
TABLE 2-continued
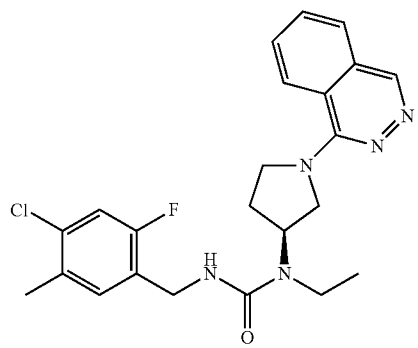 [SMILES: CCN(C(=O)NCc1cc(C)c(Cl)cc1F)[C@H]1CCN(c2nncc3ccccc23)C1]
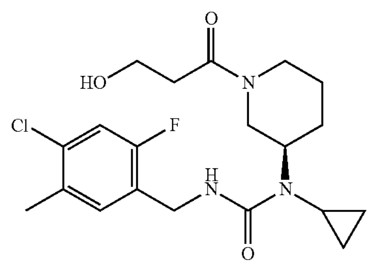 [SMILES: Cc1cc(CNC(=O)N(C2CC2)[C@@H]2CCCN(C(=O)CCO)C2)c(F)cc1Cl]
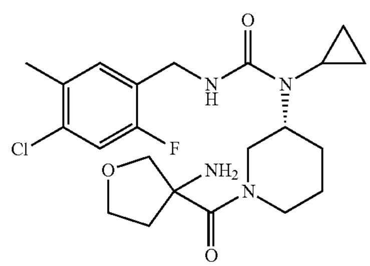
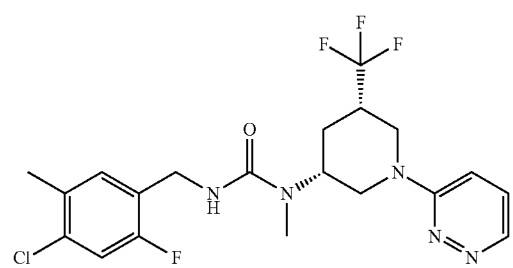 [SMILES: Cc1cc(CNC(=O)N(C)[C@@H]2C[C@H](C(F)(F)F)CN(c3cccnn3)C2)c(F)cc1Cl]
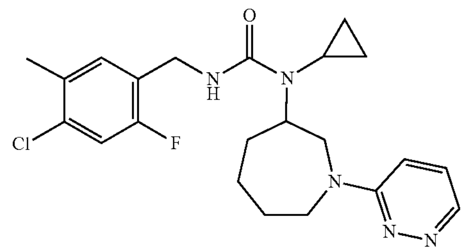 [SMILES: Cc1cc(CNC(=O)N(C2CC2)C2CCCCN(c3cccnn3)C2)c(F)cc1Cl]

TABLE 2-continued
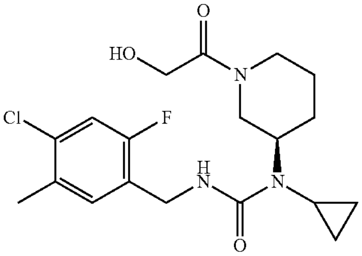 [SMILES: Cc1cc(CNC(=O)N(C2CC2)[C@@H]2CCCN(C(=O)CO)C2)c(F)cc1Cl]
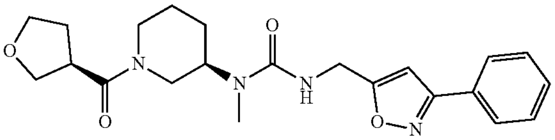 [SMILES: CN(C(=O)NCc1cc(-c2ccccc2)no1)[C@@H]1CCCN(C(=O)[C@@H]2CCOC2)C1]
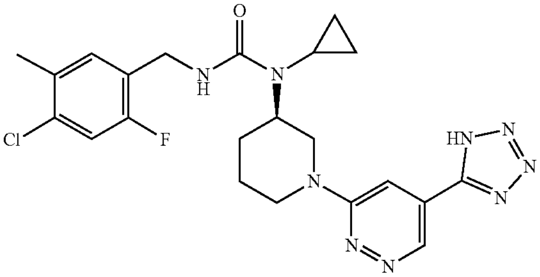 [SMILES: Cc1cc(CNC(=O)N(C2CC2)[C@@H]2CCCN(c3cc(-c4nnn[nH]4)cnn3)C2)c(F)cc1Cl]
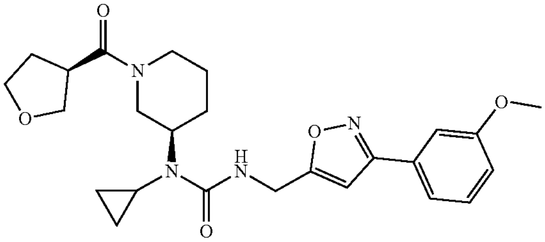 [SMILES: COc1cccc(-c2cc(CNC(=O)N(C3CC3)[C@@H]3CCCN(C(=O)[C@@H]4CCOC4)C3)on2)c1]
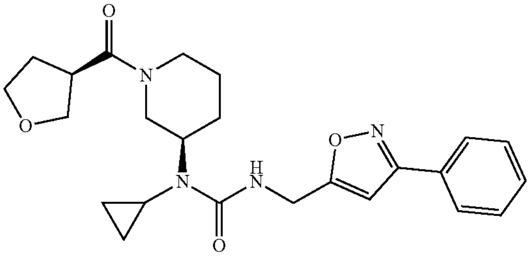 [SMILES: O=C([C@@H]1CCOC1)N1CCC[C@@H](N(C(=O)NCc2cc(-c3ccccc3)no2)C2CC2)C1]
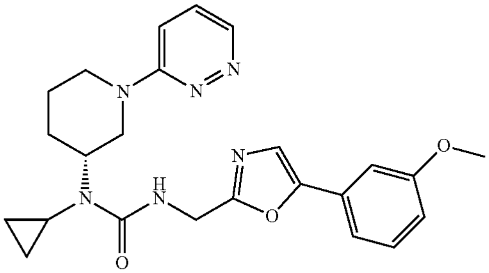 [SMILES: COc1cccc(-c2cnc(CNC(=O)N(C3CC3)[C@@H]3CCCN(c4cccnn4)C3)o2)c1]
TABLE 2-continued
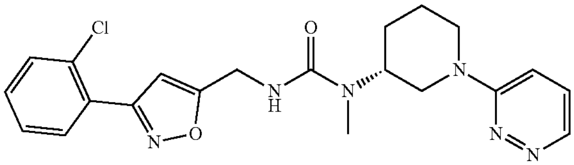 [SMILES: CN(C(=O)NCc1cc(-c2ccccc2Cl)no1)[C@@H]1CCCN(c2cccnn2)C1]
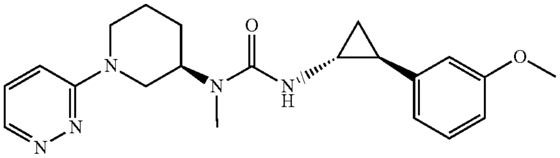
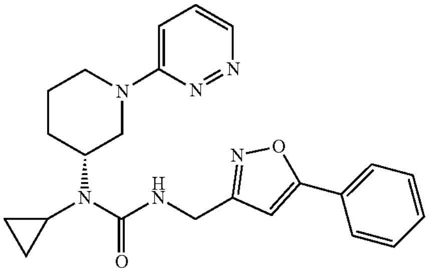 [SMILES: O=C(NCc1cc(-c2ccccc2)on1)N(C1CC1)[C@@H]1CCCN(c2cccnn2)C1]
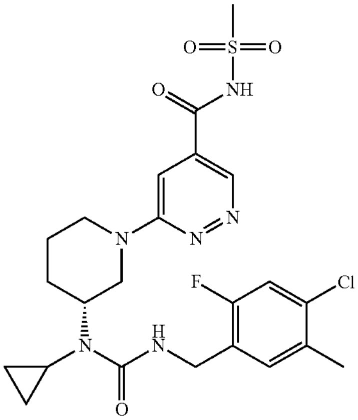 [SMILES: Cc1cc(CNC(=O)N(C2CC2)[C@@H]2CCCN(c3cc(C(=O)NS(C)(=O)=O)cnn3)C2)c(F)cc1Cl]
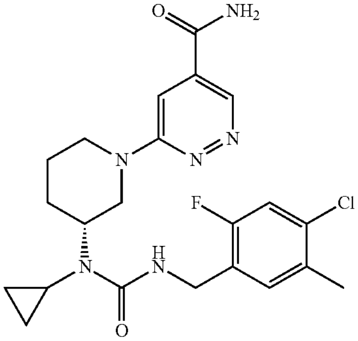 [SMILES: Cc1cc(CNC(=O)N(C2CC2)[C@@H]2CCCN(c3cc(C(N)=O)cnn3)C2)c(F)cc1Cl]

TABLE 2-continued
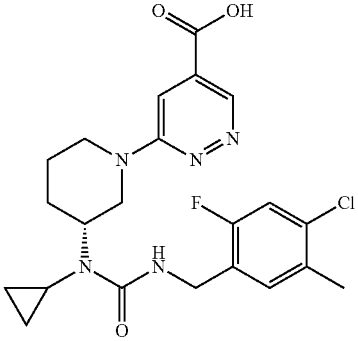 [SMILES: Cc1cc(CNC(=O)N(C2CC2)[C@@H]2CCCN(c3cc(C(=O)O)cnn3)C2)c(F)cc1Cl]
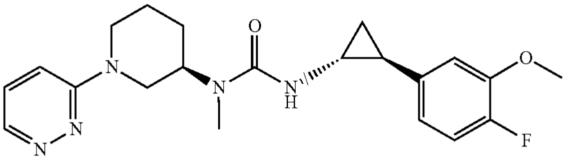
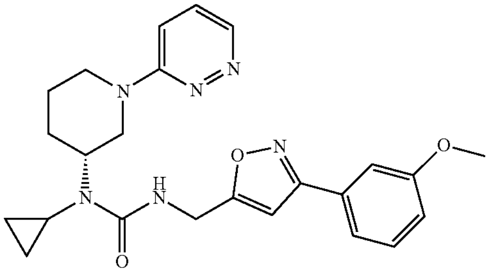 [SMILES: COc1cccc(-c2cc(CNC(=O)N(C3CC3)[C@@H]3CCCN(c4cccnn4)C3)on2)c1]
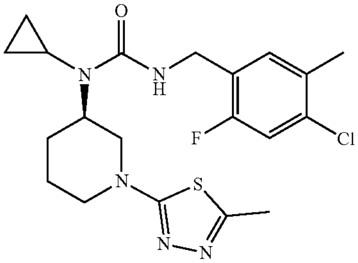 [SMILES: Cc1nnc(N2CCC[C@@H](N(C(=O)NCc3cc(C)c(Cl)cc3F)C3CC3)C2)s1]
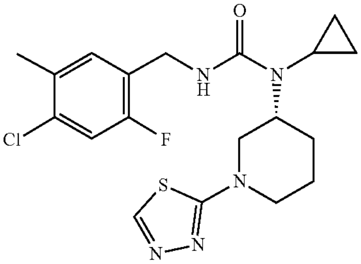 [SMILES: Cc1cc(CNC(=O)N(C2CC2)[C@@H]2CCCN(c3nncs3)C2)c(F)cc1Cl]
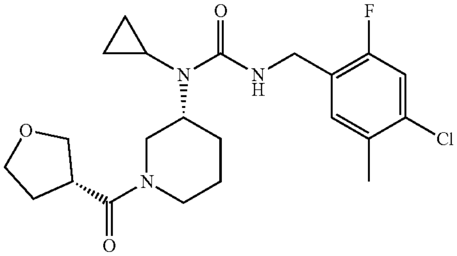 [SMILES: Cc1cc(CNC(=O)N(C2CC2)[C@@H]2CCCN(C(=O)[C@@H]3CCOC3)C2)c(F)cc1Cl]
TABLE 2-continued
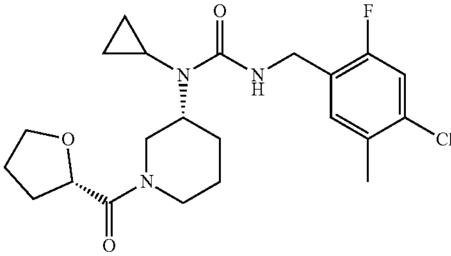
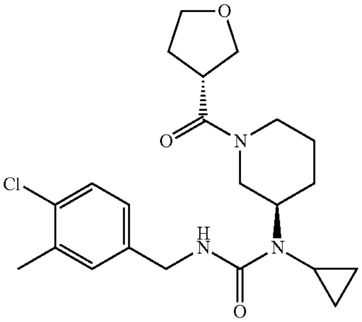 [SMILES: Cc1cc(CNC(=O)N(C2CC2)[C@@H]2CCCN(C(=O)[C@@H]3CCOC3)C2)ccc1Cl]
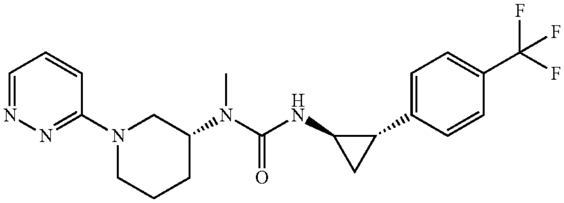 [SMILES: CN(C(=O)N[C@@H]1C[C@H]1c1ccc(C(F)(F)F)cc1)[C@@H]1CCCN(c2cccnn2)C1]
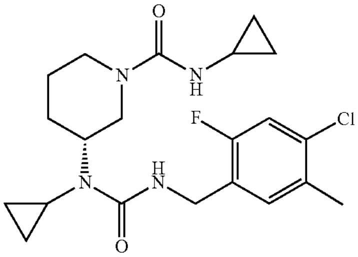 [SMILES: Cc1cc(CNC(=O)N(C2CC2)[C@@H]2CCCN(C(=O)NC3CC3)C2)c(F)cc1Cl]
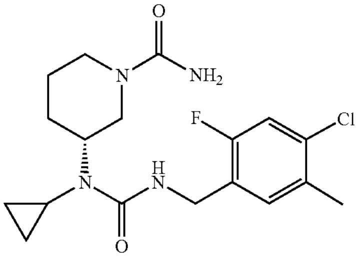 [SMILES: Cc1cc(CNC(=O)N(C2CC2)[C@@H]2CCCN(C(N)=O)C2)c(F)cc1Cl]
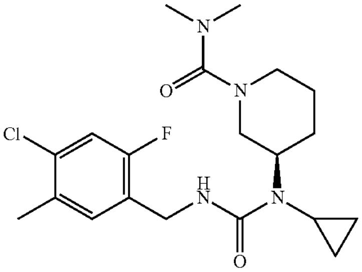 [SMILES: Cc1cc(CNC(=O)N(C2CC2)[C@@H]2CCCN(C(=O)N(C)C)C2)c(F)cc1Cl]

TABLE 2-continued
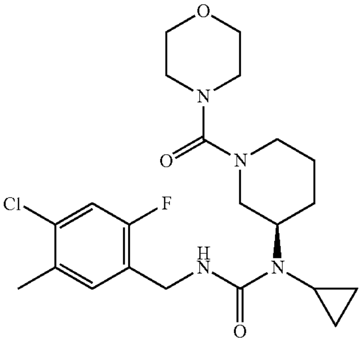 [SMILES: Cc1cc(CNC(=O)N(C2CC2)[C@@H]2CCCN(C(=O)N3CCOCC3)C2)c(F)cc1Cl]
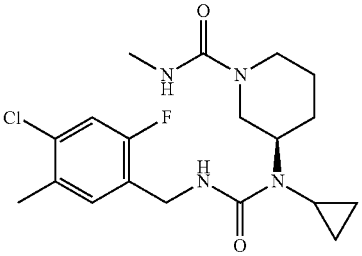 [SMILES: CNC(=O)N1CCC[C@@H](N(C(=O)NCc2cc(C)c(Cl)cc2F)C2CC2)C1]
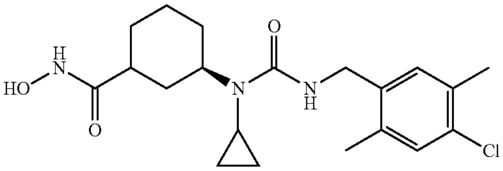 [SMILES: Cc1cc(CNC(=O)N(C2CC2)[C@@H]2CCCC(C(=O)NO)C2)c(C)cc1Cl]
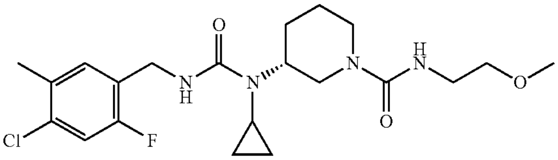
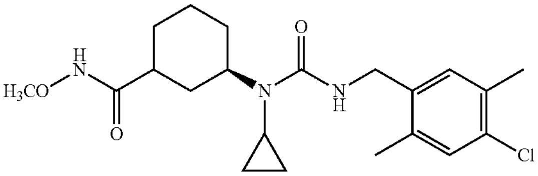 [SMILES: CONC(=O)C1CCC[C@@H](N(C(=O)NCc2cc(C)c(Cl)cc2C)C2CC2)C1]
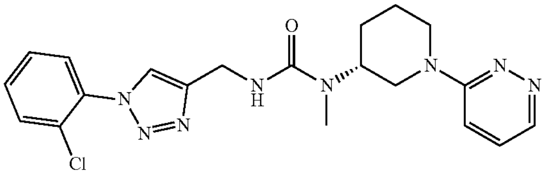 [SMILES: CN(C(=O)NCc1cn(-c2ccccc2Cl)nn1)[C@@H]1CCCN(c2cccnn2)C1]
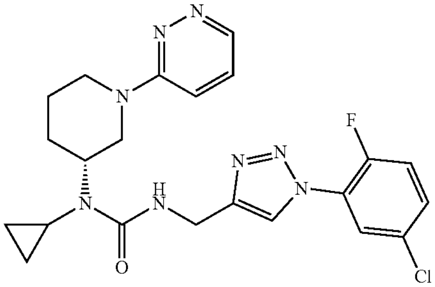 [SMILES: O=C(NCc1cn(-c2cc(Cl)ccc2F)nn1)N(C1CC1)[C@@H]1CCCN(c2cccnn2)C1]
TABLE 2-continued
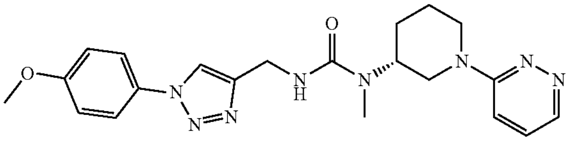 [SMILES: COc1ccc(-n2cc(CNC(=O)N(C)[C@@H]3CCCN(c4cccnn4)C3)nn2)cc1]
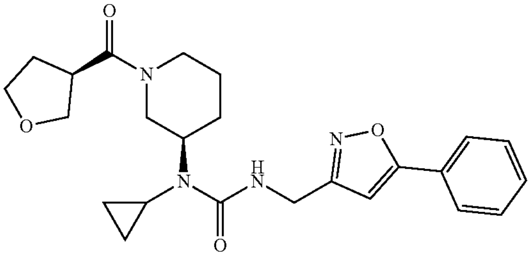 [SMILES: O=C([C@@H]1CCOC1)N1CCC[C@@H](N(C(=O)NCc2cc(-c3ccccc3)on2)C2CC2)C1]
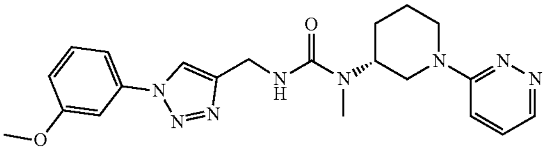
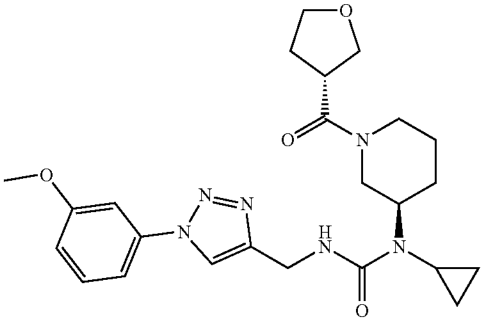 [SMILES: COc1cccc(-n2cc(CNC(=O)N(C3CC3)[C@@H]3CCCN(C(=O)[C@@H]4CCOC4)C3)nn2)c1]
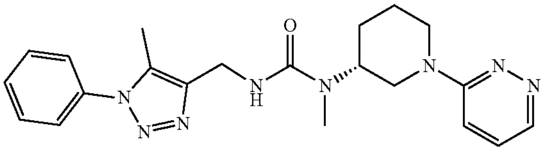
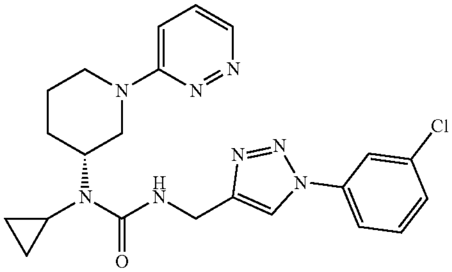 [SMILES: O=C(NCc1cn(-c2cccc(Cl)c2)nn1)N(C1CC1)[C@@H]1CCCN(c2cccnn2)C1]
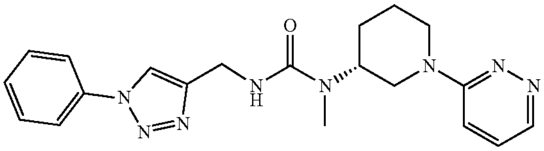

TABLE 2-continued
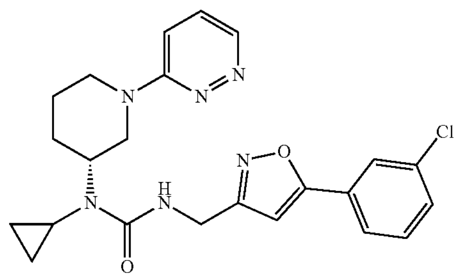 [SMILES: O=C(NCc1cc(-c2cccc(Cl)c2)on1)N(C1CC1)[C@@H]1CCCN(c2cccnn2)C1]
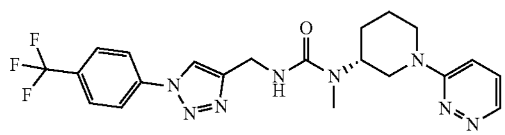
In some embodiments, the compound is selected from the following Table 3:
TABLE 3
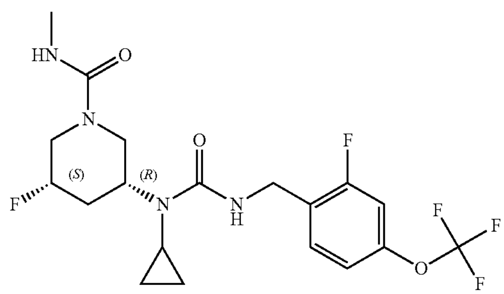
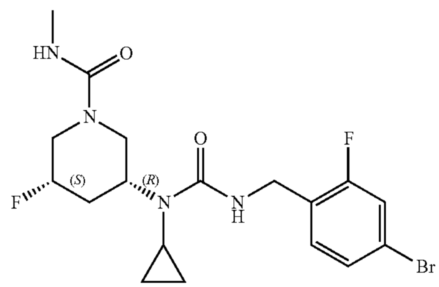
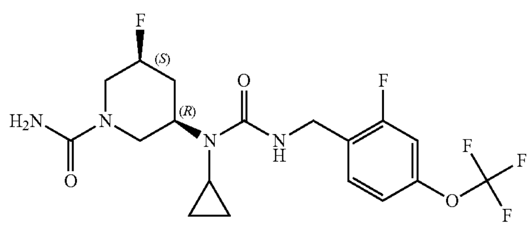
TABLE 3-continued
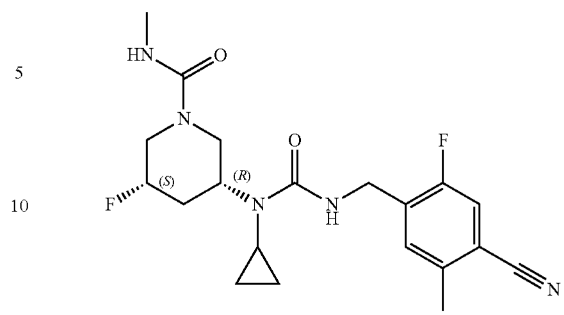
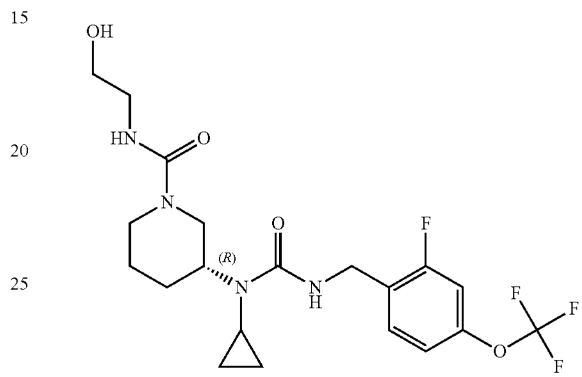
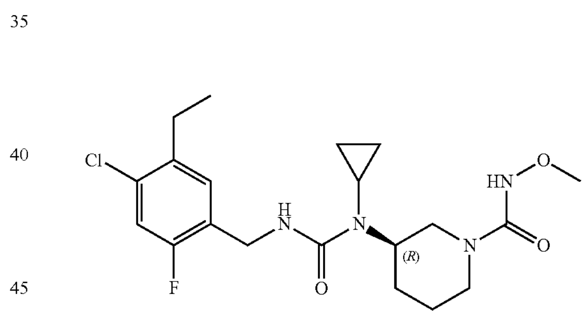
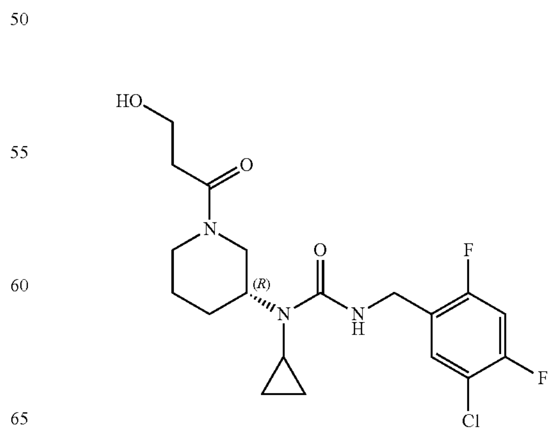

TABLE 3-continued
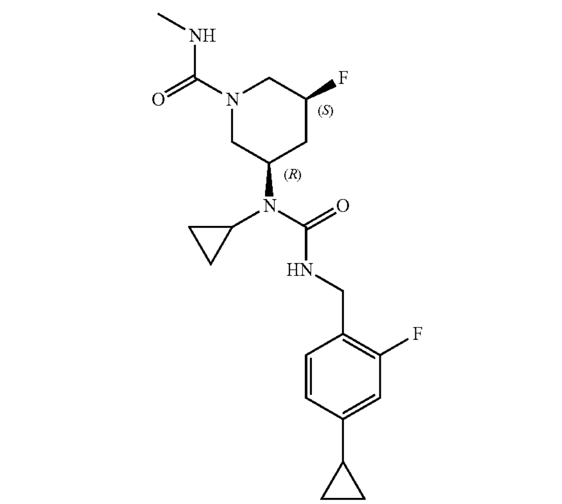
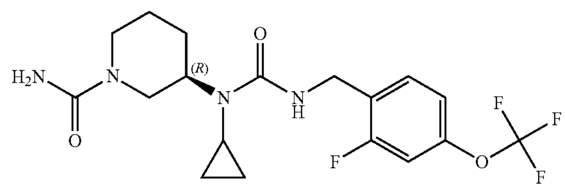
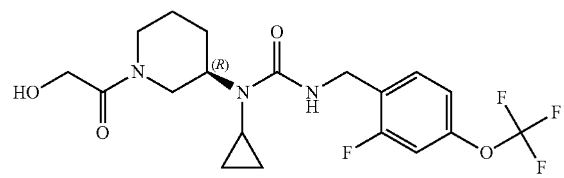
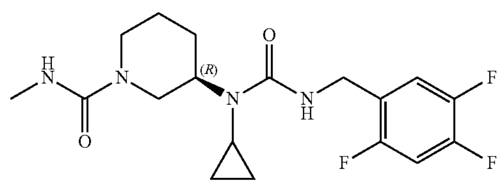
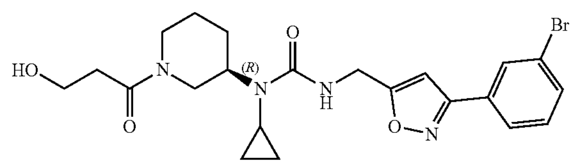
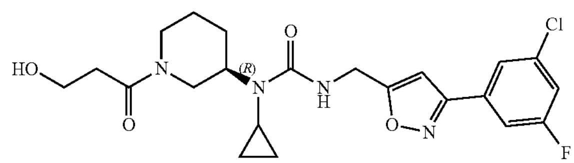
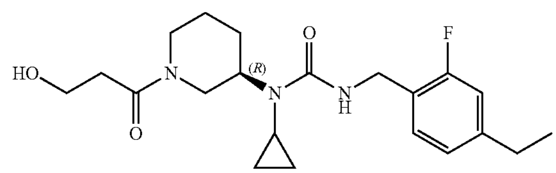
TABLE 3-continued
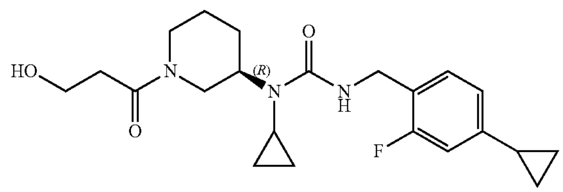
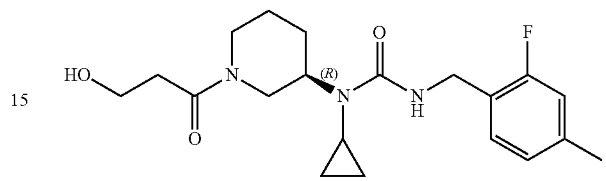
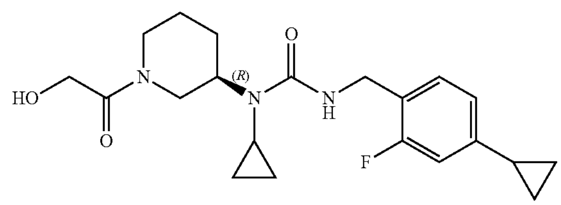
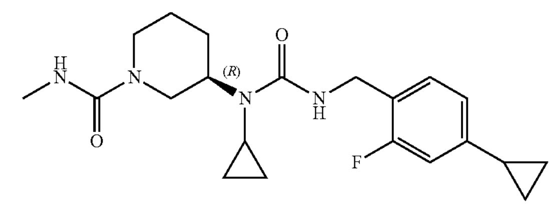
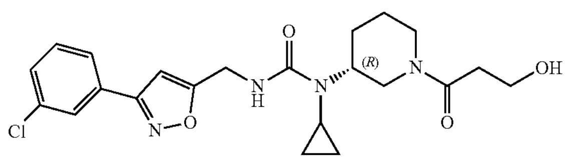
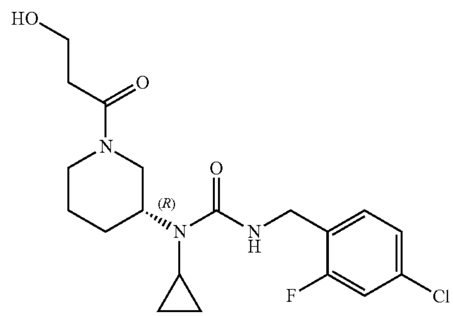
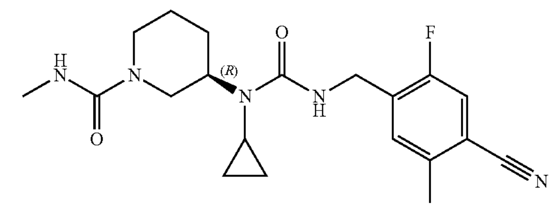

TABLE 3-continued
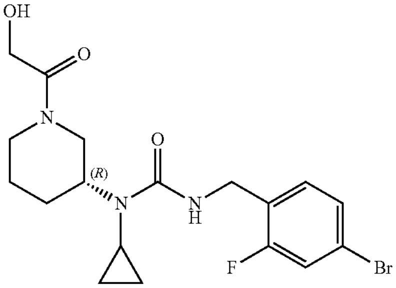
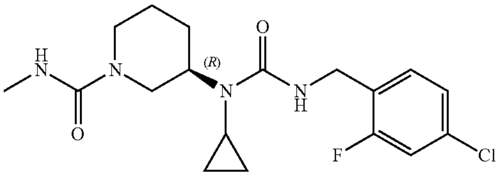
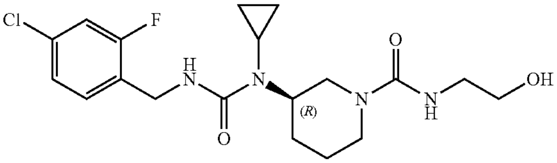
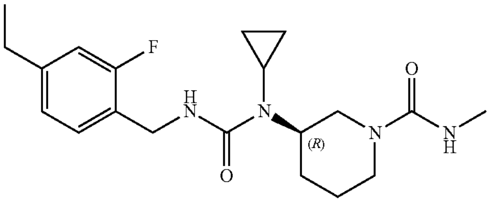
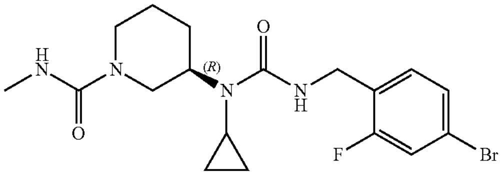
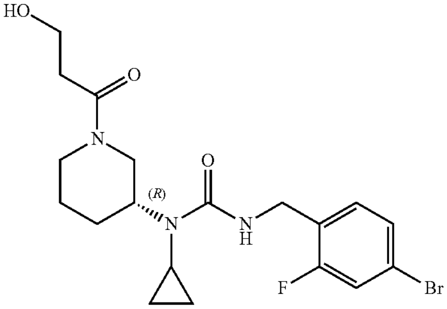
In some embodiments, the compound is selected from the following Table 4:
TABLE 4
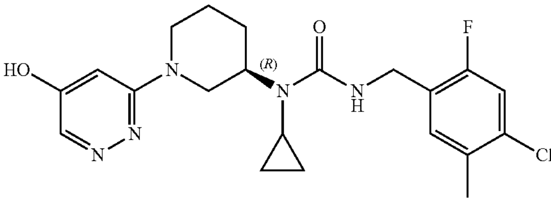
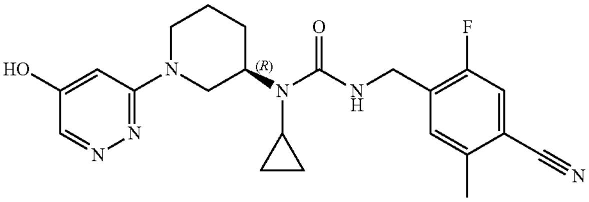
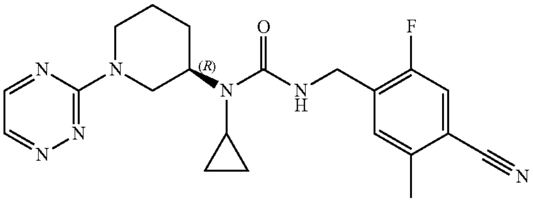
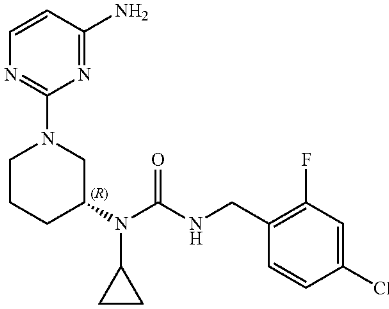
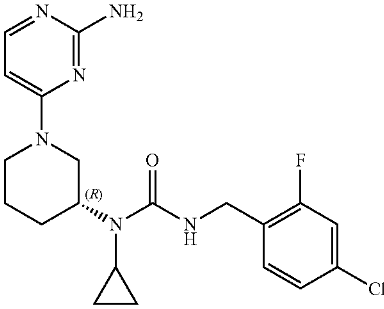
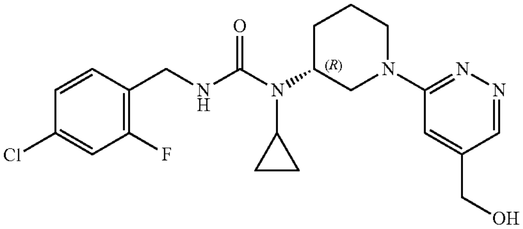

TABLE 4-continued
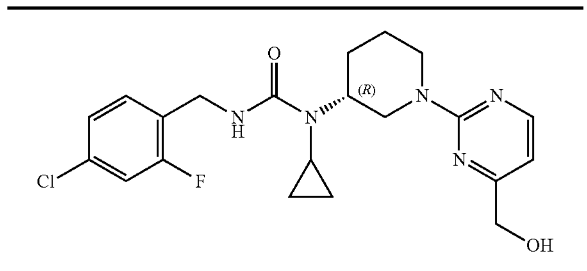
In some embodiments, the compound is selected from the following Table 5:
TABLE 5
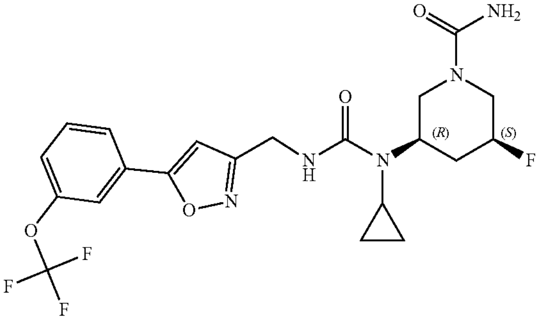
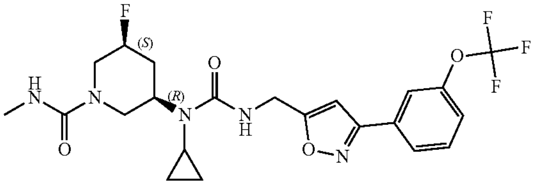
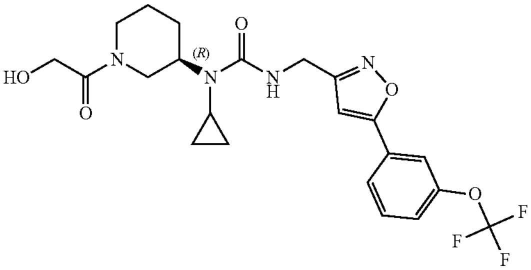
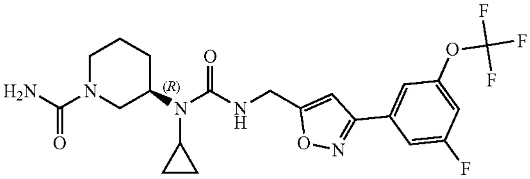
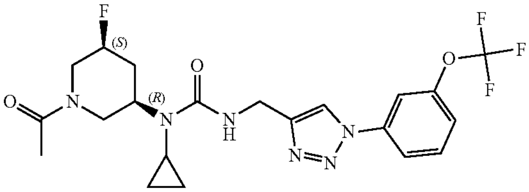
TABLE 5-continued
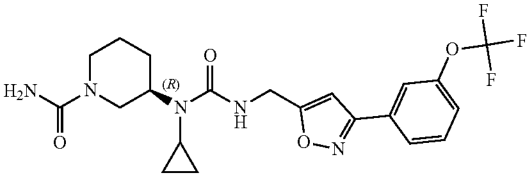
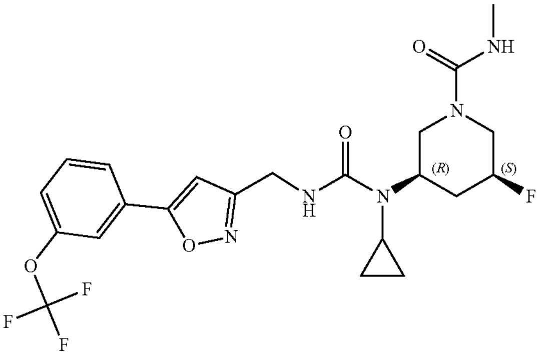
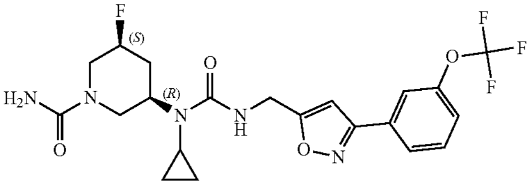
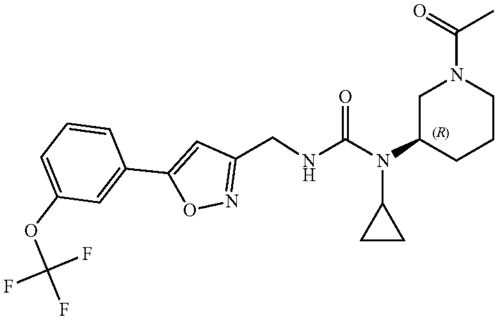
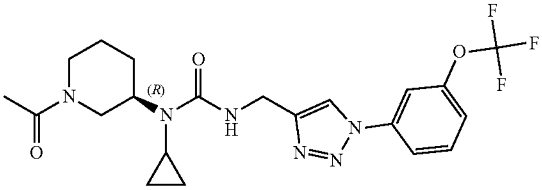
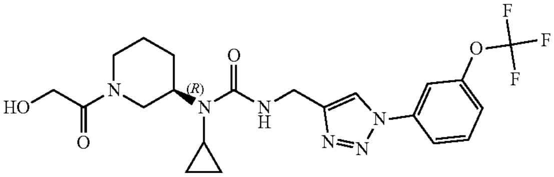
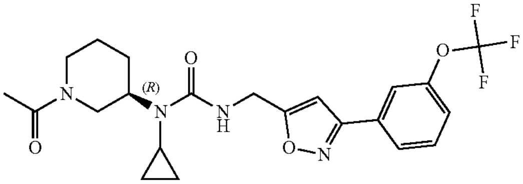

TABLE 5-continued

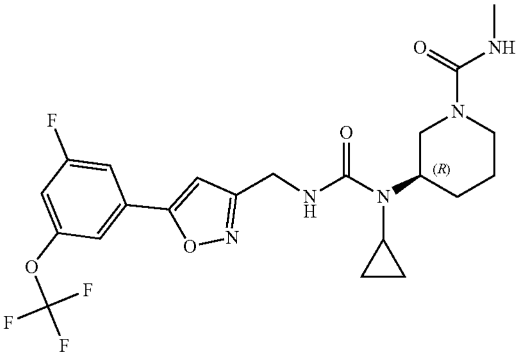

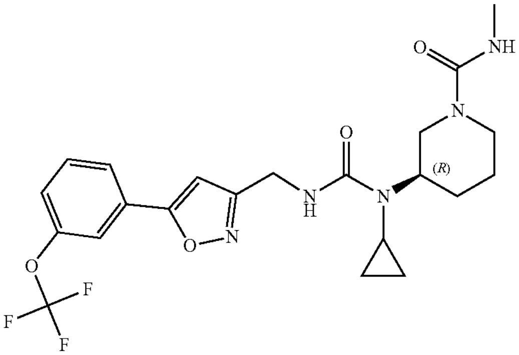

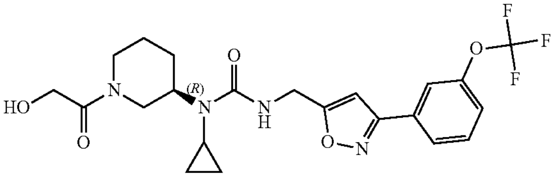

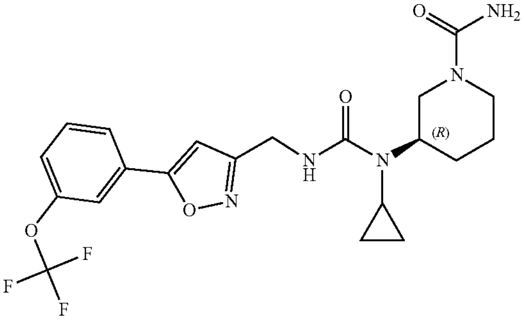

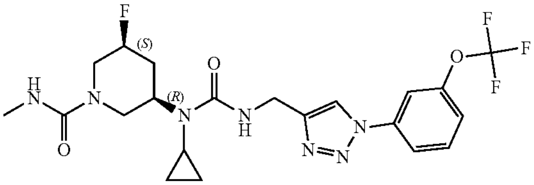

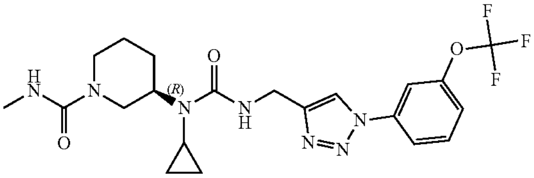

TABLE 5-continued

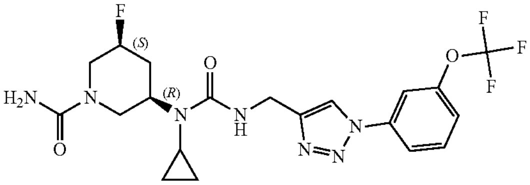

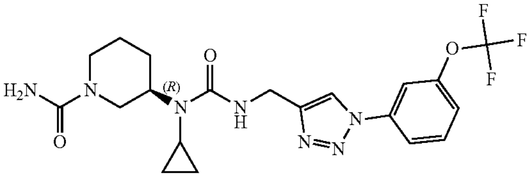

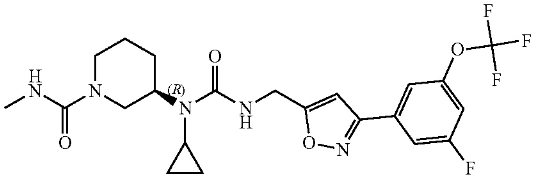

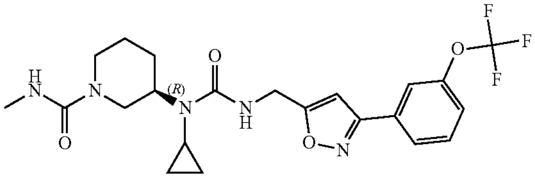

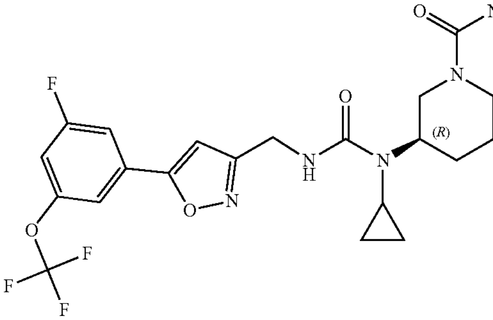

In some embodiments, the compounds are atropisomers. Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention. For example, in the case of variable $R^1$, the $(C_1-C_4)$alkyl or the —O—$(C_1-C_4)$alkyl can be suitably deuterated (e.g., —$CD_3$, —$OCD_3$).

Any compound of the invention can also be radiolabeled for the preparation of a radiopharmaceutical agent.

Methods of Treatment

One aspect of the invention provides compounds, compositions, and methods useful for treating or preventing a disease or disorder associated with abnormal levels of amino acids by modulation of SLC6A19 transport.

Another aspect of the invention relates to methods of modulating SLC6A19 transport in a subject in need thereof comprising administering to the subject an effective amount of a compound of Formula (I).

Another aspect of the invention relates to methods of treating or preventing a disease or disorder associated with a genetic defect in phenylalanine hydroxylase in a subject in need thereof comprising administering to the subject an effective amount of a compound of Formula (I).

In some embodiments, the invention relates to methods of treating or preventing phenylketonuria in a subject in need thereof comprising administering to the subject an effective amount of a compound of Formula (I).

In some embodiments, the invention relates to methods of treating or preventing hyperphenylalaninemia in a subject in need thereof comprising administering to the subject an effective amount of a compound of Formula (I).

In some embodiments, the compound reduces systemic phenylalanine levels in the subject.

In some embodiments, the invention relates to methods of treating or preventing tyrosinemia (Type I, II, or III) in a subject in need thereof comprising administering to the subject an effective amount of a compound of Formula (I).

In some embodiments, the compound reduces systemic glycine levels in the subject.

In some embodiments, the invention relates to methods of treating or preventing isovaleric acidemia, methylmalonic acidemia, propionic acidemia, maple syrup urine disease, DNAJC12 deficiency, urea cycle disorders, or hyperammonemia in a subject in need thereof comprising administering to the subject an effective amount of a compound of Formula (I).

In some embodiments of any one of the disclosed methods, the compound modulates SLC6A19 in the subject.

In some embodiments of any one of the disclosed methods, the compound inhibits SLC6A19 in the subject.

In some embodiments of any one of the disclosed methods, the compound modulates SLC6A19 transport in the subject.

In some embodiments of any one of the disclosed methods, the compound inhibits SLC6A19 transport in the subject.

In some embodiments, the compound reduces systemic levels of an amino acid in the subject.

In some embodiments of any one of the disclosed methods, wherein the subject is a mammal. In some embodiments of any one of the disclosed methods, the mammal is a human.

In some embodiments of any one of the disclosed methods, the compound of Formula (I) is defined as:

(I)

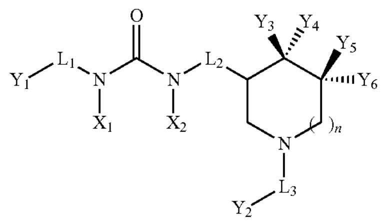

wherein:

n is 0, 1, or 2;

$L_1$ is absent or selected from -alkyl-, -hydroxyalkyl-, -cycloalkyl-, and -heteroaryl-$CH_2$—;

$L_2$ is absent or —$CH_2$—;

$L_3$ is absent or —C(O)—;

$X_1$ and $X_2$ are independently selected from —H, alkyl, haloalkyl, cycloalkyl, alkyl-cycloalkyl, and heterocyclyl; provided that $X_1$ and $X_2$ are not both —H;

$Y_1$ is selected from aryl and heteroaryl;

$Y_2$ is selected from alkyl, alkenyl, alkynyl, alkoxy, alkoxyalkyl, hydroxyalkyl, aralkyl, hetaralkyl, cycloalkyl, heterocyclyl, aryl, heteroaryl, —NH($Y_2$'), and —N($Y_2$")$_2$;

$Y_2$' is selected from —H, —OH, alkyl, alkoxy, alkoxyalkyl, and cycloalkyl;

each $Y_2$" is alkyl, or both instances taken together with the nitrogen atom to which they are bonded form a 5 or 6 membered heterocyclyl;

$Y_3$, $Y_4$, $Y_5$, and $Y_6$ are independently selected from —H, —OH, halide, alkyl, haloalkyl, and alkoxy; provided that $Y_3$ and $Y_4$ or $Y_5$ and $Y_6$ are not both —OH, or a pharmaceutically acceptable salt thereof.

In some embodiments of any one of the disclosed methods, the compound is selected from:

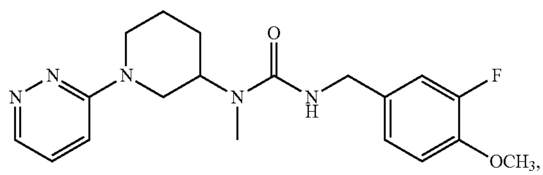

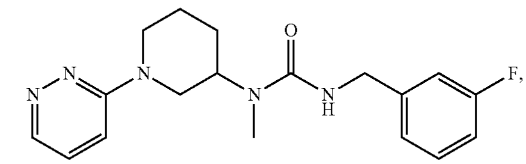

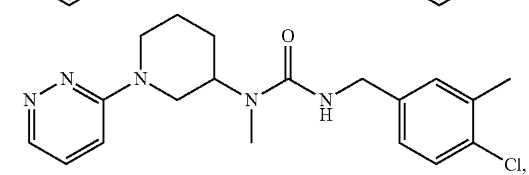

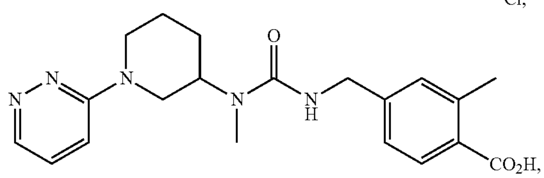

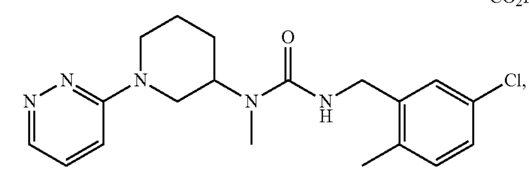

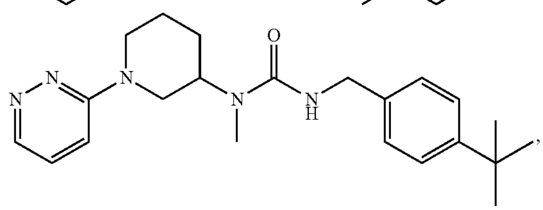

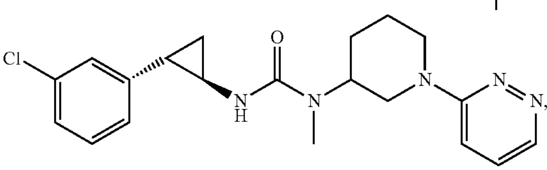

-continued

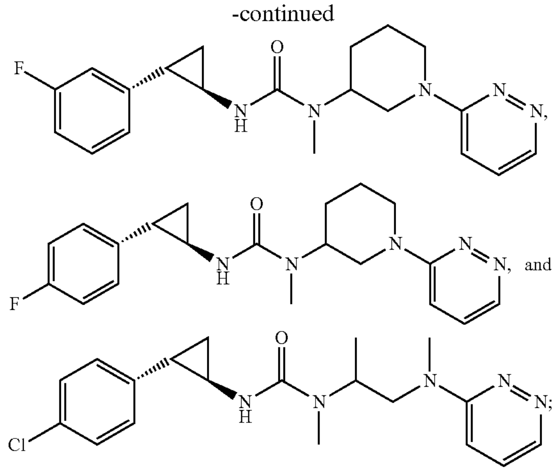

or a pharmaceutically acceptable salt thereof.

In some embodiments of any one of the disclosed methods, the compound is selected from:

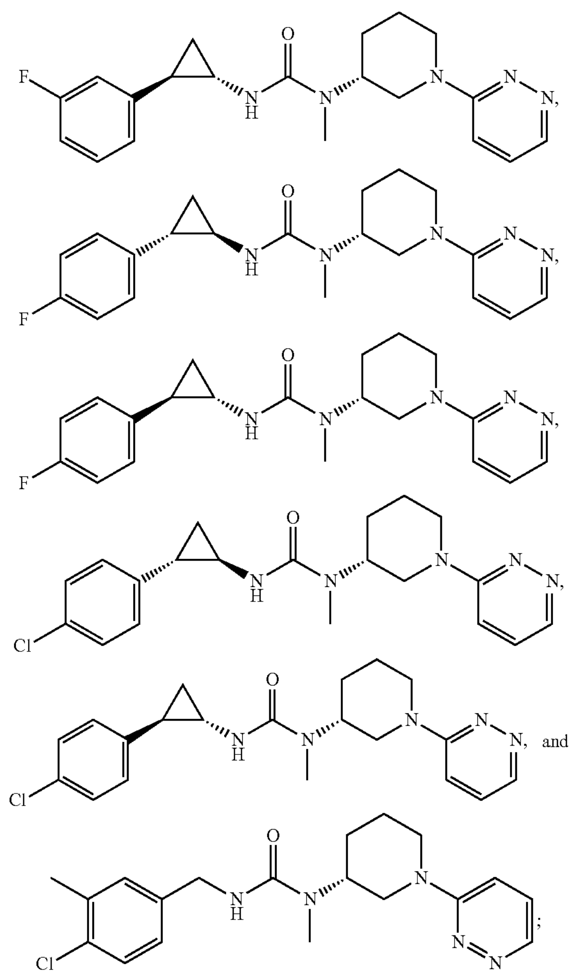

or a pharmaceutically acceptable salt thereof.

In some embodiments of any one of the disclosed methods, the compound is selected from the structure of any one of the compounds recited in Table 1.

In some embodiments of any one of the disclosed methods, the compound is selected from the structure of any one of the compounds recited in Table 2.

In some embodiments of any one of the disclosed methods, the compound is selected from the structure of any one of the compounds recited in Table 3.

In some embodiments of any one of the disclosed methods, the compound is selected from the structure of any one of the compounds recited in Table 4.

In some embodiments of any one of the disclosed methods, the compound is selected from the structure of any one of the compounds recited in Table 5.

Pharmaceutical Compositions, Routes of Administration, and Dosing

In certain embodiments, the invention is directed to a pharmaceutical composition, comprising a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of ischemia-reperfusion injury.

Pharmaceutical compositions of the invention can be prepared by combining one or more compounds of the invention with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

In certain embodiments, intravenous administration of a compound may typically be from 0.1 mg/kg/day to 20 mg/kg/day. In one embodiment, intravenous administration of a compound may typically be from 0.1 mg/kg/day to 2 mg/kg/day. In one embodiment, intravenous administration of a compound may typically be from 0.5 mg/kg/day to 5 mg/kg/day. In one embodiment, intravenous administration of a compound may typically be from 1 mg/kg/day to 20 mg/kg/day. In one embodiment, intravenous administration of a compound may typically be from 1 mg/kg/day to 10 mg/kg/day.

Generally, daily oral doses of a compound will be, for human subjects, from about 0.01 milligrams/kg per day to 1000 milligrams/kg per day. It is expected that oral doses in the range of 0.5 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the invention can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. For pharmaceutical usage, as indicated above, polyethylene glycol moieties are suitable.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds disclosed herein (or salts thereof). The compound is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Cin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise a compound of the invention (or derivative) dissolved in water at a concentration of about 0.1 to 25 mg of biologically active compound of the invention per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (m), most preferably 0.5 to 5 m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990).

The compound of the invention and optionally other therapeutics may be administered per se (neat) or in the form of a pharmaceutically acceptable salt or cocrystal. When used in medicine the salts or cocrystals should be pharmaceutically acceptable, but non-pharmaceutically acceptable salts or cocrystals may conveniently be used to prepare pharmaceutically acceptable salts or cocrystals thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to a compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles.

The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

The invention is further described in the following examples, which do not limit the scope of the invention described in the claims.

Example 1: SLC6A19 Isoleucine Transport Assay

Cell Line Generation and Maintenance

The Flp-In™ T-REx™ 293 cell line was purchased from Thermo Fisher Scientific. The line was used to generate a stable cell line inducibly expressing human SLC6A19 with a C-terminal V5 tag and stably expressing human TMEM27 (also known as Collectrin) with a C-terminal myc-DDK tag. The stable cell line was generated by transfecting SLC6A19- and TMEM27-encoding plasmids using standard protocols, followed by antibiotic selection. Stable cells were maintained in DMEM/F12 supplemented with Glutamax, 10% fetal bovine serum, 100 U/mL penicillin, 100 μg/mL streptomycin, 200 μg/mL hygromycin, 10 μg/mL blasticidin and 300 μg/mL neomycin (Thermo Fisher).

Assay: Isoleucine Transport Assay in 96-Well Format

Stable cell lines were seeded at a density of 35,000 cells per well in a poly-D-lysine coated 96-well cell culture-treated plate on day 0. On day 1 the expression of SLC6A19 was induced by dispensing tetracycline at a final concentration of 1 ug/mL using a Tecan D300e digital dispenser. On day 2 the transport assay was run. Media was removed from the plate using the GentleSpin setting of a Centrifugal Blue Washer (Blue Cat Bio) and cells were washed with 175 uL live cell imaging solution (Thermo Fisher) using the Blue Washer. Following washing, cells were treated with 70 uL of either DMSO, positive control or compound, diluted in Krebs buffer (140 mM NaCl, 4.7 mM KCl, 2.5 mM $CaCl_2$), 1.2 mM $MgCl_2$, 11 mM HEPES, 10 mM Glucose, pH 7.4) at room temperature. After 20-60 minutes 30 uL of a 3.3 mM solution of 13C6,15N-L-isoleucine (Cambridge Isotope Laboratories) was added. After 20 min incubation with the isoleucine substrate at room temperature cells were washed with 175 uL live cell imaging solution using the Blue Washer. Cells were then lysed in 150 uL of 15 uM D-Leucine-d10 (CDN Isotopes) in ultrapure water. Plates were put on a shaker at 700 rpm for a minimum of 40 minutes to facilitate lysis. Following lysis, a standard dilution curve of 13C6,15N-L-isoleucine was added to wells containing lysates of untreated cells. Plates were returned to the shaker for a minimum of 2 minutes to ensure proper mixing of the standard curve. Plates were then centrifuged for 5 min at 4,000 rpm to pellet cellular debris and precipitate. Supernatants were diluted 1:10 in acetonitrile+0.1% formic acid in polypropylene plates.

Assay: Isoleucine Transport Assay in 384-Well Format

On day 0, stable cell lines were seeded at a density of 20,000 cells per well in a poly-D-lysine coated 384-well cell culture-treated plate in media containing 1 ug/mL tetracycline using a Viaflo 384-well pipette. Transport assays were run the following day (day 1). Media was removed from the plate using the GentleSpin setting of a Centrifugal Blue Washer (Blue Cat Bio) and cells were washed with 80 uL live cell imaging solution (Thermo Fisher) using the Blue Washer. Following washing, cells were treated with 20 uL of either DMSO, positive control or compound, diluted in Krebs buffer (140 mM NaCl, 4.7 mM KCl, 2.5 mM $CaCl_2$), 1.2 mM $MgCl_2$, 11 mM HEPES, 10 mM Glucose, pH 7.4) using a TECAN liquid handler. After 20-60 minutes incubation at room temperature 8.6 uL of a 3.3 mM solution of 13C6,15N-L-isoleucine (Cambridge Isotope Laboratories) was added. After 20 min incubation with the isoleucine substrate at room temperature cells were washed with 80 uL live cell imaging solution using the Blue Washer. Cells were then lysed in 80 uL of 15 uM D-Leucine-d10 (CDN Isotopes) in ultrapure water. Plates were put on a shaker at 700 rpm for a minimum of 2 hours to facilitate lysis. Following lysis, a standard dilution curve of 13C6,15N-L-isoleucine was added to wells containing lysates of untreated cells. Plates were returned to the shaker for a minimum of 5 minutes to ensure proper mixing of the standard curve. Plates were then centrifuged for 10 min at 4,000 rpm to pellet cellular debris and precipitate. Supernatants were diluted 1:10 in acetonitrile+0.1% formic acid in polypropylene plates.

13C6,15N-L-isoleucine analysis was performed using a RapidFire365-QTOF 6545 (Agilent). Quantitative sample analysis utilizes automated solid-phase extraction (HILIC H6 cartridge) prior to mass spec injection. Samples were loaded using 95% acetonitrile, 0.1% formic acid and eluted from the cartridge with 5% acetonitrile, 0.1% formic acid directly for ESI-MS (electrospray ionization) analysis. Quantification of the analytes were performed using Agilent Masshunter Quant software from the high-resolution full scan data.

General Procedure A:

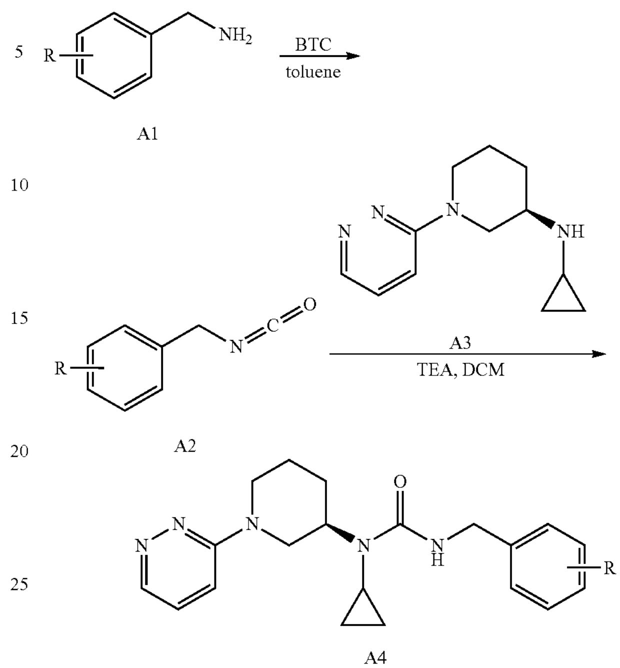

Step 1: Synthesis of Compound A2

To a solution of compound A1 (1 eq.) in toluene was added a solution of bistrichloromethyl carbonate (BTC) (0.5 eq.) in toluene at 0° C. dropwise under $N_2$ atmosphere. The resulting mixture was stirred at r.t. for 15 mins and then the mixture was heated to 130° C. and stirred for 2 hours under $N_2$ atmosphere. After cooling, the mixture was concentrated to dryness under reduced pressure to give crude compound A2, which was used at the next step directly without further purification.

Step 2: Synthesis of Compound A4

To a mixture of compound A3 (1 eq.) and TEA (3 eq.) in anhydrous DCM was added a solution of compound A2 (1 eq.) in anhydrous DCM at 0° C. dropwise under $N_2$ atmosphere. The resulting mixture was stirred at 0° C. for 1 hour under $N_2$ atmosphere. Then the mixture was diluted with water and extracted with EtOAc twice. The combined organic layer was separated, washed with brine, dried over anhydrous $Na_2SO_4$, filtered and concentrated to dryness. The residue was purified via flash column chromatography (eluted with DCM/MeOH) to give compound A4.

Example 2. Synthesis of 3-[(4-chloro-2-fluoro-5-methylphenyl)methyl]-1-cyclopropyl-1-[(3R)-1-(pyridazin-3-yl)piperidin-3-yl]urea

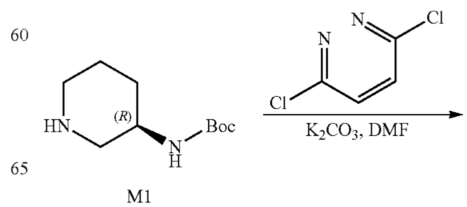

-continued

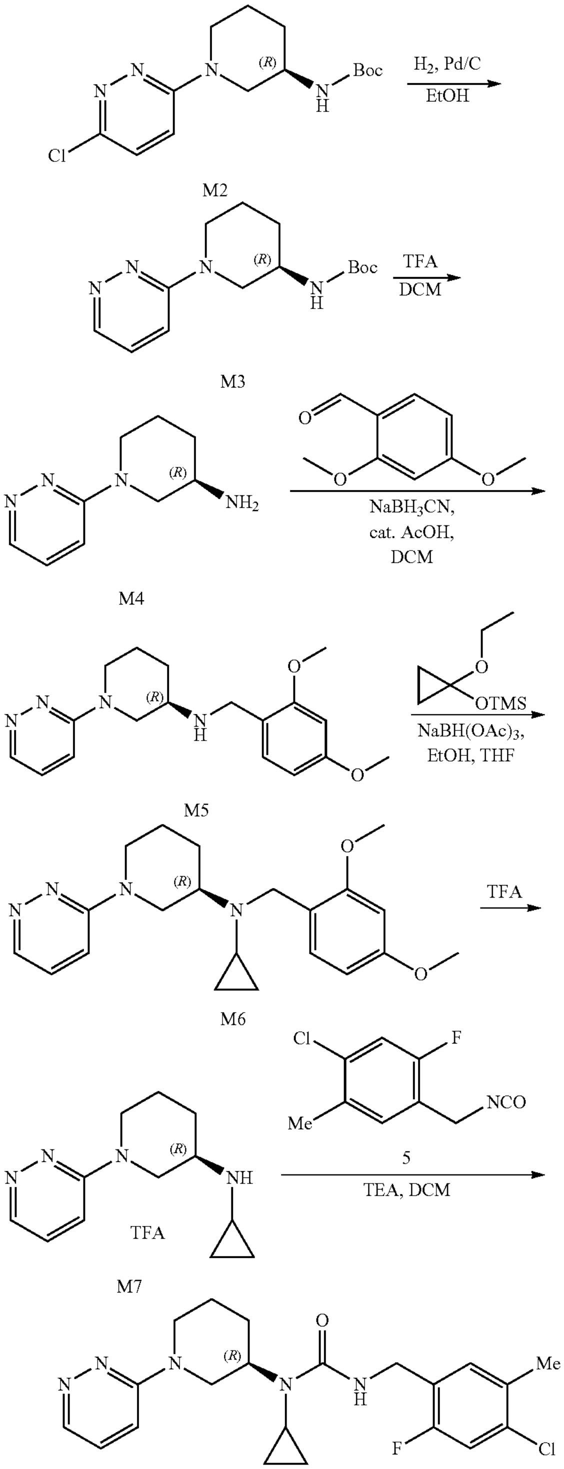

M2

M3

M4

M5

M6

TFA

M7

Example 2

Step 1: Synthesis of M2

To a mixture of M1 (10 g, 49.93 mmol) and $K_2CO_3$ (20.7 g, 149.8 mmol) in DMF (200 mL) was added 3,6-dichloropyridazine (7.44 g, 49.93 mmol). The resulting mixture was stirred at 80° C. for 16 hrs. After cooling, the resulting mixture was poured into water (800 mL). The precipitated solid was collected by filtration, washed with water (100 mL) and then dissolved with EtOAc, the organic layer was dried over $Na_2SO_4$, separated and concentrated under reduced pressure to give M2 (12 g, 38.36 mmol, 76.83% yield) as a yellow solid. LC/MS (ESI) m/z: 313 $(M+H)^+$.

Step 2: Synthesis of M3

To a solution of M2 (12 g, 38.36 mmol) in MeOH (200 mL) were added Pd/C (4.0 g, 10%). The resulting mixture was stirred at room temperature for 3 hrs under hydrogen atmosphere. Then the mixture was filtered, the filtrate was concentrated under reduced pressure to give M3 (10 g, 35.93 mmol, 93.63% yield) as yellow solid. LC/MS (ESI) m/z: 279 $(M+H)^+$.

Step 3: Synthesis of M4

To a solution of compound M3 (10 g, 35.93 mmol) in DCM (60 mL) were added TFA (60 mL). The resulting mixture was stirred at room temperature for 4 hrs. The resulting mixture was concentrated to dryness under reduced pressure. The residue was diluted with MeOH and added with $NaHCO_3$. The mixture was stirred at r.t. for 40 mins to switch pH=8-9. Then the mixture was filtered, the filtrate was concentrated under reduced pressure to give M4 (6 g, 33.7 mmol, 93.7% yield) as yellow oil. LC/MS (ESI) m/z: 179 $(M+H)^+$.

Step 4: Synthesis of M5

To a mixture of compound M4 (5.8 g, 32.54 mmol) and 2,4-dimethoxybenzaldehyde (5.41 g, 32.54 mmol) in DCM (100 mL) was added AcOH (5.86 g, 97.62 mmol). The mixture was stirred for 1 hr at room temperature. Then $NaBH(OAc)_3$ (20.7 g, 97.62 mmol) was added into the above mixture. The resulting mixture was stirred for 3 hrs. Then the mixture was concentrated under reduced pressure. The residue was diluted with EtOAc and washed with aq. $NaHCO_3$ to pH=8. The organic layer was washed with brine, dried over anhydrous $Na_2SO_4$ and concentrated to dryness. The crude product was purified by column chromatography on silica gel (eluting with 5% MeOH in DCM) to give M5 (5 g, 13.7 mmol, 42.10% yield) as yellow solid. LC/MS (ESI) m/z: 329 $(M+H)^+$.

Step 5: Synthesis of M6

To a mixture of M5 (800 mg, 2.436 mmol) and (1-ethoxycyclopropoxy)trimethylsilane (1.06 g, 6.09 mmol) in EtOH (10 mL) and THF (20 mL) was added AcOH (2.19 g, 36.54 mmol) and $NaBH_3CN$ (538 mg, 8.526 mmol). The resulting mixture was stirred for 16 hrs at 80° C. After cooling, the resulting mixture was concentrated under reduced pressure. The residue was diluted with EtOAc and washed with water and brine. The organic layer was dried over anhydrous $Na_2SO_4$ and concentrated to dryness. The crude product was purified by column chromatography on silica (eluting with 4% MeOH in DCM) to afford M6 (560 mg, 1.52 mmol, 62.40% yield) as yellow solid. LC/MS (ESI) m/z: 369 $(M+H)^+$.

Synthesis of M7

Compound M6 (560 mg, 1.520 mmol) was added into TFA (18 mL) and the resulting mixture was stirred at 80° C. for 4 hrs. After cooling, the mixture was concentrated under reduced pressure to give crude M7 (274 mg, 0.825 mmol, 54.26%) as TFA salt. LC/MS (ESI) m/z: 219 $(M+H)^+$.

3-[(4-Chloro-2-fluoro-5-methylphenyl)methyl]-1-cyclopropyl-1-[(3R)-1-(pyridazin-3-yl)piperidin-3-yl]urea To a mixture of M7 (274 mg, 0.824 mmol) in DCM (10 mL) were added TEA (251 mg, 2.473 mmol). After stirring at r.t. for 30 mins, a solution of 2 (160 mg, 0.824 mmol) in DCM (2 mL) was added into the above mixture at 0° C. The resulting mixture was stirred for 30 mins at room temperature. Then the mixture was concentrated under reduced pressure to dryness. The crude product was purified by column chromatography on silica gel (eluting with 5% MeOH in DCM) to give Example 2 (103 mg, 0.247 mmol, 30.0% yield) as light-yellow solid. LC/MS (ESI) m/z: 418 $(M+H)^+$.

$^1$H NMR (400 MHz, DMSO-d6) δ 8.50 (dd, J=4.4, 1.0 Hz, 1H), 7.36-7.30 (m, 2H), 7.28-7.21 (m, 2H), 6.89 (t, J=5.8 Hz, 1H), 4.41-4.25 (m, 4H), 3.68-3.60 (m, 1H), 3.23-3.16 (m, 1H), 2.81-2.67 (m, 1H), 2.50-2.44 (m, 1H), 2.29 (s, 3H), 2.15-2.07 (m, 1H), 1.91-1.70 (m, 2H), 1.54-1.42 (m, 1H), 0.93-0.86 (m, 2H), 0.74-0.62 (m, 2H). $^{19}$F NMR (400 MHz, DMSO-d6) δ −121.05 (s).

The compounds in the table below were prepared from the appropriate starting materials, described above or commercially available, using the above general procedure A and intermediate M7 in Example 2.

| Example | Structure and name | Data |
|---|---|---|
| 3 | 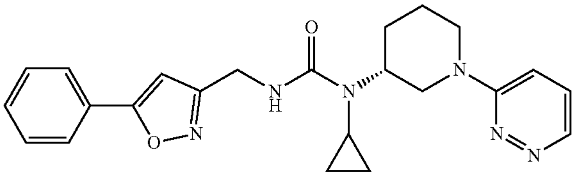 [SMILES: O=C(NCc1cc(-c2ccccc2)on1)N(C1CC1)[C@@H]1CCCN(c2cccnn2)C1] 1-cyclopropyl-3-[(3-phenyl-1,2-oxazol-5-yl)methyl]-1-[(3R)-1-(pyridazin-3-yl)piperidin-3-yl]urea | LC-MS: m/z 419 (M + H). 1H NMR (400 MHz, MeOD) δ 8.42 (d, J = 3.9 Hz, 1H), 7.87-7.77 (m, 2H), 7.52-7.43 (m, 3H), 7.36 (dd, J = 9.4, 4.4 Hz, 1H), 7.28 (dd, J = 9.4, 1.2 Hz, 1H), 6.67 (s, 1H), 4.56 (s, 2H), 4.45-4.31 (m, 2H), 3.88-3.71(m, 1H), 3.34(d, J = 12.5 Hz, 1H), 2.89 (td, J = 13.0,2.7 Hz, 1H), 2.62-2.53(m, 1H), 2.27(dd, J = 12.6, 4.1Hz, 1H), 1.98(d, J = 11.5 Hz, 1H), 1.86 (d, J = 13.8 Hz, 1H), 1.63 (d, J = 13.2 Hz, 1H), 1.01-0.93 (m, 2H), 0.84 (dd, J = 8.0, 4.5 Hz, 2H). |
| 4 | 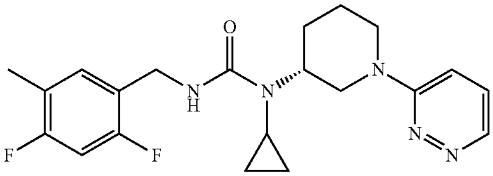 [SMILES: Cc1cc(CNC(=O)N(C2CC2)[C@@H]2CCCN(c3cccnn3)C2)c(F)cc1F] 1-cyclopropyl-3-[(2, 4-difluoro-5-methylphenyl)methyl]-1-[(3R)-1-(pyridazin-3-yl)piperidin-3-yl]urea | LC-MS: m/z 402.2 (M + H). 1H NMR (400 MHz, MeOD) δ 8.42 (dd, J = 4.4, 1.2 Hz, 1H), 7.36 (dd, J = 9.4, 4.4 Hz, 1H), 7.28 (dd, J =9.4,1.2 Hz, 1H), 7.21(t, J = 8.5 Hz, 1H), 6.84 (t, J = 9.9 Hz, 1H), 4.43-4.30(m, 4H), 3.77 (tt, J = 11.8, 3.9 Hz, 1H), 3.34 (s, 1H), 2.88 (td, J = 13.0, 2.7 Hz, 1H), 2.60-2.49 (m, 1H), 2.31-2.23 (m, 1H), 2.22 (s, 3H), 1.96 (d, J = 12.3 Hz, 1H), 1.90-1.81 (m, 1H), 1.70-1.54 (m, 1H), 0.99-0.91 (m, 2H), 0.78 (dd, J = 6.6, 4.1 Hz, 2H). |
| 5 | 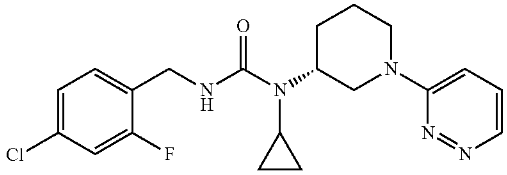 [SMILES: O=C(NCc1ccc(Cl)cc1F)N(C1CC1)[C@@H]1CCCN(c2cccnn2)C1] 3-[(4-chloro-2-fluorophenyl)methyl]-1-cyclopropyl-1-[(3R)-1-(pyridazin-3-yl)piperidin-3-yl]urea | LC-MS: m/z 404.1 (M + H). 1H NMR (400 MHz, MeOD) δ 8.42 (dd, J = 4.4, 1.2 Hz, 1H), 7.38-7.31 (m, 2H), 7.27 (dd, J = 9.4, 1.2 Hz, 1H), 7.20-7.14 (m, 2H), 4.42 (s, 2H), 4.41-4.30 (m, 2H), 3.76 (ddd, J = 15.8, 7.8, 3.9 Hz, 1H), 3.28 (s, 1H), 2.88 (td, J = 13.1, 2.7 Hz, 1H), 2.62-2.50 (m, 1H), 2.25 (qd, J = 12.5, 4.1 Hz, 1H), 2.03-1.78 (m, 2H), 1.71-1.54 (m, 1H), 1.00-0.91 (m, 2H), 0.83-0.76 (m, 2H). |
| 6 | 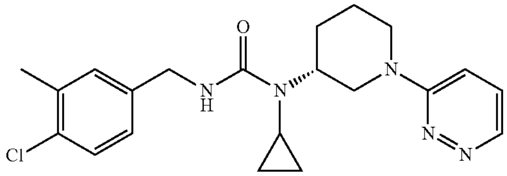 [SMILES: Cc1cc(CNC(=O)N(C2CC2)[C@@H]2CCCN(c3cccnn3)C2)ccc1Cl] 3-[(4-chloro-3-methylphenyl)methyl]-1-cyclopropyl-1-[(3R)-1-(pyridazin-3-yl)piperidin-3-yl]urea | LC-MS: m/z 400.2 (M + H). 1H NMR (400 MHz, MeOD) δ 8.43 (d, J = 3.6 Hz, 1H), 7.36 (dd, J = 9.6, 4.4 Hz, 1H), 7.28(d, J = 8.4 Hz, 2H), 7.22(s, 1H), 7.11 (d, J = 8.4 Hz, 1H), 6.93(t, J = 5.6 Hz, 1H), 4.40 (d, J = 13.6 Hz, 1H), 4.34(d, J = 6.0 Hz, 3H), 3.77(tt, J = 11.6, 4.0 Hz, 1H), 3.35 (s, 1H), 2.88 (td, J = 13.2, 2.8 Hz, 1H), 2.59-2.48 (m, 1H), 2.35 (s, 3H), 2.26 (qd, J = 12.4, 4.0 Hz, 1H), 1.96 (d, J = 12.0 Hz, 1H), 1.86 (d, J = 13.2 Hz, 1H), 1.68-1.56 (m, 1H), 0.94 (dd, J = 8.4, 5.6 Hz, 2H), 0.83-0.75 (m, 2H). |

Examples 7-127 The compounds in the table below were prepared from the appropriate starting materials, described above or commercially available, using the above general procedure and (R)—N-methyl-1-(pyridazin-3-yl)piperidin-3-amine (A3), or by using intermediate M7 from Example 2.

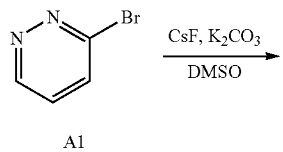

A1

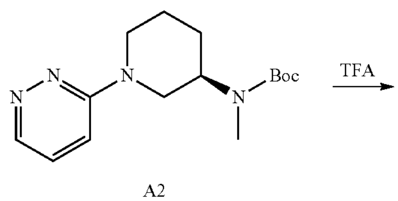

A2

-continued

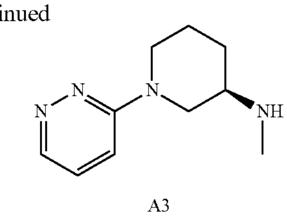

A3 tert-Butyl N-methyl-N-[(3R)-3-piperidyl]carbamate (2.14 g, 10 mmol), 3-bromopyridazine (2.38 g, 15.00 mmol), cesium Fluoride (151.90 mg, 1.00 mmol, 36.87 uL), and potassium carbonate (3.46 g, 25.00 mmol, 1.51 mL) were dissolved in DMSO (100 mL) and heated to 150 C overnight. The reaction mixture was then cooled to room temperature, poured into 600 mL of water, and extracted with ethyl acetate (3×200 mL). The combined organic layers were washed with water (1×200 mL) and brine (1×200 ml), dried with anhydrous sodium sulfate and concentrated under reduced pressure to provide a crude product which was purified by flash column chromatography (ethyl acetate: heptane, 0:100 to 40:60) to provide A2, tert-butyl N-methyl-N-[(3R)-1-pyridazin-3-yl-3-piperidyl]carbamate (1.57 g, 5.37 mmol, 53.70% yield). A2 (1.57 g, 5.37 mmol) was dissolved in DCM (4.2 mL) and TFA (6.12 g, 53.70 mmol, 4.14 mL) was added. The reaction mixture was stirred for four hours. The reaction mixture was then concentrated under reduced pressure by rotary evaporation. The crude residue was dissolved in ethyl acetate, washed with 1 M NaOH, brine and concentrated to provide A3, (R)—N-methyl-1-(pyridazin-3-yl)piperidin-3-amine (450 mg, 2.34 mmol, 43.59% yield) which was used without further purification.

| Example | Structure and name | Data |
|---|---|---|
| 7 | 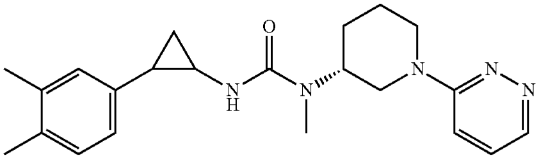 [SMILES: Cc1ccc(C2CC2NC(=O)N(C)[C@@H]2CCCN(c3cccnn3)C2)cc1C] 3-[2-(3,4-dimethylphenyl)cyclopropyl]-1-methyl-1-[(3R)-1-(pyridazin-3-yl)piperidin-3-yl]urea | LC-MS: m/z 380.1 (M + H). 1H NMR (400 MHz, MeOD) δ 8.46 (s, 1H), 7.37 (s, 1H), 7.30 (dd, J = 9.5, 4.2 Hz, 1H), 7.01-6.90 (m, 2H), 6.84 (d, J = 9.0 Hz, 1H), 4.31 (d, J = 33.8 Hz, 2H), 4.07 (s, 1H), 3.03 (t, J = 11.5 Hz, 1H), 2.91 (d, J = 13.0 Hz, 1H), 2.85 (s, 3H), 2.72 (dd, J = 7.4, 3.2 Hz, 1H), 2.20 (d, J = 7.7 Hz, 6H), 1.98 (d, J = 3.7 Hz, 1H), 1.87 (s, 3H), 1.68 (s, 1H), 1.11 (dd, J = 16.7, 10.3 Hz, 2H). |
| 8 | 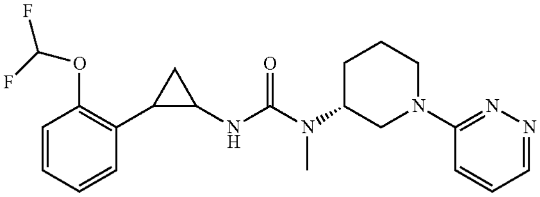 [SMILES: CN(C(=O)NC1CC1c1ccccc1OC(F)F)[C@@H]1CCCN(c2cccnn2)C1] 3-{2-[2-(difluoromethoxy)phenyl]cyclopropyl}-1-methyl-1-[(3R)-1-(pyridazin-3-yl)piperidin-3-yl]urea | LC-MS: m/z 418.1 (M + H). 1H NMR (400 MHz, MeOD) δ 8.45 (dd, J = 3.2, 1.2 Hz, 1H), 7.37 (ddd, J = 9.4, 4.4, 0.7 Hz, 1H), 7.28 (ddd, J = 9.4, 2.3, 1.2 Hz, 1H), 7.20-7.08 (m, 3H), 7.02 (dd, J = 7.2, 1.9 Hz, 1H), 7.00-6.60 (m, 1H), 4.39 (t, J = 15.6 Hz, 1H), 4.25 (t, J = 15.7 Hz, 1H), 4.07 (d, J = 4.6 Hz, 1H), 3.08 3.00 (m, 1H), 2.91 (dt, J = 7.6, 3.4 Hz, 2H), 2.86 (s, 3H), 2.25 (dtd, J = 9.9, 6.6, 3.5 Hz, 1H), 1.87 (d, J = 6.8 Hz, 3H), 1.67(d, J = 11.5 Hz, 1H), 1.36-1.30 (m, 1H), 1.21-1.13 (m, 1H). |

-continued

| Example | Structure and name | Data |
|---|---|---|
| 9 | 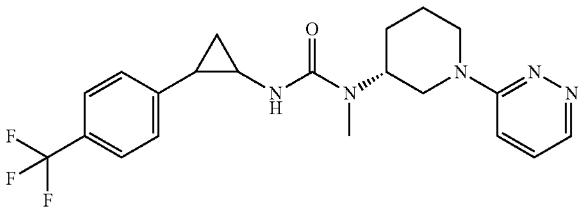 [SMILES: CN(C(=O)NC1CC1c1ccc(C(F)(F)F)cc1)[C@@H]1CCCN(c2cccnn2)C1] 1-methyl-1-[(3R)-1-(pyridazin-3-yl)piperidin-3-yl]-3-{2-[4-(trifluoromethyl)phenyl]cyclopropyl} urea | LC-MS: m/z 420 (M + H). 1H NMR (400 MHz, MeOD) δ 8.49-8.44 (m, 1H), 7.53 (d, J = 8.2 Hz, 2H), 7.38 (ddd, J = 9.3, 4.4, 2.9 Hz, 1H), 7.30 (dd, J = 14.5, 5.4 Hz, 3H), 4.39-4.25 (m, 2H), 4.05 (s, 1H), 3.03 (t, J = 11.9 Hz, 1H), 2.92 (d, J = 14.7 Hz, 1H), 2.86 (s, 3H), 2.83 (dd, J = 7.6, 4.3 Hz, 1H), 2.13 (qd, J = 6.6, 3.5 Hz, 1H), 1.87 (d, J = 5.9 Hz, 3H), 1.67(s,1H), 1.39-1.33 (m, 1H), 1.26(d, J = 7.5 Hz, 1H). |
| 10 | 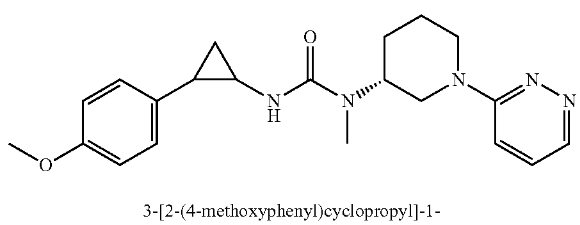 3-[2-(4-methoxyphenyl)cyclopropyl]-1-methyl-1-/(3R)-1-(pyridazin-3-yl)piperidin-3-yl]urea | LC-MS: m/z 382 (M + H). 1H NMR (400 MHz, MeOD) δ 8.47 (d, J = 4.4 Hz, 1H), 7.42-7.35 (m, 1H), 7.33-7.27 (m, 1H), 7.09 (d, J = 8.7 Hz, 2H), 6.81 (d, J = 8.4 Hz, 2H), 4.37 (d, J = 13.5 Hz, 1H), 4.32-4.22 (m, 1H), 4.07 (s, 1H), 3.75 (s, 3H), 3.03 (t, J = 11.9 Hz, 1H), 2.92 (d, J = 12.7 Hz, 1H), 2.86 (s, 3H), 2.72-2.65 (m, 1H), 2.04-1.96 (m, 1H), 1.88 (dd, J = 11.4, 4.1 Hz, 3H), 1.68 (s, 1H), 1.19-1.12 (m, 1H), 1.10-1.04 (m, 1H). |
| 11 | 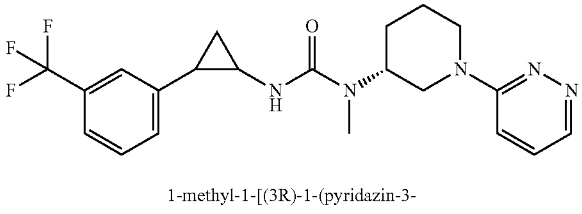 1-methyl-1-[(3R)-1-(pyridazin-3-yl)piperidin-3-yl]-3-{2-[3-(trifluoromethyl)phenyl]cyclopropyl}urea | LC-MS: m/z 420 (M + H). 1H NMR (400 MHz, MeOD) δ 8.47 (dt, J = 4.4, 1.4 Hz, 1H), 8.24 (s, 1H), 7.48 (s, 1H), 7.44 (d, J = 5.1 Hz, 2H), 7.42-7.36 (m, 2H), 7.33-7.28 (m, 1H), 4.40-4.25 (m, 2H), 4.05 (s, 1H), 3.08-2.97 (m, 1H), 2.96-2.88 (m, 1H), 2.86 (s, 3H), 2.83-2.77 (m, 1H), 2.18-2.11 (m, 1H), 1.92-1.83 (m, 3H), 1.68 (s, 1H), 1.37-1.30 (m, 1H), 1.28-1.20 (m, 1H). |
| 12 | 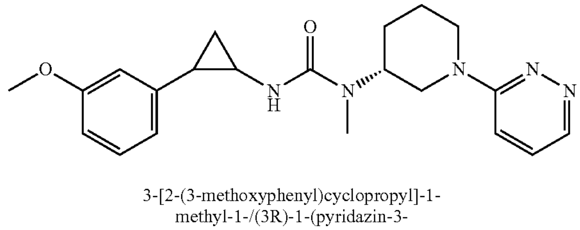 3-[2-(3-methoxyphenyl)cyclopropyl]-1-methyl-1-/(3R)-1-(pyridazin-3-yl)piperidin-3-ylurea | LC-MS: m/z 382 (M + H). 1HNMR (400 MHz, MeOD) δ 8.46 (d, J = 4.3 Hz, 1H), 7.38 (ddd, J = 9.4, 4.4,2.0 Hz, 1H), 7.30 (ddd, J = 9.4, 3.9,1.2 Hz, 1H), 7.13 (t, J = 7.9 Hz, 1H), 6.75- 6.66 (m, 3H), 4.41-4.23 (m, 2H), 4.06 (s. 1H), 3.76 (d, J = 0.8 Hz, 3H), 3.07-2.97 (m, 1H), 2.95-2.81 (m, 4H), 2.76 (dt, J = 7.7, 3.9 Hz, 1H), 2.06-1.99 (m, 1H), 1.88 (dd, J = 10.9, 4.5 Hz, 3H), 1.67 (s. 1H), 1.23-1.13 (m, 2H). |
| 13 | 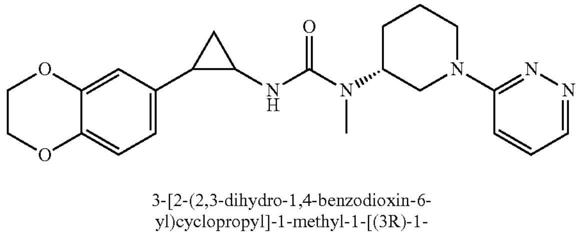 3-[2-(2,3-dihydro-1,4-benzodioxin-6-yl)cyclopropyl]-1-methyl-1-[(3R)-1-(pyridazin-3-yl)piperidin-3-yl]urea | LC-MS: m/z 410 (M + H). 1H NMR (400 MHz, MeOD) δ 8.46 (d, J = 4.4 Hz, 1H), 7.38 (ddd, J = 9.4, 4.4, 1.9 Hz, 1H), 7.32-7.28 (m, 1H), 6.69 (d, J = 8.0 Hz, 1H), 6.65-6.58 (m, 2H), 4.37 (d, J = 13.0 Hz, 1H), 4.29-4.24 (m, 1H), 4.19 (d, J = 5.1Hz, 4H), 4.06(s, 1H), 3.02(s,1H), 2.91(d, J = 12.8 Hz, 1H), 2.85(d, J = 5.2 Hz, 3H), 2.67(dd, J = 7.5, 3.6 Hz, 1H), 1.97-1.92 (m,1H), 1.87(t, J = 8.0 Hz, 3H), 1.68(s, 1H), 1.14-1.09(m,1H), 1.05(d, J = 7.4 Hz, 1H). |

-continued

| Example | Structure and name | Data |
|---|---|---|
| 14 | 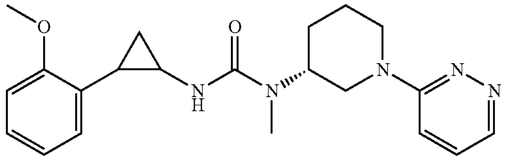 [SMILES: COc1ccccc1C1CC1NC(=O)N(C)[C@@H]1CCCN(c2cccnn2)C1] 3-[2-(2-methoxyphenyl)cyclopropyl]-1-methyl-1-[(3R)-1-(pyridazin-3-yl)piperidin-3-yl]urea | LC-MS: m/z 382 (M + H). 1H NMR (400 MHz, MeOD) δ 8.46 (s, 1H), 7.39 (dd, J = 9.3, 4.3 Hz, 1H), 7.30 (d, J = 9.4 Hz, 1H), 7.15-7.08 (m, 1H), 6.93-6.87 (m, 2H), 6.86-6.80 (m, 1H), 4.39 (d, J = 12.0 Hz, 1H), 4.27 (d, J = 12.6 Hz, 1H), 4.14-4.03 (m, 1H), 3.84 (d, J = 2.3 Hz, 3H), 3.08-2.98 (m, 1H), 2.94-2.87 (m, 2H), 2.86 (s, 3H), 2.34-2.25 (m, 1H), 1.88 (t, J = 7.0 Hz, 3H), 1.77-1.60 (m, 1H), 1.21-1.12 (m, 1H), 1.07-1.01 (m, 1H). |
| 15 | 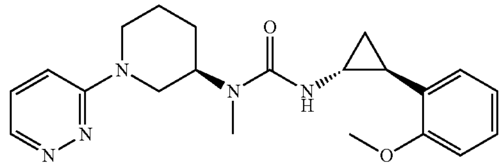 [SMILES: COc1ccccc1[C@@H]1C[C@H]1NC(=O)N(C)[C@@H]1CCCN(c2cccnn2)C1] 3-[(1R,2S)-2-(2-methoxyphenyl)cyclopropyl]-1-methyl-1-[(3R)-1-(pyridazin-3-yl)piperidin-3-yl]urea | LC-MS: m/z 382 (M + H). 1H NMR (400 MHz, MeOD) δ 8.46 (d, J = 4.2 Hz, 1H), 7.38 (dd, J = 9.3, 4.4 Hz, 1H), 7.33-7.28 (m, 1H), 7.15-7.09 (m, 1H), 6.93-6.88 (m, 2H), 6.86-6.81 (m, 1H), 4.39 (d, J = 12.8 Hz, 1H), 4.27 (d, J = 12.0 Hz, 1H), 4.09 (d, J = 4.1 Hz, 1H), 3.84 (s, 3H), 3.09-3.00 (m, 1H), 2.95-2.88 (m, 2H), 2.86 (s, 3H), 2.34-2.24 (m, 1H), 1.92-1.84 (m, 3H), 1.69 (s, 1H), 1.21-1.15 (m, 1H), 1.08-1.00 (m, 1H). |
| 16 | 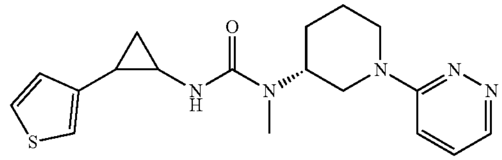 [SMILES: CN(C(=O)NC1CC1c1ccsc1)[C@@H]1CCCN(c2cccnn2)C1] 1-methyl-1-[(3R)-1-(pyridazin-3-yl)piperidin-3-yl]-3-[2-(thiophen-3-yl)cyclopropyl]urea | LC-MS: m/z 358 (M + H). 1H NMR (400 MHz, MeOD) δ 8.48-8.45 (m, 1H), 7.38 (ddd, J = 9.4, 4.4, 1.7 Hz, 1H), 7.32-7.26 (m, 2H), 7.00 (d, J = 2.9 Hz, 1H), 6.95 (dt, J = 5.0, 1.1 Hz, 1H), 4.36 (d, J = 13.3 Hz, 1H), 4.31-4.24 (m, 1H), 4.06 (s, 1H), 3.02 (t, J = 11.6 Hz, 1H), 2.91 (d, J = 13.0 Hz, 1H), 2.85 (s, 3H), 2.73 (td, J = 7.4, 4.1 Hz, 1H), 2.08 (ddt, J = 9.4, 6.3, 3.2 Hz, 1H), 1.90-1.82 (m, 3H), 1.68 (s, 1H), 1.20-1.14 (m, 1H), 1.10 (dd, J = 13.2, 5.9 Hz, 1H). |
| 17 | 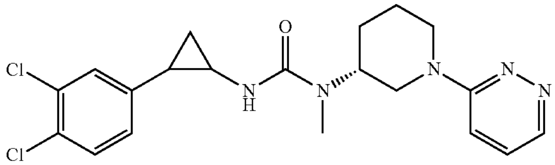 [SMILES: CN(C(=O)NC1CC1c1ccc(Cl)c(Cl)c1)[C@@H]1CCCN(c2cccnn2)C1] 3-[2-(3,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.47 (d, J = 3.9 Hz, 1H), 7.41-7.33 (m, 3H), 7.32-7.24 (m, 1H), 7.08 (dd, J = 8.3, 2.0 Hz, 1H), 4.40-4.22 (m, 2H), 4.10-3.96 (m, 1H), 3.07-2.97 (m, 1H), 2.94-2.87 (m, 1H), 2.86 (s, 3H), 2.78-2.72 (m, 1H), 2.07-1.98 (m, 1H), 1.92-1.82 (m, 3H), 1.73-1.58 (m, 1H), 1.31-1.28 (m, 1H), 1.23-1.16 (m, 1H). |
| 18 | 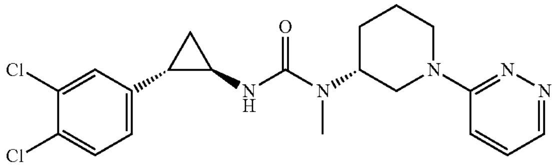 3-[(1R,2S)-2-(3,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.50-8.45 (m, 1H), 7.41-7.34 (m, 3H), 7.31 (dd, J = 9.4, 1.2 Hz, 1H), 7.08 (dd, J = 8.3, 2.1 Hz, 1H), 4.31 (dd, J = 21.5, 8.9 Hz, 2H), 4.09-3.98 (m, 1H), 3.07-2.99 (m, 1H), 2.95-2.87 (m, 1H), 2.86 (s, 3H), 2.78-2.73 (m, 1H), 2.06-2.00 (m, 1H), 1.92-1.84 (m, 3H), 1.74-1.60 (m, 1H), 1.35-1.28 (m, 1H), 1.23-1.16 (m, 1H). |
| 19 | 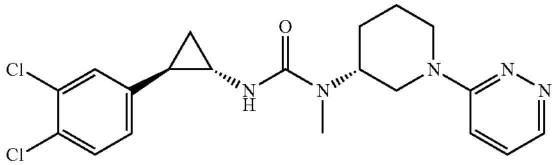 3-[(1S,2R)-2-(3,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.50-8.42 (m, 1H), 7.41-7.34 (m, 3H), 7.29 (dd, J = 9.4, 1.2 Hz, 1H), 7.08 (dd, J = 8.3, 2.1 Hz, 1H), 4.39-4.24 (m, 2H), 4.09-3.99 (m, 1H), 3.03 (dd, J = 12.5, 11.3 Hz, 1H), 2.95-2.87 (m, 1H), 2.86 (s, 3H), 2.09-2.00 (m, 1H), 1.92-1.83 (m, 3H), 1.73-1.61 (m, 1H), 1.33-1.27 (m, 1H), 1.24-1.16 (m, 1H). |

-continued

| Example | Structure and name | Data |
|---|---|---|
| 20 | 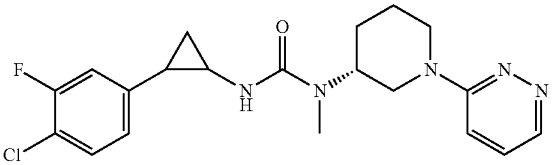 3-[2-(4-chloro-3-fluorophenyl)cyclopropyl]-1-methyl-1-[(3R)-1-(pyridazin-3-yl)piperidin-3-yl]urea | LC-MS: m/z 404 (M + H). 1H NMR (400 MHz, MeOD) δ 8.50-8.44 (m, 1H), 7.39 (ddd, J = 9.4, 4.4, 2.5 Hz, 1H), 7.35-7.27 (m, 2H), 7.06 (d, J = 10.7 Hz, 1H), 6.97 (dd, J = 8.3, 1.8 Hz, 1H), 4.31 (dd, J = 22.2, 10.9 Hz, 2H), 4.05 (d, J = 5.4 Hz, 1H), 3.03 (t, J = 11.9 Hz, 1H), 2.95-2.84 (m, 4H), 2.76 (td, J = 7.7, 4.3 Hz, 1H), 2.05 (dq, J = 6.7, 3.6 Hz, 1H), 1.88 (t, J = 7.1 Hz, 3H), 1.66 (d, J = 8.0 Hz, 1H), 1.33-1.27 (m, 1H), 1.19 (dd, J = 13.7, 6.1 Hz, 1H). |
| 21 | 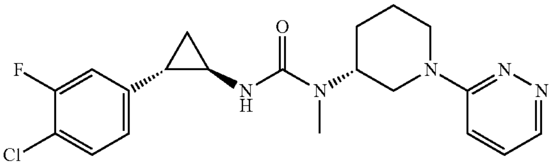 3-[(1R,2S)-2-(4-chloro-3-fluorophenyl)cyclopropyl]-1-methyl-1-[(3R)-1-(pyridazin-3-yl)piperidin-3-yl]urea | LC-MS: m/z 404 (M + H). 1H NMR (400 MHz, MeOD) δ 8.47 (d, J = 3.8 Hz, 1H), 7.40 (dd, J = 9.4, 4.4 Hz, 1H), 7.35-7.29 (m, 2H), 7.05 (dd, J = 10.7, 2.0 Hz, 1H), 6.97 (dd, J = 8.3, 1.8 Hz, 1H), 4.35-4.27 (m, 2H), 4.04 (d, J = 3.7 Hz, 1H), 3.08-3.00 (m, 1H), 2.95-2.83 (m, 4H), 2.76 (ddd, J = 7.7, 4.5, 3.3 Hz, 1H), 2.05 (ddd, J = 9.4, 6.2, 3.5 Hz, 1H), 1.93-1.83 (m, 3H), 1.72-1.59 (m, 1H), 1.33-1.28 (m, 1H), 1.19 (dt, J = 7.5, 6.1 Hz, 1H). |
| 22 | 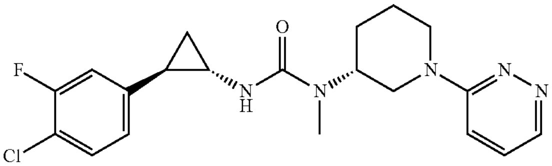 | LC-MS: m/z 404 (M + H). 1H NMR (400 MHz, MeOD) δ 8.47 (d, J = 3.9 Hz, 1H), 7.38 (dd, J = 9.4, 4.3 Hz, 1H), 7.34-7.26 (m, 2H), 7.06 (dd, J = 10.7, 2.0 Hz, 1H), 6.97 (dd, J = 8.3, 1.9 Hz, 1H), 4.38-4.25 (m, 2H), 4.10-3.99 (m, 1H), 3.02 (dd, J = 12.4, 11.4 Hz, 1H), 2.96-2.82 (m, 4H), 2.75 (ddd, J = 7.7, 4.5, 3.3 Hz, 1H), 2.05 (ddd, J = 9.5, 6.3, 3.3 Hz, 1H), 1.93-1.81 (m, 3H), 1.74-1.61 (m, 1H), 1.33-1.28 (m, 1H), 1.19 (dt, J = 7.5, 6.1 Hz, 1H). |
| 23 | 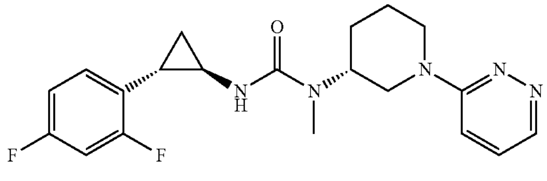 [SMILES: CN(C(=O)N[C@@H]1C[C@H]1c1ccc(F)cc1F)[C@@H]1CCCN(c2cccnn2)C1] 3-[(1R,2S)-2-(2,4-difluorophenyl)cyclopropyl]-1-methyl-1-[(3R)-1-(-94-yridazine-3-yl)piperidin-3-yl]urea | LC-MS: m/z 388 (M + H). 1HNMR (400 MHz, MeOD) δ 8.46 (dd, J = 4.4,1.1Hz, 1H), 7.38 (dd, J = 9.4, 4.4 Hz, 1H), 7.30 (dd, J = 9.4,1.2 Hz, 1H), 7.11 (td, J = 8.8,6.4 Hz, 1H), 6.90- 6.81 (m, 2H), 4.41-4.24 (m, 2H), 4.06 (dd, J = 9.6, 5.8 Hz, 1H), 3.03 (dd, J = 12.5, 11.3 Hz, 1H), 2.91 (ddd, J = 17.6, 9.0, 5.0 Hz, 2H), 2.86 (s, 3H), 2.12 (ddd, J = 9.6, 6.3, 3.4 Hz, 1H), 1.93-1.82 (m, 3H), 1.67 (dt, J = 14.1, 9.1 Hz, 1H), 1.31-1.27 (m, 1H), 1.14 (dt, J = 7.5, 6.0 Hz, 1H). |
| 24 | 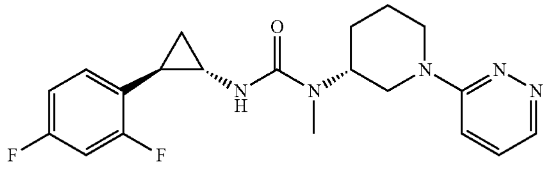 [SMILES: CN(C(=O)N[C@H]1C[C@@H]1c1ccc(F)cc1F)[C@@H]1CCCN(c2cccnn2)C1] 3-[(1S,2R)-2-(2,4-difluorophenyl)cyclopropyl]-1-methyl-1-[(3R)-1-(pyridazin-3-yl)piperidin-3-yl]urea | LC-MS: m/z 388 (M + H). 1HNMR (400 MHz, MeOD) δ 8.46 (dd, J = 4.4,1.2 Hz, 1H), 7.38 (dd, J = 9.4, 4.4 Hz, 1H), 7.29(dd, J = 9.4, 1.2 Hz, 1H), 7.11 (td, J = 8.8,6.4 Hz, 1H), 6.90-6.81 (m, 2H), 4.41-4.23 (m, 2H), 4.13-4.01 (m, 1H), 3.03 (dd, J = 12.5, 11.3 Hz, 1H), 2.96-2.87 (m, 2H), 2.86 (s, 3H), 2.14 (ddd, J = 9.7, 6.3, 3.4 Hz, 1H), 1.88 (dd, J = 10.9, 4.4 Hz, 3H), 1.68 (dd, J = 11.3, 6.4 Hz, 1H), 1.28 (dd, J = 7.0, 2.6 Hz, 1H), 1.14 (dt, J = 7.5, 6.0 Hz, 1H). |
| 25 | 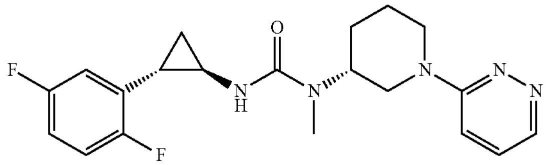 [SMILES: CN(C(=O)N[C@@H]1C[C@H]1c1cc(F)ccc1F)[C@@H]1CCCN(c2cccnn2)C1] 3-[(1R,2S)-2-(2,5-difluorophenyl)cyclopropyl]-1-methyl-1-[(3R)-1-(pyridazin-3-yl)piperidin-3-yl]urea | LC-MS: m/z 388 (M + H). 1H NMR (400 MHz, MeOD) δ 8.46 (dd, J = 4.4, 1.2 Hz, 1H), 7.38 (dd, J = 9.4, 4.4 Hz, 1H), 7.30 (dd, J = 9.4, 1.2 Hz, 1H), 7.02 (td, J = 9.3, 4.6 Hz, 1H), 6.92-6.77 (m, 2H), 4.39-4.32 (m, 1H), 4.28 (dd, J = 12.7, 3.7 Hz, 1H), 4.05 (dt, J = 11.2, 7.7 Hz, 1H), 3.03 (dd, J = 12.5, 11.3 Hz, 1H), 2.96-2.93 (m, 1H), 2.92-2.86 (m, 1H), 2.86 (s, 3H), 2.17 (ddd, J = 9.6, 6.2, 3.4 Hz, 1H), 1.92-1.84 (m, 3H), 1.73-1.60 (m, 1H), 1.39-1.32 (m, 1H), 1.18 (dt, J = 7.6, 6.0 Hz, 1H). |

-continued

| Example | Structure and name | Data |
|---|---|---|
| 26 | 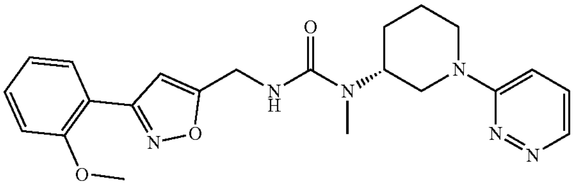 [SMILES: COc1ccccc1-c1cc(CNC(=O)N(C)[C@@H]2CCCN(c3cccnn3)C2)on1] 3-{[3-(2-methoxyphenyl)-1,2-oxazol-5-yl]methyl}-1-methyl-1-[(3R)-1-(pyridazin-3-yl)piperidin-3-yl]urea | LC-MS: m/z 423.41 (M + H). 1H NMR (400 MHz, cdcl3) δ 8.59-8.52 (m, 1H), 7.87-7.80 (m, 1H), 7.43-7.33 (m, 1H), 7.28-7.15 (m, 1H), 7.05-6.93 (m, 3H), 6.72 (s, 1H), 6.21 (s, 1H), 4.75-4.59 (m, 2H), 4.41-4.32 (m, 1H), 4.24 (d, J = 13.9 Hz, 1H), 4.01 (t, J = 12.0 Hz, 1H), 3.86 (s, 3H), 3.03-2.92 (m, 2H), 2.90 (s, 3H), 2.02-1.95 (m, 1H), 1.90-1.75 (m, 2H), 1.72-1.61 (m, 1H). |
| 27 | 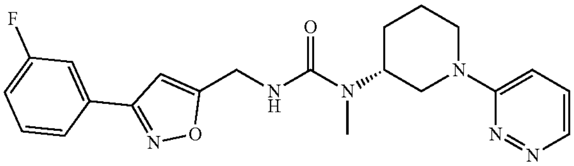 [SMILES: CN(C(=O)NCc1cc(-c2cccc(F)c2)no1)[C@@H]1CCCN(c2cccnn2)C1] 3-{[3-(3-fluorophenyl)-1,2-oxazol-5-yl]methyl}-1-methyl-1-[(3R)-1-(pyridazin-3-yl)piperidin-3-yl]urea | LC-MS: m/z 411.4 (M + H). 1H NMR (400 MHz, cdcl3) δ 8.57 (dd, J = 4.4, 1.3 Hz, 1H), 7.64-7.55 (m, 1H), 7.52 (ddd, J = 9.7, 2.7, 1.5 Hz, 1H), 7.39 (td, J = 7.9, 5.7 Hz, 1H), 7.22 (dd, J = 9.3, 4.4 Hz, 1H), 7.10 (tdd, J = 8.4, 2.6, 1.1 Hz, 1H), 7.01 (dd, J = 9.3, 1.3 Hz, 1H), 6.75 (s, 1H), 6.60 (s, 1H), 4.69 (dd, J = 5.7, 2.8 Hz, 2H), 4.50-4.41 (m, 2H), 4.10 (d, J = 12.6 Hz, 1H), 3.98-3.87 (m, 1H), 3.12-2.90 (m, 5H), 2.02 (dd, J = 8.1, 2.6 Hz, 1H), 1.94-1.80 (m, 1H), 1.62 (tdd, J = 13.6, 9.1, 4.2 Hz, 1H). |
| 28 | 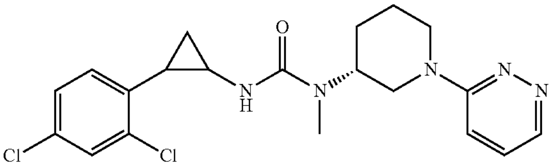 [SMILES: CN(C(=O)NC1CC1c1ccc(Cl)cc1Cl)[C@@H]1CCCN(c2cccnn2)C1] 3-[2-(2,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.46 (dd, J = 4.4, 1.2 Hz, 1H), 7.43-7.35 (m, 2H), 7.30 (ddd, J = 9.4, 2.1, 1.3 Hz, 1H), 7.25-7.20 (m, 1H), 7.13 (dd, J = 8.4, 2.1 Hz, 1H), 4.32 (dd, J = 28.6, 13.0 Hz, 2H), 4.07 (d, J = 4.4 Hz, 1H), 3.08-3.00 (m, 1H), 2.97 (dt, J = 8.0, 3.6 Hz, 1H), 2.94-2.88 (m, 1H), 2.87 (s, 3H), 2.27 (dtd, J = 10.0, 6.7, 3.6 Hz, 1H), 1.88 (d, J = 6.9 Hz, 3H), 1.75-1.63 (m, 1H), 1.37 (ddd, J = 9.6, 5.6, 4.5 Hz, 1H), 1.12-1.02 (m, 1H). |
| 29 | 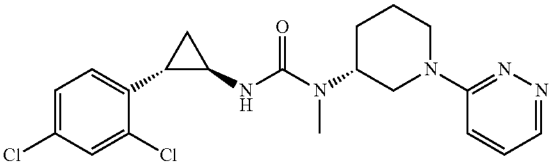 [SMILES: CN(C(=O)N[C@@H]1C[C@H]1c1ccc(Cl)cc1Cl)[C@@H]1CCCN(c2cccnn2)C1] 3-[(1R,2S)-2-(2,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.46 (dd, J = 4.4, 1.1 Hz, 1H), 7.42-7.33 (m, 2H), 7.29 (d, J = 9.4 Hz, 1H), 7.23 (dd, J = 8.4, 2.1 Hz, 1H), 7.13 (d, J = 8.4 Hz, 1H), 4.38-4.26 (m, 2H), 4.07 (dd, J = 11.7, 7.5 Hz, 1H), 3.03 (t, J = 11.9 Hz, 1H), 2.99-2.94 (m, 1H), 2.91 (dd, J = 12.8, 2.2 Hz, 1H), 2.87 (s, 3H), 2.28 (ddd, J = 9.8, 6.3, 3.6 Hz, 1H), 1.87 (d, J = 5.7 Hz, 3H), 1.68 (dd, J = 11.5, 6.7 Hz, 1H), 1.37 (dq, J = 5.6, 4.5 Hz, 1H), 1.08 (dt, J = 7.5, 6.0 Hz, 1H). |
| 30 | 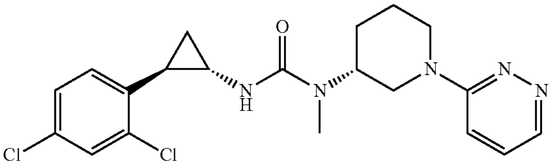 [SMILES: CN(C(=O)N[C@H]1C[C@@H]1c1ccc(Cl)cc1Cl)[C@@H]1CCCN(c2cccnn2)C1] 3-[(1S,2R)-2-(2,4-dichlorophenyl)cyclopropyl]-1-methyl-1-[(3R)-1-(pyridazin-3-yl)piperidin-3-yl]urea | LC-MS: m/z 420 (M + H). 1H NMR (400 MHz, MeOD) δ 8.46 (dd, J = 4.4, 1.1 Hz, 1H), 7.42-7.33 (m, 2H), 7.29 (d, J = 9.4 Hz, 1H), 7.23 (dd, J = 8.4, 2.1 Hz, 1H), 7.13 (d, J = 8.4 Hz, 1H), 4.38-4.26 (m, 2H), 4.07 (dd, J = 11.7, 7.5 Hz, 1H), 3.03 (t, J = 11.9 Hz, 1H), 2.99-2.94 (m, 1H), 2.91 (dd, J = 12.8, 2.2 Hz, 1H), 2.87 (s, 3H), 2.28 (ddd, J = 9.8, 6.3, 3.6 Hz, 1H), 1.87 (d, J = 5.7 Hz, 3H), 1.68 (dd, J = 11.5, 6.7 Hz, 1H), 1.37 (dq, J = 5.6, 4.5 Hz, 1H), 1.08 (dt, J = 7.5, 6.0 Hz, 1H). |
| 31 | 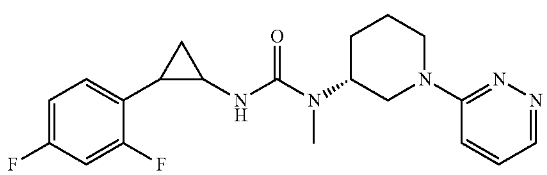 [SMILES: CN(C(=O)NC1CC1c1ccc(F)cc1F)[C@@H]1CCCN(c2cccnn2)C1] 3-[2-(2,4-difluorophenyl)cyclopropyl]-1-methyl-1-[(3R)-1-(pyridazin-3-yl)piperidin-3-yl]urea | LC-MS: m/z 388.1 (M + H). 1H NMR (400 MHz, MeOD) δ 8.46 (d, J = 4.4 Hz, 1H), 7.38 (dd, J = 9.4, 4.4 Hz, 1H), 7.33-7.27 (m, 1H), 7.11 (dd, J = 15.2, 8.6 Hz, 1H), 6.89-6.83 (m, 2H), 4.32 (dd, J = 33.0,12.8 Hz, 2H), 4.07 (s, 1H), 3.03 (t, J = 11.9 Hz, 1H), 2.91 (dd, J = 8.3, 3.9 Hz, 2H), 2.86 (s, 3H), 2.13(d, J = 4.4 Hz, 1H), 1.87 (d, J = 5.5 Hz, 3H), 1.68 (s, 1H), 1.29 (s, 1H), 1.14 (dd, J = 13.0, 6.6 Hz, 1H). |

-continued

| Example | Structure and name | Data |
|---|---|---|
| 32 | 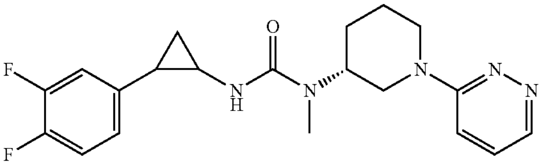 [SMILES: CN(C(=O)NC1CC1c1ccc(F)c(F)c1)[C@@H]1CCCN(c2cccnn2)C1] 3-[2-(3,4-difluorophenyl)cyclopropyl]-1-methyl-1-[(3R)-1-(pyridazin-3-yl)piperidin-3-yl]urea | LC-MS: m/z 388.1 (M + H). 1H NMR (400 MHz, MeOD) δ 8.47 (d, J = 4.0 Hz, 1H), 7.44-7.33 (m, 1H), 7.30 (dd, J = 9.3, 3.8 Hz, 1H), 7.10 (dt, J = 13.7, 7.6 Hz, 2H), 6.96 (dd, J = 6.3, 2.0 Hz, 1H), 4.41-4.21 (m, 2H), 4.14-3.90 (m, 1H), 3.01 (d, J = 11.8 Hz, 1H), 2.94-2.79 (m, 4H), 2.71 (tt, J = 8.6, 4.3 Hz, 1H), 2.04 (qd, J = 6.5, 3.4 Hz, 1H), 1.89 (dd, J = 18.7, 9.2 Hz, 3H), 1.67 (s, 1H), 1.30-1.21 (m, 1H), 1.16 (dd, J = 13.3, 6.3 Hz, 1H). |
| 33 | 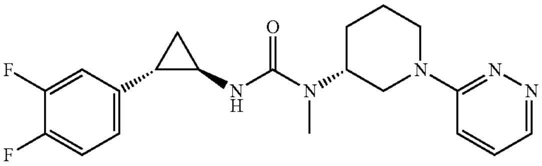 [SMILES: CN(C(=O)N[C@@H]1C[C@H]1c1ccc(F)c(F)c1)[C@@H]1CCCN(c2cccnn2)C1] 3-[(1R,2S)-2-(3,4-difluorophenyl)cyclopropyl]-1-methyl-1-[(3R)-1-(pyridazin-3-yl)piperidin-3-yl]urea | LC-MS: m/z 388.1 (M + H). 1H NMR (400 MHz, MeOD) δ 8.47 (dd, J = 4.4, 1.1 Hz, 1H), 7.39 (dd, J = 9.4, 4.4 Hz, 1H), 7.30 (dd, J = 9.4, 1.2 Hz, 1H), 7.16-7.04 (m, 2H), 7.00-6.93 (m, 1H), 4.40-4.24 (m, 2H), 4.04 (dd, J = 9.6, 5.7 Hz, 1H), 3.09-2.96 (m, 1H), 2.95-2.82 (m, 4H), 2.76-2.67 (m, 1H), 2.03 (ddd, J = 9.5, 6.3, 3.2 Hz, 1H), 1.94-1.83 (m, 3H), 1.65 (ddd, J = 22.2, 11.9, 5.9 Hz, 1H), 1.29-1.21 (m, 1H), 1.16 (dt, J = 7.4, 6.1 Hz, 1H). |
| 34 | 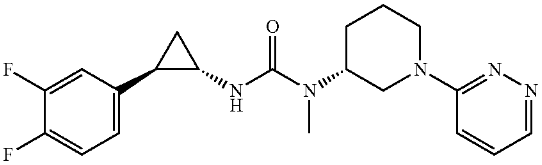 [SMILES: CN(C(=O)N[C@H]1C[C@@H]1c1ccc(F)c(F)c1)[C@@H]1CCCN(c2cccnn2)C1] 3-[(1S,2R)-2-(3,4-difluorophenyl)cyclopropyl]-1-methyl-1-[(3R)-1-(pyridazin-3-yl)piperidin-3-yl]urea | LC-MS: m/z 388.1 (M + H). 1H NMR (400 MHz, MeOD) δ 8.47 (d, J = 4.1 Hz, 1H), 7.38 (dd, J = 9.3, 4.3 Hz, 1H), 7.29 (d, J = 9.3 Hz, 1H), 7.15-7.04 (m, 2H), 6.96 (dd, J = 6.2, 1.8 Hz, 1H), 4.40-4.24 (m, 2H), 4.11-4.00 (m, 1H), 3.02(t, J = 11.9 Hz, 1H), 2.95-2.83 (m, 4H), 2.71 (dq, J = 8.7, 4.3 Hz, 1H), 2.04 (ddd, J = 9.4,6.3, 3.3 Hz, 1H), 1.88 (t, J = 13.8 Hz, 3H), 1.66(d, J = 9.9 Hz, 1H), 1.29-1.22(m,1H), 1.16(dd, J = 13.5, 6.2 Hz, 1H). |
| 35 | 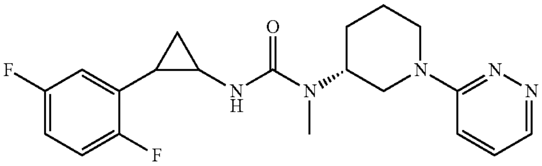 [SMILES: CN(C(=O)NC1CC1c1cc(F)ccc1F)[C@@H]1CCCN(c2cccnn2)C1] 3-[2-(2,5-difluorophenyl)cyclopropyl]-1-methyl-1-[(3R)-1-(pyridazin-3-yl)piperidin-3-yl]urea | LC-MS: m/z 388.1 (M + H). 1H NMR (400 MHz, MeOD) δ 8.46 (dt, J = 4.4, 1.3 Hz, 1H), 7.41-7.34 (m, 1H), 7.29 (ddd, J = 9.4, 3.8, 1.2 Hz, 1H), 7.05-6.97 (m, 1H), 6.83 (dddd, J = 24.0, 9.2, 6.4, 3.1 Hz, 2H), 4.32 (dd, J = 32.7, 12.2 Hz, 2H), 4.06 (dd, J = 11.5, 7.3 Hz, 1H), 3.07-2.99 (m, 1H), 2.94 (dd, J = 7.8, 4.4 Hz, 1H), 2.90 (dd, J = 5.9, 3.2 Hz, 1H), 2.86 (s, 3H), 2.17 (td, J = 9.8, 4.2 Hz, 1H), 1.92-1.83 (m, 3H), 1.74-1.60 (m, 1H), 1.39-1.32 (m, 1H), 1.18 (dt, J = 7.6, 6.0 Hz, 1H). |
| 36 | 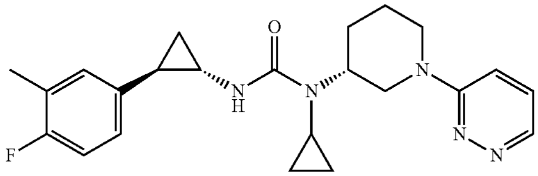 [SMILES: Cc1cc([C@H]2C[C@@H]2NC(=O)N(C2CC2)[C@@H]2CCCN(c3cccnn3)C2)ccc1F] 1-cyclopropyl-3-[(1S,2R)-2-(4-fluoro-3-methylphenyl)cyclopropyl]-1-[(3R)-1-(pyridazin-3-yl)piperidin-3-yl]urea | LC-MS: m/z 410.2 (M + H). 1H NMR (400 MHz, $CDCl_3$) δ 8.53 (d, J = 2.9 Hz, 1H), 7.17 (dd, J = 9.1, 4.2 Hz, 1H), 7.03-6.92 (m, 3H), 6.91-6.85 (m, 1H), 5.69 (s, 1H), 4.45 (d, J = 13.3 Hz, 1H), 4.35-4.26 (m, 1H), 3.83 (tt, J = 11.9, 3.9 Hz, 1H), 3.34-3.19 (m, 1H), 2.88 (td, J = 13.0, 2.7 Hz, 1H), 2.80 (dt, J = 12.3, 5.1 Hz, 1H), 2.48-2.40 (m, 1H), 2.33-2.17 (m, 4H), 2.03-1.91 (m, 2H), 1.84 (d, J = 12.9 Hz, 1H), 1.69 (s, 1H), 1.19-1.07 (m, 2H), 0.96-0.85 (m, 2H), 0.84-0.72 (m, 2H). |
| 37 | 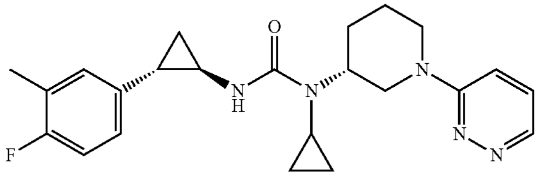 [SMILES: Cc1cc([C@@H]2C[C@H]2NC(=O)N(C2CC2)[C@@H]2CCCN(c3cccnn3)C2)ccc1F] 1-cyclopropyl-3-[(1R,2S)-2-(4-fluoro-3-methylphenyl)cyclopropyl]-1-[(3R)-1-(pyridazin-3-yl)piperidin-3-yl]urea | LC-MS: m/z 410.2 (M + H). 1H NMR (400 MHz, CDCl3) δ 8.53 (dd, J = 4.4, 1.0 Hz, 1H), 7.18 (dd, J = 9.3, 4.4 Hz, 1H), 7.02-6.92 (m, 3H), 6.92-6.85 (m, 1H), 5.75 (s, 1H), 4.48-4.27 (m, 2H), 3.81 (tt, J = 11.8, 3.9 Hz, 1H), 3.33-3.18 (m, 1H), 2.90 (td, J = 13.0, 2.7 Hz, 1H), 2.84-2.76 (m, 1H), 2.48-2.41 (m, 1H), 2.32-2.19 (m, 4H), 2.03-1.93 (m, 2H), 1.87-1.81 (m, 1H), 1.68-1.56 (m, 1H), 1.20-1.11 (m, 2H), 0.93-0.85 (m, 2H), 0.84-0.73 (m, 2H). |

-continued

| Example | Structure and name | Data |
|---|---|---|
| 38 | 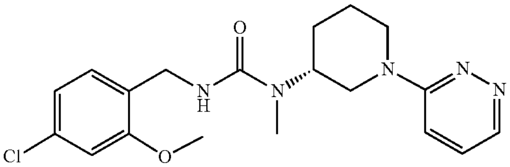 [SMILES: COc1cc(Cl)ccc1CNC(=O)N(C)[C@@H]1CCCN(c2cccnn2)C1] 3-[(4-chloro-2-methoxyphenyl)methyl]-1-methyl-1-[(3R)-1-(pyridazin-3-yl)piperidin-3-yl]urea | LC-MS: m/z 390 (M + H). 1H NMR (400 MHz, MeOD) δ 8.44 (s, 1H), 7.37 (dd, J = 9.1, 3.9 Hz, 1H), 7.27 (d, J = 9.2 Hz, 1H), 7.17 (d, J = 8.1 Hz, 1H), 6.99-6.84 (m, 2H), 4.41-4.25 (m, 4H), 4.10 (dt, J = 11.2, 7.8 Hz, 1H), 3.83 (s, 3H), 3.07-2.99 (m, 1H), 2.90 (s, 3H), 2.86 (dd, J = 13.1, 2.4 Hz, 1H), 1.94-1.83 (m, 3H), 1.74-1.61 (m, 1H). |
| 39 | 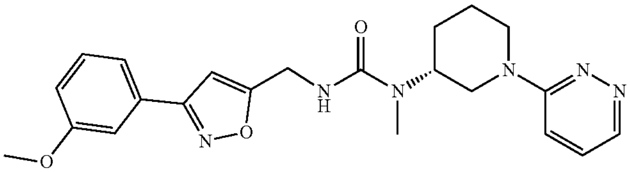 3-{[3-(3-methoxyphenyl)-1,2-oxazol-5-yl]methyl}-1-methyl-1-[(3R)-1-(pyridazin-3-yl)piperidin-3-yl]urea | LC-MS: m/z 423.4 (M + H). 1H NMR (400 MHz, cdcl3) δ 8.60-8.53 (m, 1H), 7.39-7.28 (m, 2H), 7.28-7.18 (m, 2H), 7.05-6.98 (m, 1H), 6.98-6.92 (m, 1H), 6.61 (s, 1H), 6.57 (s, 1H), 4.75-4.60 (m, 2H), 4.47-4.38 (m, 1H), 4.13 (d, 1H), 3.96 (m, 1H), 3.85-3.82 (m, 3H), 3.09-2.94 (m, 2H), 2.94-2.90 (m, 3H), 2.02 (m, 1H), 1.92-1.78 (m, 2H), 1.64 (m, 1H). |
| 40 | 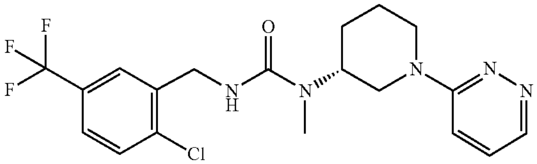 1-{[2-chloro-5-(trifluoromethyl)phenyl]methyl}-3-methyl-3-[(3R)-1-(pyridazin-3-yl)piperidin-3-yl]urea | LC-MS: m/z 423.4 (M + H). 1H NMR (400 MHz, cdcl3) δ 8.56-8.49 (m, 1H), 7.72 (s, 1H), 7.43 (m, 2H), 7.22-7.17 (m, 1H), 7.02-6.97 (m, 1H), 6.37 (s, 1H), 4.73-4.55 (m, 2H), 4.45-4.37 (m, 1H), 4.23-4.15 (m, 1H), 4.05-3.94 (m, 1H), 3.06-2.93 (m, 2H), 2.92 (s, 3H), 2.06-1.99 (m, 1H), 1.93-1.78 (m, 2H), 1.73-1.60 (m, 1H). |
| 41 | 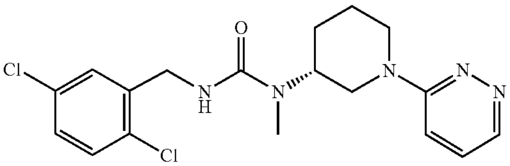 [SMILES: CN(C(=O)NCc1cc(Cl)ccc1Cl)[C@@H]1CCCN(c2cccnn2)C1] 1-[(2,5-dichlorophenyl)methyl]-3-methyl-3-[(3R)-1-(pyridazin-3-yl)piperidin-3-yl]urea | LC-MS: m/z 394.1 (M + H). 1H NMR (400 MHz, cdcl3) δ 8.55 (d, 1H), 7.43-7.40 (m, 1H), 7.27-7.18 (m, 2H), 7.16-7.12 (m, 1H), 7.03-6.99 (m, 1H), 6.12 (br, 1H), 4.62-4.46 (m, 2H), 4.37 (d, 1H), 4.24 (d, 1H), 4.08-3.96 (m, 1H), 3.01-2.92 (m, 2H), 2.90 (s, 3H), 2.04-1.95 (m, 1H), 1.90-1.76 (m, 2H), 1.72-1.59 (m, 1H). |
| 42 | 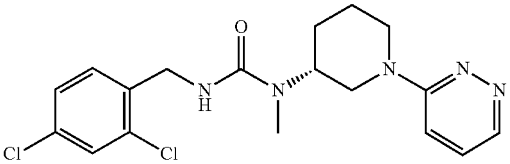 [SMILES: CN(C(=O)NCc1ccc(Cl)cc1Cl)[C@@H]1CCCN(c2cccnn2)C1] 1-[(2,4-dichlorophenyl)methyl]-3-methyl-3-[(3R)-1-(pyridazin-3-yl)piperidin-3-yl]urea | LC-MS: m/z 394.1 (M + H). 1H NMR (400 MHz, cdcl3) δ 8.56-8.51 (m, 1H), 7.40 (d, 1H), 7.36-7.33 (m, 1H), 7.22-7.16 (m, 2H), 7.00-6.95 (d, 1H), 6.06 (br, 1H), 4.52 (d, 2H), 4.38 (d, 1H), 4.21 (d, 1H), 4.07-3.95 (m, 1H), 3.01-2.90 (m, 2H), 2.88 (s, 3H), 2.02-1.92 (m, 1H), 1.90-1.75 (m, 2H), 1.73-1.56 (m, 1H). |

-continued

| Example | Structure and name | Data |
|---|---|---|
| 43 | 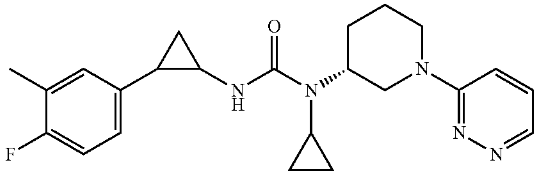 [SMILES: Cc1cc(C2CC2NC(=O)N(C2CC2)[C@@H]2CCCN(c3cccnn3)C2)ccc1F] 1-cyclopropyl-3-[2-(4-fluoro-3-methylphenyl)cyclopropyl]-1-[(3R)-1-(pyridazin-3-yl)piperidin-3-yl]urea | LC-MS: m/z 410.2 (M + H). 1H NMR (400 MHz, MeOD) δ 8.43 (dd, J = 4.4, 1.1 Hz, 1H), 7.37 (dd, J = 9.4, 4.4 Hz, 1H), 7.29 (ddd, J = 9.4, 2.6, 1.3 Hz, 1H), 7.04 (d, J = 7.5 Hz, 1H), 6.99-6.93 (m, 1H), 6.92-6.85 (m, 1H), 6.67 (s, 1H), 4.37 (dd, J = 26.9, 12.9 Hz, 2H), 3.76 (tt, J = 11.9, 3.9 Hz, 1H), 3.28-3.09 (m, 1H), 2.89 (td, J = 13.1, 2.5 Hz, 1H), 2.71 (dt, J = 7.0, 3.6 Hz, 1H), 2.53-2.44 (m, 1H), 2.31-2.18 (m, 4H), 2.04-1.93 (m, 2H), 1.86 (d, J = 13.0 Hz, 1H), 1.62 (dtd, J = 13.0, 9.0, 4.0 Hz, 1H), 1.21-1.10 (m, 2H), 0.98-0.87 (m, 2H), 0.76 (d, J = 2.5 Hz, 2H). |
| 44 | 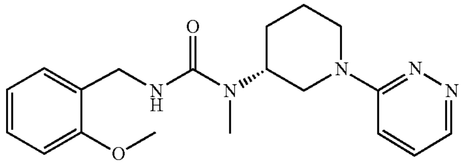 [SMILES: COc1ccccc1CNC(=O)N(C)[C@@H]1CCCN(c2cccnn2)C1] 3-[(2-methoxyphenyl)methyl]-1-methyl-1-[(3R)-1-(pyridazin-3-yl)piperidin-3-yl]urea | LC-MS: m/z 356 (M + H). 1H NMR (400 MHz, MeOD) δ 8.44 (dd, J = 4.4, 1.2 Hz, 1H), 7.36 (dd, J = 9.4, 4.4 Hz, 1H), 7.27 (dd, J = 9.4, 1.2 Hz, 1H), 7.23-7.18 (m, 2H), 6.95-6.85 (m, 2H), 4.38 (d, J = 6.2 Hz, 3H), 4.28 (dd, J = 12.5, 3.9 Hz, 1H), 4.11 (dt, J = 11.1, 7.8 Hz, 1H), 3.83 (s, 3H), 3.10-3.01 (m, 1H), 2.92-2.84 (m, 4H), 1.93-1.84 (m, 3H), 1.76-1.62 (m, 1H). |
| 45 | 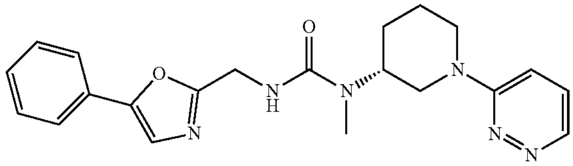 [SMILES: CN(C(=O)NCc1ncc(-c2ccccc2)o1)[C@@H]1CCCN(c2cccnn2)C1] 1-methyl-3-[(5-phenyl-1,3-oxazol-2-yl)methyl]-1-[(3R)-1-(pyridazin-3-yl)piperidin-3-yl]urea | LC-MS: m/z 392.1 (M + H). 1H NMR (400 MHz, MeOD) δ 8.44 (dd, J = 4.3, 1.1 Hz, 1H), 7.73-7.62 (m, 2H), 7.48-7.38 (m, 3H), 7.38-7.26 (m, 3H), 4.56 (s, 2H), 4.36 (ddd, J = 16.7, 12.9, 2.0 Hz, 2H), 4.11 (ddd, J = 15.6, 11.3, 4.3 Hz, 1H), 3.11-3.02 (m, 1H), 2.94 (s, 3H), 2.93-2.84 (m, 1H), 1.90 (dd, J = 13.4, 6.0 Hz, 3H), 1.76-1.61 (m, 1H). |
| 46 | 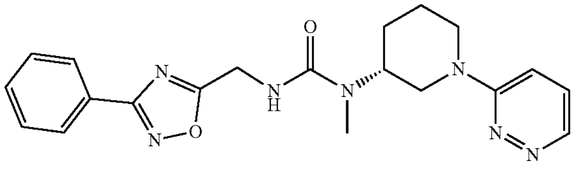 1-methyl-3-[(3-phenyl-1,2,4-oxadiazol-5-yl)methyl]-1-[(3R)-1-(pyridazin-3-yl)piperidin-3-yl]urea | LC-MS: m/z 393.1 (M + H). 1H NMR (400 MHz, MeOD) δ 8.44 (dd, J = 4.3, 1.2 Hz, 1H), 8.10-7.99 (m, 2H), 7.56-7.47 (m, 3H), 7.33 (ddd, J = 10.6, 9.4, 2.8 Hz, 2H), 4.68 (s, 2H), 4.35 (dd, J = 15.6, 7.4 Hz, 2H), 4.08 (d, J = 4.2 Hz, 1H), 3.08 (dd, J = 12.5, 11.3 Hz, 1H), 2.99-2.89 (m, 4H), 1.97-1.87 (m, 3H), 1.69 (dd, J = 8.1, 4.3 Hz, 1H). |
| 47 | 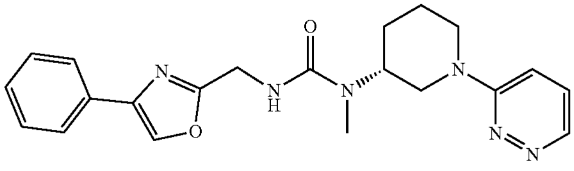 1-methyl-3-[(4-phenyl-1,3-oxazol-2-yl)methyl]-1-[(3R)-1-(pyridazin-3-yl)piperidin-3-yl]urea | LC-MS: m/z 392.1 (M + H). 1H NMR (400 MHz, MeOD) δ 8.43 (dd, J = 4.3, 1.1 Hz, 1H), 8.18 (s, 1H), 7.73 (dd, J = 5.2, 3.3 Hz, 2H), 7.41-7.33 (m, 3H), 7.30 (ddd, J = 6.3, 3.6, 1.3 Hz, 2H), 4.54 (s, 2H), 4.42-4.29 (m, 2H), 4.11 (d, J = 3.6 Hz, 1H), 3.06 (dd, J = 12.5, 11.3 Hz, 1H), 2.97-2.86 (m, 4H), 1.90 (dd, J = 13.8, 5.9 Hz, 3H), 1.68 (dd, J = 10.3, 5.4 Hz, 1H). |
| 48 | 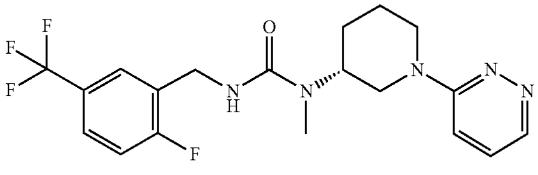 [SMILES: CN(C(=O)NCc1cc(C(F)(F)F)ccc1F)[C@@H]1CCCN(c2cccnn2)C1] 1-{[2-fluoro-5-(trifluoromethyl)phenyl]methyl}-3-methyl-3-[(3R)-1-(pyridazin-3-yl)piperidin-3-yl]urea | LC-MS: m/z 412.4 (M + H). |

-continued

| Example | Structure and name | Data |
|---|---|---|
| 49 | 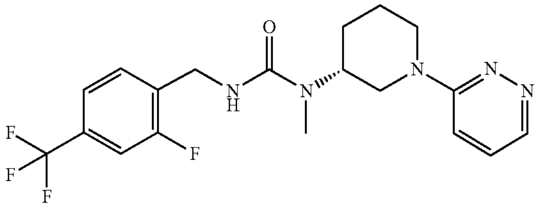 [SMILES: CN(C(=O)NCc1ccc(C(F)(F)F)cc1F)[C@@H]1CCCN(c2cccnn2)C1] 1-{[2-fluoro-4-(trifluoromethyl)phenyl]methyl}-3-methyl-3-[(3R)-1-(pyridazin-3-yl)piperidin-3-yl]urea | LC-MS: m/z 412.4 (M + H). |
| 50 | 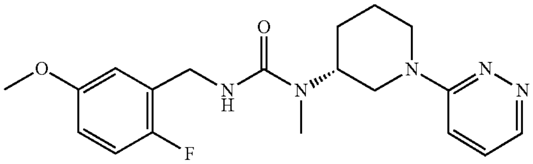 [SMILES: COc1ccc(F)c(CNC(=O)N(C)[C@@H]2CCCN(c3cccnn3)C2)c1] 3-[(2-fluoro-5-methoxyphenyl)methyl]-1-methyl-1-[(3R)-1-(pyridazin-3-yl)piperidin-3-yl]urea | LC-MS: m/z 374.3 (M + H). |
| 51 | 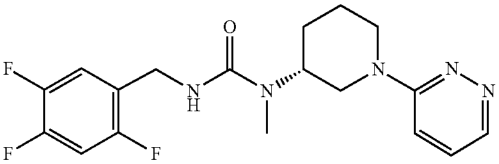 [SMILES: CN(C(=O)NCc1cc(F)c(F)cc1F)[C@@H]1CCCN(c2cccnn2)C1] 3-methyl-3-[(3R)-1-(pyridazin-3-yl)piperidin-3-yl]-1-[(2,4,5-trifluorophenyl)methyl]urea | 1H NMR (400 MHz, cdcl3) δ 8.56 (d, 1H), 7.35-7.37 (m, 1H), 7.25-7.20 (m, 1H), 7.04-7.98 (m, 1H), 6.92-6.83 (m, 1H), 6.46 (br, 1H), 4.49 (d, 2H), 4.42 (d, 1H), 4.13 (d, 1H), 10 |
| 52 | 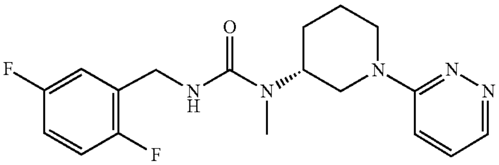 [SMILES: CN(C(=O)NCc1cc(F)ccc1F)[C@@H]1CCCN(c2cccnn2)C1] 1-[(2,5-difluorophenyl)methyl]-3-methyl-3-[(3R)-1-(pyridazin-3-yl)piperidin-3-yl]urea | LC-MS: m/z 362.36 (M + H). |
| 53 | 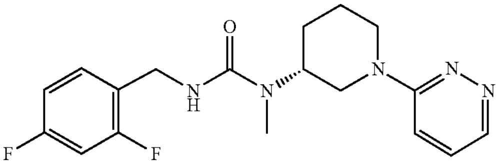 [SMILES: CN(C(=O)NCc1ccc(F)cc1F)[C@@H]1CCCN(c2cccnn2)C1] 1-[(2,4-difluorophenyl)methyl]-3-methyl-3-[(3R)-1-(pyridazin-3-yl)piperidin-3-yl]urea | LC-MS: m/z 362.26 (M + H). |

-continued

| Example | Structure and name | Data |
| --- | --- | --- |
| 54 | 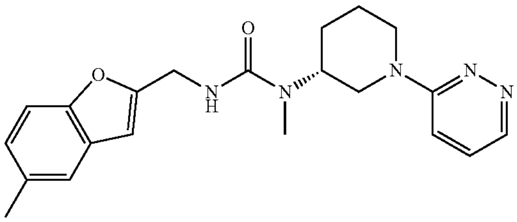 [SMILES: Cc1ccc2oc(CNC(=O)N(C)[C@@H]3CCCN(c4cccnn4)C3)cc2c1] 1-methyl-3-[(5-methyl-1-benzofuran-2-yl)methyl]-1-[(3R)-1-(pyridazin-3-yl)piperidin-3-yl]urea | LC-MS: m/z 380.3 (M + H). |
| 55 | 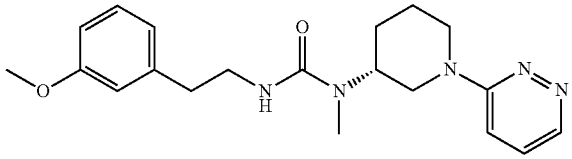 [SMILES: COc1cccc(CCNC(=O)N(C)[C@@H]2CCCN(c3cccnn3)C2)c1] 3-[2-(3-methoxyphenyl)ethyl]-1-methyl-1-[(3R)-1-(pyridazin-3-yl)piperidin-3-yl]urea | LC-MS: m/z 370.4 (M + H). |
| 56 | 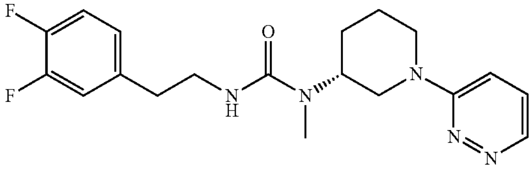 [SMILES: CN(C(=O)NCCc1ccc(F)c(F)c1)[C@@H]1CCCN(c2cccnn2)C1] 1-[2-(3,4-difluorophenyl)ethyl]-3-methyl-3-[(3R)-1-(pyridazin-3-yl)piperidin-3-yl]urea | LC-MS: m/z 376.37 (M + H). |
| 57 | 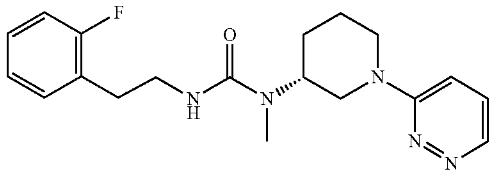 [SMILES: CN(C(=O)NCCc1ccccc1F)[C@@H]1CCCN(c2cccnn2)C1] 1-[2-(2-fluorophenyl)ethyl]-3-methyl-3-[(3R)-1-(pyridazin-3-yl)piperidin-3-yl]urea | LC-MS: m/z 358.36 (M + H). |
| 58 | 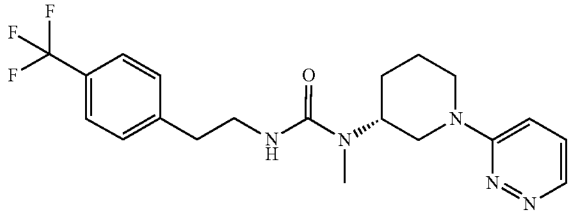 [SMILES: CN(C(=O)NCCc1ccc(C(F)(F)F)cc1)[C@@H]1CCCN(c2cccnn2)C1] 3-methyl-3-[(3R)-1-(pyridazin-3-yl)piperidin-3-yl]-1-{2-[4-(trifluoromethyl)phenyl]ethyl}urea | LC-MS: m/z 408.4 (M + H). |

-continued

| Example | Structure and name | Data |
|---|---|---|
| 59 | 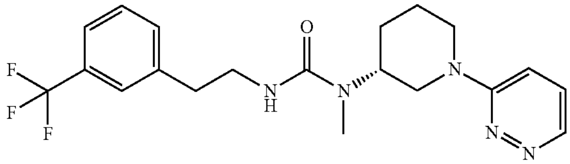 [SMILES: CN(C(=O)NCCc1cccc(C(F)(F)F)c1)[C@@H]1CCCN(c2cccnn2)C1] 3-methyl-3-[(3R)-1-(pyridazin-3-yl)piperidin-3-yl]-1-{2-[3-(trifluoromethyl)phenyl]ethyl}urea | LC-MS: m/z 408.4(M + H). |
| 60 | 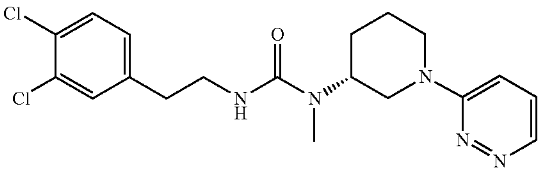 [SMILES: CN(C(=O)NCCc1ccc(Cl)c(Cl)c1)[C@@H]1CCCN(c2cccnn2)C1] 1-[2-(3,4-dichlorophenyl)ethyl]-3-methyl-3-[(3R)-1-(pyridazin-3-yl)piperidin-3-yl]urea | LC-MS: m/z 408.3(M + H). |
| 61 | 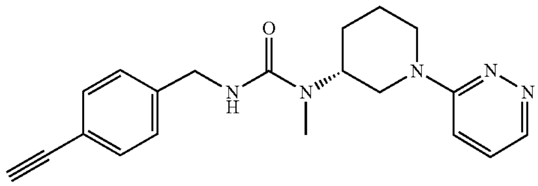 [SMILES: C#Cc1ccc(CNC(=O)N(C)[C@@H]2CCCN(c3cccnn3)C2)cc1] 1-[(4-ethynylphenyl)methyl]-3-methyl-3-[(3R)-1-(pyridazin-3-yl)piperidin-3-yl]urea | LC-MS: m/z 350.35 (M + H). |
| 62 | 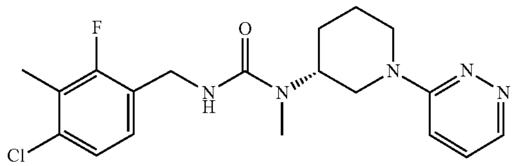 [SMILES: Cc1c(Cl)ccc(CNC(=O)N(C)[C@@H]2CCCN(c3cccnn3)C2)c1F] 3-[(4-chloro-2-fluoro-3-methylphenyl)methyl]-1-methyl-1-[(3R)-1-(pyridazin-3-yl)piperidin-3-yl]urea | LC-MS: m/z 392.2 (M + H). 1H NMR (400 MHz, MeOD) δ 8.44 (dd, J = 4.4, 1.1 Hz, 1H), 7.37 (dd, J = 9.4, 4.4 Hz, 1H), 7.28 (dd, J = 9.4, 1.0 Hz, 1H), 7.18-7.12 (m, 2H), 4.40 (s, 2H), 4.38-4.25 (m, 2H), 4.09 (dd, J = 9.8, 5.6 Hz, 1H), 3.04 (dd, J = 12.4, 11.5 Hz, 1H), 2.93-2.85 (m, 4H), 2.29 (d, J = 2.4 Hz, 3H), 1.92-1.84 (m, 3H), 1.74-1.61 (m, 1H). |
| 63 | 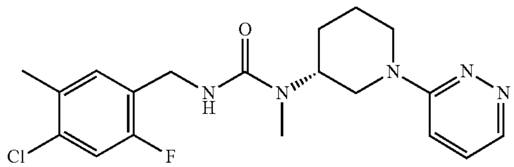 [SMILES: Cc1cc(CNC(=O)N(C)[C@@H]2CCCN(c3cccnn3)C2)c(F)cc1Cl] 3-[(4-chloro-2-fluoro-5-methylphenyl)methyl]-1-methyl-1-[(3R)-1-(pyridazin-3-yl)piperidin-3-yl]urea | LC-MS: m/z 392.2 (M + H). 1H NMR (400 MHz, MeOD) δ 8.45 (d, J = 4.0 Hz, 1H), 7.38 (dd, J = 9.4, 4.4 Hz, 1H), 7.31-7.23 (m, 2H), 7.11 (d, J = 9.7 Hz, 1H), 4.39-4.26 (m, 4H), 4.09 (dd, J = 9.6, 5.7 Hz, 1H), 3.04 (dd, J = 12.4, 11.4 Hz, 1H), 2.93-2.85 (m, 4H), 2.31 (s, 3H), 1.88 (dt, J = 9.6, 3.9 Hz, 3H), 1.74-1.62 (m, 1H). |

-continued

| Example | Structure and name | Data |
|---|---|---|
| 64 | 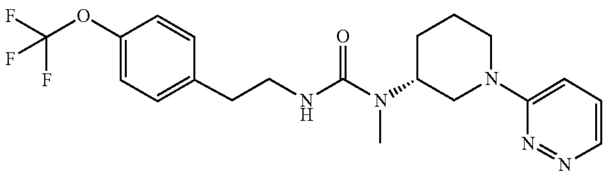 [SMILES: CN(C(=O)NCCc1ccc(OC(F)(F)F)cc1)[C@@H]1CCCN(c2cccnn2)C1] 1-methyl-1-[(3R)-1-(pyridazin-3-yl)piperidin-3-yl]-3-{2-[4-(trifluoromethoxy)phenyl]ethyl}urea | LC-MS: m/z 424.2 (M + H). 1H NMR (400 MHz, MeOD) δ 8.46 (dd, J = 4.4, 1.1 Hz, 1H), 7.39 (dd, J = 9.4, 4.4 Hz, 1H), 7.29 (dd, J = 12.7, 4.7 Hz, 3H), 7.16 (d, J = 8.0 Hz, 2H), 4.38-4.21 (m, 2H), 4.01 (s, 1H), 3.41 (t, J = 7.3 Hz, 2H), 3.00 (dd, J = 12.4, 11.4 Hz, 1H), 2.93-2.81 (m, 6H), 1.92-1.80 (m, 3H), 1.65 (dd, J = 14.5, 10.3 Hz, 1H). |
| 65 | 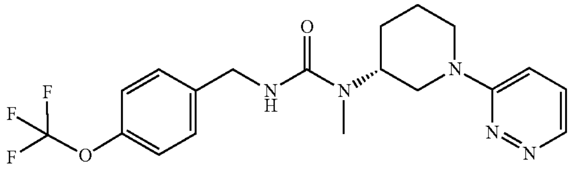 [SMILES: CN(C(=O)NCc1ccc(OC(F)(F)F)cc1)[C@@H]1CCCN(c2cccnn2)C1] 1-methyl-1-[(3R)-1-(pyridazin-3-yl)piperidin-3-yl]-3-{[4-(trifluoromethoxy)phenyl]methyl}urea | LC-MS: m/z 410 (M + H). 1H NMR (400 MHz, MeOD) δ 8.45 (d, J = 3.5 Hz, 1H), 7.44-7.34 (m, 3H), 7.28 (d, J = 9.3 Hz, 1H), 7.20 (d, J = 8.0 Hz, 2H), 4.40 (s, 2H), 4.38-4.26 (m, 2H), 4.10 (dt, J = 11.1, 7.7 Hz, 1H), 3.09-2.99 (m, 1H), 2.95-2.84 (m, 4H), 1.97-1.82 (m, 3H), 1.67 (dt, J = 8.2, 6.1 Hz, 1H). |
| 66 | 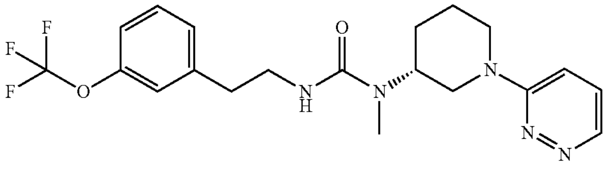 1-methyl-1-[(3R)-1-(pyridazin-3-yl)piperidin-3-yl]-3-{2-[3-(trifluoromethoxy)phenyl]ethyl}urea | LC-MS: m/z 410 (M + H). 1H NMR (400 MHz, MeOD) δ 8.46 (dd, J = 4.4, 1.1 Hz, 1H), 7.41-7.34 (m, 2H), 7.29-7.21 (m, 2H), 7.14(s, 1H), 7.09(d, J = 8.2 Hz, 1H), 4.37-4.20(m,2H), 4.00(d, J = 9.4 Hz, 1H), 3.43(t, J = 7.3 Hz, 2H), 2.99 (dd, J = 12.4, 11.5 Hz, 1H), 2.91 (d, J = 12.1 Hz, 1H), 2.86 (d, J = 7.1 Hz, 2H), 2.82 (s, 3H), 1.91-1.81 (m, 3H), 1.70-1.58 (m, 1H). |
| 67 | 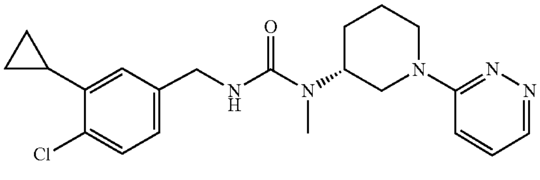 [SMILES: CN(C(=O)NCc1ccc(Cl)c(C2CC2)c1)[C@@H]1CCCN(c2cccnn2)C1] 3-[(4-chloro-3-cyclopropylphenyl)methyl]-1-methyl-1-[(3R)-1-(pyridazin-3-yl)piperidin-3-yl]urea | LC-MS: m/z 400.1 (M + H). 1H NMR (400 MHz, MeOD) δ 8.45 (d, J = 4.0 Hz, 1H), 7.38 (dd, J = 9.4, 4.4 Hz, 1H), 7.33-7.24 (m, 2H), 7.08 (dd, J = 8.1, 2.0 Hz, 1H), 6.94 (d, J = 1.9 Hz, 1H), 4.36 (d, J = 13.1 Hz, 1H), 4.30 (s, 2H), 4.30-4.24 (m, 1H), 4.13-4.03 (m, 1H), 3.08-3.00 (m, 1H), 2.94-2.86 (m, 4H), 2.16 (ddd, J = 8.4, 5.2, 3.2 Hz, 1H), 1.94-1.82 (m, 3H), 1.68 (dd, J = 10.6, 7.8 Hz, 1H), 1.04-0.93 (m, 2H), 0.66 (dt, J = 9.9, 5.1 Hz, 2H). |
| 68 | 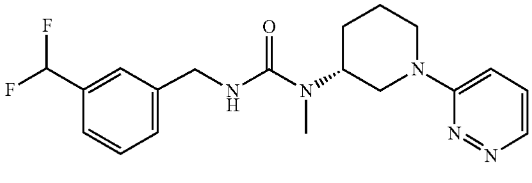 [SMILES: CN(C(=O)NCc1cccc(C(F)F)c1)[C@@H]1CCCN(c2cccnn2)C1] 3-{[3-(difluoromethyl)phenyl]methyl}-1-methyl-1-[(3R)-1-(pyridazin-3-yl)piperidin-3-yl]urea | LC-MS: m/z 376.2(M + H). 1H NMR (400 MHz, MeOD) δ 8.45 (dd, J = 4.4, 1.2 Hz, 1H), 7.50-7.36 (m, 5H), 7.29 (dd, J = 9.4, 1.2 Hz, 1H), 6.74 (t, J = 56.3 Hz, 1H), 4.44-4.26 (m, 4H), 4.17-4.05 (m, 1H), 3.05 (dd, J = 12.4, 11.4 Hz, 1H), 2.93-2.86 (m, 4H), 1.93-1.86 (m, 3H), 1.74-1.62 (m, 1H). |
| 69 | 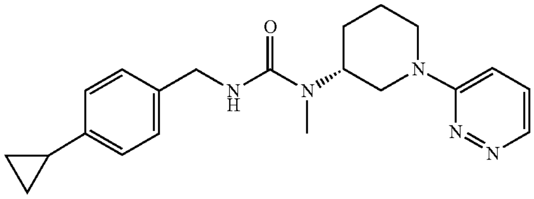 [SMILES: CN(C(=O)NCc1ccc(C2CC2)cc1)[C@@H]1CCCN(c2cccnn2)C1] 3-[(4-cyclopropylphenyl)methyl]-1-methyl-1-[(3R)-1-(pyridazin-3-yl)piperidin-3-yl]urea | LC-MS: m/z 366.2 (M + H). 1H NMR (400 MHz, MeOD) δ 8.44 (dd, J = 4.4, 1.1 Hz, 1H), 7.38 (dd, J = 9.4, 4.4 Hz, 1H), 7.28(dd, J = 9.4, 1.2 Hz, 1H), 7.17(d, J = 8.2 Hz, 2H), 7.00(d, J = 8.1 Hz, 2H), 4.42-4.23 (m, 4H), 4.17-4.05 (m, 1H), 3.03 (dd, J = 12.4, 11.4 Hz, 1H), 2.93-2.82 (m, 4H), 1.93-1.82 (m, 4H), 1.68 (s, 1H), 0.92 (ddd, J = 8.4, 6.3, 4.3 Hz, 2H), 0.67-0.58 (m, 2H). |

-continued

| Example | Structure and name | Data |
|---|---|---|
| 70 | 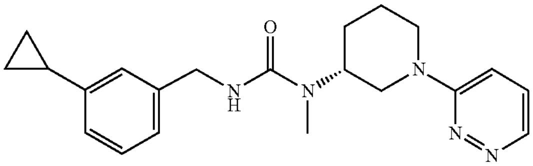 [SMILES: CN(C(=O)NCc1cccc(C2CC2)c1)[C@@H]1CCCN(c2cccnn2)C1] 3-[(3-cyclopropylphenyl)methyl]-1-methyl-1-[(3R)-1-(pyridazin-3-yl)piperidin-3-yl]urea | LC-MS: m/z 366.2 (M + H). 1H NMR (400 MHz, MeOD) δ 8.45 (d, J = 3.5 Hz, 1H), 7.38 (dd, J = 9.4, 4.4 Hz, 1H), 7.29 (dd, J = 9.4, 1.1 Hz, 1H), 7.16 (t, J = 7.6 Hz, 1H), 7.08-6.97 (m, 2H), 6.92 (d, J = 7.6 Hz, 1H), 4.43-4.22 (m, 4H), 4.10 (dt, J = 11.3, 7.6 Hz, 1H), 3.09-2.99 (m, 1H), 2.94-2.84 (m, 4H), 1.95-1.82 (m, 4H), 1.75-1.62 (m, 1H), 0.96-0.85 (m, 2H), 0.69-0.57 (m, 2H). |
| 71 | 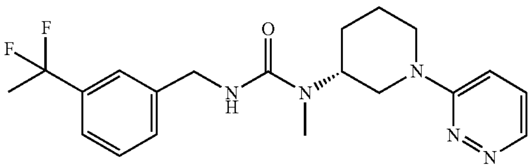 [SMILES: CN(C(=O)NCc1cccc(C(C)(F)F)c1)[C@@H]1CCCN(c2cccnn2)C1] 3-{[3-(1,1-difluoroethyl)phenyl]methyl}-1-methyl-1-[(3R)-1-(pyridazin-3-yl)piperidin-3-yl]urea | LC-MS: m/z 390.1 (M + H). 1H NMR (400 MHz, DMSO) δ 8.52 (dd, J = 4.4, 1.2 Hz, 1H), 7.47-7.33 (m, 5H), 7.24 (dd, J = 9.3, 1.2 Hz, 1H), 7.06 (t, J = 5.8 Hz, 1H), 4.37-4.21 (m, 4H), 4.06-3.94 (m, 1H), 3.02-2.94 (m, 1H), 2.85-2.77 (m, 4H), 1.95 (t, J = 18.8 Hz, 3H), 1.83-1.70 (m, 3H), 1.62-1.50 (m, 1H). |
| 72 | 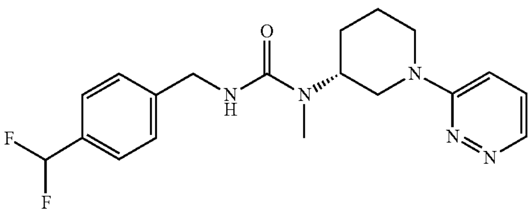 [SMILES: CN(C(=O)NCc1ccc(C(F)F)cc1)[C@@H]1CCCN(c2cccnn2)C1] 3-{[4-(difluoromethyl)phenyl]methyl}-1-methyl-1-[(3R)-1-(pyridazin-3-yl)piperidin-3-yl]urea | LC-MS: m/z 376.2 (M + H). 1H NMR (400 MHz, MeOD) δ 8.44 (d, J = 2.5 Hz, 1H), 7.40 (ddd, J = 16.3, 13.6, 6.2 Hz, 5H), 7.27 (dd, J = 9.4, 0.9 Hz, 1H), 6.72 (t, J = 56.4 Hz, 1H), 4.43 (s, 2H), 4.38-4.26 (m, 2H), 4.10 (dt, J = 11.1, 7.8 Hz, 1H), 3.03 (dd, J = 12.4, 11.4 Hz, 1H), 2.94-2.82 (m, 4H), 1.92-1.81 (m, 3H), 1.72-1.59 (m, 1H). |
| 73 | 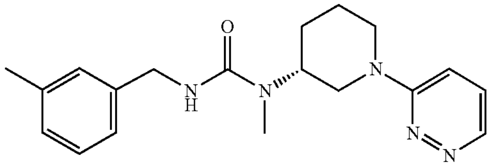 [SMILES: Cc1cccc(CNC(=O)N(C)[C@@H]2CCCN(c3cccnn3)C2)c1] 1-methyl-3-[(3-methylphenyl)methyl]-1-[(3R)-1-(pyridazin-3-yl)piperidin-3-yl]urea | LC-MS: m/z 340.2 (M + H). 1H NMR (400 MHz, MeOD) δ 8.44 (dd, J = 4.4, 0.9 Hz, 1H), 7.37 (dd, J = 9.4, 4.4 Hz, 1H), 7.28 (dd, J = 9.4, 1.2 Hz, 1H), 7.10 (ddd, J = 31.1, 19.2, 7.5 Hz, 4H), 4.41-4.24 (m, 4H), 4.11 (dd, J = 9.7, 5.5 Hz, 1H), 3.04 (dd, J = 12.5, 11.3 Hz, 1H), 2.95-2.84 (m, 4H), 2.31 (s, 3H), 1.93-1.83 (m, 3H), 1.74-1.61 (m, 1H). |
| 75 | 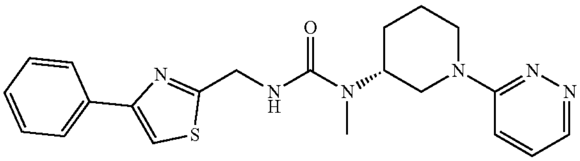 [SMILES: CN(C(=O)NCc1nc(-c2ccccc2)cs1)[C@@H]1CCCN(c2cccnn2)C1] 1-methyl-3-[(4-phenyl-1,3-thiazol-2-yl)methyl]-1-[(3R)-1-(pyridazin-3-yl)piperidin-3-yl]urea | LC-MS: m/z 409.2 (M + H). 1H NMR (400 MHz, MeOD) δ 8.44 (dd, J = 4.4, 1.2 Hz, 1H), 7.88 (dd, J = 5.2, 3.3 Hz, 2H), 7.69 (s, 1H), 7.43-7.25 (m, 5H), 4.72 (s, 2H), 4.36 (t, J = 14.0 Hz, 2H), 4.18-4.05 (m, 1H), 3.15-3.04 (m, 1H), 2.99-2.85 (m, 4H), 1.97-1.85 (m, 3H), 1.76-1.62 (m, 1H). |

-continued

| Example | Structure and name | Data |
|---|---|---|
| 76 | 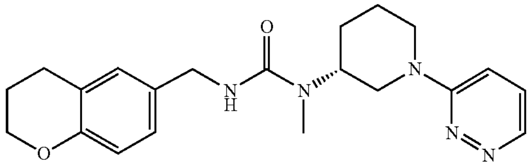 [SMILES: CN(C(=O)NCc1ccc2c(c1)CCCO2)[C@@H]1CCCN(c2cccnn2)C1] 3-[(3,4-dihydro-2H-1-benzopyran-6-yl)methyl]-1-methyl-1-[(3R)-1-(pyridazin-3-yl)piperidin-3-yl]urea | LC-MS: m/z 382 (M + H). |
| 77 | 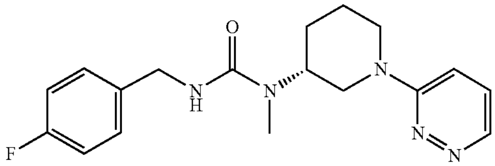 [SMILES: CN(C(=O)NCc1ccc(F)cc1)[C@@H]1CCCN(c2cccnn2)C1] 3-[(4-fluorophenyl)methyl]-1-methyl-1-[(3R)-1-(pyridazin-3-yl)piperidin-3-yl]urea | LC-MS: m/z 344.2(M + H). 1H NMR (400 MHz, DMSO) δ 8.52 (dd, J = 4.4, 1.0 Hz, 1H), 7.30 (tdd, J = 10.3, 9.3, 2.7 Hz, 4H), 7.13 (t, J = 8.9 Hz, 2H), 7.00 (s, 1H), 4.38-4.15 (m, 4H), 3.99 (dd, J = 13.3, 9.4 Hz, 1H), 3.02-2.90 (m, 1H), 2.80 (s, 4H), 1.86-1.66 (m, 3H), 1.54 (d, J = 12.8 Hz, 1H). |
| 78 | 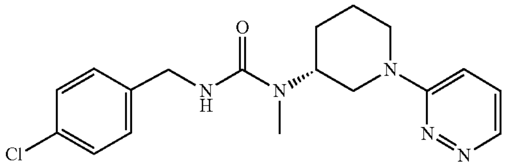 [SMILES: CN(C(=O)NCc1ccc(Cl)cc1)[C@@H]1CCCN(c2cccnn2)C1] 3-[(4-chlorophenyl)methyl]-1-methyl-1-[(3R)-1-(pyridazin-3-yl)piperidin-3-yl]urea | LC-MS: m/z 360.2 (M + H). 1H NMR (400 MHz, DMSO) § 8.52 (d, J = 3.5 Hz, 1H), 7.44-7.16 (m, 6H), 7.02 (t, J = 5.7 Hz, 1H), 4.38-4.17(m, 4H), 3.99(t, J = 11.3 Hz, 1H),2.96(t, J = 11.8 Hz, 1H), 2.86-2.74 (m, 4H), 1.76 (dd, J = 22.8, 7.9 Hz, 3H), 1.55 (t, J = 13.1 Hz, 1H). |
| 79 | 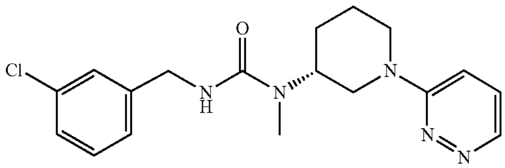 [SMILES: CN(C(=O)NCc1cccc(Cl)c1)[C@@H]1CCCN(c2cccnn2)C1] 3-[(3-chlorophenyl)methyl]-1-methyl-1-[(3R)-1-(pyridazin-3-yl)piperidin-3-yl]urea | LC-MS: m/z 360.2 (M + H). 1H NMR (400 MHz, MeOD) δ 8.45 (s, 1H), 7.38 (dd, J = 9.2, 4.2 Hz, 1H), 7.34-7.16 (m, 5H), 4.41-4.25 (m, 4H), 4.15-4.05 (m, 1H), 3.05 (dd, J = 12.5, 11.3 Hz, 1 H), 2.95-2.85 (m, 4H), 1.94-1.84 (m, 3H), 1.74-1.62 (m, 1H). |
| 80 | 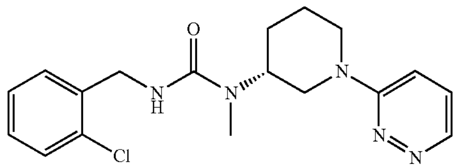 3-[(2-chlorophenyl)methyl]-1-methyl-1-[(3R)-1-(pyridazin-3-yl)piperidin-3-yl]urea | LC-MS: m/z 360.2 (M + H). 1H NMR (400 MHz, MeOD) δ 8.44 (d, J = 3.9 Hz, 1H), 7.42-7.18 (m, 6H), 4.48 (s, 2H), 4.41-4.28 (m, 2H), 4.12 (dd, J = 9.8, 5.5 Hz, 1H), 3.06 (dd, J = 12.5, 11.3 Hz, 1H), 2.96-2.85 (m, 4H), 1.95-1.84 (m, 3H), 1.76-1.63 (m, 1H). |
| 81 | 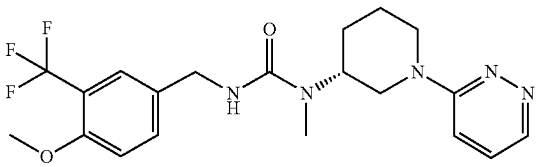 [SMILES: COc1ccc(CNC(=O)N(C)[C@@H]2CCCN(c3cccnn3)C2)cc1C(F)(F)F] 3-{[4-methoxy-3-(trifluoromethyl)phenyl]methyl}-1-methyl-1-[(3R)-1-(pyridazin-3-yl)piperidin-3-yl]urea | LC-MS: m/z 424.2 (M + H). 1H NMR (400 MHz, MeOD) δ 8.45 (dd, J = 4.4, 1.0 Hz, 1H), 7.52 (d, J = 7.7 Hz, 2H), 7.37(dd, J = 9.4, 4.4 Hz, 1H), 7.28(dd, J = 9.4, 1.1Hz, 1H), 7.11(d, J = 8.4 Hz, 1H), 4.41-4.23 (m, 4H), 4.14-4.03 (m, 1H), 3.87 (s, 3H), 3.04 (dd, J = 12.4, 11.3 Hz, 1H), 2.95-2.84 (m, 4H), 1.88 (dt, J = 9.5, 4.2 Hz, 3H), 1.67 (dd, J = 11.4, 7.3 Hz, 1H). |

-continued

| Example | Structure and name | Data |
|---|---|---|
| 82 | 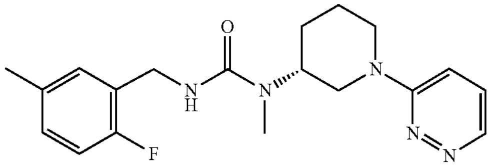 [SMILES: Cc1ccc(F)c(CNC(=O)N(C)[C@@H]2CCCN(c3cccnn3)C2)c1] 3-[(2-fluoro-5-methylphenyl)methyl]-1-methyl-1-[(3R)-1-(pyridazin-3-yl)piperidin-3-yl]urea | LC-MS: m/z 358.2 (M + H). 1H NMR (400 MHz, MeOD) δ 8.44 (dd, J = 4.4, 0.9 Hz, 1H), 7.37 (dd, J = 9.4, 4.4 Hz, 1H), 7.28 (dd, J = 9.4, 1.2 Hz, 1H), 7.14 (dd, J = 7.3, 1.7 Hz, 1H), 7.06-7.00 (m, 1H), 6.90 (dd, J = 10.1, 8.4 Hz, 1H), 4.41-4.24 (m, 4H), 4.11 (dt, J = 11.2, 7.8 Hz, 1H), 3.04 (dd, J = 12.5, 11.3 Hz, 1H), 2.92-2.84 (m, 4H), 2.29 (s, 3H), 1.93-1.84 (m, 3H), 1.69 (ddd, J = 12.6, 8.1, 3.4 Hz, 1H). |
| 83 | 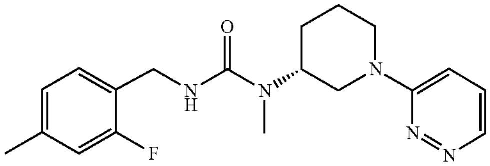 [SMILES: Cc1ccc(CNC(=O)N(C)[C@@H]2CCCN(c3cccnn3)C2)c(F)c1] 3-[(2-fluoro-4-methylphenyl)methyl]-1-methyl-1-[(3R)-1-(pyridazin-3-yl)piperidin-3-yl]urea | LC-MS: m/z 358.2 (M + H). 1H NMR (400 MHz, MeOD) δ 8.44 (dd, J = 4.4, 1.1 Hz, 1H), 7.37 (dd, J = 9.4, 4.4 Hz, 1H), 7.28 (d, J = 9.3 Hz, 1H), 7.21 (t, J = 7.9 Hz, 1H), 6.93(d, J = 7.8 Hz, 1H),6.87(d, J = 11.4 Hz, 1H), 4.38 (d, J = 10.8 Hz, 3H), 4.28 (dd, J = 12.5, 3.9 Hz, 1H), 4.10 (dd, J = 9.6, 5.7 Hz, 1H), 3.09-3.00 (m, 1H), 2.92 (m, 4H), 2.31 (s, 3H), 1.93-1.83 (m, 3H), 1.68 (dd, J = 12.8, 5.2 Hz, 1H). |
| 84 | 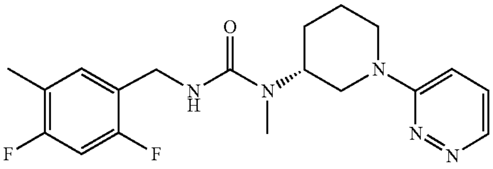 [SMILES: Cc1cc(CNC(=O)N(C)[C@@H]2CCCN(c3cccnn3)C2)c(F)cc1F] 3-[(2,4-difluoro-5-methylphenyl)methyl]-1-methyl-1-[(3R)-1-(pyridazin-3-yl)piperidin-3-yl]urea | LC-MS: m/z 376.2 (M + H). 1H NMR (400 MHz, MeOD) δ 8.45 (d, J = 3.9 Hz, 1H), 7.39 (dd, J = 9.4, 4.4 Hz, 1H), 7.30(dd, J = 9.4,1.1Hz, 1H), 7.21(t, J = 8.6 Hz, 1H), 6.82(t, J = 9.9 Hz, 1H), 4.41-4.25 (m, 4H), 4.15-4.05 (m, 1H), 3.04 (dd, J = 12.5, 11.3 Hz, 1H), 2.93-2.84 (m, 4H), 2.21 (s, 3H), 1.93-1.82 (m, 3H), 1.75-1.61 (m, 1H). |
| 85 | 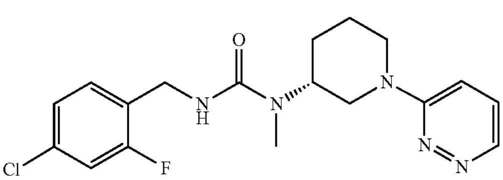 [SMILES: CN(C(=O)NCc1ccc(Cl)cc1F)[C@@H]1CCCN(c2cccnn2)C1] 3-[(4-chloro-2-fluorophenyl)methyl]-1-methyl-1-[(3R)-1-(pyridazin-3-yl)piperidin-3-yl]urea | LC-MS: m/z 378.1(M + H). 1H NMR (400 MHz, MeOD) δ 8.45 (dd, J = 4.4, 0.9 Hz, 1H), 7.41-7.26 (m, 3H), 7.20-7.06 (m, 2H), 4.43-4.25 (m, 4H), 4.09 (dt, J = 11.3, 7.6 Hz, 1H), 3.04 (dd, J = 12.4, 11.4 Hz, 1H), 2.94-2.84 (m, 4H), 1.93-1.82 (m, 3H), 1.74-1.61 (m, 1H). |
| 86 | 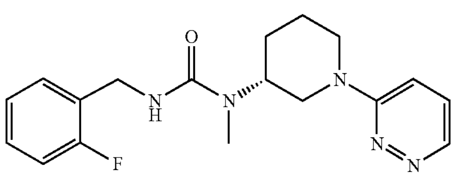 [SMILES: CN(C(=O)NCc1ccccc1F)[C@@H]1CCCN(c2cccnn2)C1] 3-[(2-fluorophenyl)methyl]-1-methyl-1-[(3R)-1-(pyridazin-3-yl)piperidin-3-yl]urea | LC-MS: m/z 344.2(M + H). 1H NMR (400 MHz, MeOD) δ 8.44 (d, J = 3.4 Hz, 1H), 7.40-7.32 (m, 2H), 7.30-7.20 (m, 2H), 7.15-7.08 (m, 1H), 7.07-7.00 (m, 1H), 4.45 (s, 2H), 4.36 (d, J = 13.2 Hz, 1H), 4.28 (dd, J = 12.6, 3.7 Hz, 1H), 4.10 (dd, J = 9.6, 5.5 Hz, 1H), 3.03 (dd, J = 12.3, 11.5 Hz, 1H), 2.92-2.84 (m, 4H), 1.87 (dd, J = 10.6, 4.6 Hz, 3H), 1.72-1.60 (m, 1H). |
| 87 | 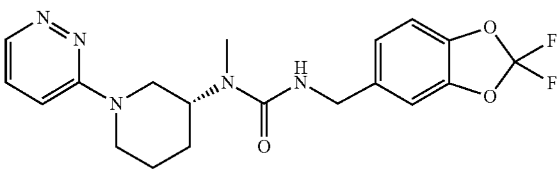 [SMILES: CN(C(=O)NCc1ccc2c(c1)OC(F)(F)O2)[C@@H]1CCCN(c2cccnn2)C1] 3-[(2,2-difluoro-2H-1,3-benzodioxol-5-yl)methyl]-1-methyl-1-[(3R)-1-(pyridazin-3-yl)piperidin-3-yl]urea | LC-MS: m/z 406 (M + H). 1H NMR (400 MHz, MeOD) δ 8.45 (s, 1H), 7.38 (s, 1H), 7.29 (d, J = 9.3 Hz, 1H), 7.17 (s, 1H), 7.11 (d, J = 0.8 Hz, 2H), 4.37 (s, 2H), 4.36-4.25 (m, 2H), 4.13-4.05 (m, 1H), 3.07-3.01 (m, 1H), 2.94-2.86 (m, 4H), 1.89 (dd, J = 9.9, 4.8 Hz, 3H), 1.72-1.62 (m, 1H). |

-continued

| Example | Structure and name | Data |
|---|---|---|
| 88 | 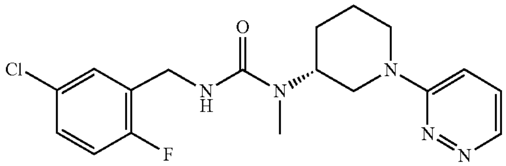 [SMILES: CN(C(=O)NCc1cc(Cl)ccc1F)[C@@H]1CCCN(c2cccnn2)C1] 3-[(5-chloro-2-fluorophenyl)methyl]-1-methyl-1-[(3R)-1-(pyridazin-3-yl)piperidin-3-yl]urea | LC-MS: m/z 378.2 (M + H). 1H NMR (400 MHz, MeOD) δ 8.45 (dd, J = 4.4, 1.1 Hz, 1H), 7.40 (dd, J = 9.4, 4.4 Hz, 1H), 7.35-7.29 (m, 2H), 7.24 (ddd, J = 8.6, 4.4, 2.7 Hz, 1H), 4.43-4.26 (m, 4H), 4.10 (dd, J = 9.6, 5.7 Hz, 1H), 3.07 (dd, J = 12.5, 11.3 Hz, 1H), 2.95-2.87 (m, 4H), 1.93-1.85 (m, 3H), 1.75-1.63 (m, 1H). |
| 89 | 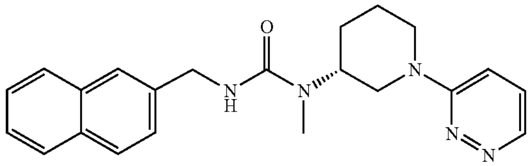 [SMILES: CN(C(=O)NCc1ccc2ccccc2c1)[C@@H]1CCCN(c2cccnn2)C1] 1-methyl-3-[(naphthalen-2-yl)methyl]-1-[(3R)-1-(pyridazin-3-yl)piperidin-3-yl]urea | LC-MS: m/z 376.1 (M + H). 1H NMR (400 MHz, MeOD) δ 8.43 (d, J = 3.7 Hz, 1H), 7.84-7.77 (m, 3H), 7.74 (s, 1H), 7.48-7.39 (m, 3H), 7.34 (dd, J = 9.4, 4.4 Hz, 1H), 7.25 (dd, J = 9.4, 1.2 Hz, 1H), 4.55 (s, 2H), 4.39-4.26 (m, 2H), 4.18-4.09 (m, 1H), 3.04 (dd, J = 12.4, 11.3 Hz, 1H), 2.92 (s, 3H), 2.91-2.84 (m, 1H), 1.88 (dd, J = 13.6, 5.5 Hz, 3H), 1.73-1.62 (m, 1H). |
| 90 | 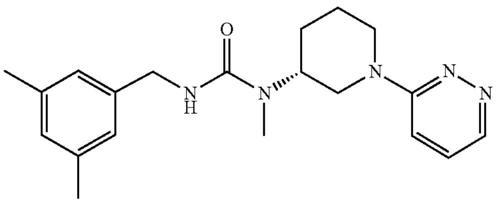 [SMILES: Cc1cc(C)cc(CNC(=O)N(C)[C@@H]2CCCN(c3cccnn3)C2)c1] 3-[(3,5-dimethylphenyl)methyl]-1-methyl-1-[(3R)-1-(pyridazin-3-yl)piperidin-3-yl]urea | LC-MS: m/z 376.1 (M + H). 1H NMR (400 MHz, MeOD) δ 8.45 (s, 1H), 7.37 (dd, J = 9.3, 4.1 Hz, 1H), 7.28 (d, J = 9.3 Hz, 1 H), 6.90 (s, 2H), 6.85 (s, 1H), 4.38 (d, J = 13.6 Hz, 1H), 4.30 (s, 2H), 4.26 (d, J = 3.9 Hz, 1H), 4.11 (dd, J = 9.7, 5.4 Hz, 1H), 3.04 (dd, J = 12.4, 11.3 Hz, 1H), 2.95-2.83 (m, 3H), 2.26 (s, 5H), 1.89 (dd, J = 10.8, 4.4 Hz, 2H), 1.76-1.58 (m, 1H). |
| 91 | 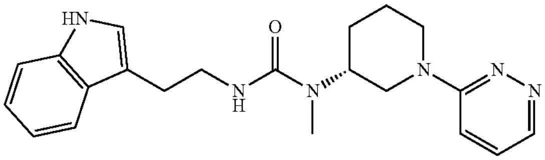 [SMILES: CN(C(=O)NCCc1c[nH]c2ccccc12)[C@@H]1CCCN(c2cccnn2)C1] 3-[2-(1H-indol-3-yl)ethyl]-1-methyl-1-[(3R)-1-(pyridazin-3-yl)piperidin-3-yl]urea | LC-MS: m/z 379.4 (M + H). 1H NMR (400 MHz, MeOD) δ 8.45 (s, 1H), 7.56 (d, J = 7.7 Hz, 1H), 7.35 (s, 1H), 7.30 (d, J = 8.1 Hz, 1H), 7.20 (d, J = 8.8 Hz, 1H), 7.09-7.02 (m, 2H), 7.01-6.93 (m, 1H), 4.36 (d, J = 13.8 Hz, 1H), 4.17 (dd, J = 12.7, 3.8 Hz, 1H), 3.98 (s, 1H), 3.54-3.44 (m, 2H), 3.02-2.93 (m, 3H), 2.85 (dd, J = 18.5, 8.0 Hz, 1H), 2.79 (s, 3H), 1.92-1.78 (m, 3H), 1.61 (d, J = 8.6 Hz, 1H). |
| 92 | 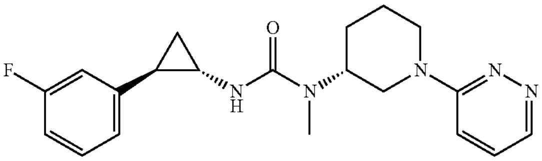 [SMILES: CN(C(=O)N[C@H]1C[C@@H]1c1cccc(F)c1)[C@@H]1CCCN(c2cccnn2)C1] 3-[(1S,2R)-2-(3-fluorophenyl)cyclopropyl]-1-methyl-1-[(3R)-1-(pyridazin-3-yl)piperidin-3-yl]urea | LC-MS: m/z 370.2(M + H). |
| 93 | 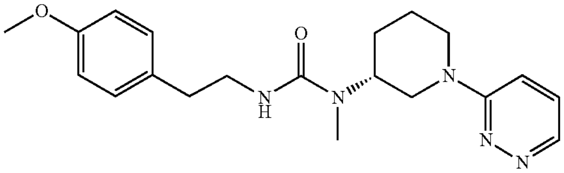 [SMILES: COc1ccc(CCNC(=O)N(C)[C@@H]2CCCN(c3cccnn3)C2)cc1] 3-[2-(4-methoxyphenyl)ethyl]-1-methyl-1-[(3R)-1-(pyridazin-3-yl)piperidin-3-yl]urea | LC-MS: m/z 370.4(M + H). 1H NMR (400 MHz, MeOD) δ 8.46 (dd, J = 4.4, 1.1 Hz, 1H), 7.40 (dd, J = 9.4, 4.4 Hz, 1H), 7.28 (dd, J = 9.4, 1.2 Hz, 1H), 7.16-7.06 (m, 2H), 6.87-6.77 (m, 2H), 4.36 (d, J = 13.2 Hz, 1H), 4.22 (dd, J = 12.7, 3.8 Hz, 1H), 4.01(d, J = 5.5 Hz, 1H), 3.73 (d, J = 3.5 Hz, 3H), 3.40-3.33 (m, 2H), 3.00 (dd, J = 12.5, 11.3 Hz, 1H), 2.93-2.81 (m, 4H), 2.74 (t, J = 7.4 Hz, 2H), 1.95-1.80 (m, 3H), 1.73-1.57 (m, 1H). |

-continued

| Example | Structure and name | Data |
|---|---|---|
| 94 | 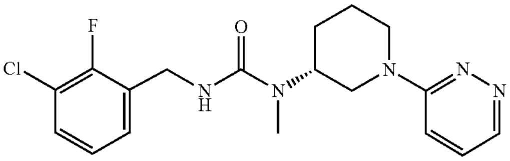 [SMILES: CN(C(=O)NCc1cccc(Cl)c1F)[C@@H]1CCCN(c2cccnn2)C1] 3-[(3-chloro-2-fluorophenyl)methyl]-1-methyl-1-[(3R)-1-(pyridazin-3-yl)piperidin-3-yl]urea | LC-MS: m/z 378.3 (M + H). 1H NMR (400 MHz, MeOD) δ 8.45 (s, 1H), 7.43-7.25 (m, 4H), 7.11 (td, J = 7.9, 1.1 Hz, 1H), 4.46 (s, 2H), 4.40-4.25 (m, 2H), 4.09 (dt, J = 11.2, 7.6 Hz, 1H), 3.05 (dd, J = 12.5, 11.3 Hz, 1H), 2.94-2.86 (m, 4H), 1.89 (tt, J = 9.6, 5.0 Hz, 3H), 1.75-1.63 (m, 1H). |
| 95 | 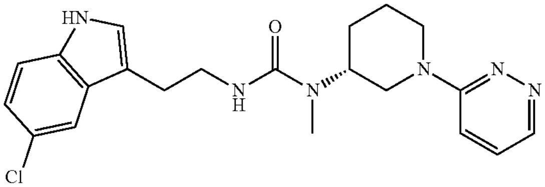 3-[2-(5-chloro-1H-indol-3-yl)ethyl]-1-methyl-1-[(3R)-1-(pyridazin-3-yl)piperidin-3-yl]urea | LC-MS: m/z 378.3 (M + H). 1HNMR (400 MHz, MeOD) δ8.45 (d, J = 3.9 Hz, 1H), 7.54(d, J = 2.0 Hz, 1H), 7.37 (dd, J = 9.4, 4.3 Hz, 1H), 7.26(d, J = 8.6 Hz, 1H), 7.20(d, J = 8.7 Hz, 1H), 7.12 (s,1H), 7.02 (dd, J = 8.6,2.0 Hz, 1H), 4.36 (d, J = 13.8 Hz, 1H), 4.13 (d, J = 12.3 Hz, 1H), 3.94 (s, 1H), 3.50-3.42 (m, 2H), 3.01-2.83 (m, 4H), 2.81 (s, 3H), 1.84 (t, J = 7.6 Hz, 3H), 1.60 (d, J = 9.1Hz, 1H). |
| 96 | 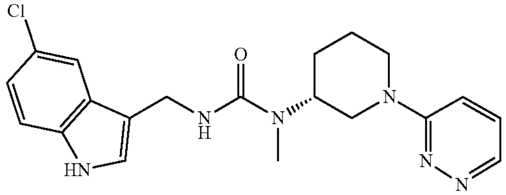 3-[(5-chloro-1H-indol-3-yl)methyl]-1-methyl-1-[(3R)-1-(pyridazin-3-yl)piperidin-3-yl]urea | LC-MS: m/z 388.3 (M + H). 1H NMR (400 MHz, DMSO) δ 11.04 (s, 1H), 8.57-8.47 (m, 1H), 7.73 (d, J = 2.0 Hz, 1H), 7.37-7.31 (m, 2H), 7.28 (d, J = 2.2 Hz, 1H), 7.20 (dd, J = 9.3, 1.0 Hz, 1H), 7.05 (dd, J = 8.6, 2.1 Hz, 1H), 6.77 (t, J = 5.5 Hz, 1H), 4.43-4.29 (m, 3H), 4.16 (d, J = 12.5 Hz, 1H), 4.00 (t, J = 11.3 Hz, 1H), 2.98-2.91 (m, 1H), 2.76 (s, 4H), 1.81-1.67 (m, 3H), 1.55 (t, J = 13.1 Hz, 1H). |
| 97 | 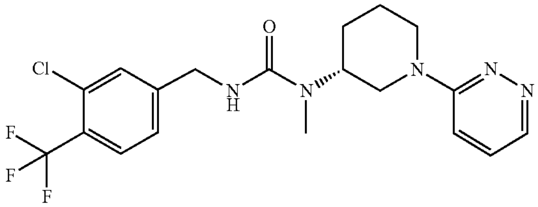 [SMILES: CN(C(=O)NCc1ccc(C(F)(F)F)c(Cl)c1)[C@@H]1CCCN(c2cccnn2)C1] 3-{[3-chloro-4-(trifluoromethyl)phenyl]methyl}-1-methyl-1-[(3R)-1-(pyridazin-3-yl)piperidin-3-yl]urea | LC-MS: m/z 428.3 (M + H). 1H NMR (400 MHz, DMSO) δ 8.52 (dd, J = 4.4, 1.1 Hz, 1H), 7.81 (d, J = 8.1 Hz, 1H), 7.59 (s, 1H), 7.44 (d, J = 8.3 Hz, 1H), 7.35 (dd, J = 9.3, 4.4 Hz, 1H), 7.25 (dd, J = 9.3,1.1Hz, 1H), 7.14(t, J = 5.7 Hz, 1H), 4.40-4.18(m, 4H), 4.03-3.93 (m, 1H), 3.03-2.92 (m, 1H), 2.87-2.76 (m, 4H), 1.78 (dt, J = 9.8, 8.7 Hz, 3H), 1.61-1.46 (m, 1H). |
| 98 | 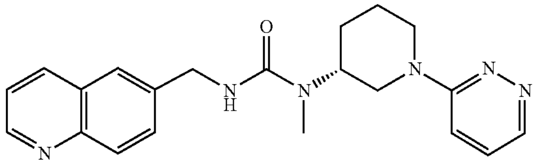 [SMILES: CN(C(=O)NCc1ccc2ncccc2c1)[C@@H]1CCCN(c2cccnn2)C1] 1-methyl-1-[(3R)-1-(pyridazin-3-yl)piperidin-3-yl]-3-[(quinolin-6-yl)methyl]urea | LC-MS: m/z 377.4 (M + H). 1H NMR (400 MHz, MeOD) δ 8.80 (dd, J = 4.3, 1.7 Hz, 1H), 8.44 (d, J = 3.3 Hz, 1H), 8.35(d, J = 7.5 Hz, 1H), 7.99(d, J = 8.7 Hz, 1H), 7.84(s, 1H), 7.77 (dd, J = 8.7, 1.9 Hz, 1H), 7.52 (dd, J = 8.3, 4.3 Hz, 1H), 7.37 (dd, J = 9.4, 4.4 Hz, 1H), 7.29 (dd, J = 9.4, 1.2 Hz, 1H), 4.59 (s, 2H), 4.35 (t, J = 14.5 Hz, 2H), 4.12 (s, 1H), 3.11-3.03 (m, 1H), 2.96-2.87 (m, 4H), 1.91 (t, J = 7.6 Hz, 3H), 1.68 (s, 1H). |

-continued

| Example | Structure and name | Data |
| --- | --- | --- |
| 99 | 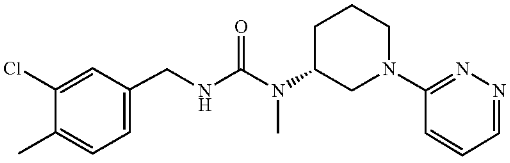 [SMILES: Cc1ccc(CNC(=O)N(C)[C@@H]2CCCN(c3cccnn3)C2)cc1Cl] 3-[(3-chloro-4-methylphenyl)methyl]-1-methyl-1-[(3R)-1-(pyridazin-3-yl)piperidin-3-yl]urea | LC-MS: m/z 374.4 (M + H). 1H NMR (400 MHz, DMSO) δ 8.52 (dd, J = 4.4, 1.0 Hz, 1H), 7.35 (dd, J = 9.3, 4.4 Hz, 1H), 7.31-7.22 (m, 3H), 7.14 (dd, J = 7.7, 1.3 Hz, 1H), 7.00 (t, J = 5.8 Hz, 1H), 4.34 (d, J = 11.7 Hz, 1H), 4.28-4.15 (m, 3H), 3.98 (dd, J = 13.3, 9.2 Hz, 1H), 3.01-2.91 (m, 1H), 2.85-2.76 (m, 4H), 2.29 (s, 3H), 1.85-1.66 (m, 3H), 1.60-1.47 (m, 1H). |
| 100 | 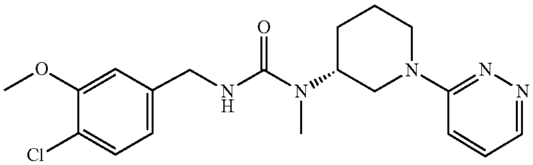 [SMILES: COc1cc(CNC(=O)N(C)[C@@H]2CCCN(c3cccnn3)C2)ccc1Cl] 3-[(4-chloro-3-methoxyphenyl)methyl]-1-methyl-1-[(3R)-1-(pyridazin-3-yl)piperidin-3-yl]urea | LC-MS: m/z 390.3 (M + H). 1H NMR (400 MHz, MeOD) δ 8.45 (dd, J = 4.4, 1.1 Hz, 1H), 7.38 (dd, J = 9.4, 4.4 Hz, 1H), 7.28 (dd, J = 14.0, 4.6 Hz, 2H), 7.03 (d, J = 1.7 Hz, 1H), 6.86 (dd, J = 8.1, 1.9 Hz, 1H), 4.42-4.25 (m, 4H), 4.09 (dd, J = 9.6, 5.5 Hz, 1H), 3.86 (s, 3H), 3.04 (dd, J = 12.4, 11.3 Hz, 1H), 2.96-2.81 (m, 4H), 1.96-1.80 (m, 3H), 1.79-1.59 (m, 1H). |
| 101 | 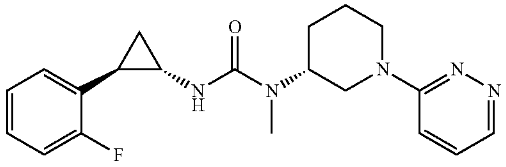 [SMILES: CN(C(=O)N[C@H]1C[C@@H]1c1ccccc1F)[C@@H]1CCCN(c2cccnn2)C1] 3-[(1S,2R)-2-(2-fluorophenyl)cyclopropyl]-1-methyl-1-[(3R)-1-(pyridazin-3-yl)piperidin-3-yl]urea | LC-MS: m/z 370.2 (M + H). |
| 102 | 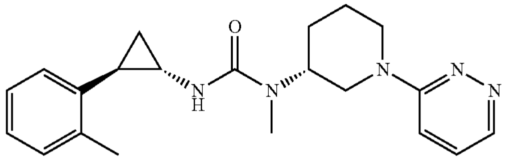 [SMILES: Cc1ccccc1[C@H]1C[C@@H]1NC(=O)N(C)[C@@H]1CCCN(c2cccnn2)C1] 1-methyl-3-[(1S,2R)-2-(2-methylphenyl)cyclopropyl]-1-[(3R)-1-(pyridazin-3-yl)piperidin-3-yl]urea | LC-MS: m/z 366.2 (M + H). |
| 103 | 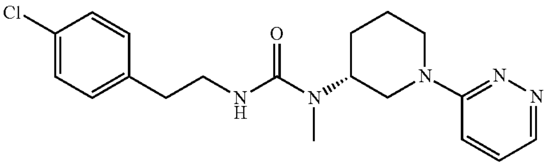 [SMILES: CN(C(=O)NCCc1ccc(Cl)cc1)[C@@H]1CCCN(c2cccnn2)C1] 3-[2-(4-chlorophenyl)ethyl]-1-methyl-1-[(3R)-1-(pyridazin-3-yl)piperidin-3-ylurea | LC-MS: m/z 374.2 (M + H). |
| 104 | 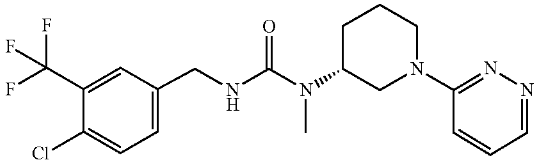 3-{[4-chloro-3-(trifluoromethyl)phenyl]methyl}-1-methyl-1-[(3R)-1-(pyridazin-3-yl)piperidin-3-yl]urea | LC-MS: m/z 374.2 (M + H). 1H NMR (400 MHz, MeOD) δ 8.45 (dd, J = 4.4, 1.2 Hz, 1H), 7.71 (s, 1H), 7.54 (d, J = 1.1 Hz, 2H), 7.38 (dd, J = 9.4, 4.4 Hz, 1H), 7.29 (dd, J = 9.4, 1.2 Hz, 1H), 4.41 (s, 2H), 4.38-4.27 (m, 2H), 4.13-4.03 (m, 1H), 3.05 (dd, J = 12.5, 11.3 Hz, 1H), 2.94-2.87 (m, 4H), 1.95-1.84 (m, 3H), 1.68 (dd, J = 11.2, 8.5 Hz, 1H). |

-continued

| Example | Structure and name | Data |
|---|---|---|
| 105 | 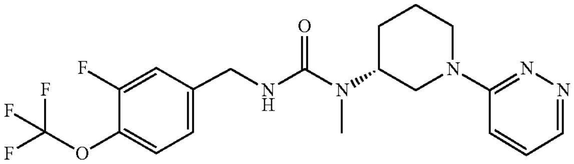 [SMILES: CN(C(=O)NCc1ccc(OC(F)(F)F)c(F)c1)[C@@H]1CCCN(c2cccnn2)C1] 3-{[3-fluoro-4-(trifluoromethoxy)phenyl]methyl}-1-methyl-1-[(3R)-1-(pyridazin-3-yl)piperidin-3-yl]urea | LC-MS: m/z 428.2 (M + H). 1H NMR (400 MHz, MeOD) δ 8.45 (d, J = 4.4 Hz, 1H), 7.54-7.14 (m, 5H), 4.47-4.21 (m, 4H), 4.09 (s, 1H), 3.09-2.98 (m, 1H), 2.96-2.82 (m, 4H), 1.88 (d, J = 7.8 Hz, 3H), 1.68 (s, 1H). |
| 106 | 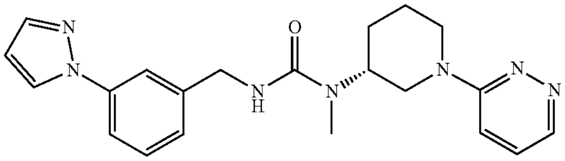 [SMILES: CN(C(=O)NCc1cccc(-n2cccn2)c1)[C@@H]1CCCN(c2cccnn2)C1] 1-methyl-3-{[3-(1H-pyrazol-1-yl)phenyl]methyl}-1-[(3R)-1-(pyridazin-3-yl)piperidin-3-yl]urea | LC-MS: m/z 392.3 (M + H). 1H NMR (400 MHz, MeOD) δ 8.44 (dd, J = 4.4, 1.1 Hz, 1H), 8.19 (d, J = 2.3 Hz, 1H), 7.76-7.66 (m, 2H), 7.59 (d, J = 8.1 Hz, 1H), 7.43 (t, J = 7.8 Hz, 1H), 7.36 (dd, J = 9.4, 4.4 Hz, 1H), 7.32-7.25 (m, 2H), 6.57-6.44 (m, 1H), 4.47 (d, J = 4.4 Hz, 2H), 4.38 (d, J = 13.2 Hz, 1H), 4.28 (d, J = 12.6 Hz, 1H), 4.18-4.05 (m, 1H), 3.10-3.00 (m, 1H), 2.92 (s, 3H), 2.91-2.81 (m, 1H), 1.90 (dd, J = 13.5, 6.0 Hz, 3H), 1.76-1.58 (m, 1H). |
| 107 | 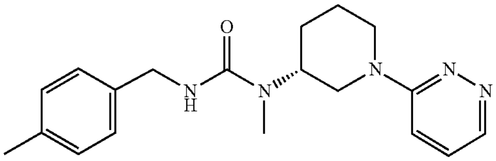 [SMILES: Cc1ccc(CNC(=O)N(C)[C@@H]2CCCN(c3cccnn3)C2)cc1] 1-methyl-3-[(4-methylphenyl)methyl]-1-[(3R)-1-(pyridazin-3-yl)piperidin-3-yl]urea | LC-MS: m/z 340.4 (M + H). 1H NMR (400 MHz, DMSO) δ 8.52 (dd, J = 4.4, 1.1 Hz, 1H), 7.36 (dd, J = 9.3, 4.4 Hz, 1H), 7.25 (dd, J = 9.3, 1.1 Hz, 1H), 7.13 (dd, J = 21.8, 8.0 Hz, 4H), 6.92 (t, J = 5.8 Hz, 1H), 4.34(d, J = 11.2 Hz, 1H), 4.28-4.14 (m, 3H), 4.05-3.95(m, 1H), 3.03-2.90 (m, 1H), 2.86-2.73 (m, 4H), 2.27 (s, 3H), 1.85-1.66 (m, 3H), 1.55 (dd, J = 15.2, 11.4 Hz, 1H). |
| 108 | 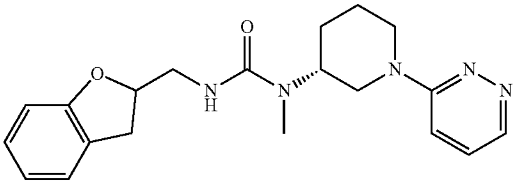 [SMILES: CN(C(=O)NCC1Cc2ccccc2O1)[C@@H]1CCCN(c2cccnn2)C1] 3-[(2,3-dihydro-1-benzofuran-2-yl)methyl]-1-methyl-1-[(3R)-1-(pyridazin-3-yl)piperidin-3-yl]urea | LC-MS: m/z 368.4 (M + H). 1H NMR (400 MHz, MeOD) δ 8.47 (s, 1H), 7.43-7.36 (m, 1H), 7.29 (dd, J = 8.6, 4.6 Hz, 1H), 7.16-6.97(m,2H), 6.77 (t, J = 7.4 Hz, 1H), 6.69 (d, J = 7.8 Hz, 1H), 6.60 (d, J = 8.0 Hz, 1H), 4.88 (dd, J = 9.5, 5.2 Hz, 1H), 4.39-4.21 (m, 2H), 4.03-3.87 (m, 1H), 3.56-3.41 (m, 2H), 3.28-3.21 (m, 1H), 3.04-2.85 (m, 3H), 2.80 (s, 3H), 1.90-1.76 (m, 3H), 1.62 (s, 1H). |
| 109 | 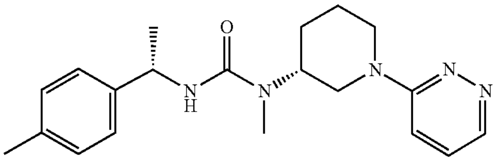 [SMILES: Cc1ccc([C@H](C)NC(=O)N(C)[C@@H]2CCCN(c3cccnn3)C2)cc1] 1-methyl-3-[(1S)-1-(4-methylphenyl)ethyl]-1-[(3R)-1-(pyridazin-3-yl)piperidin-3-yl]urea | LC-MS: m/z 354.4 (M + H). 1H NMR (400 MHz, MeOD) δ 8.46 (s, 1H), 7.30 (s, 2H), 7.22 (d, J = 8.1 Hz, 3H), 7.10 (d, J = 7.9 Hz, 3H), 4.92 (q, J = 7.0 Hz, 1H), 4.36 (d, J = 13.3 Hz, 1H), 4.24 (d, J = 12.2 Hz, 1H), 4.15-4.02 (m, 1H), 3.09-2.96 (m, 1H), 2.95-2.83 (m, 5H), 2.29 (s, 4H), 1.87 (t, J = 7.7 Hz, 4H), 1.65 (d, J = 9.3 Hz, 1H), 1.47 (d, J = 7.1 Hz, 4H). |
| 110 | 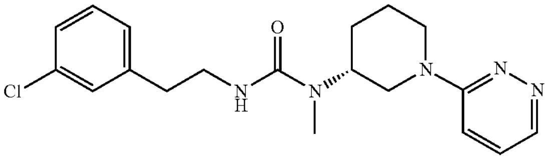 [SMILES: CN(C(=O)NCCc1cccc(Cl)c1)[C@@H]1CCCN(c2cccnn2)C1] 3-[2-(3-chlorophenyl)ethyl]-1-methyl-1-[(3R)-1-(pyridazin-3-yl)piperidin-3-yl]urea | LC-MS: m/z 374 (M + H). 1H NMR (400 MHz, MeOD) δ 8.59-8.38 (m, 1H), 7.19-7.03 (m, 5H), 6.95 (dd, J = 9.3, 1.0 Hz, 1H), 5.70 (s, 1H), 4.25 (d, J = 12.8 Hz, 1H), 4.11 (d, J = 13.3 Hz, 1H), 3.81 (t, J = 11.2 Hz, 1H), 3.49 (dd, J = 13.2, 6.1 Hz, 2H), 2.97-2.80 (m, 5H), 2.77 (s, 3H), 1.90 (d, J = 11.0 Hz, 1H), 1.83-1.68 (m, 2H), 1.64-1.47 (m, 1H). |

-continued

| Example | Structure and name | Data |
|---|---|---|
| 111 | 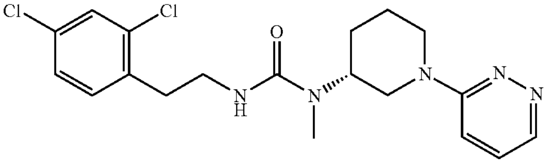 3-[2-(2,4-dichlorophenyl)ethyl]-1-methyl-1-[(3R)-1-(pyridazin-3-yl)piperidin-3-yl]urea | LC-MS: m/z 480.3 (M + H). 1H NMR (400 MHz, MeOD) δ 8.46 (s, 1H), 7.39 (dd, J = 8.7, 3.0 Hz, 2H), 7.26 (qd, J = 8.2, 2.8 Hz, 3H), 4.35 (d, J = 14.7 Hz, 1H), 4.23 (dd, J = 12.7, 3.9 Hz, 1H), 4.00 (s, 1H), 3.58-3.37 (m, 2H), 3.09-2.84 (m, 4H), 2.82 (s, 3H), 1.96-1.79 (m, 3H), 1.74-1.55 (m, 1H). |
| 112 | 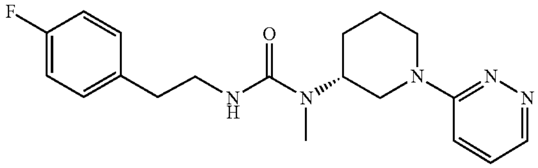 [SMILES: CN(C(=O)NCCc1ccc(F)cc1)[C@@H]1CCCN(c2cccnn2)C1] 3-[2-(4-fluorophenyl)ethyl]-1-methyl-1-[(3R)-1-(pyridazin-3-yl)piperidin-3-yl]urea | LC-MS: m/z 358.1 (M + H). 1H NMR (400 MHz, MeOD) δ 8.46 (d, J = 3.7 Hz, 1H), 7.39 (dd, J-9.4, 4.4 Hz, 1H), 7.27 (dd, J = 9.4, 1.1 Hz, 1H), 7.23-7.16 (m, 2H), 7.05-6.89 (m, 2H), 4.35 (d, J = 13.7 Hz, 1H), 4.24 (dd, J = 12.5, 3.8 Hz, 1H), 4.01 (s, 1H), 3.43-3.35 (m, 2H), 3.00 (dd, J = 12.5, 11.4 Hz, 1H), 2.94-2.85 (m, 1H), 2.85-2.75 (m, 5H), 1.87 (ddd, J = 12.6, 10.3, 5.4 Hz, 3H), 1.74-1.58 (m, 1H). |
| 113 | 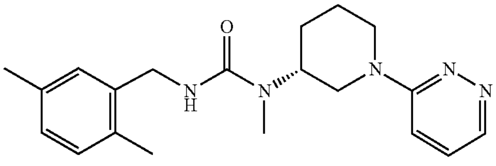 [SMILES: Cc1ccc(C)c(CNC(=O)N(C)[C@@H]2CCCN(c3cccnn3)C2)c1] 3-[(2,5-dimethylphenyl)methyl]-1-methyl-1-[(3R)-1-(pyridazin-3-yl)piperidin-3-yl]urea | LC-MS: m/z 354.1 (M + H). 1H NMR (400 MHz, MeOD) δ 8.44 (d, J = 3.8 Hz, 1H), 7.38 (dd, J = 9.4, 4.4 Hz, 1H), 7.29 (dd, J = 9.4, 1.1 Hz, 1H), 7.13-6.88 (m, 3H), 4.41-4.26 (m, 4H), 4.12 (dt, J = 11.6, 8.0 Hz, 1H), 3.10-3.02 (m, 1H), 2.94-2.84(m, 4H), 2.28 (d, J = 4.9 Hz,6H), 1.90 (dd, J = 10.9, 8.9 Hz, 3H), 1.68(d, J = 9.4 Hz, 1H). |
| 114 | 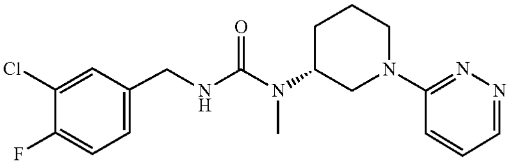 3-[(3-chloro-4-fluorophenyl)methyl]-1-methyl-1-[(3R)-1-(pyridazin-3-yl)piperidin-3-yl]urea | LC-MS: m/z 378.1 (M + H). 1H NMR (400 MHz, MeOD) δ 8.45 (d, J = 4.1 Hz, 1H), 7.45-7.33 (m, 2H), 7.33-7.23 (m, 2H), 7.16 (t, J = 8.7 Hz, 1H), 4.42-4.26 (m, 4H), 4.15-4.01 (m, 1H), 3.10-2.98 (m, 1H), 2.95-2.84 (m, 4H), 1.98-1.82 (m, 3H), 1.76-1.58 (m, 1H). |
| 115 | 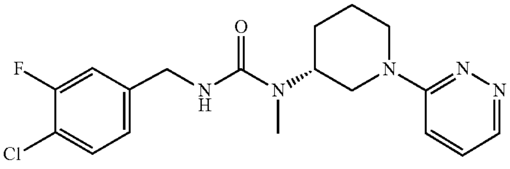 [SMILES: CN(C(=O)NCc1ccc(Cl)c(F)c1)[C@@H]1CCCN(c2cccnn2)C1] 3-[(4-chloro-3-fluorophenyl)methyl]-1-methyl-1-[(3R)-1-(pyridazin-3-yl)piperidin-3-yl]urea | LC-MS: m/z 378.1 (M + H). 1H NMR (400 MHz, DMSO) δ 8.51 (dd, J = 4.4, 1.0 Hz, 1H), 7.51 (t, J = 8.0 Hz, 1H), 7.35 (dd, J = 9.3, 4.4 Hz, 1H), 7.30-7.22 (m, 2H), 7.14 (dd, J = 8.2, 1.2 Hz, 1H), 7.06 (t, J = 5.8 Hz, 1H), 4.36-4.18 (m, 4H), 3.97 (dd, J = 13.3, 9.1 Hz, 1H), 3.01-2.91 (m, 1H), 2.86-2.74 (m, 4H), 1.86-1.67 (m, 3H), 1.59-1.46 (m, 1H). |
| 116 | 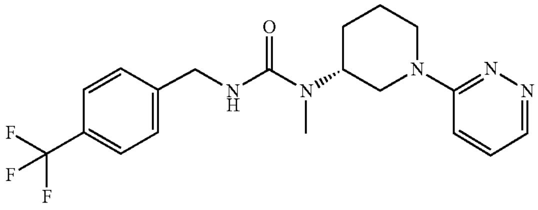 [SMILES: CN(C(=O)NCc1ccc(C(F)(F)F)cc1)[C@@H]1CCCN(c2cccnn2)C1] 1-methyl-1-[(3R)-1-(pyridazin-3-yl)piperidin-3-yl]-3-{[3-(trifluoromethyl)phenyl]methyl}urea | LC-MS: m/z 394.1(M + H). |

-continued

| Example | Structure and name | Data |
|---|---|---|
| 117 | 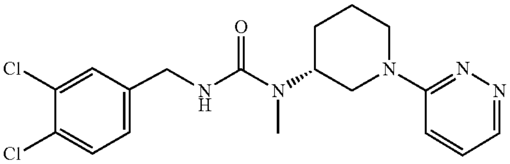 [SMILES: CN(C(=O)NCc1ccc(Cl)c(Cl)c1)[C@@H]1CCCN(c2cccnn2)C1] 3-[(3,4-dichlorophenyl)methyl]-1-methyl-1-[(3R)-1-(pyridazin-3-yl)piperidin-3-yl]urea | LC-MS: m/z 394.1(M + H). |
| 118 | 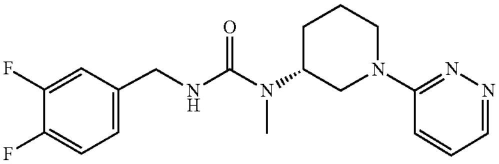 1-[(3,4-difluorophenyl)methyl]-3-methyl-3-[(3R)-1-(pyridazin-3-yl)piperidin-3-yl]urea | LC-MS: m/z 394.1(M + H). 1H NMR (400 MHz, MeOD) δ 8.48 (s, 1H), 7.40 (s, 1H), 7.31 (d, J = 9.2 Hz, 1H), 7.25-7.15 (m, 2H), 7.13 (d, J = 4.3 Hz, 1H), 4.40-4.29 (m, 4H), 4.11 (dt, J = 11.2, 7.6 Hz, 1H), 3.06 (dd, J = 12.5, 11.3 Hz, 1H), 2.96-2.87 (m, 4H), 1.91 (tt, J = 9.6, 4.9 Hz, 3H), 1.69 (dd, J = 15.6, 6.3 Hz, 1H). |
| 119 | 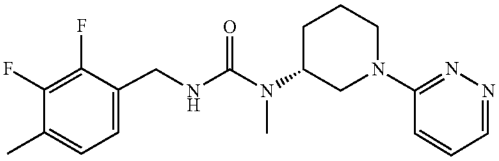 [SMILES: Cc1ccc(CNC(=O)N(C)[C@@H]2CCCN(c3cccnn3)C2)c(F)c1F] 1-[(2,3-difluoro-4-methylphenyl)methyl]-3-methyl-3-[(3R)-1-(pyridazin-3-yl)piperidin-3-yl]urea | LC-MS: m/z 376.1(M + H). 1H NMR (400 MHz, MeOD) δ 8.47 (s, 1H), 7.41 (s, 1H), 7.30 (d, J = 9.1 Hz, 1H), 6.99 (dt, J = 14.6, 7.6 Hz, 2H), 4.42 (s, 2H), 4.37 (d, J = 12.7 Hz, 1H), 4.28 (d, J = 12.6 Hz, 1H), 4.14-4.05 (m, 1H), 3.08-3.00 (m, 1H), 2.94-2.85 (m, 4H), 2.26 (d, J = 2.0 Hz, 3H), 1.93-1.83 (m, 3H), 1.67 (d, J = 9.1 Hz, 1H). |
| 120 | 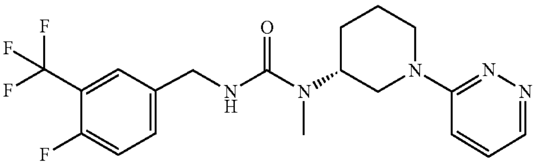 [SMILES: CN(C(=O)NCc1ccc(F)c(C(F)(F)F)c1)[C@@H]1CCCN(c2cccnn2)C1] 1-{[4-fluoro-3-(trifluoromethyl)phenyl]methyl}-3-methyl-3-[(3R)-1-(pyridazin-3-yl)piperidin-3-yl]urea | LC-MS: m/z 412.4 (M + H). 1H NMR (400 MHz, DMSO) δ 8.51 (dd, J = 4.4, 1.1 Hz, 1H), 7.64 (dd, J = 9.2, 6.1 Hz, 2H), 7.45 (dd, J = 10.8, 8.4 Hz, 1H), 7.35 (dd, J = 9.3, 4.4 Hz, 1H), 7.24 (dd, J = 9.3,1.1Hz, 1H), 7.10 (t, J = 5.8 Hz, 1H), 4.38-4.18 (m, 4H), 3.97 (dd, J = 13.2, 9.2 Hz, 1H), 3.00-2.92 (m, 1H), 2.87-2.74 (m, 4H), 1.77 (dt, J = 24.0, 11.8 Hz, 3H), 1.62-1.47 (m, 1H). |
| 121 | 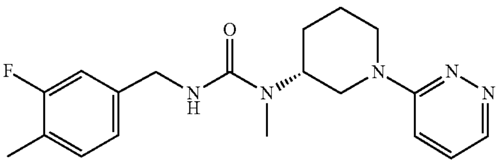 [SMILES: Cc1ccc(CNC(=O)N(C)[C@@H]2CCCN(c3cccnn3)C2)cc1F] 1-[(3-fluoro-4-methylphenyl)methyl]-3-methyl-3-[(3R)-1-(pyridazin-3-yl)piperidin-3-yl]urea | LC-MS: m/z 358.4 (M + H). 1H NMR (400 MHz, MeOD) δ 8.46 (s, 1H), 7.29 (d, J = 9.4 Hz, 1H), 7.14 (t, J = 7.7 Hz, 1H), 6.98 (dd, J = 11.9, 9.4 Hz, 2H), 4.44-4.23 (m, 5H), 4.10 (s, 1H), 3.10-2.98 (m, 1H), 2.95-2.83 (m, 5H), 2.22 (d, J = 1.6 Hz, 4H), 1.97-1.80 (m, 4H), 1.68 (s, 1H). |

-continued

| Example | Structure and name | Data |
|---|---|---|
| 122 | 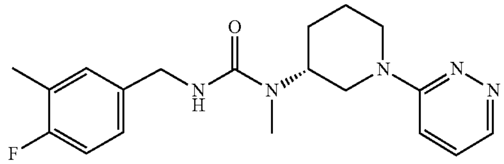 1-[(4-fluoro-3-methylphenyl)methyl]-3-methyl-3-[(3R)-1-(pyridazin-3-yl)piperidin-3-yl]urea | LC-MS: m/z 358.1 (M + H). 1H NMR (400 MHz, MeOD) δ 8.46 (s, 1H), 7.39 (dd, J = 9.2, 4.3 Hz, 1H), 7.30 (d, J = 8.7 Hz, 1H), 7.17(d, J = 7.5 Hz, 1H), 7.12(ddd, J = 7.3, 4.9, 2.1Hz, 1H),6.98-6.91(m, 1H), 4.38(d, J = 13.3 Hz, 1H), 4.32 (s, 2H), 4.28 (d, J = 3.9 Hz, 1H), 4.15-4.07 (m, 1H), 3.04 (dd, J = 12.5, 11.3 Hz, 1H), 2.93-2.87 (m, 4H), 2.24 (d, J = 1.8 Hz, 3H), 1.89 (dt, J = 9.5, 3.9 Hz, 3H), 1.75-1.63 (m, 1H). |
| 123 | 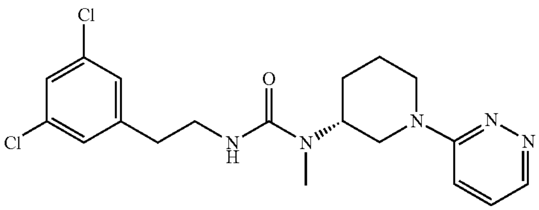 [SMILES: CN(C(=O)NCCc1cc(Cl)cc(Cl)c1)[C@@H]1CCCN(c2cccnn2)C1] 3-[2-(3,5-dichlorophenyl)ethyl]-1-methyl-1-[(3R)-1-(pyridazin-3-yl)piperidin-3-yl]urea | LC-MS: m/z 408.3 (M + H). 1H NMR (400 MHz, DMSO) δ 8.52 (dd, J = 4.4, 1.2 Hz, 1H), 7.41 (t, J = 1.9 Hz, 1H), 7.36 (dd, J = 9.3, 4.4 Hz, 1H), 7.29-7.16 (m, 3H), 6.47 (t, J = 5.5 Hz, 1H), 4.32 (d, J = 12.7 Hz, 1H), 4.13 (d, J = 12.0 Hz, 1H), 3.91 (dd, J = 13.4, 9.2 Hz, 1H), 3.30-3.26 (m, 3H), 3.00-2.88 (m, 1H), 2.86-2.71 (m, 6H), 1.84-1.64 (m, 3H), 1.52 (t, J = 13.1 Hz, 1H). |
| 124 | 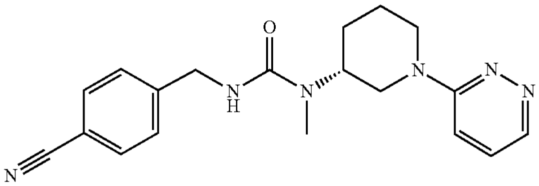 [SMILES: CN(C(=O)NCc1ccc(C#N)cc1)[C@@H]1CCCN(c2cccnn2)C1] 3-[(4-cyanophenyl)methyl]-1-methyl-1-[(3R)-1-(pyridazin-3-yl)piperidin-3-yl]urea | LC-MS: m/z 351.4 (M + H). 1H NMR (400 MHz, DMSO) δ 8.51 (dd, J = 4.4, 1.2 Hz, 1H), 7.81-7.74 (m, 2H), 7.46(d, J = 8.4 Hz, 2H),7.35(dd, J = 9.3, 4.4 Hz, 1H), 7.24(dd, J = 9.3,1.2 Hz, 1H), 7.11 (t, J = 5.8 Hz, 1H), 4.38-4.22 (m, 4H), 3.98 (dd, J = 13.4, 9.3 Hz, 1H), 3.01-2.91 (m, 1H), 2.85-2.75 (m, 4H), 1.77 (dt, J = 8.9, 8.4 Hz, 3H), 1.54 (dd, J = 15.2, 11.2 Hz, 1H). |
| 125 | 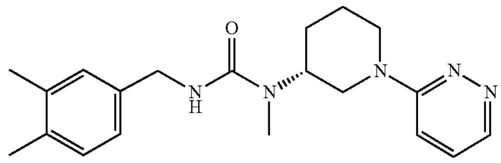 [SMILES: Cc1ccc(CNC(=O)N(C)[C@@H]2CCCN(c3cccnn3)C2)cc1C] | LC-MS: m/z 354.4 (M + H). 1H NMR (400 MHz, MeOD) δ 8.44 (dd, J = 4.4, 1.0 Hz, 1H), 7.37 (dd, J = 9.4, 4.4 Hz, 1H), 7.27 (dd, J = 9.4, 1.2 Hz, 1H), 7.10-6.96 (m, 3H), 4.47-4.22 (m, 4H), 4.16-4.02 (m, 1H), 3.03 (dd, J = 12.5, 11.3 Hz, 1H), 2.93-2.81 (m, 4H), 2.22 (d, J = 6.3 Hz, 6H), 1.88 (dt, J = 9.7, 4.1 Hz, 3H), 1.77-1.58 (m, 1H). |
| 126 | 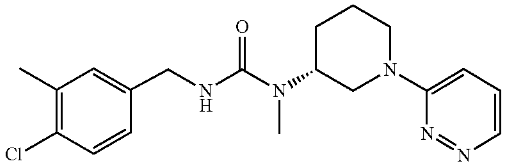 [SMILES: Cc1cc(CNC(=O)N(C)[C@@H]2CCCN(c3cccnn3)C2)ccc1Cl] 1-[(4-chloro-3-methylphenyl)methyl]-3-methyl-3-[(3R)-1-(pyridazin-3-yl)piperidin-3-yl]urea | LC-MS: m/z 374.2 (M + H). 1H NMR (400 MHz, MeOD) δ 8.45 (dd, J = 4.4, 1.1 Hz, 1H), 7.39 (dd, J = 9.4, 4.4 Hz, 1H), 7.28 (dd, J = 15.2, 8.3 Hz, 2H), 7.22 (s, 1H), 7.10 (dd, J = 8.2, 1.8 Hz, 1H), 4.40-4.25 (m, 4H), 4.09 (dd, J = 9.7, 5.7 Hz, 1H), 3.08-3.00 (m, 1H), 2.94-2.85 (m, 4H), 2.33 (s, 3H), 1.89 (dd, J = 11.2, 4.4 Hz, 3H), 1.74-1.61 (m, 1H) |
| 127 | 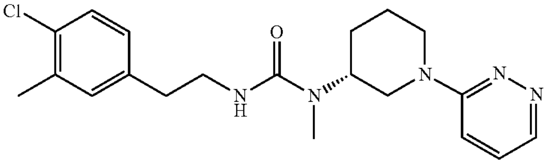 [SMILES: Cc1cc(CCNC(=O)N(C)[C@@H]2CCCN(c3cccnn3)C2)ccc1Cl] 3-[2-(4-chloro-3-methylphenyl)ethyl]-1-methyl-1-[(3R)-1-(pyridazin-3-yl)piperidin-3-yl]urea | LC-MS: m/z 388 (M + H). 1H NMR (400 MHz, MeOD) δ 8.46 (dd, J = 4.4, 1.1 Hz, 1H), 7.39 (dd, J = 9.4, 4.4 Hz, 1H), 7.27(dd, J = 9.4,1.2 Hz, 1H), 7.22(d, J = 8.1Hz, 1H), 7.13(d, J = 1.6 Hz, 1H), 7.01 (dd, J = 8.1, 1.9 Hz, 1H), 4.34 (d, J = 11.9 Hz, 1H), 4.23 (dd, J = 12.7, 4.0 Hz, 1H), 3.97 (d, J = 10.2 Hz, 1H), 3.39 (tt, J = 8.4, 4.4 Hz, 2H), 3.00 (dd, J = 12.5, 11.3 Hz, 1H), 2.89 (dd, J = 18.7, 8.0 Hz, 1H), 2.82 (s, 3H), 2.76 (t, J = 7.3 Hz, 2H), 2.31 (s, 3H), 1.92-1.80 (m, 3H), 1.71-1.57 (m, 1H). |

Example 128: Synthesis of 3-(4-chloro-3-methylbenzyl)-1-cyclopropyl-1-((R)-1-((S)-tetrahydrofuran-2-carbonyl)piperidin-3-yl)urea

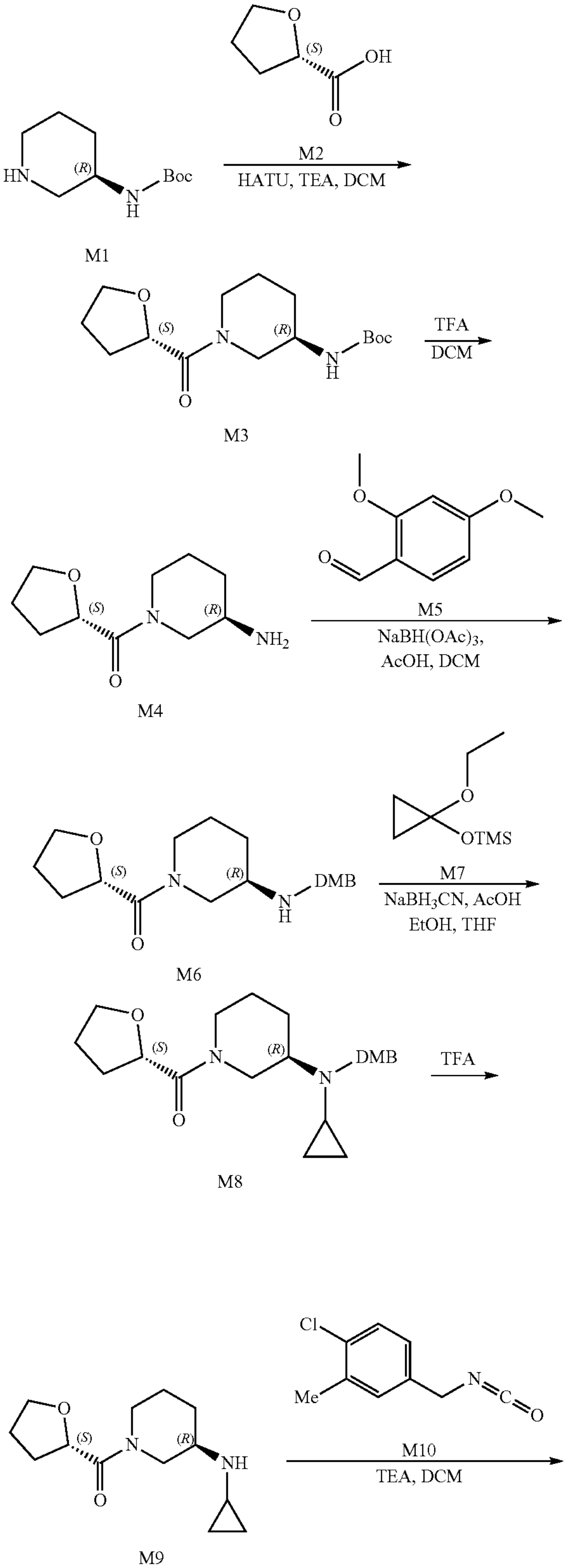

-continued

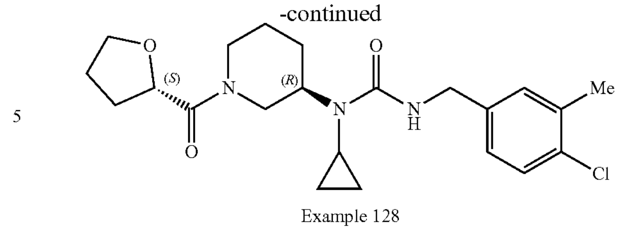

Example 128

To a mixture of M2 (116 mg, 1.0 mmol) and HATU (474 mg, 1.29 mmol) in DCM (20 mL) was added TEA (253 mg, 2.5 mmol) at 0° C. dropwise. After stirring at r.t. for 30 mins, M1 (200 mg, 0.83 mmol) was added into the above mixture. The resulting mixture was stirred at r.t. for 2 hrs under $N_2$ atmosphere. Then the mixture was diluted with DCM (20 mL) and washed with water (30 mL) and brine (30 mL). The organic layer was dried over anhydrous $Na_2SO_4$, filtered and concentrated to dryness. The residue was purified via flash column chromatography (eluted with PE/EtOAc=100:0 to 3:1) to give M3 (250 mg, 88.8%) as colorless oil. LC/MS (ESI) m/z: 299 $(M+H)^+$. To a solution of M3 (250 mg, 0.84 mmol) in DCM (6 mL) was added TFA (2 mL) at 0° C. dropwise. The resulting mixture was stirred at room temperature for 2 hrs. Then the reaction mixture was evaporated to dryness under reduced pressure to give crude M4 (160 mg, 96.3%) as yellow oil without further purification. LC/MS (ESI) m/z: 199 $(M+H)^+$. To a solution of M4 (160 mg, 0.81 mmol) and M5 (148 mg, 0.89 mmol) in DCM (10 mL) was added AcOH (145 mg, 2.42 mmol) at 0° C. The resulting mixture was stirred at r.t. for 1 hr. Then $NaBH(OAc)_3$ (510 mg, 2.42 mmol) was added into the above mixture dropwise at 0° c. The resulting mixture was stirred at r.t. overnight under $N_2$ atmosphere. The mixture was quenched with saturated $NaHCO_3$ solution (20 mL) and extracted with EtOAc (30 mL) twice. The combined organic layer was washed with brine (20 mL), dried over anhydrous $Na_2SO_4$, filtered. The filtrate was evaporated to dryness under reduced pressure. The residue was purified by column chromatography on silica gel (eluted with PE/EtOAc=100:0 to =2:1) to give M6 (100 mg, 35.6%) as colorless oil. LC/MS (ESI) m/z: 349 $(M+H)^+$. To a mixture of M6 (100 mg, 0.29 mmol), M7 (125 mg, 0.72 mmol) and AcOH (52 mg, 0.86 mmol) in THF (12 mL) and EtOH (6 mL) was added $NaBH_3CN$ (55 mg, 0.86 mmol). The resulting mixture was stirred at 80° C. overnight under $N_2$ atmosphere. After cooling, the reaction was quenched with saturated aq. $NaHCO_3$ (20 mL) and extracted with EtOAc (30 mL) twice. The combined organic layer was washed with brine (20 mL), dried over anhydrous $Na_2SO_4$, filtered. The filtrate was evaporated to dryness under reduced pressure. The residue was purified by flash column chromatography (eluted with PE/EtOAc=100:0 to =2:1) to give M8 (50 mg, 44.8%) as colorless oil. LC/MS (ESI) m/z: 389 $(M+H)^+$. A solution of M8 (50 mg, 0.13 mmol) in TFA (4 mL) was stirred at 80° C. for 3 hrs under $N_2$ atmosphere. After cooling, the mixture was concentrated to dryness under reduced pressure to give crude M9 (30 mg, 97.8%) as purple oil without further purification. LC/MS (ESI) m/z: 239 $(M+H)^+$.

To a mixture of M9 (30 mg, 0.13 mmol) and TEA (39 mg, 0.39 mmol) in anhydrous DCM (10 mL) was added a solution of M10 (22.9 mg, 0.13 mmol) in anhydrous DCM (2 mL) at 0° C. dropwise. The resulting mixture was stirred at 0° C. for 1 hour under $N_2$ atmosphere. Then the reaction mixture was diluted with water (20 mL) and extracted with DCM (20 mL) twice. The combined organic layers were separated, dried over anhydrous $Na_2SO_4$, filtered and concentrated to dryness. The residue was purified via flash column chromatography (eluted with DCM/MeOH=100:0 to 20:1) to give crude product. The crude product was purified via prep-HPLC (Gemini 5 μm C18 250*21.2 mm, $H_2O$/MeCN (5-95%)/0.1% HCOOH) to give Example 128 (11 mg, 0.026 mmol, 20.81% yield) as white solid. LC/MS (ESI) m/z: 420 $(M+H)^+$. 1H NMR (400 MHz, MeOD) δ 7.28 (dd, J=8.2, 2.7 Hz, 1H), 7.21 (d, J=5.1 Hz, 1H), 7.10 (dd, J=10.5, 4.1 Hz, 1H), 4.74-4.67 (m, 1H), 4.53-4.39 (m, 1H), 4.39-4.26 (m, 2H), 4.02-3.87 (m, 2H), 3.86-3.44 (m, 2H), 3.30-3.10 (m, 1H), 3.00-2.46 (m, 2H), 2.33 (d, J=9.2 Hz, 3H), 2.32-2.13 (m, 2H), 2.05-1.79 (m, 5H), 1.66-1.39 (m, 1H), 1.02-0.87 (m, 2H), 0.85-0.66 (m, 2H).

The compounds in the following table were made by the same route as Example 128, starting with the appropriate commercially available amide M2, and other previously described or commercially available intermediates.

| Example | Structure and name | Data |
| --- | --- | --- |
| 129 | 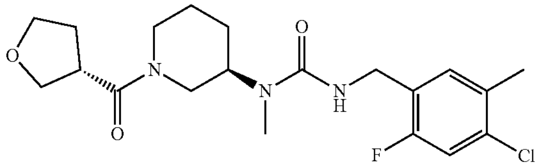 [SMILES: Cc1cc(CNC(=O)N(C)[C@@H]2CCCN(C(=O)[C@H]3CCOC3)C2)c(F)cc1Cl] 1-[(4-chloro-2-fluoro-5-methylphenyl)methyl]-3-methyl-3-[(3R)-1-[(3S)-oxolane-3-carbonyl]piperidin-3-yl]urea | LC-MS: m/z 412 (M + H). 1H NMR (400 MHz, MeOD) δ 7.24 (dd, J = 8.0, 3.5 Hz, 1H), 7.11 (dd, J = 9.7, 6.2 Hz, 1H), 4.52-4.29 (m, 3H), 4.12-3.98 (m, 1H), 3.95-3.74 (m, 5H), 3.48-3.39 (m, 1H), 3.17-3.09 (m, 1H), 3.05-2.96 (m, 1H), 2.85 (d, J = 7.5 Hz, 3H), 2.74 (t, J = 11.9 Hz, 1H), 2.51 (td, J = 13.0, 2.3 Hz, 1H), 2.31 (s, 3H), 2.12 (ddt, J = 17.1, 13.6, 7.6 Hz, 2H), 1.89-1.77 (m, 3H), 1.59-1.44 (m, 1H). |
| 130 | 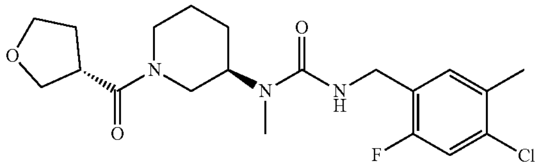 [SMILES: Cc1cc(CNC(=O)N(C)[C@@H]2CCCN(C(=O)[C@H]3CCOC3)C2)c(F)cc1Cl] 1-[(4-chloro-2-fluoro-5-methylphenyl)methyl]-3-methyl-3-[(3R)-1-[(2R)-oxolane-3-carbonyl]piperidin-3-yl]urea | LC-MS: m/z 412 (M + H). 1H NMR (400 MHz, MeOD) δ 7.24 (d, J = 8.0 Hz, 1H), 7.11 (dd, J = 9.7, 6.6 Hz, 1H), 4.70 (dd, J = 14.1, 8.0 Hz, 1H), 4.50-4.29 (m, 3H), 4.13-3.98 (m, 1H), 3.97-3.79 (m, 3H), 3.17-3.08 (m, 1H), 2.93 (dd, J = 18.6, 7.7 Hz, 1H), 2.85 (d, J = 4.9 Hz, 3H), 2.74 (t, J = 11.8 Hz, 1H), 2.52 (td, J = 13.0, 2.3 Hz, 1H), 2.31 (s, 3H), 2.28-2.12 (m, 1H), 2.03 (ddd, J = 12.9, 10.3, 6.6 Hz, 1H), 1.97-1.87 (m, 2H), 1.86-1.78 (m, 3H), 1.65 (d, J = 7.3 Hz, 1H), 1.48 (d, J = 9.6 Hz, 1H). |
| 131 | 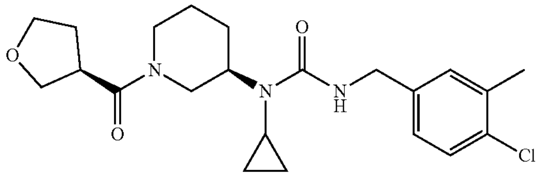 [SMILES: Cc1cc(CNC(=O)N(C2CC2)[C@@H]2CCCN(C(=O)[C@@H]3CCOC3)C2)ccc1Cl] 3-[(4-chloro-3-methylphenyl)methyl]-1-cyclopropyl-1-[(3R)-1-[(3S)-oxolane-3-carbonyl]piperidin-3-yl]urea | LC-MS: m/z 420.2 (M + H). 1H NMR (400 MHz, MeOD) δ 7.18 (dd, J = 8.2, 2.8 Hz, 1H), 7.12 (d, J = 7.9 Hz, 1H), 7.04-6.97 (m, 1H), 6.81 (dt, J = 26.1, 5.9 Hz, 1H), 4.45-4.34 (m, 1H), 4.23 (dd, J = 12.3, 5.8 Hz, 2H), 3.88 (ddd, J = 16.4, 14.3, 8.2 Hz, 2H), 3.79-3.65 (m, 3H), 3.45-3.29 (m, 2H), 3.07-2.83 (m, 1H), 2.49-2.36 (m, 2H), 2.25 (s, 3H), 2.17-1.91 (m, 3H), 1.90-1.68 (m, 2H), 1.51-1.28 (m, 1H), 0.92-0.78 (m, 2H), 0.74-0.54 (m, 2H). |

The following examples were synthesized according to General Procedure A, using commercially available building blocks:

| Example | Structure and name | Data |
|---|---|---|
| 132 | 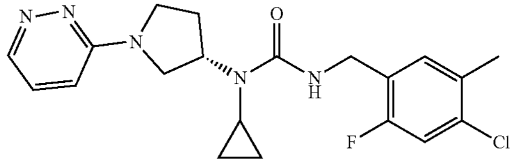 [SMILES: Cc1cc(CNC(=O)N(C2CC2)[C@H]2CCN(c3cccnn3)C2)c(F)cc1Cl]<br>1-[(4-chloro-2-fluoro-5-methylphenyl)methyl]-3-methyl-3-cyclopropyl-3-[(3S)-1-(pyridazin-3-yl)pyrrolidin-3-yl]urea | LC-MS: m/z 404 (M + H). 1H NMR (400 MHz, MeOD) δ 8.30 (dd, J = 4.5, 1.1 Hz, 1H), 7.25 (dd, J = 9.2, 4.5 Hz, 1H), 7.15 (d, J = 8.0 Hz, 1H), 7.02 (d, J = 9.8 Hz, 1H), 6.81 (dd, J = 9.2, 1.2 Hz, 1H), 4.48 (dd, J = 9.2, 7.9 Hz, 1H), 4.28 (s, 2H), 3.65 (dd, J = 15.3, 6.8 Hz, 2H), 3.50 (dd, J = 10.2, 8.1 Hz, 1H), 3.34 (dd, J = 17.7, 9.0 Hz, 1H), 2.50-2.39 (m, 2H), 2.23-2.14 (m, 4H), 0.85 (ddd, J = 6.9, 4.8, 2.8 Hz, 2H), 0.66 (qd, J = 6.4, 3.1 Hz, 2H), (m, 1H), 2.49-2.36 (m, 2H), 2.25 (s, 3H), 2.17-1.91 (m, 3H), 1.90-1.68 (m, 2H), 1.51-1.28 (m, 1H), 0.92-0.78 (m, 2H), 0.74-0.54 (m, 2H). |
| 133 | 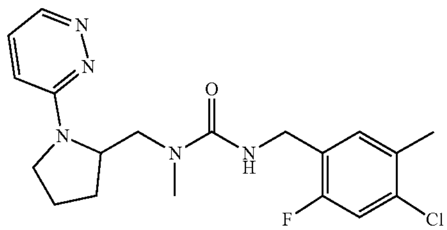 [SMILES: Cc1cc(CNC(=O)N(C)CC2CCCN2c2cccnn2)c(F)cc1Cl]<br>1-[(4-chloro-2-fluoro-5-methylphenyl)methyl]-3-methyl-3-{[1-(pyridazin-3-yl)pyrrolidin-2-yl]methyl}urea | LC-MS: m/z 392 (M + H). 1H NMR (400 MHz, MeOD) δ 8.42 (d, J = 4.4 Hz, 1H), 7.35 (dd, J = 9.2, 4.5 Hz, 1H), 7.28 (d, J = 8.0 Hz, 1H), 7.09 (d, J = 9.7 Hz, 1H), 7.02 (d, J = 9.2 Hz, 1H), 4.45 (s, 2H), 4.36 (s, 1H), 3.68 (d, J = 14.5 Hz, 1H), 3.57 (t, J = 8.7 Hz, 1H), 3.31 (s, 1H), 3.18 (d, J = 7.3 Hz, 1H), 3.02 (s, 3H), 2.29 (d, J = 15.1 Hz, 3H), 2.12 (ddd, J = 26.3, 13.1, 5.9 Hz, 4H). |
| 134 | 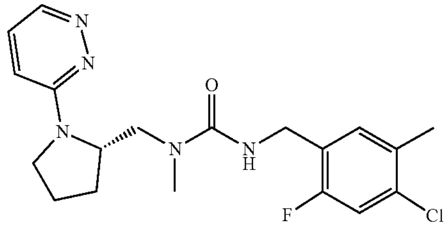 [SMILES: Cc1cc(CNC(=O)N(C)C[C@@H]2CCCN2c2cccnn2)c(F)cc1Cl]<br>1-[(4-chloro-2-fluoro-5-methylphenyl)methyl]-3-methyl-3-{[(2S)-1-(pyridazin-3-yl)pyrrolidin-2-yl]methyl}urea | LC-MS: m/z 392 (M + H). 1HNMR (400 MHz, MeOD) δ 8.42 (d, J = 4.3 Hz, 1H), 7.35 (dd, J = 9.2, 4.4 Hz, 1H), 7.28(d, J = 8.0 Hz, 1H), 7.09 (d, J = 9.7 Hz, 1H), 7.02 (d, J = 9.1 Hz, 1H), 4.45 (s, 2H), 4.36(s, 1H), 3.68(d, J = 14.1 Hz, 1H), 3.57 (t, J = 8.7 Hz, 1H), 3.31 (s, 4H), 3.17 (s, 1H), 3.02 (s, 3H), 2.27 (s, 3H), 2.12 (ddd, J = 26.1, 13.1, 5.8 Hz, 4H). |
| 135 | 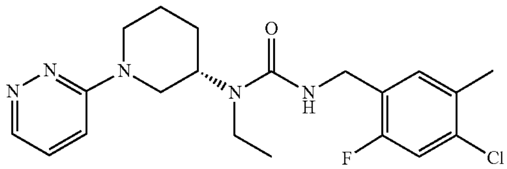<br>3[(4-chloro-2-fluoro-5-methylphenyl)methyl]-1-ethyl-1-[(3R)-1-(pyridazin-3-yl)piperidin-3-yl]urea | LC-MS: m/z 392 (M + H). 1H NMR (400 MHz, MeOD) δ 8.44 (dd, J = 4.4, 1.1 Hz, 1H), 7.38 (dd, J = 9.4, 4.4 Hz, 1H), 7.31-7.20 (m, 2H), 7.11 (d, J = 9.8 Hz, 1H), 4.44-4.30 (m, 4H), 4.05-3.95 (m, 1H), 3.36 (ddd, J = 14.3, 7.2, 3.5 Hz, 2H), 3.09-3.01 (m, 1H), 2.92 (td, J = 13.1, 2.4 Hz, 1H), 2.30 (s, 3H), 1.98-1.83 (m, 3H), 1.74-1.58 (m, 1H), 1.19 (t, J = 7.1 Hz, 3H). |

-continued

| Example | Structure and name | Data |
|---|---|---|
| 136 | 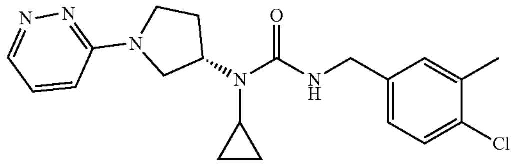 [SMILES: Cc1cc(CNC(=O)N(C2CC2)[C@H]2CCN(c3cccnn3)C2)ccc1Cl] 1-[(4-chloro-3-methylphenyl)methyl]-3-cyclopropyl-3-[(3S)-1-(pyridazin-3-yl)pyrrolidin-3-yl]urea | LC-MS: m/z 386 (M + H). 1H NMR (400 MHz, MeOD) δ 8.40 (dd, J = 4.4, 1.1 Hz, 1H), 7.36 (dd, J = 9.2, 4.5 Hz, 1H), 7.27 (d, J = 8.2 Hz, 1H), 7.21 (s, 1H), 7.10 (dd, J = 8.2, 1.8 Hz, 1H), 6.97 (t, J = 6.0 Hz, 1H), 6.92 (d, J = 9.3 Hz, 1H), 4.65-4.52(m, 1H), 4.33 (d,J = 4.4 Hz, 2H), 3.75 (t, J = 9.3 Hz, 2H), 3.61(dd, J = 10.1, 8.1 Hz, 1H), 3.45 (dd, J = 17.7, 9.0 Hz, 1H), 2.55 (ddd, J = 13.1, 8.4, 4.7 Hz, 2H), 2.34 (s, 3H), 2.31-2.24 (m, 1H), 0.98-0.91 (m, 2H), 0.81-0.71 (m, 2H). |
| 137 | 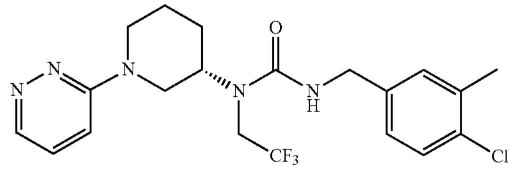 [SMILES: Cc1cc(CNC(=O)N(CC(F)(F)F)[C@H]2CCCN(c3cccnn3)C2)ccc1Cl] 3[(4-chloro-3-methylphenyl)methyl]-1[(3R)-1-(pyridazin-3-yl)piperidin-3-yl]-1-(2,2,2-trifluoroethyl)urea | LC-MS: m/z 442(M + H). 1HNMR (400 MHz, MeOD) δ 8.50 (d, J = 4.0 Hz, 1H), 7.40(dd, J = 9.4, 4.4 Hz, 1H), 7.30(dd, J = 9.4, 1.1 Hz, 1H), 7.25(d, J = 8.3 Hz, 2H), 7.14(dd, J = 8.2, 1.8 Hz, 1H), 4.50(d, J = 13.0 Hz, 1H), 4.42(d, J = 4.6 Hz, 2H), 4.38-4.29 (m, 1H), 4.20 (d, J = 13.7 Hz, 1H), 3.97(dd, J = 16.4, 8.7 Hz, 1H), 3.80 (td, J = 11.3, 5.6 Hz, 1H), 3.11-3.01 (m, 2H), 2.01-1.87 (m, 3H), 1.70-1.59 (m, 1H). |
| 138 | 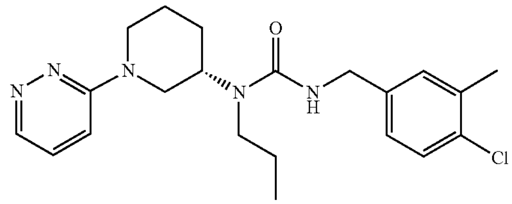 [SMILES: CCCN(C(=O)NCc1ccc(Cl)c(C)c1)[C@H]1CCCN(c2cccnn2)C1] 3[(4-chloro-3-methylphenyl)methyl]-1-propyl-1-[(3R)-1-(pyridazin-3-yl)piperidin-3-yl]urea | LC-MS: m/z 402 (M + H). 1H NMR (400 MHz, DMSO) δ 8.51 (dd, J = 4.4, 1.1 Hz, 1H), 7.37-7.32 (m, 2H), 7.26-7.21 (m, 2H), 7.10 (dd, J = 8.2, 1.8 Hz, 1H), 6.98(d, J = 5.6 Hz, 1H), 4.31-4.18(m, 4H), 3.87(d, J = 11.6 Hz, 1H), 3.11 (dd, J = 12.7, 6.8 Hz, 2H), 2.97 (t, J = 11.8 Hz, 1H), 2.84 (t, J = 12.2 Hz, 1H), 2.30 (s, 3H), 1.79 (t, J = 15.2 Hz, 3H), 1.50 (dd, J = 14.6, 7.0 Hz, 3H), 0.85 (t, J = 7.3 Hz, 3H). |
| 139 | 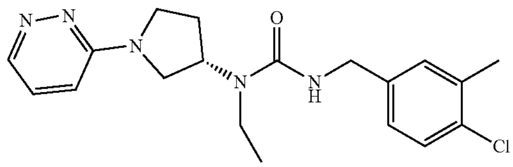 [SMILES: CCN(C(=O)NCc1ccc(Cl)c(C)c1)[C@H]1CCN(c2cccnn2)C1] 1-[(4-chloro-3-methylphenyl)methyl]-3-ethyl-3-[(3S)-1-(pyridazin-3-yl)pyrrolidin-3-yl]urea | LC-MS: m/z 374.1 (M + H). 1H NMR (400 MHz, MeOD) δ 8.42 (d, J = 4.4 Hz, 1H), 8.21 (s, 1H), 7.40 (dd, J = 9.2, 4.4 Hz, 1H), 7.27 (d, J = 8.4 Hz, 1H), 7.21(s, 1H), 7.10 (d, J = 8.0 Hz, 1H), 6.98 (dd, J = 9.2, 1.2 Hz, 1H), 4.87-4.80(m, 1H), 4.32 (s, 2H), 3.78-3.71 (m, 2H), 3.50-3.39 (m, 2H), 3.37-3.33 (m, 2H), 2.34 (s, 3H), 2.26 (dd, J = 8.4, 6.0 Hz, 2H), 1.20 (t, J = 7.2 Hz, 3H). |
| 140 | 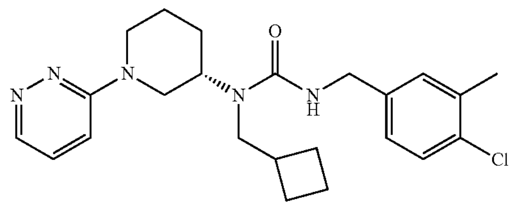 [SMILES: Cc1cc(CNC(=O)N(CC2CCC2)[C@H]2CCCN(c3cccnn3)C2)ccc1Cl] 3[(4-chloro-3-methylphenyl)methyl]-1-(cyclobutylmethyl)-1-[(3R)-1-(pyridazin-3-yl)piperidin-3-yl]urea | LC-MS: m/z 428.2 (M + H). 1H NMR (400 MHz, MeOD) δ 8.46 (d, J = 3.5 Hz, 1H), 7.38 (dd, J = 9.4, 4.4 Hz, 1H), 7.31-7.22 (m, 3H), 7.14-7.08 (m, 1H), 4.44-4.22 (m, 4H), 3.75 (ddd, J = 15.2, 7.7, 3.9 Hz, 1H), 3.42 (dd, J = 15.1, 7.6 Hz, 1H), 3.26 (dd, J = 15.2, 6.8 Hz, 1H), 3.14-3.05 (m, 1H), 2.97 (td, J = 13.2, 2.5 Hz, 1H), 2.59 (dt, J = 15.0, 7.5 Hz, 1H), 2.33 (s, 3H), 2.11-1.74 (m, 9H), 1.70-1.56 (m, 1H). |

-continued

| Example | Structure and name | Data |
| --- | --- | --- |
| 141 | 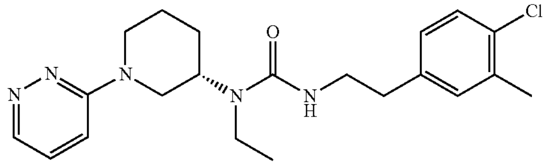 3-[2-(4-chloro-3-methylphenyl)ethyl]-1-ethyl-1-[(3R)-1-(pyridazin-3-yl)piperidin-3-yl]urea | LC-MS: m/z 428.2 (M + H). 1H NMR (400 MHz, MeOD) δ 8.46 (dd, J = 4.4, 1.2 Hz, 1H), 7.39 (dd, J = 9.6, 4.4 Hz, 1H), 7.27 (dd, J = 9.6, 1.2 Hz, 1H), 7.20 (d, J = 8.0 Hz, 1H), 7.13(d, J = 1.6 Hz, 1H), 7.01 (dd, J = 8.0, 2.0 Hz, 1H), 4.34-4.23(m, 2H), 3.87(d, J = 4.8 Hz, 1H), 3.42 (t, J = 7.2 Hz, 2H), 3.37-3.32 (m, 1H), 3.25 (dd, J = 15.2, 7.2 Hz, 1H), 3.03-2.88 (m, 2H), 2.78 (t, J = 7.2 Hz, 2H), 2.29 (s, 3H), 1.94-1.83 (m, 3H), 1.71-1.52 (m, 1H), 1.11 (t, J = 7.2 Hz, 3H). |
| 142 | 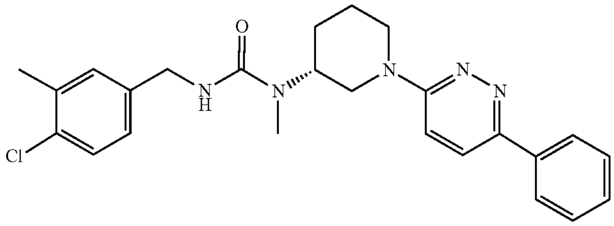 [SMILES: Cc1cc(CNC(=O)N(C)[C@@H]2CCCN(c3ccc(-c4ccccc4)nn3)C2)ccc1Cl] 3-[(4-chloro-3-methylphenyl)methyl]-1-methyl-1-[(3R)-1-(6-phenylpyridazin-3-yl)piperidin-3-yl]urea | LC-MS: m/z 450.2 (M + H). 1H NMR (400 MHz, MeOD) δ 7.93-7.88 (m, 2H), 7.83 (d, J = 9.6 Hz, 1H), 7.50-7.40 (m, 3H), 7.35 (d, J = 9.6 Hz, 1H), 7.29-7.23 (m, 2H), 7.12 (dd, J = 8.2, 1.8 Hz, 1H), 4.45-4.32 (m, 4H), 4.14 (dt, J = 13.7, 7.0 Hz, 1H), 3.10 (dd, J = 12.4, 11.4 Hz, 1H), 2.97 (dd, J = 12.9, 2.3 Hz, 1H), 2.91 (s, 3H), 2.33 (s, 3H), 1.92 (dd, J = 15.3, 5.2 Hz, 3H), 1.71 (d, J = 12.4 Hz, 1H). |
| 143 | 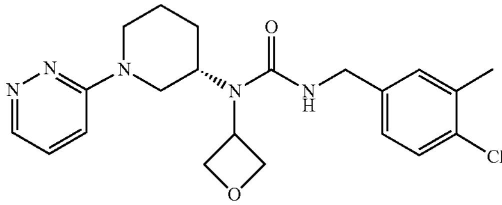 [SMILES: Cc1cc(CNC(=O)N(C2COC2)[C@H]2CCCN(c3cccnn3)C2)ccc1Cl] 3-[(4-chloro-3-methylphenyl)methyl]-1-(oxetan-3-yl)-1-[(3R)-1-(pyridazin-3-yl)piperidin-3-yl]urea | LC-MS: m/z 416 (M + H). 1H NMR (400 MHz, MeOD) δ 8.47 (d, J = 4.0 Hz, 1H), 7.38 (dd, J = 9.6, 4.4 Hz, 1H), 7.30-7.16 (m, 3H), 7.12-7.05 (m, 1H), 4.98 (t, J = 5.6 Hz, 1H), 4.84-4.73 (m, 3H), 4.56-4.48 (m, 1H), 4.32 (s, 2H), 4.27 (s, 1H), 4.20 (d, J = 13.2 Hz, 1H), 3.68-3.62 (m, 1H), 3.30-3.21 (m, 1H), 3.00 (td, J = 13.2, 2.8 Hz, 1H), 2.32 (s, 3H), 2.08-1.78 (m, 3H), 1.62 (dt, J = 13.2, 4.0 Hz, 1H). |
| 144 | 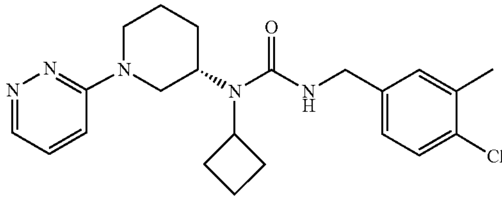 [SMILES: Cc1cc(CNC(=O)N(C2CCC2)[C@H]2CCCN(c3cccnn3)C2)ccc1Cl] 3-[(1R,2S)-2-(4-fluorophenyl)cyclopropyl]-1-methyl-1-[(3R)-1-(pyridazin-3-yl)piperidin-3-yl]urea | LC-MS: m/z 414.4 (M + H). |
| 145 | 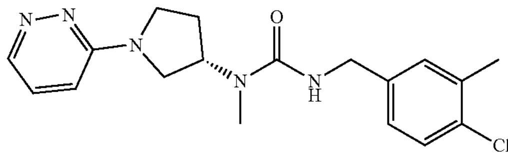 [SMILES: Cc1cc(CNC(=O)N(C)[C@H]2CCN(c3cccnn3)C2)ccc1Cl] 1-[(4-chloro-3-methylphenyl)methyl]-3-methyl-3-[(3S)-1-(pyridazin-3-yl)pyrrolidin-3-yl]urea | LC-MS: m/z 360.2 (M + H). 1H NMR (400 MHz, MeOD) δ 8.43 (dd, J = 4.5, 1.2 Hz, 1H), 7.39 (dd, J = 9.2, 4.5 Hz, 1H), 7.27 (d, J = 8.2 Hz, 1H), 7.22 (s, 1H), 7.10 (dd, J = 8.2, 1.7 Hz, 1H), 6.97 (dd, J = 9.2, 1.2 Hz, 1H), 5.04 (p, J = 7.8 Hz, 1H), 4.32 (s, 2H), 3.80-3.64 (m, 2H), 3.46 (ddd, J = 18.1, 13.5, 7.9 Hz, 2H), 2.89 (s, 3H), 2.36 (d, J = 9.7 Hz, 3H), 2.27-2.14 (m, 2H). |

General Intermediate Synthesis, Methods B-G

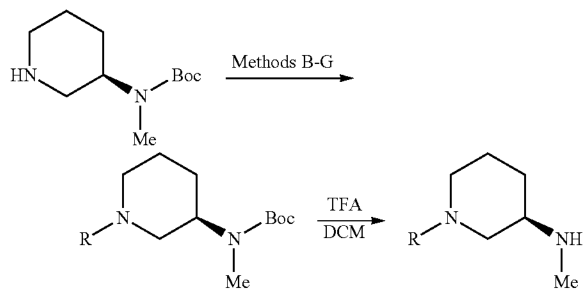

Method B: $K_2CO_3$/CsF/DMSO at 90° C. for 16 hrs

Method C: $Pd(OAc)_2$/DavePhos/t-BuONa/toluene at 100° C. for 16 hrs

Method D: $Pd(OAc)_2$/RuPhos/LiHMDS/THF at 70° C. for 2~8 hrs

Method E: XPhos-Pd-G1/XPhos/LiHMDS/THF at 70° C. for 2~8 hrs

Method F: RuPhos-Pd-G2/RuPhos/LiHMDS/THF at 70° C. for 2~16 hrs

Method G: CuI/L-proline/$K_2CO_3$/DMSO

General Procedure B:

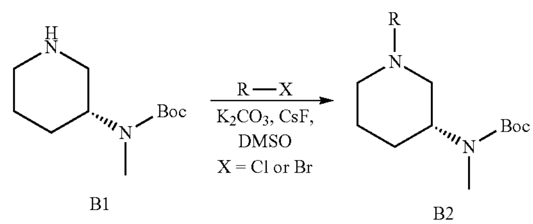

B1 B2

To a mixture of compound B1 (1.0 eq) and aryl halide (1.1 eq) in DMSO (0.1 mol/L) were added $K_2CO_3$ (3.0 eq) and CsF (0.2 eq). The resulting mixture was stirred at 90° C. for 16 hrs. Then the mixture was diluted with $H_2O$ and extracted with EtOAc twice. The combined organic layers were washed with brine, dried over anhydrous $Na_2SO_4$, filtered and concentrated to dryness. The residue was purified by column chromatography on silica gel to give compound B2.

Example Synthesis of General Procedure B:

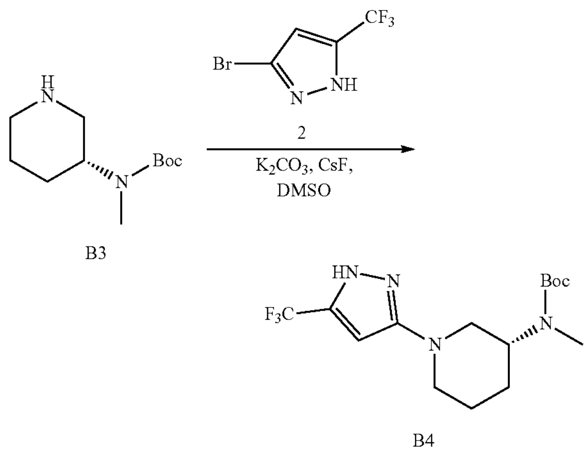

B3

B4

To a mixture of compound B3 (100 mg, 0.47 mmol) and compound 2 (101 mg, 0.47 mmol) in DMSO (8 mL) were added $K_2CO_3$ (194 mg, 1.40 mmol) and CsF (15 mg, 0.09 mmol). The resulting mixture was stirred at 90° C. for 16 hrs. Then the mixture was diluted with $H_2O$ (30 mL) and extracted with EtOAc (20 mL*2). The combined organic layers were washed with brine, dried over anhydrous $Na_2SO_4$ and concentrated to dryness. The residue was purified by column chromatography on silica gel (eluted with PE:EtOAc=10:1 to 2:1) to give compound B4 (140 mg, 87.5% yield) as yellow solid. LC/MS (ESI) m/z: 349 $(M+H)^+$.

General Procedure C:

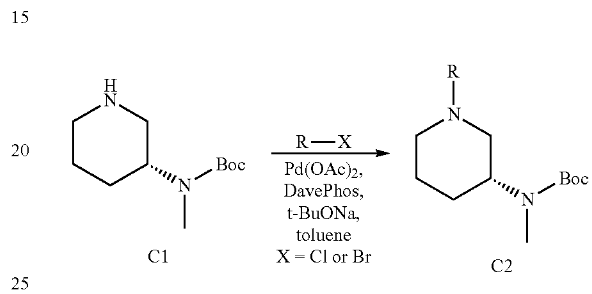

C1 C2

To a mixture of compound C1 (1.2 eq.) and aryl halide (1.0 eq.) in toluene was added t-BuONa (2.0 eq.), DavePhos (0.1 eq.) and $Pd(OAc)_2$ (0.1 eq.) under $N_2$ atmosphere. The resulting mixture was stirred at 100° C. for 16 hrs under $N_2$ atmosphere. Then the mixture was diluted with EtOAc, filtered and concentrated to dryness. The residue was purified by column chromatography on silica gel to give compound C2.

Example Synthesis of General Procedure C:

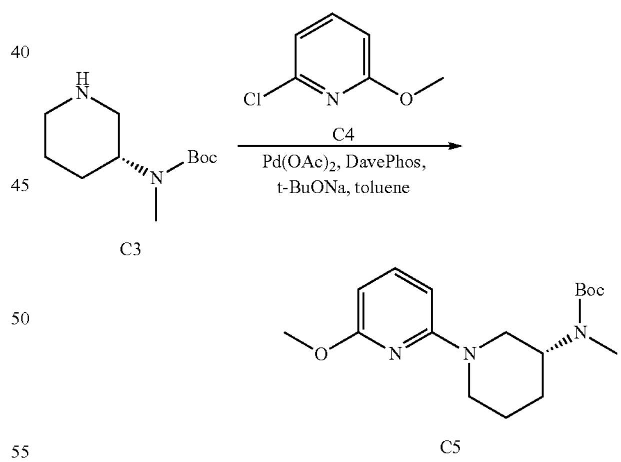

C3

C5

To a mixture of C3 (0.58 g, 2.72 mmol) and C4 (0.3 g, 2.09 mmol) in toluene (15 mL) was added t-BuONa (410 mg, 4.18 mmol), DavePhos (83 mg, 0.21 mmol) and $Pd(OAc)_2$ (47 mg, 0.21 mmol) under $N_2$ atmosphere. The resulting mixture was stirred at 120° C. for 16 hrs under $N_2$ atmosphere. Then the mixture was diluted with EtOAc (30 mL), filtered and concentrated to dryness. The residue was purified by column chromatography on silica gel (eluted with PE:EtOAc=50:1 to 20:1) to give compound C5 (0.58 g, 87% yield) as colorless oil. LC/MS (ESI) m/z: 322 $(M+H)^+$.

General Procedure D:

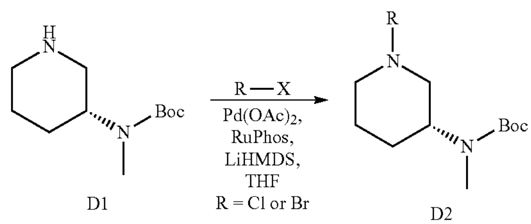

D1 D2

To a mixture of amine D1 (1.1 eq.) and aryl halide (1.0 eq.) in THF were added a solution of LiHMDS in THF (5.0 eq., 1 M), RuPhos (0.1 eq.) and $Pd(OAc)_2$ (0.1 eq.) under $N_2$ atmosphere. The resulting mixture was stirred at 80° C. for 4 hrs under $N_2$ atmosphere. Then the mixture was quenched with aq. $NH_4Cl$ and extracted with EtOAc twice. The combined organic layers were dried over anhydrous $Na_2SO_4$, filtered and concentrated to dryness under reduced pressure. The residue was purified by column chromatography on silica gel to give compound D2.

Example Synthesis of General Procedure D:

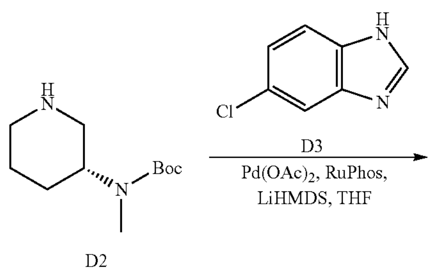

D2

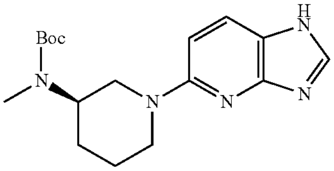

D4

To a mixture of D2 (153 mg, 0.72 mmol) and D3 (100 mg, 0.65 mmol) in THF (12 mL) were added LiHMDS (3.3 mL, 1 M in THF), RuPhos (31 mg, 0.07 mmol) and $Pd(OAc)_2$ (15 mg, 0.07 mmol) under $N_2$ atmosphere. The resulting mixture was stirred at 80° C. for 4 hrs under $N_2$ atmosphere. Then the mixture quenched with aq. $NH_4Cl$ (30 mL) and extracted with EtOAc (20 mL) twice. The combined organic layers were dried over anhydrous $Na_2SO_4$, filtered and concentrated to dryness under reduced pressure. The residue was purified by column chromatography on silica gel (eluted with PE:EtOAc=50:1 to 5:1) to give D4 (115 mg, 53% yield) as light-yellow solid. LC/MS (ESI) m/z: 332 $(M+H)^+$.

Example of General Procedure E:

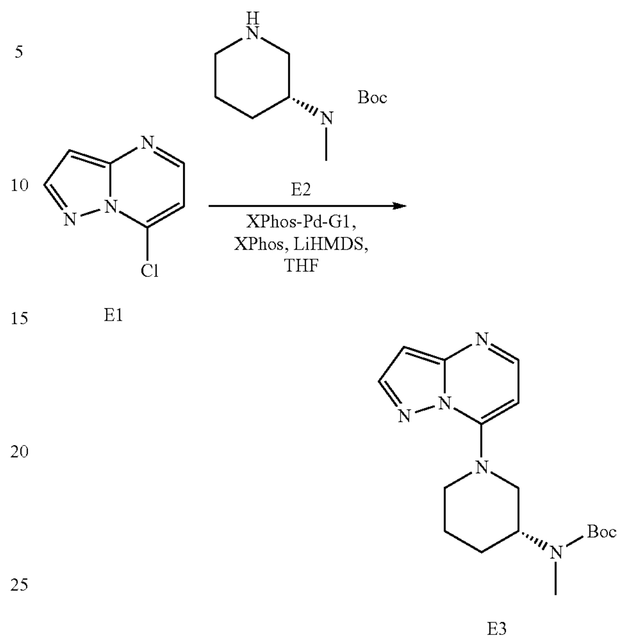

E1 E3

To a mixture of E1 (100 mg, 0.65 mmol) and E2 (182 mg, 0.85 mmol) in THF (18 mL) was added XPhos-Pd-G1 (25 mg, 0.03 mmol), XPhos (33 mg, 0.07 mmol) and LiHMDS (2.6 mL, 1 M in THF). The resulting mixture was stirred at 80° C. for 16 hrs under $N_2$ atmosphere. Then the mixture was quenched with aq. $NH_4Cl$ (40 mL) and extracted with EtOAc (25 mL) twice. The combined organic layers were dried over anhydrous $Na_2SO_4$, filtered and concentrated to dryness under reduced pressure. The residue was purified by column chromatography on silica gel (eluted with PE:EtOAc=20:1 to 3:1) to give E3 (130 mg, 60% yield) a light yellow oil. LC/MS (ESI) m/z: 332 $(M+H)^+$.

Example of General Procedure F:

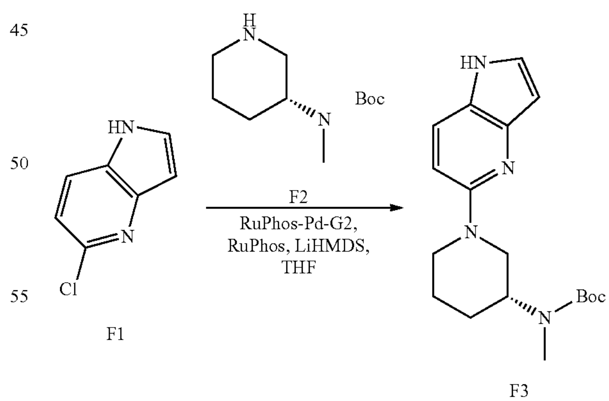

F1 F3

To a mixture of F1 (200 mg, 1.311 mmol) and F2 (280 mg, 1.311 mmol) in THF (20 mL) was added RuPhos (61 mg, 0.131 mmol) and RuPhos-Pd-G2 (101 mg, 0.131 mmol). After stirring at 0° C. for 10 min, LiHMDS (3.14 mL, 1M in THF) was added drop-wisely and the resulting mixture was stirred at 70° C. for another 3 hrs under $N_2$ atmosphere. After cooling, the mixture quenched with aq. $NH_4Cl$ (30 mL) and extracted with EtOAc (20 mL) twice. The combined organic layers were dried over anhydrous $Na_2SO_4$, filtered and concentrated to dryness under reduced pressure. The residue was purified by column chromatography on silica gel (eluted with PE:EtOAc=50:1 to 2:1) to give F3 (160 mg, 37% yield) as a yellow oil. LC/MS (ESI) m/z: 331 $(M+H)^+$.

Example of General Procedure G:

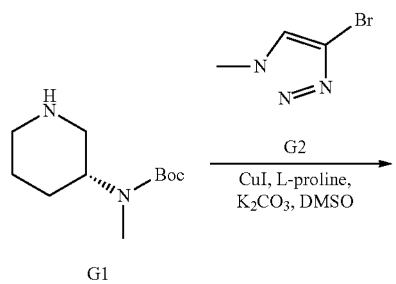

G1

-continued

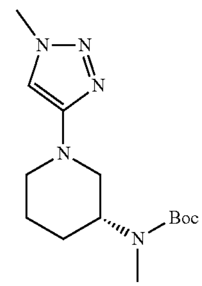

G3

To a solution of G2 (200 mg, 1.235 mmol) and G1 (265 mg, 1.235 mmol) in DMSO (10 mL) was added CuI (47 mg, 0.247 mmol), L-proline (28 mg, 0.247 mmol) and $K_2CO_3$ (512 mg, 3.704 mmol) and the resulting mixture was stirred at 100° C. for 16 hrs under $N_2$ atmosphere. After cooling, the mixture quenched with aq. $NH_4Cl$ (30 mL) and extracted with EtOAc (20 mL) twice. The combined organic layers were dried over anhydrous $Na_2SO_4$, filtered and concentrated to dryness under reduced pressure. The residue was purified by column chromatography on silica gel (eluted with DCM:MeOH=100:1 to 20:1) to give G3 (160 mg, 44% yield) as yellow oil. LC/MS (ESI) m/z: 296 $(M+H)^+$.

The examples in table below were prepared from the appropriate starting materials described previously or commercially available starting materials using the similar methods above.

| Example | Method | Structure and Name | Data |
|---|---|---|---|
| 146 | B | 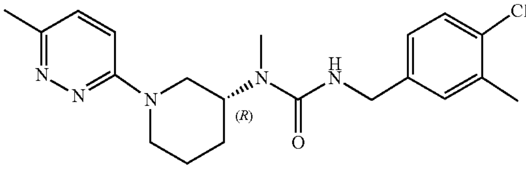 (R)-3-(4-chloro-3-methylbenzyl)-1-methyl-1-(1-(6-methylpyridazin-3-yl)piperidin-3-yl)urea | LC-MS: m/z 416 (M + H). 1H NMR (400 MHz, MeOD) δ 7.38 (d, J = 0.8 Hz, 2H), 7.26 (d, J = 8.2 Hz, 1H), 7.21 (s, 1H), 7.10 (dd, J = 8.2, 1.8 Hz, 1H), 4.32 (s, 2H), 4.31-4.18 (m, 2H), 4.11 (dt, J = 11.2, 7.7 Hz, 1H), 3.07-2.99 (m, 1H), 2.94-2.85 (m, 4H), 2.49 (s, 3H), 2.33 (s, 3H), 1.92-1.83 (m, 3H), 1.74-1.61 (m, 1H). |
| 147 | B | 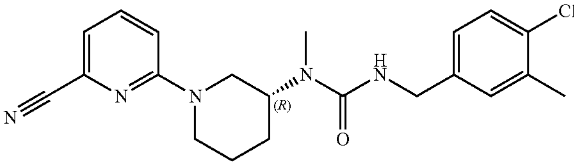 (R)-3-(4-chloro-3-methylbenzyl)-1-(1-(6-cyanopyridin-2-yl)piperidin-3-yl)-1-methyl]urea | 1H NMR (400 MHz, MeOD) δ 7.59 (dd, J = 8.9, 7.2 Hz, 1H), 7.27 (d, J = 8.2 Hz, 1H), 7.21 (s, 1H), 7.12-7.05 (m, 2H), 7.01 (d, J = 7.0 Hz, 1H), 4.37-4.24 (m, 4H), 4.11-4.01 (m, 1H), 2.96 (dd, J = 12.5, 11.3 Hz, 1H), 2.89 (s, 3H), 2.81 (td, J = 13.0, 2.4 Hz, 1H), 2.33 (d, J = 5.1 Hz, 3H), 1.89-1.81 (m, 3H), 1.69-1.57 (m, 1H). |

-continued

| Example | Method | Structure and Name | Data |
|---|---|---|---|
| 148 | C | 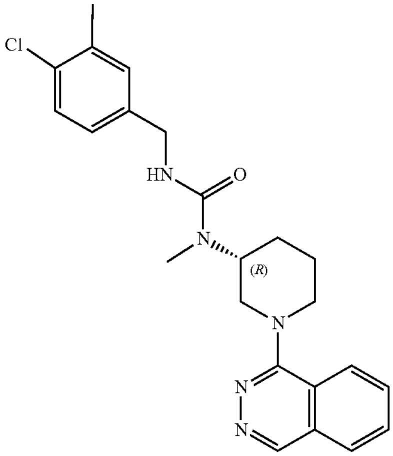 (R)-3-(4-chloro-3-methylbenzyl)-1-methyl-1-(1-(phthalazin-1-yl)piperidin-3-yl)urea | LC-MS: m/z 424 (M + H). 1H NMR (400 MHz, MeOD) δ 9.15 (s, 1H), 8.19 (dd, J = 6.0, 3.5 Hz, 1H), 8.05 (dd, J = 6.1, 3.1 Hz, 1H), 7.96-7.90 (m, 2H), 7.26-7.21 (m, 2H), 7.10 (dd, J = 8.2, 1.8 Hz, 1H), 4.53 (s, 1H), 4.35 (s, 2H), 3.89 (dd, J = 27.3, 12.2 Hz, 2H), 3.12 (t, J = 11.6 Hz, 1H), 3.03 (s, 1H), 2.91 (s, 3H), 2.30 (s, 3H), 1.97 (dd, J = 6.4, 3.5 Hz, 3H), 1.92-1.84 (m, 1H). |
| 149 | C | 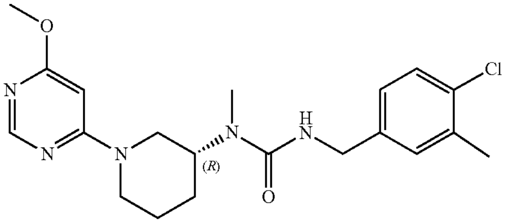 (R)-3-(4-chloro-3-methylbenzyl)-1-(1-(6-methoxypyrimidin-4-yl)piperidin-3-yl)-1-methyl]urea | LC-MS: m/z 404 (M + H). |
| 150 | C | 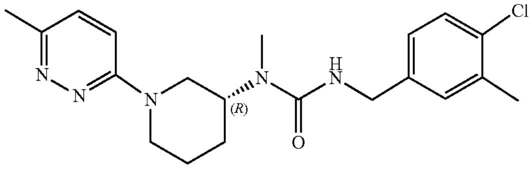 (R)-3-(4-chloro-3-methylbenzyl)-1-methyl-1-(1-(5-methylpyridin-2-yl)piperidin-3-yl)urea | LC-MS: m/z 387 (M + H). 1H NMR (400 MHz, DMSO) δ 8.18 (s, 1H), 7.82 (d, J = 2.0 Hz, 1H), 7.34 (d, J = 8.0 Hz, 2H), 7.24 (s, 1H), 7.12 (dd, J = 8.2, 1.8 Hz, 1H), 6.93(t, J-5.7 Hz,1H),6.75(d, J = 8.7 Hz, 1H), 4.27– 4.16 (m, 2H), 4.15-4.05 (m, 2H), 3.93 (d, J = 5.1 Hz, 1H), 2.76 (d, J = 10.3 Hz, 4H), 2.70-2.62 (m, 1H), 2.31 (s, 3H), 2.11 (s, 3H), 1.75-1.65 (m, 3H), 1.51 (dd, J = 14.0, 9.7 Hz, 1H). |
| 151 | C | 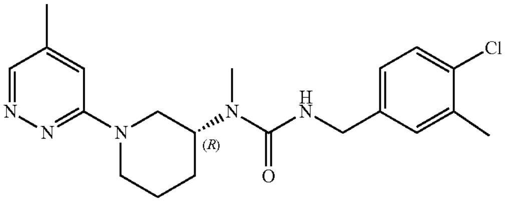 (R)-3-(4-chloro-3-methylbenzyl)-1-methyl-1-(1-(5-methylpyridazin-3-yl)piperidin-3-yl)urea | LC-MS: m/z 388 (M + H). 1H NMR (400 MHz, MeOD) δ 8.34 (s, 1H), 7.26 (d, J = 8.2 Hz, 1H), 7.22 (s, 1H), 7.13-7.08 (m, 2H), 4.38-4.24 (m, 4H), 4.08 (dd, J = 9.9, 5.4 Hz, 1H), 3.05-2.97 (m, 1H), 2.89 (s, 3H), 2.88-2.82 (m, 1H), 2.33 (s, 3H), 2.27 (s, 3H), 1.92-1.82 (m, 3H), 1.74-1.60 (m, 1H). |

-continued

| Example | Method | Structure and Name | Data |
|---|---|---|---|
| 152 | B | 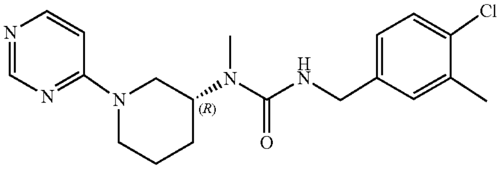 (R)-3-(4-chloro-3-methylbenzyl)-1-methyl-1-(1-(pyrimidin-4-yl)piperidin-3-yl)urea | LC-MS: m/z 374 (M + H). 1H NMR (400 MHz, MeOD) δ 8.47 (s, 1H), 8.09 (d, J = 6.8 Hz, 1H), 7.27 (d, J = 8.2 Hz, 1H), 7.22 (s, 1H), 7.10 (dd, J = 8.2, 1.7 Hz, 1H), 6.90 (d, J = 6.3 Hz, 1H), 4.48 (d, J = 20.4 Hz, 2H), 4.36-4.27(m, 2H), 4.13-4.02 (m, 1H), 3.10 (t, J = 12.0 Hz, 1H), 2.94 (dd, J = 9.8, 6.3 Hz, 1H), 2.90 (s, 3H), 2.34 (s, 3H), 1.98-1.82 (m, 3H), 1.61 (dt, J = 12.5, 3.5 Hz, 1H). |
| 153 | E | 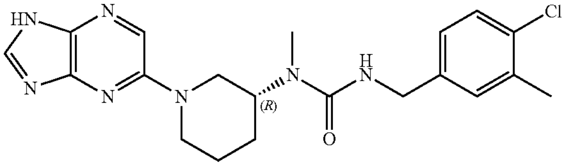 (R)-1-(1-(1H-imidazo[4,5-b]pyridin-5-yl)piperidin-3-yl)-3-(4-chloro-3-methylbenzyl)-1-methyl]urea | LC-MS: m/z 413 (M + H). |
| 154 | C | 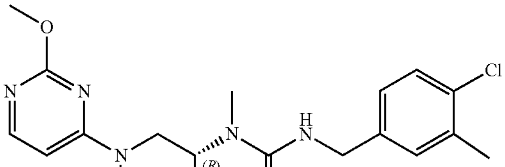 (R)-3-(4-chloro-3-methylbenzyl)-1-(1-(2-methoxypyrimidin-4-yl)piperidin-3-yl)-1-methyl]urea | LC-MS: m/z 404.2 (M + H). 1H NMR (400 MHz, MeOD) δ 7.90 (d, J = 6.3 Hz, 1H), 7.29-7.19 (m, 2H), 7.09 (dd, J = 8.0,1.8 Hz,1H), 6.42 (d, J-6.3 Hz, 1H), 4.40(s, 1H), 4.31 (d, J = 4.7 Hz, 2H), 4.11-4.03 (m, 1H), 3.85 (s, 3H), 3.03 (t, J = 11.9 Hz, 1H), 2.87 (d, J = 11.8 Hz, 4H), 2.34 (s, 3H), 1.99-1.80 (m, 4H), 1.65-1.54 (m, 1H). |
| 155 | B | 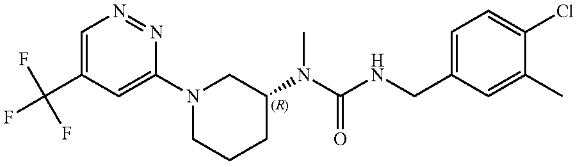 (R)-3-(4-chloro-3-methylbenzyl)-1-methyl-1-(1-(5-(trifluoromethyl)pyridazin-3-yl)piperidin-3-yl)urea | LC-MS: m/z 442 (M + H). 1H NMR (400 MHz, MeOD) δ 8.70 (d, J = 1.3 Hz, 1H), 7.53 (s, 1H), 7.26 (d, J = 8.2 Hz, 1H), 7.22 (s, 1H), 7.11 (dd, J = 8.2, 1.6 Hz, 1H), 4.48 (d, J = 12.7 Hz, 1H), 4.39 (dd, J = 12.6, 3.7 Hz, 1H), 4.32 (s, 2H), 4.17-4.07 (m, 1H), 3.15-3.07 (m, 1H), 3.00-2.93 (m, 1H), 2.91 (d, J = 6.2 Hz, 3H), 2.34 (s, 3H), 1.91 (ddd, J = 12.7, 10.2, 5.5 Hz, 3H), 1.75-1.61 (m, 1H). |
| 156 | C | 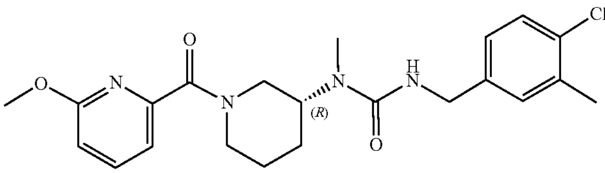 (R)-3-(3-chloro-2-methylbenzyl)-1-(1-(6-methoxypicolinoyl)piperidin-3-yl)-1-methyl]urea | LC-MS: m/z 431.2 (M + H). 1H NMR (400 MHz, MeOD) δ 7.79-7.67 (m, 1H), 7.25 (dd, J = 13.3, 8.3 Hz, 1H), 7.13 (dd, J = 13.9, 6.7 Hz, 2H), 7.04-6.79 (m, 2H), 4.65-4.51 (m, 1H), 4.36-4.11 (m, 3H), 3.94-3.77 (m, 4H), 3.20 (t, J = 12.0 Hz, 1H), 3.03-2.88 (m, 3H), 2.81-2.66 (m, 2H), 2.33 (d, J = 10.4 Hz, 3H), 1.96-1.67 (m, 4H). |

-continued

| Example | Method | Structure and Name | Data |
|---|---|---|---|
| 157 | B | 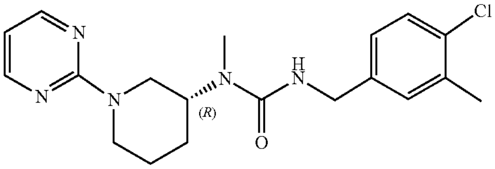 (R)-3-(4-chloro-3-methylbenzyl)-1-methyl-1-(1-(pyrimidin-2-yl)piperidin-3-yl)urea | LC-MS: m/z 374.1 (M + H). 1H NMR (400 MHz, MeOD) δ 8.24 (d, J = 4.8 Hz, 2H), 7.31-7.20 (m, 2H), 7.11 (d, J = 8.1 Hz,1H),6.91(d, J = 5.5 Hz, 1H), 6.54(t, J = 4.8 Hz, 1H), 4.71-4.59 (m, 2H), 4.34-4.26 (m, 2H), 3.97 (dd, J = 10.1, 5.2 Hz, 1H), 2.97 (t, J = 11.9 Hz, 1H), 2.89 (s, 3H), 2.85-2.76 (m, 1H), 2.34 (s, 3H), 1.91-1.79 (m, 3H), 1.66-1.53 (m, 1H). |
| 158 | B | 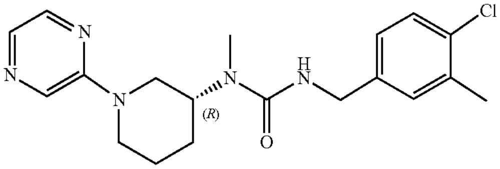 3-[(4-chloro-3-methylphenyl)methyl]-1-methyl-1-[(3R)-1-(pyrazin-2-yl)piperidin-3-yl]urea | LC-MS: m/z 374.2 (M + H). 1H NMR (400 MHz, MeOD) δ 8.20 (d, J = 1.2 Hz, 1H), 7.99 (dd, J = 2.4,1.5 Hz, 1H), 7.71 (d, J-2.7 Hz,1H), 7.27(d, J = 8.2 Hz, 1H), 7.22 (s, 1H), 7.10 (dd, J = 8.1, 1.6 Hz, 1H), 4.36-4.26 (m, 4H), 4.07 (dd, J = 9.6, 5.5 Hz, 1H), 3.01-2.94 (m, 1H), 2.89 (s, 3H), 2.87-2.79 (m, 1H), 2.34 (s, 3H), 1.90-1.81 (m, 3H), 1.71-1.59 (m, 1H). |
| 159 | B | 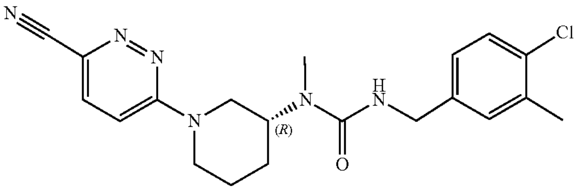 (R)-3-(4-chloro-3-methylbenzyl)-1-(1-(6-cyanopyridazin-3-yl)piperidin-3-yl)-1-methyl]urea | LC-MS: m/z 374.2 (M + H). 1H NMR (400 MHz, DMSO) δ 7.84 (d, J = 9.7 Hz, 1H), 7.34 (dd, J = 9.0, 4.9 Hz, 2H), 7.22 (s, 1H), 7.11 (dd, J = 8.2, 1.7 Hz, 1H), 6.97 (t, J = 5.8 Hz, 1H), 4.44 (dd, J = 31.8, 11.2 Hz, 2H), 4.20 (qd, J = 15.5, 5.8 Hz, 2H), 4.04-3.94 (m, 1H), 3.11 (t, J = 12.0 Hz, 1H), 2.99-2.89 (m, 1H), 2.80 (s, 3H), 2.31 (s, 3H), 1.87-1.65 (m, 3H), 1.58-1.45 (m, 1H). |
| 160 | B | 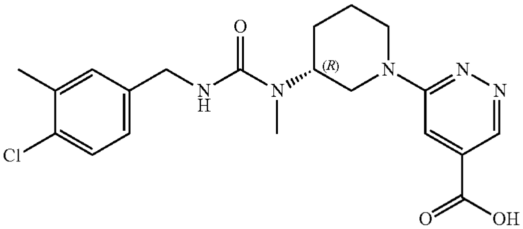 (R)-6-(3-(3-(4-chloro-3-methylbenzyl)-1-methylureido)piperidin-1-yl)pyridazine-4-carboxylic acid | LC-MS: m/z 418.1 (M + H). 1H NMR (400 MHz, MeOD) δ 8.84 (d, J = 1.2 Hz, 1H), 7.78 (d, J = 1.4 Hz, 1H), 7.26 (d, J = 8.2 Hz, 1H), 7.22 (s, 1H), 7.11 (dd, J = 8.1, 1.8 Hz, 1H), 4.44-4.33 (m, 2H), 4.32 (s, 2H), 4.13 (dd, J = 10.2, 5.9 Hz, 1H), 3.16-3.09 (m, 1H), 3.02-2.94 (m, 1H), 2.90 (s, 3H), 2.34 (s, 3H), 1.97-1.87 (m, 3H), 1.72 (dd, J = 14.0, 9.8 Hz, 1H). |
| 161 | C | 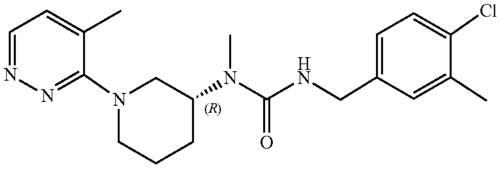 3-[(4-chloro-3-methylphenyl)methyl]-1-methyl-1-[(3R)-1-(4-methylpyridazin-3-yl)piperidin-3-yl]urea | LC-MS: m/z 388.4 (M + H). |

-continued

| Example | Method | Structure and Name | Data |
|---|---|---|---|
| 162 | B | 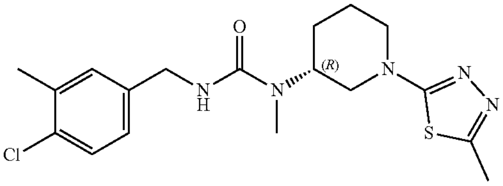 (R)-3-(4-chloro-3-methylbenzyl)-1-methyl-1-(1-(5-methyl-1,3,4-thiadiazol-2-yl)piperidin-3-yl)urea | LC-MS: m/z 394.2 (M + H). 1H NMR (400 MHz, MeOD) δ 7.27 (d, J = 8.2 Hz, 1H), 7.21 (s, 1H), 7.10 (dd, J = 8.2, 1.7 Hz, 1H), 4.30 (d, J = 2.8 Hz, 2H), 4.20 (ddd, J = 11.2, 10.3, 4.8 Hz, 1H), 3.83-3.72 (m, 2H), 3.20 (t, J = 11.8 Hz, 1H), 3.09-3.01 (m, 1H), 2.86 (s, 3H), 2.54 (s, 3H), 2.34 (s, 3H), 1.90-1.80 (m, 3H), 1.79-1.70 (m, 1H). |
| 163 | B | 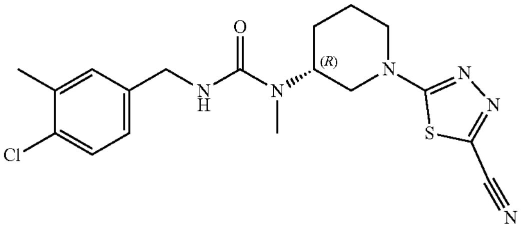 (R)-3-(4-chloro-3-methylbenzyl)-1-(1-(5-cyano-1,3,4-thiadiazol-2-yl)piperidin-3-yl)-1-methyl]urea | LC-MS: m/z 405.1 (M + H). 1HNMR (400 MHz,MeOD) δ 7.27 (d, J = 8.2 Hz, 1H), 7.21 (s, 1H), 7.10 (dd, J = 8.2,1.7 Hz, 1H), 4.31 (d, J = 4.1 Hz, 2H), 4.22 (d, J = 7.3 Hz, 1H), 4.00 (d, J = 11.3 Hz, 1H), 3.91 (dd, J = 12.4, 4.3 Hz, 1H), 3.43-3.35 (m, 1H), 3.23 (td, J = 12.7, 2.9 Hz, 1H), 2.88 (s, 3H), 2.35 (s, 3H), 1.97-1.74 (m, 4H). |
| 164 | B | 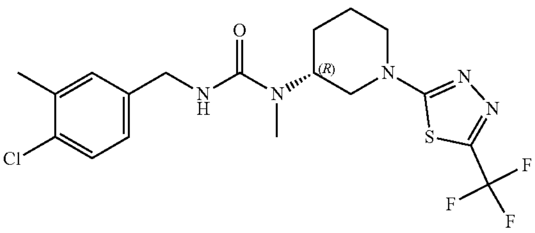 3-[(4-chloro-3-methylphenyl)methyl]-1-methyl-1-[(3R)-1-[5-(trifluoromethyl)-1,3,4-thiadiazol-2-yl]piperidin-3-yl]urea | LC-MS: m/z 448.1 (M + H). 1H NMR (400 MHz, MeOD) δ 7.27 (d, J = 8.2 Hz, 1H), 7.21 (s, 1H), 7.10 (dd, J = 8.2, 1.9 Hz, 1H), 4.31 (d, J = 5.0 Hz, 2H), 4.26-4.19 (m, 1H), 3.96 (d, J = 12.8 Hz, 1H), 3.88 (dd, J = 12.4, 4.5 Hz, 1H), 3.36 (d, J = 11.9 Hz, 1H), 3.19 (td, J = 12.7, 2.7 Hz, 1H), 2.88 (s, 3H), 2.33 (d, J = 6.3 Hz, 3H), 1.95-1.84 (m, 3H), 1.82-1.72 (m, 1H). |
| 165 | B | 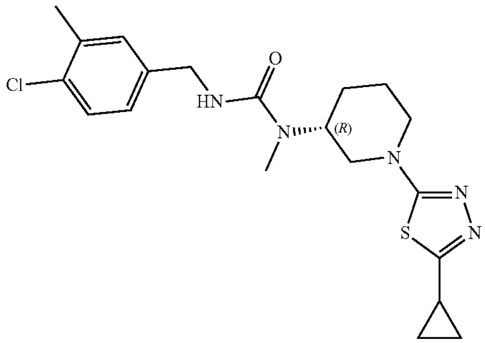 (R)-3-(4-chloro-3-methylbenzyl)-1-(1-(5-cyclopropyl-1,3,4-thiadiazol-2-yl)piperidin-3-yl)-1-methyl]urea | LC-MS: m/z 420 (M + H). 1H NMR (400 MHz, MeOD) δ 7.27 (d, J = 8.2 Hz, 1H), 7.21 (s, 1H), 7.10 (dd, J = 8.2, 1.8 Hz, 1H), 4.36-4.26 (m, 2H), 4.18 (td, J = 10.8, 5.5 Hz, 1H), 3.83-3.70 (m, 2H), 3.19 (t, J = 11.8 Hz, 1H), 3.08-3.00 (m, 1H), 2.86 (s, 3H), 2.34 (s, 3H), 2.20 (tt, J = 8.3, 5.0 Hz, 1H), 1.90-1.72 (m, 4H), 1.14-1.08 (m, 2H), 0.95-0.89 (m, 2H). |

-continued

| Example | Method | Structure and Name | Data |
|---|---|---|---|
| 166 | B | 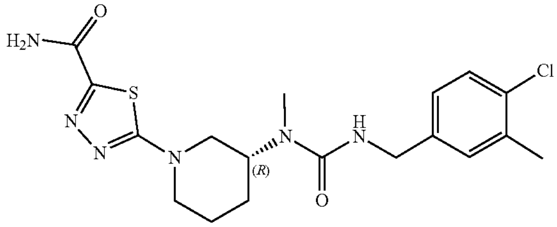 (R)-5-(3-(3-(4-chloro-3-methylbenzyl)-1-methylureido)piperidin-1-yl)-1,3,4-thiadiazole-2-carboxamide | LC-MS: m/z 420 (M + H). 1H NMR (400 MHz, MeOD) δ 7.30-7.24 (m, 1H), 7.21 (s, 1H), 7.09 (dd, J = 8.2, 1.7 Hz, 1H), 4.29 (d, J = 6.6 Hz, 2H), 4.22 (dd, J = 7.7, 3.5 Hz, 1H), 3.92 (d, J = 12.5 Hz, 2H), 3.35-3.31 (m, 1H), 3.16 (td, J = 12.8, 2.8 Hz, 1H), 2.87 (s, 3H), 2.34 (s, 3H), 1.95-1.82 (m, 3H), 1.81-1.72 (m, 1H). |
| 167 | E | 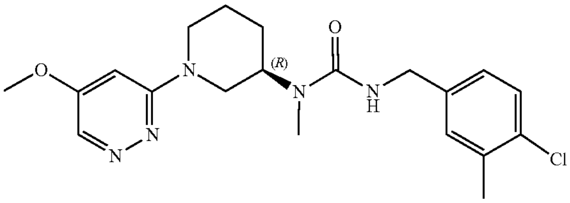 (R)-3-(4-chloro-3-methylbenzyl)-1-(1-(5-methoxypyridazin-3-yl)piperidin-3-yl)-1-methyl]urea | LC-MS: m/z 404 (M + H). 1H NMR (400 MHz, MeOD) δ 8.20 (s, 1H), 7.30-7.19 (m, 2H), 7.10 (dd, J = 8.2, 1.7 Hz, 1H), 6.69 (d, J = 2.3 Hz, 1H), 4.34(d, J = 18.1 Hz,3H), 4.23 (dd, J = 12.7,3.5 Hz, 1H), 4.10 (dt, J = 10.3,7.4 Hz, 1H), 3.89 (s, 3H), 3.04 (dd, J = 12.4, 11.4 Hz, 1H), 2.96-2.85 (m, 4H), 2.33 (s, 3H), 1.94-1.82 (m, 3H), 1.77-1.59 (m, 1H). |
| 168 | C | 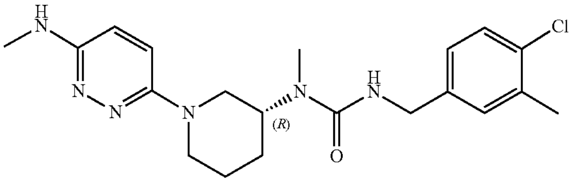 (R)-3-(4-chloro-3-methylbenzyl)-1-methyl-1-(1-(6-(methylamino)pyridazin-3-yl)piperidin-3-yl)urea | LC-MS: m/z 403.4 (M + H). 1H NMR (400 MHz, MeOD) δ 8.50 (s, 1H), 7.36 (d, J = 9.9 Hz, 1H), 7.28-7.20 (m, 2H), 7.10 (dd, J = 8.2, 1.8 Hz, 1H), 6.97 (d, J = 9.8 Hz, 1H), 4.32 (s, 2H), 4.22-4.13 (m, 1H), 4.05-3.90 (m, 2H), 2.95-2.88 (m, 4H), 2.87 (s, 3H), 2.83-2.75 (m, 1H), 2.33 (s, 3H), 1.90-1.77 (m, 3H), 1.77-1.62 (m, 1H). |

-continued
| Example | Method | Structure and Name | Data |
|---|---|---|---|
| 169 | F | 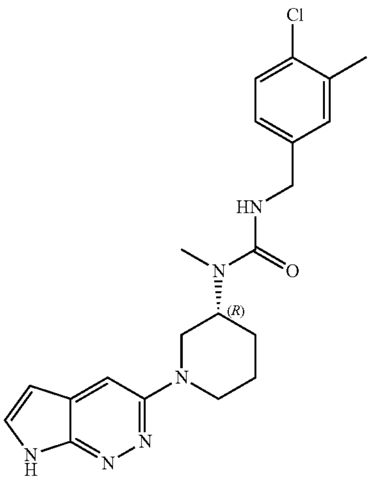 (R)-1-(1-(7H-pyrrolo[2,3-c]pyridazin-3-yl)piperidin-3-yl)-3-(4-chloro-3-methylbenzyl)-1-methyl]urea | LC-MS: m/z 413.2 (M + H). |
| 170 | E | 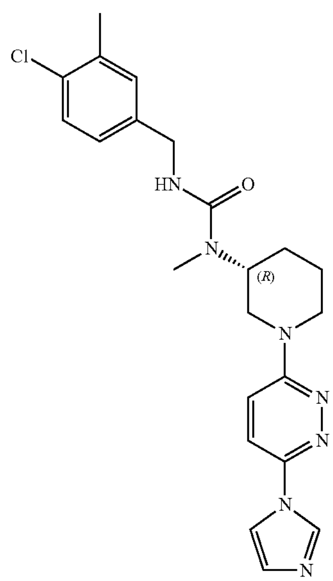 (R)-1-(1-(6-(1H-imidazol-1-yl)pyridazin-3-yl)piperidin-3-yl)-3-(4-chloro-3-methylbenzyl)-1-methyl]urea | LC-MS: m/z 440.1 (M + H). 1H NMR (400 MHz, DMSO) δ 8.43 (s, 1H), 7.92-7.87 (m, 2H), 7.56 (d, J = 9.8 Hz,1H), 7.34(d, J = 8.2 Hz, 1H), 7.23(s, 1 H), 7.14-7.09 (m, 2H), 6.96 (t, J = 5.8 Hz, 1H), 4.35 (d, J = 11.2 Hz, 1H), 4.28-4.17 (m, 3H), 4.00 (d, J = 11.0 Hz, 1H), 3.06-2.99 (m, 1H), 2.86 (t, J = 11.9 Hz, 1H), 2.81 (s, 3H), 2.31 (s, 3H), 1.84-1.69 (m, 3H), 1.56 (d, J = 12.8 Hz, 1H). |

-continued

| Example | Method | Structure and Name | Data |
|---|---|---|---|
| 171 | B | 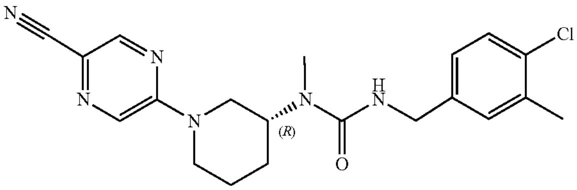 (R)-3-(4-chloro-3-methylbenzyl)-1-(1-(5-cyanopyrazin-2-yl)piperidin-3-yl)-1-methyl]urea | LC-MS: m/z 399.2 (M + H). 1H NMR (400 MHz, MeOD) δ 8.31 (d, J = 12.6 Hz, 2H), 7.28 (d, J = 8.2 Hz, 1H), 7.22 (s, 1H), 7.10 (dd, J = 8.2, 1.7 Hz, 1H), 4.49 (dd, J = 27.4, 12.4 Hz, 2H), 4.36-4.26 (m, 2H), 4.07 (td, J = 11.2, 5.6 Hz, 1H), 3.13-3.06 (m, 1H), 2.98-2.88 (m, 4H), 2.35 (s, 3H), 1.94-1.85 (m, 3H), 1.63 (dt, J = 22.3, 8.6 Hz, 1H). |
| 172 | B | 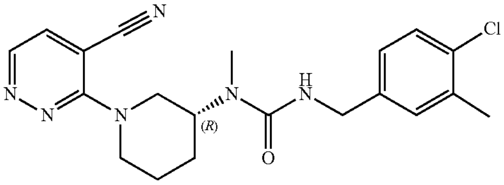 (R)-3-(4-chloro-3-methylbenzyl)-1-(1-(4-cyanopyridazin-3-yl)piperidin-3-yl)-1-methyl]urea | LC-MS: m/z 399.2 (M + H). 1H NMR (400 MHz, MeOD) δ 8.77 (d, J = 4.9 Hz, 1H), 7.78 (d, J = 4.9 Hz, 1H), 7.23 (dd, J = 12.7, 4.8 Hz, 2H), 7.10 (dd, J = 8.1, 1.8 Hz, 1H), 4.39 (dd, J = 13.4, 2.2 Hz, 1H), 4.35-4.28 (m, 3H), 4.25-4.13 (m, 1H), 3.24 (dd, J = 12.4, 11.3 Hz, 1H), 3.14-3.05 (m,1H), 2.90(d, J = 4.9 Hz,3H), 2.31 (d, J = 7.9 Hz, 3H), 1.97-1.77 (m, 4H). |
| 173 | D | 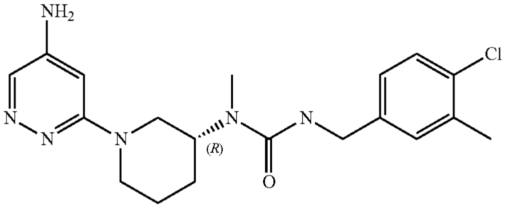 (R)-1-(1-(5-aminopyridazin-3-yl)piperidin-3-yl)-3-(4-chloro-3-methylbenzyl)-1-methyl]urea | LC-MS: m/z 389.1 (M + H). 1H NMR (400 MHz, MeOD) δ 8.49 (s, 1H), 7.94 (d, J = 2.2 Hz, 1H), 7.27 (d, J = 8.2 Hz, 1H), 7.21 (s, 1H), 7.10 (dd, J = 8.1, 1.9 Hz, 1H), 6.33 (d, J = 2.3 Hz, 1H), 4.32 (s, 2H), 4.18-4.09 (m, 1H), 4.05 (d, J = 13.3 Hz, 1H), 3.94 (d, J = 12.7 Hz, 1H), 3.12– 3.05 (m, 1H), 2.96 (dd, J = 18.7, 7.8 Hz, 1H), 2.89 (s, 3H), 2.34 (s, 3H), 1.88 (dd, J = 10.1, 4.8 Hz, 3H), 1.74-1.62 (m, 1H). |
| 174 | E | 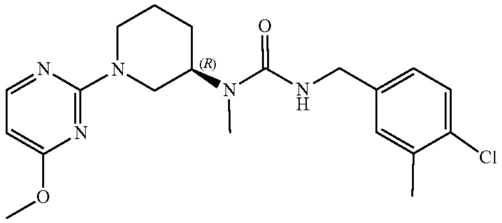 (R)-3-(4-chloro-3-methylbenzyl)-1-(1-(4-methoxypyrimidin-2-yl)piperidin-3-yl)-1-methyl]urea | LC-MS: m/z 404.2 (M + H). 1H NMR (400 MHz, MeOD) δ 7.92 (d, J = 5.7 Hz, 1H), 7.26 (d, J = 8.2 Hz, 1H), 7.21 (s, 1H), 7.12-7.07 (m, 1H), 5.99 (d, J = 5.7 Hz, 1H), 4.71-4.54 (m, 2H), 4.37-4.24 (m, 2H), 4.06-3.95 (m, 1H), 3.83 (s, 3H), 2.97 (t, J = 11.8 Hz, 1H), 2.88 (s, 3H), 2.81 (dd, J = 19.3, 7.8 Hz, 1H), 2.31 (d, J = 14.5 Hz, 3H), 1.91-1.77 (m, 3H), 1.67-1.52 (m, 1H). |

-continued

| Example | Method | Structure and Name | Data |
|---|---|---|---|
| 175 | B | 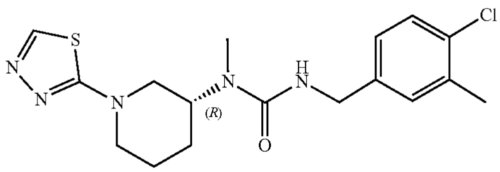 (R)-1-(1-(1,3,4-thiadiazol-2-yl)piperidin-3-yl)-3-(4-chloro-3-methylbenzyl)-1-methyl]urea | LC-MS: m/z 404.2 (M + H). 1H NMR (400 MHz, DMSO) δ 8.79 (s, 1H), 7.33 (d, J = 8.2 Hz, 1H), 7.22 (s, 1H), 7.11 (dd, J = 8.1, 1.9 Hz, 1H), 6.97 (t, J = 5.8 Hz, 1H), 4.23-4.17 (m, 2H), 4.15-4.08 (m, 1H), 3.79 (d, J = 12.0 Hz, 1H), 3.69 (dd, J = 12.0, 4.4 Hz, 1H), 3.18 (d, J = 11.7 Hz, 1H), 3.04 (dt, J = 12.6, 6.2 Hz, 1H), 2.77 (s, 3H), 2.31 (s, 3H), 1.81-1.62 (m, 4H). |
| 176 | G | 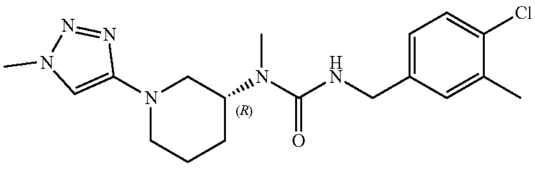 (R)-3-(4-chloro-3-methylbenzyl)-1-methyl-1-(1-(1-methyl-1H-1,2,3-triazol-4-yl)piperidin-3-yl)urea | LC-MS: m/z 377.2 (M + H). 1H NMR (400 MHz, MeOD) δ 7.31 (s, 1H), 7.27 (d, J = 8.2 Hz, 1H), 7.21 (d, J = 1.4 Hz, 1H), 7.10 (dd, J = 8.1, 1.7 Hz, 1H), 4.31 (s, 2H), 4.25 (dt, J = 8.9, 3.9 Hz, 1H), 3.98 (s, 3H), 3.62 (d, J = 11.1 Hz, 1H), 3.53 (dd, J = 11.4, 4.2 Hz, 1H), 2.86 (s, 3H), 2.77 (t, J = 11.3 Hz, 1H), 2.63 (td, J = 11.8, 2.9 Hz, 1H), 2.34 (s, 3H), 1.87-1.67 (m, 4H). |
| 177 | C | 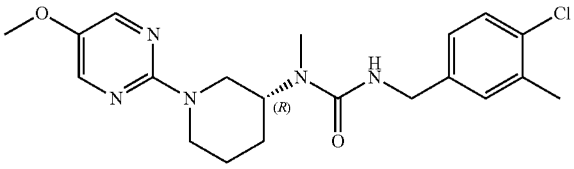 3-[(4-chloro-3-methylphenyl)methyl]-1-[(3R)-1-(5-methoxypyrimidin-2-yl)piperidin-3-yl]-1-methyl]urea | LC-MS: m/z 404.2 (M + H). 1H NMR (400 MHz, MeOD) δ 7.98 (s, 2H), 7.28 (d, J = 8.2 Hz, 1H), 7.23 (s, 1H), 7.12 (dd, J = 8.2, 1.7 Hz, 1H), 4.60-4.51 (m, 1H), 4.46 (dd, J = 12.5, 4.1 Hz, 1H), 4.38-4.28 (m, 2H), 3.98-3.87 (m, 1H), 3.76 (s, 3H), 2.94 (dd, J = 12.4, 11.4 Hz, 1H), 2.88 (s, 3H), 2.79 (td, J = 12.9, 2.5 Hz, 1H), 2.34 (s, 3H), 1.83 (ddd, J = 16.9, 11.3, 3.2 Hz, 3H), 1.64-1.53 (m, 1H). |
| 178 | D | 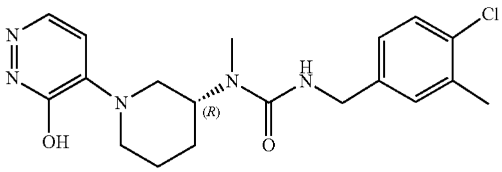 (R)-3-(4-chloro-3-methylbenzyl)-1-(1-(3-hydroxypyridazin-4-yl)piperidin-3-yl)-1- | LC-MS: m/z 390.2 (M + H). 1H NMR (400 MHz, MeOD) δ 7.67 (d, J = 5.0 Hz, 1H), 7.30-7.19 (m, 2H), 7.10 (dd, J = 8.2, 1.8 Hz, 1H), 6.59 (d, J = 5.0 Hz, 1H), 4.28 (d, J = 18.3 Hz, 3H), 4.11 (dd, J = 50.5, 11.3 Hz, 2H), 2.95-2.88 (m, 1H), 2.87 (s, 3H), 2.72 (t, J = 11.2 Hz, 1H), 2.34 (s, 3H), 1.90-1.71 (m, 4H). |
| 179 | B | 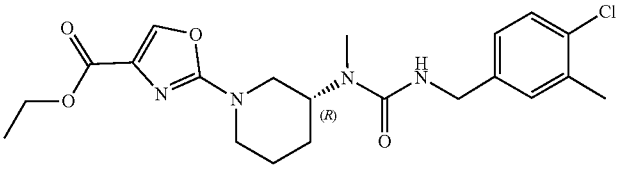 ethyl (R)-2-(3-(3-(4-chloro-3-methylbenzyl)-1-methylureido)piperidin-1-yl)oxazole-4-carboxylate | LC-MS: m/z 435.2 (M + H). 1H NMR (400 MHz, MeOD) δ 7.98 (s, 1H), 7.26 (d, J = 8.2 Hz, 1H), 7.21 (s, 1H), 7.10 (dd, J = 8.2, 1.7 Hz, 1H), 4.32-4.28 (m, 4H), 4.13 (s, 1H), 3.98 (d, J = 12.6 Hz, 2H), 3.09 (t, J = 11.8 Hz, 1H), 2.93 (d, J = 2.8 Hz, 1H), 2.86 (s, 3H), 2.34 (s, 3H), 1.89-1.70 (m, 4H), 1.32 (t, J = 7.1 Hz, 3H). |

-continued

| Example | Method | Structure and Name | Data |
|---|---|---|---|
| 180 | C | 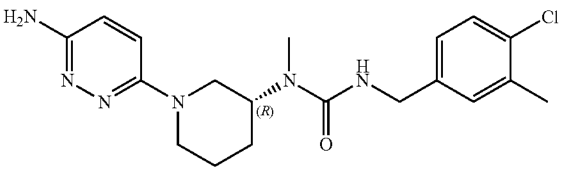 1-[(3R)-1-(6-aminopyridazin-3-yl)piperidin-3-yl]-3-[(4-chloro-3-methylphenyl)methyl]-1-methyl]urea | LC-MS: m/z 389.2 (M + H). |
| 181 | C | 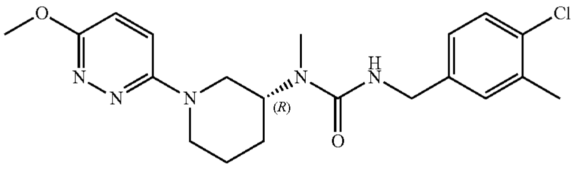 (R)-3-(4-chloro-3-methylbenzyl)-1-(1-(6-methoxypyridazin-3-yl)piperidin-3-yl)-1-methyl]urea | LC-MS: m/z 4031 (M + H). 1H NMR (400 MHz, MeOD) δ 7.36 (d, J = 9.7 Hz, 1H), 7.29-7.21 (m, 2H), 7.12 (dd, J = 8.2, 1.7 Hz, 1H), 6.98 (d, J = 9.7 Hz, 1H), 4.33 (s, 2H), 4.17-4.03 (m, 3H), 3.94 (s, 3H), 2.97 (t, J = 11.6 Hz, 1H), 2.88 (s, 3H), 2.88-2.80 (m, 1H), 2.33 (s, 3H), 1.90-1.76 (m, 3H), 1.75-1.60 (m, 1H). |
| 182 | C | 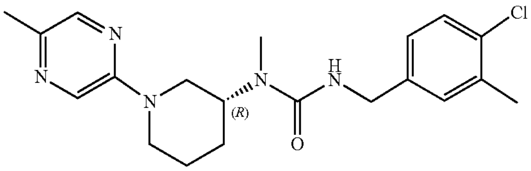 (R)-3-(4-chloro-3-methylbenzyl)-1-methyl-1-(1-(5-methylpyrazin-2-yl)piperidin-3-yl)urea | LC-MS: m/z 388.4 (M + H). 1H NMR (400 MHz, MeOD) δ 8.10 (d, J = 1.5 Hz, 1H), 7.80 (s, 1H), 7.28 (d, J = 8.2 Hz, 1H), 7.23 (s, 1H), 7.11 (dd, J = 8.1, 1.7 Hz, 1H), 4.32 (s, 2H), 4.27-4.17 (m, 2H), 4.07 (dd, J = 11.8, 7.4 Hz, 1H), 2.98-2.90 (m, 1H), 2.89 (s, 3H), 2.84 (td, J = 13.2, 2.4 Hz, 1H), 2.35 (s, 3H), 2.33 (s, 3H), 1.85 (t, J = 9.8 Hz, 3H), 1.74-1.57 (m, 1H). |
| 183 | B | 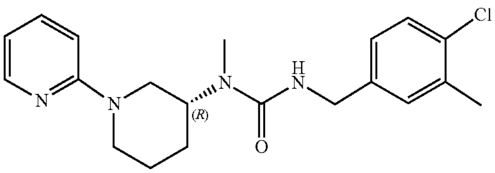 (R)-3-(4-chloro-3-methylbenzyl)-1-methyl-1-(1-(pyridin-2-yl)piperidin-3-yl)urea | LC-MS: m/z 388.4 (M + H). 1H NMR (400 MHz, MeOD) δ 7.93 (dd, J = 5.1, 1.1 Hz, 1H), 7.52 (ddd, J = 8.9, 7.1, 2.0 Hz, 1H), 7.31-7.16 (m, 2H), 7.11 (dd, J = 8.2, 1.7 Hz, 1H), 6.85 (d, J = 8.7 Hz, 1H), 6.61 (dd, J = 6.7, 5.4 Hz, 1H), 4.34 (d, J = 1.9 Hz,2H), 4.23-4.12(m,2H), 4.05(d, J = 10.7 Hz,1H), 2.97-2.75(m,5H), 2.33 (d, J = 10.8 Hz, 3H), 1.85 (td, J = 12.6, 5.9 Hz, 3H), 1.65 (dd, J = 12.3, 3.4 Hz, 1H). |

General Procedure H:

As a general procedure, the examples below were synthesized according the following general scheme

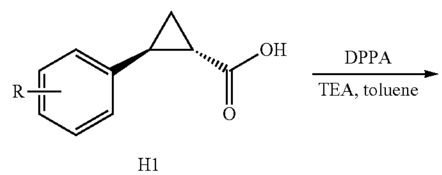

H1

-continued

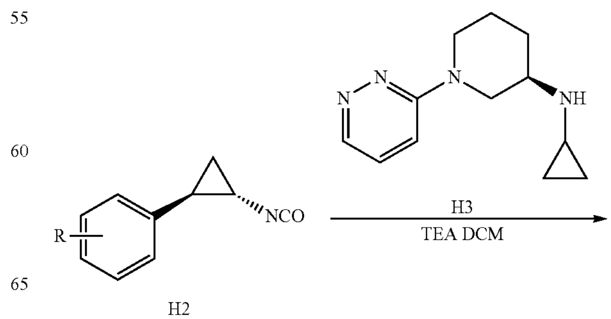

H2

-continued

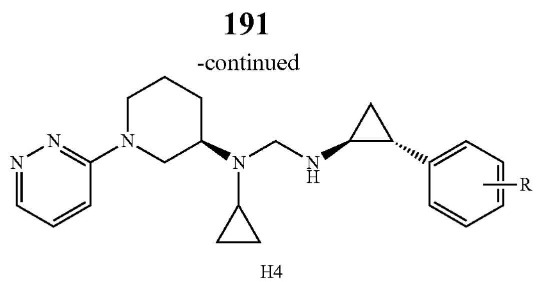

H4

-continued

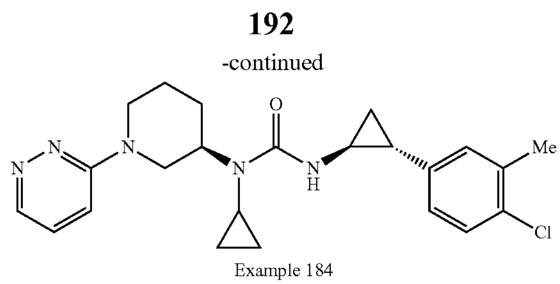

Example 184

To a solution of compound H1 (1 eq.) in toluene were added TEA (2 eq.) and DPPA (1.2 eq.). The resulting mixture was stirred at 110° C. for 2 hrs under $N_2$ atmosphere. After cooling, the resulting mixture was concentrated under reduced pressure to dryness. The crude compound was used at the next step directly without further purification. To a solution of compound H3 (1 eq.) in DCM were added TEA (3 eq.) and compound H2 (1 eq.) at 0° C. The resulting mixture was stirred for 30 mins at room temperature under $N_2$ atmosphere. Then the mixture was concentrated under reduced pressure to dryness. The crude product was purified via column chromatography on silica gel (eluted with DCM/MeOH) to afford compound H4.

Example 184: Synthesis of 3-((1S,2R)-2-(4-chloro-3-methylphenyl)cyclopropyl)-1-cyclopropyl-1-((R)-1-(pyridazin-3-yl)piperidin-3-yl)urea

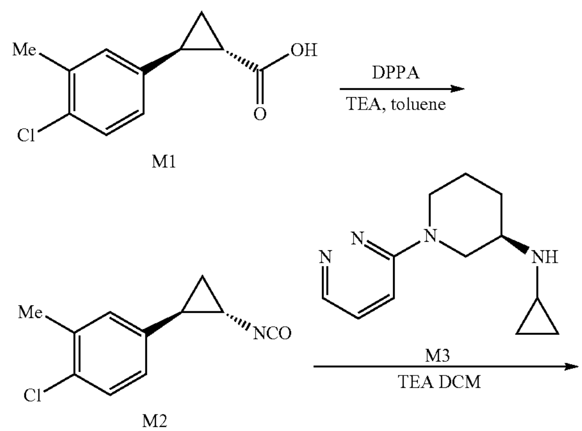

To a solution of M1 (200 mg, 0.952 mmol) in toluene (10 mL) were added TEA (192 mg, 1.904 mmol) and DPPA (314 mg, 1.142 mmol). The resulting mixture was stirred at 110° C. for 2 hrs under $N_2$ atmosphere. After cooling, the mixture was concentrated under reduced pressure to give crude M2 (197 mg, 99.9% yield) without further purification. To a solution of M3 (207 mg, 0.952 mmol) in dry DCM (10 mL) were added TEA (288 mg, 2.856 mmol) and M2 (197 mg, 0.952 mmol) under 0° C. The resulting mixture was stirred for 30 mins at room temperature under $N_2$ atmosphere. Then the mixture was concentrated under reduced pressure to dryness. The crude product was purified via column chromatography on silica gel (eluted with 1% MeOH in DCM to 5% MeOH in DCM) to afford Example 184 (61.1 mg, 15.1% yield) as white solid. LC-MS: m/z 426 $(M+H)^+$. 1H NMR (400 MHz, MeOD) δ 8.43 (dd, J=4.4, 1.2 Hz, 1H), 7.37 (dd, J=9.4, 4.4 Hz, 1H), 7.29 (dd, J=9.4, 1.2 Hz, 1H), 7.21 (d, J=8.2 Hz, 1H), 7.09 (d, J=1.9 Hz, 1H), 6.95 (dd, J=8.2, 2.1 Hz, 1H), 6.69 (s, 1H), 4.43-4.31 (m, 2H), 3.80-3.69 (m, 1H), 2.91-2.81 (m, 1H), 2.78-2.71 (m, 1H), 2.51-2.45 (m, 1H), 2.32 (s, 3H), 2.30-2.20 (m, 1H), 2.03-1.94 (m, 2H), 1.90-1.83 (m, 1H), 1.66-1.57 (m, 1H), 1.24-1.14 (m, 2H), 0.95-0.89 (m, 2H), 0.79-0.72 (m, 2H).

The compounds in the table below were prepared from the appropriate starting materials, described above or commercially available, using the above general procedure B as detailed in Example 184.

| Example | Structure and name | Data |
| --- | --- | --- |
| 185 | 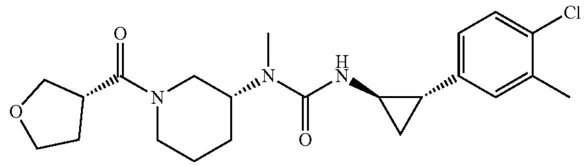 [SMILES: Cc1cc([C@@H]2C[C@H]2NC(=O)N(C)[C@@H]2CCCN(C(=O)[C@@H]3CCOC3)C2)ccc1Cl] 3-[(1R,2S)-2-(4-chloro-3-methylphenyl)cyclopropyl]-1-methyl-1-[(3R)-1-[(3R)-oxolane-3-carbonyl]piperidin-3-yl]urea | LC-MS: m/z 420 (M + H). 1H NMR (400 MHz, MeOD) δ 7.20 (dd, J = 8.2, 3.4 Hz, 1H), 7.08 (s, 1H), 6.93 (dd, J = 8.2, 2.1 Hz, 1H), 4.53-4.40 (m, 1H), 4.14-3.99 (m, 1H), 3.96-3.77 (m, 5H), 3.51-3.40 (m, 1H), 3.16-3.08 (m, 1H), 2.99 (dd, J = 18.7, 7.8 Hz, 1H), 2.80 (d, J = 3.9 Hz, 3H), 2.71 (ddd, J = 10.3, 8.9, 4.4 Hz, 1H), 2.55-2.47 (m, 1H), 2.31 (s, 3H), 2.27-2.21 (m, 1H), 2.11 (ddd, J = 20.5, 14.1, 6.7 Hz, 2H), 2.00-1.94 (m, 1H), 1.88-1.76 (m, 3H), 1.58-1.43 (m, 1H), 1.21-1.11 (m, 2H). |

-continued

| Example | Structure and name | Data |
|---|---|---|
| 186 | 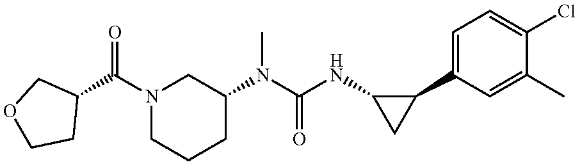 [SMILES: Cc1cc([C@H]2C[C@@H]2NC(=O)N(C)[C@@H]2CCCN(C(=O)[C@@H]3CCOC3)C2)ccc1Cl] 3-[(1S,2R)-2-(4-chloro-3-methylphenyl)cyclopropyl]-1-methyl-1-[(3R)-1-[(3R)-oxolane-3-carbonyl]piperidin-3-yl]urea | LC-MS: m/z 420 (M + H). 1H NMR (400 MHz, MeOD) δ 7.20 (dd, J = 8.2, 3.0 Hz, 1H), 7.07 (s, 1H), 6.93 (dd, J = 8.2, 2.2 Hz, 1H), 4.54-4.39 (m, 1H), 4.14-3.98 (m, 1H), 3.96-3.74 (m, 5H), 3.45 (t, J = 9.5 Hz, 1H), 3.15-3.08 (m, 1H), 2.99 (dd, J = 18.8, 7.8 Hz, 1H), 2.80 (d, J = 4.3 Hz, 3H), 2.76-2.67 (m, 2H), 2.51 (dd, J = 13.0, 10.7 Hz, 1H), 2.31 (s, 3H), 2.22 (ddd, J = 12.6, 9.7, 6.1 Hz, 1H), 2.09 (tt, J = 13.9, 7.0 Hz, 2H), 1.95 (ddt, J = 9.2, 6.0, 2.9 Hz, 1H), 1.90-1.76 (m, 3H), 1.52 (dd, J = 22.8, 15.9 Hz, 1H), 1.22-1.10 (m, 2H). |
| 187 | 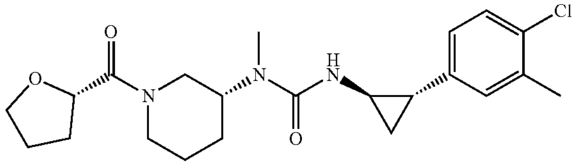 [SMILES: Cc1cc([C@@H]2C[C@H]2NC(=O)N(C)[C@@H]2CCCN(C(=O)[C@@H]3CCCO3)C2)ccc1Cl] 3-[(1R,2S)-2-(4-chloro-3-methylphenyl)cyclopropyl]-1-methyl 1-[(3R)-1-[(2S)-oxolane-2-carbonyl]piperidin-3-yl]urea | LC-MS: m/z 420.1 (M + H). 1H NMR (400 MHz, MeOD) δ 7.10 (dd, J = 8.2, 3.7 Hz, 1H), 6.98 (d, J = 1.8 Hz, 1H), 6.83 (dd, J = 8.2, 1.9 Hz, 1H), 4.62 (dd, J = 8.5, 4.4 Hz, 1H), 4.42-4.25 (m, 1H), 3.94 (dd, J = 37.3, 10.8 Hz, 1H), 3.86-3.68 (m, 3H), 3.05-2.94(m, 1H), 2.82 (dd, J = 19.0, 8.1 Hz, 1H), 2.71 (d, J = 9.5 Hz, 3H), 2.62(tt, J = 7.5, 4.4 Hz, 2H), 2.46-2.36 (m, 1H), 2.23 (d, J = 11.1 Hz, 3H), 2.20-2.14 (m, 1H), 2.12-2.02 (m,1H), 1.98-1.90 (m, 1H), 1.86 (ddd, J = 18.3, 9.8, 5.0 Hz, 3H), 1.76-1.65 (m, 3H), 1.59-1.46 (m, 1H), 1.38 (dd, J = 10.6, 4.9 Hz, 1H), 1.13-0.99 (m, 2H). |
| 188 | 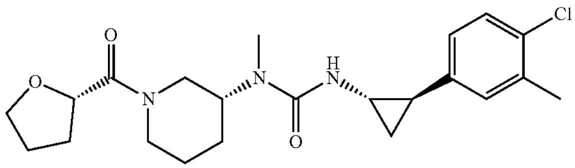 [SMILES: Cc1cc([C@H]2C[C@@H]2NC(=O)N(C)[C@@H]2CCCN(C(=O)[C@@H]3CCCO3)C2)ccc1Cl] 3-[(1S,2R)-2-(4-chloro-3-methylphenyl)cyclopropyl]-1-methyl-1-[(3R)-1-[(2S)-oxolane-2-carbonyl]piperidin-3-yl]urea | LC-MS: m/z 420.1 (M + H). 1H NMR (400 MHz, MeOD) δ 7.10 (dd, J = 8.2, 3.3 Hz, 1H), 6.98 (d, J = 1.6 Hz, 1H), 6.83 (dd, J = 8.2, 1.7 Hz, 1H), 4.61 (dd, J = 10.4, 4.9 Hz, 1H), 4.41-4.25 (m, 1H), 3.94 (dd, J = 36.8, 10.8 Hz, 1H), 3.77 (ddd, J = 21.1, 14.8, 7.4 Hz, 3H), 3.05-2.96 (m, 1H), 2.83 (t, J = 12.2 Hz, 1H), 2.71 (d, J = 9.3 Hz, 3H), 2.66-2.57 (m, 2H), 2.45-2.37 (m, 1H), 2.22 (s, 3H), 2.20-2.13 (m, 1H), 2.07 (dd, J = 12.1, 7.0 Hz, 1H), 1.93 (dd, J = 12.4, 6.6 Hz, 1H), 1.83 (td, J = 13.5, 6.8 Hz, 3H), 1.78-1.66 (m, 3H), 1.61-1.48 (m, 1H), 1.39 (s, 1H), 1.06 (tdd, J = 13.5, 6.5, 2.6 Hz, 2H). |
| 189 | 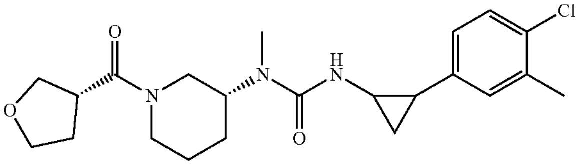 [SMILES: Cc1cc(C2CC2NC(=O)N(C)[C@@H]2CCCN(C(=O)[C@@H]3CCOC3)C2)ccc1Cl] 3-[2-(4-chloro-3-methylphenyl)cyclopropyl]-1-methyl-1-[(3R)-1-[(3R)-oxolane-3-carbonyl]piperidin-3-yl]urea | LC-MS: m/z 420.1 (M + H). 1H NMR (400 MHz, MeOD) δ 7.20 (dd, J = 8.2, 3.0 Hz, 1H), 7.07 (s, 1H), 6.93 (dd, J = 8.2, 1.9 Hz, 1H), 4.46 (dd, J = 31.7, 11.9 Hz, 1H), 4.14-3.98 (m, 1H), 3.87 (dddd, J = 30.0, 21.6, 11.4, 5.5 Hz, 5H), 3.45 (dd, J = 17.7, 6.1 Hz, 1H), 3.12 (t, J = 12.1 Hz, 1H), 2.99 (dd, J = 19.0, 7.8 Hz, 1H), 2.80 (d, J = 4.4 Hz, 3H), 2.71 (ddd, J = 10.8, 10.2, 4.8 Hz, 2H), 2.55-2.47 (m, 1H), 2.31 (s, 3H), 2.28-2.19 (m, 1H), 2.11 (ddd, J = 22.0, 10.8, 5.2 Hz, 1H), 2.00-1.92 (m, 1H), 1.90-1.76 (m, 3H), 1.60-1.43 (m, 1H), 1.22-1.09 (m, 2H). |

-continued

| Example | Structure and name | Data |
|---|---|---|
| 190 | 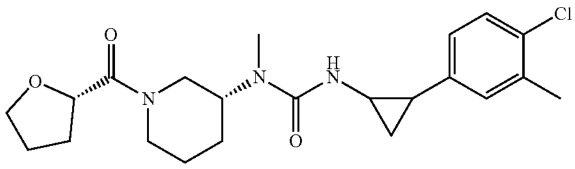 [SMILES: Cc1cc(C2CC2NC(=O)N(C)[C@@H]2CCCN(C(=O)[C@@H]3CCCO3)C2)ccc1Cl] 3-[2-(4-chloro-3-methylphenyl)cyclopropyl]-1-methyl-1-[(3R)-1-[(2S)-oxolane-2-carbonyl]piperidin-3-yl]urea | LC-MS: m/z 420.1 (M + H). 1H NMR (400 MHz, MeOD) δ 7.20 (dd, J = 8.2, 3.5 Hz, 1H), 7.08 (s, 1H), 6.94 (d, J = 8.2 Hz, 1H), 4.72 (dd, J = 11.6, 5.5 Hz, 1H), 4.43 (dd, J = 34.1, 10.5 Hz, 1H), 4.14-3.98 (m, 1H), 3.89 (ddd, J = 22.1, 13.8, 6.9 Hz, 3H), 3.10 (t, J = 12.2 Hz, 1H), 2.93 (t, J = 12.3 Hz, 1H), 2.80 (d, J = 5.4 Hz, 3H), 2.75-2.66 (m, 2H), 2.52 (t, J = 12.0 Hz, 1H), 2.32 (s, 3H), 2.27 (dd, J = 12.8, 6.8 Hz, 1H), 2.21-2.12 (m, 1H), 2.05 (dd, J = 10.9, 6.6 Hz, 1H), 1.95 (dt, J = 12.4, 6.5 Hz, 3H), 1.82 (d, J = 13.0 Hz, 3H), 1.64 (s, 1H), 1.49 (s, 1H), 1.21-1.10 (m, 2H). |
| 191 | 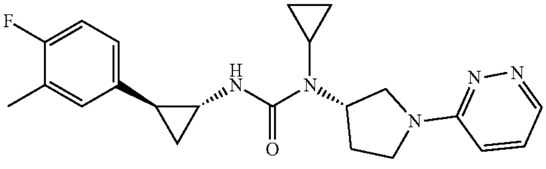 [SMILES: Cc1cc([C@@H]2C[C@H]2NC(=O)N(C2CC2)[C@H]2CCN(c3cccnn3)C2)ccc1F] 1-cyclopropyl-3-[(1R,2S)-2-(4-fluoro-3-methylphenyl)cyclopropyl]-1-[(3S)-1-(pyridazin-3-yl)pyrrolidin-3-yl]urea | LC-MS: m/z 396.1 (M + H). 1H NMR (400 MHz, MeOD) δ 8.41 (d, J = 3.8 Hz, 1H), 7.37 (dd, J = 9.2, 4.5 Hz, 1H), 7.06-7.01 (m, 1H), 6.99-6.92 (m, 2H), 6.91-6.84 (m, 1H), 6.71 (s, 1H), 4.58 (dd, J = 9.3, 7.8 Hz, 1H), 3.77 (t, J = 9.2 Hz, 2H), 3.62 (dd, J = 10.2, 8.1 Hz, 1H), 3.50-3.42 (m, 1H), 2.70 (dd, J = 7.4, 3.3 Hz, 1H), 2.53 (ddd, J = 10.1, 9.4, 6.1 Hz, 2H), 2.34-2.24 (m, 1H), 2.21 (d, J = 1.8 Hz, 3H), 2.00 (ddd, J = 9.5, 6.4, 3.3 Hz, 1H), 1.20-1.10 (m, 2H), 0.93 (ddd, J = 9.4, 5.9, 3.2 Hz, 2H), 0.81-0.67 (m, 2H). |
| 192 | 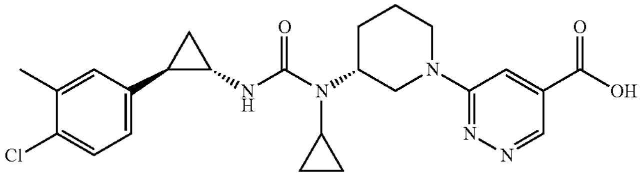 6-[(3R)-3-(1-cyclopropyl{[(1S,2R)-2-(4-chloro-3-methylphenyl)cyclopropyl]carbamoyl} amino)piperidin-1-yl]pyridazine-4-carboxylic acid | LC-MS: m/z 396.1 (M + H). 1H NMR (400 MHz, MeOD) δ 8.73 (s, 1H), 7.58 (s, 1H), 7.10 (d, J = 8.2 Hz, 1H), 6.99 (s, 1H), 6.85 (dd, J = 8.1, 2.0 Hz, 1H), 4.30 (t, J = 14.7 Hz, 2H), 3.64 (t, J = 11.7 Hz, 1H), 3.32 (t, J = 11.8 Hz, 1H), 2.85 (t, J = 12.1 Hz, 1H), 2.67-2.60 (m, 1H), 2.41 (dd, J = 6.8, 3.2 Hz, 1H), 2.24-2.11 (m, 4H), 1.94-1.75 (m, 3H), 1.54 (d, J = 13.1 Hz, 1H), 1.15-1.04 (m, 2H), 0.85-0.78 (m, 2H), 0.69 (dd, J = 10.4, 6.8 Hz, 2H). |
| 193 | 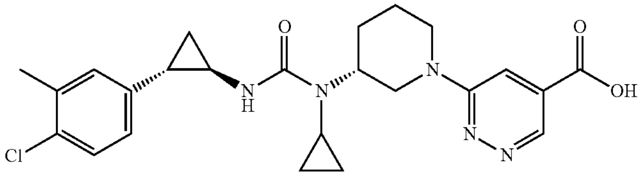 6-[(3R)-3-(1-cyclopropyl{[(1R,2S)-2-(4-chloro-3-methylphenyl)cyclopropyl]carbamoyl} amino)piperidin-1-yl]pyridazine-4-carboxylic acid | LC-MS: m/z 396.1 (M + H). 1H NMR (400 MHz, MeOD) δ 8.83 (s, 1H), 7.69 (s, 1H), 7.20 (d, J = 8.2 Hz, 1H), 7.09 (s, 1H), 6.95 (d, J = 8.2 Hz, 1H), 4.40 (t, J = 15.0 Hz, 2H), 3.74 (t, J = 12.0 Hz, 1H), 3.40 (t, J = 12.0 Hz, 1H), 2.95 (t, J = 11.8 Hz, 1H), 2.77-2.70 (m, 1H), 2.51 (dd, J = 6.7, 3.5 Hz, 1H), 2.34-2.23 (m, 4H), 2.05-1.86 (m, 3H), 1.64 (d, J = 12.8 Hz, 1H), 1.19 (ddd, J = 19.3, 11.3, 5.1 Hz, 2H), 0.95-0.88 (m, 2H), 0.81-0.71 (m, 2H) |
| 194 | 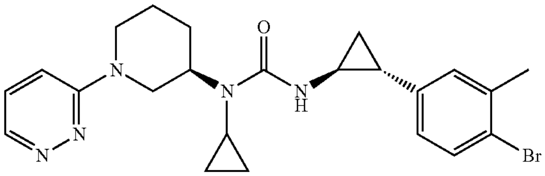 [SMILES: Cc1cc([C@H]2C[C@@H]2NC(=O)N(C2CC2)[C@@H]2CCCN(c3cccnn3)C2)ccc1Br] 3-[(1S,2R)-2-(4-bromo-3-methylphenyl)cyclopropyl]-1-cyclopropyl-1-[(3R)-1-(pyridazin-3-yl)piperidin-3-yl]urea | LC-MS: m/z 472 (M + H). 1H NMR (400 MHz, MeOD) δ 8.34 (s, 1H), 7.29 (d, J = 8.3 Hz, 2H), 7.20 (d, J = 9.3 Hz, 1H), 7.00 (s, 1H), 6.77 (dd, J = 8.2, 2.0 Hz, 1H), 4.33-4.20 (m, 2H), 3.66 (tt, J = 11.9, 3.8 Hz, 1H), 3.24 (d, J = 7.3 Hz, 1H), 2.79 (td, J = 13.1, 2.5 Hz, 1H), 2.64 (dt, J = 7.5, 3.9 Hz, 1H), 2.43-2.34 (m, 1H), 2.22 (d, J = 16.6 Hz, 3H), 2.19-2.08 (m, 1H), 1.89 (ddd, J = 23.0, 11.4, 8.3 Hz, 2H), 1.76 (d, J = 13.3 Hz, 1H), 1.52 (dtd, J = 13.0, 9.2, 4.0 Hz, 1H), 1.10 (ddd, J = 19.5, 11.2, 5.2 Hz, 2H), 0.86-0.79 (m, 2H), 0.70-0.59 (m, 2H). |

-continued

| Example | Structure and name | Data |
|---|---|---|
| 195 | 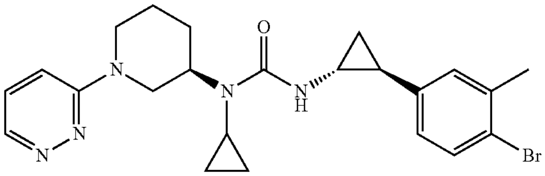 [SMILES: Cc1cc([C@@H]2C[C@H]2NC(=O)N(C2CC2)[C@@H]2CCCN(c3cccnn3)C2)ccc1Br] 3-[(1R,2S)-2-(4-bromo-3-methylphenyl)cyclopropyl]-1-cyclopropyl-1-[(3R)-1-(pyridazin-3-yl)piperidin-3-yl]urea | LC-MS: m/z 472 (M + H). 1H NMR (400 MHz, MeOD) δ 8.34 (d, J = 3.6 Hz, 1H), 7.33-7.23 (m, 2H), 7.22-7.15 (m, 1H), 7.00 (d, J = 1.9 Hz, 1H), 6.77 (dd, J = 8.2, 2.1 Hz, 1H), 6.60 (d, J = 2.0 Hz, 1H), 4.35-4.19 (m, 2H), 3.66 (tt, J = 11.9, 3.9 Hz, 1H), 3.18 (d, J = 12.2 Hz, 1H), 2.79 (td, J = 13.1, 2.6 Hz, 1H), 2.65 (td, J = 7.5, 4.1 Hz, 1H), 2.44-2.35 (m, 1H), 2.23 (d, J = 15.9 Hz, 3H), 2.14 (td, J = 12.5, 4.0 Hz, 1H), 1.95-1.82 (m, 2H), 1.76 (d, J = 13.0 Hz, 1H), 1.58-1.47 (m, 1H), 1.10 (ddd, J = 19.5, 11.4, 5.2 Hz, 2H), 0.81 (dt, J = 11.4, 7.3 Hz, 2H), 0.74-0.58 (m, 2H). |
| 196 | 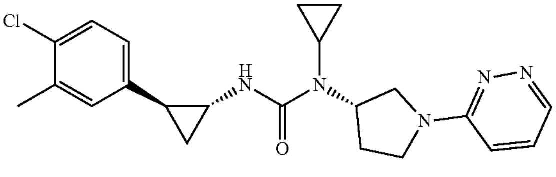 [SMILES: Cc1cc([C@@H]2C[C@H]2NC(=O)N(C2CC2)[C@H]2CCN(c3cccnn3)C2)ccc1Cl] 3-[(1R,2S)-2-(4-chloro-3-methylphenyl)cyclopropyl]-1-cyclopropyl-1-[(3S)-1-(pyridazin-3 yl)pyrrolidin-3-yl]urea | LC-MS: m/z 412 (M + H). 1H NMR (400 MHz, MeOD) δ 8.41 (d, J = 4.0 Hz, 1H), 7.38 (dd, J = 9.2, 4.4 Hz, 1H), 7.20 (d, J = 8.2 Hz, 1H), 7.09 (d, J = 1.9 Hz, 1H), 6.95 (ddd, J = 5.3, 4.1, 1.6 Hz, 2H), 6.73 (s, 1H), 4.62-4.54 (m, 1H), 3.81-3.73 (m, 2H), 3.61 (dd, J = 10.2, 8.0 Hz, 1H), 3.46 (dd, J = 17.8, 8.8 Hz, 1H), 2.74 (dd, J = 7.4, 3.4 Hz, 1H), 2.54 (ddd, J = 9.6, 8.6, 6.1 Hz, 2H), 2.31 (s, 3H), 2.29 (dd, J = 8.4, 3.9 Hz, 1H), 2.00 (ddd, J = 9.5, 6.3, 3.2 Hz, 1H), 1.24-1.13 (m, 2H), 0.96-0.89 (m, 2H), 0.80-0.69 (m, 2H). |
| 197 | 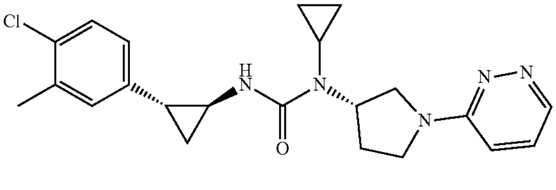 [SMILES: Cc1cc([C@H]2C[C@@H]2NC(=O)N(C2CC2)[C@H]2CCN(c3cccnn3)C2)ccc1Cl] 3-[(1S,2R)-2-(4-chloro-3 methylphenyl)cyclopropyl]-1-cyclopropyl-1-[(3S)-1-(pyridazin-3-yl)pyrrolidin-3-yl]urea | LC-MS: m/z 412 (M + H). 1H NMR (400 MHz, MeOD) δ 8.41 (d, J = 3.6 Hz, 1H), 7.37 (dd, J = 9.2, 4.5 Hz, 1H), 7.20 (d, J = 8.2 Hz, 1H), 7.08 (d, J = 1.9 Hz, 1H), 6.94 (dd, J = 7.6, 1.6 Hz, 2H), 6.73 (s, 1H), 4.58 (dd, J = 9.3, 7.9 Hz, 1H), 3.76 (t, J = 9.3 Hz, 2H), 3.61 (dd, J = 10.2, 8.1 Hz, 1H), 3.46 (dd, J = 17.7, 9.0 Hz, 1H), 2.78-2.69 (m, 1H), 2.59-2.47 (m, 2H), 2.31 (s, 3H), 2.30-2.24 (m, 1H), 2.00 (ddd, J = 9.6, 6.3, 3.3 Hz, 1H), 1.25-1.15 (m, 2H), 0.93 (ddd, J = 9.0, 4.6, 1.9 Hz, 2H), 0.75 (dt, J = 8.1, 3.9 Hz, 2H). |
| 198 | 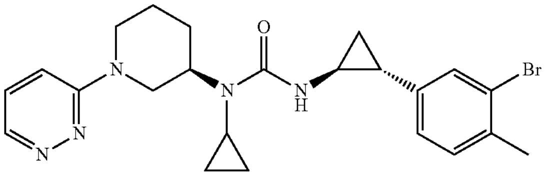 [SMILES: Cc1ccc([C@H]2C[C@@H]2NC(=O)N(C2CC2)[C@@H]2CCCN(c3cccnn3)C2)cc1Br] 3-[(1S,2R)-2-(3-bromo-4-methylphenyl)cyclopropyl]-1-cyclopropyl-1-[(3R)-1-(pyridazin-3-yl)piperidin-3-yl]urea | LC-MS: m/z 472 (M + H). 1H NMR (400 MHz, MeOD) δ 8.43 (d, J = 4.4 Hz, 1H), 7.37 (dd, J = 9.4, 4.4 Hz, 2H), 7.31-7.27 (m, 1H), 7.16 (d, J = 8.0 Hz, 1H), 7.04-7.00 (m, 1H), 4.37 (dd, J = 33.8, 13.1 Hz, 2H), 3.76 (t, J = 11.7 Hz, 1H), 3.27 (s, 1H), 2.89 (dd, J = 13.2, 10.4 Hz, 1H), 2.75-2.70 (m, 1H), 2.48 (dd, J = 7.1, 3.3 Hz, 1H), 2.32 (s, 3H), 2.25 (dd, J = 12.6, 4.0 Hz, 1H), 2.05-1.94 (m, 2H), 1.86 (d, J = 12.8 Hz, 1H), 1.62 (d, J = 13.0 Hz, 1H), 1.24-1.14 (m, 2H), 0.94-0.90 (m, 2H), 0.77 (d, J = 2.1 Hz, 2H). |
| 199 | 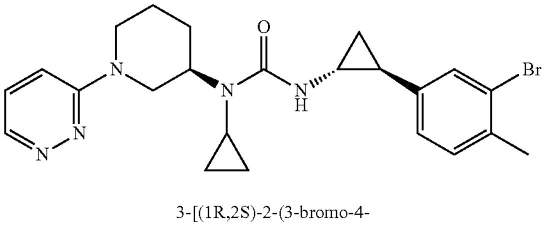 3-[(1R,2S)-2-(3-bromo-4-methylphenyl)cyclopropyl]-1-cyclopropyl-1-[(3R)-1-(pyridazin-3-yl)piperidin-3-yl]urea | LC-MS: m/z 472 (M + H). 1H NMR (400 MHz, MeOD) δ 8.43 (dd, J = 4.4, 1.2 Hz, 1H), 7.40-7.35 (m, 2H), 7.30 (dd, J = 9.4, 1.2 Hz, 1H), 7.16 (d, J = 7.8 Hz, 1H), 7.02 (dd, J = 7.8, 1.8 Hz, 1H), 4.37 (dd, J = 27.0, 12.1 Hz, 2H), 3.79-3.72 (m, 1H), 3.26 (s, 1H), 2.94-2.84 (m, 1H), 2.77-2.70 (m, 1H), 2.52-2.44 (m, 1H), 2.33 (s, 3H), 2.25 (dd, J = 12.5, 3.9 Hz, 1H), 2.05-1.96 (m, 2H), 1.91-1.82 (m, 1H), 1.62 (dd, J = 9.0, 4.0 Hz, 1H), 1.25-1.15 (m, 2H), 0.92 (dd, J = 7.6, 5.4 Hz, 2H), 0.79-0.73 (m, 2H). |

-continued

| Example | Structure and name | Data |
|---|---|---|
| 200 | 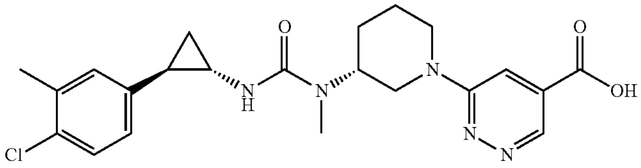 [SMILES: Cc1cc([C@H]2C[C@@H]2NC(=O)N(C)[C@@H]2CCCN(c3cc(C(=O)O)cnn3)C2)ccc1Cl] 6-[(3R)-3-({[(1S,2R)-2-(4-chloro-3-methylphenyl)cyclopropyl]carbamoyl}(methyl)amino)piperidin-1-yl]pyridazine-4-carboxylic acid | LC-MS: m/z 444.2 (M + H). 1H NMR (400 MHz, MeOD) δ 8.86 (s, 1H), 7.70 (s, 1H), 7.20 (d, J = 8.2 Hz, 1H), 7.10 (d, J = 1.7 Hz, 1H), 6.95 (dd, J = 8.2, 2.0 Hz, 1H), 4.42-4.32 (m, 2H), 4.05 (s, 1H), 3.15-3.05 (m, 1H), 3.03-2.93 (m, 1H), 2.87 (s, 3H), 2.78-2.70 (m, 1H), 2.32 (s, 3H), 2.05-1.98 (m, 1H), 1.97-1.85 (m, 3H), 1.70 (s, 1H), 1.27-1.21 (m, 1H), 1.18-1.10 (m, 1H). |
| 201 | 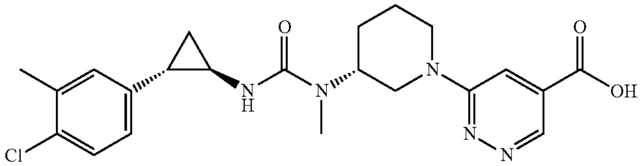 [SMILES: Cc1cc([C@@H]2C[C@H]2NC(=O)N(C)[C@@H]2CCCN(c3cc(C(=O)O)cnn3)C2)ccc1Cl] 6-[(3R)-3-({[(1R,2S)-2-(4-chloro-3-methylphenyl)cyclopropyl]carbamoyl}(methyl)amino)piperidin-1-yl]pyridazine-4-carboxylic acid | LC-MS: m/z 444.2 (M + H). 1H NMR (400 MHz, MeOD) δ 8.87 (s, 1H), 7.72 (s, 1H), 7.20 (d, J = 8.2 Hz, 1H), 7.09 (s, 1H), 7.00-6.90 (m, 1H), 4.37 (d, J = 12.5 Hz, 2H), 4.06 (s, 1H), 3.16-3.05 (m, 1H), 3.04-2.93 (m, 1H), 2.87 (s, 3H), 2.80-2.71 (m, 1H), 2.32 (s, 3H), 2.04-1.98 (m, 1H), 1.95-1.85 (m, 3H), 1.69 (d, J = 11.3 Hz, 1H), 1.27-1.21 (m, 1H), 1.19-1.10 (m, 1H). |
| 202 | 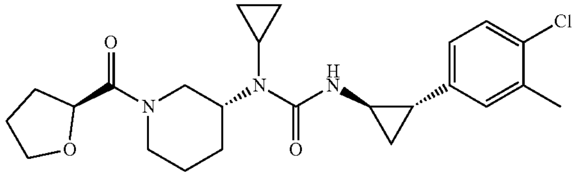 [SMILES: Cc1cc([C@@H]2C[C@H]2NC(=O)N(C2CC2)[C@@H]2CCCN(C(=O)[C@@H]3CCCO3)C2)ccc1Cl] 3-[(1R,2S)-2-(4-chloro-3-methylphenyl)cyclopropyl]-1-cyclopropyl-1-[(3R)-1-[(2S)-oxolane-2-carbonyl]piperidin-3-yl]urea | LC-MS: m/z 446.2 (M + H). 1H NMR (400 MHz, CDCl3) δ 7.14 (dd, J = 8.1, 5.5 Hz, 1H), 6.94 (d, J = 1.8 Hz, 1H), 6.84 (dd, J = 8.2, 2.0 Hz, 1H), 5.51 (d, J = 26.8 Hz, 1H), 4.65-4.37 (m, 2H), 4.05-3.72 (m, 4H), 3.31-2.80 (m, 2H), 2.78-2.69 (m, 1H), 2.45-2.15 (m, 6H), 2.13-1.76 (m, 6H), 1.75-1.69 (m, 1H), 1.50-1.41 (m, 1H), 1.11-1.05 (m, 2H), 0.89-0.78 (m, 3H), 0.68-0.60 (m, 1H). |
| 203 | 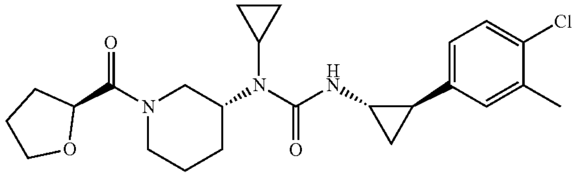 [SMILES: Cc1cc([C@H]2C[C@@H]2NC(=O)N(C2CC2)[C@@H]2CCCN(C(=O)[C@@H]3CCCO3)C2)ccc1Cl] 3-[(1S,2R)-2-(4-chloro-3-methylphenyl)cyclopropyl]-1-cyclopropyl-1-[(3R)-1-[(2S)-oxolane-2-carbonyl]piperidin-3-yl]urea | LC-MS: m/z 446.2 (M + H). 1H NMR (400 MHz, CDCl3) δ 7.14 (dd, J = 8.2, 3.6 Hz, 1H), 6.95 (d, J = 5.3 Hz, 1H), 6.83 (d, J = 8.2 Hz, 1H), 5.50 (d, J = 23.3 Hz, 1H), 4.67-4.38 (m, 2H), 4.08-3.69 (m, 4H), 3.27-2.80 (m, 2H), 2.78-2.67 (m, 1H), 2.44-2.15 (m, 6H), 2.11-1.75 (m, 6H), 1.72 (d, J = 13.1 Hz, 1H), 1.47-1.37 (m, 1H), 1.14-1.04 (m, 2H), 0.89-0.75 (m, 3H), 0.69-0.56 (m, 1H). |
| 204 | 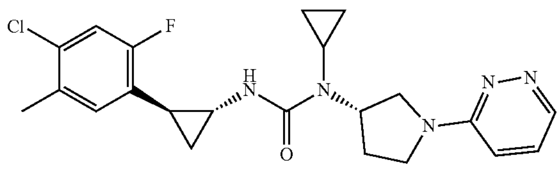 [SMILES: Cc1cc([C@@H]2C[C@H]2NC(=O)N(C2CC2)[C@H]2CCN(c3cccnn3)C2)c(F)cc1Cl] 3-[(1R,2S)-2-(4-chloro-2-fluoro-5-methylphenyl)cyclopropyl]-1-cyclopropyl-1-[(3S)-1-(pyridazin-3-yl)pyrrolidin-3-yl]urea | LC-MS: m/z 430.2 (M + H). 1H NMR (400 MHz, MeOD) δ 8.41 (dd, J = 4.4, 1.1 Hz, 1H), 7.37 (dd, J = 9.2, 4.5 Hz, 1H), 7.07 (d, J = 9.9 Hz, 1H), 6.95 (dd, J = 16.7, 8.6 Hz, 2H), 4.58 (p, J = 8.2 Hz, 1H), 3.77 (t, J = 9.3 Hz, 2H), 3.61 (ddd, J = 10.3,8.1,4.4 Hz, 1H), 3.46 (dd, J = 17.4,9.1 Hz, 1H), 2.91 (dt, J = 7.5,3.8 Hz, 1H), 2.65-2.45(m,2H), 2.36-2.23 (m,4H), 2.11 (d, J-8.5 Hz,1H), 1.31-1.24 (m,1H), 1.19 (dd, J = 12.7, 6.1 Hz, 1H), 0.97-0.88 (m, 2H), 0.83-0.69 (m, 2H). |

-continued

| Example | Structure and name | Data |
|---|---|---|
| 205 | 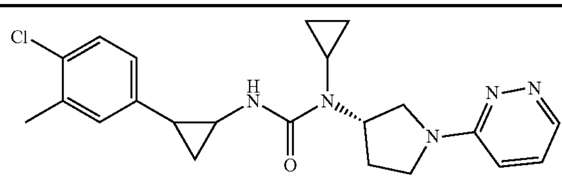 1-cyclopropyl-3-[2-(4-fluoro-3-methylphenyl)cyclopropyl]-1-[(3S)-1-(pyridazin-3-yl)pyrrolidin-3-yl]urea | LC-MS: m/z 396.2 (M + H). 1H NMR (400 MHz, MeOD) δ 8.41 (dd, J = 4.4, 1.1 Hz, 1H), 7.42 (ddd, J = 9.2, 4.4, 2.4 Hz, 1H), 7.06-6.97 (m, 2H), 6.95 (dd, J = 6.7, 4.1 Hz, 1H), 6.88 (t, J = 9.0 Hz, 1H), 6.72 (s, 1H), 4.66-4.48 (m, 1H), 3.85-3.70 (m, 2H), 3.68-3.58 (m, 1H), 3.51-3.43 (m, 1H), 2.70 (dt, J = 7.4, 3.6 Hz, 1H), 2.62-2.45 (m, 2H), 2.36-2.25 (m, 1H), 2.21 (s, 3H), 2.00 (ddd, J = 9.5, 6.3, 3.3 Hz, 1H), 1.22-1.09 (m, 2H), 0.98-0.88 (m, 2H), 0.82-0.65 (m, 2H). |
| 206 | 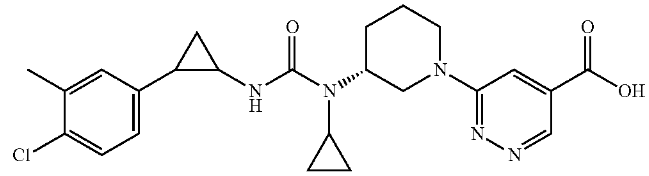 [SMILES: Cc1cc(C2CC2NC(=O)N(C2CC2)[C@@H]2CCCN(c3cc(C(=O)O)cnn3)C2)ccc1Cl] 6-[(3R)-3-(1-cyclopropyl { [2-(4-chloro-3-methylphenyl)cyclopropyl]carbamoyl} amino)piperidin-1-yl]pyridazine-4-carboxylic acid | LC-MS: m/z 470.2 (M + H). 1H NMR (400 MHz, MeOD) δ 8.84 (s, 1H), 7.64 (s, 1H), 7.20 (dd, J = 8.2, 1.5 Hz, 1H), 7.08 (s, 1H), 6.97-6.91 (m, 1H), 6.68 (s, 1H), 4.39 (t, J = 12.0 Hz, 2H), 3.74 (dd, J = 15.5, 7.9 Hz, 1H), 3.36 (t, J = 11.7 Hz, 1H), 2.92 (t, J = 12.3 Hz, 1H), 2.80-2.69 (m, 1H), 2.56-2.43 (m, 1H), 2.31 (s, 3H), 2.29-2.19 (m, 1H), 2.04-1.84 (m, 3H), 1.64 (dd, J = 14.8, 11.3 Hz, 1H), 1.19 (ddd, J = 18.1, 10.7, 5.2 Hz, 2H), 0.91 (dd, J = 12.2, 9.3 Hz, 2H), 0.82-0.71 (m, 2H). |
| 207 | 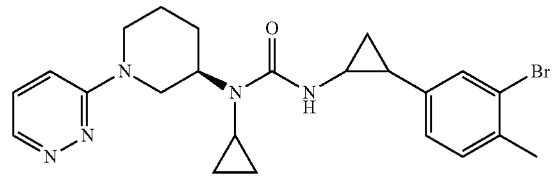 [SMILES: Cc1ccc(C2CC2NC(=O)N(C2CC2)[C@@H]2CCCN(c3cccnn3)C2)cc1Br] 3-[2-(3-bromo-4-methylphenyl)cyclopropyl]-1-cyclopropyl-1-[(3R)-1-(pyridazin-3-yl)piperidin-3-yl]urea | LC-MS: m/z 472 (M + H). 1H NMR (400 MHz, MeOD) δ 8.43 (dd, J = 4.4, 1.1 Hz, 1H), 7.40-7.34 (m, 2H), 7.29 (ddd, J = 9.4, 3.1, 1.2 Hz, 1H), 7.16 (d, J = 7.5 Hz, 1H), 7.02 (d, J = 7.7 Hz, 1H), 4.37 (dd, J = 30.0, 12.7 Hz, 2H), 3.75 (ddd, J = 12.2, 7.5, 4.1 Hz, 1H), 3.26 (d, J = 4.2 Hz, 1H), 2.89 (td, J = 13.1, 2.5 Hz, 1H), 2.73 (td, J = 7.6, 3.2 Hz, 1H), 2.52-2.46 (m, 1H), 2.32 (s, 3H), 2.28-2.19 (m, 1H), 2.05-1.94 (m, 2H), 1.86 (d, J = 12.9 Hz, 1H), 1.68-1.58 (m, 1H), 1.25-1.14 (m, 2H), 0.96-0.89 (m, 2H), 0.81-0.71 (m, 2H). |
| 208 | 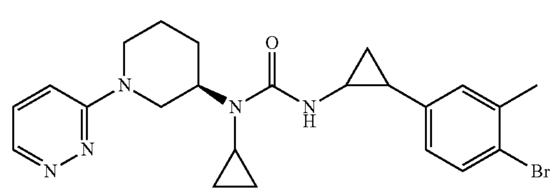 [SMILES: Cc1cc(C2CC2NC(=O)N(C2CC2)[C@@H]2CCCN(c3cccnn3)C2)ccc1Br] 3-[2-(4-bromo-3-methylphenyl)cyclopropyl]-1-cyclopropyl-1-[(3R)-1-(pyridazin-3-yl)piperidin-3-yl]urea | LC-MS: m/z 470.2 (M + H). 1H NMR (400 MHz, MeOD) δ 8.43 (dd, J = 4.4, 1.0 Hz, 1H), 7.41-7.34 (m, 2H), 7.29 (ddd, J = 9.4, 2.6, 1.3 Hz, 1H), 7.10 (s, 1H), 6.87 (d, J = 8.2 Hz, 1H), 6.69 (s, 1H), 4.37 (dd, J = 26.7, 12.9 Hz, 2H), 3.75 (ddd, J = 15.8,7.8,3.9 Hz, 1H), 3.26 (d, J-3.7 Hz, 1H), 2.89 (td, J = 13.0,2.5 Hz, 1H), 2.75 (dt, J-6.9,3.5 Hz, 1H), 2.53-2.44 (m, 1H), 2.34 (d, J = 1.4 Hz,3H), 2.31-2.18(m,1H), 2.04-1.93 (m,2H), 1.86 (d, J = 13.1 Hz, 1H), 1.68-1.54 (m, 1H), 1.26-1.14 (m, 2H), 0.96-0.88 (m, 2H), 0.80-0.71 (m, 2H). |
| 209 | 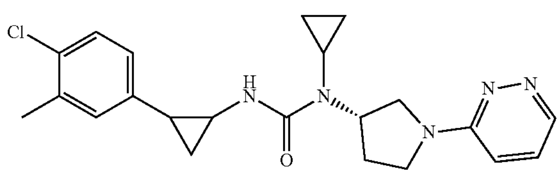 [SMILES: Cc1cc(C2CC2NC(=O)N(C2CC2)[C@H]2CCN(c3cccnn3)C2)ccc1Cl] 3-[2-(4-chloro-3-methylphenyl)cyclopropyl]-1-cyclopropyl-1-[(3S)-1-(pyridazin-3-yl)pyrrolidin-3-yl]urea | LC-MS: m/z 412.1 (M + H). 1H NMR (400 MHz, MeOD) δ 8.41 (d, J = 4.0 Hz, 1H), 7.38 (dd, J = 9.2, 4.4 Hz, 1H), 7.20 (d, J = 8.2 Hz, 1H), 7.08 (s, 1H), 6.99-6.91 (m, 2H), 6.73 (d, J = 2.0 Hz, 1H), 4.63-4.52 (m, 1H), 3.77 (dd, J = 10.3, 8.0 Hz, 2H), 3.65-3.58 (m, 1H), 3.46 (dd, J = 17.8, 8.9 Hz, 1H), 2.73 (ddd, J = 6.1, 4.4, 3.1 Hz, 1H), 2.61-2.47 (m, 2H), 2.31 (s, 3H), 2.28 (dd, J = 8.5, 4.0 Hz, 1H), 2.00 (ddd, J = 9.5, 6.3, 3.3 Hz, 1H), 1.25-1.13 (m, 2H), 0.95-0.89 (m, 2H), 0.81-0.67 (m, 2H). |

-continued

| Example | Structure and name | Data |
|---|---|---|
| 210 | 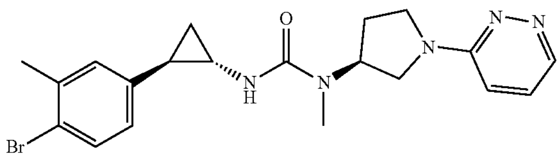 [SMILES: Cc1cc([C@H]2C[C@@H]2NC(=O)N(C)[C@H]2CCN(c3cccnn3)C2)ccc1Br] 3-[(1S,2R)-2-(4-bromo-3-methylphenyl)cyclopropyl]-1-methyl-1-[(3S)-1-(pyridazin-3-yl)pyrrolidin-3-yl]urea | LC-MS: m/z 430 (M + H). 1H NMR (400 MHz, MeOD) δ 8.35 (d, J = 4.4 Hz, 1H), 7.36 (d, J = 4.7 Hz, 1H), 7.29 (d, J = 8.2 Hz, 1H), 7.00 (d, J = 6.8 Hz, 2H), 6.77 (dd, J = 8.2, 2.1 Hz, 1H), 4.98-4.90 (m, 1H), 3.70-3.58 (m, 2H), 3.43-3.30 (m, 2H), 2.74 (s, 3H), 2.67-2.61 (m, 1H), 2.24 (s, 3H), 2.13 (t, J = 7.7 Hz, 2H), 1.86 (ddd, J = 9.5, 6.3, 3.3 Hz, 1H), 1.13-1.04 (m, 2H) |
| 211 | 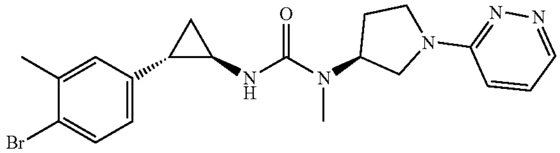 [SMILES: Cc1cc([C@@H]2C[C@H]2NC(=O)N(C)[C@H]2CCN(c3cccnn3)C2)ccc1Br] 3-[(1R,2S)-2-(4-bromo-3-methylphenyl)cyclopropyl]-1-methyl-1-[(3S)-1-(pyridazin-3-yl)pyrrolidin-3-yl]urea | LC-MS: m/z 431.9 (M + H). 1H NMR (400 MHz, MeOD) δ 8.44 (dd, J = 4.4, 1.2 Hz, 1H), 7.44 (dd, J = 9.3, 4.5 Hz, 1H), 7.39 (d, J = 8.2 Hz, 1H), 7.10 (d, J = 2.0 Hz, 1H), 7.05 (dd, J = 9.3, 1.2 Hz, 1H), 6.87 (dd, J = 8.2, 2.2 Hz, 1H), 5.06-5.00 (m, 1H), 3.78-3.67 (m, 2H), 3.52-3.40 (m, 2H), 2.84 (s, 3H), 2.76-2.71 (m, 1H), 2.34 (s, 3H), 2.25-2.17 (m, 2H), 2.00-1.93 (m, 1H), 1.22-1.14 (m, 2H). |
| 212 | 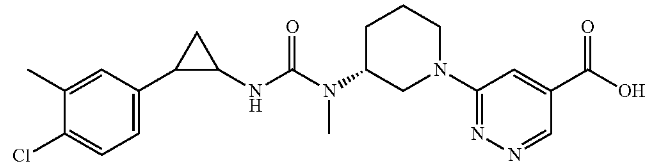 [SMILES: Cc1cc(C2CC2NC(=O)N(C)[C@@H]2CCCN(c3cc(C(=O)O)cnn3)C2)ccc1Cl] 6-[(3R)-3-({[2-(4-chloro-3-methylphenyl)cyclopropyl]carbamoyl}(methyl)amino)piperidin-1-yl]pyridazine-4-carboxylic acid | LC-MS: m/z 444.2 (M + H). 1H NMR (400 MHz, MeOD) δ 8.86 (s, 1H), 7.73 (d, J = 3.4 Hz, 1H), 7.20 (d, J = 8.2 Hz, 1H), 7.09 (s, 1H), 6.95 (d, J = 8.1 Hz, 1H), 4.39-4.28(m, 2H), 4.07 (s, 1H), 3.16-3.06 (m, 1H), 3.02-2.92 (m, 1H), 2.87 (s, 3H), 2.77-2.71 (m, 1H), 2.31 (s, 3H), 2.02 (d, J = 9.2 Hz, 1H), 1.97-1.84 (m, 3H), 1.70 (s, 1H), 1.19-1.11 (m, 1H), 0.89 (d, J = 7.6 Hz, 1H). |
| 213 | 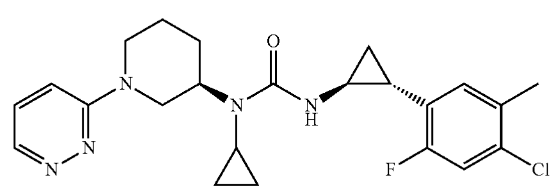 [SMILES: Cc1cc([C@H]2C[C@@H]2NC(=O)N(C2CC2)[C@@H]2CCCN(c3cccnn3)C2)c(F)cc1Cl] 3-[(1S,2R)-2-(4-chloro-2-fluoro-5-methylphenyl)cyclopropyl]-1-cyclopropyl-1-[(3R)-1-(pyridazin-3-yl)piperidin-3-yl]urea | LC-MS: m/z 444.1 (M + H). 1H NMR (400 MHz, MeOD) δ 8.33 (dd, J = 4.4, 1.1 Hz, 1H), 7.26 (dt, J = 19.6, 9.8 Hz, 1H), 7.19 (d, J = 9.4 Hz, 1H), 6.98 (d, J = 9.9 Hz, 1H), 6.86 (t, J = 12.3 Hz, 1H), 6.59 (d, J = 2.5 Hz, 1H), 4.27 (dd, J = 27.1, 12.8 Hz, 2H), 3.66 (tt, J = 12.0, 3.9 Hz, 1H), 3.19 (d, J = 8.8 Hz, 1H), 2.80 (ddd, J = 16.7, 10.4, 7.6 Hz, 2H), 2.44-2.34 (m, 1H), 2.25-2.10 (m, 4H), 2.03 (ddd, J = 9.7, 6.3, 3.4 Hz, 1H), 1.86 (d, J = 11.8 Hz, 1H), 1.76 (d, J = 13.4 Hz, 1H), 1.53 (ddd, J = 21.6, 12.8, 8.1 Hz, 1H), 1.20 (dd, J = 8.3, 3.8 Hz, 1H), 1.10 (dd, J = 13.5, 6.1 Hz, 1H), 0.85-0.79 (m, 2H), 0.72-0.62 (m, 2H). |
| 214 | 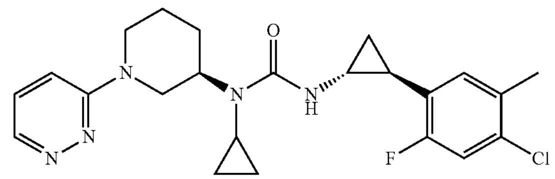 [SMILES: Cc1cc([C@@H]2C[C@H]2NC(=O)N(C2CC2)[C@@H]2CCCN(c3cccnn3)C2)c(F)cc1Cl] 3-[(1R,2S)-2-(4-chloro-2-fluoro-5-methylphenyl)cyclopropyl]-1-cyclopropyl-1-[(3R)-1-(pyridazin-3-yl)piperidin-3-yl]urea | LC-MS: m/z 444.1 (M + H). 1H NMR (400 MHz, MeOD) δ 8.43 (dd, J = 4.4, 1.2 Hz, 1H), 7.36 (dd, J = 9.4, 4.4 Hz, 1H), 7.29 (d, J = 9.2 Hz, 1H), 7.08 (d, J = 9.9 Hz, 1H), 6.98 (d, J = 8.1 Hz, 1H), 6.70 (d, J = 2.4 Hz, 1H), 4.35 (ddd, J = 15.1, 12.6, 7.5 Hz, 2H), 3.76 (tt, J = 11.9, 3.9 Hz, 1H), 3.26 (s, 1H), 2.97-2.83 (m, 2H), 2.54-2.43 (m, 1H), 2.32-2.18 (m, 4H), 2.11 (ddd, J = 9.7, 6.3, 3.4 Hz, 1H), 1.96 (d, J = 12.8 Hz, 1H), 1.86 (d, J = 13.3 Hz, 1H), 1.70-1.53 (m, 1H), 1.31 (dd, J = 9.8, 5.4 Hz, 1H), 1.19 (dd, J = 13.5, 6.1 Hz, 1H), 0.99-0.88 (m, 2H), 0.83-0.71 (m, 2H). |

-continued

| Example | Structure and name | Data |
|---|---|---|
| 215 | 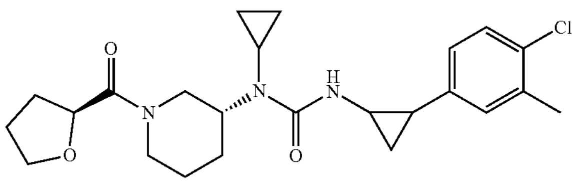 [SMILES: Cc1cc(C2CC2NC(=O)N(C2CC2)[C@@H]2CCCN(C(=O)[C@@H]3CCCO3)C2)ccc1Cl] 3-[2-(4-chloro-3-methylphenyl)cyclopropyl]-1-cyclopropyl-1-[(3R)-1-[(2S)-oxolane-2-carbonyl]piperidin-3-yl]urea | LC-MS: m/z 446.2 (M + H). 1H NMR (400 MHz, CDCl3) δ 7.24-7.16 (m, 1H), 7.02 (d, J = 4.8 Hz, 1H), 6.90 (d, J = 8.1 Hz, 1H), 5.58 (dd, J = 23.2, 2.0 Hz, 1H), 4.72-4.40 (m, 2H), 4.07-3.68 (m, 4H), 3.42-2.86 (m, 2H), 2.85-2.74 (m, 1H), 2.53-2.42 (m, 1H), 2.40-2.30 (m, 4H), 2.28-1.86 (m, 6H), 1.80 (d, J = 14.5 Hz, 1H), 1.55-1.44 (m, 1H), 1.19-1.10 (m, 2H), 0.87 (ddd, J = 22.2, 14.4, 7.2 Hz, 3H), 0.77-0.66 (m, 1H). |
| 216 | 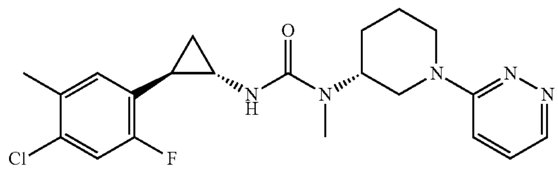 [SMILES: Cc1cc([C@H]2C[C@@H]2NC(=O)N(C)[C@@H]2CCCN(c3cccnn3)C2)c(F)cc1Cl] 3-[(1S,2R)-2-(4-chloro-2-fluoro-5-methylphenyl)cyclopropyl]-1-methyl-1-[(3R)-1-(pyridazin-3-yl)piperidin-3-yl]urea | LC-MS: m/z 418.1 (M + H). 1H NMR (400 MHz, MeOD) δ 8.46 (dd, J = 4.4, 1.2 Hz, 1H), 7.38 (dd, J = 9.4, 4.4 Hz, 1H), 7.30 (dd, J = 9.4, 1.1 Hz, 1H), 7.07 (d, J = 9.9 Hz, 1H), 6.98 (d, J = 8.1 Hz, 1H), 4.36 (d, J = 13.4 Hz, 1H), 4.28 (dd, J = 12.6, 3.7 Hz, 1H), 4.06 (dt, J = 11.3, 7.7 Hz, 1H), 3.03 (dd, J = 12.5, 11.4 Hz, 1H), 2.96-2.87 (m, 2H), 2.86 (s, 3H), 2.28 (s, 3H), 2.10 (ddd, J = 9.7, 6.3, 3.4 Hz, 1H), 1.88 (dt, J = 9.4, 4.3 Hz, 3H), 1.74-1.59 (m, 1H), 1.33-1.29 (m, 1H), 1.16 (dt, J = 7.5, 6.0 Hz, 1H). |
| 217 | 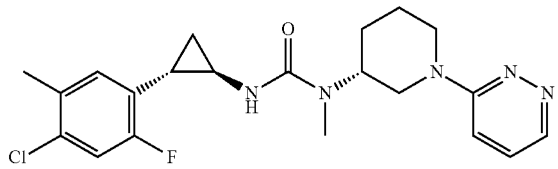 [SMILES: Cc1cc([C@@H]2C[C@H]2NC(=O)N(C)[C@@H]2CCCN(c3cccnn3)C2)c(F)cc1Cl] 3-[(1R,2S)-2-(4-chloro-2-fluoro-5-methylphenyl)cyclopropyl]-1-methyl-1-[(3R)-1-(pyridazin-3-yl)piperidin-3-yl]urea | LC-MS: m/z 418.1 (M + H). 1H NMR (400 MHz, MeOD) δ 8.48-8.42 (m, 1H), 7.38 (dd, J = 9.4, 4.4 Hz, 1H), 7.29 (d, J = 9.4 Hz, 1H), 7.06 (d, J = 9.9 Hz, 1H), 6.98 (d, J = 8.1 Hz, 1H), 4.36 (d, J = 12.0 Hz, 1H), 4.32-4.23 (m, 1H), 4.14-4.00 (m, 1H), 3.03 (t, J = 11.9 Hz, 1H), 2.96-2.87 (m, 2H), 2.86 (s, 3H), 2.28 (s, 3H), 2.11 (ddd, J = 9.7, 6.3, 3.4 Hz, 1H), 1.87 (t, J = 6.5 Hz, 3H), 1.67 (s, 1H), 1.33-1.27 (m, 1H), 1.16 (dd, J = 13.5, 6.0 Hz, 1H). |
| 218 | 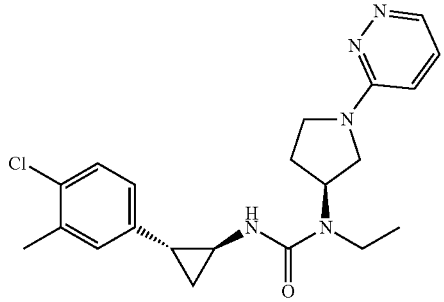 [SMILES: CCN(C(=O)N[C@H]1C[C@@H]1c1ccc(Cl)c(C)c1)[C@H]1CCN(c2cccnn2)C1] 3-[(1S,2R)-2-(4-chloro-3-methylphenyl)cyclopropyl]-1-ethyl-1-[(3S)-1-(pyridazin-3-yl)pyrrolidin-3-yl]urea | LC-MS: m/z 400.2 (M + H). 1H NMR (400 MHz, Chloroform-d) δ 8.55 (d, J = 3.9 Hz, 1H), 7.23-7.16 (m, 2H), 7.05 (d, J = 1.9 Hz, 1H), 6.94 (dd, J = 8.2, 2.2 Hz, 1H), 6.62 (dd, J = 9.1, 1.1 Hz, 1H), 5.08-4.94 (m, 1H), 4.85 (s, 1H), 3.88-3.71 (m, 2H), 3.54-3.42 (m, 1H), 3.37 (dd, J = 10.5, 8.1 Hz, 1H), 3.25-3.16 (m, 2H), 2.82 (qd, J = 4.6, 1.8 Hz, 1H), 2.33 (s, 3H), 2.27 (ddd, J = 14.3, 6.2, 2.8 Hz, 1H), 2.16-2.07 (m, 1H), 1.99 (ddd, J = 9.5, 6.3, 3.3 Hz, 1H), 1.23-1.10 (m, 5H). |

-continued

| Example | Structure and name | Data |
|---|---|---|
| 219 | 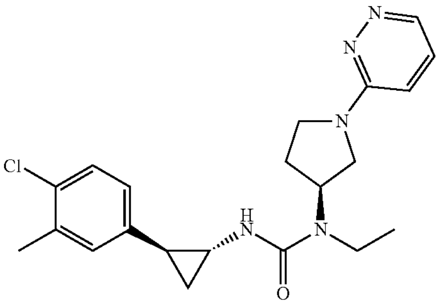 [SMILES: CCN(C(=O)N[C@@H]1C[C@H]1c1ccc(Cl)c(C)c1)[C@H]1CCN(c2cccnn2)C1] 3-[(1R,2S)-2-(4-chloro-3-methylphenyl)cyclopropyl]-1-ethyl-1-[(3S)-1-(pyridazin-3-yl)pyrrolidin-3-yl]urea | LC-MS: m/z 400.2 (M + H). 1H NMR (400 MHz, Chloroform-d) δ 8.56 (d, J = 3.6 Hz, 1H), 7.26-7.18 (m, 2H), 7.06 (d, J = 1.9 Hz, 1H), 6.95 (dd, J = 8.2, 2.2 Hz, 1H), 6.67 (dd, J = 9.2, 1.2 Hz, 1H), 5.06-4.93 (m, 2H), 3.86-3.75 (m, 2H), 3.50 (td, J = 9.9, 7.2 Hz, 1H), 3.37 (dd, J = 10.4, 8.2 Hz, 1H), 3.29-3.16 (m, 2H), 2.83 (dt, J = 7.2, 3.5 Hz, 1H), 2.34 (s, 3H), 2.29 (ddd, J = 14.2, 6.2, 2.7 Hz, 1H), 2.16-2.08 (m, 1H), 2.01 (ddd, J = 9.5, 6.5, 3.3 Hz, 1H), 1.26-1.13 (m, 5H). |
| 220 | 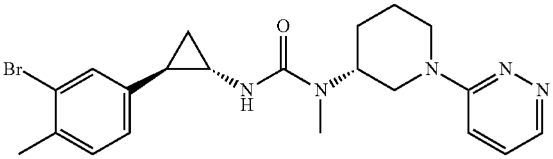 [SMILES: Cc1ccc([C@H]2C[C@@H]2NC(=O)N(C)[C@@H]2CCCN(c3cccnn3)C2)cc1Br] 3-[(1S,2R)-2-(3-bromo-4-methylphenyl)cyclopropyl]-1-methyl-1-[(3R)-1-(pyridazin-3-yl)piperidin-3-yl]urea | LC-MS: m/z 444.1 (M + H). 1H NMR (400 MHz, MeOD) δ 8.47 (dd, J = 4.4, 1.2 Hz, 1H), 7.42-7.35 (m, 2H), 7.30 (dd, J = 9.4, 1.1 Hz, 1H), 7.15 (d, J = 7.8 Hz, 1H), 7.02 (dd, J = 7.9, 1.7 Hz, 1H), 4.32 (dd, J = 28.5, 13.1 Hz, 2H), 4.05 (s, 1H), 3.07-2.99 (m, 1H), 2.89 (dd, J = 18.4, 7.7 Hz, 1H), 2.85 (s, 3H), 2.75-2.70 (m, 1H), 2.32 (s, 3H), 2.00 (ddd, J = 9.4, 6.2, 3.3 Hz, 1H), 1.92-1.83 (m, 3H), 1.67 (s, 1H), 1.22 (dd, J = 9.5, 4.4 Hz, 1H), 1.17-1.11 (m, 1H). |
| 221 | 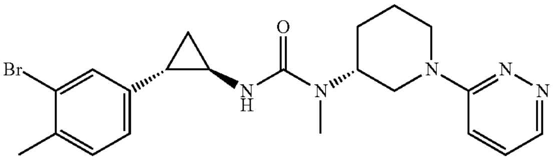 [SMILES: Cc1ccc([C@@H]2C[C@H]2NC(=O)N(C)[C@@H]2CCCN(c3cccnn3)C2)cc1Br] 3-[(1R,2S)-2-(3-bromo-4-methylphenyl)cyclopropyl]-1-methyl-1-[(3R)-1-(pyridazin-3-yl)piperidin-3-yl]urea | LC-MS: m/z 446.1 (M + H). 1H NMR (400 MHz, MeOD) δ 8.47 (dd, J = 4.4, 1.2 Hz, 1H), 7.41-7.35 (m, 2H), 7.29 (dd, J = 9.4, 1.2 Hz, 1H), 7.15 (d, J = 7.8 Hz, 1H), 7.02 (dd, J = 7.9, 1.8 Hz, 1H), 4.31 (dd, J = 37.5, 13.1 Hz, 2H), 4.05 (s, 1H), 3.07-2.98 (m, 1H), 2.94-2.87 (m, 1H), 2.85 (s, 3H), 2.75-2.69 (m, 1H), 2.32 (s, 3H), 2.01 (ddd, J = 9.4, 6.2, 3.2 Hz, 1H), 1.88 (dd, J = 10.5, 4.7 Hz, 3H), 1.68 (s, 1H), 1.26-1.19 (m, 1H), 1.17-1.10 (m, 1H). |
| 222 | 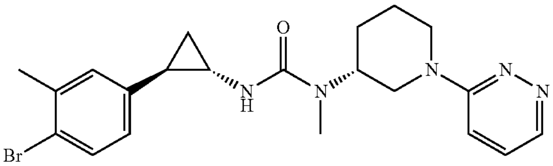 3-[(1S,2R)-2-(4-bromo-3-methylphenyl)cyclopropyl]-1-methyl-1-[(3R)-1-(pyridazin-3-yl)piperidin-3-yl]urea | LC-MS: m/z 446.1 (M + H). 1H NMR (400 MHz, MeOD) δ 8.47 (dd, J = 4.4, 1.2 Hz, 1H), 7.39 (dd, J = 9.1, 4.4 Hz, 2H), 7.30 (dd, J = 9.4, 1.1 Hz, 1H), 7.10 (d, J = 1.8 Hz, 1H), 6.87 (dd, J = 8.3, 2.2 Hz, 1H), 4.32 (dd, J = 23.0, 14.8 Hz, 2H), 4.05 (s, 1H), 3.07-2.98 (m, 1H), 2.92 (d, J = 13.1 Hz, 1H), 2.85 (s, 3H), 2.77-2.72 (m, 1H), 2.34 (s, 3H), 1.99 (ddd, J = 9.4, 6.2, 3.2 Hz, 1H), 1.88 (dd, J = 11.6, 4.6 Hz, 3H), 1.67 (s, 1H), 1.27-1.20 (m, 1H), 1.15 (dd, J = 13.5, 6.0 Hz, 1H). |
| 223 | 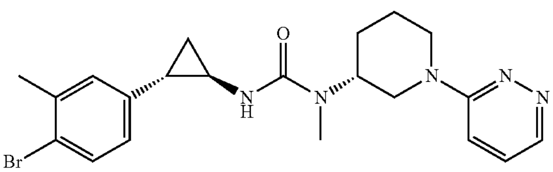 | LC-MS: m/z 444.1 (M + H). 1H NMR (400 MHz, CDCl3) δ 8.46 (dd, J = 4.4, 1.2 Hz, 1H), 7.10 (d, J = 2.1 Hz, 1H), 6.87 (dd, J = 8.3, 2.2 Hz, 1H), 4.3 1 (dd, J = 35.1, 12.7 Hz, 2H), 4.06 (s, 1H), 3.06-2.99 (m, 1H), 2.90 (t, J = 11.8 Hz, 1H), 2.85 (s, 3H), 2.76-2.71 (m, 1H), 2.34 (s, 3H), 2.00 (ddd, J = 9.4, 6.3, 3.2 Hz, 1H), 1.88 (t, J =7.7 Hz, 3H), 1.68 (s, 1H), 1.26-1.20 (m, 1H), 1.15 (dt, J = 12.0, 6.0 Hz, 1H). |

-continued

| Example | Structure and name | Data |
|---|---|---|
| 224 | 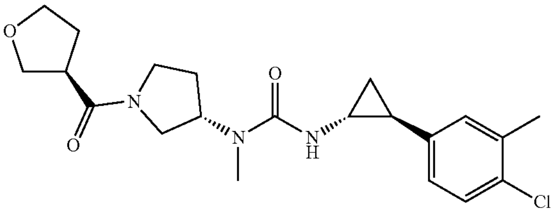 [SMILES: Cc1cc([C@@H]2C[C@H]2NC(=O)N(C)[C@H]2CCN(C(=O)[C@@H]3CCOC3)C2)ccc1Cl] 3-[(1R,2S)-2-(4-chloro-3-methylphenyl)cyclopropyl]-1-methyl-1-[(3S)-1-[(3R)-oxolane-3-carbonyl]pyrrolidin-3-yl]urea | LC-MS: m/z 406.2 (M + H). 1H NMR (400 MHz, CDCl3) δ 7.21 (dd, J = 8.2, 1.9 Hz, 1H), 7.05 (d, J = 1.9 Hz, 1H), 6.94 (d, J = 8.1 Hz, 1H), 5.12-5.00 (m, 1H), 4.92 (d, J = 13.2 Hz, 1H), 4.03 (td, J = 8.2, 4.4 Hz, 1H), 3.96-3.81 (m, 3H), 3.79-3.60 (m, 2H), 3.53-3.32 (m, 1H), 3.31-3.22 (m, 1H), 3.18-3.04 (m, 1H), 2.82-2.70 (m, 4H), 2.33 (s, 3H), 2.25-1.94 (m, 5H), 1.22-1.08 (m, 2H). |
| 225 | 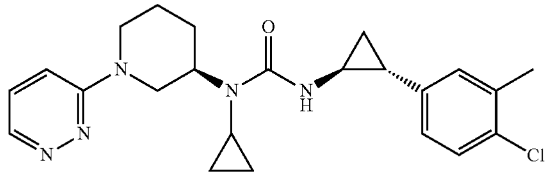 [SMILES: Cc1cc([C@H]2C[C@@H]2NC(=O)N(C2CC2)[C@@H]2CCCN(c3cccnn3)C2)ccc1Cl] 3-[(1S,2R)-2-(4-chloro-3-methylphenyl)cyclopropyl]-1-cyclopropyl-1-[(3R)-1-(pyridazin-3-yl)piperidin-3-yl]urea | LC-MS: m/z 426.2 (M + H). 1H NMR (400 MHz, MeOD) δ 8.33 (dd, J = 4.4, 1.2 Hz, 1H), 7.26 (dd, J = 9.4, 4.4 Hz, 1H), 7.18 (dd, J = 9.4, 1.2 Hz, 1H), 7.10 (d, J = 8.2 Hz, 1H), 6.99 (d, J = 1.9 Hz, 1H), 6.84 (dd, J = 8.2, 2.2 Hz, 1H), 4.25 (ddd, J = 15.0, 12.5, 7.6 Hz, 2H), 3.72-3.60 (m, 1H), 2.78 (td, J = 13.1, 2.6 Hz, 1H), 2.63 (ddd, J = 7.6, 4.4, 3.4 Hz, 1H), 2.42-2.35 (m, 1H), 2.22 (s, 3H), 2.13 (td, J = 12.6, 4.1 Hz, 1H), 1.93-1.83 (m, 2H), 1.75 (dd, J = 10.1, 2.8 Hz, 1H), 1.58-1.46 (m, 1H), 1.14-1.04 (m, 2H), 0.86-0.78 (m, 2H), 0.71-0.62 (m, 2H). |
| 226 | 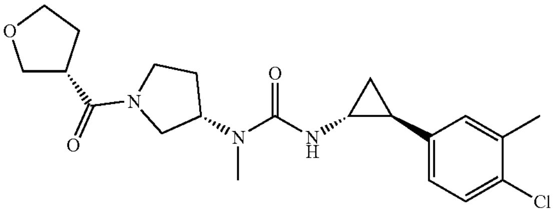 [SMILES: Cc1cc([C@@H]2C[C@H]2NC(=O)N(C)[C@H]2CCN(C(=O)[C@H]3CCOC3)C2)ccc1Cl] 3-[(1R,2S)-2-(4-chloro-3-methylphenyl)cyclopropyl]-1-methyl-1-[(3S)-1-[(3S)-oxolane-3-carbonyl]pyrrolidin-3-yl]ure | LC-MS: m/z 406.2 (M + H). 1H NMR (400 MHz, CDCl3) δ 7.21 (dd, J = 8.2, 2.4 Hz, 1H), 7.04 (d, J = 1.9 Hz, 1H), 6.93 (dd, J = 8.2, 2.1 Hz, 1H), 5.13-4.97 (m, 1H), 4.85 (d, J = 13.8 Hz, 1H), 4.01 (q, J = 8.3 Hz, 1H), 3.94-3.79 (m, 3H), 3.79-3.63 (m, 2H), 3.49-3.35 (m, 1H), 3.25 (ddd, J = 18.5, 11.2, 8.5 Hz, 1H), 3.16-3.02 (m, 1H), 2.84-2.70-(m, 4H), 2.32 (s, 3H), 2.23-2.03 (m, 3H), 2.03 1.84 (m, 2H), 1.22-1.08 (m, 2H). |
| 227 | 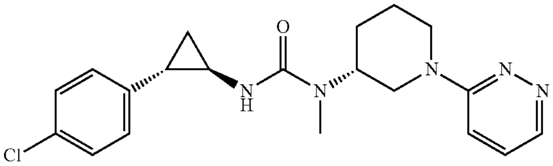 [SMILES: CN(C(=O)N[C@@H]1C[C@H]1c1ccc(Cl)cc1)[C@@H]1CCCN(c2cccnn2)C1] 3-[(1R,2S)-2-(4-chlorophenyl)cyclopropyl]-1-methyl-1-[(3R)-1-(pyridazin-3-yl)piperidin-3-yl]urea | LC-MS: m/z 386.1 (M + H). 1H NMR (400 MHz, MeOD) δ 8.47 (d, J = 4.0 Hz, 1H), 7.38 (dd, J = 9.4, 4.4 Hz, 1H), 7.30 (dd, J = 9.4, 1.1 Hz, 1H), 7.27-7.19 (m, 2H), 7.14 (d, J = 8.4 Hz, 2H), 4.39-4.23 (m, 2H), 4.05 (dd, J = 9.4, 5.6 Hz, 1H), 3.10-2.97 (m, 1H), 2.90 (td, J = 13.2, 2.5 Hz, 1H), 2.86 (s, 3H), 2.78-2.72 (m, 1H), 2.03 (ddd, J = 9.5, 6.3, 3.3 Hz, 1H), 1.88 (t, J = 8.0 Hz, 3H), 1.67 (dd, J = 10.7, 8.3 Hz, 1H), 1.27-1.21 (m, 1H), 1.16 (dt, J = 12.1, 6.0 Hz, 1H). |

-continued

| Example | Structure and name | Data |
|---|---|---|
| 228 | 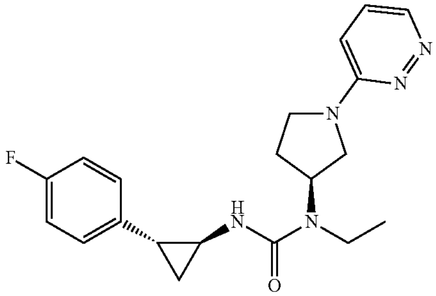 [SMILES: CCN(C(=O)N[C@H]1C[C@@H]1c1ccc(F)cc1)[C@H]1CCN(c2cccnn2)C1]<br>1-ethyl-3-[(1S,2R)-2-(4-fluorophenyl)cyclopropyl]-1-[(3S)-1-(pyridazin-3-yl)pyrrolidin-3-yl]urea | LC-MS: m/z 370.2 (M + H).<br>1H NMR (400 MHz, MeOD) δ 8.43 (dd, J = 4.5, 1.1 Hz, 1H), 7.39 (dd, J = 9.2, 4.5 Hz, 1H), 7.18 (dd, J = 8.6, 5.4 Hz, 2H), 7.03-6.88 (m, 3H), 4.83-4.77 (m, 1H), 3.75 (dt, J = 10.4, 5.8 Hz, 2H), 3.52-3.32 (m, 4H), 2.74-2.68 (m, 1H), 2.24 (dt, J = 9.1, 6.4 Hz, 2H), 2.02 (ddd, J = 9.5, 6.3, 3.2 Hz, 1H), 1.22-1.10 (m, 5H). |
| 229 | 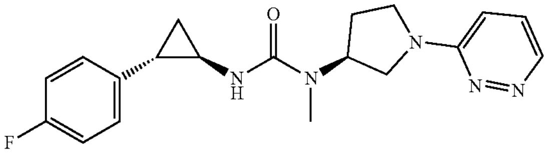 [SMILES: CN(C(=O)N[C@@H]1C[C@H]1c1ccc(F)cc1)[C@H]1CCN(c2cccnn2)C1]<br>3-[(1R,2S)-2-(4-fluorophenyl)cyclopropyl]-1-methyl-1-[(3S)-1-(pyridazin-3-yl)pyrrolidin-3-yl]urea | LC-MS: m/z 356.2 (M + H).<br>1H NMR (400 MHz, MeOD) δ 8.43 (dd, J = 4.5, 1.1 Hz, 1H), 7.39 (dd, J = 9.2, 4.5 Hz, 1H), 7.22-7.13 (m, 2H), 7.02-6.92 (m, 3H), 5.02 (p, J = 7.8 Hz, 1H), 3.82-3.63 (m, 2H), 3.56-3.37 (m, 2H), 2.83 (s, 3H), 2.74-2.68 (m, 1H), 2.20 (td, J = 7.6, 4.1 Hz, 2H), 2.01 (ddd, J = 9.5, 6.3, 3.4 Hz, 1H), 1.22-1.10 (m, 2H). |
| 230 | 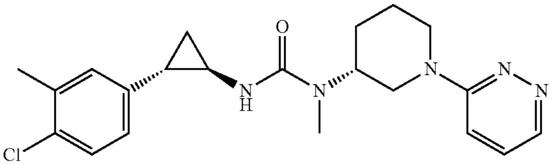 [SMILES: Cc1cc([C@@H]2C[C@H]2NC(=O)N(C)[C@@H]2CCCN(c3cccnn3)C2)ccc1Cl]<br>3-[(1R,2S)-2-(4-chloro-3-methylphenyl)cyclopropyl]-1-methyl-1-[(3R)-1-(pyridazin-3-yl)piperidin-3-yl]urea | LC-MS: m/z 400.2 (M + H).<br>1H NMR (400 MHz, MeOD) δ 8.47 (dd, J = 4.4, 1.2 Hz, 1H), 7.38 (dd, J = 9.4, 4.4 Hz, 1H), 7.30 (dd, J = 9.4, 1.0 Hz, 1H), 7.20 (d, J = 8.2 Hz, 1H), 7.09 (d, J = 1.9 Hz, 1H), 6.94 (dd, J = 8.2, 2.1 Hz, 1H), 4.37-4.25 (m, 2H), 4.12-4.00 (m, 1H), 3.06-2.99 (m, 1H), 2.94-2.87 (m, 1H), 2.85 (s, 3H), 2.74 (ddd, J = 7.6, 4.4, 3.4 Hz, 1H), 2.32 (s, 3H), 2.00 (ddd, J = 9.5, 6.3, 3.3 Hz, 1H), 1.91-1.83 (m, 3H), 1.65 (dt, J = 13.7, 8.6 Hz, 1H), 1.25-1.20 (m, 1H), 1.14 (dt, J = 7.4, 6.0 Hz, 1H). |
| 231 | 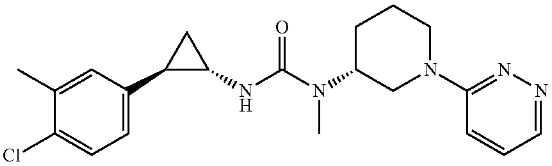 [SMILES: Cc1cc([C@H]2C[C@@H]2NC(=O)N(C)[C@@H]2CCCN(c3cccnn3)C2)ccc1Cl]<br>3-[(1S,2R)-2-(4-chloro-3-methylphenyl)cyclopropyl]-1-methyl-1-[(3R)-1-(pyridazin-3-yl)piperidin-3-yl]urea | LC-MS: m/z 400.2 (M + H).<br>1H NMR (400 MHz, MeOD) δ 8.49 (dd, J = 4.2, 1.4 Hz, 1H), 7.56-7.43 (m, 2H), 7.20 (d, J = 8.2 Hz, 1H), 7.09 (d, J = 2.0 Hz, 1H), 6.94 (dd, J = 8.2, 2.2 Hz, 1H), 4.30 (dd, J = 37.8, 12.3 Hz, 2H), 4.10 (dt, J = 11.2, 6.1 Hz, 1H), 3.12-3.04 (m, 1H), 2.95 (dd, J = 18.6, 7.8 Hz, 1H), 2.86 (s, 3H), 2.77-2.65 (m, 1H), 2.31 (s, 3H), 2.00 (ddd, J = 9.5, 6.2, 3.2 Hz, 1H), 1.93-1.85 (m, 3H), 1.72-1.66 (m, 1H), 1.25-1.20 (m, 1H), 1.17-1.12 (m, 1H). |

General Procedure I:

As a general procedure, the examples below were synthesized according to the following general scheme

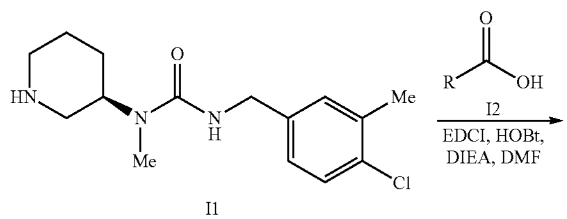

I1

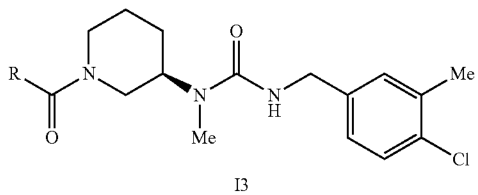

I3

To a mixture of compound I1 (1 eq.) and DIEA (5 eq.) in DMF was added corresponding acid I2 (1.2 eq.), EDCI (1.2 eq.) and HOBt (1.2 eq.). The resulting mixture was stirred at r.t. for 16 hrs. Then the mixture was diluted with water and extracted with EtOAc twice. The combined organic layers were washed with saturated $NH_4Cl$ solution and brine, dried over anhydrous $Na_2SO_4$ and filtered, the filtrate was concentrated to dryness in vacuo. The residue was purified via prep-HPLC (Xbudge prep C18 250*19 mm 5 um OBD, $H_2O$/MeCN (5-95%)/0.1% FA) to give compound 13.

Example 232: Synthesis of (R)-3-(4-chloro3-methylbenzyl)-1-methyl-1-(1-(pyrimidine-4-carbonyl) piperidin-3-yl)urea

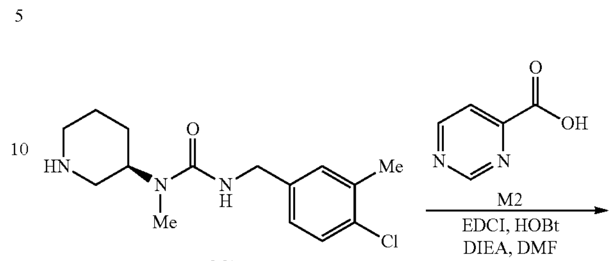

M1

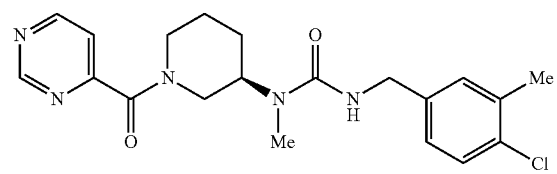

Example 232

To a mixture of compound M1 (50 mg, 0.12 mmol) and DIEA (79 mg, 0.61 mmol) in DMF was added pyrimidine-4-carboxylic acid M2 (19 mg, 0.14 mmol), EDCI (28 mg, 0.144 mmol) and HOBt (20 mg, 0.144 mmol). The resulting mixture was stirred at r.t. for 16 hrs. Then the mixture was diluted with water (20 mL) and extracted with EtOAc (20 mL) twice. The combined organic layers were washed with saturated $NH_4Cl$ solution and brine, dried over anhydrous $Na_2SO_4$, filtered and the filtrate was concentrated to dryness in vacuo. The residue was purified via prep-HPLC (Xbudge prep C18 250*19 mm 5 um OBD, $H_2O$/MeCN (5-95%)/0.1% FA) to afford Example 232 (9 mg, 18.7% yield) as white solid. LC/MS: m/z 402 $(M+H)^+$. 1H NMR (400 MHz, MeOD) δ9.21-9.12 (m, 1H), 8.94-8.90 (m, 1H), 7.66-7.63 (m, 1H), 7.28-7.23 (m, 1H), 7.14 (s, 1H), 7.12-7.00 (m, 1H), 4.64-4.49 (m, 1H), 4.38-4.11 (m, 3H), 3.70-3.54 (m, 1H), 3.28-3.18 (m, 1H), 3.08-2.42 (m, 5H), 2.36-2.29 (m, 3H), 1.98-1.76 (m, 3H), 1.76-1.62 (m, 1H).

The compounds in the table below were prepared from the appropriate starting materials, described above or commercially available, using the above General Procedure I and intermediate M1 in Example 232.

| Example | Structure and name | Data |
|---|---|---|
| 233 | 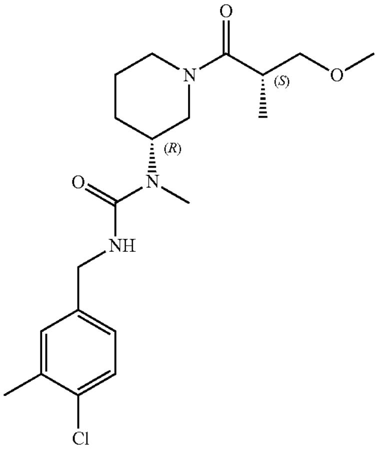 3-[(4-chloro-3-methylphenyl)methyl]-1-[(3R)-1-[(2S)-3-methoxy-2-methylpropanoyl]piperidin-3-yl]-1-methyl]urea | LC-MS: m/z 396.2 (M + H). 1H NMR (400 MHz, MeOD) δ 7.28 (dd, J = 8.2, 2.0 Hz, 1H), 7.23 (s, 1H), 7.12 (d, J = 8.1 Hz, 1H), 4.58-4.46 (m, 1H), 4.40-4.27 (m, 2H), 4.02 (dd, J = 41.8, 11.1 Hz, 2H), 3.56 (td, J = 8.7, 6.1 Hz, 1H), 3.31 (d, J = 11.4 Hz, 3H), 3.12 (ddt, J = 51.0, 24.2, 9.1 Hz, 2H), 2.87 (d, J = 7.6 Hz, 3H), 2.79-2.46 (m, 1H), 2.36 (s, 3H), 1.84 (t, J = 5.9 Hz, 3H), 1.68-1.43 (m, 1H), 1.31 (d, J = 6.5 Hz, 1H), 1.08 (dd, J = 19.5, 6.9 Hz, 3H). |
| 234 | 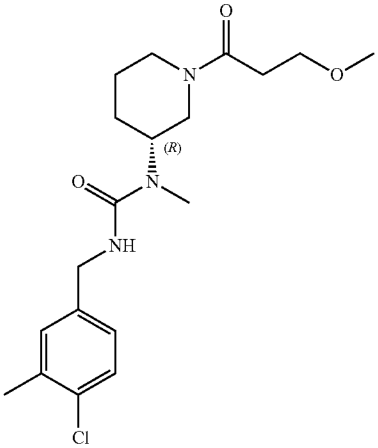 3-[(4-chloro-3-methylphenyl)methyl]-1-[(3R)-1-(3-methoxypropanoyl)piperidin-3-yl]-1-methyl]urea | LC-MS: m/z 382.2 (M + H). 1H NMR (400 MHz, MeOD) δ 7.27 (d, J = 8.2 Hz, 1H), 7.21 (s, 1H), 7.09 (dd, J = 8.2, 2.0 Hz, 1H), 4.47-4.24 (m, 3H), 4.07 (d, J = 6.0 Hz, 1H), 3.56-3.39 (m, 1H), 3.28-3.07 (m, 1H), 3.03 (t, J = 6.5 Hz, 3H), 2.99 (s, 1H), 2.91 (d, J = 3.6 Hz, 2H), 2.86 (t, J = 6.9 Hz, 3H), 2.72-2.62 (m, 1H), 2.34 (s, 3H), 1.95-1.81 (m, 3H), 1.70-1.52 (m, 1H). |
| 235 | 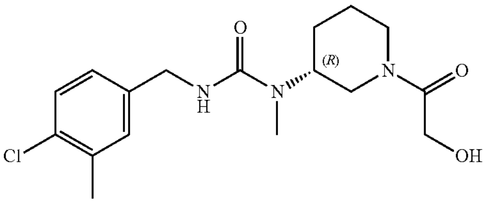 3-[(4-chloro-3-methylphenyl)methyl]-1-[(3R)-1-(2-hydroxyacetyl)piperidin-3-yl]-1-methyl]urea | LC-MS: m/z 542.2 (M + H). 1H NMR (400 MHz, MeOD) δ 7.26 (dd, J = 8.1, 1.8 Hz, 1H), 7.20 (s, 1H), 7.09 (d, J = 8.2 Hz, 1H), 4.49-4.37 (m, 1H), 4.33-4.15 (m, 4H), 4.03-3.95 (m, 1H), 3.71-3.53 (m, 1H), 3.12-2.88 (m, 1H), 2.86 (s , 3H), 2.78-2.48 (m, 1H), 2.35 (s, 3H), 1.85-1.79 (m, 3H), 1.63-1.46 (m, 1H). |

-continued

| Example | Structure and name | Data |
|---|---|---|
| 236 | 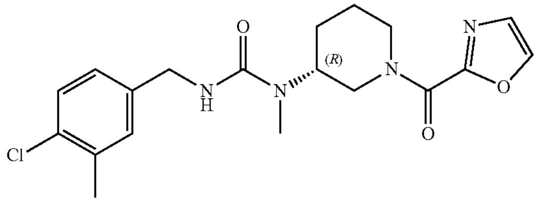 3-[(4-chloro-3-methylphenyl)methyl]-1-methyl-1-[(3R)-1-(1,3-oxazole-2-carbonyl)piperidin-3-yl]urea | LC-MS: m/z 391.1 (M + H). 1H NMR (400 MHz, MeOD) δ 8.09-8.01 (m, 1H), 7.34-7.16 (m, 3H), 7.10 (dd, J = 10.9, 4.7 Hz, 1H), 4.83-4.73 (m, 1H), 4.63-4.48 (m, 1H), 4.39-4.25 (m, 2H), 4.17-4.04 (m, 1H), 3.31-3.04 (m, 1H), 2.99-2.74 (m, 4H), 2.35 (t, J = 7.3 Hz, 3H), 1.99-1.81 (m, 3H), 1.77-1.59 (m, 1H). |
| 237 | 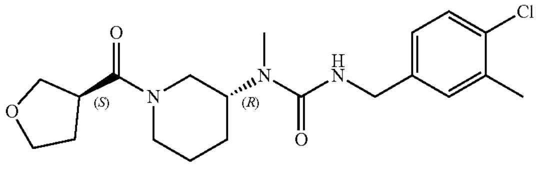 1-[(4-chloro-3-methylphenyl)methyl]-3-methyl-3-[(3R)-1-[(3S)-oxolane-3-carbonyl]piperidin-3-yl]urea | LC-MS: m/z 416.1 (M + H). 1H NMR (400 MHz, MeOD) δ 7.27 (dd, J = 8.2, 3.5 Hz, 1H), 7.21 (d, J = 3.7 Hz, 1H), 7.10 (dd, J = 9.7, 3.7 Hz, 1H), 4.54-4.41 (m, 1H), 4.37-4.25 (m, 2H), 4.09-3.89 (m, 3H), 3.89-3.74 (m, 3H), 3.51-3.40 (m, 1H), 3.20-2.95 (m, 1H), 2.85 (d, J = 8.0 Hz, 3H), 2.79-2.47 (m, 1H), 2.34 (s, 3H), 2.20-2.00 (m, 2H), 1.91-1.77 (m, 3H), 1.67-1.44 (m, 1H). |
| 238 | 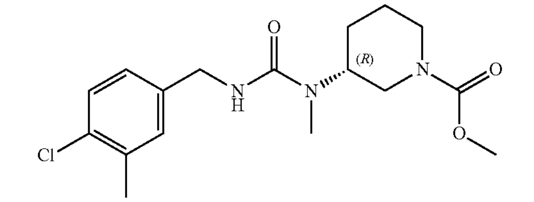 methyl (3R)-3-({[(4-chloro-3-methylphenyl)methyl]carbamoyl}(methyl)amino)piperidine-1-carboxylate | LC-MS: m/z 354.2 (M + H). 1H NMR (400 MHz, MeOD) δ 7.27 (d, J = 8.2 Hz, 1H), 7.20 (s, 1H), 7.09 (d, J = 8.1 Hz, 1H), 4.31-4.28 (m,2H),4.08-3.95(m,3H),3.67(s,3H),2.88-2.81(m, 4H),2.70-2.64 (m,1H),2.34(s,3H), 1.80- 1.68 (m, 3H), 1.60-1.50 (m, 1H). |
| 239 | 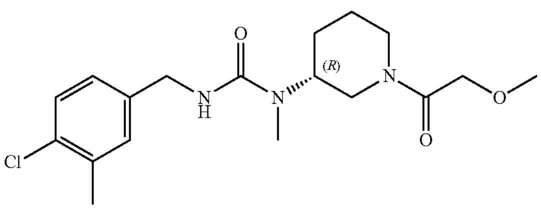 3-[(4-chloro-3-methylphenyl)methyl]-1-[(3R)-1-(2-methoxyacetyl)piperidin-3-yl]-1-methyl]urea | LC-MS: m/z 368.2 (M + H). 1H NMR (400 MHz, MeOD) δ 7.27 (dd, J = 8.1, 2.6 Hz, 1H), 7.21 (s, 1H), 7.09 (d, J = 8.1 Hz, 1H), 4.50-4.38 (m, 1H), 4.37-4.25 (m, 2H), 4.23-4.08 (m, 2H), 4.07-3.95 (m, 1H), 3.84-3.65 (m, 1H), 3.38 (s, 3H), 3.16-2.90 (m, 1H), 2.85 (d, J = 1.7 Hz, 3H), 2.78-2.47 (m, 1H), 2.34 (s, 3H), 1.85-1.76 (m, 3H), 1.67-1.44 (m, 1H). |
| 240 | 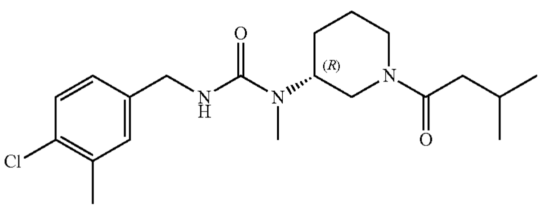 3-[(4-chloro-3-methylphenyl)methyl]-1-methyl-1-[(3R)-1-(3-methylbutanoyl)piperidin-3-yl]urea | LC-MS: m/z 380.2 (M + H). 1H NMR (400 MHz, MeOD) δ 7.29-7.15 (m, 2H), 7.09 (dd, J = 6.4, 3.8 Hz, 1H), 4.59-4.42 (m, 1H), 4.39-4.22 (m, 2H), 4.15-3.77 (m, 2H), 3.15-2.93 (m, 1H), 2.84 (d, J = 5.5 Hz, 3H), 2.74-2.42 (m, 1H), 2.33 (s , 3H), 2.28-220 (m, 2H), 2.12-1.99 (m, 1H), 1.88-1.71 (m, 3H), 1.62-1.42 (m, 1H), 0.98-0.88 (m, 6H). |

-continued

| Example | Structure and name | Data |
|---|---|---|
| 241 | 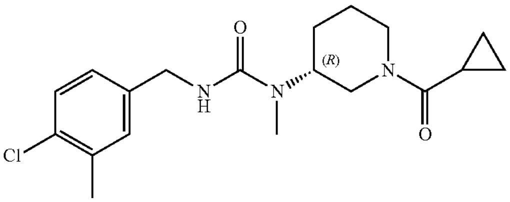 3-[(4-chloro-3-methylphenyl)methyl]-1-[(3R)-1-cyclopropanecarbonylpiperidin-3-yl]-1-methyl]urea | LC-MS: m/z 364.2 (M + H). 1H NMR (400 MHz, MeOD) δ 7.26 (d, J-8.2 Hz, 1H), 7.21 (s, 1H), 7.09 (d, J = 7.7 Hz, 1H), 4.63-4.22 (m, 4H), 4.19-3.90 (m, 1H), 3.25-2.98 (m, 1H), 2.94-2.82 (m, 3H), 2.79-2.45 (m, 1H), 2.34 (s, 3H), 2.01-1.73 (m, 4H), 1.67-1.48 (m, 1H), 0.93-0.72 (m, 4H). |
| 242 | 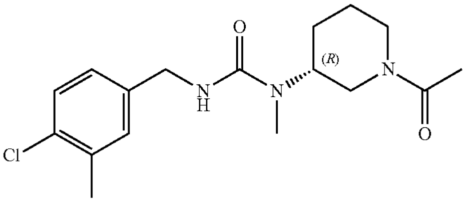 1-[(3R)-1-acetylpiperidin-3-yl]-3-[(4-chloro-3-methylphenyl)methyl]-1-methyl]urea | LC-MS: m/z 338.2 (M + H). 1H NMR (400 MHz, MeOD) δ 7.28-7.25 (m, 1H), 7.21 (s, 1H), 7.14-7.05 (m, 1H), 4.52-4.40 (m, 1H), 4.38-4.22 (m, 2H), 4.10-3.95 (m, 1H), 3.89-3.73 (m, 1H), 3.18-2.96 (m, 1H), 2.86 (s , 3H), 2.74-2.43 (m, 1H), 2.35 (s, 3H), 2.18-2.03 (m, 3H), 1.88-1.72 (m, 3H), 1.65-1.44 (m, 1H). |
| 243 | 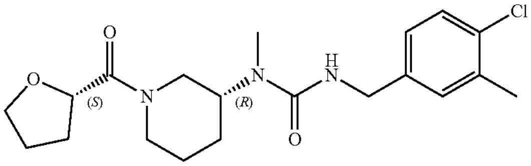 1-[(4-chloro-3-methylphenyl)methyl]-3-methyl-3-[(3R)-1-[(2S)-oxolane-2-carbonyl]piperidin-3-yl]urea | LC-MS: m/z 394 (M + H). 1H NMR (400 MHz, MeOD) δ 7.27 (dd, J = 8.2, 3.9 Hz, 1H), 7.21 (s, 1H), 7.10 (dd, J = 5.7, 2.3 Hz, 1H), 4.78-4.65 (m, 1H), 4.51-4.25 (m, 3H), 4.13-3.79 (m, 4H), 3.19-2.90 (m, 1H), 2.85 (d, J = 5.7 Hz, 3H), 2.78-2.47 (m, 1H), 2.34 (s, 3H), 2.29-2.10 (m, 1H), 2.06-1.78 (m, 6H), 1.69-1.42 (m, 1H). |
| 244 | 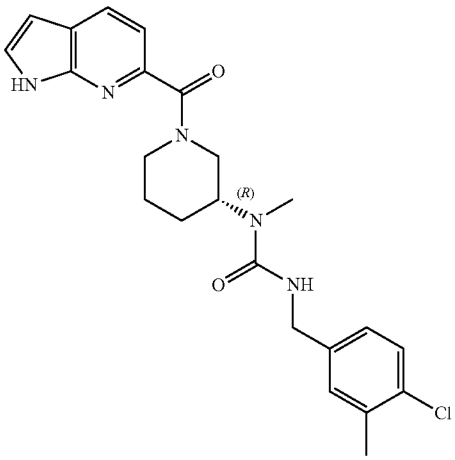 1-[(4-chloro-3-methylphenyl)methyl]-3-methyl-3-[(3R)-1-{1H-pyrrolo[2,3-b]pyridine-6-carbonyl}piperidin-3-yl]urea | LC-MS: m/z 440.2 (M + H). 1H NMR (400 MHz, MeOD) δ 8.09-8.00(m,1H), 7.53-7.41(m,1H), 7.33-7.20(m,2H), 7.12(d, J = 7.8 Hz, 1H), 7.06-6.87 (m, 1H), 6.57-6.50 (m, 1H), 4.69-4.55 (m, 1H), 4.42-4.14 (m, 3H), 3.88-3.82 (m, 1H), 3.26-3.00 (m, 1H), 2.99-2.71 (m, 4H), 2.38-2.19 (m, 3H), 1.99-1.65 (m, 4H). |

-continued

| Example | Structure and name | Data |
|---|---|---|
| 245 | 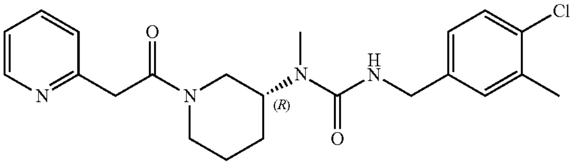 1-[(4-chloro-3-methylphenyl)methyl]-3-methyl-3-[(3R)-1-[2-(pyridin-2-yl)acetyl]piperidin-3-yl]urea | LC-MS: m/z 415.2 (M + H). 1H NMR (400 MHz, MeOD) δ 8.64 (s, 1H), 8.25-8.13 (m, 1H), 7.73-7.60 (m, 2H), 7.30-7.16 (m, 2H), 7.11-7.05 (m, 1H), 4.56-4.41 (m, 1H), 4.37-4.26 (m, 2H), 4.14-3.86(m, 2H), 3.23-3.02 (m, 1H), 2.92-2.83 (m, 3H), 2.81-2.48 (m, 1H), 2.33 (s, 3H), 1.93-1.78 (m, 3H), 1.64-1.44( m, 1H). |
| 246 | 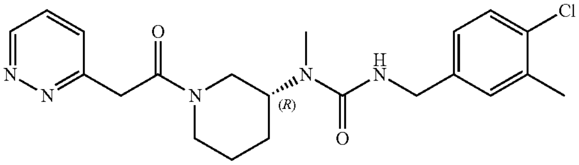 1-[(4-chloro-3-methylphenyl)methyl]-3-methyl-3-[(3R)-1-[2-(pyridazin-3-yl)acetyl]piperidin-3-yl]urea | LC-MS: m/z 416.2 (M + H). 1H NMR (400 MHz, MeOD) δ 9.15-9.03 (m, 1H), 7.67 (dd, J = 8.5, 4.7 Hz, 2H), 7.30-7.16 (m, 2H), 7.11-7.06 (m, 1H), 4.52-3.93 (m, 7H), 3.28-3.03 (m, 1H), 2.91-2.53 (m, 4H), 2.32 (d, J = 5.6 Hz, 3H), 1.92-1.78 (m, 3H), 1.65-1.45 (m, 1H). |
| 247 | 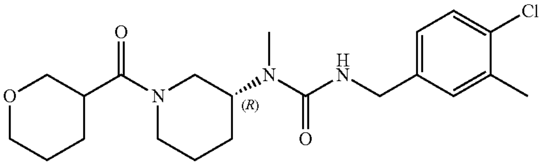 1-[(4-chloro-3-methylphenyl)methyl]-3-methyl-3-[(3R)-1-(oxane-3-carbonyl)piperidin-3-yl]urea | LC-MS: m/z 408.2 (M + H). 1H NMR (400 MHz, MeOD) δ 7.28-7.25 (m, 1H), 7.21 (d, J = 6.9 Hz, 1H), 7.09 (t, J = 7.8 Hz, 1H), 4.53-4.24 (m, 3H), 4.14-3.81 (m, 4H), 3.54-3.33 (m, 2H), 3.19-2.79 (m, 5H), 2.74-2.39 (m, 1H), 2.34 (s, 3H), 2.08-1.54 (m, 8H). |
| 248 | 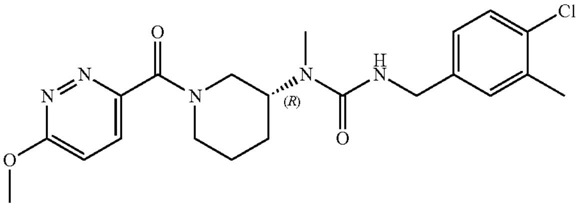 1-[(4-chloro-3-methylphenyl)methyl]-3-[(3R)-1-(6-methoxypyridazine-3-carbonyl)piperidin-3-yl]-3-methyl]urea | LC-MS: m/z 432.2 (M + H). 1H NMR (400 MHz, MeOD) δ 7.72-7.86 (m, 1H), 7.30-7.00 (m, 4H), 4.70-4.54 (m, 1H), 4.42-4.30 (m, 2H), 4.20-3.99 (m, 4H), 3.98-3.84 (m, 1H), 3.15-2.95 (m, 1H), 2.93-2.74 (m, 4H), 2.36-2.28 (m, 3H), 2.01-1.67 (m, 4H). |
| 249 | 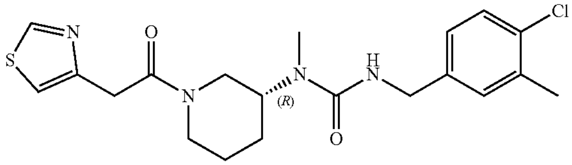 1-[(4-chloro-3-methylphenyl)methyl]-3-methyl-3-[(3R)-1-[2-(1,3-thiazol-4-yl)acetyl]piperidin-3-yl]urea | LC-MS: m/z 421.1 (M + H). 1H NMR (400 MHz, MeOD) δ 8.95-8.81 (m, 1H), 7.42-7.33 (m, 1H), 7.24 (dd, J = 8.2, 3.2 Hz, 1H), 7.18 (d, J = 4.1 Hz, 1H), 7.07 (d, J = 8.3 Hz, 1H), 4.59-4.45 (m, 1H), 4.37-4.22 (m, 2H), 4.08-3.86 (m, 4H), 3.24-2.95 (m, 1H), 2.84 (d, J = 9.6 Hz, 3H), 2.80-2.46 (m, 1H), 2.31 (d, J = 7.5 Hz, 3H), 1.89-1.73 (m, 3H), 1.55-1.39 (m, 1H). |
| 250 | 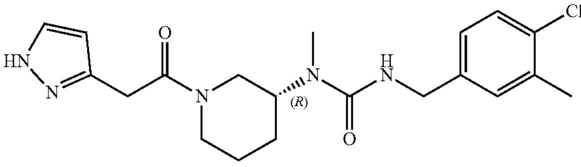 1-[(4-chloro-3-methylphenyl)methyl]-3-methyl-3-[(3R)-1-[2-(1H-pyrazol-3-yl)acetyl]piperidin-3-yl]urea | LC-MS: m/z 404.2 (M + H). 1H NMR (400 MHz, CDCl3) δ 7.55-7.51 (m, 1H), 7.25 (dd, J = 8.2, 1.5 Hz, 1H), 7.19 (d, J = 4.3 Hz, 1H), 7.07 (d, J = 8.1 Hz, 1H), 6.24-6.14 (m, 1H), 4.57-4.40 (m, 1H), 4.37-4.21 (m, 2H), 4.02-3.72 (m, 4H), 3.15-2.93 (m, 1H), 2.82 (d, J = 1.5 Hz, 3H), 2.81-2.45 (m, 1H), 2.32 (d, J = 5.6 Hz, 3H), 1.87-1.70 (m, 3H), 1.58-1.36 (m, 1H). |

-continued

| Example | Structure and name | Data |
|---|---|---|
| 251 | 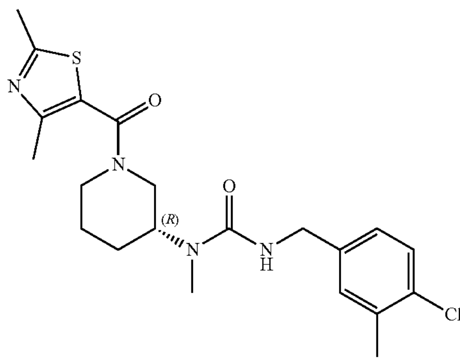 1-[(4-chloro-3-methylphenyl)methyl]-3-[(3R)-1-(2,4-dimethyl-1,3-thiazole-5-carbonyl)piperidin-3-yl]-3-methyl]urea | LC-MS: m/z 435.1 (M + H). 1H NMR (400 MHz, CDCl3) δ 7.30-7.02 (m, 3H), 4.70-3.94 (m, 5H), 3.23-2.73 (m, 5H), 2.66 (s, 3H), 2.36 (s, 3H), 2.33 (s, 3H), 1.91-1.76 (m, 3H), 1.60 (s, 1H). |
| 252 | 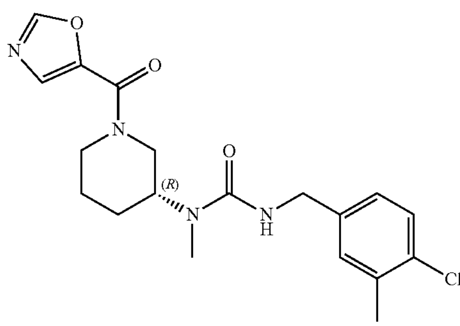 1-[(4-chloro-3-methylphenyl)methyl]-3-methyl-3-[(3R)-1-(1,3-oxazole-5-carbonyl)piperidin-3-yl]urea | LC-MS: m/z 391.1 (M + H). 1H NMR (400 MHz, MeOD) δ 8.31 (s, 1H), 7.73-7.62 (m, 1H), 7.26 (d, J = 8.2 Hz, 1H), 7.20 (s, 1H), 7.09 (d, J = 7.9 Hz, 1H), 4.61-4.13 (m, 5H), 3.21-2.68 (m, 5H), 2.34 (s, 3H), 1.94-1.85 (m, 3H), 1.65 (s, 1H). |
| 253 | 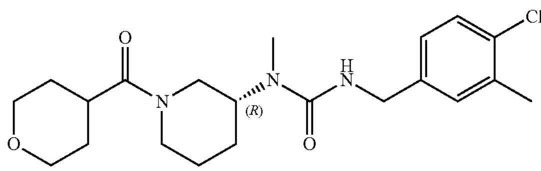 1-[(4-chloro-3-methylphenyl)methyl]-3-methyl-3-[(3R)-1-(oxane-4-carbonyl)piperidin-3-yl]urea | LC-MS: m/z 480.2 (M + H). 1H NMR (400 MHz, MeOD) δ 7.26 (dd, J = 8.1, 5.3 Hz, 1H), 7.20 (s, 1H), 7.11-7.06 (m, 1H), 4.61-4.41(m, 1H), 4.36-4.23 (m, 2H), 4.14-3.84 (m, 4H), 3.55-3.41 (m, 2H), 3.16-2.89 (m, 2H), 2.84 (d, J = 9.1 Hz, 3H), 2.75-2.43 (m, 1H), 2.34 (s , 3H), 1.91- 1.40 (m, 8H). |
| 254 | 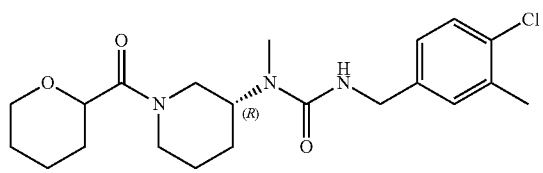 1-[(4-chloro-3-methylphenyl)methyl]-3-methyl-3-[(3R)-1-(oxane-2-carbonyl)piperidin-3-yl]urea | LC-MS: m/z 480.2 (M + H). 1H NMR (400 MHz, MeOD) δ 7.29-7.16 (m, 2H), 7.09 (t, J = 7.7 Hz, 1H), 4.51-4.14 (m, 4H), 4.10-3.80 (m, 3H), 3.63-3.38 (m, 1H), 3.15-2.87 (m, 1H), 2.84 (d, J = 6.4 Hz, 3H), 2.76-2.44 (m, 1H), 2.33 (s, 3H), 1.95-1.76 (m, 4H), 1.75-1.39 (m, 6H). |

-continued

| Example | Structure and name | Data |
|---|---|---|
| 255 | 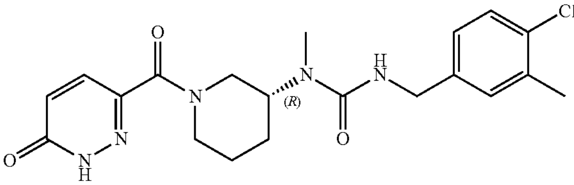 1-[(4-chloro-3-methylphenyl)methyl]-3-methyl-3-[(3R)-1-(6-oxo-1,6-dihydropyridazine-3-carbonyl)piperidin-3-yl]urea | LC-MS: m/z 418.1 (M + H). 1H NMR (400 MHz, MeOD) δ 7.43 (dd, J = 9.8, 3.8 Hz, 1H), 7.06 (dd, J = 8.2, 3.8 Hz, 1H), 7.04-6.96 (m, 1H), 6.91-6.68 (m, 2H), 4.37-4.27 (m, 1H), 4.13-3.76 (m, 4H), 3.07-2.81 (m, 1H), 2.77-2.48 (m, 4H), 2.13 (d, J = 7.2 Hz, 3H), 1.78-1.57 (m, 3H), 1.57-1.33 (m, 1H). |
| 256 | 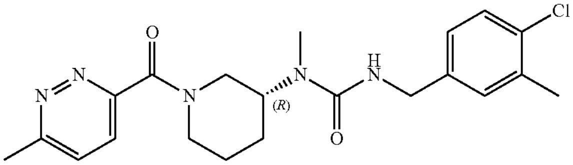 1-[(4-chloro-3-methylphenyl)methyl]-3-methyl-3-[(3R)-1-(6-methylpyridazine-3-carbonyl)piperidin-3-yl]urea | LC-MS: m/z 416.1 (M + H). 1H NMR (400 MHz, MeOD) δ 7.82-7.66 (m, 2H), 7.29-6.96 (m, 3H), 4.72-4.54 (m, 1H), 4.39-4.26 (m, 2H), 4.24-4.01 (m, 1H), 3.80-3.72 (m, 1H), 3.11-2.96 (m, 1H), 2.95-2.74 (m, 4H), 2.74-2.66 (m, 3H), 2.35-2.28 (m, 3H), 2.01-1.62 (m, 4H). |
| 257 | 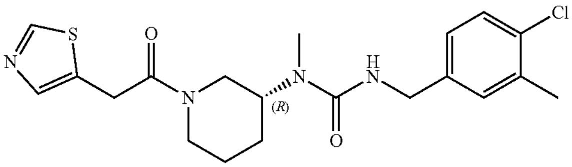 1-[(4-chloro-3-methylphenyl)methyl]-3-methyl-3-[(3R)-1-[2-(1,3-thiazol-5-yl)acetyl]piperidin-3-yl]urea | LC-MS: m/z 421.1 (M + H). 1H NMR (400 MHz, MeOD) δ 8.98 (s, 1H), 7.75 (d, J = 9.6 Hz, 1H), 7.30-7.18 (m, 2H), 7.14-7.05 (m, 1H), 4.53-4.41 (m, 1H), 4.35-4.27 (m, 2H), 4.16-3.87 (m, 4H), 3.24-2.98 (m, 1H), 2.90-2.83 (m, 3H), 2.81-2.52 (m, 1H), 2.34 (s, 3H), 1.92-1.77 (m, 3H), 1.62-1.45 (m, 1H). |
| 258 | 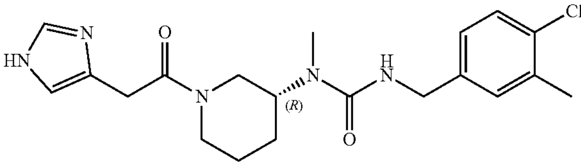 1-[(4-chloro-3-methylphenyl)methyl]-3-[(3R)-1-[2-(1H-imidazol-4-yl)acetyl]piperidin-3-yl]-3-methyl]urea | LC-MS: m/z 404.1 (M + H). 1H NMR (400 MHz, MeOD) δ 7.84 (s, 1H), 7.26-7.19 (m, 2H), 7.13-6.99 (m, 2H), 4.56-4.39 (m, 1H), 4.32 (d, J = 7.3 Hz, 2H), 4.00-3.92 (m, 2H), 3.82-3.71 (m, 2H), 3.20-2.95 (m, 1H), 2.84 (d, J = 10.0 Hz, 3H), 2.77-2.48 (m, 1H), 2.31 (d, J = 5.5 Hz, 3H), 1.85-1.74 (m, 3H), 1.055-1.39 (m, 1H). |
| 259 | 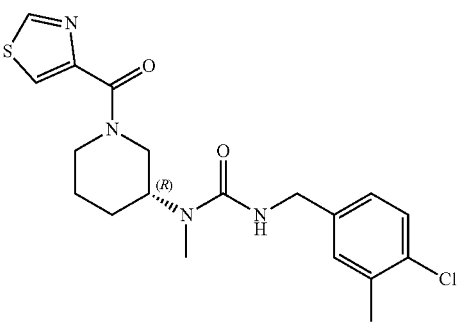 1-[(4-chloro-3-methylphenyl)methyl]-3-methyl-3-[(3R)-1-(1,3-thiazole-4-carbonyl)piperidin-3-yl]urea | LC-MS: m/z 407.1 (M + H). 1H NMR (400 MHz, MeOD) δ 8.89-9.03 (m, 1H), 8.11-8.00 (m, 1H), 7.26 (d, J = 8.1 Hz, 1H), 7.22-7.18 (m, 1H), 7.14-7.03 (m, 1H), 4.63-4.54 (m, 1H), 4.35-4.24 (m, 2H), 4.13 (d, J = 8.0 Hz, 2H), 3.27-2.69 (m, 5H), 2.33 (s, 3H), 1.98-1.74 (m, 3H), 1.74-1.57 (m, 1H). |

-continued

| Example | Structure and name | Data |
|---|---|---|
| 260 | 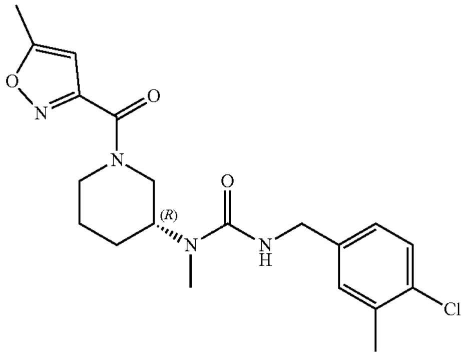 1-[(4-chloro-3-methylphenyl)methyl]-3-methyl-3-[(3R)-1-(5-methyl-1,2-oxazole-3-carbonyl)piperidin-3-yl]urea | LC-MS: m/z 405.1 (M + H). 1H NMR (400 MHz, MeOD) δ 7.25 (dd, J = 8.2, 4.2 Hz, 1H), 7.19 (d, J = 14.2 Hz, 1H), 7.15- 7.03 (m, 1H), 6.32 (dd, J = 11.6, 0.7 Hz, 1H), 4.65-4.52 (m, 1H), 4.37-4.23 (m, 2H), 4.14-3.99 (m, 2H), 3.28-2.99 (m, 1H), 2.97-2.70 (m, 4H), 2.44 (d, J = 16.7 Hz, 3H), 2.33 (d, J = 3.8 Hz, 3H), 1.95-1.80 (m, 3H), 1.67-1.55(m, 1H). |
| 261 | 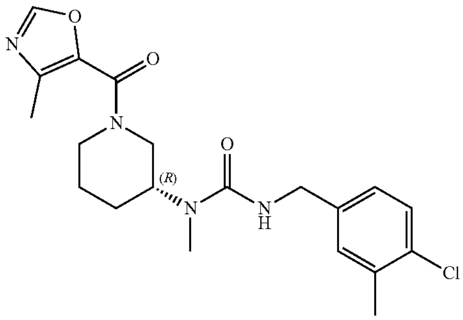 1-[(4-chloro-3-methylphenyl)methyl]-3-methyl-3-[(3R)-1-(4-methyl-1,3-oxazole-5-carbonyl)piperidin-3-yl]urea | LC-MS: m/z 405.1 (M + H). 1H NMR (400 MHz, MeOD) δ 8.24-8.08 (m, 1H), 7.26 (d, J = 8.2 Hz, 1H), 7.19 (s, 1H), 7.07 (d, J = 7.6 Hz, 1H), 4.51-3.98 (m, 5H), 3.15-2.67 (m, 5H), 2.33 (s, 3H), 2.31 (s, 3H), 1.94-1.80 (m, 3H), 1.71-1.57 (m, 1H). |
| 262 | 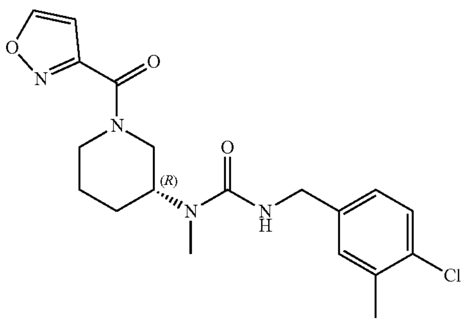 1-[(4-chloro-3-methylphenyl)methyl]-3-methyl-3-[(3R)-1-(1,2-oxazole-3-carbonyl)piperidin-3-yl]urea | LC-MS: m/z 391.1 (M + H). 1H NMR (400 MHz, MeOD) δ 8.77 (dd, J = 9.2, 1.6 Hz, 1H), 7.26 (dd, J = 8.2, 5.4 Hz, 1H), 7.25-7.22 (m, 1H), 7.14-7.04 (m, 1H), 6.70 (dd, J = 12.6, 1.8 Hz, 1H), 4.68-4.52 (m, 1H), 4.39-4.21 (m, 2H), 4.20-4.02 (m, 2H), 3.13-2.71 (m, 5H), 2.34 (d, J = 5.2 Hz, 3H), 1.98-1.79 (m, 3H), 1.74-1.58 (m, 1H). |

-continued

| Example | Structure and name | Data |
|---|---|---|
| 263 | 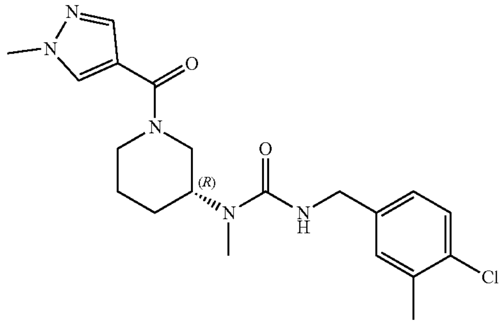 1-[(4-chloro-3-methylphenyl)methyl]-3-methyl-3-[(3R)-1-(1-methyl-1H-pyrazole-4-carbonyl)piperidin-3-yl]urea | LC-MS: m/z 404.2 (M + H). 1H NMR (400 MHz, CDCl3) δ 8.03 (s, 1H), 7.75 (s, 1H), 7.27 (d, J = 8.2 Hz, 1H), 7.20 (s, 1H), 7.09 (d, J = 8.2 Hz, 1H), 4.66-4.41 (m, 1H), 4.31 (s, 2H), 4.26-3.99 (m, 2H), 3.86 (s, 3H), 3.26-2.98 (m, 1H), 2.93-2.60 (m, 4H), 2.33 (s, 3H), 1.97-1.79 (m, 3H), 1.71-1.53 (m, 1H). |
| 264 | 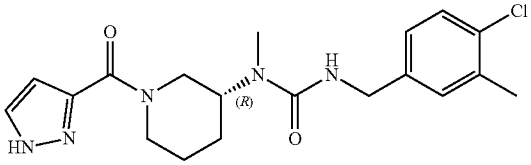 1-[(4-chloro-3-methylphenyl)methyl]-3-methyl-3-[(3R)-1-(1H-pyrazole-3-carbonyl)piperidin-3-yl]urea | LC-MS: m/z 390 (M + H). 1H NMR (400 MHz, MeOD) δ 7.67 (d, J = 6.4 Hz, 1H), 7.30-6.99 (m, 3H), 6.62 (s, 1H), 4.67-4.36 (m, 2H), 4.30 (s, 2H), 4.10 (s, 1H), 3.29-2.98 (m, 1H), 2.96-2.63 (m, 4H), 2.33 (d, J = 5.8 Hz, 3H), 1.86-1.52 (m, 4H). |
| 265 | 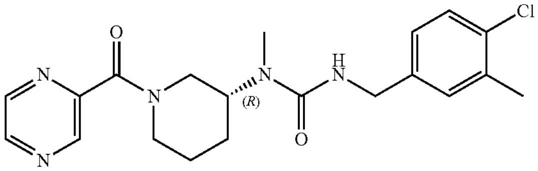 1-[(4-chloro-3-methylphenyl)methyl]-3-methyl-3-[(3R)-1-(pyrazine-2-carbonyl)piperidin-3-yl]urea | LC-MS: m/z 402.1 (M + H). 1H NMR (400 MHz, MeOD) δ 8.82 (dd, J = 5.1, 1.3 Hz, 1H), 8.68-8.50 (m,, 2H), 7.29-6.99 (m, 3H), 4.67-4.54 (m, 1H), 4.36-4.10 (m, 3H), 3.83-3.71 (m, 1H), 3.09-2.95 (m, 1H), 2.92-2.71 (m, 4H), 2.33 (s, 3H), 1.95-1.65 (m, 4H). |
| 266 | 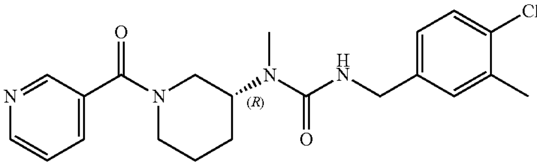 1-[(4-chloro-3-methylphenyl)methyl]-3-methyl-3-[(3R)-1-(pyridine-3-carbonyl)piperidin-3-yl]urea | LC-MS: m/z 400.2 (M + H). 1H NMR (400 MHz, MeOD) δ 8.55 (d, J = 3.9 Hz, 1H), 7.23-7.16 (m, 2H), 7.05 (d, J = 1.9 Hz, 1H), 6.94 (dd, J = 8.2, 2.2 Hz, 1H), 6.62 (dd, J = 9.1, 1.1 Hz, 1H), 5.08-4.94 (m, 1H), 4.85 (s, 1H), 3.88-3.71 (m, 2H), 3.54-3.42 (m, 1H), 3.37 (dd, J = 10.5, 8.1 Hz, 1H), 3.25-3.16 (m, 2H), 2.82 (qd, J = 4.6, 1.8 Hz, 1H), 2.33 (s, 3H), 2.27 (ddd, J = 14.3, 6.2, 2.8 Hz, 1H), 2.16-2.07 (m, 1H), 1.99 (ddd, J = 9.5, 6.3, 3.3 Hz, 1H), 1.23-1.10 (m, 5H). |
| 267 | 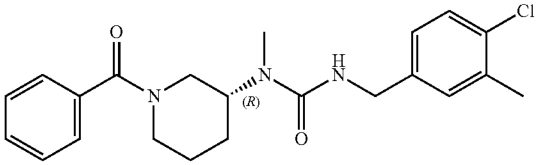 3-[(3R)-1-benzoylpiperidin-3-yl]-1-[(4-chloro-3-methylphenyl)methyl]-3-methyl]urea | LC-MS: m/z 400.1 (M + H). 1H NMR (400 MHz, MeOD) δ 7.45-7.40 (m, 5H), 7.29-6.95 (m, 3H), 4.56 (br, 1H), 4.32-4.10 (m, 3H), 3.64 (br, 1H), 3.19-2.67 (m, 5H), 2.32 (s, 3H), 1.94-1.70 (m, 3H), 1.61 (br, 1H). |

-continued

| Example | Structure and name | Data |
|---|---|---|
| 268 | 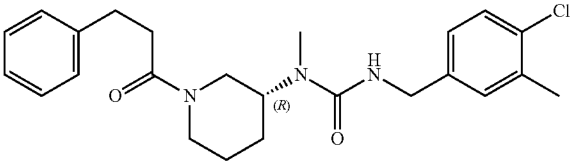 1-[(4-chloro-3-methylphenyl)methyl]-3-methyl-3-[(3R)-1-(3-phenylpropanoyl)piperidin-3-yl]urea | LC-MS: m/z 428.4 (M + H). 1H NMR (400 MHz, DMSO) δ 7.35-7.13 (m, 7H), 7.08 (t, J = 8.4 Hz, 1H), 6.91 (t, J = 5.7 Hz, 1H), 4.38-4.15 (m,, 3H), 3.95-3.61 (m, 2H), 3.05-2.70 (m, 6H), 2.6-2.52 (m, 3H), 2.28 (s, 3H), 1.77-.55 (m, 3H), 1.41-1.22 (m, 1H). |
| 269 | 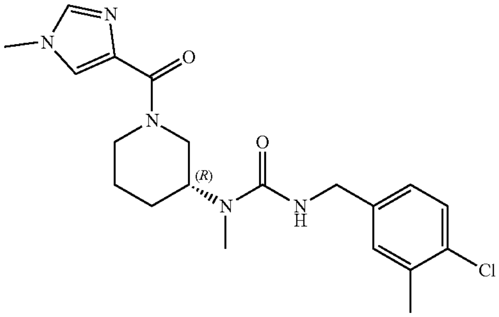 1-[(4-chloro-3-methylphenyl)methyl]-3-methyl-3-[(3R)-1-(1-methyl-1H-imidazole-4-carbonyl)piperidin-3-yl]urea | LC-MS: m/z 404.4 (M + H). 1H NMR (400 MHz, DMSO) δ 7.60 (s, 2H), 7.32 (d, J = 8.2 Hz, 1H), 7.21 (s, 1H), 7.09 (d, J = 8.0 Hz, 1H), 7.06-6.78 (m, 1H), 5.09 (d, J = 83.9 Hz, 1H), 4.35 (s, 1H), 4.20 (d, J = 5.6 Hz, 2H), 3.91 (s, 1H), 3.66 (s, 3H), 3.13 (s, 1H), 2.71 (d, J = 34.3 Hz, 4H), 2.30 (s, 3H), 1.72 (s, 3H), 1.45 (d, J = 12.4 Hz, 1H). |
| 270 | 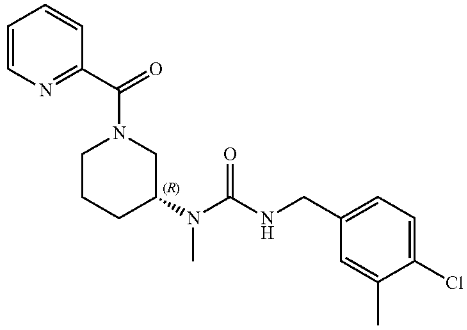 1-[(4-chloro-3-methylphenyl)methyl]-3-methyl-3-[(3R)-1-(pyridine-2-carbonyl)piperidin-3-yl]urea | LC-MS: m/z 401.4 (M + H). 1H NMR (400 MHz, DMSO) δ 8.55 (dd, J = 29.7, 4.5 Hz, 1H), 7.95-7.85 (m, 1H), 7.53 (d, J = 7.8 Hz, 1H), 7.45 (ddd, J = 11.8, 6.2, 3.0 Hz, 1H), 7.38-7.20 (m, 2H), 7.12 (d, J = 8.4 Hz, 1H), 7.02-6.92 (m, 1H), 4.41 (dd, J = 48.2, 12.2 Hz, 1H), 4.26-3.91 (m, 3H), 3.52 (dd, J = 42.7, 10.9 Hz, 1H), 3.20-2.89 (m, 1H), 2.73 (d, J = 50.5 Hz, 3H), 2.29 (d, J = 16.6 Hz, 3H), 1.84-1.61 (m, 3H), 1.57-1.43 (m, 1H). |
| 271 | 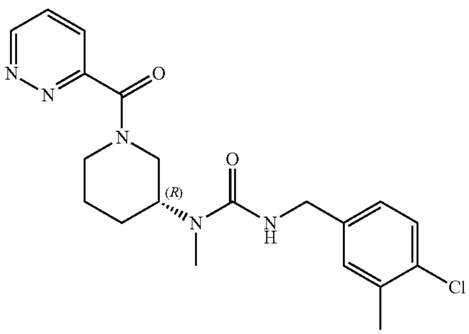 1-[(4-chloro-3-methylphenyl)methyl]-3-methyl-3-[(3R)-1-(pyridazine-3-carbonyl)piperidin-3-yl]urea | LC-MS: m/z 402.2 (M + H). 1H NMR (400 MHz, MeOD) δ 9.24 (ddd, J = 14.4, 5.0, 1.8 Hz, 1H), 7.94-7.79 (m, 2H), 7.30-6.99 (m, 3H), 4.70-4.57 (m, 1H), 4.34 (t, J = 9.2 Hz, 1H), 4.28 (s, 1H), 4.25-4.03 (m, 1H), 3.73 (dd, J = 29.6, 12.1 Hz, 2H), 3.14-2.97 (m, 1H), 2.96-2.75 (m, 4H), 2.33 (d, J = 15.4 Hz, 3H), 2.01-1.65 (m, 4H). |

General Procedure J:

Example 272: Synthesis of (R)-3-(4-chloro-3-methylbenzyl)-1-(1-(cyclopropanecarbonyl)piperidin-3-yl)-1-cyclopropylurea

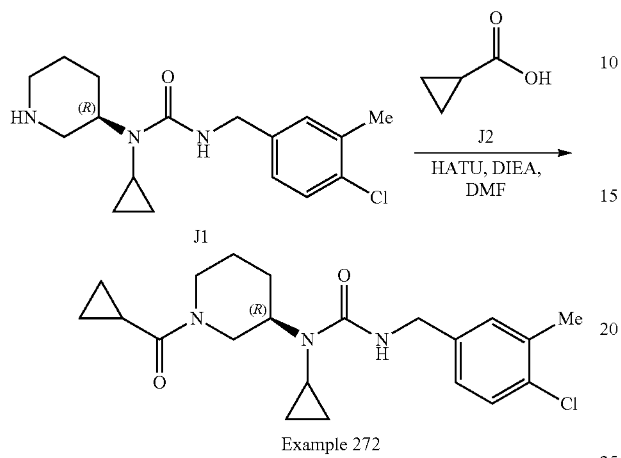

J1

Example 272

To a mixture of J1 (67 mg, 0.21 mmol) and DIEA (81 mg, 0.63 mmol) in anhydrous DMF (5 mL) was added cyclopropane carboxylic acid J2 (19 mg, 0.22 mmol) and HATU (84 mg, 0.22 mmol). The resulting mixture was stirred at r.t. for 1 hr. Then the mixture was poured into water (10 mL) and extracted with EtOAc (20 mL) twice. The combined organic layers were washed with saturated $NH_4Cl$ solution and brine, dried over anhydrous $Na_2SO_4$, filtered and concentrated to dryness. The residue was purified via prep-HPLC to afford Example 272 (17 mg, 20.73% yield) as light-yellow solid. LC/MS (ESI) m/z: 390 $(M+H)^+$. 1H NMR (400 MHz, MeOD) δ 7.27 (d, J=8.2 Hz, 1H), 7.24-7.17 (m, 1H), 7.13-7.05 (m, 1H), 4.54-4.39 (m, 1H), 4.37-4.21 (m, 3H), 3.57-3.34 (m, 1H), 3.22-2.91 (m, 1H), 2.65-2.43 (m, 2H), 2.34 (s, 3H), 2.28-2.12 (m, 1H), 1.99-1.76 (m, 3H), 1.62-1.36 (m, 1H), 0.97-0.68 (m, 8H).

The compounds in the table below were prepared from the appropriate starting materials, described above or commercially available, using the above General Procedure J and intermediate J1 in Example 272.

| Example | Structure and name | Data |
| --- | --- | --- |
| 273 | 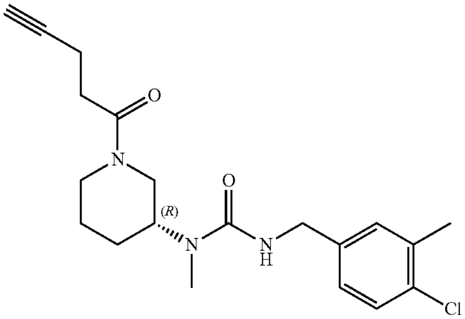 1-[(4-chloro-3-methylphenyl)methyl]-3-methyl-3-[(3R)-1-(pent-4-ynoyl)piperidin-3-yl]urea | LC-MS: m/z 376.3 (M + H). 1H NMR (400 MHz, $CDCl_3$) δ 7.32-7.24 (m, 1H), 7.18 (s, 1H), 7.11-7.04 (m, 1H), 4.97-4.67 (m, 1H), 4.65-4.49 (m, 1H), 4.45-4.26 (m, 2H), 4.22-4.11 (m, 1H), 3.85-3.72 (m, 1H), 2.98-2.86 (m, 1H), 2.80 (s, 3H), 2.70-2.47 (m, 5H), 2.43-2.37 (m, 1H), 2.35 (s, 3H), 1.95 (s, 1H), 1.91-1.46 (m, 3H). |

General Procedure K:

Example 274: Synthesis of (R)-3-(4-chloro-3-methylbenzyl)-1-methyl-1-(1-(6-(trifluoromethyl) pyridazin-3-yl)piperidin-3-yl)urea

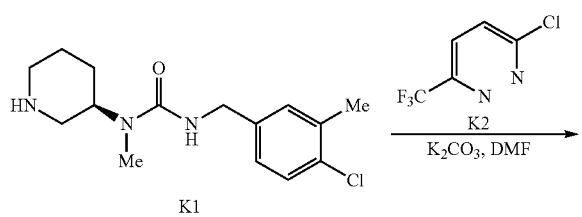

K1

-continued

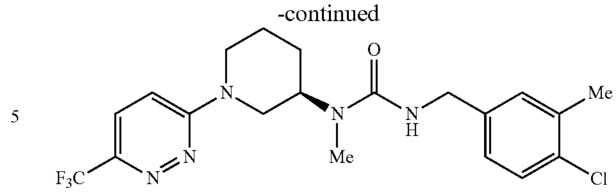

Example 274

To a mixture of K1 (59 mg, 0.2 mmol) and $K_2CO_3$ (56 mg, 0.4 mmol) in DMF (6 mL) was added 3-chloro-6-(trifluoromethyl) pyridazine $K_2$ (44 mg, 0.24 mmol). The resulting mixture was stirred at 80° C. for 10 hrs. After cooling, the mixture was diluted with saturated $NH_4Cl$ solution (20 mL) and extracted with EtOAc (20 mL) twice. The combined organic layers were washed with saturated $NH_4Cl$ solution and brine, dried over anhydrous $Na_2SO_4$, filtered and concentrated to dryness. The residue was purified via prep-HPLC to afford Example 274 (8 mg, 9.1% yield) as white solid. LC/MS (ESI) m/z: 442 $(M+H)^+$. 1H NMR (400 MHz, MeOD) δ 7.64 (d, J=9.7 Hz, 1H), 7.35 (d, J=9.7 Hz, 1H), 7.27 (d, J=8.2 Hz, 1H), 7.24-7.20 (m, 1H), 7.11 (dd, J=8.2, 1.7 Hz, 1H), 4.57-4.47 (m, 1H), 4.45-4.36 (m, 1H), 4.31 (s, 2H), 4.12-4.02 (m, 1H), 3.19-3.09 (m, 1H), 3.04-2.94 (m, 1H), 2.90 (s, 3H), 2.33 (s, 3H), 1.98-1.84 (m, 3H), 1.75-1.60 (m, 1H).

| Example | Structure and name | Data |
| --- | --- | --- |
| 275 | 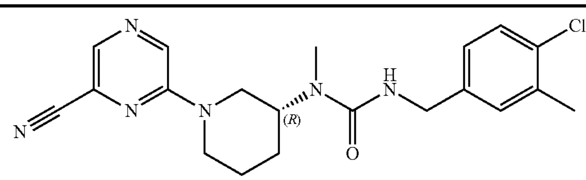 3-[(4-chloro-3-methylphenyl)methyl]-1-[(3R)-1-(6-cyanopyrazin-2-yl)piperidin-3-yl]-1-methylurea | LC-MS: m/z 399.2 (M + H). 1H NMR (400 MHz, MeOD) δ 8.47 (s, 1H), 8.09 (s, 1H), 7.27 (d, J = 8.2 Hz, 1H), 7.21 (s, 1H), 7.10 (dd, J = 8.2, 1.7 Hz, 1H), 4.46-4.29 (m, 4H), 4.10 (dt, J = 10.9, 7.5 Hz, 1H), 3.04 (dd, J = 12.5, 11.5 Hz, 1H), 2.94-2.83 (m, 4H), 2.34 (s, 3H), 1.89 (ddd, J = 15.8, 9.8, 3.4 Hz, 3H), 1.73-1.58 (m, 1H). |

The following examples were prepared by General Procedure A

| Example | Structure/name | Data |
| --- | --- | --- |
| 278 | 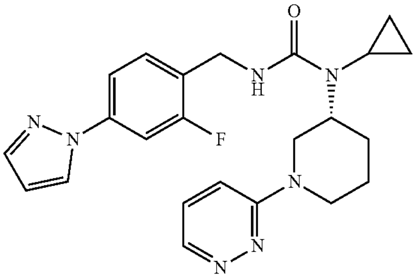 [SMILES: O=C(NCc1ccc(-n2cccn2)cc1F)N(C1CC1)[C@@H]1CCCN(c2cccnn2)C1] 3-cyclopropyl-1-{[2-fluoro-4-(1H-pyrazol-1-yl)phenyl]methyl}-3-[(3R)-1-(pyridazin-3-yl)piperidin-3-yl]urea | LC-MS: 435.2 m/z (M + H). 1H NMR (400 MHz, MeOD) δ 8.42 (dd, J = 4.4, 1.2 Hz, 1H), 8.25 (d, J = 2.5 Hz, 1H), 7.72 (d, J = 1.6 Hz, 1H), 7.59-7.51 (m, 2H), 7.46 (dd, J = 16.5, 8.4 Hz, 1H), 7.37 (dd, J = 9.4, 4.4 Hz, 1H), 7.29 (dd, J = 9.4, 1.2 Hz, 1H), 6.53 (dd, J = 2.5, 1.9 Hz, 1H), 4.53-4.44 (m, 2H), 4.43-4.31 (m, 2H), 3.78 (tt, J = 11.8, 3.9 Hz, 1H), 3.33 (d, J = 12.4 Hz, 1H), 2.88 (td, J = 13.0, 2.7 Hz, 1H), 2.62-2.51 (m, 1H), 2.26 (qd, J = 12.5, 4.0 Hz, 1H), 2.01-1.81 (m, 2H), 1.69-1.56 (m, 1H), 1.04-0.93 (m, 2H), 0.88-0.74 (m, 2H). |

-continued

| Example | Structure/name | Data |
| --- | --- | --- |
| 279 | 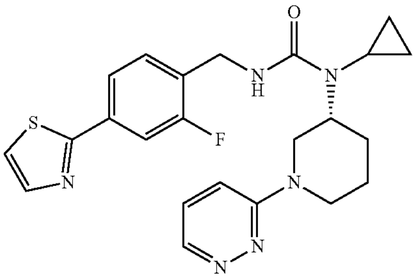 [SMILES: O=C(NCc1ccc(-c2nccs2)cc1F)N(C1CC1)[C@@H]1CCCN(c2cccnn2)C1] 3-cyclopropyl-1-{[2-fluoro-4-(1,3-thiazol-2-yl)phenyl]methyl}-3-[(3R)-1-(pyridazin-3-yl)piperidin-3-yl]urea | LC-MS: 453 m/z (M + H). 1H NMR (400 MHz, MeOD) δ 8.42 (d, J = 4.3 Hz, 1H), 7.89-7.84 (m, 1H), 7.71 (dd, J = 18.7, 9.5 Hz, 2H), 7.64-7.60 (m, 1H), 7.46 (t, J = 7.7 Hz, 1H), 7.36 (dd, J = 8.8, 3.8 Hz, 1H), 7.27 (d, J = 9.4 Hz, 1H), 6.98 (d, J = 5.7 Hz, 1H), 4.50 (d, J = 4.9 Hz, 2H), 4.37 (dd, J = 23.6, 12.7 Hz, 2H), 3.78 (t, J = 11.8 Hz, 1H), 3.35 (s, 1H), 2.88 (t, J = 12.9 Hz, 1H), 2.58 (s, 1H), 2.32-2.20 (m, 1H), 1.92 (dd, J = 46.2, 12.0 Hz, 2H), 1.62 (q, J = 13.3 Hz, 1H), 0.98 (d, J = 6.7 Hz, 2H), 0.82 (s, 2H). |
| 280 | 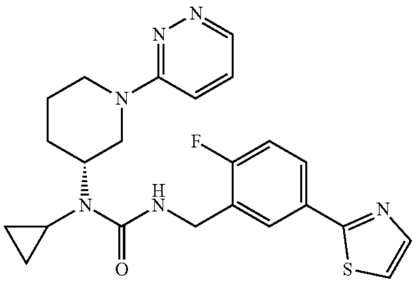 [SMILES: O=C(NCc1cc(-c2nccs2)ccc1F)N(C1CC1)[C@@H]1CCCN(c2cccnn2)C1] 3-cyclopropyl-1-{[2-fluoro-5-(1,3-thiazol-2-yl)phenyl]methyl}-3-[(3R)-1-(pyridazin-3-yl)piperidin-3-yl]urea | LC-MS: 453 m/z (M + H). 1H NMR (400 MHz, MeOD) δ 8.44-8.38 (m, 1H), 7.95 (dd, J = 7.1, 2.2 Hz, 1H), 7.90-7.82 (m, 2H), 7.58(d, J = 3.3 Hz, 1H), 7.34 (dd, J = 9.4, 4.4 Hz, 1H), 7.30-7.16 (m, 2H), 7.07 (t, J = 6.0 Hz, 1H), 4.52 (d, J = 2.5 Hz, 2H), 4.36 (ddd, J = 13.2, 12.6, 7.7 Hz, 2H), 3.78 (tt, J = 12.0, 3.9 Hz, 1H), 3.36 (d, J = 12.3 Hz, 1H), 2.88 (td, J = 13.1, 2.6 Hz, 1H), 2.67-2.57 (m, 1H), 2.28 (qd, J = 12.6, 4.1 Hz, 1H), 1.92 (dd, J = 53.6, 12.6 Hz, 2H), 1.63 (ddt, J = 17.1, 13.1, 6.6 Hz, 1H), 1.02-0.95 (m, 2H), 0.89-0.82 (m, 2H). |
| 281 | 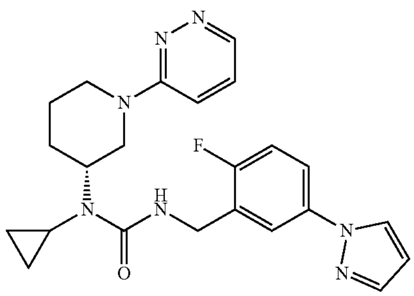 [SMILES: O=C(NCc1cc(-n2cccn2)ccc1F)N(C1CC1)[C@@H]1CCCN(c2cccnn2)C1] 3-cyclopropyl-1-{[2-fluoro-5-(1H-pyrazol-1-yl)phenyl]methyl}-3-[(3R)-1-(pyridazin-3-yl)piperidin-3-yl]urea | LC-MS: 436 m/z (M + H). 1H NMR (400 MHz, MeOD) δ 8.41 (dd, J = 4.4, 1.2 Hz, 1H), 8.15 (d, J = 2.4 Hz, 1H), 7.74 (dd, J = 6.4, 2.8 Hz, 1H), 7.70 (d, J = 1.7 Hz, 1H), 7.61 (ddd, J = 8.7, 4.2, 2.9 Hz, 1H), 7.34 (dd, J = 9.4, 4.4 Hz, 1H), 7.29-7.18 (m, 2H), 6.52-6.49 (m, 1H), 4.56-4.47 (m, 2H), 4.35 (ddd, J = 18.6, 12.5, 7.5 Hz, 2H), 3.78 (tt, J = 11.9, 3.9 Hz, 1H), 3.33 (d, J = 12.8 Hz, 1H), 2.87 (td, J = 13.0, 2.7 Hz, 1H), 2.65-2.52 (m, 1H), 2.26 (qd, J = 12.6, 4.2 Hz, 1H), 1.97 (d, J = 11.5 Hz, 1H), 1.85 (d, J = 12.8 Hz, 1H), 1.68-1.54 (m, 1H), 1.02-0.92 (m, 2H), 0.87-0.75 (m, 2H). |
| 282 | 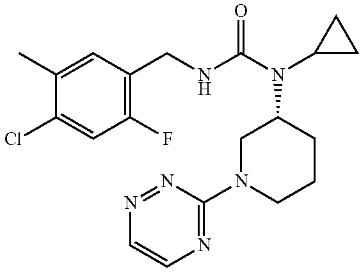 [SMILES: Cc1cc(CNC(=O)N(C2CC2)[C@@H]2CCCN(c3nccnn3)C2)c(F)cc1Cl] 1-[(4-chloro-2-fluoro-5-methylphenyl)methyl]-3-cyclopropyl-3-[(3R)-1-(1,2,4-triazin-3-yl)piperidin-3-yl]urea | LC-MS: 419 m/z (M + H). 1H NMR (400 MHz, MeOD) δ 8.45 (d, J = 2.2 Hz, 1H), 8.26 (d, J = 2.2 Hz, 1H), 7.25 (d, J = 8.0 Hz, 1H), 7.13 (d, J = 9.8 Hz, 1H), 6.86 (t, J = 5.7 Hz, 1H), 4.75 (d, J = 8.6 Hz, 2H), 4.39 (d, J = 5.4 Hz, 2H), 3.71-3.63 (m, 1H), 3.42 (t, J = 11.9 Hz, 1H), 2.87 (td, J = 13.1, 2.7 Hz, 1H), 2.60-2.55 (m, 1H), 2.32 (s, 3H), 2.31-2.23 (m, 1H), 1.90 (dd, J = 27.9, 12.4 Hz, 2H), 1.57 (dt, J = 13.0, 4.0 Hz, 1H), 0.94 (ddd, J = 9.9, 6.9, 3.7 Hz, 2H), 0.83-0.73 (m, 2H). |

-continued

| Example | Structure/name | Data |
|---|---|---|
| 283 | 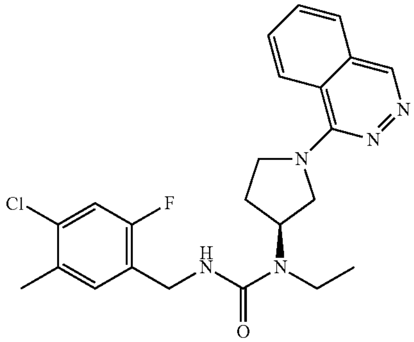 [SMILES: CCN(C(=O)NCc1cc(C)c(Cl)cc1F)[C@H]1CCN(c2nncc3ccccc23)C1] 1-[(4-chloro-2-fluoro-5-methylphenyl)methyl]-3-ethyl-3-[(3S)-1-(phthalazin-1-yl)pyrrolidin-3-yl]urea | LC-MS: 442 m/z (M + H). 1H NMR (400 MHz, MeOD) δ 8.88 (s, 1H), 8.42-8.38 (m, 1H), 7.94 (tdd, J = 6.9, 5.4, 2.0 Hz, 3H), 7.24 (d, J = 8.0 Hz, 1H), 7.10 (d, J = 9.8 Hz, 1H), 4.80 (d, J = 9.0 Hz, 1H), 4.38 (s, 2H), 4.04-3.90 (m, 4H), 3.42 (dd, J = 7.1, 1.7 Hz, 2H), 2.29 (d, J = 5.8 Hz, 5H), 1.23 (t, J = 7.0 Hz, 3H). |
| 284 | 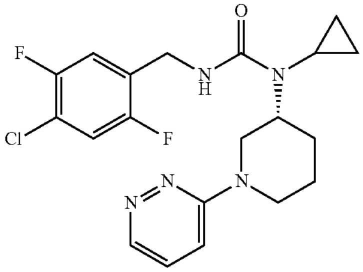 [SMILES: O=C(NCc1cc(F)c(Cl)cc1F)N(C1CC1)[C@@H]1CCCN(c2cccnn2)C1] 3-[(4-chloro-2,5-difluorophenyl)methyl]-1-cyclopropyl-1-[(3R)-1-(pyridazin-3-yl)piperidin-3-yl]urea | LC-MS: 422 m/z (M + H). 1H NMR (400 MHz, MeOD) δ 8.43 (dd, J = 4.3, 1.0 Hz, 1H), 7.37 (dd, J = 9.4, 4.4 Hz, 1H), 7.29 (ddd, J = 9.3, 3.5, 2.3 Hz, 2H), 7.21 (dd, J = 9.5, 6.5 Hz, 1H), 7.02 (t, J = 5.7 Hz, 1H), 4.42-4.30 (m, 4H), 3.76 (tt, J = 11.9, 3.9 Hz, 1H), 3.35 (s, 1H), 2.88 (td, J = 13.1, 2.7 Hz, 1H), 2.61-2.51 (m, 1H), 2.25 (qd, J = 12.6, 4.2 Hz, 1H), 1.96 (d, J = 11.5 Hz, 1H), 1.86 (d, J = 13.1 Hz, 1H), 1.68-1.54 (m, 1H), 1.02-0.92 (m, 2H), 0.81 (dd, J = 6.6, 4.1 Hz, 2H). |
| 285 | 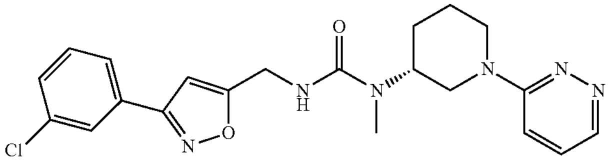 [SMILES: CN(C(=O)NCc1cc(-c2cccc(Cl)c2)no1)[C@@H]1CCCN(c2cccnn2)C1] 3-{[3-(3-chlorophenyl)-1,2-oxazol-5-yl]methyl}-1-methyl-1-[(3R)-1-(pyridazin-3-yl)piperidin-3-yl]urea | LC-MS: 427.3 m/z (M + H). 1H NMR (400 MHz, CDCl3) δ 8.58 (dt, J = 4.4, 1.3 Hz, 1H), 7.84-7.78 (m, 1H), 7.69 (dq, J = 6.9, 1.5 Hz, 1H), 7.43-7.32 (m, 2H), 7.29-7.19 (m, 4H), 7.01 (dd, J = 9.3, 1.3 Hz, 1H), 6.61 (t, J = 0.8 Hz, 1H), 4.77-4.62 (m, 2H), 4.47 (d, J = 12.9 Hz, 1H), 4.09 (d, J = 13.8 Hz, 1H), 3.98-3.88 (m, 1H), 3.07 (t, J = 12.9 Hz, 1H), 3.02-2.91 (m, 5H), 2.03 (s, OH), 1.89 (td, J = 12.9, 4.5 Hz, 2H), 1.77-1.54 (m, 8H), 1.26 (s, 3H).). |
| 286 | 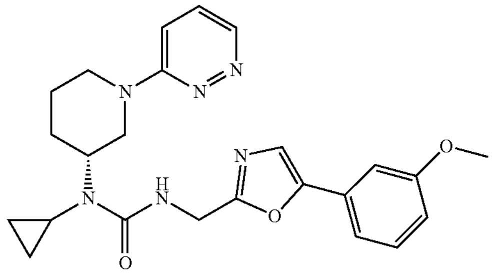 [SMILES: COc1cccc(-c2cnc(CNC(=O)N(C3CC3)[C@@H]3CCCN(c4cccnn4)C3)o2)c1] 1-cyclopropyl-3-{[5-(3-methoxyphenyl)-1,3-oxazol-2-yl]methyl}-1-[(3R)-1-(pyridazin-3-yl)piperidin-3-yl]urea | LC-MS: 449 m/z (M + H). 1H NMR (400 MHz, MeOD) δ 8.42 (dd, J = 4.4, 1.2 Hz, 1H), 7.41 (d, J = 8.5 Hz, 1H), 7.37-7.24 (m, 4H), 7.23-7.19 (m, 1H), 6.91 (dd, J = 8.2, 1.7 Hz, 1H), 4.57 (s, 2H), 4.38 (dd, J = 27.6, 13.2 Hz, 2H), 3.84-3.78 (m, 4H), 2.95-2.82 (m, 1H), 2.65-2.57 (m, 1H), 2.27 (tt, J = 13.0, 6.4 Hz, 1H), 1.82 (ddd, J = 94.5, 29.2, 12.5 Hz, 4H), 1.01-0.95 (m, 2H), 0.92-0.86 (m, 2H). |

-continued

| Example | Structure/name | Data |
|---|---|---|
| 287 | 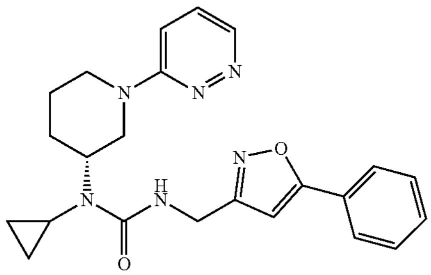 [SMILES: O=C(NCc1cc(-c2ccccc2)on1)N(C1CC1)[C@@H]1CCCN(c2cccnn2)C1] 1-cyclopropyl-3-[(5-phenyl-1,2-oxazol-3-yl)methyl]-1-[(3R)-1-(pyridazin-3-yl)piperidin-3-yl]urea | LC-MS: 419 m/z (M + H). 1H NMR (400 MHz, MeOD) δ 8.43 (s, 1H), 7.81 (dd, J = 7.8, 1.4 Hz, 2H), 7.51-7.41 (m, 3H), 7.35 (d, J = 3.2 Hz, 1H), 7.29 (d, J = 9.3 Hz, 1H), 7.04 (t, J = 5.8 Hz, 1H), 6.72 (s, 1H), 4.53-4.44 (m, 2H), 4.44-4.27 (m, 2H), 3.80 (tt, J = 11.9, 3.9 Hz, 1H), 3.36-3.31(m, 1H), 2.87 (dd, J = 18.4, 7.6 Hz, 1H), 2.61-2.51(m, 1H), 2.26 (qd, J = 12.6, 4.0 Hz, 1H), 1.98 (d, J = 11.6 Hz, 1H), 1.86 (d, J = 13.3 Hz, 1H), 1.62 (dtd, J = 13.0, 9.3, 4.0 Hz, 1H), 1.02-0.91 (m, 2H), 0.88-0.77 (m, 2H). |
| 288 | 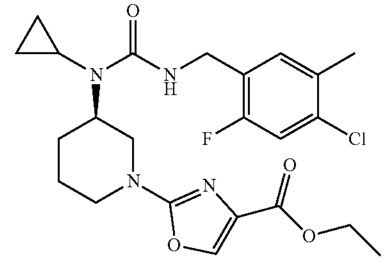 [SMILES: CCOC(=O)c1coc(N2CCC[C@@H](N(C(=O)NCc3cc(C)c(Cl)cc3F)C3CC3)C2)n1] ethyl 2-[(3R)-3-(1-cyclopropyl{[(4-chloro-2-fluoro-5-methylphenyl)methyl]carbamoyl}amino)piperidin-1-yl]-1,3-oxazole-4-carboxylate | LC-MS: 479 m/z (M + H). 1H NMR (400 MHz, MeOD) δ 7.99 (s, 1H), 7.25 (d, J = 8.0 Hz, 1H), 7.13 (d, J = 9.8 Hz, 1H), 4.38 (s, 2H), 4.30 (q, J = 7.1 Hz, 2H), 4.03 (dd, J = 12.4, 4.0 Hz, 2H), 3.82-3.69 (m, 1H), 3.46-3.37 (m, 1H), 2.97-2.87 (m, 1H), 2.61-2.51 (m, 1H), 2.32 (s, 3H), 2.22-2.10 (m, 1H), 1.95-1.82 (m, 2H), 1.72-1.58 (m, 1H), 1.36-1.29 (m, 3H), 0.99-0.89 (m, 2H), 0.81-0.72 (m, 2H). |
| 289 | 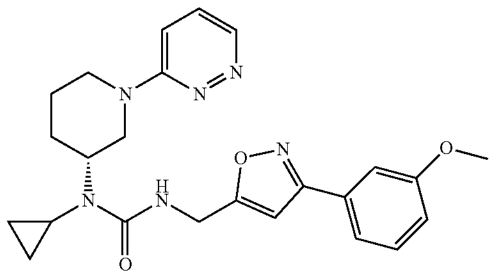 [SMILES: COc1cccc(-c2cc(CNC(=O)N(C3CC3)[C@@H]3CCCN(c4cccnn4)C3)on2)c1] 1-cyclopropyl-3-{[3-(3-methoxyphenyl)-1,2-oxazol-5-yl]methyl}-1-[(3R)-1-(pyridazin-3-yl)piperidin-3-yl]urea | LC-MS: 449 m/z (M + H). 1H NMR (400 MHz, MeOD) δ 8.42 (dd, J = 4.3, 1.0 Hz, 1H), 7.42-7.34 (m, 4H), 7.29 (dd, J = 9.4, 1.2 Hz, 1H), 7.16 (t, J = 5.9 Hz, 1H), 7.06-6.99 (m, 1H), 6.66 (s, 1H), 4.55 (d, J = 5.7 Hz, 2H), 4.42-4.30 (m, 2H), 3.84 (s, 3H), 3.78 (ddd, J = 15.8, 7.9, 4.0 Hz, 1H), 3.36-3.32 (m, 1H), 2.89 (td, J = 13.0, 2.7 Hz, 1H), 2.62-2.54 (m, 1H), 2.25 (td, J = 12.5, 4.1 Hz, 1H), 1.92 (dd, J = 46.8, 12.7 Hz, 2H), 1.70-1.55 (m, 1H), 1.03-0.95 (m, 2H), 0.84 (dd, J = 7.9, 4.4 Hz, 2H). |

General Procedure M:

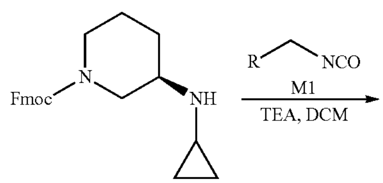

-continued

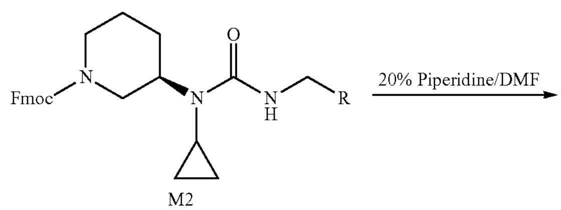

M2

-continued

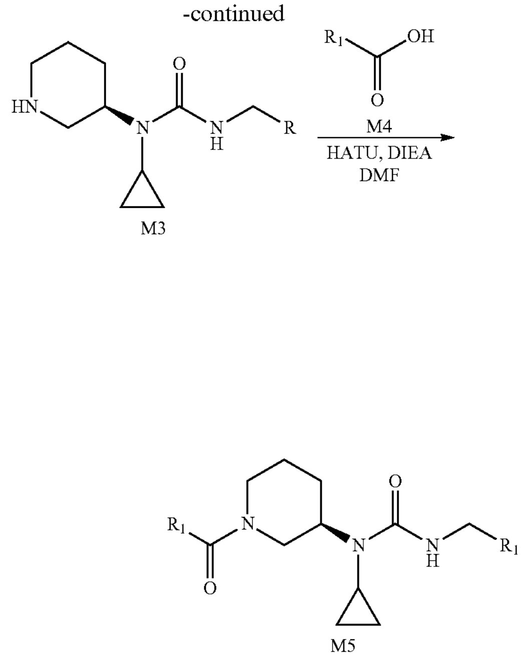

M3

M5

Step 1

To a solution of compound (9H-fluoren-9-yl)methyl (R)-3-(cyclopropylamino)piperidine-1-carboxylate (1 eq.) and TEA (3 eq.) in anhydrous DCM was added a solution of compound M1 (1 eq.) in anhydrous DCM at 0° C. dropwise under $N_2$ atmosphere. The resulting mixture was stirred at 0° C. for 1 hour under $N_2$ atmosphere. Then the mixture was diluted with water and extracted with EtOAc twice. The combined organic layers were separated, washed with brine, dried over anhydrous $Na_2SO_4$, filtered and concentrated to dryness. The residue was purified via flash column chromatography (eluted with Heptane/Ethyl Acetate) to give compound M2.

Step 2

M2 (1 eq) was dissolved in 20% Piperidine/DMF (0.1M) and the reaction mixture was stirred at r.t. for 1-2 hours. The reaction mixture was then concentrated under vacuum and the crude product was purified by flash column chromatography using DCM/DCM:7N NH4 MeOH (10:0 to 0:10) to afford product M3.

Step 3

M3 (1 eq), the appropriate carboxylic acid M4 (1.2 eqs) and HATU (1.3 eqs) were dissolved in DMF (0.1M), then DIEA (2 eqs) was added and the reaction was stirred at r.t. until full conversion. Water was added and the reaction mixture was extracted with DCM twice. The combined organic layers were dried over anhydrous $Na_2SO_4$, filtrated and concentrated under vacuum. The crude product was purified by prep HPLC to give pure product M5.

Synthesis of 1-cyclopropyl-1-[(3R)-1-(2-hydroxyacetyl)piperidin-3-yl]-3-[(3-phenyl-1,2-oxazol-5-yl)methyl]urea, Example 290

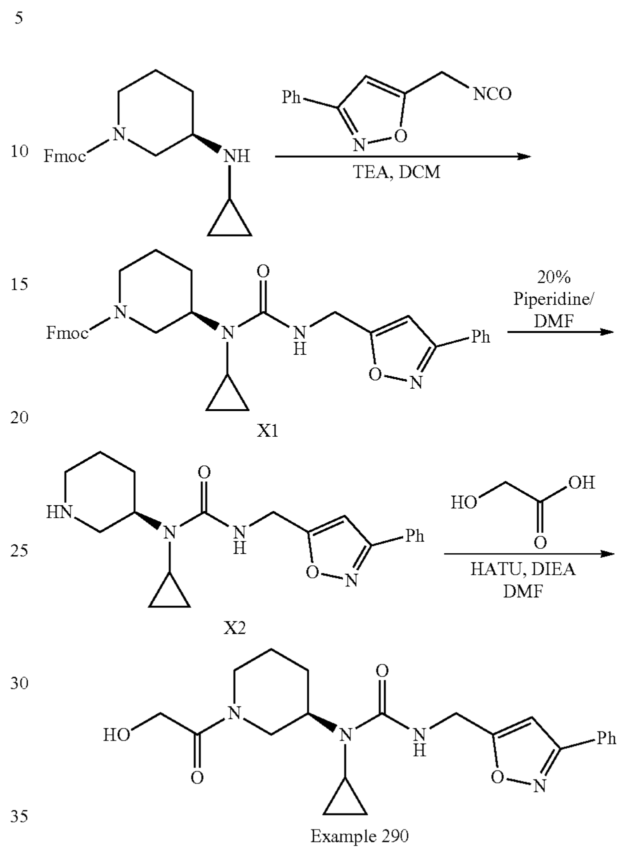

X1

X2

Example 290

To a solution of (9H-fluoren-9-yl)methyl (R)-3-(cyclopropylamino)piperidine-1-carboxylate (400 mg, 1.10 mmol) and TEA (0.460 mL, 3.30 mmol.) in anhydrous DCM (11 mL) was added a solution of 5-(isocyanatomethyl)-3-phenylisoxazole (220 mg, 1.10 mmol) in anhydrous DCM (5.5 mL) at 0° C. dropwise under $N_2$ atmosphere. The resulting mixture was stirred at 0° C. for 1 hour under $N_2$ atmosphere. Then the mixture was diluted with water and extracted with EtOAc twice. The combined organic layers were separated, washed with brine, dried over anhydrous $Na_2SO_4$, filtered and concentrated to dryness. The residue was purified via flash column chromatography (eluted with Heptane/Ethyl Acetate) to give X1 (280 mg, 45% yield). X1 (280 mg, 0.498 mmol) was dissolved in 20% Piperidine/DMF (4.98 mL) and the reaction mixture was stirred at r.t. for 1 hour. The reaction mixture was then concentrated under vacuum and the crude product was purified by flash column chromatography using DCM/DCM:7N NH4 MeOH (10/0 to 0/10) to afford X2 (150 mg, 88% yield) X2 (20 mg, 0.06 mmol), 2-hydroxyacetic acid (5.4 mg, 0.072 mmol) and HATU (29 mg, 0.076 mmol) were dissolved in DMF (0.56 mL), then DIEA (21 uL, 0.12 mmol) was added and the reaction was stirred at r.t. for 5 minutes. Water was added and the reaction mixture was extracted with DCM twice. The combined organic layers were dried over anhydrous $Na_2SO_4$, filtrated and concentrated under vacuum. The crude product was purified by prep HPLC to give Example 290 (11 mg, 47% yield) as a white powder. LC/MS (ESI) m/z: 399.1 $(M+H)^+$.

Examples below were prepared by General Procedure M

| Example | Structure/name | Data |
|---|---|---|
| 291 | 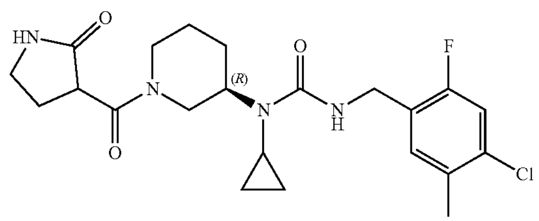 1-[(4-chloro-2-fluoro-5-methylphenyl)methyl]-3-cyclopropyl-3-[(3R)-1-(2-oxopyrrolidine-3-carbonyl)piperidin-3-yl]urea | LC-MS: m/z 451 (M + H). 1H NMR (400 MHz, MeOD) δ 7.28-7.20 (m, 1H), 7.13 (dd, J = 9.8, 3.8 Hz, 1H), 6.91 (s, 1H), 6.83 (dd, J = 11.8, 5.9 Hz, 1H), 4.53 (d, J = 12.3 Hz, 1H), 4.45-4.31 (m, 2H), 4.12 (dd, J = 25.2, 12.2 Hz, 1H), 4.01-3.88 (m, 1H), 3.87-3.59 (m, 1H), 3.59-3.32 (m, 3H), 3.26-2.94 (m, 1H), 2.64-2.54 (m, 1H), 2.51-2.44 (m, 1H), 2.38-2.14 (m, 5H), 1.99-1.77 (m, 2H), 1.62-1.37 (m, 1H), 1.03-0.88 (m, 2H), 0.87-0.60 (m, 2H). |
| 292 | 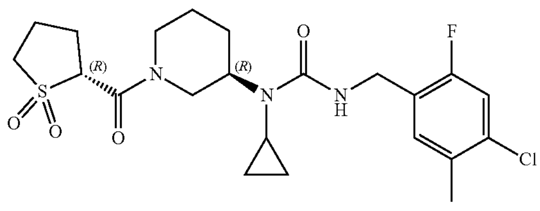 1-[(4-chloro-2-fluoro-5-methylphenyl)methyl]-3-cyclopropyl-3-[(3R)-1-[(2R)-1,1-dioxo-1$\lambda^6$-thiolane-2-carbonyl]piperidin-3-yl]urea | LC-MS: m/z 486 (M + H). 1H NMR (400 MHz, MeOD) δ 7.27-7.21 (m, 1H), 7.13 (dd, J = 9.8, 2.5 Hz, 1H), 4.54 (dd, J = 39.0, 7.8 Hz, 2H), 4.44-4.33 (m, 2H), 4.12 (d, J = 12.9 Hz, 1H), 3.88-3.81 (m, 1H), 3.51-3.44 (m, 1H), 3.26 (s, 1H), 3.22-3.01 (m, 3H), 2.74-2.43 (m, 3H), 2.32 (s, 3H), 2.30-2.21 (m, 2H), 2.18-2.12 (m, 1H), 2.01 (s, 1H), 1.90-1.77 (m, 2H), 1.55-1.44 (m, 1H), 0.99-0.89 (m, 2H), 0.82-0.68 (m, 2H). |
| 293 | 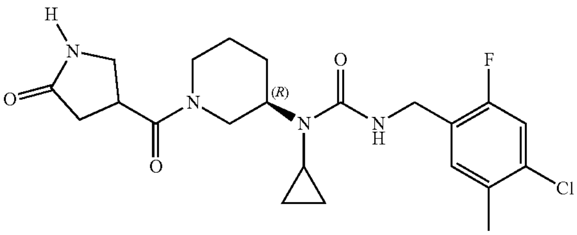 1-[(4-chloro-2-fluoro-5-methylphenyl)methyl]-3-cyclopropyl-3-[(3R)-1-(5-oxopyrrolidine-3-carbonyl)piperidin-3-yl]urea | LC-MS: m/z 451 (M + H). 1H NMR (400 MHz, MeOD) δ 7.29-7.21 (m, 1H), 7.13 (dd, J = 9.8, 4.6 Hz, 1H), 4.49 (t, J = 14.4 Hz, 1H), 4.44-4.32 (m, 2H), 3.91 (t, J = 14.0 Hz, 1H), 3.85-3.65 (m, 2H), 3.60-3.42 (m, 2H), 3.30-3.21 (m, 1H), 3.19-3.08 (m, 1H), 3.07-2.93 (m, 1H), 2.68-2.58 (m, 1H), 2.58-2.50 (m, 2H), 2.50-2.44 (m, 1H), 2.32 (s, 3H), 2.19 (dtd, J = 8.6, 6.8, 4.5 Hz, 1H), 2.03 (s, 1H), 2.02-1.79 (m, 2H), 1.57-1.43 (m, 1H), 1.03-0.87 (m, 2H), 0.86-0.64 (m, 2H). |
| 294 | 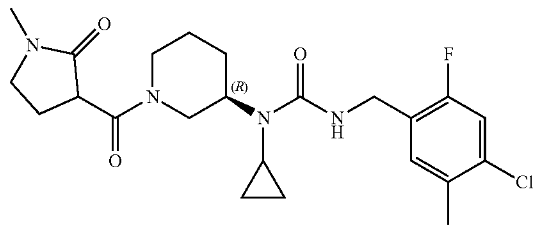 1-[(4-chloro-2-fluoro-5-methylphenyl)methyl]-3-cyclopropyl-3-[(3R)-1-(1-methyl-2-oxopyrrolidine-3-carbonyl)piperidin-3-yl]urea | LC-MS: m/z 465 (M + H). 1H NMR (400 MHz, MeOD) δ 7.24 (t, J = 7.0 Hz, 1H), 7.13 (dd, J = 9.8, 3.2 Hz, 1H), 4.51 (d, J = 12.9 Hz, 1H), 4.41-4.31 (m, 2H), 4.15-3.92 (m, 2H), 3.78 (d, J = 25.7 Hz, 1H), 3.64-3.37 (m, 3H), 3.21-2.93 (m, 1H), 2.87-2.80 (m, 3H), 2.59-2.46 (m, 2H), 2.42-2.34 (m, 1H), 2.31 (s, 3H), 2.28-2.14 (m, 2H), 1.95-1.77 (m, 2H), 1.64-1.35 (m, 1H), 0.98-0.67 (m, 4H). |

-continued

| Example | Structure/name | Data |
|---|---|---|
| 295 | 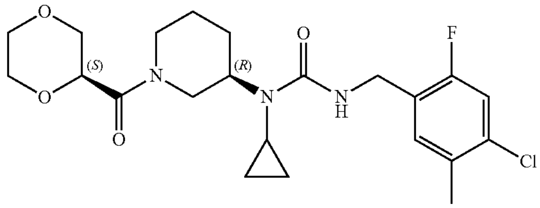 1-[(4-chloro-2-fluoro-5-methylphenyl)methyl]-3-cyclopropyl-3-[(3R)-1-[(2S)-1,4-dioxane-2-carbonyl]piperidin-3-yl]urea | LC-MS: m/z 454 (M + H). 1H NMR (400 MHz, MeOD) δ 7.29-7.21 (m, 1H), 7.13 (dd, J = 9.8, 3.8 Hz, 1H), 4.48-4.33 (m, 4H), 3.98 (dd, J = 44.7, 12.1 Hz, 1H), 3.86-3.74 (m, 3H), 3.73-3.67 (m, 2H), 3.66-3.55 (m, 2H), 3.51 (dd, J = 11.4, 6.5 Hz, 1H), 3.17-2.92 (m, 1H), 2.60-2.52 (m, 1H), 2.48 (dd, J = 13.0, 2.7 Hz, 1H), 2.32 (s, 3H), 2.30-2.17 (m, 1H), 1.94-1.77 (m, 2H), 1.60-1.37 (m, 1H), 0.99-0.87 (m, 2H), 0.83-0.68 (m, 2H). |
| 296 | 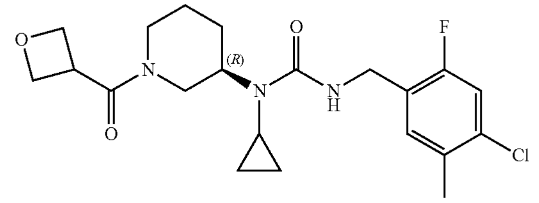 1-[(4-chloro-2-fluoro-5-methylphenyl)methyl]-3-cyclopropyl-3-[(3R)-1-(oxetane-3-carbonyl)piperidin-3-yl]urea | LC-MS: m/z 424 (M + H). 1H NMR (400 MHz, MeOD) 8 7.24 (t, J = 8.1 Hz, 1H), 7.13 (dd, J = 9.8, 5.5 Hz, 1H), 4.84-4.76 (m, 4H), 4.53-4.35 (m, 3H), 4.21-4.14 (m, 1H), 3.71-3.61 (m, 1H), 3.51 (td, J = 11.8, 5.7 Hz, 1H), 3.36 (dd, J = 17.0, 8.4 Hz, 1H), 3.15 (dd, J = 23.8, 12.1 Hz, 1H), 2.90 (td, J = 13.3, 2.7 Hz, 1H), 2.57-2.45 (m, 2H), 2.32 (d, J = 3.2 Hz, 3H), 2.14 (ddd, J = 23.0, 13.2, 3.5 Hz, 1H), 1.97-1.77 (m, 2H), 1.53-1.39 (m, 1H), 0.94 (ddd, J = 16.0, 8.7, 4.3 Hz, 2H), 0.81-0.63 (m, 2H). |
| 297 | 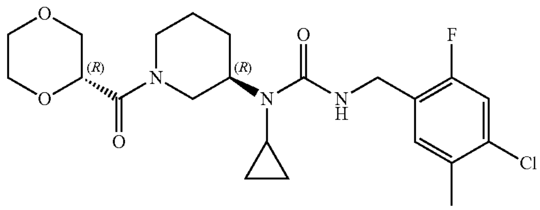 1-[(4-chloro-2-fluoro-5-methylphenyl)methyl]-3-cyclopropyl-3-[(3R)-1-[(2R)-1,4-dioxane-2-carbonyl]piperidin-3-yl]urea | LC-MS: m/z 454 (M + H). 1H NMR (400 MHz, CDCl3) δ 7.21 (dd, J = 17.7, 8.0 Hz, 1H), 7.08 (dd, J = 9.6, 6.9 Hz, 1H), 5.80-5.64 (m, 1H), 4.58-4.24 (m, 4H), 4.06-3.59 (m, 8H), 3.37-3.17 (m, 2H), 2.91 (t, J = 11.7 Hz, 1H), 2.56-2.33 (m, 2H), 2.31 (d, J = 2.6 Hz, 3H), 1.96-1.75 (m, 2H), 1.59-1.47 (m, 1H), 0.94-0.66 (m, 4H). |
| 298 | 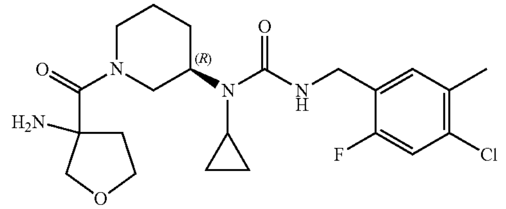 1-[(3R)-1-(3-aminooxolane-3-carbonyl)piperidin-3-yl]-3-[(4-chloro-2-fluoro-5-methylphenyl)methyl]-1-cyclopropylurea | LC-MS: m/z 453.1 (M + H). 1H NMR (400 MHz, MeOD) δ 7.24 (d, J = 8.0 Hz, 1H), 7.13 (d, J = 9.8 Hz, 1H), 4.53-4.22 (m, 4H), 4.12 (dd, J = 19.6, 9.3 Hz, 1H), 4.01-3.74 (m, 3H), 3.62 (dd, J = 9.2, 4.2 Hz, 2H), 3.16 (dd, J = 24.0, 7.3 Hz, 1H), 2.54-2.38 (m, 2H), 2.32 (s, 3H), 2.25-2.15 (m, 1H), 2.00-1.77 (m, 3H), 1.53 (d, J = 11.4 Hz, 1H), 0.94 (d, J = 5.8 Hz, 2H), 0.75 (s, 2H). |

-continued

| Example | Structure/name | Data |
|---|---|---|
| 299 | 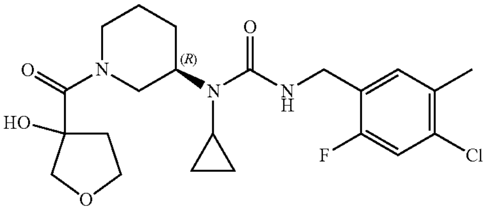 3-[(4-chloro-2-fluoro-5-methylphenyl)methyl]-1-cyclopropyl-1-[(3R)-1-(3-hydroxyoxolane-3-carbonyl)piperidin-3-yl]urea | LC-MS: m/z 454 (M + H). 1H NMR (400 MHz, MeOD) δ 7.23 (d, J = 8.0 Hz, 1H), 7.13 (d, J = 9.8 Hz, 1H), 4.42 (d, J = 14.8 Hz, 2H), 4.37 (s, 2H), 4.24-4.01 (m, 1H), 4.00-3.82 (m, 2H), 3.77 (dd, J = 13.5, 9.6 Hz, 1H), 3.70-3.32 (m, 2H), 3.22-2.79 (m, 1H), 2.71-2.50 (m, 2H), 2.32 (s, 3H), 2.26-1.97 (m, 2H), 1.85 (d, J = 48.8 Hz, 2H), 1.49 (s, 1H), 1.01-0.88 (m, 2H), 0.83-0.68 (m, 2H). |
| 300 | 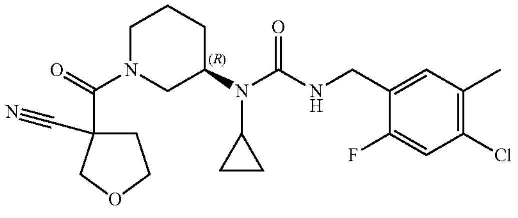 3-[(4-chloro-2-fluoro-5-methylphenyl)methyl]-1-[(3R)-1-(3-cyanooxolane-3-carbonyl)piperidin-3-yl]-1-cyclopropylurea | LC-MS: m/z 463 (M + H). 1H NMR (400 MHz, CDCl3) δ 7.19 (d, J = 8.0 Hz, 1H), 7.12-7.05 (m, 1H), 5.76 (d, J = 29.9 Hz, 1H), 4.59-4.45 (m, 1H), 4.41-4.22 (m, 4H), 3.98 (ddd, J = 27.0, 12.5, 4.7 Hz, 3H), 3.68 (t, J = 11.1 Hz, 2H), 3.49-3.28 (m, 1H), 3.10 (d, J = 13.1 Hz, 1H), 2.90-2.68 (m, 1H), 2.58-2.47 (m, 2H), 2.29 (d, J = 25.8 Hz, 4H), 1.93-1.82 (m, 2H), 1.57-1.47 (m, 1H), 0.87 (dd, J = 13.1, 6.8 Hz, 3H), 0.76 (d, J = 19.4 Hz, 1H). |
| 301 | 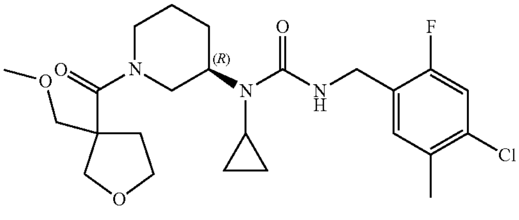 3-[(4-chloro-2-fluoro-5-methylphenyl)methyl]-1-cyclopropyl-1-[(3R)-1-[3-(methoxymethyl)oxolane-3-carbonyl]piperidin-3-yl]urea | LC-MS: m/z 482 (M + H). 1H NMR (400 MHz, CDCl3) δ 7.20 (dd, J = 8.0, 2.6 Hz, 1H), 7.08 (d, J = 9.7 Hz, 1H), 5.73 (t, J = 5.6 Hz, 1H), 4.39 (d, J = 5.9 Hz, 2H), 4.04-3.75 (m, 5H), 3.56 (d, J = 8.0 Hz, 1H), 3.49 (q, J = 8.9 Hz, 2H), 3.35 (d, J = 4.6 Hz, 3H), 3.23 (t, J = 11.3 Hz, 1H), 2.46 (s, 1H), 2.31 (s, 3H), 2.29-2.14 (m, 2H), 1.99 (dt, J = 13.3, 8.1 Hz, 1H), 1.86 (d, J = 11.6 Hz, 1H), 1.77 (dd, J = 13.6, 2.6 Hz, 1H), 1.62 (s, 3H), 1.53-1.42 (m, 1H), 0.88 (d, J = 6.0 Hz, 2H), 0.75 (d, J = 12.6 Hz, 2H). |

-continued

| Example | Structure/name | Data |
|---|---|---|
| 302 | 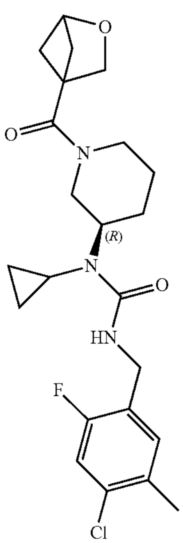 3-[(4-chloro-2-fluoro-5-methylphenyl)methyl]-1-cyclopropyl-1-[(3R)-1-{2-oxabicyclo[2.1.1]hexane-4-carbonyl}piperidin-3-yl]urea | LC-MS: m/z 450.1 (M + H). 1H NMR (400 MHz, MeOD) δ 7.28-7.20 (m, 1H), 7.13 (d, J = 9.8 Hz, 1H), 4.54-4.30 (m, 4H), 3.86 (dd, J = 33.0, 5.6 Hz, 1H), 3.78-3.46 (m, 3H), 3.28 (d, J = 10.9 Hz, 1H), 3.07 (dt, J = 24.5, 12.7 Hz, 1H), 2.56-2.47 (m, 1H), 2.31 (s, 3H), 2.24-2.07 (m, 3H), 1.97-1.76 (m, 4H), 1.48 (qd, J = 13.3, 6.6 Hz, 1H), 1.00-0.87 (m, 2H), 0.73 (ddd, J = 25.6, 15.2, 8.2 Hz, 2H). |
| 303 | 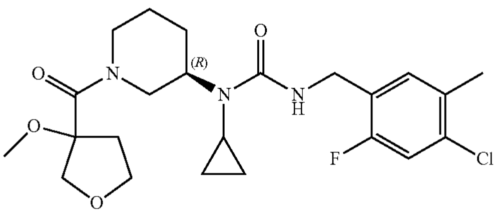 3-[(4-chloro-2-fluoro-5-methylphenyl)methyl]-1-cyclopropyl-1-[(3R)-1-(3-methoxyoxolane-3-carbonyl)piperidin-3-yl]urea | LC-MS: m/z 468 (M + H). 1H NMR (400 MHz, MeOD) δ 7.24 (d, J = 8.1 Hz, 1H), 7.13 (d, J = 9.7 Hz, 1H), 6.85 (s, 1H), 4.49 (t, J = 13.0 Hz, 1H), 4.38 (s, 3H), 4.06 (d, J = 9.8 Hz, 1H), 3.97-3.85 (m, 2H), 3.82 (dt, J = 8.2, 4.1 Hz, 1H), 3.51 (dd, J = 47.8, 10.0 Hz, 1H), 3.26-3.22 (m, 3H), 3.16-2.89 (m, 1H), 2.61-2.43 (m, 3H), 2.32 (s, 3H), 2.21 (dd, J = 16.7, 11.4 Hz, 2H), 1.94-1.81 (m, 2H), 1.58-1.44 (m, 1H), 0.98-0.90 (m, 2H), 0.75 (s, 2H). |
| 304 | 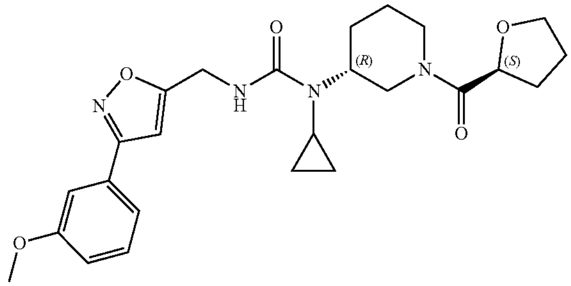 1-cyclopropyl-3-{[3-(3-methoxyphenyl)-1,2-oxazol-5-yl]methyl}-1-[(3R)-1-[(2S)-oxolane-2-carbonyl]piperidin-3-yl]urea | LC-MS: m/z 469 (M + H). 1H NMR (400 MHz, MeOD) δ 7.38 (dd, J = 4.4, 1.8 Hz, 3H), 7.21 (s, 1H), 7.05-7.00 (m, 1H), 6.65 (d, J = 6.9 Hz, 1H), 4.69-4.34 (m, 4H), 3.92 (ddd, J = 21.4, 13.8, 6.4 Hz, 3H), 3.84 (d, J = 6.6 Hz, 3H), 3.79 (d, J = 6.1 Hz, 1H), 3.56-3.32 (m, 1H), 3.08 (t, J = 47.9 Hz, 1H), 2.51 (dd, J = 6.8, 2.9 Hz, 1H), 2.32-2.14 (m, 2H), 2.05-1.84 (m, 5H), 1.63-1.43 (m, 1H), 1.06-0.94 (m, 2H), 0.85-0.73 (m, 2H). |

-continued

| Example | Structure/name | Data |
|---|---|---|
| 305 | 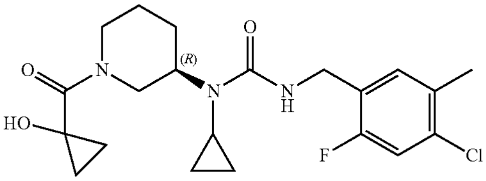 3-[(4-chloro-2-fluoro-5-methylphenyl)methyl]-1-cyclopropyl-1-[(3R)-1-(1-hydroxycyclopropanecarbonyl)piperidin-3-yl]urea | LC-MS: m/z 424 (M + H). 1H NMR (400 MHz, CDCl3) δ 7.21 (d, J = 8.0 Hz, 1H), 7.07 (d, J = 9.7 Hz, 1H), 5.74 (t, J = 5.8 Hz, 1H), 4.48 (t, J = 13.6 Hz, 2H), 4.39 (d, J = 5.9 Hz, 2H), 3.75 (s, 1H), 3.10 (t, J = 11.8 Hz, 1H), 2.61 (s, 1H), 2.45-2.38 (m, 1H), 2.31 (s, 3H), 2.23-2.12 (m, 1H), 1.97 (d, J = 11.8 Hz, 1H), 1.81 (d, J = 13.5 Hz, 1H), 1.58 (dt, J = 13.2, 4.1 Hz, 1H), 1.15 (d, J = 7.4 Hz, 1H), 1.00-0.86 (m, 5H), 0.75 (t, J = 4.3 Hz, 2H). |
| 306 | 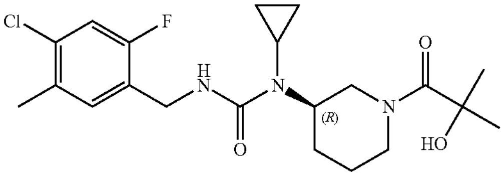 3-[(4-chloro-2-fluoro-5-methylphenyl)methyl]-1-cyclopropyl-1-[(3R)-1-(2-hydroxy-2-methylpropanoyl)piperidin-3-yl]urea | LC-MS: m/z 426 (M + H). 1H NMR (400 MHz, CDCl3) δ 7.20 (d, J = 8.0 Hz, 1H), 7.08 (d, J = 9.7 Hz, 1H), 5.74 (t, J = 5.7 Hz, 1H), 4.80-4.10 (m, 5H), 3.45 (dd, J = 78.1, 29.3 Hz, 2H), 2.46 (s, 1H), 2.31 (s, 3H), 2.25 (d, J = 11.1 Hz, 1H), 1.93-1.78 (m, 3H), 1.53 (s, 3H), 1.48 (s, 3H), 0.89 (t, J = 5.8 Hz, 2H), 0.74 (s, 2H). |
| 307 | 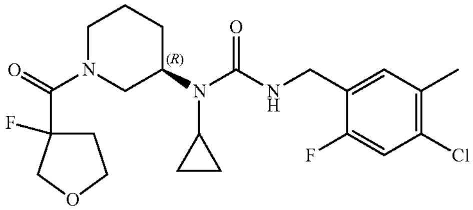 3-[(4-chloro-2-fluoro-5-methylphenyl)methyl]-1-cyclopropyl-1-[(3R)-1-(3-fluorooxolane-3-carbonyl)piperidin-3-yl]urea | LC-MS: m/z 456 (M + H). 1H NMR (400 MHz, MeOD) δ 7.24 (d, J = 8.0 Hz, 1H), 7.13 (d, J = 9.8 Hz, 1H), 6.85 (s, 1H), 4.41 (dd, J = 27.0, 12.4 Hz, 3H), 4.24-3.87 (m, 5H), 3.79-3.40 (m, 2H), 3.15 (dd, J = 49.8, 38.8 Hz, 1H), 2.76-2.43 (m, 3H), 2.32 (s, 3H), 2.23 (d, J = 13.1 Hz, 1H), 1.99-1.79 (m, 2H), 1.51 (d, J = 13.4 Hz, 1H), 0.94 (s, 2H), 0.74 (d, J = 10.6 Hz, 2H). |
| 308 | 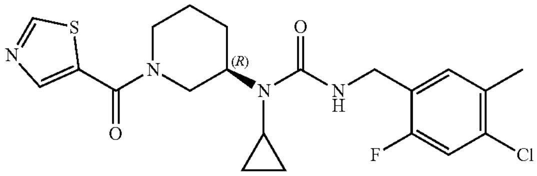 3-[(4-chloro-2-fluoro-5-methylphenyl)methyl]-1-cyclopropyl-1-[(3R)-1-(1,3-thiazole-5-carbonyl)piperidin-3-yl]urea | LC-MS: m/z 451 (M + H). 1H NMR (400 MHz, MeOD) δ 9.11 (s, 1H), 8.25 (s, 1H), 7.23 (d, J = 8.0 Hz, 1H), 7.12 (d, J = 9.8 Hz, 1H), 6.85 (s, 1H), 4.61-4.02 (m, 4H), 3.85-3.57 (m, 1H), 3.50-3.35 (m, 1H), 3.11-2.67 (m, 1H), 2.60-2.44 (m, 1H), 2.32-2.21 (m, 4H), 2.02-1.82 (m, 2H), 1.61 (dd, J = 26.3, 13.2 Hz, 1H), 0.94 (d, J = 6.4 Hz, 2H), 0.81-0.56 (m, 2H). |

-continued

| Example | Structure/name | Data |
|---|---|---|
| 309 | 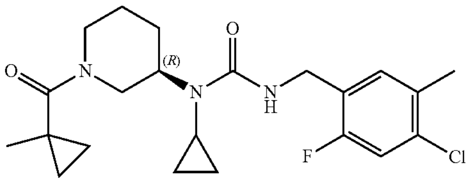<br>3-[(4-chloro-2-fluoro-5-methylphenyl)methyl]-1-cyclopropyl-1-[(3R)-1-(1-methylcyclopropanecarbonyl) piperidin-3-yl]urea | LC-MS: m/z 422 (M + H). 1H NMR (400 MHz, MeOD) δ 7.24 (d, J = 8.0 Hz, 1H), 7.13 (d, J = 9.8 Hz, 1H), 4.36 (t, J = 9.9 Hz, 4H), 3.71-3.54 (m, 1H), 3.29-3.02 (m, 1H), 2.53 (ddd, J = 10.4, 6.7, 3.9 Hz, 1H), 2.32 (s, 3H), 2.19 (qd, J = 12.6, 4.1 Hz, 1H), 1.87 (dd, J = 28.7, 12.7 Hz, 2H), 1.57-1.41 (m, 1H), 1.38-1.12 (m, 4H), 0.98-0.83 (m, 4H), 0.75 (s, 2H), 0.60 (d, J = 1.4 Hz, 2H). |
| 310 | 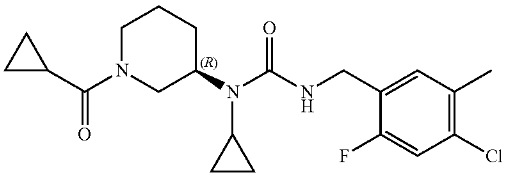<br>3-[(4-chloro-2-fluoro-5-methylphenyl)methyl]-1-[(3R)-1-cyclopropanecarbonylpiperidin-3-yl]-1-cyclopropylurea | LC-MS: m/z 408 (M + H). 1H NMR (400 MHz, MeOD) δ 7.32-7.19 (m, 1H), 7.13 (d, J = 9.6 Hz, 1H), 4.44 (d, J = 9.3 Hz, 1H), 4.38 (d, J = 8.7 Hz, 2H), 4.32-4.22 (m, 1H), 3.75 (d, J = 11.4 Hz, 1H), 3.56-3.35 (m, 1H), 3.20-2.98 (m, 1H), 2.52 (d, J = 11.0 Hz, 2H), 2.31 (s, 3H), 2.26-2.14 (m, 1H), 2.01-1.75 (m, 3H), 1.63-1.40 (m, 1H), 1.02-0.90 (m, 2H), 0.88-0.75 (m, 5H), 0.72 (s, 1H). |
| 311 | 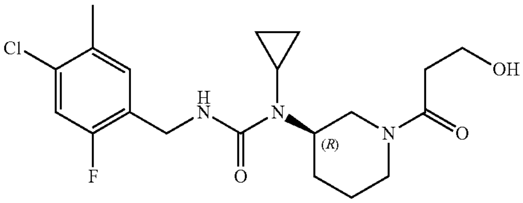<br>3-[(4-chloro-2-fluoro-5-methylphenyl)methyl]-1-cyclopropyl-1-[(3R)-1-(3-hydroxypropanoyl)piperidin-3-yl]urea | LC-MS: m/z 412.1 (M + H). 1H NMR (400 MHz, MeOD) δ 7.24 (t, J = 7.6 Hz, 1H), 7.13 (dd, J = 9.8, 3.7 Hz, 1H), 6.85 (dt, J = 11.7, 5.6 Hz, 1H), 4.51 (t, J = 10.1 Hz, 1H), 4.36 (dd, J = 9.8, 5.9 Hz, 2H), 3.93 (t, J = 11.6 Hz, 1H), 3.79 (dt, J = 16.1, 5.4 Hz, 2H), 3.75-3.44 (m, 1H), 3.38-3.31 (m, 1H), 3.16-2.90 (m, 1H), 2.79-2.61 (m, 1H), 2.59-2.49 (m, 2H), 2.32 (s, 3H), 2.26-2.09 (m, 1H), 1.99-1.74 (m, 2H), 1.63-1.41 (m, 1H), 0.94 (ddd, J = 16.8, 10.1, 4.6 Hz, 2H), 0.74 (dddd, J = 12.3, 8.4, 5.6, 2.2 Hz, 2H). |
| 312 | 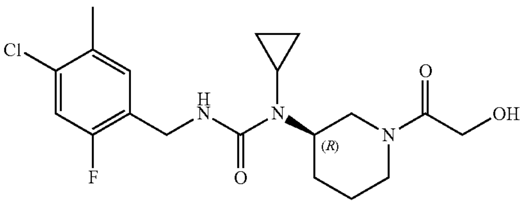<br>3-[(4-chloro-2-fluoro-5-methylphenyl)methyl]-1-cyclopropyl-1-[(3R)-1-(2-hydroxyacetyl)piperidin-3-yl]urea | LC-MS: m/z 398 (M + H). 1H NMR (400 MHz, MeOD) δ 7.28-7.21 (m, 1H), 7.13 (d, J = 9.6 Hz, 1H), 4.59-4.33 (m, 3H), 4.31-4.13 (m, 2H), 3.73-3.48 (m, 2H), 3.26 (d, J = 12.5 Hz, 1H), 3.17-2.86 (m, 1H), 2.57-2.49 (m, 1H), 2.32 (s, 3H), 2.18 (dd, J = 24.7, 14.2 Hz, 1H), 1.99-1.76 (m, 2H), 1.58-1.42 (m, 1H), 1.01-0.84 (m, 2H), 0.75 (dd, J = 21.6, 8.8 Hz, 2H). |

-continued

| Example | Structure/name | Data |
|---|---|---|
| 313 | 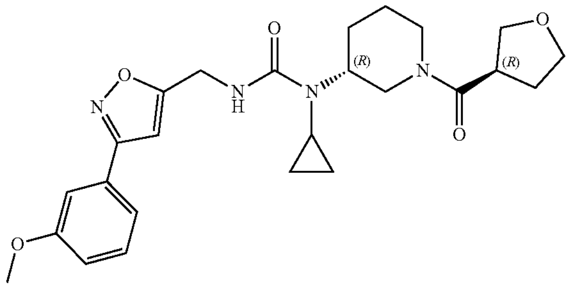 1-cyclopropyl-3-{[3-(3-methoxyphenyl)-1,2-oxazol-5-yl]methyl}-1-[(3R)-1-[(3R)-oxolane-3-carbonyl]piperidin-3-yl]urea | LC-MS: m/z 469 (M + H). 1H NMR (400 MHz, MeOD) δ 7.44-7.33 (m, 3H), 7.22-7.07 (m, 1H), 7.03 (ddd, J = 6.5, 4.2, 2.6 Hz, 1H), 6.66 (d, J = 7.7 Hz, 1H), 4.57-4.48 (m, 4H), 4.04-3.86 (m, 3H), 3.85 (s, 3H), 3.84-3.71 (m, 3H), 3.55-3.44 (m, 1H), 3.43-3.32 (m, 1H), 3.05 (ddd, J = 24.4, 18.5, 11.6 Hz, 1H), 2.60-2.52 (m, 1H), 2.25-2.05 (m, 3H), 1.99-1.78 (m, 2H), 1.55-1.41 (m, 1H), 1.03-0.91 (m, 2H), 0.87-0.72 (m, 2H). |
| 314 | 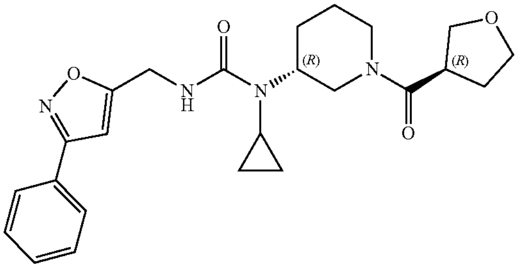 1-cyclopropyl-1-[(3R)-1-[(3R)-oxolane-3-carbonyl]piperidin-3-yl]-3-[(3-phenyl-1,2-oxazol-5-yl)methyl]urea | LC-MS: m/z 439 (M + H). 1H NMR (400 MHz, CDCl3) δ 7.79 (dd, J = 6.5, 2.9 Hz, 2H), 7.48-7.42 (m, 3H), 6.50 (s, 1H), 5.87 (s, 1H), 4.60 (d, J = 4.4 Hz, 2H), 3.97 (d, J = 8.1 Hz, 1H), 3.92-3.79 (m, 4H), 3.29-3.15 (m, 2H), 2.68-2.01 (m, 5H), 1.92 (s, 1H), 1.82 (d, J = 13.2 Hz, 1H), 1.68 (s, 2H), 1.48 (s, 1H), 0.88 (d, J = 56.6 Hz, 4H). |
| 314A | 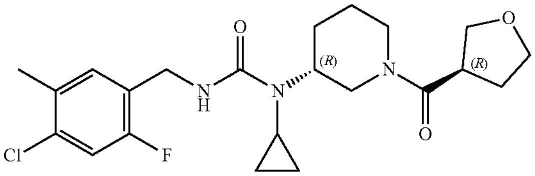 1-[(4-chloro-2-fluoro-5-methylphenyl)methyl]-3-cyclopropyl-3-[(3R)-1-[(3R)-oxolane-3-carbonyl]piperidin-3-yl]urea | LC-MS: m/z 438 (M + H). 1H NMR (400 MHz, MeOD) δ 7.24 (t, J = 8.5 Hz, 1H), 7.13 (dd, J = 9.8, 4.8 Hz, 1H), 6.86 (d, J = 23.0 Hz, 1H), 4.42 (dt, J = 26.8, 12.8 Hz, 3H), 4.04-3.72 (m, 6H), 3.45 (dt, J = 14.7, 9.6 Hz, 2H), 3.27 (d, J = 12.4 Hz, 1H), 3.12 (t, J = 11.8 Hz, 1H), 2.99 (t, J = 12.1 Hz, 1H), 2.59-2.43 (m, 2H), 2.28 (d, J = 25.5 Hz, 3H), 2.22-2.00 (m, 3H), 1.99-1.78 (m, 2H), 1.55-1.35 (m, 1H), 1.04-0.84 (m, 2H), 0.82-0.60 (m, 2H). |
| 315 | 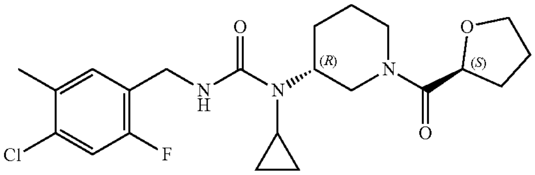 1-[(4-chloro-2-fluoro-5-methylphenyl)methyl]-3-cyclopropyl-3-[(3R)-1-[(2S)-oxolane-2-carbonyl]piperidin-3-yl]urea | LC-MS: m/z 438.1 (M + H). 1H NMR (400 MHz, MeOD) δ 7.24 (t, J = 7.9 Hz, 1H), 7.13 (dd, J = 9.8, 4.4 Hz, 1H), 6.85 (dt, J = 18.8, 5.7 Hz, 1H), 4.70 (dd, J = 9.8, 4.0 Hz, 1H), 4.52-4.32 (m, 3H), 4.0-3.87 (m, 2H), 3.86-3.73 (m, 2H), 3.48 (ddd, J = 15.6, 7.9, 3.9 Hz, 1H), 3.26 (s, 1H), 3.13 (t, J = 11.8 Hz, 1H), 2.99-2.85 (m, 1H), 2.61-2.45 (m, 2H), 2.32 (s, 3H), 2.28-2.11 (m, 2H), 2.05-1.79 (m, 5H), 1.62-1.40 (m, 1H), 1.00-0.86 (m, 2H), 0.84-0.64 (m, 2H). |

-continued

| Example | Structure/name | Data |
|---|---|---|
| 316 | 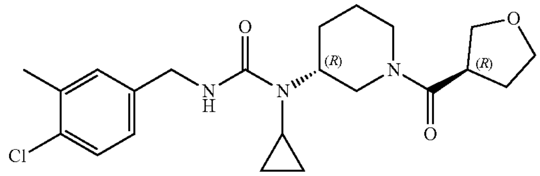 1-[(4-chloro-3-methylphenyl)methyl]-3-cyclopropyl-3-[(3R)-1-[(3R)-oxolane-3-carbonyl]piperidin-3-yl]urea | LC-MS: m/z 420 (M + H). 1H NMR (400 MHz, MeOD) δ 7.27 (dt, J = 14.1, 7.0 Hz, 1H), 7.21 (d, J = 6.9 Hz, 1H), 7.10 (dd, J = 10.9, 4.5 Hz, 1H), 6.91 (d, J = 29.3 Hz, 1H), 4.55-4.43 (m, 1H), 4.40-4.27 (m, 2H), 3.86 (dddd, J = 19.0, 17.4, 14.8, 11.4 Hz, 6H), 3.53-3.38 (m, 2H), 3.27 (d, J = 12.0 Hz, 1H), 3.13 (t, J = 11.9 Hz, 1H), 2.99 (t, J = 13.1 Hz, 1H), 2.57-2.46 (m, 2H), 2.34 (s, 3H), 2.25-2.04 (m, 3H), 2.01-1.80 (m, 2H), 1.55-1.37 (m, 1H), 0.98-0.86 (m, 2H), 0.83-0.61 (m, 2H). |

General Procedure N

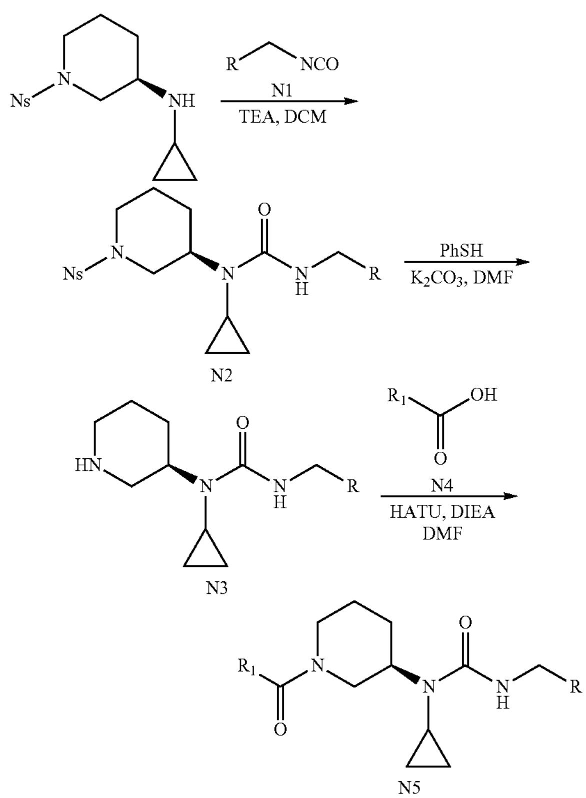

N2

N3

N5

To a solution of compound (R)—N-cyclopropyl-1-((2-nitrophenyl)sulfonyl)piperidin-3-amine (1 eq.) and TEA (3 eq.) in anhydrous DCM was added a solution of compound Ni (1 eq.) in anhydrous DCM at 0° C. dropwise under $N_2$ atmosphere. The resulting mixture was stirred at 0° C. for 1 hour under $N_2$ atmosphere. Then the mixture was diluted with water and extracted with EtOAc twice. The combined organic layers were separated, washed with brine, dried over anhydrous $Na_2SO_4$, filtered and concentrated to dryness. The residue was purified via flash column chromatography (eluted with Heptane/Ethyl Acetate) to give compound $N_2$. $N_2$ (1 eq) was dissolved in DMF (0.1M) followed by potassium carbonate (2 eqs) and thiophenol (1.5 eqs) and the reaction mixture was stirred at r.t. for 1-2 hours. 1 M HCl was added till pH 2-3 and the resulting mixture was extracted with DCM twice. The acidic solution was then brought to pH 10-11 by a carefully addition of NaOH 6N. The resulting basic solution was then extracted with DCM (×3). The combined organic layers were dried over $Na_2SO_4$, filtered and concentrated under vacuum. Crude $N_3$ was used for next step without any further purification. $N_3$ (1 eq), the appropriate carboxylic acid $N_4$ (1.2 eqs) and HATU (1.3 eqs) were dissolved in DMF (0.1M), then DIEA (2 eqs) was added and the reaction was stirred at r.t. until full conversion. Water was added and the reaction mixture was extracted with DCM twice. The combined organic layers were dried over anhydrous $Na_2SO_4$, filtrated and concentrated under vacuum. The crude product was purified by prep HPLC to give pure product $N_5$.

General Procedure O:

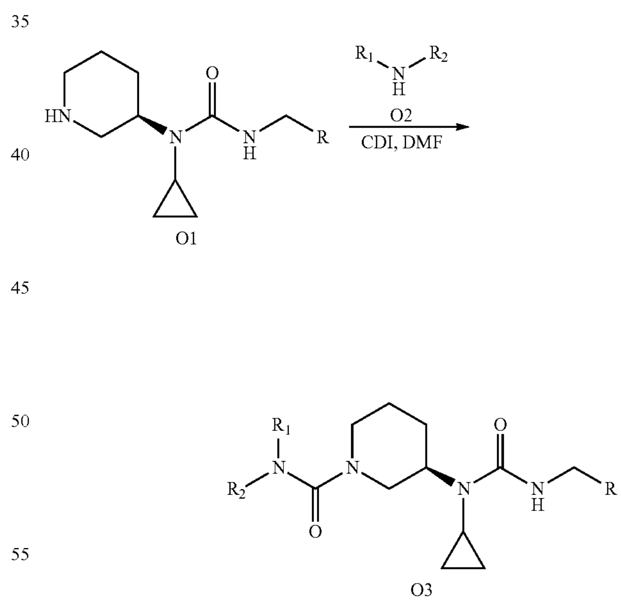

O1

O3

O1 was synthesized using Procedure M or N

Synthesis of O3

The appropriate amine O2 (2 eqs) and CDI (2 eqs) were dissolved in DMF (0.1M) and reaction was stirred at r.t for 2-3 hours. Then O1 (1 eq) was added and reaction was stirred at 50° C. until full conversion (1 to 4 hours). The reaction mixture was concentrated under vacuum and the crude was purified by prep HPLC to give product O3.

Synthesis of (3R)—N-cyclopropyl-3-(3-cyclopropyl{[(4-chloro-2-fluoro-5-methylphenyl)methyl]carbamoyl}amino)piperidine-1-carboxamide, (Example 317)

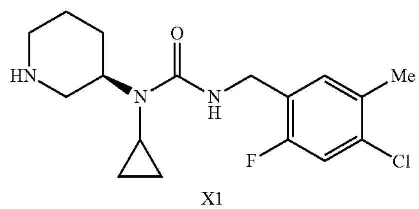

X1

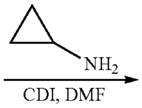

CDI, DMF

-continued

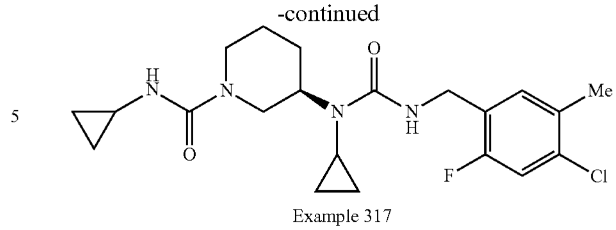

Example 317

Cyclopropylamine (8.3 uL, 0.12 mmol) and CDI (19.5 mg, 0.12 mmol) were dissolved in DMF and reaction was stirred at r.t for 2 hours. Then X1 (20 mg, 0.06 mmol) was added and reaction was warmed to 50° C. and stirred for 2 hours. The reaction mixture was then cooled to r.t. and concentrated under vacuum. The crude was purified by prep HPLC to give X1 (10 mg, 39% yield) as a white powder. LC/MS (ESI) m/z: 423.1 $(M+H)^+$. 1H NMR (400 MHz, MeOD) δ 7.24 (d, J=8.0 Hz, 1H), 7.13 (d, J=9.8 Hz, 1H), 6.86 (t, J=5.7 Hz, 1H), 4.37 (t, J=4.7 Hz, 2H), 3.96 (d, J=12.8 Hz, 1H), 3.84 (d, J=12.5 Hz, 1H), 3.61 (ddd, J=11.8, 7.9, 4.1 Hz, 1H), 3.13-3.06 (m, 1H), 2.61 (td, J=13.0, 2.4 Hz, 1H), 2.55-2.47 (m, 2H), 2.32 (s, 3H), 2.07 (td, J=12.5, 3.8 Hz, 1H), 1.87 (d, J=11.6 Hz, 1H), 1.74 (d, J=13.0 Hz, 1H), 1.47 (dt, J=13.3, 4.2 Hz, 1H), 0.96-0.89 (m, 2H), 0.73 (d, J=3.6 Hz, 2H), 0.66-0.60 (m, 2H), 0.47-0.40 (m, 2H).

| Example | Structure/name | Data |
| --- | --- | --- |
| 318 | 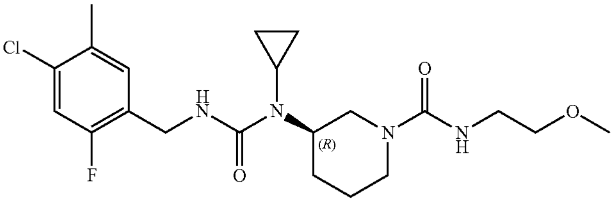 (3R)-3-(3-cyclopropyl{[(4-chloro-2-fluoro-5-methylphenyl)methyl]carbamoyl}amino)-N-(2-methoxyethyl)piperidine-1-carboxamide | LC-MS: m/z 441 (M + H). 1H NMR (400 MHz, MeOD) δ 7.24 (d, J = 8.0 Hz, 1H), 7.13 (d, J = 9.8 Hz, 1H), 4.43-4.30 (m, 2H), 4.00-3.84 (m, 2H), 3.66-3.56 (m, 1H), 3.45-3.40 (m, 2H), 3.33 (s, 3H), 3.31-3.28 (m, 2H), 3.19-3.08 (m, 1H), 2.68-2.57 (m, 1H), 2.55-2.47 (m, 1H), 2.31 (s, 3H), 2.18-2.04 (m, 1H), 1.90 (t, J = 13.4 Hz, 1H), 1.80-1.69 (m, 1H), 1.56-1.40 (m, 1H), 1.00-0.85 (m, 2H), 0.80-0.67 (m, 2H). |
| 319 | 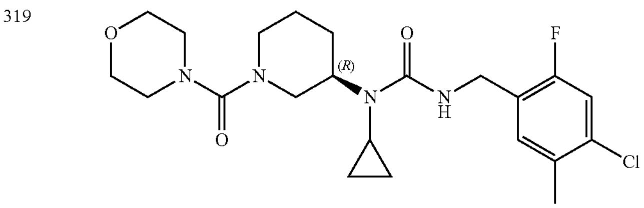 [(4-chloro-2-fluoro-5-methylphenyl)methyl]-3-cyclopropyl-3-[(3R)-1-(morpholine-4-carbonyl)piperidin-3-yl]urea | LC-MS: m/z 453.1 (M + H). 1H NMR (400 MHz, MeOD) δ 7.24 (d, J = 8.0 Hz, 1H), 7.13 (d, J = 9.8 Hz, 1H), 6.84 (t, J = 5.7 Hz, 1H), 4.44-4.29 (m, 2H), 3.82-3.73 (m, 1H), 3.67-3.56 (m, 6H), 3.27-3.16 (m, 4H), 3.07 (t, J = 11.8 Hz, 1H), 2.77-2.62 (m, 1H), 2.53-2.42 (m, 1H), 2.32 (s, 3H), 2.17-2.01 (m, 1H), 1.96-1.85 (m, 1H), 1.82-1.73 (m, 1H), 1.63-1.47 (m, 1H), 0.99-0.87 (m, 2H), 0.80-0.63 (m, 2H). |

-continued

| Example | Structure/name | Data |
|---|---|---|
| 320 | 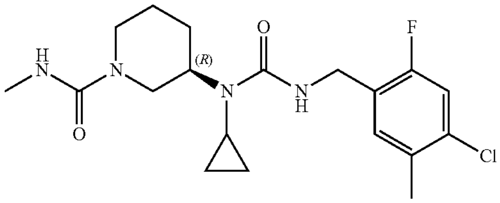 (3R)-3-(3-cyclopropyl{[(4-chloro-2-fluoro-5-methylphenyl)methyl]carbamoyl}amino)-N-methylpiperidine-1-carboxamide | LC-MS: m/z 397 (M + H). 1H NMR (400 MHz, MeOD) δ 7.24 (d, J = 8.0 Hz, 1H), 7.13 (d, J = 9.8 Hz, 1H), 4.43-4.31 (m, 2H), 3.99-3.91 (m, 1H), 3.90-3.80 (m, 1H), 3.66-3.55 (m, 1H), 3.17-3.06 (m, 1H), 2.69 (s, 3H), 2.68-2.60 (m, 1H), 2.55-2.47 (m, 1H), 2.31 (s, 3H), 2.18-2.04 (m, 1H), 1.88 (d, J = 11.4 Hz, 1H), 1.79-1.70 (m, 1H), 1.58-1.42 (m, 1H), 1.58-1.42 (m, 1H), 0.97-0.89 (m, 2H), 0.79-0.67 (m, 2H), 0.79-0.70 (m, 2H). |
| 321 | 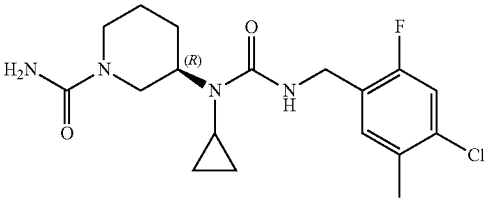 (3R)-3-(3-cyclopropyl{[(4-chloro-2-fluoro-5-methylphenyl)methyl]carbamoyl}amino)piperidine-1-carboxamide | LC-MS: m/z 383 (M + H). 1H NMR (400 MHz, MeOD) δ 7.24 (d, J = 8.0 Hz, 1H), 7.13 (d, J = 9.8 Hz, 1H), 6.89-6.81 (m, 1H), 4.42-4.32 (m, 2H), 4.01-3.85 (m, 2H), 3.69-3.58 (m, 1H), 3.23-3.14 (m, 1H), 2.72-2.61 (m, 1H), 2.56-2.48 (m, 1H), 2.31 (s, 3H), 2.17-2.05 (m, 1H), 1.93-1.84 (m, 1H), 1.79-1.69 (m, 1H), 1.58-1.45 (m, 1H), 0.97-0.89 (m, 2H), 0.77-0.70 (m, 2H). |
| 322 | 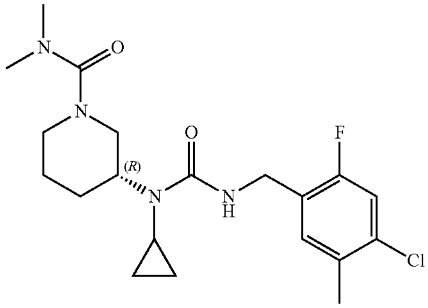 (3R)-3-(3-cyclopropyl{[(4-chloro-2-fluoro-5-methylphenyl)methyl]carbamoyl}amino)-N,N-dimethylpiperidine-1-carboxamide | LC-MS: m/z 411 (M + H). 1H NMR (400 MHz, CD3OD) δ 7.24 (d, J = 8.0 Hz, 1H), 7.12 (d, J = 9.8 Hz, 1H), 4.37 (s, 2H), 3.78 (ddd, J = 15.5, 8.0, 3.9 Hz, 1H), 3.61-3.53 (m, 2H), 3.08 (t, J = 11.8 Hz, 1H), 2.82 (s, 6H), 2.67 (dt, J = 13.0, 6.6 Hz, 1H), 2.52-2.47 (m, 1H), 2.31 (s, 3H), 2.09 (td, J = 12.5, 8.5 Hz, 1H), 1.89 (d, J = 12.3 Hz, 1H), 1.79-1.73 (m, 1H), 1.63-1.53 (m, 1H), 0.96-0.90 (m, 2H), 0.76-0.70 (m, 2H). |

General Procedure P:

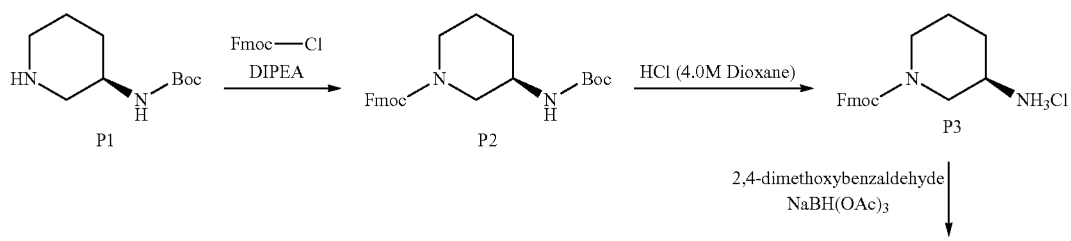

P1 P2 P3

-continued

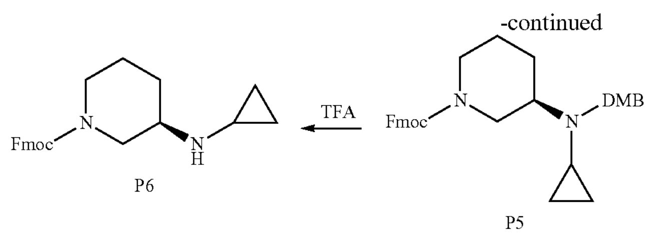

P6

P5

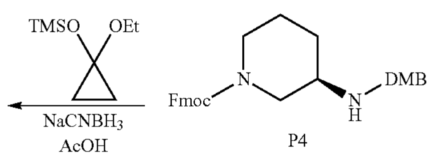

P4

Protected intermediate 3-amino-piperidines can be prepared by the general route shown above or by general procedure Q.

A solution of tert-butyl N-[(3R)-3-piperidyl]carbamate P1 (25 g, 124.83 mmol) and DIPEA (19.36 g, 149.79 mmol, 26.09 mL) in 500 mL of DCM was added dropwise to solution of Fmoc-Cl (44.28 g, 137.31 mmol) in DCM (150 mL), in an ice bath, dropwise over two hours. Afterwards, the reaction mixture was stirred for an additional hour, then warmed to rt, filtered and concentrated to provide 9H-fluoren-9-ylmethyl (3R)-3-(tert-butoxycarbonylamino)piperidine-1-carboxylate P2 (81 g, 191.71 mmol, 153.58% yield) as a crude white solid which was used without further purification. To a suspension of 9H-fluoren-9-ylmethyl (3R)-3-(tert-butoxycarbonylamino)piperidine-1-carboxylate P2 (20 g, 47.34 mmol) in THF (200 mL) was added dioxane/HCl (4.0M) (4.0 M, 59.17 mL) and the reaction mixture was stirred at 60 C from three hours. The reaction mixture was then concentrated under reduced pressure by rotary evaporation and the resultant solid was washed 2× with Et2O to afford 9H-fluoren-9-ylmethyl (3R)-3-aminopiperidine-1-carboxylate P3 (13.91 g, 38.76 mmol, 81.89% yield, HCl) as a white solid. To a suspension of 9H-fluoren-9-ylmethyl (3R)-3-aminopiperidine-1-carboxylate P3 (13.91 g, 38.76 mmol, HCl) in DCM (250 mL) was added 2,4-dimethoxybenzaldehyde (6.12 g, 36.82 mmol), DIPEA (5.51 g, 42.64 mmol, 7.43 mL), and Sodium triacetoxyborohydride (8.22 g, 38.76 mmol). The reaction mixture was allowed to stir overnight, and then washed with 1 M NaOH, brine, and dried over anhydrous sodium sulfate. The reaction mixture was then concentrated and purified by chromatography (DCM:MeOH 100:0 to 95:5) to afford 9H-fluoren-9-ylmethyl (3R)-3-[(2,4-dimethoxyphenyl)methylamino]piperidine-1-carboxylate P4 (9.26 g, 19.59 mmol, 50.55% yield) as a yellow oil. To a solution of 9H-fluoren-9-ylmethyl (3R)-3-[(2,4-dimethoxyphenyl)methylamino]piperidine-1-carboxylate (5.75 g, 12.17 mmol) P4 in THF (50 mL) and Ethanol (100 mL) was added (1-ethoxycyclopropoxy)-trimethyl-silane (5.30 g, 30.43 mmol, 6.12 mL), Acetic Acid (10.96 g, 182.55 mmol, 10.44 mL), and Sodium cyanoborohydride (2.68 g, 42.60 mmol). The reaction mixture was stirred overnight at 80 C, then concentrated and the residue dissolved in DCM. The organic layer was washed with sat. aq. sodium carbonate, brine, and dried over anhydrous sodium sulfate. The organic layer was concentrated and purified by chromatography (DCM:MeOH 10:0 to 9:1) to provide 9H-fluoren-9-ylmethyl (3R)-3-[cyclopropyl-[(2,4-dimethoxyphenyl)methyl]amino]piperidine-1-carboxylate P5 as a white foam. A solution of 9H-fluoren-9-ylmethyl (3R)-3-[cyclopropyl-[(2,4-dimethoxyphenyl)methyl]amino] piperidine-1-carboxylate P5 (2.0 g, 3.90 mmol) in TFA (59.20 g, 519.19 mmol, 40 mL) was heated to 80 C and stirred for 6 hours. The reaction mixture was then cooled to room temperature and concentrated. The residue was dissolved in DCM and washed with sat. aq. $Na_2CO_3$, dried over anhydrous $Na_2SO_4$ and concentrated to provide 9H-fluoren-9-ylmethyl (3R)-3-(cyclopropylamino)piperidine-1-carboxylate P6 (1.35 g, 3.72 mmol, 95.47% yield) as a brown oil which was used stored at −20 C and used without further purification.

General Procedure Q:

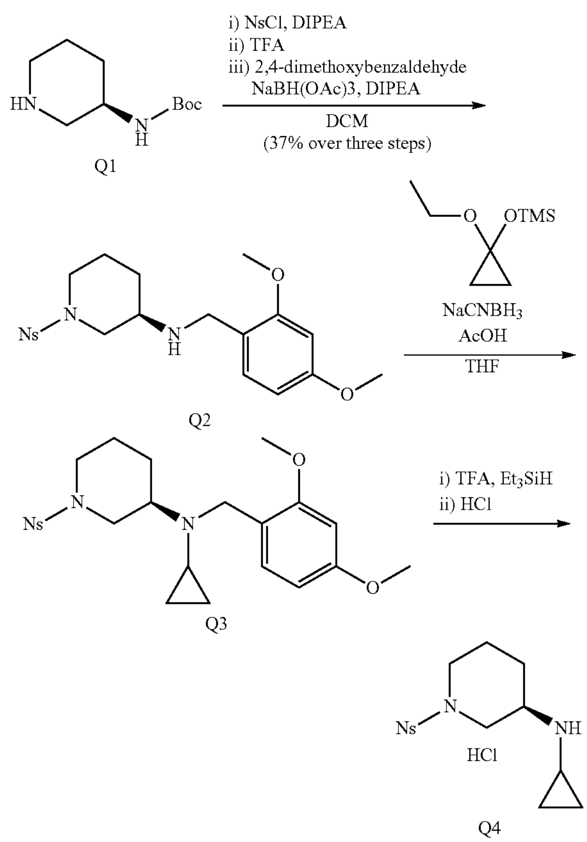

Q1

Q2

Q3

Q4

To a solution of tert-butyl N-[(3R)-3-piperidyl]carbamate (10 g, 49.93 mmol) Q1 and DIPEA (7.10 g, 54.92 mmol, 9.57 mL) in DCM (500 mL) was added 2-nitrobenzenesulfonyl chloride (11.62 g, 52.43 mmol) as a solid, portionwise. The reaction mixture was allowed to stir for 15 minutes at ambient temperature and then TFA (56.93 g, 499.31 mmol, 38.47 mL) was slowly added. The reaction mixture was stirred at ambient temperature for an additional two hours and then concentrated under reduced pressure by rotary evaporation. The crude residue was then resuspended in 500 mL of DCM, and to this solution was added DIPEA (11.29 g, 87.38 mmol, 15.22 mL), 2,4-dimethoxybenzaldehyde (7.88 g, 47.43 mmol), and Sodium triacetoxyborohydride (26.46 g, 124.83 mmol). The reaction mixture was allowed to stir at ambient temperature overnight. The reaction mixture was then washed with 1 M NaOH (500 mL) and then the organic layer was separated, dried with anhydrous sodium sulfate, and concentrated under reduced pressure by rotary evaporation. The crude reside was purified by flash column chromatrography (DCM:MeOH, 100:0 to 96:4) to provide (3R)—N-[(2,4-dimethoxyphenyl)methyl]-1-(2-nitrophenyl)sulfonyl-piperidin-3-amine (7.94 g, 18.23 mmol, 36.52% yield) Q2. To a solution of (3R)—N-[(2,4-dimethoxyphenyl)methyl]-1-(2-nitrophenyl)sulfonyl-piperidin-3-amine (7.93 g, 18.21 mmol) Q2 in THF (240 mL) and EtOH (120 mL) was added 1-ethoxy-1-trimethylsiloxycyclopropane (7.94 g, 45.52 mmol, 9.15 mL), Sodium cyanoborohydride (4.01 g, 63.73 mmol), and acetic acid (16.40 g, 273.14 mmol, 15.62 mL). The reaction mixture was stirred at 80 C overnight, after which it was cooled to rt, and concentrated under reduced pressure by rotary evaporation. The residue was then dissolved in ethyl acetate (250 mL) and washed with 1 M NaOH (250 mL), brine (250 mL), dried with $Na_2SO_4$, filtered and concentrated under reduced pressure by rotary evaporation to provide (3R)—N-cyclopropyl-N-[(2,4-dimethoxyphenyl)methyl]-1-(2-nitrophenyl)sulfonyl-piperidin-3-amine (8.58 g, 18.04 mmol, 99.08% yield) Q3 which was used without further purification. (3R)—N-cyclopropyl-N-[(2,4-dimethoxyphenyl)methyl]-1-(2-nitrophenyl)sulfonyl-piperidin-3-amine (8.58 g, 18.04 mmol) was dissolved in TFA (100 mL) Q3 and Et3SiH (10 mL) and heated to 80 C. After four hours an additional portion of Triethyl silane (7.28 g, 62.61 mmol, 10 mL) was added to suppress the formation of the dimethoxytolyl cation. The reaction mixture was then allowed to stir overnight. The reaction mixture was then concentrated under reduced pressure by rotary evaporation and the crude residue was dissolved in 200 mL Ethyl acetate. The organic layer was washed with 3M NaOH (~200 mL), brine (~200 mL) dried with Na2SO4, filtered and concentrated under reduced pressure by rotary evaporation. The crude residue was then dissolved in 100 mL diethyl ether and Hydrogen chloride solution 2.0 M in diethyl ether (2.0 M, 9.02 mL) was slowly added dropwise. The product was filtered from the solution to provide (3R)—N-cyclopropyl-1-(2-nitrophenyl)sulfonyl-piperidin-3-amine (5.5 g, 15.20 mmol, 84.25% yield, HCl) Q4 as a tan solid.

General Procedure R

Intermediate benzylic amines attached to heterocycles on the aromatic ring were prepared by the general procedure

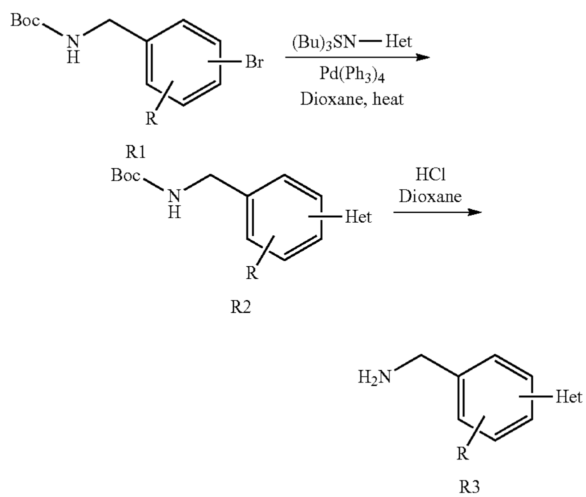

R1

R2

R3

The appropriate aryl bromide R1 (1 eq) was dissolved in Dioxane (0.3M), then the corresponding thin reagent R2 (1.1 eqs) and Palladium (0) tetrakis(triphenylphosphine) (0.1 eqs) were added and reaction was stirred at 110° C. overnight. The reaction mixture was then cooled down and concentrated under vacuum. The crude was purified by flash column chromatography using Heptane/Ethyl Acetate to give pure product R3. R3 (1 eq) was dissolved in HCl 4M Dioxane (20 eqs) and reaction stirred at r.t. until full deprotection. Saturated $NaHCO_3$ solution was added and the reaction mixture was extracted with DCM (×3). The combined organic layers were dried over anhydrous $Na_2SO_4$, filtered and concentrated under vacuum. Crude product R4 was used for next step without further purification.

Synthesis of (2-fluoro-4-(oxazol-2-yl)phenyl)methanamine R6 through general procedure R

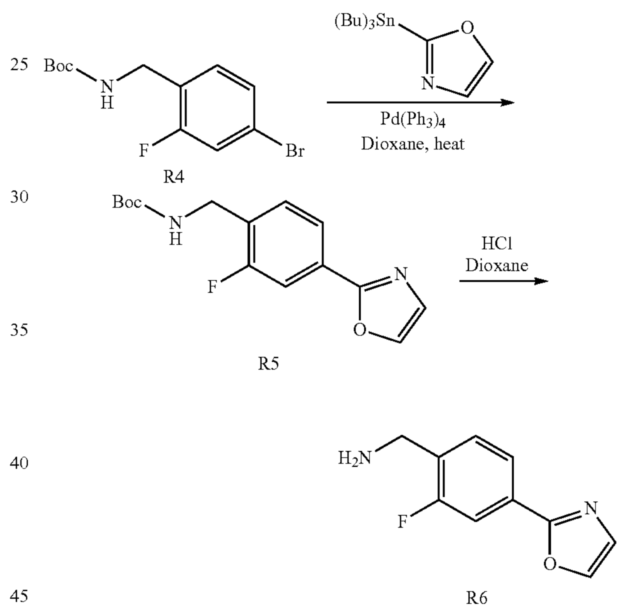

R4

R5

R6

R4 (520 mg, 1.71 mmol) was dissolved in Dioxane (5.12 mL), then 2-(tributylstannyl)oxazole (673 mg, 1.88 mmol) and Palladium (0) tetrakis(triphenylphosphine) (198 mg, 0.17 mmol) were added and reaction was stirred at 110° C. overnight. The reaction mixture was then cooled down and concentrated under vacuum. The crude was purified by flash column chromatography using Heptane/Ethyl Acetate to give pure product R5 (350 mg, 70% yield) as a white powder. R5 (350 mg, 1.20 mmol) was dissolved in HCl 4M Dioxane (6 mL, 24 mmol) and reaction stirred at r.t. until full deprotection. Saturated $NaHCO_3$ solution was added and the reaction mixture was extracted with DCM (×3). The combined organic layers were dried over anhydrous $Na_2SO_4$, filtered and concentrated under vacuum. Crude product (2-fluoro-4-(oxazol-2-yl)phenyl)methanamine R6 was used for next step without further purification.

Examples 323-333 were prepared from the corresponding aryl or heteroaryl-benzyl amine and the general procedures described above

| Entry | General Procedure | Structure, name | Data |
|---|---|---|---|
| 323 | A | 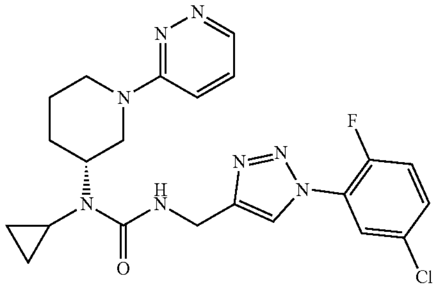 [SMILES: O=C(NCc1cn(-c2cc(Cl)ccc2F)nn1)N(C1CC1)[C@@H]1CCCN(c2cccnn2)C1] 3-{[1-(5-chloro-2-fluorophenyl)-1H-1,2,3-triazol-4-yl]methyl}-1-cyclopropyl-1-[(3R)-1-(pyridazin-3-yl)pieridin-3-yl]urea | LC-MS: m/z 471 (M + H). 1H NMR (400 MHz, MeOD) δ 8.42 (d, J = 3.8 Hz, 1H), 8.27 (d, J = 2.3 Hz, 1H), 7.94 (dd, J = 6.4, 2.6 Hz, 1H), 7.60-7.53 (m, 1H), 7.49-7.41 (m, 1H), 7.37 (dd, J = 9.4, 4.3 Hz, 1H), 7.29 (d, J = 9.1 Hz, 1H), 7.04 (t, J = 5.6 Hz, 1H), 4.56 (d, J = 5.7 Hz, 2H), 4.37 (dd, J = 28.3, 12.8 Hz, 2H), 3.85-3.73 (m, 1H), 3.34 (s, 1H), 2.87 (dt, J = 12.9, 6.6 Hz, 1H), 2.55 (dt, J = 10.1, 3.4 Hz, 1H), 2.25 (qd, J = 12.6, 4.0 Hz, 1H), 1.96 (d, J = 11.6 Hz, 1H), 1.86 (d, J = 13.2 Hz, 1H), 1.69-1.54 (m, 1H), 0.95 (dd, J = 8.4, 5.6 Hz, 2H), 0.81 (d, J = 3.3 Hz, 2H). |
| 324 | B | 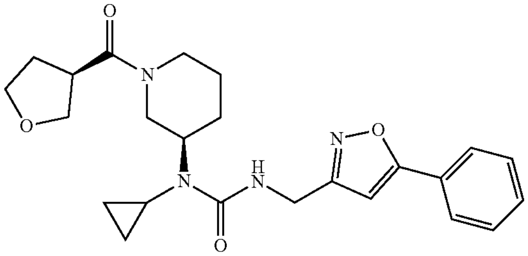 [SMILES: O=C([C@@H]1CCOC1)N1CCC[C@@H](N(C(=O)NCc2cc(-c3ccccc3)on2)C2CC2)C1] 1-cyclopropyl-1-[(3R)-1-[(3R)-oxolane-3-carbonyl]piperidin-3-yl]-3-[(5-phenyl-1,2-oxazol-3-yl)methyl]urea | LC-MS: m/z 439.2 (M + H). 1H NMR (400 MHz, MeOD) δ 7.81 (d, J = 6.5 Hz, 2H), 7.58-7.38 (m, 3H), 7.00 (dd, J = 16.7, 11.5 Hz, 1H), 6.71 (d, J = 5.8 Hz, 1H), 4.57-4.41 (m, 3H), 4.06-3.74 (m, 6H), 3.59-3.38 (m, 2H), 3.26 (s, 1H), 3.13 (t, J = 11.8 Hz, 1H), 3.00 (t, J = 12.2 Hz, 1H), 2.59-2.47 (m, 2H), 2.29-1.82 (m, 5H), 1.50 (ddd, J = 19.7, 16.9, 8.6 Hz, 1H), 0.95 (ddd, J = 22.2, 12.9, 7.6 Hz, 2H), 0.88-0.71 (m, 2H). |
| 325 | B | 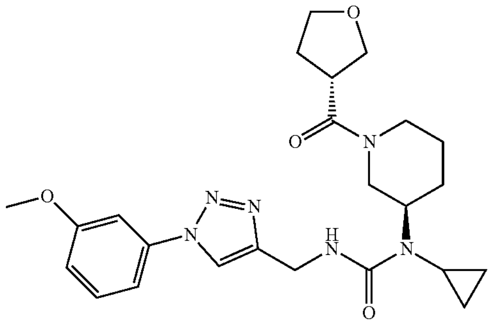 1-cyclopropyl-1-[(3R)-1-[(3R)-oxolane-3-carbonyl]piperidin-3-yl]-3-[(5-phenyl-1,2-oxazol-3-yl)methyl]urea | LC-MS: m/z 439.2 (M + H). 1H NMR (400 MHz, MeOD) δ 7.81 (d, J = 6.5 Hz, 2H), 7.58-7.38 (m, 3H), 7.00 (dd, J = 16.7, 11.5 Hz, 1H), 6.71 (d, J = 5.8 Hz, 1H), 4.57-4.41 (m, 3H), 4.06-3.74 (m, 6H), 3.59-3.38 (m, 2H), 3.26 (s, 1H), 3.13 (t, J = 11.8 Hz, 1H), 3.00 (t, J = 12.2 Hz, 1H), 2.59-2.47 (m, 2H), 2.29-1.82 (m, 5H), 1.50 (ddd, J = 19.7, 16.9, 8.6 Hz, 1H), 0.95 (ddd, J = 22.2, 12.9, 7.6 Hz, 2H), 0.88-0.71 (m, 2H). |
| 326 | A | 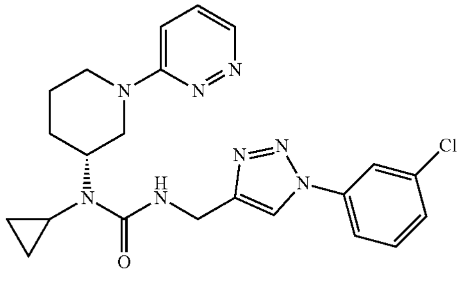 [SMILES: O=C(NCc1cn(-c2cccc(Cl)c2)nn1)N(C1CC1)[C@@H]1CCCN(c2cccnn2)C1] 3-{[1-(3-chlorophenyl)-1H-1,2,3-triazol-4-yl]methyl}-1-cyclopropyl-1-[(3R)-1-(pyridazin-3-yl)piperidin-3-yl]urea | LC-MS: m/z 453.2 (M + H). 1H NMR (400 MHz, MeOD) δ 8.42 (dd, J = 3.9, 2.7 Hz, 2H), 7.95 (t, J = 2.0 Hz, 1H), 7.82 (ddd, J = 8.0, 2.0, 1.0 Hz, 1H), 7.56 (t, J = 8.1 Hz, 1H), 7.50 (ddd, J = 8.1, 1.9, 1.0 Hz, 1H), 7.36 (dd, J = 9.4, 4.4 Hz, 1H), 7.29 (dd, J = 9.4, 1.2 Hz, 1H), 7.01 (t, J = 5.6 Hz, 1H), 4.54 (d, J = 5.6 Hz, 2H), 4.44-4.32 (m, 2H), 3.80 (ddd, J = 15.9, 7.9, 4.0 Hz, 1H), 3.33 (s, 1H), 2.88 (td, J = 13.1, 2.8 Hz, 1H), 2.60-2.49 (m, 1H), 2.25 (qd, J = 12.6, 4.2 Hz, 1H), 1.99 (t, J = 9.6 Hz, 1H), 1.86 (d, J = 13.2 Hz, 1H), 1.62 (dtd, J = 13.0, 8.9, 4.1 Hz, 1H), 1.00-0.91 (m, 2H), 0.82 (t, J = 4.8 Hz, 2H). |

-continued

| Entry | General Procedure | Structure, name | Data |
|---|---|---|---|
| 327 | A | 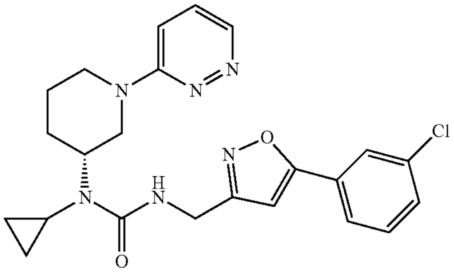 [SMILES: O=C(NCc1cc(-c2cccc(Cl)c2)on1)N(C1CC1)[C@@H]1CCCN(c2cccnn2)C1] 3-{[5-(3-chlorophenyl)-1,2-oxazol-3-yl]methyl}-1-cyclopropyl-1-[(3R)-1-(pyridazin-3-yl)piperidin-3-yl]urea | LC-MS: m/z 453.2 (M + H). 1H NMR (400 MHz, MeOD) δ 8.43 (dd, J = 4.4, 1.1 Hz, 1H), 7.84 (s, 1H), 7.79-7.71 (m, 1H), 7.52-7.44 (m, 2H), 7.36 (dd, J = 9.4, 4.4 Hz, 1H), 7.29 (dd, J = 9.4, 1.2 Hz, 1H), 6.81 (s, 1H), 4.49 (s, 2H), 4.45-4.33 (m, 2H), 3.81 (tt, J = 11.9, 3.9 Hz, 1H), 3.33 (d, J = 12.7 Hz, 1H), 2.89 (td, J = 13.0, 2.6 Hz, 1H), 2.60-2.53 (m, 1H), 2.27 (qd, J = 12.4, 4.0 Hz, 1H), 1.99 (d, J = 13.2 Hz, 1H), 1.87 (d, J = 13.5 Hz, 1H), 1.63 (tdd, J = 13.0, 9.0, 4.1 Hz, 1H), 1.02-0.92 (m, 2H), 0.88-0.79 (m, 2H). |
| 328 | A | 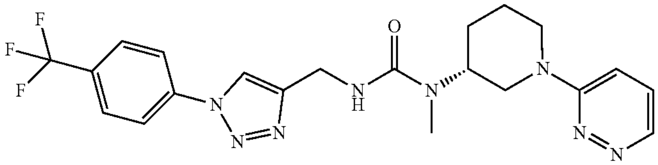 [SMILES: CN(C(=O)NCc1cn(-c2ccc(C(F)(F)F)cc2)nn1)[C@@H]1CCCN(c2cccnn2)C1] 1-methyl-1-[(3R)-1-(pyridazin-3-yl)piperidin-3-yl]-3-({1-[4-(trifluoromethyl)phenyl]-1H-1,2,3-triazol-4-yl}methyl)urea | LC-MS: m/z 461.35 (M + H). |
| 329 | A | 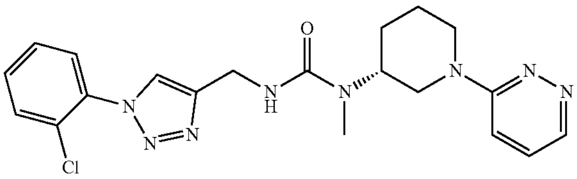 [SMILES: CN(C(=O)NCc1cn(-c2ccccc2Cl)nn1)[C@@H]1CCCN(c2cccnn2)C1] 3-{[1-(2-chlorophenyl)-1H-1,2,3-triazol-4-yl]methyl}-1-methyl-1-[(3R)-1-(pyridazin-3-yl)piperidin-3-yl]urea | LC-MS: m/z 427.42 (M + H). |
| 330 | A | 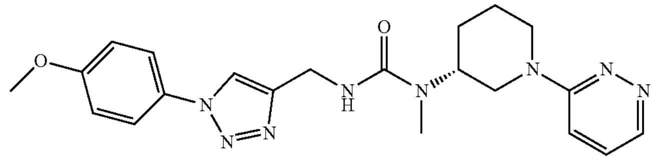 [SMILES: COc1ccc(-n2cc(CNC(=O)N(C)[C@@H]3CCCN(c4cccnn4)C3)nn2)cc1] 3-{[1-(4-methoxyphenyl)-1H-1,2,3-triazol-4-yl]methyl}-1-methyl-1-[(3R)-1-(pyridazin-3-yl)piperidin-3-yl]urea | LC-MS: m/z 423.32 (M + H). |
| 331 | A | 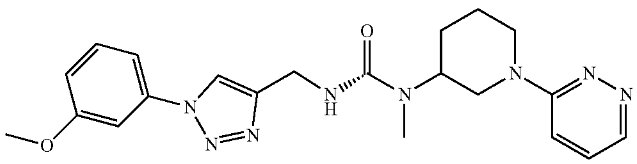 3-{[1-(3-methoxyphenyl)-1H-1,2,3-triazol-4-yl]methyl}-1-methyl-1-[(3R)-1-(pyridazin-3-yl)piperidin-3-yl]urea | LC-MS: m/z 423.41 (M + H). |

-continued
| Entry | General Procedure | Structure, name | Data |
|---|---|---|---|
| 332 | A | 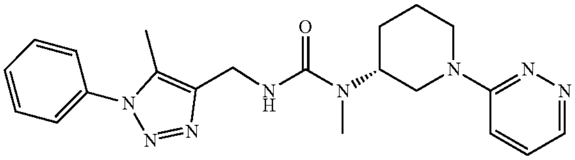 1-methyl-3-[(5-methyl-1-phenyl-1H-1,2,3-triazol-4-yl)methyl]-1-[(3R)-1-(pyridazin-3-yl)piperidin-3-yl]urea | LC-MS: m/z 407.3 (M + H). |
| 333 | A | 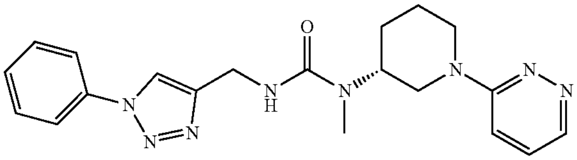 [SMILES: CN(C(=O)NCc1cn(-c2ccccc2)nn1)[C@@H]1CCCN(c2cccnn2)C1] 1-methyl-3-[(1-phenyl-1H-1,2,3-triazol-4-yl)methyl]-1-[(3R)-1-(pyridazin-3-yl)piperidin-3-yl]urea | LC-MS: m/z 393.3 (M + H). |
The general procedure R' as described below was used to prepare Examples 334-339 and 343 and similar compounds.
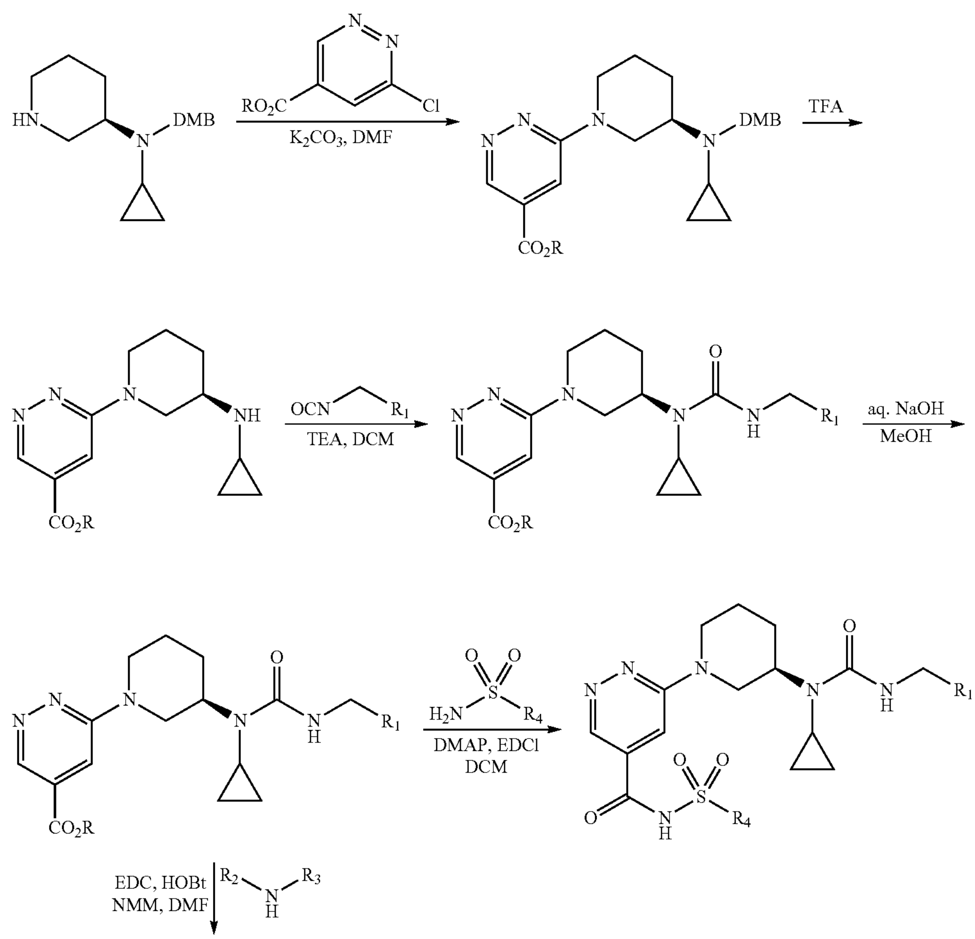

-continued
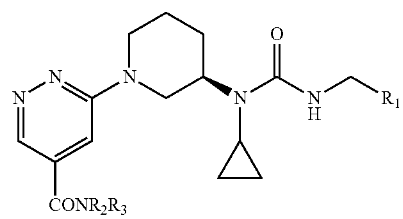
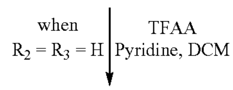
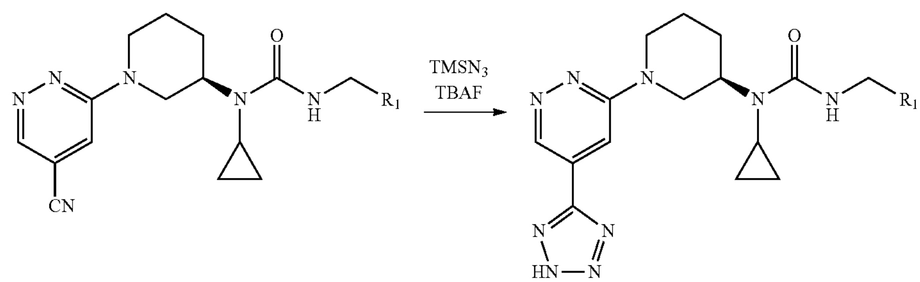
The general procedure S as described below was used to prepare Examples 340, 341, and 342 and 343 and similar compounds.
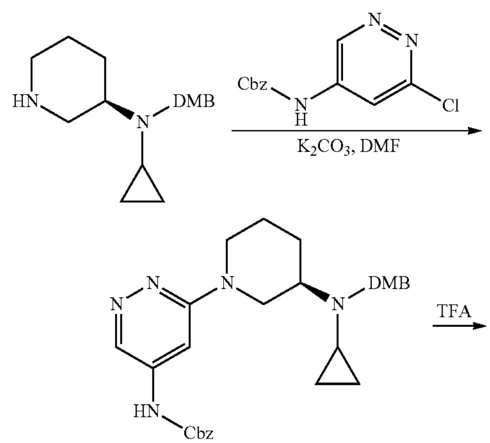
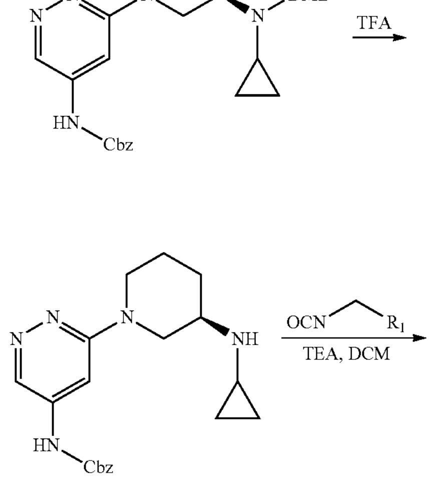
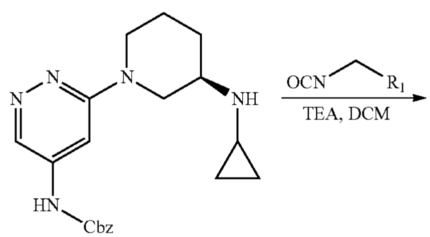
-continued
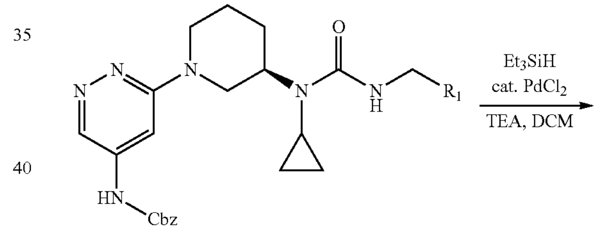
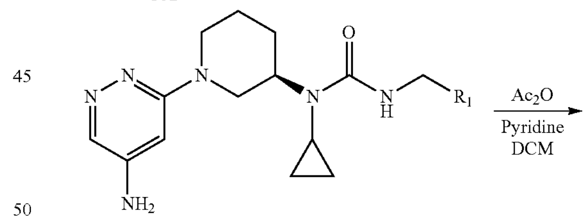
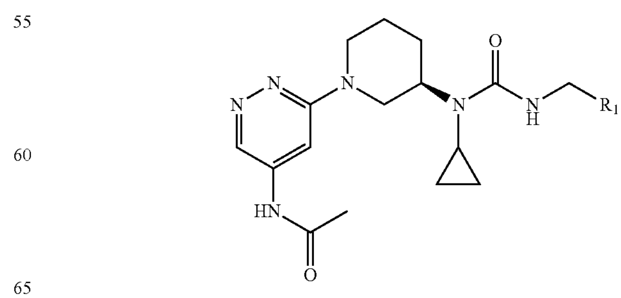

Examples 334-343

| Example | Procedure | Structure, name | Data |
|---|---|---|---|
| 334 | R | 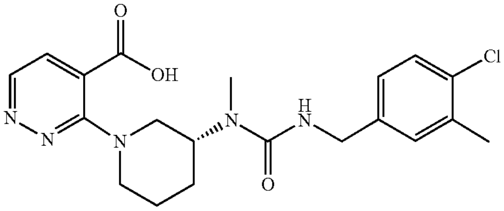 [SMILES: Cc1cc(CNC(=O)N(C)[C@@H]2CCCN(c3nnccc3C(=O)O)C2)ccc1Cl] 3-[(3R)-3-({[(4-chloro-3-methylphenyl)methyl]carbamoyl}(methyl) amino)piperidin-1-yl]pyridazine-4-carboxylic acid | LC-MS: 418.2 (M + H). 1H NMR (400 MHz, MeOD) δ 8.71 (d, J = 4.8 Hz, 1H), 7.73 (d, J = 4.8 Hz, 1H), 7.25 (d, J = 8.2 Hz, 1H), 7.22 (s, 1H), 7.10 (dd, J = 8.2, 1.8 Hz, 1H), 4.33 (d, J = 1.6 Hz, 2H), 4.18 (d, J = 3.8 Hz, 1H), 3.95 (dd, J = 19.1, 15.1 Hz, 2H), 3.22-3.14 (m, 1H), 3.04 (dd, J = 17.8, 7.4 Hz, 1H), 2.89 (s, 3H), 2.33 (s, 3H), 1.93-1.84 (m, 3H), 1.84-1.75 (m, 1H). |
| 335 | R | 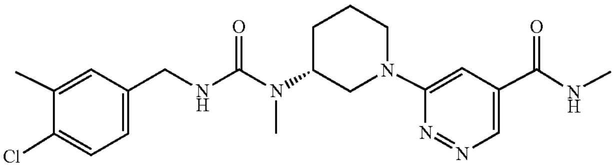 6-[(3R)-3-({[(4-chloro-3-methylphenyl)methyl]carbamoyl}(methyl)amino)piperidin-1-yl]-N-methylpyridazine-4-carboxamide | LC-MS: 431.4 (M + H). |
| 336 | R | 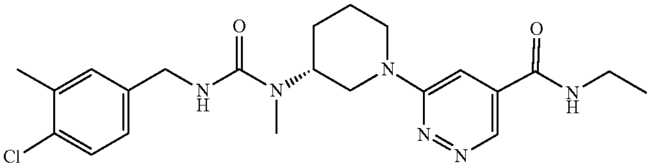 [SMILES: CCNC(=O)c1cnnc(N2CCC[C@@H](N(C)C(=O)NCc3ccc(Cl)c(C)c3)C2)c1] 6-[(3R)-3-({[(-chloro-3-methylphenyl)methyl]carbamoyl}(methyl)amino)piperidin-1-yl]-N-ethylpyridazine-4-carboxamide | LC-MS: 445.43 (M + H). |
| 337 | R | 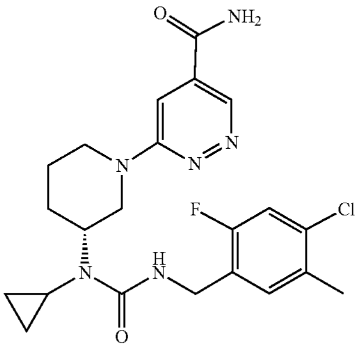 [SMILES: Cc1cc(CNC(=O)N(C2CC2)[C@@H]2CCCN(c3cc(C(N)=O)cnn3)C2)c(F)cc1Cl] 6-[(3R)-3-(1-cyclopropyl{[(4-chloro-2-fluoro-5-methylphenyl)methyl]carbamoyl}amino)piperidin-1-yl]pyridazine-4-carboxamide | LC-MS: 461 (M + H) 1H NMR (400 MHz, MeOD) δ 8.77 (d, J = 1.6 Hz, 1H), 7.59 (d, J = 1.7 Hz, 1H), 7.26 (d, J = 8.0 Hz, 1H), 7.13 (d, J = 9.8 Hz, 1H), 6.91 (t, J = 5.9 Hz, 1H), 4.48 (d, J = 12.0 Hz, 1H), 4.42-4.36 (m, 3H), 3.78 (ddd, J = 15.7, 7.8, 3.9 Hz, 1H), 3.40-3.33 (m, 1H), 2.93 (td, J = 13.1, 2.7 Hz, 1H), 2.59-2.52 (m, 1H), 2.32 (s, 3H), 2.30-2.21 (m, 1H), 1.97 (d, J = 11.6 Hz, 1H), 1.89 (d, J = 13.3 Hz, 1H), 1.70-1.59 (m, 1H), 0.99-0.92 (m, 2H), 0.82-0.75 (m, 2H). |

-continued

| Example | Procedure | Structure, name | Data |
|---|---|---|---|
| 338 | R | 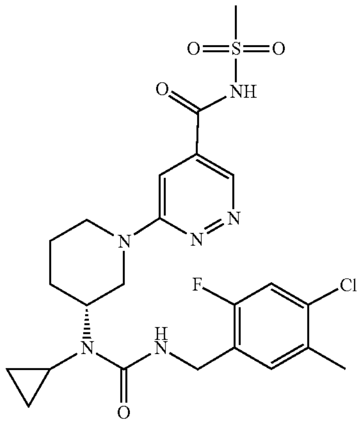 [SMILES: Cc1cc(CNC(=O)N(C2CC2)[C@@H]2CCCN(c3cc(C(=O)NS(C)(=O)=O)cnn3)C2)c(F)cc1Cl] 6-[(3R)-3-(1-cyclopropyl{[(4-chloro-2-fluoro-5-methylphenyl)methyl]carbamoyl}amino)piperidin-1-yl]-N-methanesulfonylpyridazine-4-carboxamide | LC-MS: 539 (M + H). 1H NMR (400 MHz, MeOD) δ 8.82 (s, 1H), 7.97 (s, 1H), 7.26 (d, J = 8.1 Hz, 1H), 7.13 (d, J = 9.8 Hz, 1H), 4.44-4.34 (m, 4H), 3.82-3.74 (m, 1H), 3.49 (d, J = 11.7 Hz, 1H), 3.21 (s, 3H), 3.03 (dd, J = 13.1, 10.7 Hz, 1H), 2.58 (dt, J = 10.3, 3.5 Hz, 1H), 2.32 (s, 3H), 2.27 (dd, J = 12.4, 8.5 Hz, 1H), 2.01-1.90 (m, 2H), 1.67 (q, J = 12.8 Hz, 1H), 0.99-0.93 (m, 2H), 0.81-0.76 (m, 2H). |
| 339 | R | 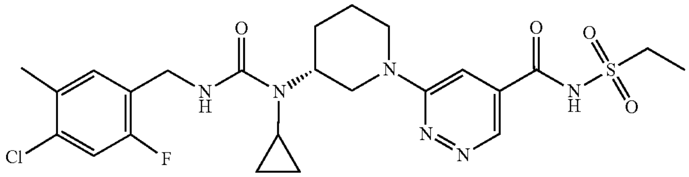 [SMILES: CCS(=O)(=O)NC(=O)c1cnnc(N2CCC[C@@H](N(C(=O)NCc3cc(C)c(Cl)cc3F)C3CC3)C2)c1] 6-[(3R)-3-(3-cyclopropyl{[(4-chloro-2-fluoro-5-methylphenyl)methyl]carbamoyl}amino)piperidin-1-yl]-N-(ethanesulfonyl)pyridazine-4-carboxamide | LC-MS: 553 (M + H). 1H NMR (400 MHz, MeOD) δ 8.82 (s, 1H), 7.90 (s, 1H), 7.26 (d, J = 8.0 Hz, 1H), 7.13 (d, J = 9.7 Hz, 1H), 4.45-4.35 (m, 4H), 3.77 (t, J = 11.8 Hz, 1H), 3.51-3.38 (m, 3H), 3.01 (t, J = 12.0 Hz, 1H), 2.61-2.55 (m, 1H), 2.32 (s, 3H), 2.27 (dd, J = 12.0, 8.1 Hz, 1H), 2.01-1.90 (m, 2H), 1.68 (t, J = 13.0 Hz, 1H), 1.34 (t, J = 7.4 Hz, 3H), 0.97 (d, J = 6.2 Hz, 2H), 0.79 (s, 2H). |
| 340 | S | 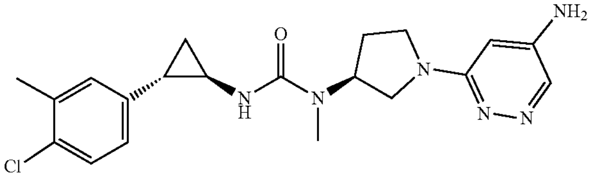 [SMILES: Cc1cc([C@@H]2C[C@H]2NC(=O)N(C)[C@H]2CCN(c3cc(N)cnn3)C2)ccc1Cl] 1-[(3S)-1-(5-aminopyridazin-3-yl)pyrrolidin-3-yl]-3-[(1R,2S)-2-(4-chloro-3-methylphenyl)cyclopropyl]-1-methylurea | LC-MS: 401 (M + H). 1H NMR (400 MHz, MeOD) δ 7.95 (d, J = 2.3 Hz, 1H), 7.20 (d, J = 8.2 Hz, 1H), 7.09 (d, J = 1.9 Hz, 1H), 6.94 (dd, J = 8.3, 2.2 Hz, 1H), 5.92 (d, J = 2.2 Hz, 1H), 4.96 (dd, J = 15.6, 7.7 Hz, 1H), 3.66-3.56 (m, 2H), 3.43-3.33 (m, 2H), 2.82 (s, 3H), 2.75-2.70 (m, 1H), 2.32 (s, 3H), 2.17 (dd, J = 10.7, 6.5 Hz, 2H), 1.97 (td, J = 6.4, 3.1 Hz, 1H), 1.22-1.12 (m, 2H). |
| 341 | S | 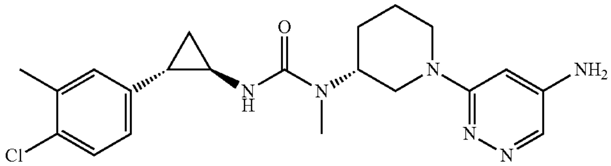 [SMILES: Cc1cc([C@@H]2C[C@H]2NC(=O)N(C)[C@@H]2CCCN(c3cc(N)cnn3)C2)ccc1Cl] 1-[(3R)-1-(5-aminopyridazin-3-yl)piperidin-3-yl]-3-[(1R,2S)-2-(4-chloro-3-methylphenyl)cyclopropyl]-1-methylurea | LC-MS: 415 (M + H). 1H NMR (400 MHz, MeOD) δ 7.99 (t, J = 2.3 Hz, 1H), 7.20 (d, J = 8.3 Hz, 1H), 7.09 (s, 1H), 6.95 (d, J = 8.3 Hz, 1H), 6.25 (d, J = 2.3 Hz, 1H), 4.12 (dd, J = 27.2, 12.0 Hz, 3H), 2.94 (t, J = 11.7 Hz, 1H), 2.82 (d, J = 17.5 Hz, 4H), 2.77-2.70 (m, 1H), 2.32 (s, 3H), 1.98 (d, J = 9.3 Hz, 1H), 1.83 (d, J = 8.8 Hz, 3H), 1.66 (s, 1H), 1.26-1.20 (m, 1H), 1.14 (dd, J = 13.5, 6.0 Hz, 1H). |

-continued

| Example | Procedure | Structure, name | Data |
|---|---|---|---|
| 342 | S | 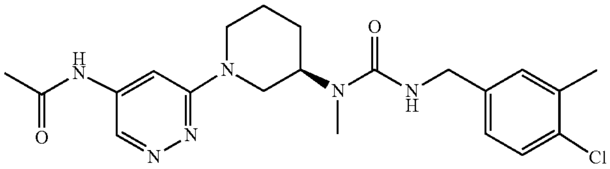 [SMILES: CC(=O)Nc1cnnc(N2CCC[C@@H](N(C)C(=O)NCc3ccc(Cl)c(C)c3)C2)c1] N-{6-[(3R)-3-({[(4-chloro-3-methylphenyl)methyl]carbamoyl}(methyl)amino)piperidin-1-yl]pyridazin-4-yl}acetamide | LC-MS: 431 (M + H). 1H NMR (400 MHz, MeOD) δ 8.53 (d, J = 2.0 Hz, 1H), 7.65 (d, J = 2.0 Hz, 1H), 7.29-7.20 (m, 2H), 7.10 (dd, J = 8.2, 1.7 Hz, 1H), 4.58 (s, 1H), 4.32 (s, 2H), 4.25 (t, J = 12.4 Hz, 2H), 4.08 (d, J = 8.3 Hz, 1H), 3.08-3.00 (m, 1H), 2.89 (s, 3H), 2.33 (s, 3H), 2.16 (s, 3H), 1.88 (dd, J = 9.8, 4.4 Hz, 3H), 1.68 (s, 1H). |
| 343 | R | 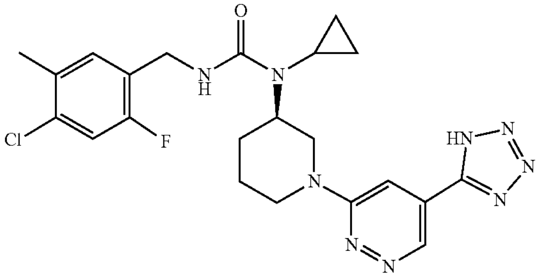 3-[(4-chloro-2-fluoro-5-methylphenyl)methyl]-1-cyclopropyl-1-[(3R)-1-[5-(1H-1,2,3,4-tetrazol-5-yl)pyridazin-3-yl]piperidin-3-yl]urea | LC-MS: 486 (M + H). 1H NMR (400 MHz, DMSO) δ 9.05 (d, J = 1.3 Hz, 1H), 7.74 (s, 1H), 7.34 (d, J = 9.8 Hz, 1H), 7.28 (d, J = 8.1 Hz, 1H), 6.91 (t, J = 5.9 Hz, 1H), 4.40 (t, J = 12.8 Hz, 2H), 4.29 (d, J = 5.7 Hz, 2H), 3.68 (d, J = 11.7 Hz, 1H), 3.34 (s, 1H), 2.89 (d, J = 11.6 Hz, 1H), 2.53 (d, J = 3.7 Hz, 1H), 2.29 (s, 3H), 2.19-2.10 (m, 1H), 1.83 (d, J = 12.3 Hz, 2H), 1.55 (d, J = 13.4 Hz, 1H), 0.91 (d, J = 6.6 Hz, 2H), 0.78-0.69 (m, 2H). |

General procedure R was used to prepare the final acids, amides or sulfonamides in the final step with the preceding General procedures in the following examples:

Examples 160 was prepared by General procedure C followed by General procedure R.

Examples 166, 192, 193, 201, 206, 212 were prepared by General procedure B followed by General procedure R.

Examples 335 was prepared by General procedure C followed by General procedure R.

Examples 200 was prepared by General procedure D followed by General procedure R.

General procedure S was used to prepare the final amines or amides in the final step with the preceding General procedures in the following example: Examples 180 was prepared by General procedure C, followed by General procedure S.

Representative compounds selected from above were tested in the isoleucine transport assay described in Example 1. The results are tabulated in FIG. 1.

General Procedure S'

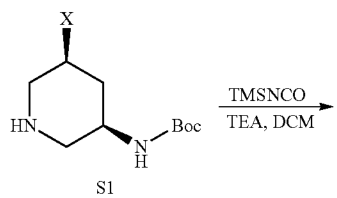

S1

-continued

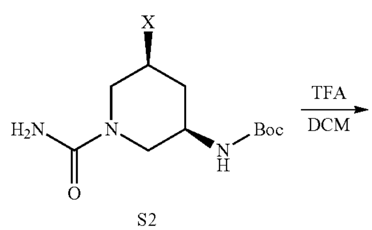

S2

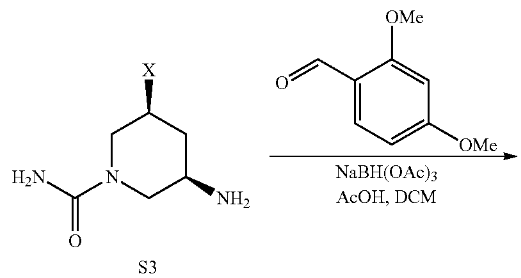

S3

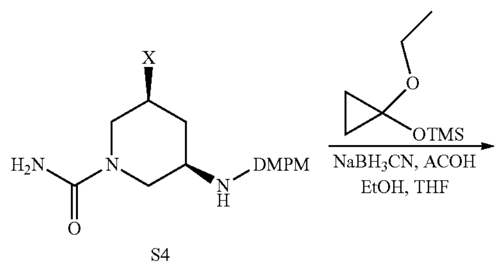

S4

-continued

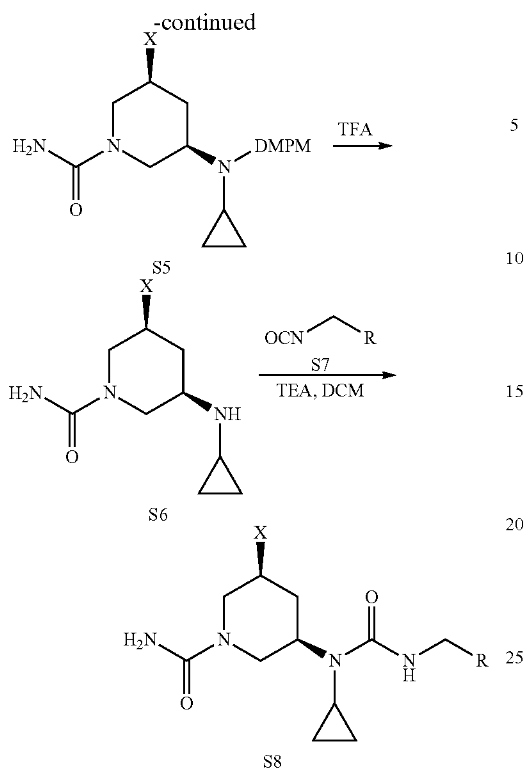

S5

S6

S8

Step 1: Synthesis of S2

To a mixture of compound S1 (1 eq) and TEA (4 eq) in anhydrous THF (0.05M) was added TMSNCO (1.5 eq) dropwise at 0° C. under $N_2$ atmosphere, and the resulting mixture was stirred at room temperature for 16 hours. The mixture was then poured into $H_2O$ and washed with EtOAc twice. The combined organic layers were dried over anhydrous $Na_2SO_4$, filtered and concentrated to dryness. The residue was purified via flash column chromatography (eluted with DCM:MeOH) to give compound S2.

Step 2: Synthesis of S3

S2 (1 eq) was dissolved in a solution of DCM/TFA 5:1 (0.1M) and the resulting mixture was stirred at room temperature for 2 hours. The mixture was then concentrated under reduced pressure to give crude compound S3 which was used for the next step without any further purification.

Step 3: Synthesis of S4

To a solution of S3 (1 eq) in anhydrous DCM (0.03M) were added 2,4-dimethoxybenzaldehyde (1.2 eq) and acetic acid (2 eq), and the resulting mixture was stirred at room temperature for 1 hour. $NaBH(OAc)_3$ (2 eq) was then added into the above mixture and the resulting mixture was stirred at 45° C. overnight. The mixture was then poured into 5% $Na_2CO_3$ solution and extracted with DCM (×4). The combined organic layers were dried over anhydrous $Na_2SO_4$, filtered and concentrated to dryness. The residue was purified via flash column chromatography (eluted with DCM/MeOH) to give compound S4

Step 4: Synthesis of S5

To a mixture of S4 (1 eq) and acetic acid (10 eq) in THF/EtOH 1:2 (0.03M) was added (1-ethoxycyclopropoxy) trimethylsilane (1.1 eq) followed by the addition of $NaBH_3CN$ (3 eq), and the resulting mixture was stirred at 80° C. for 16 hours under $N_2$ atmosphere. The mixture was then poured into 5% $Na_2CO_3$ solution and extracted with DCM (×3). The combined organic layers were dried over anhydrous $Na_2SO_4$, filtered and concentrated to dryness. The residue was purified via flash column chromatography (eluted with DCM/MeOH) to give compound S5.

Step 5: Synthesis of S6

S5 (1 eq) was added into TFA (0.1M) and the resulting mixture was stirred at 80° C. for 16 hours. The mixture was then concentrated under reduced pressure to dryness and the crude product was purified via flash column chromatography (eluted with DCM/MeOH) to give compound S6

Step 6: Synthesis of S8

To a solution of S6 (1 eq) in anhydrous DCM (0.03M) DIEA (3 eq) was added and the resulting mixture was stirred at 0° C. for 15 minutes before it was added into a mixture of the corresponding isocyanate S7 (1 eq) in anhydrous DCM (0.08M) at 0° C. under $N_2$ atmosphere. The resulting mixture was stirred from 0° C. to room temperature for 30 minutes. The mixture was then poured into saturated $NaHCO_3$ solution and extracted with DCM (×3). The combined organic layers were dried over anhydrous $Na_2SO_4$, filtered and concentrated to dryness. The residue was purified via prep-HPLC to give pure compound S8.

Synthesis of Example 346

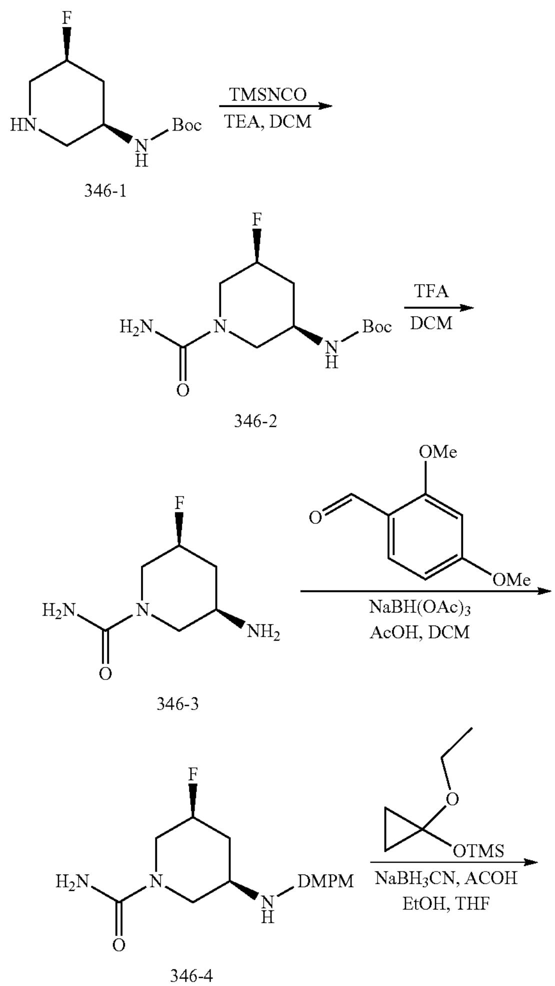

346-1

346-2

346-3

346-4

-continued

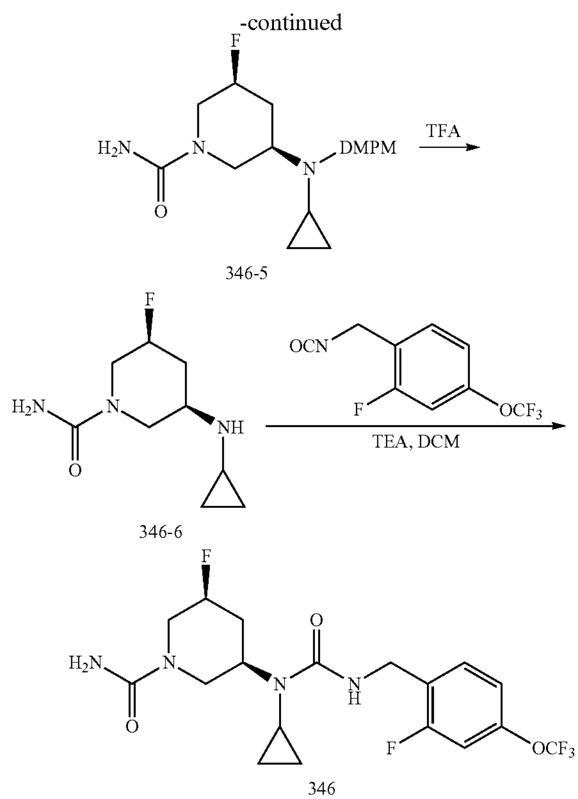

346-5

346-6

346

Step 1: Synthesis of 346-2

To a mixture of 346-1 (150 mg, 0.688 mmol) and TEA (278 mg, 2.752 mmol) in anhydrous THF (10 mL) was added TMSNCO (119 mg, 1.032 mmol) dropwise at 0° C. under $N_2$ atmosphere, and the resulting mixture was stirred at room temperature for 16 hrs. The mixture was then poured into $H_2O$ (50 mL) and washed with EtOAc (40 mL) twice. The combined organic layers were dried over anhydrous $Na_2SO_4$, filtered and concentrated to dryness. The residue was purified via flash column chromatography (eluted with DCM:MeOH=100:0 to 20:1) to give compound 346-2 (150 mg, 83.3% yield) as a white solid. LC/MS (ESI) m/z: 162 $(M-100+H)^+$.

Step 2: Synthesis of 346-3

To a solution of 346-2 (180 mg, 0.575 mmol) in DCM (5 mL) was added TFA (1 mL). The resulting mixture was stirred at room temperature for 2 hours. The mixture was then concentrated under reduced pressure to give crude compound 346-3 (158 mg, 99.0% yield) as a colorless oil which was used for the next step without any further purification. LC/MS (ESI) m/z: 162.2 $(M+H)^+$.

Step 3: Synthesis of 346-4

To a solution of 346-3 (158 mg, 0.575 mmol) in anhydrous DCM (15 mL) were added 2,4-dimethoxybenzaldehyde (115 mg, 0.693 mmol) and acetic acid (69 mg, 1.155 mmol). The mixture was then stirred at room temperature for 1 hour, before $NaBH(OAc)_3$ (244 mg, 1.155 mmol) was added into the above mixture and the resulting mixture was stirred at 45° C. overnight. The mixture was then poured into 5% $Na_2CO_3$ solution (50 mL) and extracted with DCM (30 mL×4). The combined organic layers were dried over anhydrous $Na_2SO_4$, filtered and concentrated to dryness. The residue was purified via flash column chromatography (eluted with DCM/MeOH=100:0 to 12:1) to give compound 346-4 (176 mg, 97.8% yield) as a colorless oil. LC/MS (ESI) m/z: 312 $(M+H)^+$.

Step 4: Synthesis of 346-5

To a mixture of 346-4 (176 mg, 0.566 mmol) and acetic acid (348 mg, 5.788 mmol) in THF (5 mL) and EtOH (10 mL) was added (1-ethoxycyclopropoxy)trimethylsilane (111 mg, 0.637 mmol) followed by the addition of $NaBH_3CN$ (109 mg, 1.736 mmol). The resulting mixture was stirred at 80° C. for 16 hours under $N_2$ atmosphere. The mixture was then poured into 5% $Na_2CO_3$ solution (50 mL) and extracted with DCM (30 mL×3). The combined organic layers were dried over anhydrous $Na_2SO_4$, filtered and concentrated to dryness. The residue was purified via flash column chromatography (eluted with DCM/MeOH=100:0 to 20:1) to give compound 346-5 (193 mg, 97.5% yield) as a colorless oil. LC/MS (ESI) m/z: 352 $(M+H)^+$.

Step 5: Synthesis of 346-6

346-5 (193 mg, 0.55 mmol) was added into TFA (5 mL) and the resulting mixture was stirred at 80° C. for 16 hours. The mixture was then concentrated under reduced pressure to dryness. The crude product was purified via flash column chromatography (eluted with DCM/MeOH=100:0 to 15:1) to give compound 346-6 (78 mg, 70.9% yield) as a colorless oil. LC/MS (ESI) m/z: 202 $(M+H)^+$.

Step 6: Synthesis of 346

To a solution of 346-6 (78 mg, 0.388 mmol) in anhydrous DCM (10 mL) DIEA (150 mg, 1.164 mmol) was added and the resulting mixture was stirred at 0° C. for 15 minutes before it was added into a mixture of 2-fluoro-1-(isocyanatomethyl)-4-(trifluoromethoxy)benzene (92 mg, 0.388 mmol) in anhydrous DCM (5 mL) at 0° C. under $N_2$ atmosphere. The resulting mixture was stirred from 0° C. to room temperature for 30 minutes. The mixture was then poured into saturated $NaHCO_3$ solution (50 mL) and extracted with DCM (30 mL×3). The combined organic layers were dried over anhydrous $Na_2SO_4$, filtered and concentrated to dryness. The residue was purified via prep-HPLC to give pure 346 (27 mg, 16.0% yield) as a white solid. LC/MS (ESI) m/z: 437.2 $(M+H)^+$. $^1H$ NMR (400 MHz, MeOD-d4) δ 7.43 (t, J=8.6 Hz, 1H), 7.09 (t, J=7.8 Hz, 2H), 7.00 (t, J=5.7 Hz, 1H), 4.59-4.37 (m, 3H), 4.30 (d, J=12.6 Hz, 1H), 3.84 (d, J=12.6 Hz, 1H), 3.69 (t, J=11.9 Hz, 1H), 3.18 (t, J=12.1 Hz, 1H), 2.72-2.63 (m, 1H), 2.59-2.53 (m, 1H), 2.37-2.24 (m, 2H), 1.01-0.92 (m, 2H), 0.83-0.73 (m, 2H).

General Procedure T

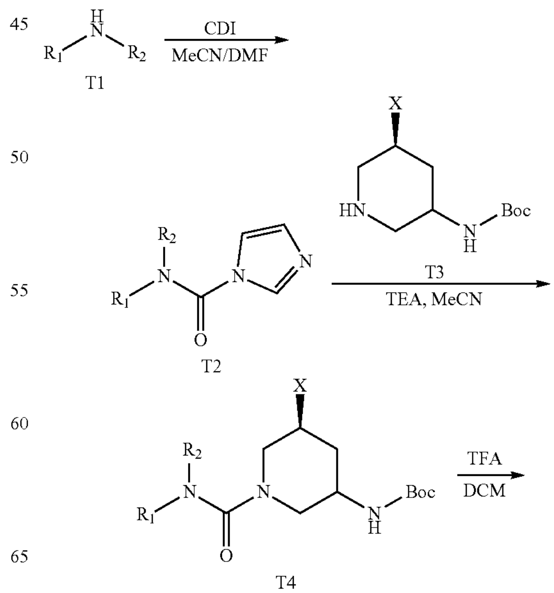

T1

T2

T4

-continued

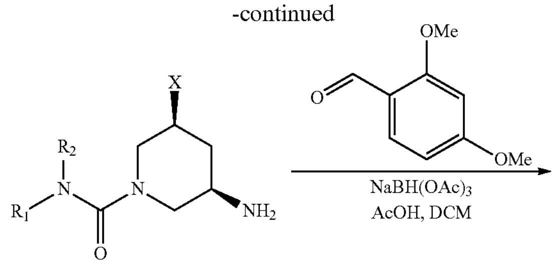

T5

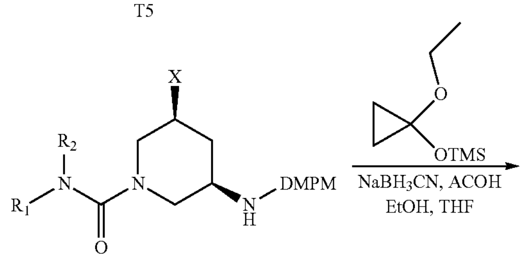

T6

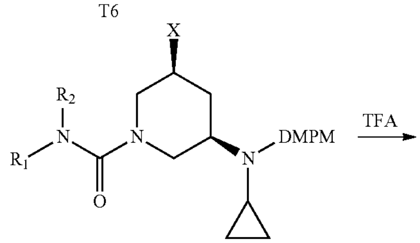

T7

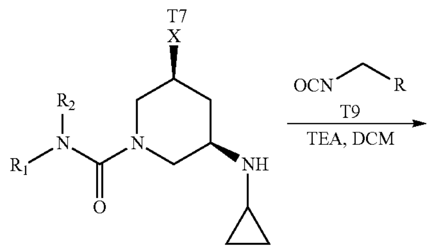

T8

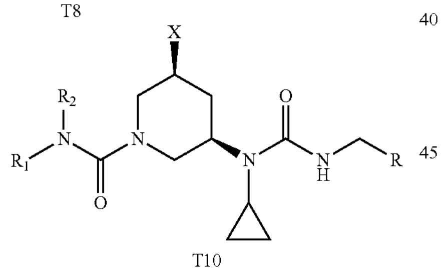

T10

Step 1: Synthesis of T2

To a mixture of the corresponding amine T1 (1 eq) in a mixture of MeCN/DMF 5:1 (0.4M) CDI (1 eq) was added at room temperature and the resulting mixture was stirred for 2 hours. The mixture was then concentrated under reduced pressure to give crude T2 which was used for the next step without any further purification.

Step 2: Synthesis of T4

To a mixture of T2 (0.5 eq) and the appropriate T3 (1 eq) in MeCN (0.15M) was added TEA (4 eq) and the resulting mixture was stirred at 50° C. for 16 hours. The mixture was then concentrated to dryness, and the residue was dissolved in EtOAc, and washed with water and brine. The organic layer was then dried over anhydrous $Na_2SO_4$, filtered and concentrated to dryness. The residue was purified via flash column chromatography (eluted with DCM: MeOH) to give T4.

Step 3 to Step 7 are the Same as Step 2 to Step 6 in the General Procedure S'.

Synthesis of Example 347

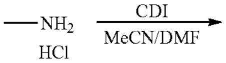

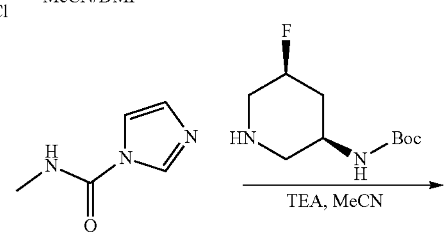

347-1

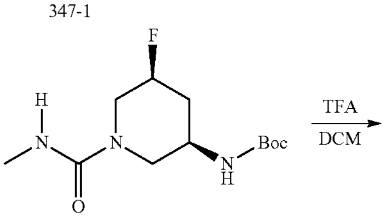

347-2

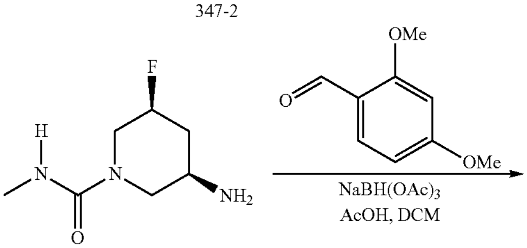

347-3

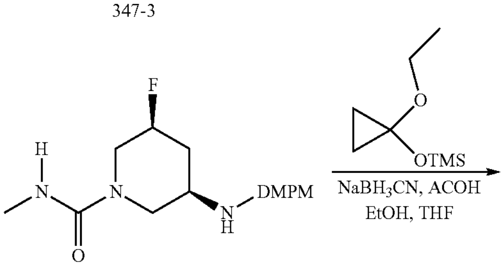

347-4

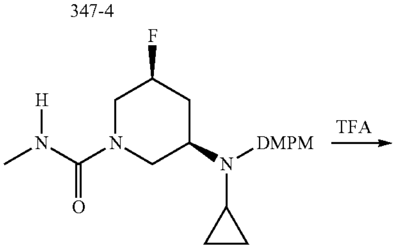

347-5

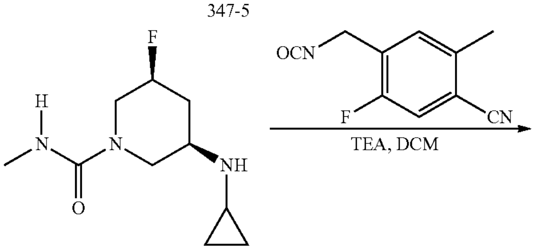

347-6

-continued

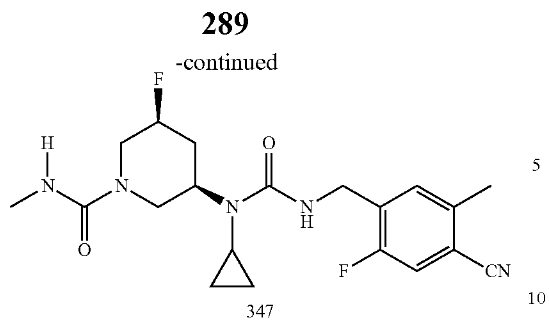

347

Step 1: Synthesis of 347-1

To a mixture of N-methylamine hydrochloride (310 mg, 4.591 mmol) in a mixture of MeCN (10 mL) and DMF (2 mL) was added CDI (744 mg, 4.588 mmol) at room temperature and the resulting mixture was stirred at room temperature for 2 hours. The mixture was then concentrated under reduced pressure to give crude 347-1 (550 mg, 95.74% yield) as a light-yellow oil which was used for the next step without any further purification. LC/MS (ESI) m/z: 126 $(M+H)^+$.

Step 2: Synthesis of 347-2

To a mixture of 347-1 (550 mg, 4.395 mmol) and tert-butyl ((3R,5S)-5-fluoropiperidin-3-yl)carbamate (480 mg, 2.199 mmol) in MeCN (15 mL) was added TEA (888 mg, 8.796 mmol) and the resulting mixture was stirred at 50° C. for 16 hours. The mixture was then concentrated to dryness, and the residue was dissolved in EtOAc (40 mL), and washed with water (50 mL) and brine (50 mL). The organic layer was then dried over anhydrous $Na_2SO_4$, filtered and concentrated to dryness. The residue was purified via flash column chromatography (eluted with DCM:MeOH=100:0 to 20:1) to give 347-2 (302 mg, 49.55% yield) as a colorless oil. LC/MS (ESI) m/z: 176 $(M-100+H)^+$.

Step 3 to Step 7 are the Same as Step 2 to Step 6 in the General Procedure S'

Compound 347 was obtained as a white solid. LC/MS (ESI) m/z: 406.2 $(M+H)^+$. $^1$H NMR (400 MHz, MeOD) δ 7.43 (d, J=9.6 Hz, 1H), 7.34 (d, J=7.1 Hz, 1H), 7.04 (t, J=5.9 Hz, 1H), 4.56-4.41 (m, 3H), 4.27 (d, J=12.4 Hz, 1H), 3.81 (d, J=12.6 Hz, 1H), 3.66 (t, J=11.0 Hz, 1H), 3.17-3.08 (m, 1H), 2.69 (s, 3H), 2.68-2.62 (m, 1H), 2.57 (dt, J=10.1, 3.4 Hz, 1H), 2.49 (s, 3H), 2.30 (m, 2H), 0.98-0.94 (m, 2H), 0.81-0.76 (m, 2H).

General Procedure U

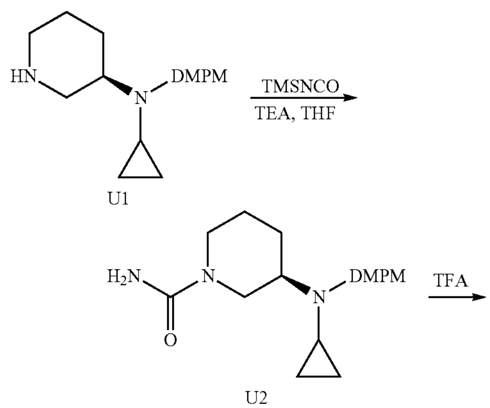

U1

U2

-continued

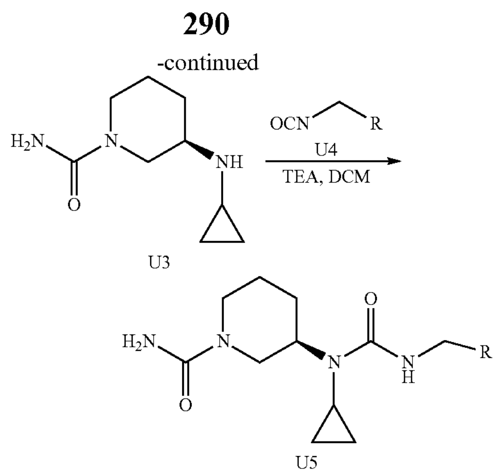

U3

U5

U1 was synthesized according to procedures P or Q through deprotection of the intermediates P5 and Q3 respectively.

Step 1: Synthesis of U2

To a mixture of compound U1 (11.5 g, 39.59 mmol) and TEA (27.5 mL, 197.95 mmol) in anhydrous THF (200 mL) was added isocyanatotrimethylsilane (11.98 g, 83.15 mmol) dropwise at 0° C. under $N_2$ atmosphere, and the resulting mixture was stirred at room temperature for 16 hours. The mixture was then concentrated under reduced pressure to dryness. The residue was diluted with EtOAc (300 mL), and washed with water and brine. The organic layer was then dried over anhydrous $Na_2SO_4$, filtered and concentrated to dryness. The crude product was purified by column chromatography on silica gel (eluted with DCM:MeOH=100:0 to 95:5) to afford compound U2 (10.0 g, 75.7% yield) as a light-yellow solid. LC/MS (ESI) m/z: 334 $(M+H)^+$.

Step 2: Synthesis of U3

Compound U2 (10 g, 29.99 mmol) was added into TFA (100 mL) portionwise at 0° C. under $N_2$ atmosphere, and the resulting mixture was then stirred at 80° C. for 4 hours. The reaction mixture was then cooled to room temperature and concentrated under reduced pressure to give crude compound U3 (5.48 g, 99.8% yield) as a purple oil which was used for the next step without any further purification. LC/MS (ESI) m/z: 184 $(M+H)^+$.

Step 3: Synthesis of U5

To a solution of U3 (1 eq) in anhydrous DCM (0.2M) a mixture of the appropriate isocyantae U4 (1 eq) and TEA (10 eq) in DCM (0.15M) was added dropwise at 0° C. under $N_2$ atmosphere. The resulting mixture was then stirred at room temperature for 1 hour and concentrated under reduced pressure to dryness. The residue was dissolved with EtOAc and washed with water and brine. The organic layer was then dried over anhydrous $Na_2SO_4$, filtered and concentrated to dryness. The crude product was purified by column chromatography on silica gel (eluted with DCM:MeOH) to afford U5.

Synthesis of Example 352

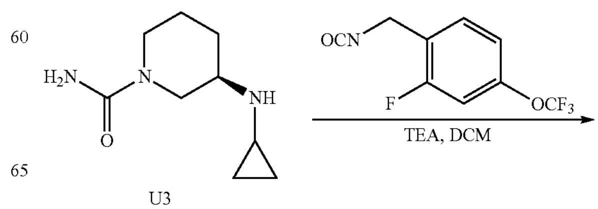

U3

-continued

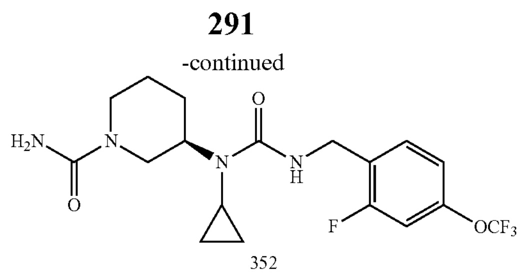

352

-continued

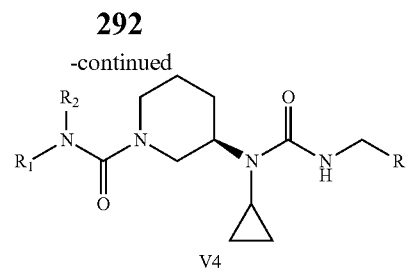

V4

To a solution of U3 (22.4 mg, 0.095 mmol) in anhydrous DCM (0.4 mL) a mixture of 2-fluoro-1-(isocyanatomethyl)-4-(trifluoromethoxy)benzene (17.4 mg, 0.095 mmol) and TEA (0.13 mL, 0.95 mmol) in DCM (0.6 mL) was added dropwise at 0° C. under $N_2$ atmosphere. The resulting mixture was stirred at room temperature for 1 hour and then concentrated under reduced pressure to dryness. The residue was dissolved in EtOAc (5 mL) and washed with water and brine. The organic layer was then dried over anhydrous $Na_2SO_4$, filtered and concentrated to dryness. The crude product was purified by column chromatography on silica gel (eluted with DCM:MeOH=100:0 to 95:5) to afford 352 (15 mg, 37.7% yield) as a white solid. LC/MS (ESI) m/z: 419.2 $(M+H)^+$. $^1$H NMR (400 MHz, MeOD) δ 7.43 (t, J=8.6 Hz, 1H), 7.09 (t, J=7.9 Hz, 2H), 6.93 (d, J=5.4 Hz, 1H), 4.43 (s, 2H), 4.02-3.86 (m, 2H), 3.69-3.59 (m, 1H), 3.18 (t, J=12.0 Hz, 1H), 2.67 (t, J=12.0 Hz, 1H), 2.59-2.49 (m, 1H), 2.18-2.05 (m, 1H), 1.94-1.84 (m, 1H), 1.80-1.71 (m, 1H), 1.59-1.45 (m, 1H), 1.00-0.89 (m, 2H), 0.82-0.71 (m, 2H).

General Procedure V:

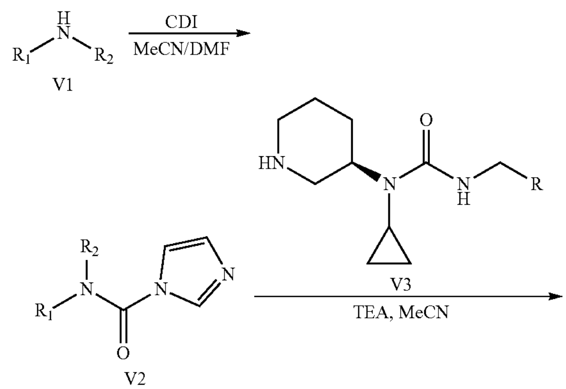

V1

V3

V2

V3 was synthesized using Procedure M or N

Step 1: Synthesis of V2

To a solution of the appropriate V1 (1 eq) in THF (0.3M) were added TEA (3 eq) and CDI (1.2 eq), and the resulting mixture was stirred at room temperature for 12 hours. The mixture was then concentrated under reduced pressure to dryness. The residue was dissolved in ethyl acetate, and washed with water and brine. The organic layer was then dried over anhydrous $Na_2SO_4$, filtered and concentrated to dryness. The crude product was purified by column chromatography on silica gel (eluting with PE:EtOAc) to afford compound V2.

Step 2: Synthesis of V4

Compound V2 (1.5 eq) was added to a mixture of compound V3 (1 eq) and TEA (3 eq) in DCM (0.05M), and the resulting mixture was stirred at 50° C. for 16 hours. The mixture was then concentrated under reduced pressure to dryness, and the residue was dissolved in EtOAc and washed with water and brine. The organic layer was then dried over anhydrous $Na_2SO_4$, filtered and concentrated to dryness. The crude product was purified by column chromatography on silica gel (eluting with PE:EtOAc) to afford compound V4.

Synthesis of Example 348

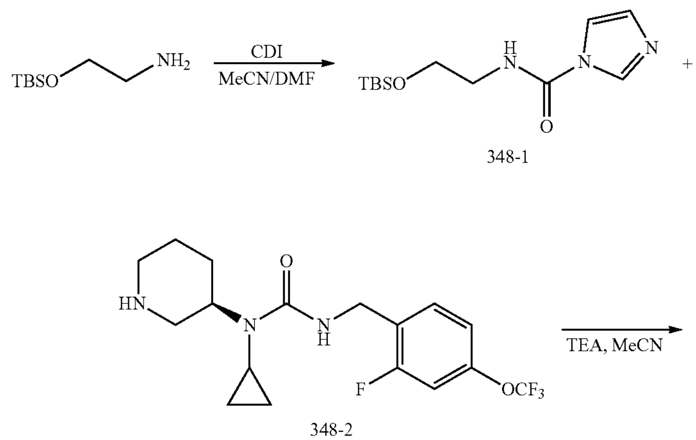

348-1

348-2

-continued

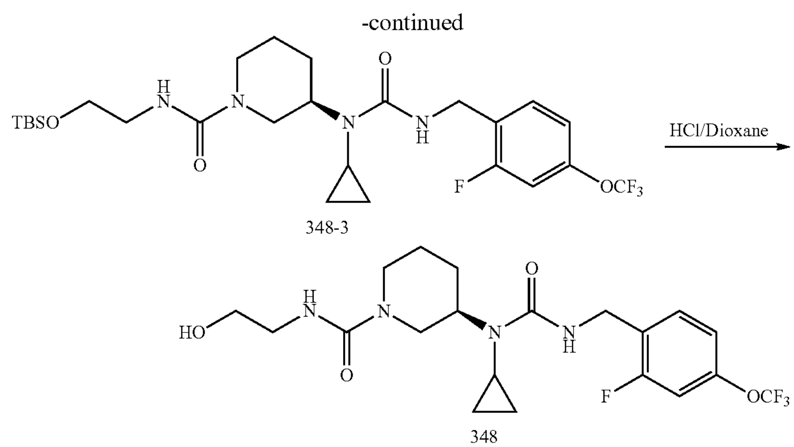

348-3

348

Step 1: Synthesis of 348-1

To a solution of 2-((tert-butyldimethylsilyl)oxy)ethan-1-amine (50 mg, 0.29 mmol) in THF (1 mL) were added TEA (86.5 mg, 0.86 mmol) and CDI (55 mg 0.34 mmol), and the resulting mixture was stirred at room temperature for 12 hours. The mixture was then concentrated under reduced pressure to dryness, and the residue was dissolved in ethyl acetate (5 mL) and washed with water (10 mL) and brine (10 mL). The organic layer was then dried over anhydrous $Na_2SO_4$, filtered and concentrated to dryness. The crude product was purified by column chromatography on silica gel (eluting with PE:EtOAc=100:0 to 4:1) to afford compound 348-1 (61 mg, 80.26% yield) as a white solid. LC/MS (ESI) m/z: 270 $(M+H)^+$.

Step 2: Synthesis of 348-3

Compound 348-1 (16 mg, 0.06 mmol) was added to a mixture of compound 348-2 (15 mg, 0.04) and TEA (12 mg, 0.12) in DCM (0.7 mL), and the resulting mixture was stirred at 50° C. for 16 hours. The mixture was then concentrated under reduced pressure to dryness, and the residue was dissolved in EtOAc (6 mL), and washed with water and brine. The organic layer was then dried over anhydrous $Na_2SO_4$, filtered and concentrated to dryness. The crude product was purified by column chromatography on silica gel (eluting with PE:EtOAc=100:0 to 1:1) to afford compound 348-3 (19.5 mg, 82.29% yield) as a yellow oil. LC/MS (ESI) m/z: 577 $(M+H)^+$.

Step 6: Synthesis of 348

Compound 348-3 (19.5 mg, 0.034 mmol) was added portionwise at 0° C. to HCl/dioxane (0.5 mL, 4 M) and the resulting mixture was stirred at room temperature for 1 hour. The mixture was then concentrated under reduced pressure and the residue was diluted with DCM/MeOH (15:1, 1 mL). A saturated $NaHCO_3$ solution was slowly added to bring the pH to 8-9, then the organic layer was separated, washed with water and brine, dried over anhydrous $Na_2SO_4$, filtered and concentrated to dryness. The residue was purified by column chromatography on silica gel (eluting with DCM: MeOH=100:0 to 20:1) to give 348 (15 mg, 96.2% yield) as a yellow oil. LC/MS (ESI) m/z: 463.3 $(M+H)^+$. $^1H$ NMR (400 MHz, MeOD) δ 7.43 (t, J=8.1 Hz, 1H), 7.08 (d, J=9.3 Hz, 2H), 4.51-4.34 (m, 2H), 3.94 (dd, J=30.8, 9.7 Hz, 2H), 3.62 (d, J=25.8 Hz, 3H), 3.28 (s, 2H), 3.14 (s, 1H), 2.70-2.66 (m, 1H), 2.55-2.51 (m, 1H), 2.11 (d, J=11.1 Hz, 1H), 1.94-1.90 (m, 1H), 1.77-1.73 (m, 1H), 1.53 (s, 1H), 0.97-0.93 (m, 2H), 0.76 (brs, 2H).

Examples 344-370

| Example | Procedure | Structure, name | Data |
|---|---|---|---|
| 344 | T (X = F) | 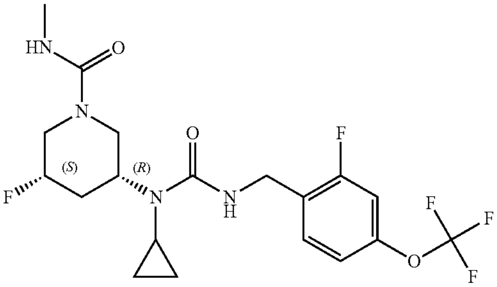 (3R,5S)-3-(1-cyclopropyl-3-(2-fluoro-4-(trifluoromethoxy)benzyl)ureido)-5-fluoro-N-methylpiperidine-1-carboxamide | LC-MS: 451.2 (M + H). 1H NMR (400 MHz, MeOD) δ 7.43 (t, J = 8.6 Hz, 1H), 7.09 (t, J = 7.8 Hz, 2H), 7.00 (s, 1H), 4.52-4.37 (m, 3H), 4.28 (d, J = 12.3 Hz, 1H), 3.81 (d, J = 11.8 Hz, 1H), 3.67 (t, J = 11.7 Hz, 1H), 3.13 (t, J = 12.0 Hz, 1H), 2.69 (s, 3H), 2.65 (s, 1H), 2.56 (dd, J = 6.7, 3.2 Hz, 1H), 2.28 (dd, J = 22.6, 11.2 Hz, 2H), 0.96 (d, J = 6.7 Hz, 2H), 0.77 (s, 2H). |

-continued

| Example | Procedure | Structure, name | Data |
|---|---|---|---|
| 345 | T (X = F) | 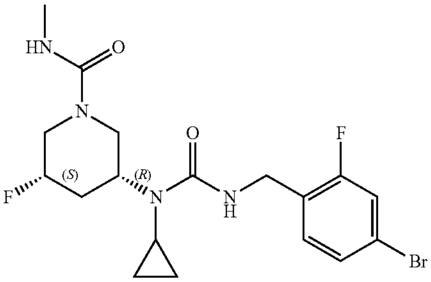 (3R,5S)-3-(3-(4-bromo-2-fluorobenzyl)-1-cyclopropylureido)-5-fluoro-N-methylpiperidine-1-carboxamide | LC-MS: 445.1 (M + H). 1H NMR (400 MHz, MeOD) δ 7.31 (t, J = 6.9 Hz, 2H), 7.26 (t, J = 8.1 Hz, 1H), 4.45 (d, J = 50.0 Hz, 3H), 4.28 (d, J = 12.8 Hz, 1H), 3.80 (d, J = 13.0 Hz, 1H), 3.66 (s, 1H), 3.13 (t, J = 12.0 Hz, 1H), 2.69 (s, 3H), 2.64 (dd, J = 16.6, 6.5 Hz, 1H), 2.57-2.52 (m, 1H), 2.27 (dd, J = 22.7, 11.3 Hz, 2H), 0.98-0.92 (m, 2H), 0.76 (s, 2H). |
| 346 | S' (X = F) | 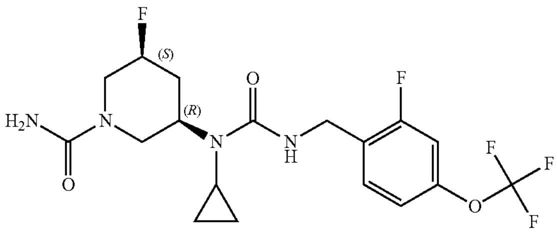 (3R,5S)-3-(1-cyclopropyl-3-(2-fluoro-4-(trifluoromethoxy)benzyl)ureido)-5-fluoropiperidine-1-carboxamide | LC-MS: 437.2 (M + H). 1H NMR (400 MHz, MeOD) δ 7.43 (t, J = 8.6 Hz, 1H), 7.09 (t, J = 7.8 Hz, 2H), 7.00 (t, J = 5.7 Hz, 1H), 4.59-4.37 (m, 3H), 4.30 (d, J = 12.6 Hz, 1H), 3.84 (d, J = 12.6 Hz, 1H), 3.69 (t, J = 11.9 Hz, 1H), 3.18 (t, J = 12.1 Hz, 1H), 2.72-2.63 (m, 1H), 2.59-2.53 (m, 1H), 2.37-2.24 (m, 2H), 1.01-0.92 (m, 2H), 0.83-0.73 (m, 2H). |
| 347 | T (X = F) | 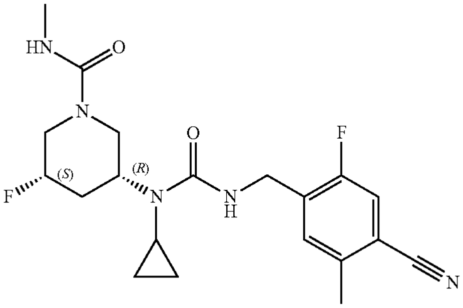 (3R,5S)-3-(3-(4-cyano-2-fluoro-5-methylbenzyl)-1-cyclopropylureido)-5-fluoro-N-methylpiperidine-1-carboxamide | LC-MS: 406.2 (M + H). 1H NMR (400 MHz, MeOD) δ 7.43 (d, J = 9.6 Hz, 1H), 7.34 (d, J = 7.1 Hz, 1H), 7.04 (t, J = 5.9 Hz, 1H), 4.56-4.41 (m, 3H), 4.27 (d, J = 12.4 Hz, 1H), 3.81 (d, J = 12.6 Hz, 1H), 3.66 (t, J = 11.0 Hz, 1H), 3.17-3.08 (m, 1H), 2.69 (s, 3H), 2.68-2.62 (m, 1H), 2.57 (dt, J = 10.1, 3.4 Hz, 1H), 2.49 (s, 3H), 2.30 (m, 2H), 0.98-0.94 (m, 2H), 0.81-0.76 (m, 2H). |
| 348 | V | 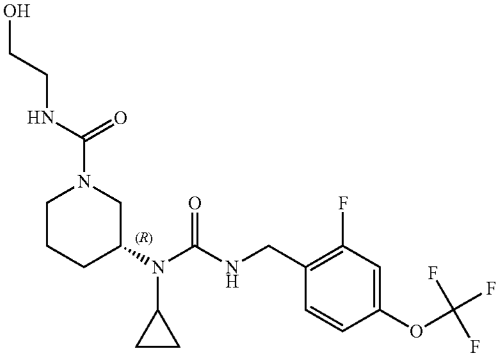 (R)-3-(1-cyclopropyl-3-(2-fluoro-4-(trifluoromethoxy)benzyl)ureido)-N-(2-hydroxyethyl)piperidine-1-carboxamide | LC-MS: 463.3 (M + H). 1H NMR (400 MHz, MeOD) δ 7.43 (t, J = 8.1 Hz, 1H), 7.08 (d, J = 9.3 Hz, 2H), 4.51-4.34 (m, 2H), 3.94 (dd, J = 30.8, 9.7 Hz, 2H), 3.62 (d, J = 25.8 Hz, 3H), 3.28 (s, 2H), 3.14 (s, 1H), 2.70-2.66 (m, 1H), 2.55-2.51 (m, 1H), 2.11 (d, J = 11.1 Hz, 1H), 1.94-1.90 (m, 1H), 1.77-1.73 (m, 1H), 1.53 (s, 1H), 0.97-0.93 (m, 2H), 0.76 (brs, 2H). |

-continued

| Example | Procedure | Structure, name | Data |
|---|---|---|---|
| 349 | O | 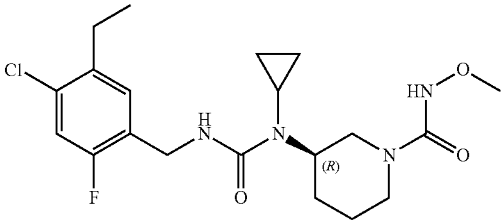 (R)-3-(3-(4-chloro-5-ethyl-2-fluorobenzyl)-1-cyclopropylureido)-N-methoxypiperidine-1-carboxamide | LC-MS: 427.2 (M + H). 1H NMR (400 MHz, MeOD) δ 7.25 (d, J = 8.1 Hz, 1H), 7.13 (d, J = 9.8 Hz, 1H), 6.89 (t, J = 5.3 Hz, 1H), 4.38 (s, 2H), 3.85 (dd, J = 32.8, 12.9 Hz, 2H), 3.65-3.57 (m, 4H), 3.17 (t, J = 12.0 Hz, 1H), 2.72 (q, J = 7.5 Hz, 2H), 2.65 (dd, J = 14.4, 12.1 Hz, 1H), 2.56-2.50 (m, 1H), 2.11 (tt, J = 12.5, 6.4 Hz, 1H), 1.82 (dd, J = 47.9, 13.0 Hz, 2H), 1.50 (q, J = 13.2 Hz, 1H), 1.21 (t, J = 7.5 Hz, 3H), 0.98-0.91 (m, 2H), 0.74 (d, J = 3.4 Hz, 2H). |
| 350 | N | 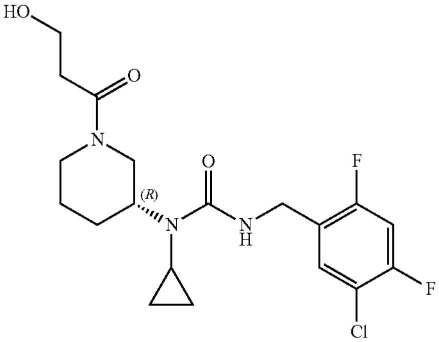 (R)-3-(5-chloro-2,4-difluorobenzyl)-1-cyclopropyl-1-(1-(3-hydroxypropanoyl)piperidin-3-yl)urea | LC-MS: 416.4 (M + H). 1H NMR (400 MHz, DMSO-d6) δ 7.53-7.37 (m, 2H), 6.99-6.81 (m, 1H), 4.39-4.20 (m, 3H), 3.86-3.68 (m, 1H), 3.59 (t, J = 6.6 Hz, 2H), 3.21-3.15 (m, 1H), 2.81 (t, J = 11.9 Hz, 1H), 2.46-2.40 (m, 2.5H), 2.38-2.27 (m, 0.5H), 2.04-1.97 m, 1H), 1.86-1.61 (m, 2H), 1.42-1.21 (m, 1H), 0.89-0.84 (m, 2H), 0.73-0.53 (m, 2H). |
| 351 | T (X = F) | 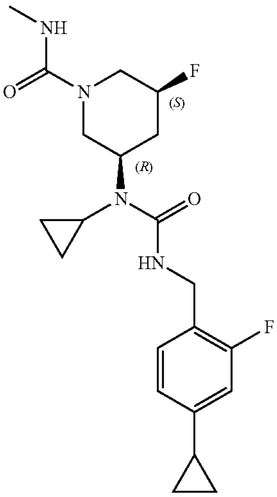 (3R,5S)-3-(1-cyclopropyl-3-(4-cyclopropyl-2-fluorobenzyl)ureido)-5-fluoro-N-methylpiperidine-1-carboxamide | LC-MS: 407.2 (M + H). 1H NMR (400 MHz, MeOD) δ 7.18 (t, J = 8.0 Hz, 1H), 6.86 (dd, J = 7.9, 1.3 Hz, 1H), 6.80 (t, J = 5.9 Hz, 1H), 6.76 (d, J = 11.8 Hz, 1H), 4.55-4.39 (m, 1H), 4.37 (s, 2H), 4.29 (d, J = 12.3 Hz, 1H), 3.79 (d, J = 12.8 Hz, 1H), 3.67 (t, J = 11.6 Hz, 1H), 3.13 (t, J = 12.0 Hz, 1H), 2.69 (s, 3H), 2.64 (dd, J = 16.6, 6.4 Hz, 1H), 2.56-2.49 (m, 1H), 2.29 (dt, J = 22.9, 8.5 Hz, 2H), 1.94-1.85 (m, 1H), 0.99-0.90 (m, 4H), 0.68 (ddd, J = 17.9, 9.7, 4.1 Hz, 4H). |

-continued

| Example | Procedure | Structure, name | Data |
|---|---|---|---|
| 352 | S' (X = H) | 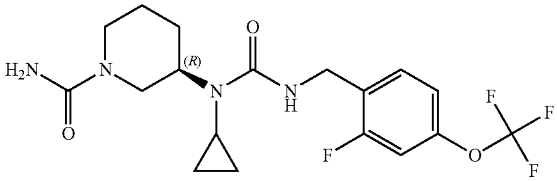 (R)-3-(1-cyclopropyl-3-(2-fluoro-4-(trifluoromethoxy)benzyl)ureido)piperidine-1-carboxamide | LC-MS: 419.2 (M + H). 1H NMR (400 MHz, MeOD) δ 7.43 (t, J = 8.6 Hz, 1H), 7.09 (t, J = 7.9 Hz, 2H), 6.93 (d, J = 5.4 Hz, 1H), 4.43 (s, 2H), 4.02-3.86 (m, 2H), 3.69-3.59 (m, 1H), 3.18 (t, J = 12.0 Hz, 1H), 2.67 (t, J = 12.0 Hz, 1H), 2.59-2.49 (m, 1H), 2.18-2.05 (m, 1H), 1.94-1.84 (m, 1H), 1.80-1.71 (m, 1H), 1.59-1.45 (m, 1H), 1.00-0.89 (m, 2H), 0.82-0.71 (m, 2H). |
| 353 | N | 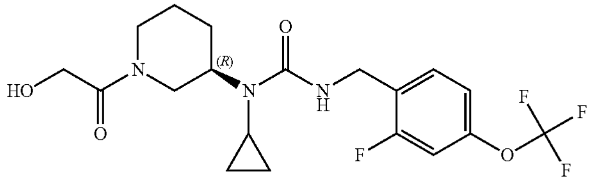 (R)-1-cyclopropyl-3-(2-fluoro-4-(trifluoromethoxy)benzyl)-1-(1-(2-hydroxyacetyl)piperidin-3-yl)urea | LC-MS: 434.4 (M + H). $^1$H NMR (400 MHz, dmso) δ 7.41 (t, J = 8.2 Hz, 1H), 7.30 (d, J = 10.7 Hz, 1H), 7.20 (d, J = 8.6 Hz, 1H), 6.90 (s, 1H), 4.44 (t, J = 5.4 Hz, 1H), 4.30 (d, J = 5.8 Hz, 3H), 4.03 (d, J = 5.4 Hz, 2H), 3.63-3.41 (m, 2H), 2.94-2.74 (m, 1H), 2.43 (s, 2H), 2.01 (d, J = 9.9 Hz, 1H), 1.83-1.63 (m, 2H), 1.32 (s, 1H), 0.87 (d, J = 6.6 Hz, 2H), 0.65 (d, J = 10.7 Hz, 2H). |
| 354 | O | 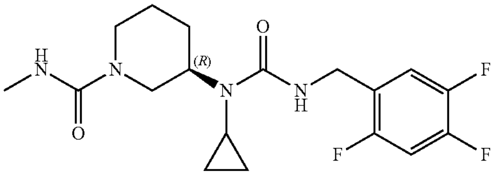 (R)-3-(1-cyclopropyl-3-(2,4,5-trifluorobenzyl)ureido)-N-methylpiperidine-1-carboxamide | LC-MS: 385.4 (M + H). 1H NMR (400 MHz, dmso) δ 7.52-7.41 (m, 1H), 7.35-7.24 (m, 1H), 6.88 (t, 1H), 6.32 (m, 1H), 4.26 (d, 2H), 3.89-3.78 (m, 2H), 3.50-3.40 (m, 1H), 2.95 (t, 1H), 2.54 (d, 3H), 2.48-2.42 (m, 2H), 1.93 (ddd, 1H), 1.76-1.58 (m, 2H), 1.37-1.25 (m, 1H), 0.90-0.83 (m, 2H), 0.66-0.60 (m, 2H). |
| 355 | N | 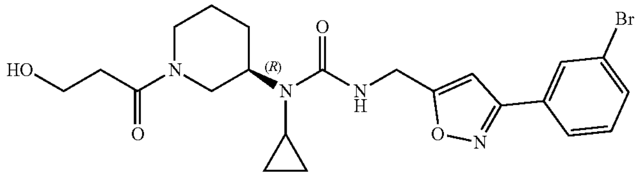 (R)-3-((3-(3-bromophenyl)isoxazol-5-yl)methyl)-1-cyclopropyl-1-(1-(3-hydroxypropanoyl)piperidin-3-yl)urea | LC-MS: 491.2 (M + H). 1H NMR (400 MHz, DMSO-d6) δ 8.05 (dd, J = 1.8, 1.8 Hz, 1H), 7.88 (dd, J = 7.9, 1.2 Hz, 1H), 7.68 (dd, J = 8.1, 1.2 Hz, 1H), 7.46 (dd, J = 7.9, 7.9 Hz, 1H), 7.05-6.98 (m, 1H), 6.87 (d, J = 4.6 Hz, 1H), 4.42 (t, J = 6.4 Hz, 2H), 4.39-4.28 (m, 1H), 3.87-3.70 (m, 1H), 3..61-3.5 (m, 2H), 3.25-3.14 (m, 2H), 2.82 (t, J = 12.0 Hz, 1H), 2.46-2.42 (m, 2.5H), 2.40-2.29 (m, 0.5H), 2.05-1.99 (m, 1H), 1.88-1.62 (m, 2H), 1.40-1.26 (m, 1H), 0.90-0.85 (m, 2H), 0.77-0.61 (m, 2H). |

-continued

| Example | Procedure | Structure, name | Data |
|---|---|---|---|
| 356 | M | 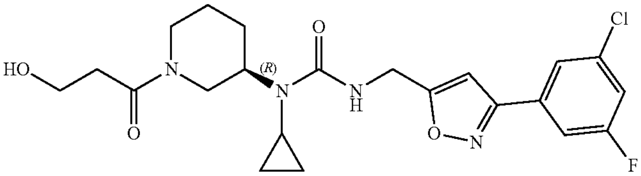 (R)-3-((3-(3-chloro-5-fluorophenyl)isoxazol-5-yl)methyl)-1-cyclopropyl-1-(1-(3-hydroxypropanoyl)piperidin-3-yl)urea | LC-MS: 465.2 (M + H). 1H NMR (400 MHz, MeOD) δ 7.72 (s, 1H), 7.57 (d, J = 9.2 Hz, 1H), 7.33 (dd, J = 8.5, 1.8 Hz, 1H), 7.22-7.12 (m, 1H), 6.74 (d, J = 4.4 Hz, 1H), 4.53 (d, J = 5.2 Hz, 2H), 4.50 (s, 1H), 4.33 (s, 1H), 4.03-3.90 (m, 1H), 3.81 (t, J = 6.3 Hz, 2H), 3.77-3.69 (m, 1H), 3.58-3.49 (m, 1H), 3.15-2.93 (m, 1H), 2.71-2.46 (m, 4H), 2.27-2.14 (m, 1H), 2.02-1.87 (m, 1H), 1.81 (d, J = 6.9 Hz, 1H), 1.60-1.43 (m, 1H), 1.04-0.93 (m, 2H), 0.88-0.73 (m, 2H). |
| 357 | N | 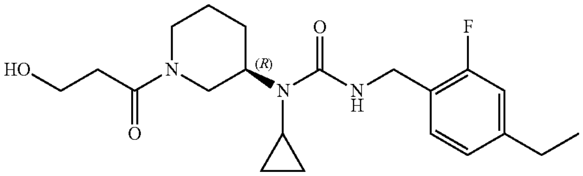 (R)-1-cyclopropyl-3-(4-ethyl-2-fluorobenzyl)-1-(1-(3-hydroxypropanoyl)piperidin-3-yl)urea | LC-MS: 392.4 (M + H). $^1$H NMR (400 MHz, dmso) δ 7.21 (q, J = 7.7 Hz, 1H), 7.03-6.96 (m, 2H), 6.82-6.71 (m, 1H), 4.45 (q, J = 5.6 Hz, 1H), 4.36 (d, J = 13.7 Hz, 1H), 4.27 (d, J = 5.5 Hz, 2H), 3.85-3.72 (m, 1H), 3.61 (q, J = 5.9 Hz, 2H), 3.57-3.39 (m, 1H), 3.20 (t, J = 12.0 Hz, 1H), 2.83 (t, J = 11.7 Hz, 1H), 2.59 (q, J = 7.6 Hz, 2H), 2.45 (t, J = 6.6 Hz, 3H), 2.10-1.95 (m, 1H), 1.84-1.66 (m, 2H), 1.45-1.23 (m, 1H), 1.16 (t, J = 7.6 Hz, 3H), 0.87 (d, J = 4.8 Hz, 2H), 0.73-0.57 (m, 2H). |
| 358 | N | 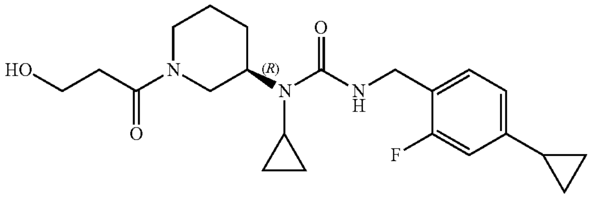 (R)-1-cyclopropyl-3-(4-cyclopropyl-2-fluorobenzyl)-1-(1-(3-hydroxypropanoyl)piperidin-3-yl)urea | LC-MS: 404.4 (M + H). 1H NMR (400 MHz, DMSO-d6) δ 7.15 (dd, J = 7.7, 7.7 Hz, 1H), 6.90-6.79 (m, 2H), 6.76-6.69 (m, 1H), 4.38-4.17 (m, 3H), 3.84-3.66 (m, 1H), 3.64-3.48 (m, 2.5H), 3.45-3.38 (m, 0.5H), 3.22-3.11 (m, 1H), 2.84-2.77 (m, 1H), 2.45-2.36 (m, 2.5H), 2.35-2.29 (m, 0.5H), 2.04-1.93 (m, 1H), 1.92-1.85 (mz, 1H), 1.83-1.60 (m, 2H), 1.43-1.16 (m, 1H), 0.95-0.78 (m, 4H), 0.71-0.52 (m, 4H). |
| 359 | N | 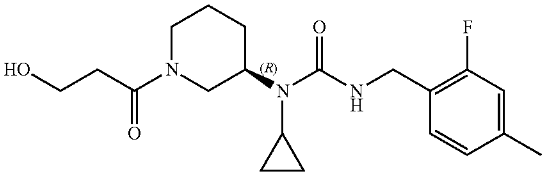 (R)-1-cyclopropyl-3-(2-fluoro-4-methylbenzyl)-1-(1-(3-hydroxypropanoyl)piperidin-3-yl)urea | LC-MS: 378.4 (M + H). $^1$H NMR (400 MHz, dmso) δ 7.22-7.12 (m, 1H), 6.96 (s, 1H), 6.94 (d, J = 4.7 Hz, 1H), 6.74 (d, J = 15.6 Hz, 1H), 4.42 (t, J = 5.6 Hz, 1H), 4.34 (d, J = 16.7 Hz, 1H), 4.25 (d, J = 5.7 Hz, 2H), 3.84-3.70 (m, 1H), 3.59 (q, J = 6.0 Hz, 2H), 3.54 (s, 1H), 3.18 (t, J = 12.0 Hz, 1H), 2.81 (t, J = 11.8 Hz, 1H), 2.43 (t, J = 6.4 Hz, 3H), 2.27 (s, 3H), 2.01 (s, 1H), 1.70 (s, 2H), 1.44-1.19 (m, 1H), 0.85 (d, J = 4.6 Hz, 2H), 0.70-0.56 (m, 2H). |

-continued

| Example | Procedure | Structure, name | Data |
|---|---|---|---|
| 360 | N | 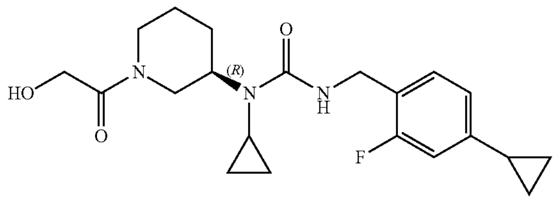 (R)-1-cyclopropyl-3-(4-cyclopropyl-2-fluorobenzyl)-1-(1-(2-hydroxyacetyl)piperidin-3-yl)urea | LC-MS: 390.4 (M + H). 1H NMR (400 MHz, DMSO-d6) δ 7.19-7.10 (m, 1H), 6.90-6.78 (m, 2H), 6.76-6.71 (m, 1H), 4.31-4.19 (m, 3H), 4.08-3.99 (m, 2H), 3.17 (t, J = 12.8 Hz, 0.5H), 2.89 (t, J = 11.7 Hz, 0.5H), 2.77 (t, J = 13.6 Hz, 0.5H), 2.46-2.39 (m, 1.5H), 2.08-1.96 (m, 1H), 1.92-1.85 (m, 1H), 1.81-1.67 (m, 2H), 1.44-1.29 (m, 1H), 0.96-0.78 (m, 4H), 0.68-0.51 (m, 4H). |
| 361 | O | 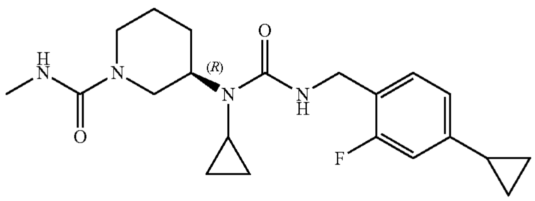 (R)-3-(1-cyclopropyl-3-(4-cyclopropyl-2-fluorobenzyl)ureido)-N-methylpiperidine-1-carboxamide | LC-MS: 389.3 (M + H). 1H NMR (400 MHz, DMSO-d6) δ 7.14 (dd, J = 8.0, 8.0 Hz, 1H), 6.87 (dd, J = 7.9, 1.8 Hz, 1H), 6.81 (dd, J = 11.8, 1.7 Hz, 1H), 6.72-6.69 (m, 1H), 6.32-6.29 (m, 1H), 4.24 (d, J = 5.8 Hz, 2H), 3.91-3.73 (m, 2H), 3.49-3.41 (m, 1H), 2.93 (t, J = 11.8 Hz, 1H), 2.52 (d, J = 4.3 Hz, 3H), 2.49-2.47 (m, 1H), 2.45-3.38 (m, 2H), 1.97-1.85 (m, 2H), 1.76-1.65 (m, 1H), 1.63-1.58 (m, 1H), 1.38-1.21 (m, 1H), 0.95-0.88 (m, 2H), 0.87-0.82 (m, 2H), 0.67-0.59 (m, 4H). |
| 362 | N | 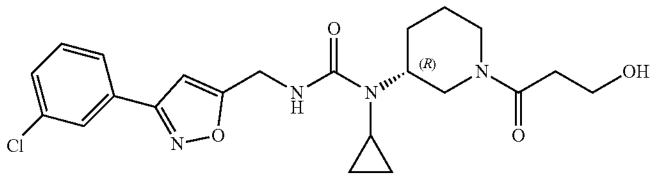 (R)-3-((3-(3-chlorophenyl)isoxazol-5-yl)methyl)-1-cyclopropyl-1-(1-(3-hydroxypropanoyl)piperidin-3-yl)urea | LC-MS: 447.3 (M + H). 1H NMR (400 MHz, DMSO-d6) δ 7.92 (d, J = 2.0 Hz, 1H), 7.84 (dt, J = 6.8, 1.8 Hz, 1H), 7.61-7.43 (m, 2H), 7.06-6.99 (m, 1H), 6.87 (d, J = 4.9 Hz, 1H), 4.42 (t, J = 6.4 Hz, 2H), 4.39-4.27 (m, 1H), 3.82-3.74 (m, 1H), 3.61-3.51 (m, 2H), 3.18 (t, J = 12.0 Hz, 1H), 2.82 (t, J = 11.9 Hz, 1H), 2.46-2.42 (m, 2H), 2.40-2.25 (m, 1H), 2.11-1.94 (m, 1H), 1.88-1.64 (m, 2H), 1.53-1.14 (m, 1H), 0.90-0.86 (m, 3H), 0.76-0.63 (m, 2H). |
| 363 | N | 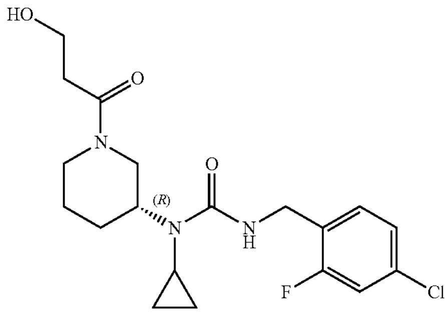 (R)-3-(4-chloro-2-fluorobenzyl)-1-cyclopropyl-1-(1-(3-hydroxypropanoyl)piperidin-3-yl)urea | LC-MS: 398.3 (M + H). 1H NMR (400 MHz, DMSO-d6) δ 7.37-7.27 (m, 2H), 7.26-7.23 (m, 1H), 6.89-6.83 (m, 1H), 4.45-4.41 (m, 1H), 4.38-4.24 (m, 3H), 3.76 (dd, J = 28.6, 13.2 Hz, 1H), 3.63-3.48 (m, 2.25H), 3.47-3.36 (m, 0.25H), 3.18 (t, J = 12.0 Hz, 0.5H), 2.81 (t, J = 12.0 Hz, 1H), 2.46-2.39 (m, 2.5H), 2.38-2.28 (m, 0.5H), 2.09-1.92 (m, 1H), 1.85-1.62 (m, 2H), 1.39-1.25 (m, 1H), 0.89-0.83 (m, 2H), 0.72-0.56 (m, 2H). |

-continued

| Example | Procedure | Structure, name | Data |
|---|---|---|---|
| 364 | N | 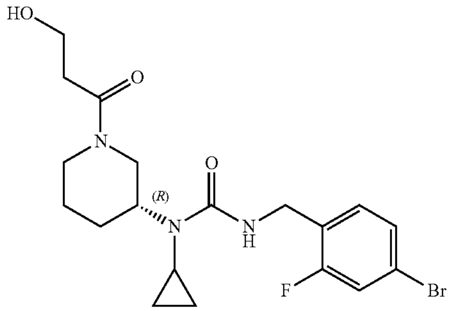 (R)-3-(4-bromo-2-fluorobenzyl)-1-cyclopropyl-1-(1-(3-hydroxypropanoyl)piperidin-3-yl)urea | LC-MS: 442.3 (M + H). 1H NMR (400 MHz, DMSO-d6) δ 7.45 (d, J = 9.9, 1H), 7.40-7.35 (m, 1H), 7.28-7.22 (m, 1H), 6.89-6.83 (m, 1H), 4.47-4.38 (m, 1H), 4.37-4.21 (m, 3H), 3.85-3.68 (m, 1H), 3.64-3.48 (m, 2.5H), 3.47-3.36 (m, 0.5H), 3.21-3.15 (m, 0.5H), 2.81 (dd, J = 13.3, 10.6 Hz, 1H), 2.46-2.39 (m, 2H), 2.36-2.30 (m, 0.5H), 2.04-1.97 (m, 1H), 1.84-1.62 (m, 2H), 1.45-1.18 (m, 1H), 0.88-0.83 (m, 2H), 0.72-0.55 (m, 2H). |
| 365 | O | 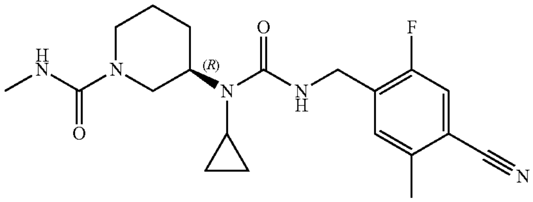 (R)-3-(3-(4-cyano-2-fluoro-5-methylbenzyl)-1-cyclopropylureido)-N-methylpiperidine-1-carboxamide | LC-MS: 388.3 (M + H). 1H NMR (400 MHz, MeOD) δ 7.42 (d, J = 9.6 Hz, 1H), 7.34 (d, J = 7.1 Hz, 1H), 6.98 (t, J = 5.8 Hz, 1H), 4.44 (d, J = 4.4 Hz, 2H), 3.98-3.84 (m, 2H), 3.61 (tt, J = 11.8, 3.9 Hz, 1H), 3.14 (t, J = 12.0 Hz, 1H), 2.70 (s, 3H), 2.64 (td, J = 13.1, 2.5 Hz, 1H), 2.57-2.51 (m, 1H), 2.49 (s, 3H), 2.10 (qd, J = 12.5, 4.0 Hz, 1H), 1.88 (d, J = 12.1 Hz, 1H), 1.74 (d, J = 13.3 Hz, 1H), 1.55-1.42 (m, 1H), 1.00-0.92 (m, 2H), 0.80-0.71 (m, 2H). |
| 366 | N | 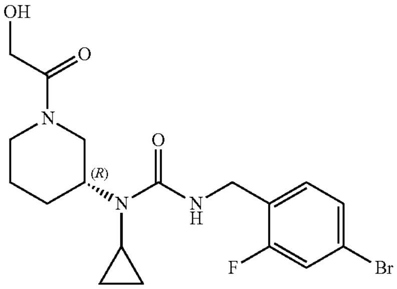 (R)-3-(4-bromo-2-fluorobenzyl)-1-cyclopropyl-1-(1-(2-hydroxyacetyl)piperidin-3-yl)urea | LC-MS: 428.3 (M + H). 1H NMR (400 MHz, DMSO-d6) δ 7.45 (dd, J = 9.8, 2.0 Hz, 1H), 7.37 (dd, J = 8.2, 1.9 Hz, 1H), 7.25 (dd, J = 8.2, 8.2 Hz, 1H), 6.89-6.84 (m, 1H), 4.25 (d, J = 6.1 Hz, 3H), 4.03 (brs, 2H), 3.60-3.42 (m, 2.5H), 3.17 (t, J = 12.9 Hz, 0.5H), 2.89 (t, J = 11.8 Hz, 0.5H), 2.82-2.70 (m, 0.5H), 2.46-2.40 (m, 1H), 2.11-1.93 (m, 1H), 1.82-1.67 (m, 2H), 1.44-1.29 (m, 1H), 0.88-0.82 (m, 2H), 0.70-0.54 (m, 2H). |
| 367 | O | 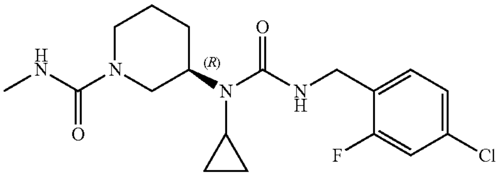 (R)-3-(3-(4-chloro-2-fluorobenzyl)-1-cyclopropylureido)-N-methylpiperidine-1-carboxamide | LC-MS: 383.3 (M + H). 1H NMR (400 MHz, DMSO) δ 7.39-7.34 (m, 1H), 7.31 (d, J = 8.1 Hz, 1H), 7.26 (dd, J = 8.3, 1.9 Hz, 1H), 6.89 (t, J = 5.8 Hz, 1H), 6.35 (d, J = 4.3 Hz, 1H), 4.28 (d, J = 5.8 Hz, 2H), 3.84 (t, J = 15.6 Hz, 2H), 3.52-3.39 (m, 2H), 2.95 (t, J = 11.8 Hz, 1H), 2.54 (d, J = 4.3 Hz, 3H), 2.48-2.40 (m, 2H), 1.93 (dd, J = 13.0, 4.3 Hz, 1H), 1.67 (dd, J = 40.5, 12.6 Hz, 2H), 1.34-1.28 (m, 1H), 0.91-0.83 (m, 2H), 0.64 (dd, J = 6.2, 3.6 Hz, 2H). |

-continued

| Example | Procedure | Structure, name | Data |
|---|---|---|---|
| 368 | V | 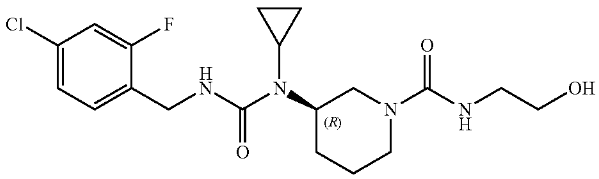 (R)-3-(3-(4-chloro-2-fluorobenzyl)-1-cyclopropylureido)-N-(2-hydroxyethyl)piperidine-1-carboxamide | LC-MS: 413.3 (M + H). 1H NMR (400 MHz, DMSO-d6) δ 7.36-7.27 (m, 2H), 7.24 (dd, J = 8.2, 2.0 Hz, 1H), 6.84 (t, J = 5.9 Hz, 1H), 6.37 (t, J = 5.5 Hz, 1H), 4.26 (d, J = 5.8 Hz, 2H), 3.91-3.77 (m, 2H), 3.50-3.42 (m, 1H), 3.35 (t, J = 6.3 Hz, 3H), 3.05 (q, J = 6.1 Hz, 2H), 2.94 (t, J = 11.8 Hz, 1H), 2.46-2.39 (m, 2H), 1.97-1.86 (m, 1H), 1.75-1.67 (m, 1H), 1.63-1.58 (m, 1H), 1.37-1.25 (m, 1H), 0.88-0.83 (m, 2H), 0.64-0.61 (m, 2H). |
| 369 | O | 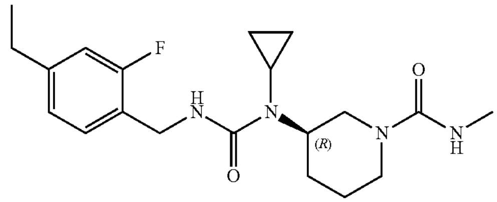 (R)-3-(1-cyclopropyl-3-(4-ethyl-2-fluorobenzyl)ureido)-N-methylpiperidine-1-carboxamide | LC-MS: 377.3 (M + H). 1H NMR (400 MHz, MeOD) δ 7.22 (t, J = 7.9 Hz, 1H), 6.97 (d, J = 7.8 Hz, 1H), 6.91 (d, J = 11.4 Hz, 1H), 6.77 (s, 1H), 4.47-4.31 (m, 2H), 4.02-3.92 (m, 1H), 3.90-3.80 (m, 1H), 3.68-3.56 (m, 1H), 3.19-3.04 (m, 1H), 2.70 (s, 3H), 2.67-2.56 (m, 3H), 2.54-2.46 (m, 1H), 2.17-2.03 (m, 1H), 1.94-1.84 (m, 1H), 1.80-1.69 (m, 1H), 1.57-1.41 (m, 1H), 1.21 (t, J = 7.6 Hz, 3H), 0.97-0.87 (m, 2H), 0.77-0.68 (m, 2H). |
| 370 | O | 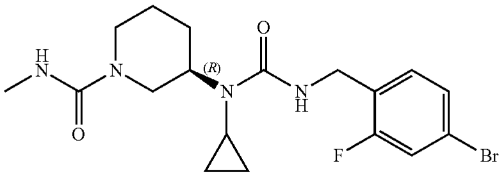 (R)-3-(3-(4-bromo-2-fluorobenzyl)-1-cyclopropylureido)-N-methylpiperidine-1-carboxamide | LC-MS: 427.2 (M + H). 1H NMR (400 MHz, MeOD) δ 7.28 (dt, J = 16.3, 7.1 Hz, 3H), 6.90 (t, J = 5.8 Hz, 1H), 4.44-4.32 (m, 2H), 3.95 (d, J = 12.0 Hz, 1H), 3.86 (d, J = 12.6 Hz, 1H), 3.61 (tt, J = 11.8, 3.9 Hz, 1H), 3.31 (s, 3H), 3.13 (t, J = 12.0 Hz, 1H), 2.70 (s, 3H), 2.63 (td, J = 13.0, 2.4 Hz, 1H), 2.55-2.48 (m, 1H), 2.16-2.02 (m, 1H), 1.88 (d, J = 11.6 Hz, 1H), 1.74 (d, J = 13.4 Hz, 1H), 1.48 (qt, J = 13.0, 4.1 Hz, 1H), 0.94 (dt, J = 5.9, 3.1 Hz, 2H), 0.74 (dd, J = 6.6, 3.2 Hz, 2H). |

Examples 371-377

The compounds recited in the following table were prepared by adapting the experimental general procedures G, R', and S recited above:

| Example | Structure and name | Data |
|---|---|---|
| 371 | 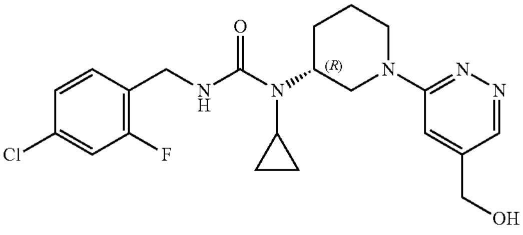 3-[(4-chloro-2-fluorophenyl)methyl]-1-cyclopropyl-1-[(3R)-1-[5-(hydroxymethyl)pyridazin-3-yl]piperidin-3-yl]urea | LC-MS: m/z = 434.2 (M + H) 1H NMR: 1H NMR (400 MHz, MeOD) δ 8.43 (s, 1H), 7.34 (t, J = 8.3 Hz, 1H), 7.27-7.14 (m, 3H), 4.59 (s, 2H), 4.46-4.32 (m, 4H), 3.77 (dd, J = 15.8, 7.6 Hz, 1H), 3.34 (d, J = 12.3 Hz, 1H), 2.89 (dd, J = 13.0, 10.7 Hz, 1H), 2.56 (dt, J = 10.6, 3.6 Hz, 1H), 2.25 (tt, J = 12.5, 6.3 Hz, 1H), 1.96 (d, J = 12.8 Hz, 1H), 1.87 (d, J = 13.2 Hz, 1H), 1.62 (dt, J = 16.9, 13.0 Hz, 1H), 0.96 (t, J = 7.3 Hz, 2H), 0.80 (d, J = 2.8 Hz, 2H). |
| 372 | 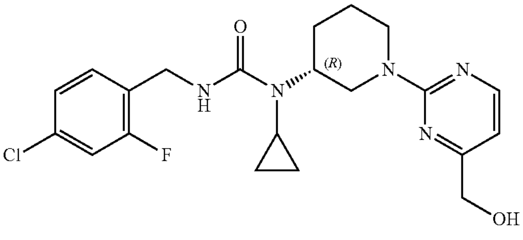 3-[(4-chloro-2-fluorophenyl)methyl]-1-cyclopropyl-1-[(3R)-1-[4-(hydroxymethyl)pyrimidin-2-yl]piperidin-3-yl]urea | LC-MS: m/z = 434.2 (M + H) 1H NMR: 1H NMR (400 MHz, MeOD) δ 8.25 (d, J = 5.0 Hz, 1H), 7.33 (t, J = 8.3 Hz, 1H), 7.20-7.13 (m, 2H), 6.69 (d, J = 5.0 Hz, 1H), 4.71 (t, J = 8.2 Hz, 2H), 4.47 (s, 2H), 4.41 (s, 2H), 3.64 (tt, J = 11.8, 3.9 Hz, 1H), 3.26 (d, J = 11.9 Hz, 1H), 2.75 (td, J = 13.0, 2.4 Hz, 1H), 2.59-2.52 (m, 1H), 2.21 (qd, J = 12.6, 4.1 Hz, 1H), 1.84 (dd, J = 41.9, 12.5 Hz, 2H), 1.58-1.45 (m, 1H), 0.98-0.88 (m, 2H), 0.86-0.72 (m, 2H). |
| 373 | 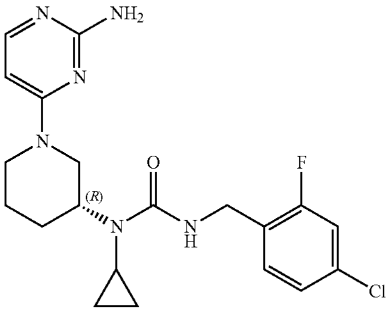 3-[(3R)-1-(2-aminopyrimidin-4-yl)piperidin-3-yl]-1-[(4-chloro-2-fluorophenyl)methyl]-3-cyclopropylurea | LC-MS: m/z = 419.2 (M + H) 1H NMR: 1H NMR (400 MHz, MeOD) δ 7.69 (d, J = 6.4 Hz, 1H), 7.33 (t, J = 8.3 Hz, 1H), 7.24-7.09 (m, 2H), 6.11 (d, J = 6.4 Hz, 1H), 4.40 (d, J = 14.8 Hz, 4H), 3.65 (t, J = 11.8 Hz, 1H), 3.21 (t, J = 11.9 Hz, 1H), 2.77 (t, J = 12.0 Hz, 1H), 2.54 (dt, J = 10.0, 3.3 Hz, 1H), 2.20 (tt, J = 12.6, 6.3 Hz, 1H), 1.92 (d, J = 12.9 Hz, 1H), 1.80 (d, J = 12.3 Hz, 1H), 1.52 (d, J = 13.1 Hz, 1H), 0.94 (dd, J = 15.3, 7.4 Hz, 2H), 0.78 (s, 2H). |

-continued

| Example | Structure and name | Data |
|---|---|---|
| 374 | 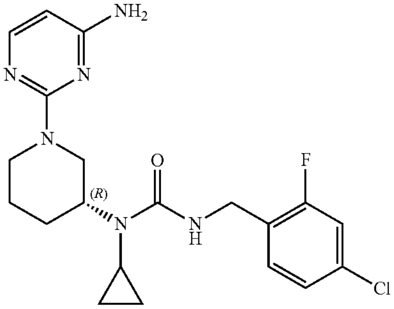 3-[(3R)-1-(4-aminopyrimidin-2-yl)piperidin-3-yl]-1-[(4-chloro-2-fluorophenyl)methyl]-3-cyclopropylurea | LC-MS: m/z = 419.2 (M + H) 1H NMR: 1H NMR (400 MHz, MeOD) δ 7.63 (d, J = 6.6 Hz, 1H), 7.33 (t, J = 8.3 Hz, 1H), 7.20-7.13 (m, 2H), 6.96 (t, J = 5.8 Hz, 1H), 5.96 (d, J = 6.6 Hz, 1H), 4.48-4.38 (m, 4H), 3.71 (ddd, J = 15.4, 8.0, 4.0 Hz, 1H), 3.33 (s, 1H), 2.85 (dd, J = 13.1, 11.1 Hz, 1H), 2.58-2.50 (m, 1H), 2.20 (qd, J = 12.5, 4.0 Hz, 1H), 1.89 (dd, J = 38.9, 12.5 Hz, 2H), 1.64-1.52 (m, 1H), 0.96 (dd, J = 8.2, 5.6 Hz, 2H), 0.78 (s, 2H). |
| 375 | 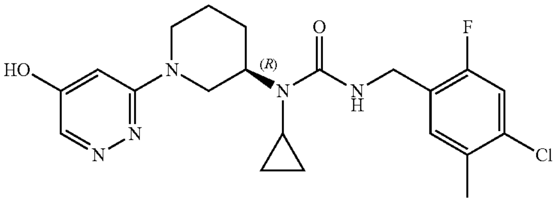 3-[(4-chloro-2-fluoro-5-methylphenyl)methyl]-1-cyclopropyl-1-[(3R)-1-(5-hydroxypyridazin-3-yl)piperidin-3-yl]urea | LC-MS: m/z = 434.2 1H NMR: 1H NMR (400 MHz, MeOD) δ 7.59 (s, 1H), 7.25 (d, J = 8.0 Hz, 1H), 7.14 (d, J = 9.8 Hz, 1H), 6.04 (s, 1H), 4.38 (q, J = 15.7 Hz, 2H), 3.80 (t, J = 11.6 Hz, 3H), 3.35 (d, J = 13.8 Hz, 1H), 2.94 (t, J = 11.9 Hz, 1H), 2.58-2.48 (m, 1H), 2.32 (s, 3H), 2.25-2.13 (m, 1H), 1.94 (dd, J = 33.2, 11.8 Hz, 2H), 1.73-1.57 (m, 1H), 0.96 (d, J = 6.5 Hz, 2H), 0.75 (dd, J = 32.5, 9.2 Hz, 2H). |
| 376 | 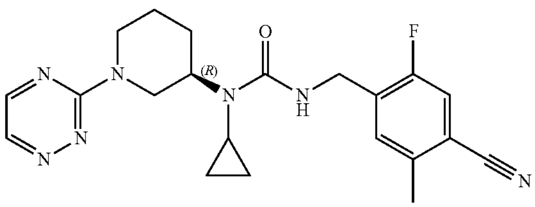 3-[(4-cyano-2-fluoro-5-methylphenyl)methyl]-1-cyclopropyl-1-[(3R)-1-(1,2,4-triazin-3-yl)piperidin-3-yl]urea | LC-MS: m/z = 410.3 (M + H) 1H NMR: 1H NMR (400 MHz, MeOD) δ 8.45 (d, J = 2.1 Hz, 1H), 8.26 (d, J = 2.1 Hz, 1H), 7.43 (d, J = 9.6 Hz, 1H), 7.36 (d, J = 7.2 Hz, 1H), 7.00 (t, J = 5.7 Hz, 1H), 4.76 (t, J = 10.5 Hz, 2H), 4.46 (d, J = 5.8 Hz, 2H), 3.67 (dd, J = 15.7, 7.9 Hz, 1H), 3.41 (t, J = 11.9 Hz, 1H), 2.87 (dd, J = 13.0, 10.8 Hz, 1H), 2.63-2.56 (m, 1H), 2.50 (s, 3H), 2.29 (dt, J = 12.7, 8.9 Hz, 1H), 1.90 (dd, J = 28.7, 13.1 Hz, 2H), 1.57 (q, J = 13.1 Hz, 1H), 0.96 (dt, J = 9.4, 6.7 Hz, 2H), 0.86-0.77 (m, 2H). |
| 377 | 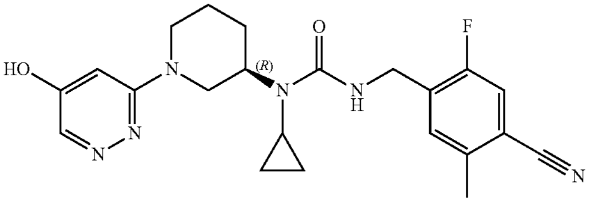 3-[(4-cyano-2-fluoro-5-methylphenyl)methyl]-1-cyclopropyl-1-[(3R)-1-(5-hydroxypyridazin-3-yl)piperidin-3-yl]urea | LC-MS: m/z = 425.2 (M + H) 1H NMR: 1H NMR (400 MHz, MeOD) δ 7.58 (s, 1H), 7.43 (d, J = 9.6 Hz, 1H), 7.36 (d, J = 7.1 Hz, 1H), 7.05 (t, J = 6.0 Hz, 1H), 6.02 (s, 1H), 4.53-4.39 (m, 2H), 3.80 (t, J = 11.8 Hz, 3H), 3.37 (s, 1H), 2.93 (t, J = 11.8 Hz, 1H), 2.60-2.53 (m, 1H), 2.49 (s, 3H), 2.19 (dd, J = 12.2, 8.7 Hz, 1H), 1.94 (dd, J = 35.5, 12.7 Hz, 2H), 1.68 (t, J = 13.1 Hz, 1H), 0.98 (d, J = 6.7 Hz, 2H), 0.79 (dd, J = 28.2, 9.6 Hz, 2H). |

Examples 378-400 recited in the following table were prepared by adapting the experimental general procedures W, X, or Y recited following the table:

| Example | Procedure | Structure | Name and Data |
|---|---|---|---|
| 378 | W | 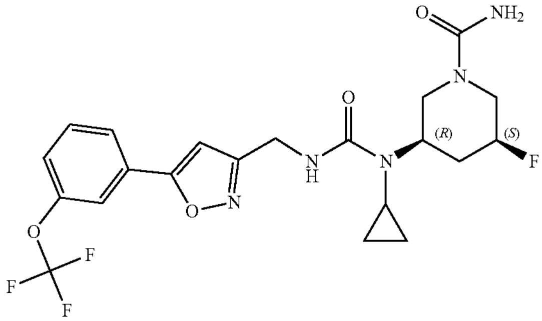 | (3R,5S)-3-{1-cyclopropyl[({5-[3-(trifluoromethoxy)phenyl]-1,2-oxazol-3-yl}methyl)carbamoyl]amino}-5-fluoropiperidine-1-carboxamide LC-MS: m/z = 486.2 (M + H) 1H NMR: 1H NMR (400 MHz, MeOD) δ 7.83 (d, J = 7.9 Hz, 1H), 7.72 (s, 1H), 7.61 (t, J = 8.1 Hz, 1H), 7.40 (d, J = 8.3 Hz, 1H), 7.08 (t, J = 5.9 Hz, 1H), 6.83 (s, 1H), 4.60-4.52 (m, 1H), 4.49 (d, J = 5.8 Hz, 2H), 4.43 (dd, J = 10.4, 5.3 Hz, 1H), 4.31(d, J = 11.2 Hz, 1H), 3.87(d, J = 12.4 Hz, 1H), 3.73 (t, J = 11.6 Hz, 1H), 3.24-3.16 (m, 1H), 2.73-2.65 (m, 1H), 2.57 (ddd, J = 10.4, 6.8, 3.9 Hz, 1H), 2.36 (d, J = 8.7 Hz, 1H), 2.33-2.26 (m, 1H), 0.97 (dd, J = 6.5, 2.9 Hz, 2H), 0.85-0.78 (m, 2H). |
| 379 | X | 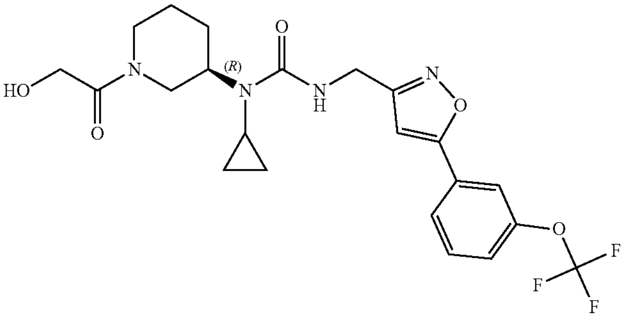 | 1-cyclopropyl-1-[(3R)-1-(2-hydroxyacetyl)piperidin-3-yl]-3-({5-[3-(trifluoromethoxy)phenyl]-1,2-oxazol-3-yl}methyl)urea LC-MS: m/z = 483.1 (M + H) 1H NMR: 1H NMR (400 MHz, MeOD) δ 7.83 (d, J = 7.9 Hz, 1H), 7.72 (s, 1H), 7.61 (t, J = 8.1 Hz, 1H), 7.39 (d, J = 8.5 Hz, 1H), 7.07-6.98 (m, 1H), 6.84 (s, 1H), 4.52-4.41 (m, 3H), 4.25 (q, J = 15.4 Hz, 2H), 3.67 (dd, J = 39.4, 25.9 Hz, 2H), 3.18 (dd, J = 30.3, 18.5 Hz, 1H), 2.96-2.48 (m, 2H), 2.20 (dd, J = 12.8, 3.8 Hz, 1H), 2.03-1.78 (m, 2H), 1.61-1.44 (m, 1H), 0.95 (t, J = 7.2 Hz, 2H), 0.87-0.73 (m, 2H). |
| 380 | Y | 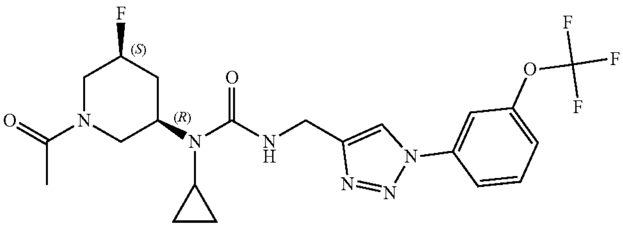 | 1-[(3R,5S)-1-acetyl-5-fluoropiperidin-3-yl]-1-cyclopropyl-3-({1-[3-(trifluoromethoxy)phenyl]-1H-1,2,3-triazol-4-yl}methyl)urea LC-MS: m/z = 485.1 (M + H) 1H NMR: 1H NMR (400 MHz, MeOD) δ 8.44 (d, J = 3.7 Hz, 1H), 7.92-7.81 (m, 2H), 7.69 (t, J = 8.2 Hz, 1H), 7.42 (d, J = 7.9 Hz, 1H), 7.04 (dd, J = 15.2, 9.7 Hz, 1H), 4.79-4.59 (m, 1H), 4.53 (t, J = 5.2 Hz, 2H), 4.49-4.33 (m, 1H), 4.13 (d, J = 14.0 Hz, 1H), 3.81 (d, J = 11.2 Hz, 1H), 3.60 (s, 1H), 3.26 (s, 1H), 3.17-2.92 (m, 1H), 2.59-2.50 (m, 2H), 2.45-2.26 (m, 2H), 2.12 (d, J = 6.5 Hz, 3H), 0.96 (dd, J = 16.5, 5.2 Hz, 2H), 0.88-0.71 (m, 2H). |

-continued

| Example | Procedure | Structure | Name and Data |
|---|---|---|---|
| 381 | X | 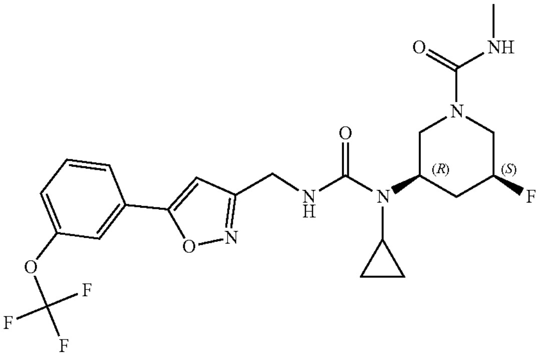 | (3R,5S)-3-{1-cyclopropyl [({5-[3-(trifluoromethoxy) phenyl]-1,2-oxazol-3-yl}methyl)carbamoyl]amino}-5-fluoro-N-methylpiperidine-1-carboxamide<br>LC-MS: m/z = 500.3 (M + H)<br>1H NMR: 1H NMR (400 MHz, MeOD) δ 7.83 (d, J = 7.9 Hz, 1H), 7.72 (s, 1H), 7.61 (t, J = 8.1 Hz, 1H), 7.40 (d, J = 8.3 Hz, 1H), 6.83 (s, 1H), 4.53 (dd, J = 10.4, 5.3 Hz, 1H), 4.48 (s, 2H), 4.45-4.37 (m, 1H), 4.29 (d, J = 12.4 Hz, 1H), 3.84 (d, J = 12.9 Hz, 1H), 3.71 (t, J = 11.0 Hz, 1H), 3.18-3.12 (m, 1H), 2.70 (s, 3H), 2.68-2.63 (m, 1H), 2.58-2.52 (m, 1H), 2.39-2.33 (m, 1H), 2.31-2.23 (m, 1H), 0.97 (dd, J = 6.6, 2.3 Hz, 2H), 0.84-0.79 (m, 2H). |
| 382 | X | 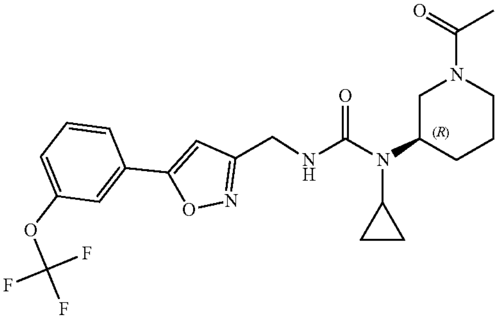 | 1-[(3R)-1-acetylpiperidin-3-yl]-1-cyclopropyl-3-({5-[3-(trifluoromethoxy)phenyl]-1,2-oxazol-3-yl}methyl)urea<br>LC-MS: m/z = 467.2 (M + H)<br>1H NMR: 1H NMR (400 MHz, MeOD) δ 7.83 (d, J = 7.9 Hz, 1H), 7.72 (s, 1H), 7.64-7.57 (m, 1H), 7.39 (d, J = 8.2 Hz, 1H), 6.84 (d, J = 3.5 Hz, 1H), 4.52-4.45 (m, 3H), 3.86 (d, J = 12.6 Hz, 1H), 3.81-3.74 (m, 0.5H), 3.59-3.46 (m, 0.5H), 3.35 (s, 0.5H), 3.14-2.96 (m, 1H), 2.56 (td, J = 6.6, 3.4 Hz, 0.5H), 2.50 (ddd, J = 16.1, 9.7, 2.9 Hz, 1H), 2.26-2.13 (m, 1H), 2.10 (d, J = 6.9 Hz, 3H), 1.94 (dd, J = 28.4, 11.9 Hz, 1H), 1.87-1.76 (m, 1H), 1.62-1.40 (m, 1H), 0.95 (ddd, J = 17.4, 8.7, 5.5 Hz, 2H), 0.87-0.73 (m, 2H). |
| 383 | Y | 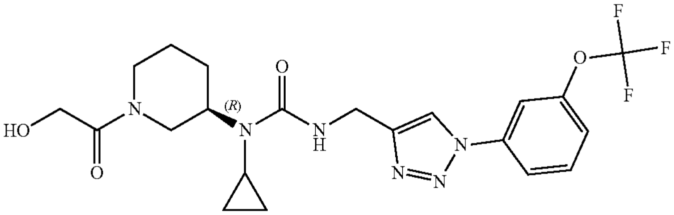 | 1-cyclopropyl-1-[(3R)-1-(2-hydroxyacetyl)piperidin-3-yl]-3-({1-[3-(trifluoromethoxy) phenyl]-1H-1,2,3-triazol-4-yl}methyl)urea<br>LC-MS: m/z = 483.2 (M + H)<br>1H NMR: 1H NMR (400 MHz, MeOD) δ 8.44 (s, 1H), 7.94-7.74 (m, 2H), 7.68 (t, J = 8.1 Hz, 1H), 7.42 (d, J = 8.3 Hz, 1H), 6.99 (d, J = 6.0 Hz, 1H), 4.53 (s, 2H), 4.46 (d, J = 12.7 Hz, 1H), 4.35-4.12 (m, 2H), 3.79-3.54 (m, 2H), 3.19 (dd, J = 39.2, 12.0 Hz, 1H), 2.63 (dd, J = 89.0, 78.0 Hz, 2H), 2.17 (dd, J = 12.7, 8.9 Hz, 1H), 2.01-1.76 (m, 2H), 1.59-1.41 (m, 1H), 0.94 (s, 2H), 0.78 (d, J = 15.8 Hz, 2H). |

-continued

| Example | Procedure | Structure | Name and Data |
|---|---|---|---|
| 384 | X | 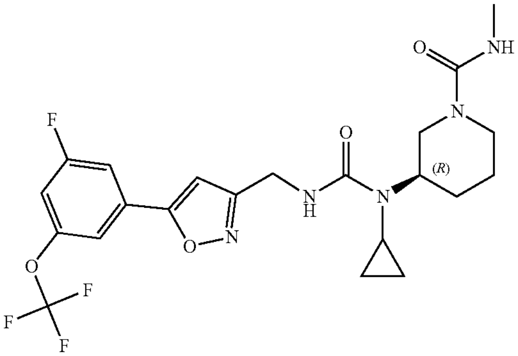 | (3R)-3-{1-cyclopropyl[({5-[3-fluoro-5-(trifluoromethoxy)phenyl]-1,2-oxazol-3-yl}methyl)carbamoyl]amino}-N-methylpiperidine-1-carboxamide LC-MS: m/z = 500.1 (M + H) 1H NMR: 1H NMR (400 MHz, MeOD) δ 7.65 (dd, J = 8.9, 1.4 Hz, 1H), 7.60 (s, 1H), 7.25 (d, J = 8.9 Hz, 1H), 7.02 (t, J = 5.8 Hz, 1H), 6.90 (s, 1H), 4.48 (d, J = 4.8 Hz, 2H), 4.03-3.80 (m, 2H), 3.72-3.58 (m, 1H), 3.14(t, J = 12.0 Hz, 1H), 2.74-2.56(m, 4H), 2.55-2.48 (m, 1H), 2.16-2.00(m, 1H), 1.91(d, J = 12.0 Hz, 1H), 1.75 (d, J = 13.4 Hz, 1H), 1.58-1.42 (m, 1H), 1.01-0.85(m, 2H), 0.80 (dd, J = 5.3, 3.4 Hz, 2H). |
| 385 | W | 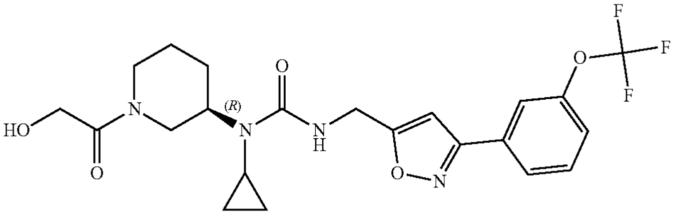 | 1-cyclopropyl-1-[(3R)-1-(2-hydroxyacetyl)piperidin-3-yl]-3-({3-[3-(trifluoromethoxy)phenyl]-1,2-oxazol-5-yl}methyl)urea LC-MS: m/z = 483.2 (M + H) 1H NMR: 1H NMR (400 MHz, MeOD) δ 7.83 (d, J = 7.8 Hz, 1H), 7.75 (s, 1H), 7.59 (t, J = 8.0 Hz, 1H), 7.39 (d, J = 8.0 Hz, 1H), 7.20-7.08 (m, 1H), 6.72 (d, J = 3.5 Hz, 1H), 4.50 (dd, J = 33.8, 8.0 Hz, 3H), 4.32-4.13 (m, 2H), 3.77-3.52 (m, 2H), 3.29-3.08 (m, 1H), 2.98-2.46 (m, 2H), 2.18 (td, J = 12.6, 4.0 Hz, 1H), 2.02-1.76 (m, 2H), 1.60-1.42 (m, 1H), 0.96 (dd, J = 13.7, 6.4 Hz, 2H), 0.88-0.69 (m, 2H). |
| 386 | Y | 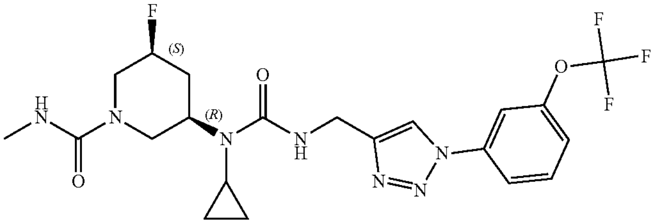 | (3R,5S)-3-{1-cyclopropyl[({1-[3-(trifluoromethoxy)phenyl]-1H-1,2,3-triazol-4-yl}methyl)carbamoyl]amino}-5-fluoro-N-methylpiperidine-1-carboxamide LC-MS: m/z = 500.2 (M + H) 1H NMR: 1H NMR (400 MHz, MeOD) δ 8.43 (s, 1H), 7.88 (dd, J = 12.0, 3.9 Hz, 2H), 7.69 (t, J = 8.2 Hz, 1H), 7.42 (d, J = 8.3 Hz, 1H), 4.52 (s, 2H), 4.52-4.47 (m, 1H), 4.40 (ddd, J = 15.6, 10.4, 5.0 Hz, 1H), 4.29 (d, J = 12.5 Hz, 1H), 3.82 (d, J = 12.8 Hz, 1H), 3.71 (t, J = 1 1.1 Hz, 1H), 3.13 (dd, J = 12.6, 11.4 Hz, 1H), 2.69 (s, 3H), 2.68-2.62 (m, 1H), 2.57-2.51 (m, 1H), 2.38-2.31 (m, 1H), 2.30-2.19 (m, 1H), 0.99-0.91 (m, 2H), 0.83-0.76 (m, 2H). |
| 387 | Y | 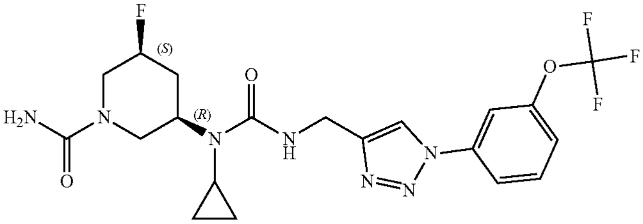 | (3R,5S)-3-{1-cyclopropyl[({1-[3-(trifluoromethoxy)phenyl]-1H-1,2,3-triazol-4-yl}methyl)carbamoyl]amino}-5-fluoropiperidine-1-carboxamide LC-MS: m/z = 486.2 (M + H) 1H NMR: 1H NMR (400 MHz, MeOD) δ 8.43 (s, 1H), 7.91-7.82 (m, 2H), 7.69 (t, J = 8.2 Hz, 1H), 7.42 (d, J = 8.4 Hz, 1H), 7.03 (t, J = 5.6 Hz, 1H), 4.58-4.42 (m, 3H), 4.30 (d, J = 11.9 Hz, 1H), 3.86 (d, J = |

-continued

| Example | Procedure | Structure | Name and Data |
|---|---|---|---|
| | | | 12.7 Hz, 1H), 3.73 (s, 1H), 3.21-3.14 (m, 1H), 2.74-2.64 (m, 1H), 2.54 (td, J = 6.7, 3.4 Hz, 1H), 2.29 (dd, J = 22.7, 11.4 Hz, 2H), 0.96 (dd, J = 10.3, 3.9 Hz, 2H), 0.84-0.76 (m, 2H). |
| 388 | W | 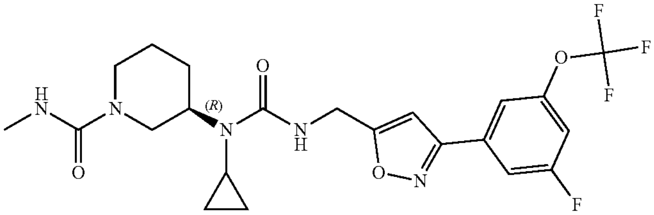 | (3R)-3-{1-cyclopropyl[({3-[3-fluoro-5-(trifluoromethoxy) phenyl]-1,2-oxazol-5-yl} methyl)carbamoyl]amino}-N-methylpiperidine-1-carboxamide LC-MS: m/z = 500.2 (M + H) 1H NMR: 1H NMR (400 MHz, MeOD) δ 7.69-7.59 (m, 2H), 7.25 (d, J = 8.1 Hz, 1H), 7.13 (t, J = 5.9 Hz, 1H), 6.75 (s, 1H), 4.53 (t, J = 10.9 Hz, 2H), 3.99-3.87 (m, 2H), 3.70-3.58 (m, 1H), 3.19-3.09 (m, 1H), 2.69 (d, J = 4.9 Hz, 3H), 2.63 (dd, J = 13. 1,2.6 Hz, 1H), 2.53 (ddd, J = 10.5, 6.6, 3.7 Hz, 1H), 2.11 (qd, J = 12.6, 4.0 Hz, 1H), 1.90 (d, J = 12.0 Hz, 1H), 1.75(d, J = 13.1 Hz, 1H), 1.57-1.42 (m, 1H), 1.02-0.90 (m, 2H), 0.85-0.72 (m, 2H). |
| 389 | X | 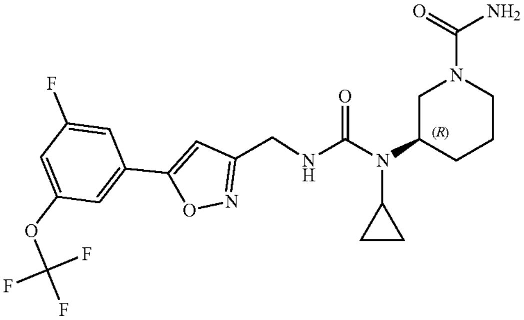 | (3R)-3-{1-cyclopropyl[({5-[3-fluoro-5-(trifluoromethoxy) phenyl]-1,2-oxazol-3-yl}methyl)carbamoyl]amino} piperidine-1-carboxamide LC-MS: m/z = 486.2 (M + H) 1H NMR: 1H NMR (400 MHz, MeOD) δ 7.65 (d, J = 8.9 Hz, 1H), 7.60 (s, 1H), 7.26 (d, J = 8.8 Hz, 1H), 7.03 (t, J = 5.8 Hz, 1H), 6.90 (s, 1H), 4.52-4.43 (m, 2H), 4.04-3.88 (m, 2H), 3.73-3.60 (m, 1H), 3.25-3.15 (m, 1H), 2.75-2.63 (m, 1H), 2.57-2.49 (m, 1H), 2.20-2.05 (m, 1H), 1.96-1.87 (m, 1H), 1.83-1.71 (m, 1H), 1.61-1.43 (m, 1H), 0.99-0.90 (m, 2H), 0.84-0.74 (m, 2H). |
| 390 | W | 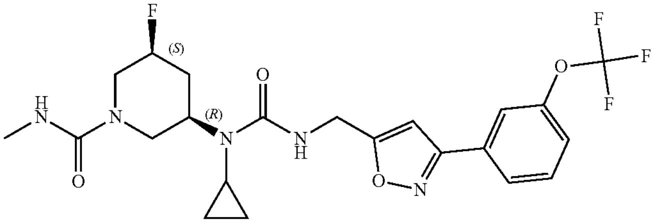 | (3R,5S)-3-{1-cyclopropyl [({3-[3-(trifluoromethoxy) phenyl]-1,2-oxazol-5-yl}methyl) carbamoyl]amino}-5-fluoro-N-methylpiperidine-1-carboxamide LC-MS: m/z = 500.2 (M + H) 1H NMR: 1H NMR (400 MHz, MeOD) δ 7.83 (d, J = 7.8 Hz, 1H), 7.75 (s, 1H), 7.59 (t, J = 8.0 Hz, 1H), 7.39 (d, J = 8.3 Hz, 1H), 6.72 (s, 1H), 4.55 (s, 2H), 4.50 (dd, J = 10.4, 5.3 Hz, 1H), 4.40 (td, J = 10.4, 5.1 Hz, 1H), 4.28 (d, J = 10.5 Hz, 1H), 3.83 (d, J = 12.7 Hz, 1H), 3.69 (t, J = 11.1 Hz, 1H), 3.18-3.11 (m, 1H), 2.69 (s, 3H), 2.68-2.62 (m, 1H), 2.56 (ddd, J = 10.5, 6.8, 3.9 Hz, 1H), 2.39-2.32 (m, 1H), 2.32-2.21 (m, 1H), 0.97 (t, J = 6.0 Hz, 2H), 0.82(d, J = 3.5 Hz, 2H). |

-continued

| Example | Procedure | Structure | Name and Data |
|---|---|---|---|
| 391 | W | 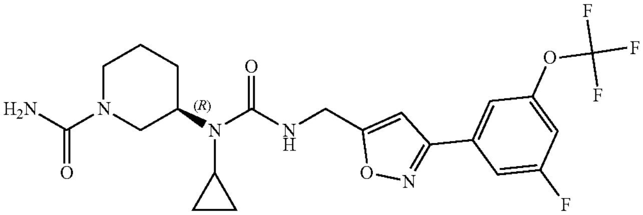 | (3R)-3-{1-cyclopropyl[({3-[3-fluoro-5-(trifluoromethoxy)phenyl]-1,2-oxazol-5-yl}methyl)carbamoyl]amino}piperidine-1-carboxamide LC-MS: m/z = 486.2 (M + H) 1H NMR: 1H NMR (400 MHz, MeOD) δ 7.68-7.60 (m, 2H), 7.25 (d, J = 9.0 Hz, 1H), 7.13 (t, J = 5.8 Hz, 1H), 6.75 (s, 1H), 4.54 (d, J = 5.4 Hz, 2H), 3.95 (t, J = 14.6 Hz, 2H), 3.66 (ddd, J = 11.7, 7.9, 4.1 Hz, 1H), 3.23-3.15 (m, 1H), 2.68 (dd, J = 12.8, 10.7 Hz, 1H), 2.58-2.51 (m, 1H), 2.12 (qd, J = 12.6, 4.0 Hz, 1H), 1.91 (d, J = 11.7 Hz, 1H), 1.76 (d, J = 13.9 Hz, 1H), 1.59-1.45 (m, 1H), 0.96 (dd, J = 8.8, 6.0 Hz, 2H), 0.83-0.76 (m, 2H). |
| 392 | W | 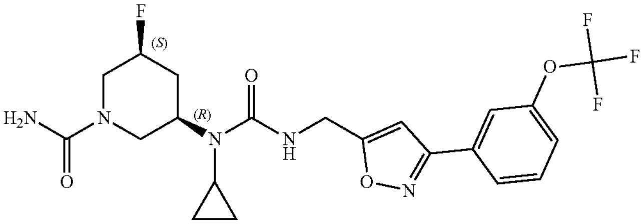 | (3R,5S)-3-{1-cyclopropyl[({3-[3-(trifluoromethoxy)phenyl]-1,2-oxazol-5-yl}methyl)carbamoyl]amino}-5-fluoropiperidine-1-carboxamide LC-MS: m/z = 486.2 (M + H) 1H NMR: 1H NMR (400 MHz, MeOD) δ 7.83 (d, J = 7.8 Hz, 1H), 7.75 (s, 1H), 7.59 (t, J = 8.0 Hz, 1H), 7.39 (d, J = 8.3 Hz, 1H), 7.19 (t, J = 5.8 Hz, 1H), 6.72 (s, 1H), 4.60-4.50 (m, 3H), 4.48-4.37 (m, 1H), 4.30 (d, J = 12.6 Hz, 1H), 3.86 (d, J = 12.4 Hz, 1H), 3.77-3.64 (m, 1H), 3.18 (dd, J = 24.4, 12.6 Hz, 1H), 2.74-2.65 (m, 1H), 2.61-2.53 (m, 1H), 2.41-2.22 (m, 2H), 1.04-0.94 (m, 2H), 0.87-0.78 (m, 2H). |
| 393 | W | 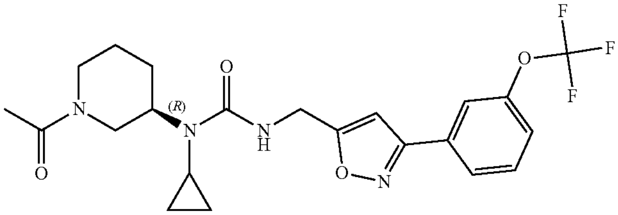 | 1-[(3R)-1-acetylpiperidin-3-yl]-1-cyclopropyl-3-({3-[3-(trifluoromethoxy)phenyl]-1,2-oxazol-5-yl}methyl)urea LC-MS: m/z = 467.1 (M + H) |
| 394 | Y | 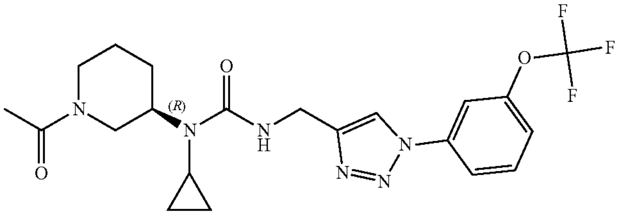 | 1-[(3R)-1-acetylpiperidin-3-yl]-1-cyclopropyl-3-({1-[3-(trifluoromethoxy)phenyl]-1H-1,2,3-triazol-4-yl}methyl)urea LC-MS: m/z = 467.2 (M + H) 1H NMR: 1H NMR (400 MHz, MeOD) δ 8.44 (d, J = 4.5 Hz, 1H), 7.92-7.81 (m, 2H), 7.68 (dd, J = 8.7, 7.8 Hz, 1H), 7.42 (d, J = 8.2 Hz, 1H), 4.53 (t, J = 5.7 Hz, 2H), 4.49 (d, J = 12.2 Hz, 1H), 3.89-3.82 (m, 1H), 3.77 (dt, J = 12.2, 3.9 Hz, 1H), 3.55 (tt, J = 12.0, 4.0 Hz, 1H), 3.33 (s, 1H), 3.11-2.96 (m, 1H), 2.58-2.44 (m, 2H), 2.27-2.12 (m, 1H), 2.10 (d, J = 6.0 Hz, 3H), 2.01-1.78 (m, 2H), 1.60-1.40 (m, 1H), 1.01-0.89 (m, 2H), 0.86-0.71 (m, 2H). |

-continued

| Example | Procedure | Structure | Name and Data |
| --- | --- | --- | --- |
| 395 | W | 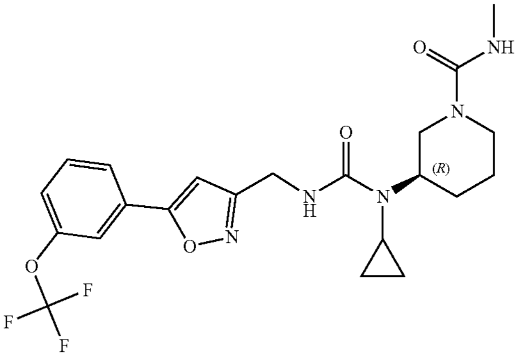 | (3R)-3-{1-cyclopropyl[({5-[3-(trifluoromethoxy)phenyl]-1,2-oxazol-3-yl}methyl)carbamoyl]amino}-N-methylpiperidine-1-carboxamide LC-MS: m/z = 482.1 (M + H) 1H NMR: 1H NMR (400 MHz, MeOD) δ 7.83 (d, J = 7.8 Hz, 1H), 7.72 (s, 1H), 7.61 (t, J = 8.1 Hz, 1H), 7.40 (d, J = 8.3 Hz, 1H), 6.83 (s, 1H), 4.48 (s, 2H), 3.93 (dd, J = 24.8, 12.3 Hz, 2H), 3.70-3.61 (m, 1H), 3.18-3.11 (m, 1H), 2.70 (d, J = 5.5 Hz, 3H), 2.65 (dd, J = 13.2, 10.6 Hz, 1H), 2.56-2.50 (m, 1H), 2.19-2.07 (m, 1H), 1.91 (d, J = 12.1 Hz, 1H), 1.76(d, J = 13.3 Hz, 1H), 1.55-1.45(m, 1H), 0.94 (dt, J = 10.0, 5.7 Hz, 2H), 0.85-0.75 (m, 2H). |
| 396 | W | 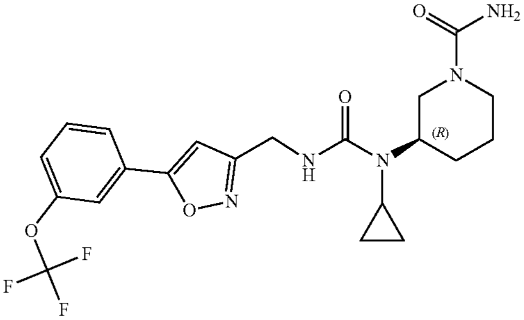 | (3R)-3-{1-cyclopropyl[({5-[3-(trifluoromethoxy)phenyl]-1,2-oxazol-3-yl}methyl)carbamoyl]amino}piperidine-1-carboxamide LC-MS: m/z = 468.1 (M + H) 1H NMR: 1H NMR (400 MHz, MeOD) δ 7.83 (d, J = 7.7 Hz, 1H), 7.72 (s, 1H), 7.61 (t, J = 8.1 Hz, 1H), 7.39 (d, J = 8.2 Hz, 1H), 7.02 (t, J = 5.9 Hz, 1H), 6.83 (s, 1H), 4.48 (d, J = 4.5 Hz, 2H), 4.03-3.89 (m, 2H), 3.72-3.62 (m, 1H), 3.22-3.12 (m, 1H), 2.68 (t, J = 11.8 Hz, 1H), 2.57-2.50 (m, 1H), 2.19-2.08 (m, 1H), 1.92 (dd, J = 8.4, 4.0 Hz, 1H), 1.79-1.73 (m, 1H), 1.54 (m, 1H), 0.95 (m, 2H), 0.81 (d, J = 3.5 Hz, 2H). |
| 397 | Y | 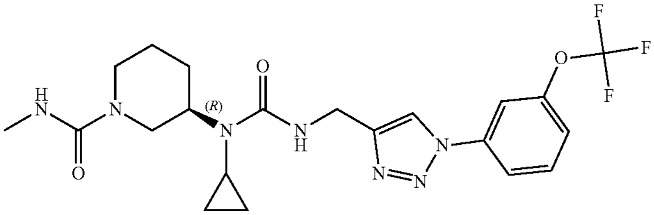 | (3R)-3-{1-cyclopropyl[({1-[3-(trifluoromethoxy)phenyl]-1H-1,2,3-triazol-4-yl}methyl)carbamoyl]amino}-N-methylpiperidine-1-carboxamide LC-MS: m/z = 482.0 (M + H) 1H NMR:1H NMR (400 MHz, MeOD) δ 8.43 (s, 1H), 7.92-7.81 (m, 2H), 7.69 (t, J = 8.2 Hz, 1H), 7.45-7.38 (m, 1H), 6.98 (t, J = 5.6 Hz, 1H), 4.52 (d, J = 4.3 Hz, 2H), 3.91 (ddd, J = 15.1, 12.6, 6.8 Hz, 2H), 3.66 (tt, J = 11.8, 4.0 Hz, 1H), 3.16-3.09 (m, 1H), 2.75-2.58 (m, 4H), 2.55-2.47 (m, 1H), 2.09 (tt, J = 12.5, 6.3 Hz, 1H), 1.90 (d, J = 12.0 Hz, 1H), 1.75 (d, J = 13.7 Hz, 1H), 1.56-1.43 (m, 1H), 0.98-0.87 (m, 2H), 0.84-0.73 (m, 2H). |
| 398 | Y | 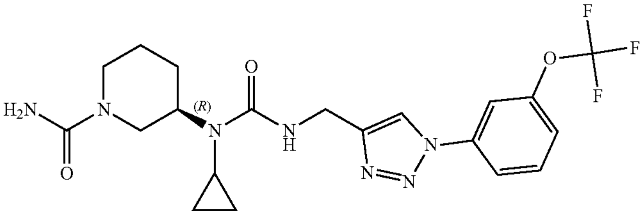 | (3R)-3-{1-cyclopropyl[({1-[3-(trifluoromethoxy)phenyl]-1H-1,2,3-triazol-4-yl}methyl)carbamoyl]amino}piperidine-1-carboxamide LC-MS: m/z = 468.0 (M + H) 1H NMR: 1H NMR (400 MHz, MeOD) δ 8.43 (s, 1H), 7.93-7.80 (m, 2H), 7.68 (t, J = 8.2 Hz, 1H), 7.46-7.38 (m, 1H), 4.52 (d, J = 4.2 Hz, 2H), 3.94 (dd, J = 24.0, 13.0 Hz, 2H), 3.74-3.62 (m, 1H), |

-continued

| Example | Procedure | Structure | Name and Data |
|---|---|---|---|
| | | | 3.22-3.12 (m, 1H), 2.72-2.62 (m, 1H), 2.55-2.48 (m, 1H), 2.18-2.03 (m, 1H), 1.90 (d, J = 11.9 Hz, 1H), 1.76 (d, J = 13.3 Hz, 1H), 1.58-1.44 (m, 1H), 1.00-0.89 (m, 2H), 0.82-0.71 (m, 2H). |
| 399 | W | 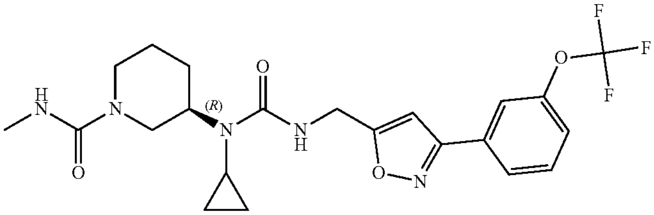 | (3R)-3-{1-cyclopropyl[({3-[3-(trifluoromethoxy)phenyl]-1,2-oxazol-5-yl}methyl)carbamoyl]amino}-N-methylpiperidine-1-carboxamide LC-MS: m/z = 482.0 (M + H) 1H NMR: 1H NMR (400 MHz, MeOD) δ 7.83 (d, J = 7.8 Hz, 1H), 7.75 (s, 1H), 7.59 (t, J = 8.0 Hz, 1H), 7.43-7.35 (m, 1H), 6.72 (s, 1H), 4.60-4.45 (m, 2H), 4.00-3.84 (m, 2H), 3.71-3.56 (m, 1H), 3.13 (t, J = 11.9 Hz, 1H), 2.73-2.60 (m, 4H), 2.57-2.48 (m, 1H), 2.19-2.03 (m, 1H), 1.96-1.86 (m, 1H), 1.75 (d, J = 13.4 Hz, 1H), 1.57-1.42 (m, 1H), 1.00-0.90 (m, 2H), 0.83-0.73 (m, 2H). |
| 400 | W | 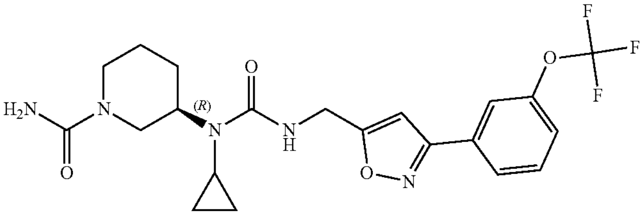 | (3R)-3-{1-cyclopropyl[({3-[3-(trifluoromethoxy)phenyl]-1,2-oxazol-5-yl}methyl)carbamoyl]amino}piperidine-1-carboxamide LC-MS: m/z = 468.2 (M + H) 1H NMR: 1H NMR (400 MHz, MeOD) δ 7.86-7.77 (m, 1H), 7.74 (s, 1H), 7.59 (t, J = 8.0 Hz, 1H), 7.43-7.31 (m, 1H), 6.71 (s, 1H), 4.59-4.44 (m, 2H), 4.05-3.84 (m, 2H), 3.72-3.56 (m, 1H), 3.24-3.14 (m, 1H), 2.75-2.61 (m, 1H), 2.58-2.48 (m, 1H), 2.22-2.05 (m, 1H), 1.97-1.84 (m, 1H), 1.81-1.68 (m, 1H), 1.61-1.45 (m, 1H), 1.03-0.90 (m, 2H), 0.88-0.75 (m, 2H). |

General Procedure W:

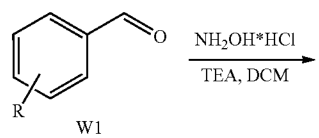

W1

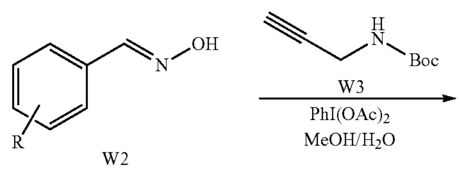

W2

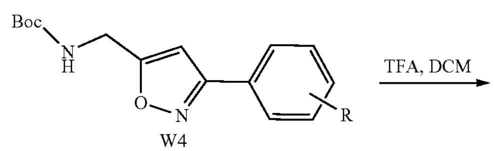

W4

-continued

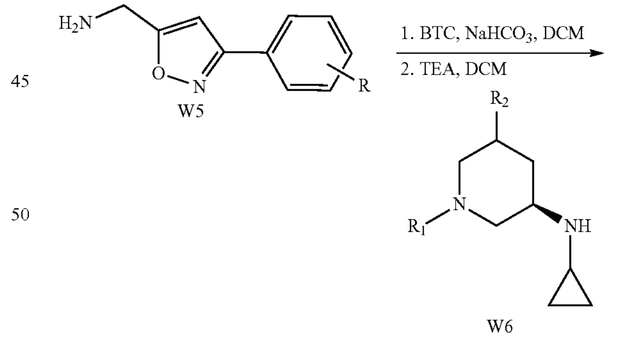

W5

W6

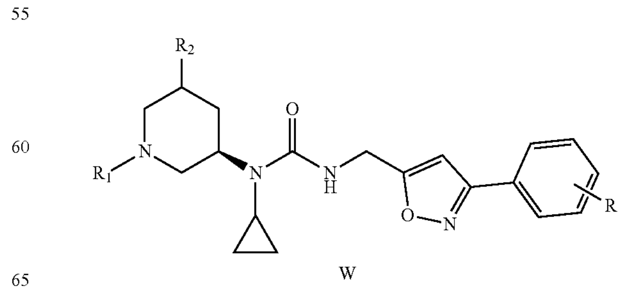

W

Step 1: Synthesis of W2

To a mixture of the appropriate aldehyde W1 (1 eq.) and hydroxylamine hydrochloride (1.1 eq.) in DCM TEA (1.1 eq.) was added dropwise at 0° C. under $N_2$ atmosphere. The resulting mixture was stirred at room temperature for 45 minutes. The mixture was then diluted with water and extracted with DCM twice. The combined organic layers were washed with brine, dried over anhydrous $Na_2SO_4$, filtered and concentrated to dryness under reduced pressure to give crude compound W2 which was used in the next step without any further purification.

Step 2: Synthesis of W4

To a mixture of W2 (1 eq.) and W3 (1 eq.) in $MeOH/H_2O$ (4:1, V/V) [Bis(trifluoroacetoxy)iodo]benzene (1.3 eq.) was added at 0° C. under $N_2$ atmosphere. The resulting mixture was stirred at room temperature for 1 hour. The mixture was then diluted with water and extracted with EtOAc twice. The combined organic layers were separated, washed with brine, dried over anhydrous $Na_2SO_4$, filtered and concentrated to dryness. The residue was purified via flash column chromatography (eluted with PE/EtOAc) to give compound W4.

Step 3: Synthesis of W5

W4 (1 eq.) was added dropwise into a mixture of TFA/DCM (1:4, V/V) at 0° C. and the resulting mixture was stirred at room temperature for 1 hour. The mixture was then concentrated to dryness under reduced pressure to give crude compound W5 which was used in the next step without any further purification.

Step 4: Synthesis of W

To a mixture of W5 (1 eq.) and $NaHCO_3$ (3 eq.) in DCM a solution of triphosgene (0.5 eq.) was added dropwise in DCM at −30° C. under $N_2$ atmosphere. The resulting mixture was stirred at room temperature for 30 minutes, then a mixture of W6 (1 eq.) and TEA (3 eq.) in anhydrous DCM was added dropwise at 0° C. under $N_2$ atmosphere. The resulting mixture was stirred at room temperature for 1 hour, then the mixture was diluted with water and extracted with DCM twice. The combined organic layers were separated, washed with brine, dried over anhydrous $Na_2SO_4$, filtered and concentrated to dryness. The residue was purified via prep-HPLC to give pure compound W.

Synthesis of Example 400

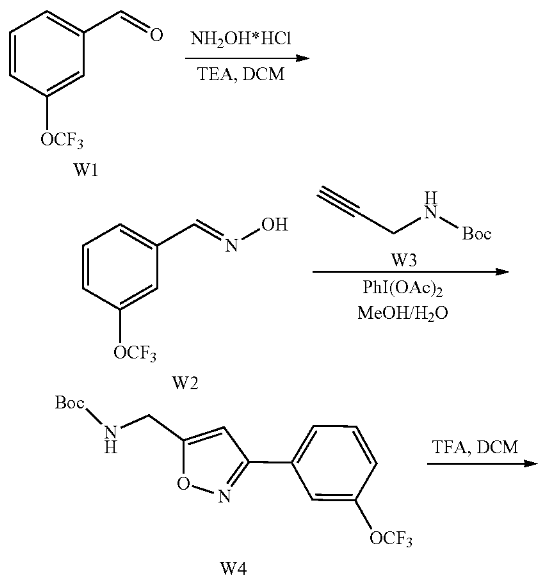

W1
W2
W3
W4

-continued

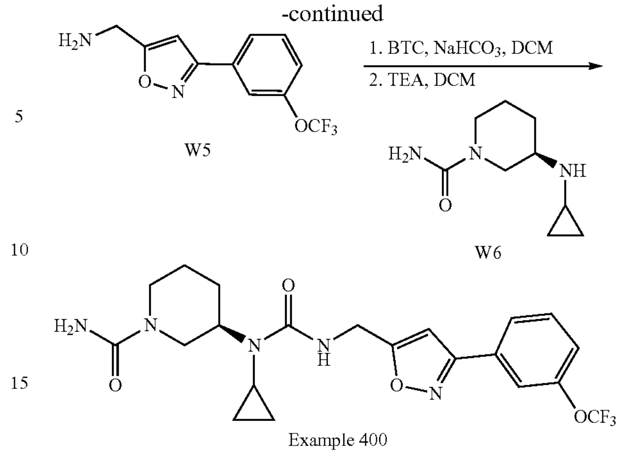

W5
W6
Example 400

Step 1: Synthesis of W2

To a solution of W1 (1.0 g, 5.26 mmol) and hydroxylamine hydrochloride (402 mg, 5.79 mmol) in DCM (25 mL) TEA (586 mg, 5.79 mmol) was added dropwise at 0° C. under $N_2$ atmosphere, and the resulting mixture was stirred at room temperature for 45 minutes. The mixture was then diluted with water (25 mL) and extracted with DCM (25 mL) twice. The combined organic layers were separated, washed with brine (30 mL), dried over anhydrous $Na_2SO_4$, filtered and concentrated to dryness under reduced pressure to give crude compound W2 (950 mg, 88.05% yield) which was used in the next step without any further purification. LC/MS (ESI) m/z: 206 $(M+H)^+$.

Step 2: Synthesis of W4

To a mixture of W2 (950 mg, 4.63 mmol) and W3 (719 mg, 4.63 mmol) in MeOH (40 mL) and $H_2O$ (10 mL) [Bis(trifluoroacetoxy)iodo]benzene (2.59 g, 6.02 mmol) was added at 0° C. under $N_2$ atmosphere, and the resulting mixture was stirred at room temperature for 1 hour. The mixture was then diluted with water (60 mL) and extracted with EtOAc (50 mL) twice. The combined organic layers were separated, washed with brine, dried over anhydrous $Na_2SO_4$, filtered and concentrated to dryness. The residue was purified via flash column chromatography (eluted with 10~50% EtOAc in PE) to give pure compound W4 (390 mg, 23.50% yield) as a white solid. LC/MS (ESI) m/z: 359 $(M+H)^+$.

Step 3: Synthesis of W5

To a mixture of W4 (390 mg, 1.09 mmol) in DCM (4 mL) TFA (1 mL) was added at 0° C. under $N_2$ atmosphere, and the resulting mixture was stirred at room temperature for 1 hour. The mixture was then concentrated to dryness under reduced pressure to give crude product W5 (550 mg) which was used in the next step without any further purification. LC/MS (ESI) m/z: 259 $(M+H)^+$.

Step 4: Synthesis of 400

A solution of triphosgene (35 mg, 0.54 mmol) in DCM (2 mL) was added dropwise at −30° C. under $N_2$ atmosphere to a solution of crude W5 (60 mg, 0.232 mmol) and $NaHCO_3$ (59 mg, 0.697 mmol) in DCM (5 mL), and the resulting mixture was stirred at room temperature for 30 minutes. A mixture of W6 (43 mg, 0.232 mmol) and TEA (71 mg, 0.697 mmol) in anhydrous DCM (5 mL) was then added dropwise at 0° C. under $N_2$ atmosphere, and the resulting mixture was stirred at room temperature for 1 hour. The mixture was then diluted with water (10 mL) and extracted with DCM (10 mL) twice. The combined organic layers were separated, washed with brine (12 mL), dried over anhydrous $Na_2SO_4$, filtered and concentrated to dryness. The residue was purified via prep-HPLC to afford 400 (22 mg, 20.25% yield) as a white solid. LC/MS: m/z 468 $(M+H)^+$. $^1H$ NMR (400 MHz, MeOD) δ 7.86-7.77 (m, 1H), 7.74 (s, 1H), 7.59 (t, J=8.0 Hz, 1H), 7.43-7.31 (m, 1H), 6.71 (s, 1H), 4.59-4.44 (m, 2H), 4.05-3.84 (m, 2H), 3.72-3.56 (m, 1H), 3.24-3.14 (m, 1H), 2.75-2.61 (m, 1H), 2.58-2.48 (m, 1H), 2.22-2.05 (m, 1H), 1.97-1.84 (m, 1H), 1.81-1.68 (m, 1H), 1.61-1.45 (m, 1H), 1.03-0.90 (m, 2H), 0.88-0.75 (m, 2H).

General Procedure X:

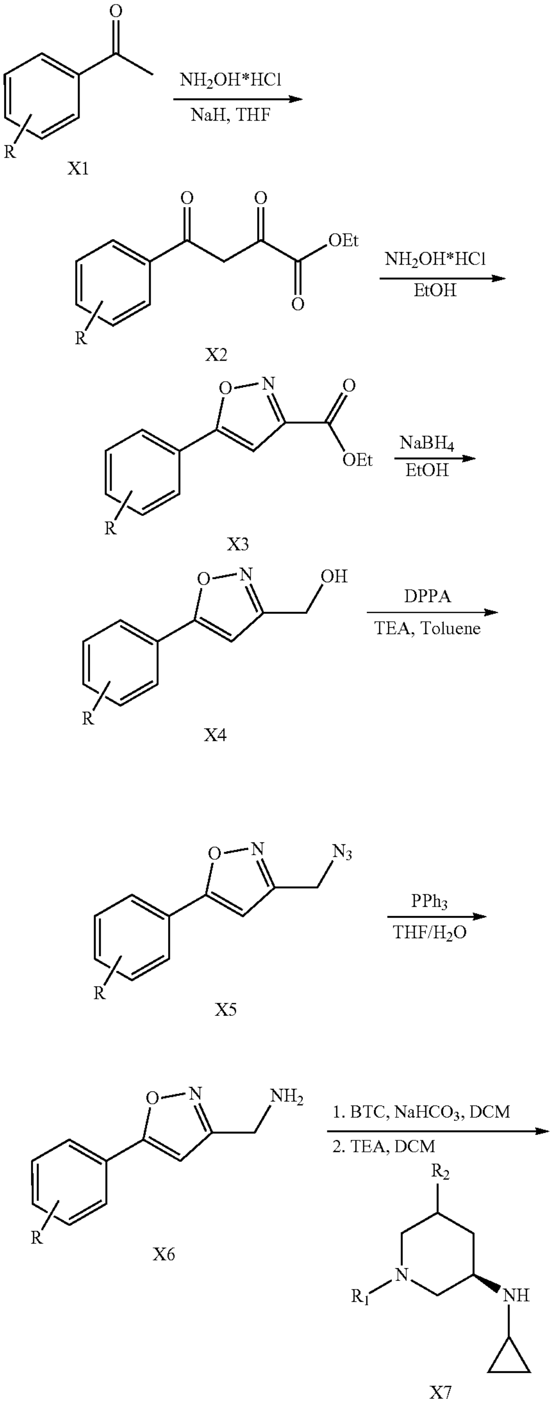

-continued

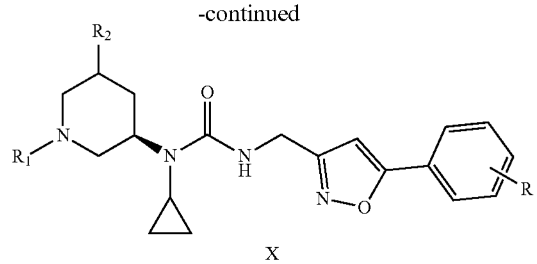

X

Step 1: Synthesis of X2

To a solution of X1 (1 eq.) and diethyl oxalate (1.1 eq.) in anhydrous THF NaH (1.1 eq.) was added at 0° C. under $N_2$ atmosphere, and the resulting mixture was stirred at room temperature for 3 hours. The mixture was then quenched with water and extracted with DCM twice. The combined organic layers were separated, washed with brine, dried over anhydrous $Na_2SO_4$, filtered and concentrated to dryness under reduced pressure to give crude compound X2 which was used in the next step without any further purification.

Step 2: Synthesis of X3

Hydroxylamine hydrochloride (2.5 eq.) was added to a solution of X2 (1 eq.) in EtOH, and the resulting mixture was stirred at 80° C. for 2 hours under $N_2$ atmosphere. After cooling, the mixture was concentrated to dryness under reduced pressure and the residue was purified via flash column chromatography (eluted with PE/EtOAc) to give compound X3.

Step 3: Synthesis of X4

To a solution of compound X3 (1 eq.) in EtOH $NaBH_4$ (2.5 eq.) was added at 0° C. portionwise, and the resulting mixture was stirred at room temperature for 2 hours. The mixture was then quenched with water and extracted with EtOAc twice. The combined organic layers were washed with brine, dried over anhydrous $Na_2SO_4$, filtered and concentrated to dryness under reduced pressure. The residue was purified by flash column chromatography (eluted with PE/EtOAc) to give compound X4.

Step 4: Synthesis of X5

TEA (2 eq.) and DPPA (1.2 eq.) were added to a solution of compound X4 (1 eq.) in toluene, and the resulting mixture was stirred at room temperature for 20 hours under $N_2$ atmosphere. The mixture was then diluted with water and extracted with EtOAc twice. The combined organic layers were washed with brine, dried over anhydrous $Na_2SO_4$, filtered and concentrated to dryness under reduced pressure to give crude product X5 which was used in the next step without any further purification.

Step 5: Synthesis of X6

$PPh_3$ (2 eq.) was added to a mixture of X5 (1 eq.) in $THF/H_2O$ (4:1, V/V), and the resulting mixture was stirred at room temperature for 17 hours under $N_2$ atmosphere. The mixture was then diluted with 2N HCl (aq.) and washed with MTBE. The aqueous layer was separated and extracted with EtOAc twice after adjusting pH to 8 with saturated aqueous $NaHCO_3$ solution. The combined organic layers were washed with brine, dried over anhydrous $Na_2SO_4$, filtered and concentrated to dryness under reduced pressure to give crude product X6 which was used in the next step without any further purification.

Step 6: Synthesis of X

To a mixture of X6 (1 eq.) and $NaHCO_3$ (3 eq.) in anhydrous DCM a solution of triphosgene (0.5 eq.) in DCM was added dropwise at −30° C. under $N_2$ atmosphere, and the resulting mixture was stirred at room temperature for 30 minutes. A mixture of X7 (1 eq.) and TEA (3 eq.) in anhydrous DCM was then added dropwise at 0° C. under $N_2$ atmosphere, and the resulting mixture was stirred at room temperature for 1 hour. The mixture was then diluted with water and extracted with DCM twice. The combined organic layers were washed with brine, dried over anhydrous $Na_2SO_4$, filtered and concentrated to dryness. The residue was purified via prep-HPLC to give compound X.

General Procedure Y:

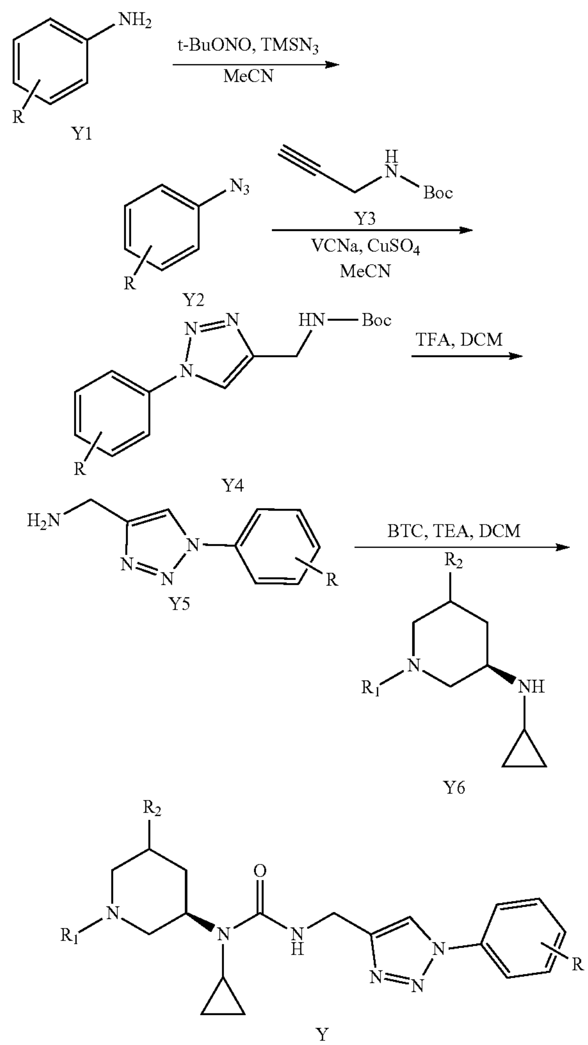

Step 1: Synthesis of Y2

To a solution of Y1 (1 eq.) in MeCN was added t-BuONO (1.2 eq.) and $TMSN_3$ (1.2 eq.) at 0° C. dropwise under $N_2$ atmosphere. The resulting mixture was stirred at room temperature for 1 hr. After TLC indicated the complete consumption of the starting material, the solution of Y2 in MeCN was used in the next step directly without further purification.

Step 2: Synthesis of Y 4

To a mixture of Y3 (1.2 eq.), sodium ascorbate (0.2 eq.) and $CuSO_4$ (0.2 eq.) in MeCN was added a solution of Y2 (1 eq.) in MeCN at 0° C. dropwise under $N_2$ atmosphere. The resulting mixture was stirred at r.t. overnight under $N_2$ atmosphere. Then the mixture was diluted with water and extracted with EtOAc twice. The combined organic layers were washed with brine, dried over anhydrous $Na_2SO_4$, filtered and concentrated to dryness. The residue was purified via flash column chromatography (eluted with PE/EtOAc) to give Y4.

Step 3: Synthesis of Y5

Y4 (1 eq.) was added into a mixture of TFA in DCM (1:3, V/V) at 0° C. dropwise. The resulting mixture was stirred at r.t. for 30 mins. Then the mixture was concentrated to dryness. The residue was dissolved in EtOAc, neutralized with aq. $NaHCO_3$ and extracted with EtOAc twice. The combined organic layers were washed with brine, dried over anhydrous $Na_2SO_4$, filtered and concentrated to obtain crude 5 which was used in the next step directly without further purification.

Step 4: Synthesis of Y7

To a mixture of Y5 (1.0 eq.) and Y6 (1.0 eq.) in DCM was added TEA (3.0 eq.) and a solution of BTC (0.5 eq.) in DCM at −78° C. dropwise under $N_2$ atmosphere. The resulting mixture was stirred at r.t. for 1 hr. Then the mixture was diluted with water and extracted with DCM twice. The combined organic layers were washed with brine, dried over anhydrous $Na_2SO_4$, filtered and concentrated to dryness. The residue was purified by prep-HPLC to give Y7.

Synthesis of Example 386

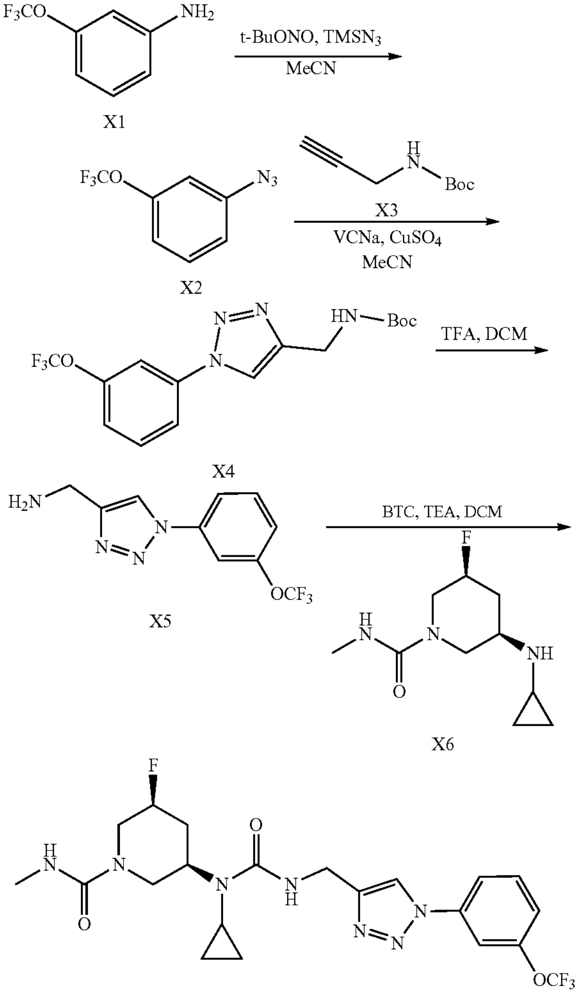

Example 386

Step 1: Synthesis of Y2

To a solution of Y1 (3.0 g, 16.95 mmol) in MeCN (30 mL) was added t-BuONO (2.10 g, 20.34 mmol) and $TMSN_3$ (2.34 g, 20.34 mmol) at 0° C. dropwise under $N_2$ atmosphere. The resulting mixture was stirred at room temperature for 1 hr. After TLC indicated the complete consumption of the starting material, the solution of Y2 in MeCN was used in the next step directly without further purification.

Step 2: Synthesis of Y4

To a mixture of Y3 (3.15 g, 20.34 mmol), sodium ascorbate (810 mg, 4.07 mmol) and $CuSO_4$ (650 mg, 4.07 mmol) in MeCN (20 mL) was added a mixture of Y2 in MeCN (30 mL) at 0° C. dropwise. The resulting mixture was stirred at r.t. overnight under $N_2$ atmosphere. Then the mixture was diluted with water and extracted with EtOAc (40 mL) twice. The combined organic layers were washed with brine (40 mL), dried over anhydrous $Na_2SO_4$, filtered and concentrated to dryness. The residue was purified by flash column chromatography (eluted with PE/EtOAc=100:0 to 3:2) to give pure Y4 (2.3 g, 37.80% yield). LC/MS (ESI) m/z: 359 $(M+H)^+$.

Step 3: Synthesis of Y5

To a solution of Y4 (80 mg, 0.223 mmol) in DCM (6 mL) was added TFA (2 mL) at 0° C. dropwise. The resulting mixture was stirred at r.t. for 30 mins. Then the mixture was concentrated to dryness. The residue was dissolved in EtOAc (4 mL), neutralized with aq. $NaHCO_3$ to pH=8. The mixture was extracted with EtOAc (10 mL) twice. The combined organic layers were washed with brine (20 mL), dried over anhydrous $Na_2SO_4$, filtered and concentrated to obtain crude Y5 (55 mg, 96.49% yield) which was used in the next step directly without further purification. LC/MS (ESI) m/z: 259 $(M+H)^+$.

Step 4: Synthesis of Example 386

To a mixture of Y5 (55 mg, 0.212 mmol) and Y6 (46 mg, 0.212 mmol) in DCM (5 mL) was added TEA (64 mg, 0.636 mmol) and a solution of BTC (31 mg, 0.106 mmol) in DCM (1 mL) at −78° C. dropwise under $N_2$ atmosphere. The resulting mixture was stirred at r.t. for 1 hr. Then the mixture was diluted with water (20 mL) and extracted with DCM (20 mL) twice. The combined organic layers were washed with brine (30 mL), dried over anhydrous $Na_2SO_4$, filtered and concentrated to dryness. The residue was purified via prep-HPLC to afford 386 (15 mg, 9.74% yield) as white solid. LC/MS (ESI) m/z: 500 $(M+H)^+$. $^1$HNMR (400 MHz, MeOD) δ 8.43 (s, 1H), 7.88 (dd, J=12.0, 3.9 Hz, 2H), 7.69 (t, J=8.2 Hz, 1H), 7.42 (d, J=8.3 Hz, 1H), 4.52 (s, 2H), 4.52-4.47 (m, 1H), 4.44-4.36 (m, 1H), 4.29 (d, J=12.5 Hz, 1H), 3.82 (d, J=12.8 Hz, 1H), 3.71 (t, J=11.1 Hz, 1H), 3.18-3.08 (m, 1H), 2.69 (s, 3H), 2.68-2.62 (m, 1H), 2.57-2.51 (m, 1H), 2.38-2.31 (m, 1H), 2.30-2.19 (m, 1H), 0.99-0.91 (m, 2H), 0.83-0.76 (m, 2H).

Representative compounds selected from above were tested in the isoleucine transport assay described in Example 1. The results are tabulated in FIG. 2 and FIG. 3.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula (I):

(I)

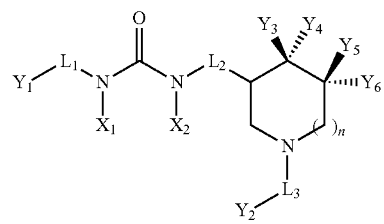

wherein:

n is 1;

$L_1$ is -alkyl-;

$L_2$ is absent;

$L_3$ is —C(O)—;

$X_1$ and $X_2$ are independently selected from —H and cycloalkyl; provided that $X_1$ and $X_2$ are not both —H;

$Y_1$ is unsubstituted or substituted aryl;

$Y_2$ is selected from hydroxyalkyl and —NH($Y_2$');

$Y_2$' is alkyl; and $Y_3$, $Y_4$, $Y_5$, and $Y_6$ are independently selected from —H, and halide;

or a pharmaceutically acceptable salt thereof.

2. The compound of claim 1, or a pharmaceutically acceptable salt thereof, wherein any one of the following statements (A)-(B) applies:

(A) $Y_1$ is selected from

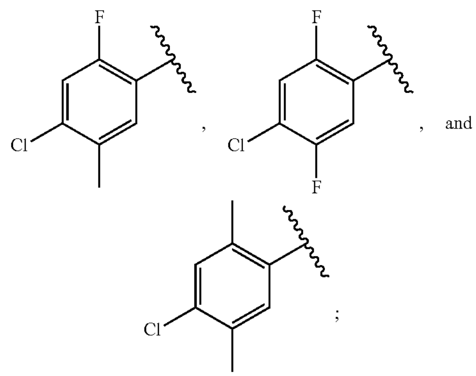

, , and ;

(B) $Y_1$ is selected from

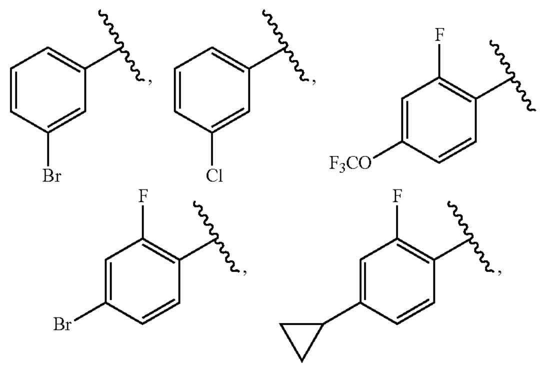

, , , , ,

-continued

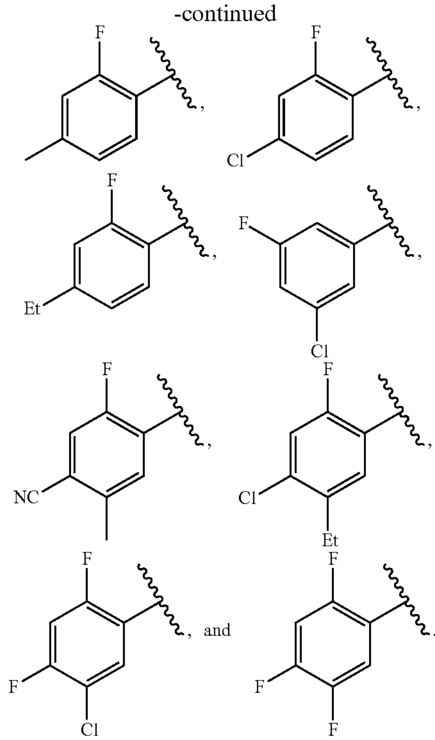

3. The compound of claim 1, or a pharmaceutically acceptable salt thereof, wherein $Y_1$ is selected from

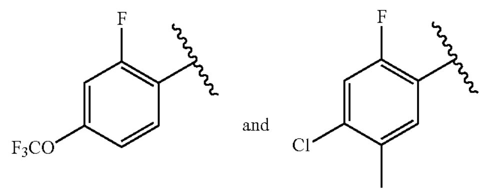

4. The compound of claim 1, or a pharmaceutically acceptable salt thereof, wherein $L_1$ is $—CH_2—$.

5. The compound of claim 2, or a pharmaceutically acceptable salt thereof, wherein $L_1$ is $—CH_2—$.

6. The compound of claim 3, or a pharmaceutically acceptable salt thereof, wherein $L_1$ is $—CH_2—$.

7. The compound of claim 1, or a pharmaceutically acceptable salt thereof, wherein $X_1$ and $X_2$ are independently selected from —H and cyclopropyl; provided that $X_1$ and $X_2$ are not both —H.

8. The compound of claim 2, or a pharmaceutically acceptable salt thereof, wherein $X_1$ and $X_2$ are independently selected from —H and cyclopropyl; provided that $X_1$ and $X_2$ are not both —H.

9. The compound of claim 3, or a pharmaceutically acceptable salt thereof, wherein $X_1$ and $X_2$ are independently selected from —H and cyclopropyl; provided that $X_1$ and $X_2$ are not both —H.

10. The compound of claim 4, or a pharmaceutically acceptable salt thereof, wherein $X_1$ and $X_2$ are independently selected from —H and cyclopropyl; provided that $X_1$ and $X_2$ are not both —H.

11. The compound of claim 1, or a pharmaceutically acceptable salt thereof, wherein:

$Y_1$ is

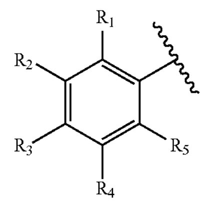

and $R_1$, $R_2$, $R_3$, $R_4$, and $R_5$ are independently selected from —H, —F, —Cl, —Br, —CN, $—CH_3$, $—CH_2CH_3$, $—OCF_3$, and

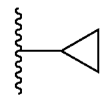

12. The compound of claim 1, or a pharmaceutically acceptable salt thereof, wherein $Y_2$ is selected from hydroxyalkyl having 1 to 3 carbons and —NH ($Y_2'$).

13. The compound of claim 2, or a pharmaceutically acceptable salt thereof, wherein $Y_2$ is selected from hydroxyalkyl having 1 to 3 carbons and —NH ($Y_2'$).

14. The compound of claim 3, or a pharmaceutically acceptable salt thereof, wherein $Y_2$ is selected from hydroxyalkyl having 1 to 3 carbons and —NH ($Y_2'$).

15. The compound of claim 4, or a pharmaceutically acceptable salt thereof, wherein $Y_2$ is selected from hydroxyalkyl having 1 to 3 carbons and —NH ($Y_2'$).

16. The compound of claim 7, or a pharmaceutically acceptable salt thereof, wherein $Y_2$ is selected from hydroxyalkyl having 1 to 3 carbons and —NH ($Y_2'$).

17. The compound of claim 11, or a pharmaceutically acceptable salt thereof, wherein $Y_2$ is selected from hydroxyalkyl having 1 to 3 carbons and —NH ($Y_2'$).

18. The compound of claim 1, or a pharmaceutically acceptable salt thereof, wherein $Y_2'$ is alkyl having 1 to 3 carbons.

19. The compound of claim 2, or a pharmaceutically acceptable salt thereof, wherein $Y_2'$ is alkyl having 1 to 3 carbons.

20. The compound of claim 3, or a pharmaceutically acceptable salt thereof, wherein $Y_2'$ is alkyl having 1 to 3 carbons.

21. The compound of claim 4, or a pharmaceutically acceptable salt thereof, wherein $Y_2'$ is alkyl having 1 to 3 carbons.

22. The compound of claim 7, or a pharmaceutically acceptable salt thereof, wherein $Y_2'$ is alkyl having 1 to 3 carbons.

23. The compound of claim 11, or a pharmaceutically acceptable salt thereof, wherein $Y_2'$ is alkyl having 1 to 3 carbons.

24. The compound of claim 12, or a pharmaceutically acceptable salt thereof, wherein $Y_2'$ is alkyl having 1 to 3 carbons.

25. The compound of claim 1, or a pharmaceutically acceptable salt thereof, wherein $Y_2$ is hydroxyalkyl having 1 to 3 carbons.

26. The compound of claim 2, or a pharmaceutically acceptable salt thereof, wherein $Y_2$ is hydroxyalkyl having 1 to 3 carbons.

27. The compound of claim 3, or a pharmaceutically acceptable salt thereof, wherein $Y_2$ is hydroxyalkyl having 1 to 3 carbons.

28. The compound of claim 4, or a pharmaceutically acceptable salt thereof, wherein $Y_2$ is hydroxyalkyl having 1 to 3 carbons.

29. The compound of claim 7, or a pharmaceutically acceptable salt thereof, wherein $Y_2$ is hydroxyalkyl having 1 to 3 carbons.

30. The compound of claim 11, or a pharmaceutically acceptable salt thereof, wherein $Y_2$ is hydroxyalkyl having 1 to 3 carbons.

* * * * *